US010647720B2

(12) United States Patent
Venkatesan et al.

(10) Patent No.: US 10,647,720 B2
(45) **Date of Patent: *May 12, 2020**

(54) PYRIMIDO-PYRIDAZINONE COMPOUNDS AND METHODS OF USE THEREOF

(71) Applicant: Asana Biosciences, LLC, Lawrenceville, NJ (US)

(72) Inventors: Aranapakam Venkatesan, Rego Park, NY (US); Roger Smith, Chester Springs, PA (US); Subramanya Hosahalli, Bangalore (IN); Vijay Potluri, Hyderabad (IN); Sunil Kumar Panigrahi, Orissa (IN); Vishnu Basetti, Hyderabad (IN); Karunasree Kunta, Hyderabad (IN)

(73) Assignee: Asan BioSciences, LLC, Lawrenceville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/206,395

(22) Filed: Nov. 30, 2018

(65) Prior Publication Data

US 2019/0092779 A1 Mar. 28, 2019

Related U.S. Application Data

(60) Continuation of application No. 15/137,950, filed on Apr. 25, 2016, now Pat. No. 10,183,944, which is a continuation of application No. 14/244,183, filed on Apr. 3, 2014, now Pat. No. 9,382,277, which is a division of application No. 13/592,511, filed on Aug. 23, 2012, now Pat. No. 8,729,079.

(60) Provisional application No. 61/526,525, filed on Aug. 23, 2011.

(51) Int. Cl.

| | |
|---|---|
| *C07D 487/04* | (2006.01) |
| *C07D 519/00* | (2006.01) |
| *A61K 31/519* | (2006.01) |
| *A61P 37/00* | (2006.01) |
| *A61P 17/00* | (2006.01) |
| *C07F 9/6561* | (2006.01) |

(52) U.S. Cl.

CPC .......... *C07D 487/04* (2013.01); *A61K 31/519* (2013.01); *C07D 519/00* (2013.01); *C07F 9/6561* (2013.01)

(58) Field of Classification Search

CPC ... A61K 31/519; C07D 487/04; C07D 519/00

USPC ........... 514/248, 234.2, 217.06, 218, 210.02; 544/118, 236, 230, 70; 540/200, 575, 540/600

See application file for complete search history.

(56) References Cited

U.S. PATENT DOCUMENTS

| | | | | |
|---|---|---|---|---|
| 3,764,598 | A | 10/1973 | Yurugi et al. | |
| 7,037,917 | B2 | 5/2006 | De Corte et al. | |
| 7,825,116 | B2 | 11/2010 | Singh et al. | |
| 8,729,079 | B2 * | 5/2014 | Venkatesan .......... | C07D 487/04 514/248 |
| 9,382,277 | B2 | 7/2016 | Venkatesan et al. | |
| 10,188,654 | B2 * | 1/2019 | Reddy .................. | A61K 31/519 |
| 2004/0176400 | A1 | 9/2004 | Capelli et al. | |
| 2006/0223741 | A1 | 10/2006 | Smith et al. | |
| 2007/0066632 | A1 | 3/2007 | Hart et al. | |
| 2008/0194656 | A1 | 8/2008 | Berwaer et al. | |
| 2009/0181993 | A1 | 7/2009 | Guillemont et al. | |
| 2010/0137313 | A1 | 6/2010 | Boriack-Sjodin et al. | |
| 2010/0216827 | A1 | 8/2010 | Ma et al. | |
| 2012/0129851 | A1 | 5/2012 | Smith et al. | |
| 2014/0038952 | A1 | 2/2014 | Smith et al. | |
| 2019/0008868 | A1 * | 1/2019 | Railkar .................. | A61P 17/00 |
| 2019/0070182 | A1 * | 3/2019 | Reddy .................. | A61K 31/519 |

FOREIGN PATENT DOCUMENTS

| | | | |
|---|---|---|---|
| CN | 1462273 | A | 12/2003 |
| CN | 101641014 | A | 2/2010 |
| DE | 2046577 | A1 | 5/1971 |
| EP | 1724268 | A1 | 11/2006 |
| EP | 1970373 | A1 | 9/2008 |

(Continued)

OTHER PUBLICATIONS

International Search Report and Written Opinion dated Jan. 4, 2013, issued in counterpart International Appln. No. PCT/US2012/051980.

(Continued)

*Primary Examiner* — Irina Neagu

(74) *Attorney, Agent, or Firm* — DLA Piper LLP (US)

(57) ABSTRACT

The present application provides novel pyrimido-pyridazinone compounds and methods for preparing and using these compounds. These compounds are useful in treating inflammation in patients by administering one or more of the compounds to a patient. In one embodiment, the novel pyrimido-pyridazinone compound is of Formula (I) and $R^1$ and $R^2$ are defined herein.

(I)

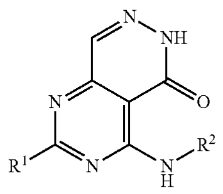

33 Claims, 3 Drawing Sheets

(56) References Cited

FOREIGN PATENT DOCUMENTS

| | | | |
|---|---|---|---|
| JP | 49048695 | | 5/1974 |
| JP | 50101387 | | 8/1975 |
| JP | 2011510990 | A | 4/2011 |
| WO | 94/025446 | A1 | 11/1994 |
| WO | 95/019774 | A1 | 7/1995 |
| WO | 99/043671 | A1 | 9/1999 |
| WO | 03/075828 | A2 | 9/2003 |
| WO | 2004/087053 | A2 | 10/2004 |
| WO | 2005/012294 | A1 | 2/2005 |
| WO | 2006/100310 | A1 | 9/2006 |
| WO | 2006/105063 | A1 | 10/2006 |
| WO | 2007/082131 | A1 | 7/2007 |
| WO | 2007/125405 | A2 | 11/2007 |
| WO | 2008/074982 | A1 | 6/2008 |
| WO | 2008/112913 | A1 | 9/2008 |
| WO | 2009/097287 | A1 | 8/2009 |
| WO | 2009/099801 | A1 | 8/2009 |
| WO | 2010/038060 | A1 | 4/2010 |
| WO | 2011/053861 | A1 | 5/2011 |
| WO | 2011/079105 | A1 | 6/2011 |

OTHER PUBLICATIONS

Prausnitz, “Transdermal Drug Delivery”, Nat. Biotechnol., 26(11): 1261-1268 (Nov. 2008).
Moore, “An analysis of the diaminopyrimidine patent estates describing spleen tyrosine kinase inhibitors by Rigel and Portola”, Expert Opin. Ther. Patents 20(12): 1703-1722 (2010; e-publication: Nov. 14, 2010).
Braselmann, “R406, an Orally Available Spleen Tyrosine Kinase Inhibitor Blocks Fc Receptor Signaling and Reduces Immune Complex-Mediated Inflammation”, Journal of Pharmacology and Experimental Therapeutics, 319(3): 998-1008 (Dec. 2006; e-publication: Aug. 31, 2006).
Arias-Palomo, 3D structure of Syk kinase determined by single particle electron microscopy, Biochem. Biophys. Acta, 1774 (12): 1493-1499 (Dec. 2007; e-publication: Oct. 26, 2007).
Villasenor, “Structural Insights for Design of Potent Spleen Tyrosine Kinase Inhibitors from Crystallographic Analysis of Three Inhibitor Complexes”, Chem. Biol. Drug Des., 73: 466-470 (Apr. 2009; e-publication: Feb. 7, 2009).
Law et al., “Molecular Cloning of Human Syk”, J. Biol. Chem. vol. 269, No. 16, 1994, pp. 12310-12319.
Yagi, “Cloning of the cDNA for the Deleted SYK Kinase Honologous to ZAP-70 from Human Basophilic Leukemia Cell Line (KU812)”, Biochem. Biophys. Res. Commun. vol. 200, No. 1, 1994, pp. 28-34.
Rossi et al., “Identification of the Syk kinase inhibitor R112 by a human mast cell screen”, J. Allergy Clin. Immunol. vol. 118, No. 3, 2006, pp. 749-755.
Eva Papp, “Steady State Kinetics of Spleen J yrosine Kinase Investigated by a Real Time Fluorescence Assay”. Biochemistry vol. 46, 2007, pp. 15103-15114.
Rodig, “Disruption of the JAK1 gene demonstrates obligatory and nonredundant roles of the JAKs in cytokine-induced biologic responses”, Cell vol. 93, No. 3, 1998, pp. 373-383.
Yamaoka, “The Janus kinases (Jkas)”, Genome Biology, 2004, vol. 5: 253.
Ghoreschi et al. Nature Immunology 2009, 10 (4), 356-360.
Walker et al. Biochimica and Biophysica Acta 2012, 1822. 57-65.
Japanese Office Action for Application No. 2014-527282 dated Mar. 22, 2016.
Fourth Chinese Office Action dated Dec. 5, 2016, of corresponding Chinese Application No. 201280051788.8 along with an English translation.
Tanaka, Yoshiya et al., “Jak and Syk: Emerging Their Relevance to the Treatment of Inflammatory Diseases”, *Inflammation and Regeneration*, vol. 31, No. 3, May 2011, pp. 237-244.
Kontzias, Apostolos, et al., “Kinase Inhibitors in the Treatment of Immune-Mediated Disease”, *F1000 Reorts Medicine*, Mar. 1, 2012, http://f1000.com/reports/m/4/5, 8 pages.
Mayers, Melissa, et al., “Intracellular Signal Pathways: Potential for Therapies”, *Curr. Rheumatoal Rep.*, vol. 11, No. 5, Oct. 2009, 13 pages.
Bhagwat, Shripad S., “Kinase Inhibitors for the Treatment of Inflammatory and Autoimmune Disorders”, *Purinergic Signalling*, vol. 5, 2009, pp. 107-115.
Office Action from corresponding Mexican Patent Application No. MX/a/2014/0021I2 dated Apr. 17, 2018, and its technical analysis.
Office Action from corresponding European Patent Application No. 12 756 865.7 dated Apr. 26, 2016.
Office Action from corresponding European Patent Application No. 12 756 865.7 dated Sep. 10, 2015.
International Preliminary Report on Patentability from corresponding International Application No. PCT/US2012/051980 dated Feb. 25, 2014.
Stedman's Medical Dictionary; Stedman's on line. Autoimmune disease; http://stedmansonline.com/content.aspx?id-mlrA2100002481 &termtype=t (accessed Mar. 11, 2017).
Janeway CA Jr, Travers P, Walport M. et al., Immunobiology: The Immune System in Health and Disease, 5th edition, New York: Garland Science, 2001, Autoimmune responses are directed against self antigens. Available from: http://www.ncbi/nlm.nih.gov/books/NBK27155/ (accessed on Jun. 30, 2017).
Extended European Search Report from corresponding European Patent Application No. 18175788.1 dated Sep. 25, 2018.
Extended European Search Report from corresponding European Patent Application No. 18182723.9 dated Nov. 13, 2018.

* cited by examiner

PYRIMIDO-PYRIDAZINONE COMPOUNDS AND METHODS OF USE THEREOF

BACKGROUND

Protein kinases constitute a large family of structurally related enzymes that are responsible for the control of a variety of signal transduction processes within cells. Almost all kinases contain a similar 250 to 300 amino acid catalytic domain. The kinases can be categorized into families by the substrates they phosphorylate.

JAK2 (Janus kinase 2) is a family of intracellular non-receptor tyrosine kinases. JAK2 is expressed ubiquitously in hematopoietic cells and abundantly in primary leukemic cells from children with acute lymphoblastic leukemia. The downstream substrates of JAK include the signal tranducer activator of transcription (STAT) proteins. STAT proteins function both as signaling molecules and transcription factors and ultimately bind to specific DNA sequences present in the promoters of cytokine-responsive genes. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Spleen tyrosine kinase (syk) is a member of the syk family of protein tyrosine kinases and plays a crucial role in inflammatory and allergic responses. Syk triggers IgE and IgG receptor mediated signaling in mast cells, basophils, and macrophages leading to degranulation and cytokine release.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, and Fc receptors in immune cells and at GPVI and FcγRIIa in platelets to downstream intracellular molecules such as Syk.

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact. The interaction of Syk with diphosphorylated ITAM sequences induces a conformation change in the kinases that allows for tyrosine phosphorylation of the kinase itself.

Not only do these kinases contribute to normal host defense, they also play roles in the pathogenesis of diseases. Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, Alzheimer's disease and hormone-related diseases. As a consequence, there have been substantial efforts in medicinal chemistry to find inhibitors of protein kinases for use as therapeutic agents.

There is a need in the art for compounds that are dual inhibitors of Syk/JAK2, as well as for methods for treating conditions that can benefit from such inhibition.

SUMMARY OF THE INVENTION

In one aspect, the present invention provides a compound of Formula (I), wherein $R^1$ and $R^2$ are defined herein.

(I)

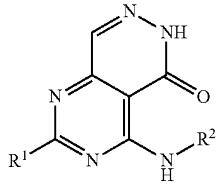

In another aspect, the invention provides a pharmaceutical composition containing a compound of Formula (I) and a pharmaceutically acceptable carrier.

In a further aspect, the invention provides a method for co-regulating JAK-2 and Syk by administering a therapeutically effective amount of a compound of Formula (I) to a patient in need thereof.

In yet another aspect, methods for treating inflammation are provided and include administering a compound of Formula (I) to a patient in need thereof.

Other aspects and advantages of the invention will be readily apparent from the following detailed description of the invention.

BRIEF DESCRIPTION OF THE DRAWINGS

FIG. 1A illustrates anti-inflammatory effects as a function of the amount of edema (mL) vs. time (days). The black diamonds (♦) represent results for the control. The triangles (▲) represent results for the compound of Example 19. The crosses (x) represent results for methotrexate.

FIG. 1B illustrates anti-inflammatory effects as a function of the amount of edema (mL) vs. time (days). The circles (●) represent results for the control. The inverted triangles (▼) represent results for the compound of Example 62. The astericks (*) represent results for the compound of Example 108. The squares (■) represent results for the compound of Example 189. The diamonds (♦) represent results for the compound of Example 191.

FIG. 2A illustrates anti-inflammatory effects as a function of arhtritic score (per rat) vs. time (days). The black diamonds (♦) represent results for the control. The triangles (▲) represent results for the compound of Example 19. The crosses (x) represent results for methotrexate.

FIG. 2B illustrates anti-inflammatory effects as a function of arhtritic score (per rat) vs. time (days). The circles (●) represent results for the control. The triangles (▲) represent results for the compound of Example 62. The astericks (*) represent results for the compound of Example 108. The squares (■) represent results for the compound of Example 189. The diamonds (♦) represent results for the compound of Example 191.

DETAILED DESCRIPTION OF THE INVENTION

Figure 1A:
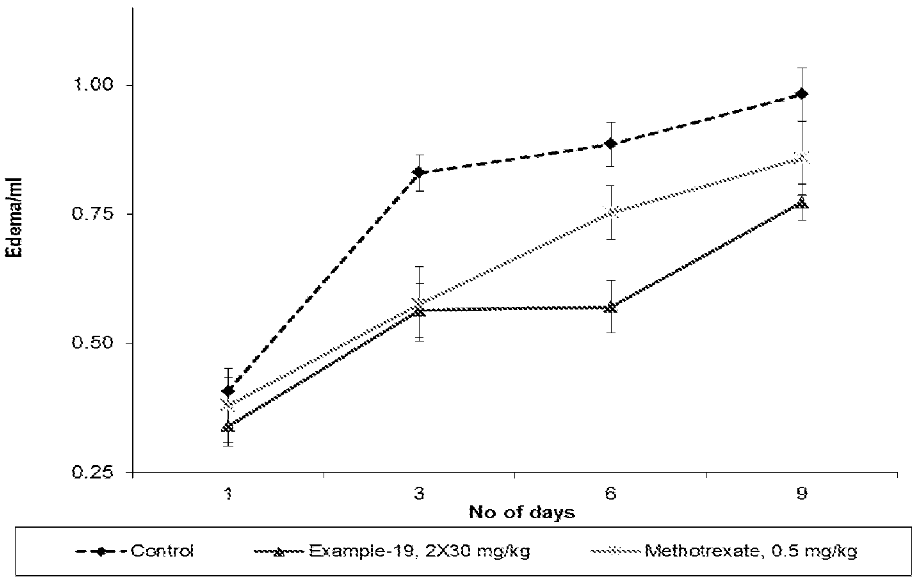
FIGS. 1A, 1B, 2A and 2B provide comparative data illustrating the anti-inflammatory effects of methotrexate, a known anti-inflammatory, and a compound described herein which is encompassed by the compound of Formula (I), using the Collagen Induced Arthritis (CIA) model of human rheumatoid arthritis (RA) in female lewis rats. After type II collagen (cII) induced CIA, the compound of Example 19 (2×30 mg/kg) and methotrexate (0.5 mg/kg) were administered daily or twice daily, respectively, to separate rats.

The invention provides compounds and pharmaceutical composition thereof, which are capable of reducing or eliminating inflammation caused by tissue insult, injury, or pathology. The invention further provides compounds and compositions which function through a protein kinase inhibitory mechanism.

In one aspect, the present invention provides a compound of Formula (I):

(I)

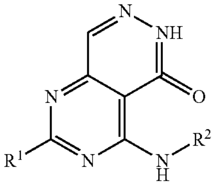

In this formula, $R^1$ is $NR^4R^5$, optionally substituted $C_1$ to $C_6$ alkoxy, optionally substituted $C_6$ to $C_{14}$ aryl, optionally substituted heteroaryl, optionally substituted 3-10 membered monocyclic or bicyclic cycloalkyl, or optionally substituted 3-10 membered monocyclic or bicyclic heterocyclyl. In one aspect, the 3-4 membered cycloalkyl and heterocyclyl are saturated. In another aspect, the hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In a further aspect, the hydrogen atoms on the same atom of the cycloalkyl or heterocyclyl are optionally replaced with O to form an oxo substituent.

i. In another embodiment, $R^1$ is N($C_1$ to $C_6$ alkyl)($C_1$ to $C_6$ alkyl) or $C_1$ to $C_6$ alkoxy.

ii. In still a further embodiment, $R^1$ is $N(CH(CH_3)_2)_2$, $N(CH_3)_2$, $OCH_2CH_3$, or $OCH_3$.

iii. In another embodiment, $R^1$ is optionally substituted phenyl.

iv. In still another embodiment, $R^1$ is of the structure:

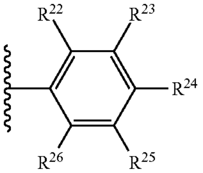

wherein, $R^{22}$, $R^{23}$, $R^{24}$, $R^{25}$, and $R^{26}$ are, independently, H, C(O)($C_1$ to $C_6$ alkoxy), C(O)OH, O($C_1$ to $C_3$ perfluoroalkyl), O($C_1$ to $C_6$ perfluoroalkoxy), $C_1$ to $C_6$ alkoxy, halogen, ($C_1$ to $C_6$ alkyl)heterocyclyl, or ($C_1$ to $C_6$ alkyl)CN.

v. In a further embodiment, $R^1$ is:

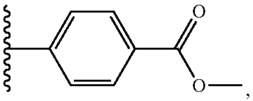 , 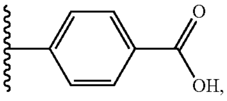 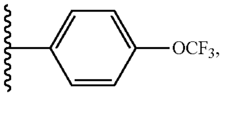 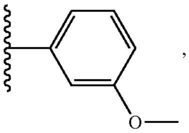 ,

-continued

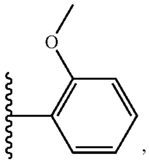 , 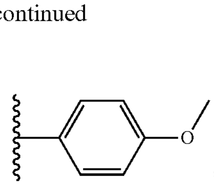 ,

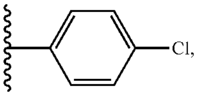 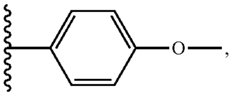 ,

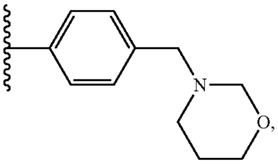 or 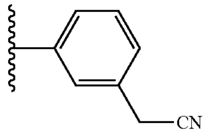

vi. In yet another embodiment, $R^1$ is optionally substituted 5-9 membered saturated heterocyclyl.

vii. In still a further embodiment, $R^1$ is of the structure:

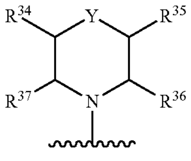

wherein, $R^{34}$, $R^{35}$, $R^{36}$, and $R^{37}$ are, independently, H, $C_1$ to $C_6$ alkyl, or CN; Y is $(C(R^8)_2)_x$, $NR^7(C(R^8)_2)_x$, O, (S═O), $SO_2$, or $NR^7$; $R^7$ and $R^8$ are, independently, H, $C_1$ to $C_6$ alkyl, C(O)OH, ($C_1$ to $C_6$ alkyl)CN, ($C_1$ to $C_6$ alkyl)C(O)OH, C(O)($C_1$ to $C_6$ alkyl)CN, or CN; and x is 0 to 2.

viii. In another embodiment, $R^1$ is:

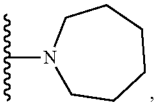 , 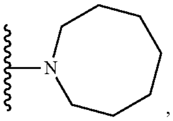 , 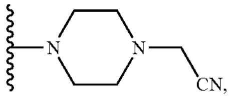

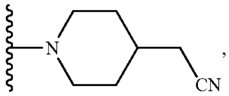 , 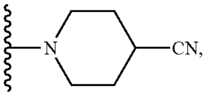

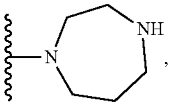 , 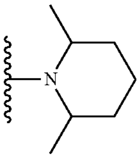 , 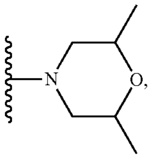

, ,

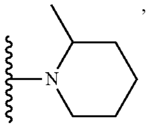 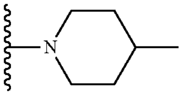 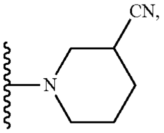

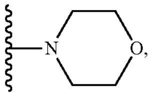 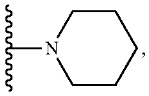 , 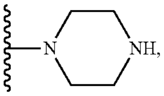

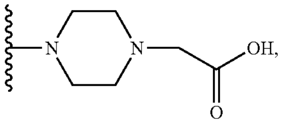 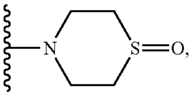

-continued

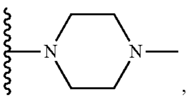, 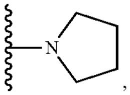, 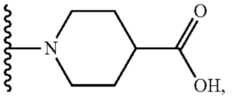

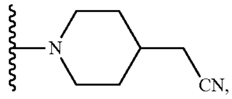 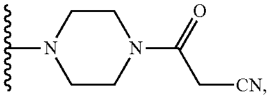 or

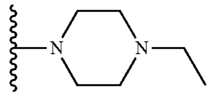

ix. In still a further embodiment, $R^1$ is of the structure:

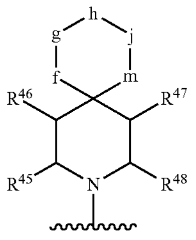

wherein, f, g, h, j, and m are, independently, absent, ($CH_2$), $CH(R^3)$, Z, or C═O; $R^3$ is H, C(O)OH, or C(O)O($C_1$ to $C_6$ alkyl); $R^{45}$, $R^{46}$, $R^{47}$, and $R^{48}$ are, independently, H or $C_1$ to $C_6$ alkyl; and Z is O, S, SO, $SO_2$, or NH.

x. In yet another embodiment, $R^1$ is:

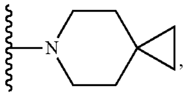, 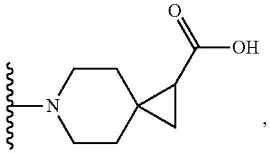, or

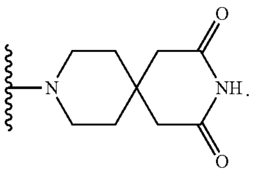

xi. In a further embodiment, $R^1$ is a heteroaryl.

xii. In yet another embodiment, $R^1$ is thiophene, benzooxole, or pyridine.

xiii. In still another embodiment, $R^1$ is a monocyclic $C_3$ to $C_8$ cycloalkyl.

xiv. In yet a further embodiment, $R^1$ is cycloheptyl or cyclohexyl, both optionally substituted with —N($C_1$ to $C_6$ alkyl)($C_1$ to $C_6$ alkyl).

xv. In another embodiment, $R^1$ is piperidine substituted with C(O)($C_1$ to $C_6$ alkyl)CN.

xvi. In still a further embodiment, $R^1$ is:

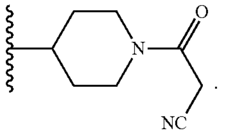 [SMILES: *C1CCN(C(=O)CC#N)CC1]

a. In one embodiment, $R^2$ is phenyl substituted with $C(O)NR^4R^5$.

b. In another embodiment, $R^2$ is phenyl substituted with

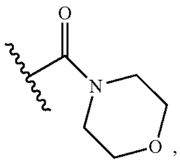, 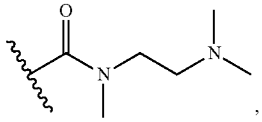, or

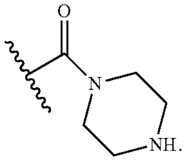

c. In a further embodiment, $R^2$ is phenyl substituted with $NR^4R^5$.

d. In yet another embodiment, $R^2$ is phenyl substituted with ($C_1$ to $C_6$ alkyl)$NR^4R^5$.

e. In another embodiment, $R^2$ is phenyl substituted with $NR^4R^5$ or ($C_1$ to $C_6$ alkyl)$NR^4R^5$ and $R^4$ and $R^5$ are taken together with the nitrogen atom to which they are attached to form a 6-membered ring.

f. In still a further embodiment, $R^2$ is phenyl substituted with $NR^4R^5$ or ($C_1$ to $C_6$ alkyl)$NR^4R^5$ and $R^4$ and $R^5$ are joined to form a heterocyclyl of the structure:

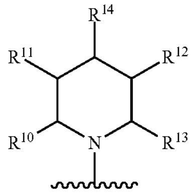 or 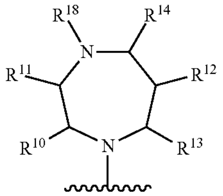

wherein, $R^{10}$, $R^1$, $R^{12}$, and $R^{13}$ are, independently, H or $C_1$ to $C_6$ alkyl; $R^{14}$ is halogen, OH, C(O)OH, $C_1$ to $C_6$ alkoxy, ($C_1$ to $C_6$ alkyl)halogen, ($C_1$ to $C_6$ alkyl)C(O)OH, $C_1$ to $C_6$ hydroxyalkyl, $C_3$ to $C_8$ cycloalkyl, ($C_1$ to $C_6$ alkyl)C(O)$NH_2$, ($C_1$ to $C_6$ alkyl)C(O)NH($C_1$ to $C_6$ hydroxyalkyl), ($C_1$ to $C_6$ alkyl)C(O)N($C_1$ to $C_6$ hydroxyalkyl)$_2$, ($C_1$ to $C_6$ alkyl)CN, ($C_1$ to $C_6$ alkyl)heteroaryl, or heteroaryl; and $R^{18}$ is $C_1$ to $C_6$ hydroxyalkyl or ($C_1$ to $C_6$ alkyl)C(O)OH.

g. In yet a further embodiment, $R^2$ is phenyl substituted with $NR^4R^5$ or ($C_1$ to $C_6$ alkyl)$NR^4R^5$ and wherein $R^4$ and $R^5$ are joined to form an optionally substituted piperidine or diazepane.

h. In another embodiment, $R^2$ is phenyl substituted with $NR^4R^5$ or ($C_1$ to $C_6$ alkyl)$NR^4R^5$ and $R^4$ and $R^5$ are joined to form:

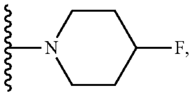, 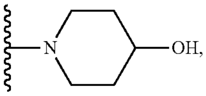,

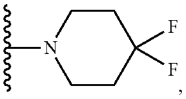, 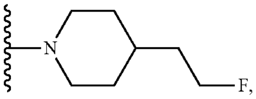,

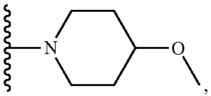, 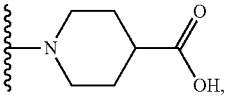,

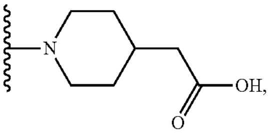, 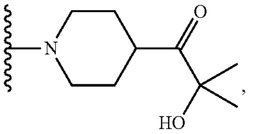,

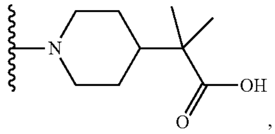, 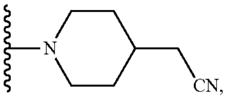,

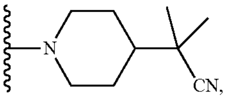, 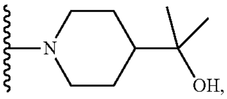,

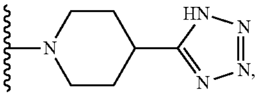, 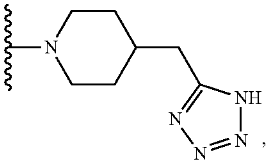,

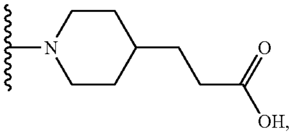, 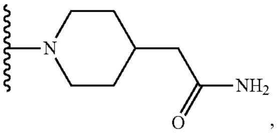,

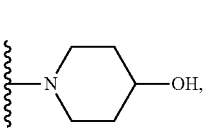, 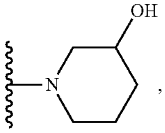,

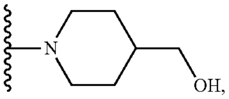, 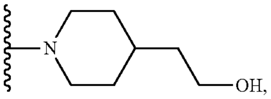,

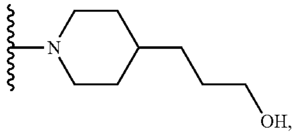,

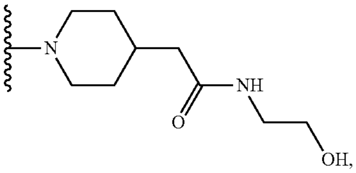,

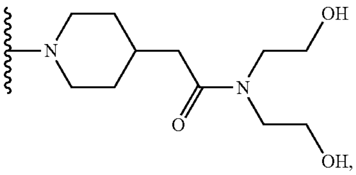,

-continued

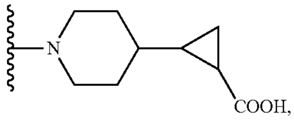,

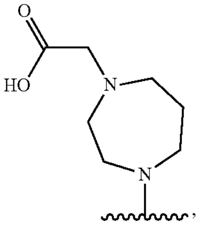, 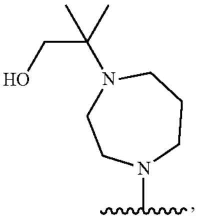, or

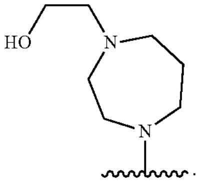.

i. In still a further embodiment, $R^2$ is phenyl substituted with $NR^4R^5$ or ($C_1$ to $C_6$ alkyl)$NR_4R^5$ and $R^4$ and $R^5$ are joined to form a heterocyclyl of the structure:

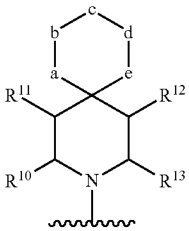

wherein, a, b, c, d, and e are, independently, absent, ($CH_2$), $CH(R^3)$, Z, or C═O; $R^3$ is H, C(O)OH, $C_1$ to $C_6$ hydroxyalkyl, or C(O)O($C_1$ to $C_6$ alkyl); $R^{10}$, $R^{11}$, $R^{12}$, and $R^{13}$ are, independently, H or $C_1$ to $C_6$ alkyl; and Z is O, S, or NH.

j. In yet another embodiment, $R^2$ is phenyl substituted with $NR^4R^5$ or ($C_1$ to $C_6$ alkyl)$NR^4R^5$ and $R^4$ and $R^5$ are joined to form:

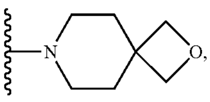, 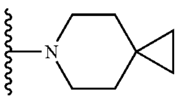,

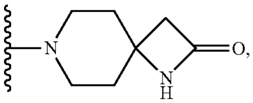, 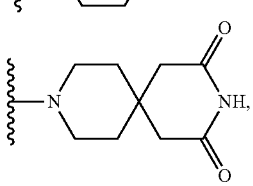,

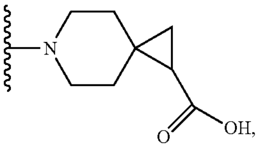, 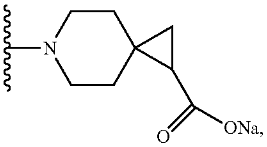,

-continued

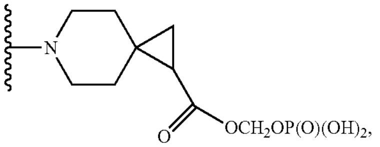

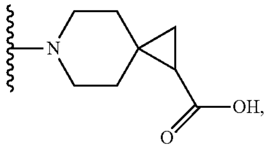

or

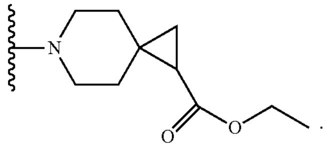

k. In a further embodiment, $R^2$ is phenyl substituted with $NR^4R^5$ or ($C_1$ to $C_6$ alkyl)$NR^4R^5$ and $R^4$ and $R^5$ are taken together to form a heterocyclyl of the structure:

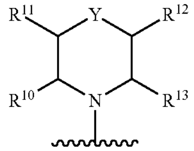

wherein, $R^{10}$, $R^{11}$, $R^{12}$, and $R^{13}$ are, independently, H or $C_1$ to $C_6$ alkyl; Y is O or $NR^9$; and $R^9$ is H, $C_1$ to $C_6$ alkyl, OH, C(O)OH, $C_1$ to $C_6$ hydroxyalkyl, ($C_1$ to $C_6$ alkyl)$NH_2$, ($C_1$ to $C_6$ alkyl)N($C_1$ to $C_6$ alkyl)($C_1$ to $C_6$ alkyl), ($C_1$ to $C_6$ alkyl)($C_1$ to $C_6$ alkoxy), C(O)($C_1$ to $C_6$ alkyl)$NH_2$, ($C_1$ to $C_6$ alkyl)C(O)OH, C(O)($C_1$ to $C_6$ hydroxyalkyl), C(O)($C_1$ to $C_6$ alkyl)CN, ($C_1$ to $C_6$ alkyl)CN, ($C_1$ to $C_6$ alkyl)halogen, or ($C_1$ to $C_6$ alkyl)O($C_1$ to $C_6$ alkyl)C(O)($C_1$ to $C_6$ alkyl)$NH_2$; wherein 2 hydrogen atoms attached to the same carbon atom are optionally replaced with =O.

l. In yet another embodiment, $R^2$ is phenyl substituted with $NR^4R^5$ or ($C_1$ to $C_6$ alkyl)$NR^4R^5$ and $R^4$ and $R^5$ are taken together to form an optionally substituted morpholine or piperazine.

m. In still a further embodiment, $R^2$ is phenyl substituted with $NR^4R^5$ or ($C_1$ to $C_6$ alkyl)$NR^4R^5$ and $R^4$ and $R^5$ are taken together to form:

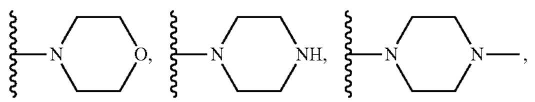

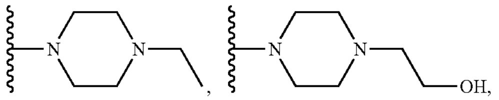

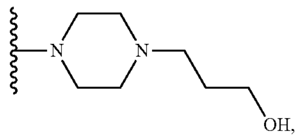

-continued

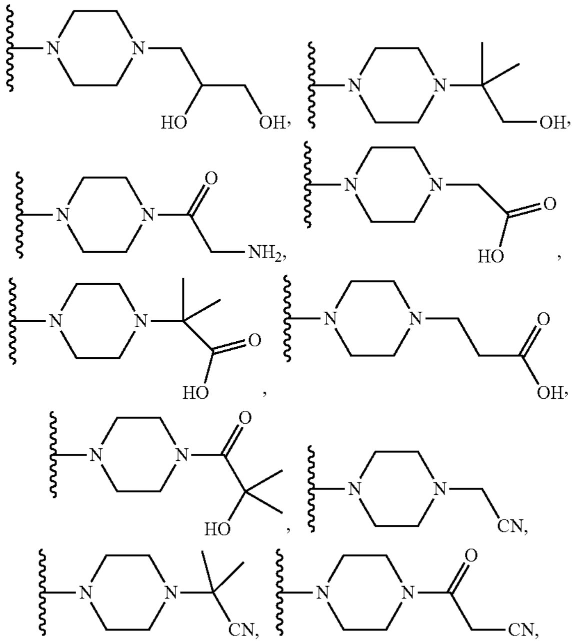

or

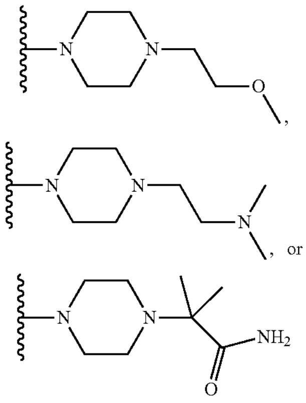

n. In another embodiment, $R^2$ is phenyl substituted with ($C_1$ to $C_6$ alkyl)$NR^4R^5$.

o. In yet a further embodiment, $R^2$ is phenyl substituted with ($C_1$ to $C_6$ alkyl)$NR^4R^5$ and $R^4$ and $R^5$ are ($C_1$ to $C_6$ hydroxyalkyl).

p. In still another embodiment, $R^2$ is phenyl substituted with ($C_1$ to $C_6$ alkyl)$NR^4R^5$ and $NR^4R^5$ is:

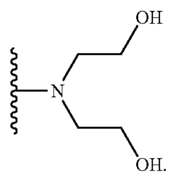 [SMILES: *N(CCO)CCO]

q. In a further embodiment, $R^2$ is phenyl substituted with ($C_1$ to $C_6$ alkyl)$NR^4R^5$ and $R^4$ and $R^5$ are joined to form an optionally substituted 6-membered ring.

r. In yet another embodiment, $R^2$ is phenyl substituted with ($C_1$ to $C_6$ alkyl)$NR^4R^5$ and $NR^4R^5$ are joined to form the 6-membered ring:

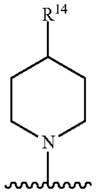

wherein, $R^{14}$ is H, OH, C(O)OH, $C_1$ to $C_6$ alkyl, or ($C_1$ to $C_6$ alkyl)CN.

s. In another embodiment, $R^2$ is phenyl substituted with ($C_1$ to $C_6$ alkyl)$NR^4R^5$ and $NR^4R^5$ are joined to form the 6-membered ring:

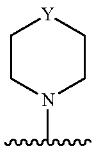

wherein, Y is O or $NR^9$; and $R^9$ is H, $C_1$ to $C_6$ alkyl, OH, $C_1$ to $C_6$ hydroxyalkyl, C(O)($C_1$ to $C_6$ hydroxyalkyl), C(O)($C_1$ to $C_6$ alkyl)CN, ($C_1$ to $C_6$ alkyl)CN, ($C_1$ to $C_6$ alkyl)$NH_2$, ($C_1$ to $C_6$ alkyl)halogen, C(O)($C_1$ to $C_6$ alkyl)CN or ($C_1$ to $C_6$ alkyl)O($C_1$ to $C_6$ alkyl)C(O)($C_1$ to $C_6$ alkyl)$NH_2$.

t. In still a further embodiment, $R^2$ is phenyl substituted with ($C_1$ to $C_6$ alkyl)$NR^4R^5$ and $NR^4R^5$ are joined to form the 6-membered ring

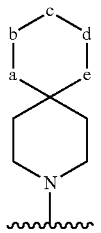

wherein, a, b, c, d, and e are, independently, absent, ($CH_2$), CH($R^3$), or O; and $R^3$ is H or C(O)OH.

u. In yet another embodiment, $R^2$ is a heteroaryl substituted with ($C_1$ to $C_6$ alkyl)$NR^4R^5$.

v. In still another embodiment, $R^2$ is:

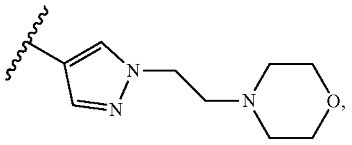

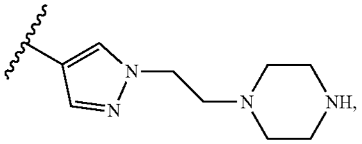

-continued

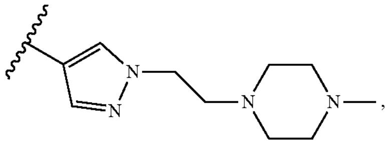

, or

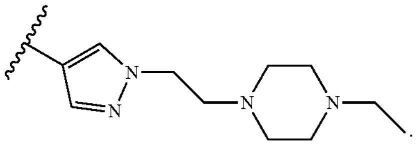

w. In a further embodiment, $R^2$ is a heteroaryl substituted with $NR^4R^5$.

x. In still another embodiment, $R^2$ is a heteroaryl substituted with $NR^4R^5$ and the heteroaryl is pyridine.

y. In yet a further embodiment, $R^2$ is of the structure:

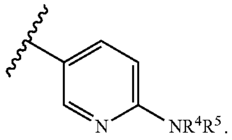

z. In another embodiment, $R^2$ is of the structure:

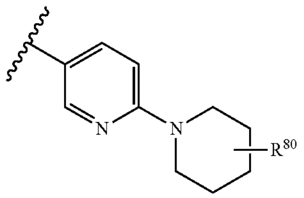

wherein, $R^{80}$ is OH, —($C_1$ to $C_6$ alkyl)CN, $C_1$ to $C_6$ hydroxyalkyl, ($C_1$ to $C_6$ alkyl)C(O)$NH_2$, ($C_1$ to $C_6$ alkyl)heterocycle or —($C_1$ to $C_6$ alkyl) C(O)OH.

aa. In still a further embodiment, $R^2$ is of the structure:

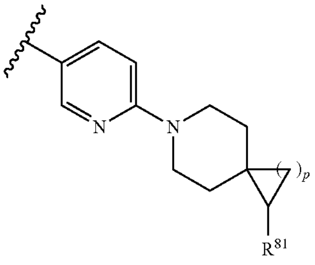

wherein, p is 1 to 6; and $R^{81}$ is H or C(O)OH.

bb. In another embodiment, $R^2$ is of the structure:

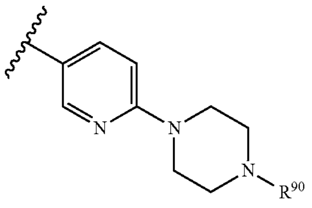

wherein, $R^{90}$ is H, $C_1$ to $C_6$ alkyl, C(O)($C_1$ to $C_6$ alkyl)CN, ($C_1$ to $C_6$ alkyl)C(O)OH, or C(O)$C_1$ to $C_6$ hydroxyalkyl.

cc. In yet another embodiment, wherein $R^2$ is phenyl substituted with one or more $C_1$ to $C_6$ alkoxy, ($C_1$ to $C_6$ alkyl)halogen, $C_1$ to $C_6$ trifluoroalkoxy, ($C_1$ to $C_6$ alkyl) C(O)OH, halogen, optionally substituted $C_3$ to $C_8$ cycloalkyl, optionally substituted heterocyclyl, optionally substituted heteroaryl, —O—($C_1$ to $C_6$ alkyl)C(O) OH, —O—($C_1$ to $C_6$ alkyl)$NR^4R^5$, —O(optionally substituted heterocycle), —O($C_1$ to $C_6$ alkyl)N($C_1$ to $C_6$ alkyl)($C_1$ to $C_6$ alkyl), —O($C_1$ to $C_6$ alkyl)$NH_2$, $C_1$ to $C_6$ hydroxyalkyl, —O($C_1$ to $C_6$ hydroxyalkyl), —O($C_1$ to $C_6$ alkyl)C(O)OH, —$C_1$ to $C_6$ alkoxy-$C_1$ to $C_6$ alkoxy, —O(heterocycle)($C_1$ to $C_6$ hydroxyalkyl), —$SO_2$($C_1$ to $C_6$ alkyl), or —($C_1$ to $C_6$ alkyl)($C_1$ to $C_6$ alkoxy)halogen.

dd. In a further embodiment, wherein $R^2$ is of the structure:

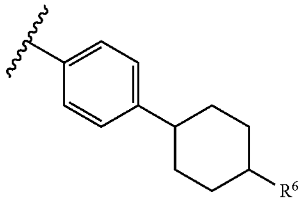

wherein, $R^6$ is H, ($C_1$ to $C_6$ alkyl)C(O)OH, or ($C_1$ to $C_6$ alkyl)CN.

ee. In still another embodiment, $R^2$ is of the structure:

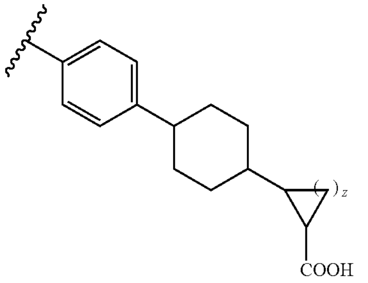

wherein, z is 1, 2, 3, 4, 5, or 6.

ff. In another embodiment, $R^2$ is of the structure:

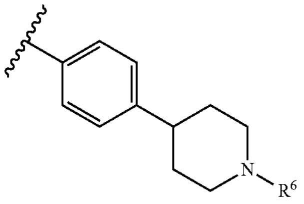

wherein, $R^6$ is H or ($C_1$ to $C_6$ alkyl)C(O)OH.

gg. In yet a further embodiment, $R^2$ is —O($C_1$ to $C_6$ alkyl)$NR^4R^5$.

hh. In still another embodiment, $R^2$ is of the structure:

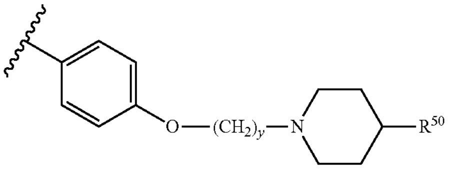

wherein, y is 2 to 6; and $R^{50}$ is H, OH, $C_1$ to $C_6$ alkyl, $C_1$ to $C_6$ hydroxyalkyl, or —($C_1$ to $C_6$ alkyl)C(O)OH.

ii. In further embodiment, $R^2$ is of the structure:

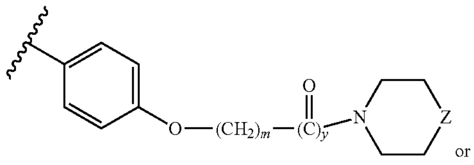

or

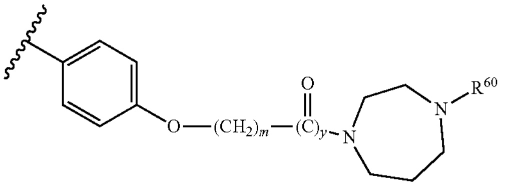

wherein, m is 2 to 6; y is 0 or 1; Z is O or $NR^{60}$; and $R^{60}$ is H, $C_1$ to $C_6$ alkyl, $C_1$ to $C_6$ hydroxyalkyl, —($C_1$ to $C_6$ alkyl)CN, —($C_1$ to $C_6$ alkyl)C(O)OH, —($C_1$ to $C_6$ alkyl)$CONH_2$, or —C(O)($C_1$ to $C_6$ alkyl)OH; wherein 2 hydrogen atoms attached to one carbon atom of the nitrogen-ring are replaced with an oxo or optionally substituted 3-8 membered spirocyclic ring.

jj. In yet another embodiment, $R^2$ is of the structure:

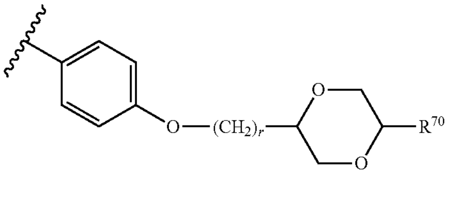

wherein, r is 2 to 6; and $R^{70}$ is H, C(O)OH or $C_1$ to $C_6$ hydroxyalkyl.

kk. In still a further embodiment, $R^2$ is:

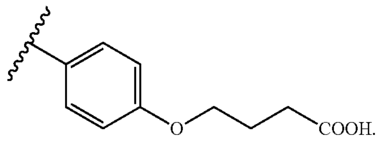 [SMILES: *c1ccc(OCCCC(=O)O)cc1]

ll. In another embodiment, $R^2$ is aryl substituted with —O—($C_1$ to $C_6$ alkyl)-heterocycle.

mm. In a further embodiment, $R^2$ is:

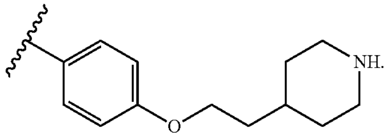 [SMILES: *c1ccc(OCCC2CCNCC2)cc1]

In one aspect, a compound of Formula (I) is provided, wherein $R^1$ is $NR^4R^5$, optionally substituted $C_1$ to $C_6$ alkoxy, optionally substituted $C_6$ to $C_{14}$ aryl, optionally substituted heteroaryl, optionally substituted 3-10 membered monocyclic or bicyclic cycloalkyl, or optionally substituted 3-10 membered monocyclic or bicyclic heterocyclyl. The 3-4 membered cycloalkyl and heterocyclyl rings are saturated. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or 5-6 membered heteroaryl containing at least one N or NH in the backbone, wherein $R^2$ is optionally substituted with one or more $R^{19}$ and when $R^2$ is 4-pyridyl, the 4-pyridyl lacks a carbonyl substituent at the $2^{nd}$ position. $R^{19}$ is $NR^4R^5$, ($C_1$ to $C_6$ alkyl)$NR^4R^5$, $C_1$ to $C_6$ alkyl, C(O)$NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, or ($C_1$ to $C_6$ alkyl)C(O)N$(CH_2CH_2OH)_2$. $R^4$ and $R^5$ are independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl). Alternatively, $R^4$ and $R^5$ are joined to form an optionally substituted 3-8 membered heterocyclyl optionally further containing one or more O, S(O)n, or $NR^9$. $R^9$ is H, OH, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, ($C_1$ to $C_6$ alkyl)C(O)N$(CH_2CH_2OH)_2$, C(O)($C_1$ to $C_6$ alkyl)$NH_2$, C(O)($C_1$ to $C_6$ alkyl)OH, $C_1$ to $C_6$ hydroxyalkyl, or $C_1$ to $C_6$ alkyl and n is 0 to 2. In one embodiment, $R^9$ is $CH_2CH_2OH$. Hydrogen atoms on the same carbon atom of the heterocyclyl are optionally replaced with a 3-6 membered cycloalkyl or heterocyclyl optionally substituted with one or more $R^{20}$ to form a spirocycloalkyl or spiroheterocyclyl. $R^{20}$ is C(O)O($C_1$ to $C_6$ alkyl), C(O)OH, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, or ($C_1$ to $C_6$ alkyl)C(O)N$(CH_2CH_2OH)_2$. Alternatively, or in addition, hydrogen atoms on the same atom of any of the heterocyclyls or cycloalkyls of $R^9$ are optionally replaced with O to form an oxo substituent; or a pharmaceutically acceptable salt or ester thereof.

In another aspect, a compound of Formula (I) is provided, wherein $R^1$ is $NR^4R^5$, $C_1$ to $C_6$ alkoxy, optionally substituted phenyl, heteroaryl, optionally substituted 3-10 membered cycloalkyl, or optionally substituted 3-10 membered monocyclic or bicyclic heterocyclyl. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or pyrazole, wherein $R^2$ is optionally substituted with one or more $R^{19}$. $R^{19}$ is $NR^4R^5$, ($C_1$ to $C_6$ alkyl)$NR^4R^5$, $C_1$ to $C_6$ alkyl, C(O)$NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, ($C_1$ to $C_6$ alkyl)C(O)N$(CH_2CH_2OH)_2$. $R^4$ and $R^5$ are (a) independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl) or (b) joined to form an optionally substituted 3-8 membered heterocyclyl optionally further containing one or more O, S(O)n, or $NR^9$. $R^9$ is H, OH, $C_1$ to $C_6$ hydroxyalkyl, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, ($C_1$ to $C_6$ alkyl)C(O)N$(CH_2CH_2OH)_2$, C(O)($C_1$ to $C_6$ alkyl)$NH_2$, C(O)($C_1$ to $C_6$ alkyl)OH, or $C_1$ to $C_6$ alkyl and n is 0 to 2. In one embodiment, $R^9$ is $CH_2CH_2OH$. Hydrogen atoms on the same carbon atom of the heterocyclyl are optionally replaced with a 3-6 membered cycloalkyl or heterocyclyl to form a spirocycloalkyl or spiroheterocyclyl optionally substituted with one or more $R^{20}$. $R^{20}$ is C(O)O($C_1$ to $C_6$ alkyl), C(O)OH, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, or ($C_1$ to $C_6$ alkyl)C(O)N$(CH_2CH_2OH)_2$. Alternatively, or in addition, hydrogen atoms on the same atom of the heterocyclyl (b) or cycloalkyl are optionally replaced with O to form an oxo substituent; or a pharmaceutically acceptable salt or ester thereof.

In a further aspect, a compound of Formula (I) is provided, wherein $R^1$ is $NR^4R^5$, $C_1$ to $C_6$ alkoxy, phenyl optionally substituted with C(O)O($C_1$ to $C_6$ alkyl), C(O)OH, O($C_1$ to $C_3$ perfluoroalkyl), $C_1$ to $C_6$ alkoxy, halogen, $CH_2$-heterocyclyl, or $CH_2CN$, 5-8 membered cycloalkyl, heteroaryl, or 3-10 membered monocyclic or bicyclic heterocyclyl optionally substituted with ($C_1$ to $C_6$ alkyl)C(O)OH, $C_1$ to $C_6$ alkyl, CN, C(O)OH, or ($C_1$ to $C_6$ alkyl)CN. Hydrogen atoms on the same carbon atom of the cycloalkyl or heterocyclyl are optionally replaced with an optionally substituted 3-6 membered cycloalkyl or heterocyclyl to form a spirocycloalkyl or spiroheterocyclyl. In addition or alternatively, hydrogen atoms on the same atom of the cycloalkyl or heterocyclyl are optionally replaced with O to form an oxo substituent. $R^2$ is phenyl or pyrazole, wherein $R^2$ is optionally substituted with one $R^{19}$. $R^{19}$ is $NR^4R^5$, ($C_1$ to $C_6$ alkyl)$NR^4R^5$, $C_1$ to $C_6$ alkyl, C(O)$NR^4R^5$, $C_3$ to $C_8$ cycloalkyl substituted with one or more $R^{21}$, or heterocyclyl substituted with one or more $R^{21}$. $R^{21}$ is ($C_1$ to $C_6$ alkyl)CN, ($C_1$ to $C_6$ alkyl)C(O)OH, ($C_1$ to $C_6$ alkyl)C(O)$NH_2$, ($C_1$ to $C_6$ alkyl)C(O)$NHCH_2CH_2OH$, or ($C_1$ to $C_6$ alkyl)C(O)N$(CH_2CH_2OH)_2$. $R^4$ and $R^5$ are (a) independently selected from among H, $C_1$ to $C_6$ alkyl, $C_1$ to $C_6$ hydroxyalkyl, and ($C_1$ to $C_6$ alkyl)N($C_1$ to $C_6$ alkyl)($C_1$ to $C_6$ alkyl). $R^4$ and $R^5$ may also be (b) joined to form a 5-8 membered heterocyclyl optionally further containing one or two O, S(O)n, or $NR^9$. $R^9$ is H, OH, $C_1$ to $C_6$ hydroxyalkyl ($C_1$ to $C_6$ alkyl)C(O)OH, C(O)($C_1$ to $C_6$ alkyl)$NH_2$, C(O)($C_1$ to $C_6$ alkyl)OH, ($C_1$ to $C_6$ alkyl)C(O)$NH_2$, ($C_1$ to $C_6$ alkyl)C(O)$NHCH_2CH_2OH$, ($C_1$ to $C_6$ alkyl)C(O)N$(CH_2CH_2OH)_2$, or $C_1$ to $C_6$ alkyl and n is 0 to 2. In one embodiment, $R^9$ is $CH_2CH_2OH$. Hydrogen atoms on the same carbon atom of the heterocyclyl are optionally replaced with a 3-5 membered cycloalkyl optionally substituted with one or more $R^{20}$ to form a spirocycloalkyl. $R^{20}$ is C(O)O($C_1$ to $C_6$ alkyl), C(O)OH, ($C_1$ to $C_6$ alkyl)C(O)OH, ($C_1$ to $C_6$ alkyl)C(O)$NH_2$, ($C_1$ to $C_6$ alkyl) C(O)$NHCH_2CH_2OH$, or ($C_1$ to $C_6$ alkyl)C(O)N$(CH_2CH_2OH)_2$. Alternatively, or in addition, hydrogen atoms on the same atom of the heterocyclyl (b) or cycloalkyl (b) are optionally replaced with O to form an oxo substituent; or a pharmaceutically acceptable salt or ester thereof.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds of the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. For example, the substituent "arylalkyloxycabonyl" refers to the group ($C_6$-$C_{14}$ aryl)-($C_1$-$C_6$ alkyl)-O—C(O)—. Terms not defined herein have the meaning commonly attributed to them by those skilled in the art.

"Alkyl" refers to a hydrocarbon chain that may be a straight chain or branched chain, containing the indicated number of carbon atoms, for example, a $C_1$-$C_{12}$ alkyl group may have from 1 to 12 (inclusive) carbon atoms in it. Examples of $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl. Examples of $C_1$-$C_8$ alkyl groups include, but are not limited to, methyl, propyl, pentyl, hexyl, heptyl, 3-methylhex-1-yl, 2,3-dimethylpent-2-yl, 3-ethylpent-1-yl, octyl, 2-methylhept-2-yl, 2,3-dimethylhex-1-yl, and 2,3,3-trimethylpent-1-yl. An alkyl group can be unsubstituted or substituted with one or more of halogen, $NH_2$, (alkyl)NH, (alkyl)(alkyl)N—, —N(alkyl)C(O)(alkyl), —NHC(O)(alkyl), —NHC(O)H, —C(O)$NH_2$, —C(O)NH(alkyl), —C(O)N(alkyl)(alkyl), CN, OH, alkoxy, alkyl, C(O)OH, —C(O)O(alkyl), —C(O)(alkyl), aryl, heteroaryl, heterocyclyl, cycloalkyl, haloalkyl, aminoalkyl-, —OC(O)(alkyl), carboxyamidoalkyl-, and $NO_2$.

"Alkoxy" refers to the group R—O— where R is an alkyl group, as defined above. Exemplary $C_1$-$C_6$ alkoxy groups include but are not limited to methoxy, ethoxy, n-propoxy, 1-propoxy, n-butoxy and t-butoxy. An alkoxy group can be unsubstituted or substituted with one or more of halogen, OH, alkoxy, $NH_2$, (alkyl)amino-, di(alkyl)amino-, (alkyl)C(O)N($C_1$-$C_3$ alkyl)-, (alkyl)carboxyamido-, HC(O)NH—, $H_2NC$(O)—, (alkyl)NHC(O)—, di(alkyl)NC(O)—, CN, C(O)OH, (alkoxy)carbonyl-, (alkyl)C(O)—, aryl, heteroaryl, cycloalkyl, haloalkyl, amino($C_1$-$C_6$ alkyl)-, (alkyl)carboxyl-, carboxyamidoalkyl-, or $NO_2$.

Aryl refers to an aromatic 6 to 14 membered hydrocarbon group. Examples of a $C_6$-$C_{14}$ aryl group include, but are not limited to, phenyl, α-naphthyl, β-naphthyl, biphenyl, anthryl, tetrahydronaphthyl, fluorenyl, indanyl, biphenylenyl, and acenanaphthyl. Examples of a $C_6$-$C_{10}$ aryl group include, but are not limited to, phenyl, α-naphthyl, β-naphthyl, biphenyl, and tetrahydronaphthyl. An aryl group can be unsubstituted or substituted with one or more of alkyl, halogen, haloalkyl, alkoxy, haloalkoxy, OH, hydroxyalkyl, —O-(hydroxyalkyl), —O-(alkyl)-C(O)OH, -(alkyl)-(alkoxy)-halogen, $NH_2$, aminoalkyl-, dialkylamino-, C(O)OH, —C(O)O-(alkyl), —OC(O)(alkyl), —O-(alkyl)-N(alkyl)(alkyl), N-alkylamido-, —C(O)$NH_2$, (alkyl)amido-, $NO_2$, (aryl)alkyl, alkoxy, aryloxy, heteroaryloxy, (aryl)amino, (alkoxy)carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl)alkyl-, heterocyclyl, —O-(heterocyclyl), heterocyclyl(alkyl)-, (hydroxyalkyl)NH—, $(hydroxyalkyl)_2N$, —$SO_2$(alkyl) or a spiro substituent.

The term "bicycle" or "bicyclic" as used herein refers to a molecule that features two fused rings, which rings are a cycloalkyl, heterocyclyl, or heteroaryl. In one embodiment, the rings are fused across a bond between two atoms. The bicyclic moiety formed therefrom shares a bond between the rings. In another embodiment, the bicyclic moiety is formed by the fusion of two rings across a sequence of atoms of the rings to form a bridgehead. Similarly, a "bridge" is an unbranched chain of one or more atoms connecting two bridgeheads in a polycyclic compound. In another embodiment, the bicyclic molecule is a "spiro" or "spirocyclic" moiety. The spirocyclic group is a carbocyclic or heterocyclic ring which bound through a single carbon atom of the spirocyclic moiety to a single carbon atom of a carbocyclic or heterocyclic moiety. In one embodiment, the spirocyclic group is a cycloalkyl and is bound to another cycloalkyl. In another embodiment, the spirocyclic group is a cycloalkyl and is bound to a heterocyclyl. In a further embodiment, the spirocyclic group is a heterocyclyl and is bound to another heterocyclyl. In still another embodiment, the spirocyclic group is a heterocyclyl and is bound to a cycloalkyl.

"(Aryl)alkyl" refers to an alkyl group, as defined above, wherein one or more of the alkyl group's hydrogen atoms has been replaced with an aryl group as defined above. ($C_6$-$C_{14}$ aryl)alkyl- moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl group can be unsubstituted or substituted with one or more of halogen, CN, $NH_2$, OH, (alkyl)amino-, di(alkyl)amino-, (alkyl)C(O)N(alkyl)-, (alkyl)carboxyamido-, HC(O)NH—, $H_2NC$(O)—, (alkyl)NHC(O)—, di(alkyl)NC(O)—, CN, OH, alkoxy, alkyl, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"(Alkoxy)carbonyl-" refers to the group alkyl-O—C(O)—. Exemplary ($C_1$-$C_6$ alkoxy)carbonyl- groups include but are not limited to methoxy, ethoxy, n-propoxy, 1-propoxy, n-butoxy and t-butoxy. An (alkoxy)carbonyl group can be unsubstituted or substituted with one or more of halogen, OH, $NH_2$, (alkyl)amino-, di(alkyl)amino-, (alkyl)C(O)N(alkyl)-, (alkyl)carboxyamido-, HC(O)NH—, $H_2NC$(O)—, (alkyl)NHC(O)—, di(alkyl)NC(O)—, CN, alkoxy, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"(Alkyl)amido-" refers to a —C(O)NH— group in which the nitrogen atom of said group is attached to a $C_1$-$C_6$ alkyl group, as defined above. Representative examples of a ($C_1$-$C_6$ alkyl)amido- group include, but are not limited to, —C(O)$NHCH_3$, —C(O)$NHCH_2CH_3$, —C(O)$NHCH_2CH_2CH_3$, —C(O)$NHCH_2CH_2CH_2CH_3$, —C(O)$NHCH_2CH_2CH_2CH_2CH_3$, —C(O)NHCH$(CH_3)_2$, —C(O)$NHCH_2CH(CH_3)_2$, —C(O)NHCH$(CH_3)CH_2CH_3$, —C(O)NH—C$(CH_3)_3$ and —C(O)$NHCH_2C(CH_3)_3$.

"(Alkyl)amino-" refers to an —NH group, the nitrogen atom of said group being attached to a alkyl group, as defined above. Representative examples of an ($C_1$-$C_6$ alkyl) amino- group include, but are not limited to $CH_3NH$—, $CH_3CH_2NH$—, $CH_3CH_2CH_2NH$—, $CH_3CH_2CH_2CH_2NH$—, $(CH_3)_2CHNH$—, $(CH_3)_2CHCH_2NH$—, $CH_3CH_2CH(CH_3)NH$— and $(CH_3)_3CNH$—. An (alkyl)amino group can be unsubstituted or substituted on the alkyl moiety with one or more of halogen, $NH_2$, (alkyl)amino-, di(alkyl)amino-, (alkyl)C(O)N(alkyl)-, (alkyl)carboxyamido-, HC(O)NH—, $H_2NC(O)$—, (alkyl)NHC(O)—, di(alkyl)NC(O)—, CN, OH, alkoxy, alkyl, C(O)OH, (alkoxy)carbonyl-, (alkyl)C(O)—, aryl, heteroaryl, cycloalkyl, haloalkyl, amino(alkyl)-, (alkyl)carboxyl-, carboxyamidoalkyl-, or $NO_2$.

"Aminoalkyl-" refers to an alkyl group, as defined above, wherein one or more of the alkyl group's hydrogen atoms has been replaced with —$NH_2$; one or both H of the $NH_2$ may be replaced by a substituent.

"Alkylcarboxyl-" refers to an alkyl group, defined above that is attached to the parent structure through the oxygen atom of a carboxyl (C(O)—O—) functionality. Examples of ($C_1$-$C_6$ alkyl)carboxyl- include acetoxy, propionoxy, propylcarboxyl, and isopentylcarboxyl.

"(Alkyl)carboxyamido-" refers to a —NHC(O)— group in which the carbonyl carbon atom of said group is attached to a $C_1$-$C_6$ alkyl group, as defined above. Representative examples of a ($C_1$-$C_6$ alkyl)carboxyamido- group include, but are not limited to, —NHC(O)$CH_3$, —NHC(O)$CH_2CH_3$, —NHC(O)$CH_2CH_2CH_3$, —NHC(O)$CH_2CH_2CH_2CH_3$, —NHC(O)$CH_2CH_2CH_2CH_2CH_3$, —NHC(O)CH$(CH_3)_2$, —NHC(O)$CH_2CH(CH_3)_2$, —NHC(O)CH$(CH_3)CH_2CH_3$, —NHC(O)—C$(CH_3)_3$ and —NHC(O)$CH_2C(CH_3)_3$.

"(Aryl)amino" refers to a radical of formula (aryl)-NH—, wherein aryl is as defined above. "(Aryl)oxy" refers to the group Ar—O— where Ar is an aryl group, as defined above.

"Cycloalkyl" refers to a non-aromatic, saturated, partially saturated, monocyclic, bicyclic or polycyclic hydrocarbon 3 to 12 membered ring system. Representative examples of a $C_3$-$C_{12}$ cycloalkyl include, but are not limited to, cyclopropyl, cyclopentyl, cycloheptyl, cyclooctyl, decahydronaphthalen-1-yl, octahydro-1H-inden-2-yl, decahydro-1H-benzo[7]annulen-2-yl, and dodecahydros-indacen-4-yl. Representative examples of a $C_3$-$C_{10}$ cycloalkyl include, but are not limited to, cyclopropyl, cyclobutyl, cyclopentyl, cyclohexyl, cycloheptyl, cyclooctyl, decahydronaphthalen-1-yl, and octahydro-1H-inden-2-yl. Representative examples of a $C_3$-$C_8$ cycloalkyl include, but are not limited to, cyclopropyl, cyclobutyl, cyclopentyl, cyclohexyl, cycloheptyl, cyclooctyl, and octahydropentalen-2-yl. A cycloalkyl can be unsubstituted or substituted with one or more of halogen, $NH_2$, (alkyl)NH, (alkyl)(alkyl)N—, —N(alkyl)C(O)(alkyl), —NHC(O)(alkyl), —NHC(O)H, —C(O)$NH_2$, —C(O)NH(alkyl), —C(O)N(alkyl)(alkyl), CN, OH, alkoxy, alkyl, C(O)OH, —C(O)O(alkyl), —C(O) alkyl), aryl, heteroaryl, cycloalkyl, haloalkyl, aminoalkyl-, —OC(O)(alkyl), carboxyamidoalkyl-, and $NO_2$. Additionally, each of any two hydrogen atoms on the same carbon atom of the carbocyclic ring can be replaced by an oxygen atom to form an oxo (=O) substituent.

"Halo" or "halogen" refers to —F, —Cl, —Br and —I.

"$C_1$-$C_6$ haloalkyl" refers to a $C_1$-$C_6$ alkyl group, as defined above, wherein one or more of the $C_1$-$C_6$ alkyl group's hydrogen atoms has been replaced with F, Cl, Br, or I. Each substitution can be independently selected from F, Cl, Br, or I. Representative examples of an $C_1$-$C_6$ haloalkyl-group include, but are not limited to, —$CH_2F$, —$CCl_3$, —$CF_3$, $CH_2CF_3$, —$CH_2C_1$, —$CH_2CH_2Br$, —$CH_2CH_2I$, —$CH_2CH_2CH_2F$, —$CH_2CH_2CH_2C_1$, —$CH_2CH_2CH_2CH_2Br$, —$CH_2CH_2CH_2CH_2I$, —$CH_2CH_2CH_2CH_2CH_2Br$, —$CH_2CH_2CH_2CH_2CH_2I$, —$CH_2CH(Br)CH_3$, —$CH_2CH(C_1)CH_2CH_3$, —CH(F)$CH_2CH_3$ and —C$(CH_3)_2(CH_2C_1)$.

"Heteroaryl" refers to a monocyclic, bicyclic, or polycyclic aromatic ring system containing at least one ring atom selected from the heteroatoms oxygen, sulfur and nitrogen. Examples of $C_1$-$C_9$ heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic $C_1$-$C_9$ hetroaryl groups include those where a phenyl, pyridine, pyrimidine or pyridazine ring is fused to a 5 or 6-membered monocyclic heteroaryl ring having one or two nitrogen atoms in the ring, one nitrogen atom together with either one oxygen or one sulfur atom in the ring, or one O or S ring atom. Examples of monocyclic $C_1$-$C_4$ heteroaryl groups include 2H-tetrazole, 3H-1,2,4-triazole, furan, thiophene, oxazole, thiazole, isoxazole, isothiazole, imidazole, and pyrrole. A heteroaryl group can be unsubstituted or substituted with one or more of $C_1$-$C_6$ alkyl, halogen, haloalkyl, OH, CN, hydroxyalkyl, $NH_2$, aminoalkyl-, dialkylamino-, C(O)OH, —C(O)O-(alkyl), —OC(O)(alkyl), N-alkylamido-, —C(O)$NH_2$, (alkyl)amido-, —$NO_2$, (aryl)alkyl, alkoxy, aryloxy, heteroaryloxy, (aryl)amino, (alkoxy)carbonyl-, (alkyl)amido-, (alkyl)amino, aminoalkyl-, alkylcarboxyl-, (alkyl)carboxyamido-, (aryl)alkyl-, (aryl)amino-, cycloalkenyl, di(alkyl)amino-, heteroaryl, (heteroaryl)alkyl-, heterocyclyl, hetyerocyclyl(alkyl)-, (hydroxyalkyl)NH—, $(hydroxyalkyl)_2N$ or a spiro substituent.

"Heterocycle" or "heterocyclyl" refers to monocyclic, bicyclic, polycyclic, or bridged head molecules in which at least one ring atom is a heteroatom. A heterocycle may be saturated or partially saturated. Exemplary $C_1$-$C_9$ heterocyclyl groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, azepane, diazepane, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3- azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, $C_1$ heterocyclyl radicals would include but are not limited to oxaziranyl, diaziridinyl, and diazirinyl, $C_2$ heterocyclyl radicals include but are not limited to aziridinyl, oxiranyl, and diazetidinyl, $C_9$ heterocyclyl radicals include but are not limited to azecanyl, tetrahydroquinolinyl, and perhydroisoquinolinyl. A heterocyclyl group can be unsubstituted or substituted with one or more of alkyl, halogen, alkoxy, haloalkyl, OH, hydroxyalkyl, —C(O)-(hydroxyalkyl), $NH_2$, aminoalkyl-, dialkylamino-, C(O)OH, —C(O)O-(alkyl), —OC(O)(alkyl), N-alkylamido-, —C(O)$NH_2$, (alkyl)amido-, —C(O)-(alkyl)-CN, (alkyl)-CN, or $NO_2$.

"Heterocyclyl(alkyl)-" refers to an alkyl group, as defined above, wherein one or more of the alkyl group's hydrogen atoms has been replaced with a heterocycle group as defined above. Heterocyclyl($C_1$-$C_6$ alkyl)- moieties include 1-piperazinylethyl, 4-morpholinylpropyl, 6-piperazinylhexyl, and the like. A heterocyclyl(alkyl) group can be unsubstituted or substituted with one or more of halogen, $NH_2$, (alkyl)amino-, di(alkyl)amino-, (alkyl)C(O)N(alkyl)-, (alkyl)carboxyamido-, HC(O)NH—, $H_2NC(O)$—, (alkyl)NHC(O)—, di(alkyl)NC(O)—, CN, OH, alkoxy, alkyl, C(O)OH, (alkoxy)carbonyl-, (alkyl)C(O)—, 4- to 7-membered monocyclic heterocycle, aryl, heteroaryl, or cycloalkyl.

"Heteroaryl(alkyl)" refers to a heteroaryl which is attached to an alkyl group and the heteroaryl is defined above.

"Hydroxyalkyl" refers to a alkyl group, as defined above, wherein one or more of the alkyl group's hydrogen atoms has been replaced with OH groups. Examples of $C_1$-$C_6$ hydroxyalkyl moieties include, for example, —$CH_2OH$, —$CH_2CH_2OH$, —$CH_2CH_2CH_2OH$, —$CH_2CH(OH)CH_2OH$, —$CH_2CH(OH)CH_3$, —$CH(CH_3)CH_2OH$ and higher homologs.

"Perfluoroalkyl-" refers to alkyl group, defined above, having two or more fluorine atoms. Examples of a $C_1$-$C_6$perfluoroalkyl- group include $CF_3$, $CH_2CF_3$, $CF_2CF_3$ and $CH(CF_3)_2$.

A "subject" is a mammal, e.g., a human, mouse, rat, guinea pig, dog, cat, horse, cow, pig, or non-human primate, such as a monkey, chimpanzee, baboon or gorilla.

With the proviso that when $R^2$ is 4-pyridyl, then there cannot be a carbonyl substituent at the 2-position of the 4-pyridyl moiety;

Representative "pharmaceutically acceptable salts" include but are not limited to, e.g., water-soluble and water-insoluble salts, such as the acetate, benzenesulfonate, benzoate, bicarbonate, bisulfate, bitartrate, bromide, butyrate, calcium, chloride, choline, citrate, edisylate (camphorsulfonate), fumarate, gluconate, glucuronate, glutamate, hydrobromide, hydrochloride, lauryl sulfate, malate, maleate, mandelate, mesylate, palmitate, pantothenate, phosphate, potassium, propionate, p-toluenesulfonate, salicylate, sodium, stearate, succinate, and sulfate salts.

The following abbreviations are used and have the indicated definitions: ACN is acetonitrile; DMSO is dimethylsulfoxide; DMF is N,N-dimethylformamide; DMF.DMA is dimethylformamide dimethylacetal; TFA is trifluroroacetic acid; mCPBA is meta-chloroperbenzoic acid; RT is room temperature; THF is tetrahydrofuran; and NMP is N-methyl pyrrolidinone.

Methods useful for making the compounds of Formula (I) are set forth in the Examples below and generalized in Schemes I-III. One of skill in the art will recognize that Schemes 1-III can be adapted to produce the compounds of Formula (I) and pharmaceutically accepted salts of compounds of Formula (I) according to the present invention. In the reactions described, reactive functional groups, such as hydroxy, amino, imino, thio or carboxy groups, where these are desired in the final product, may be protected to avoid unwanted reactions. Conventional protecting groups may be used in accordance with standard practice.

Scheme 1

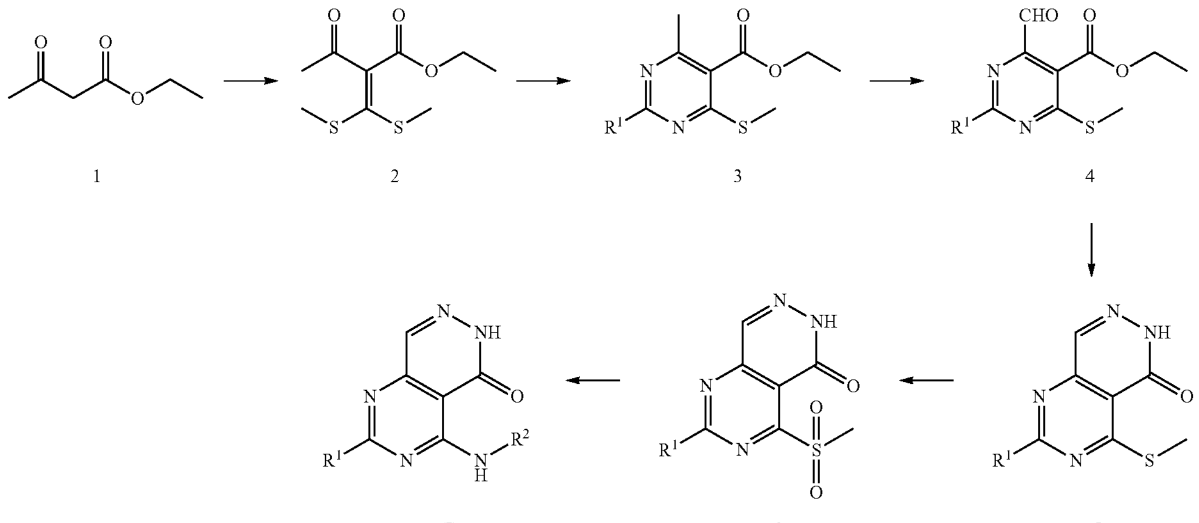

1 2 3 4

(I) 6 5

Scheme 1 provides the synthesis of compounds of Formula (I). Ethyl acetoacetate 1 is converted to the corresponding bis(methylthio)methylene derivative 2 using carbon disulfide, an organic or inorganic base such as $K_2CO_3$ and a alkylating agent. In one embodiment, the alkylating agent is an alkyl iodide, alkyl triflate, or alkyl sulfonate. In another embodiment, the alkylating agent is a methylating agent. In a further embodiment, the alkylating agent is methyl iodide. Reaction of 2 with an $R^1$-optionally substituted amidine hydrochloride in the presence of a base results in pyrimidine 3. In one embodiment, the base utilized to form pyrimidine 3 is $Et_3N$ or Hünig's base. The alkyl group on the pyrimidine group of compound 3 is then oxidized using an oxidizing agent. In one embodiment, the oxidation is performed using $SeO_2$. The resulting pyrimidine aldehyde 4 is converted to pyrimido-pyridazinone 5 using hydrazine hydrate or hydrazine hydrochloride. The methyl thio group in compound 5 is oxidized to a methane sulfonyl using meta-chloroperoxybenzoic acid (mCPBA) or hydrogen peroxide/acetic acid. Finally, the methane sulfonyl group of compound 6 is replaced with an $R^2$-substituted aniline to provide compound (I). In one embodiment, the $R^2$-substituted aniline is an aryl or heteroaryl substituted aniline.

Scheme 2

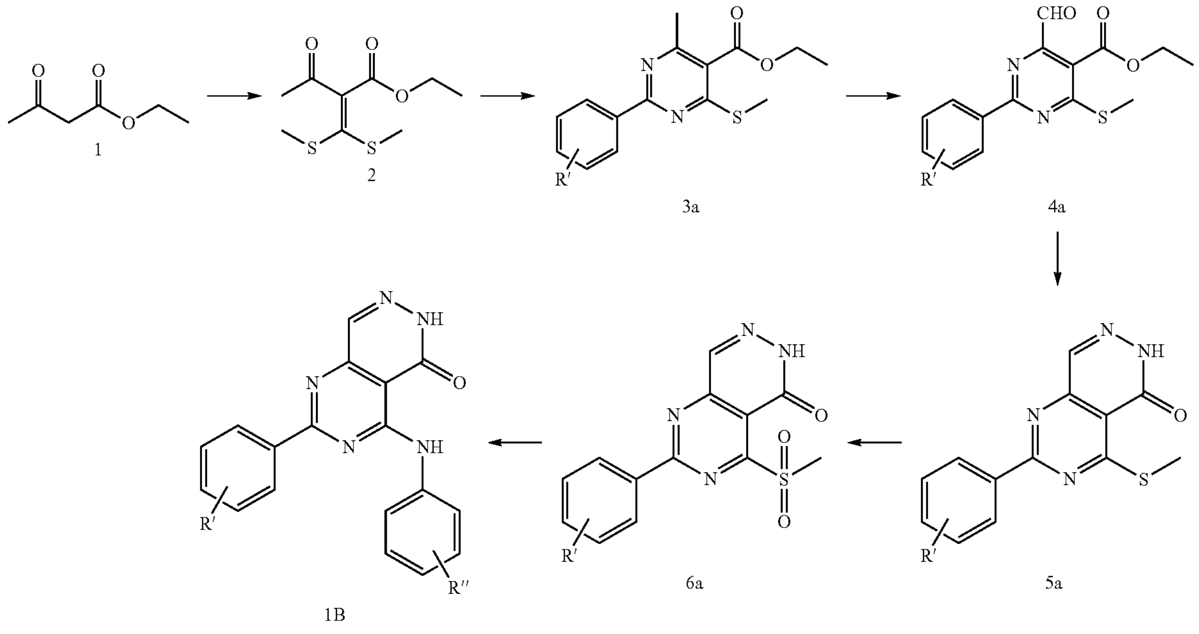

1, 2, 3a, 4a, 5a, 6a, 1B

Scheme 2 provides the synthesis of compound IB which are encompassed by the structure of Formula (I). In this embodiment, ethyl acetoacetate 1 is converted to the corresponding bis(methylthio)methylene derivative 2 using carbon disulfide, $K_2CO_3$ and methyl iodide. Reaction of 2 with an R'-substituted benzamidine hydrochloride in the presence of $Et_3N$ results in pyrimidine 3a. The methyl group bound to the C-atom of pyrimidine 3a is then oxidized using $SeO_2$. The resulting pyrimidine aldehyde 4a is converted to pyrimido-pyridazinone 5a using hydrazine hydrate or hydrazine hydrochloride. The methyl thio group in compound 5a is oxidized to a methane sulfonyl group using mCPBA. Finally, the methane sulfonyl group is replaced with an R"-substituted aniline to give compound 1B.

Scheme 3

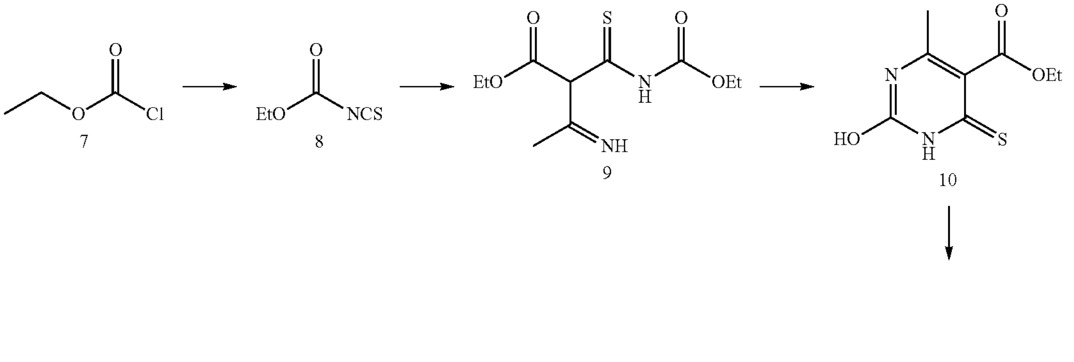

7, 8, 9, 10

-continued

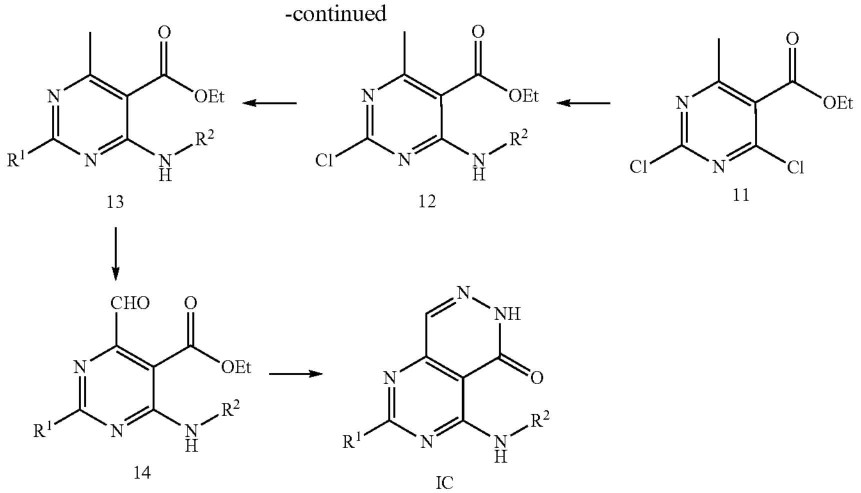

13 12 11

14 IC

Scheme 3 provides the synthesis of compounds IC which are encompassed by the structure of Formula (I). Treatment of ethyl chloroformate 7 with ammonium thiocyanate results in the production of ethyl thiocyanato formate 8 which upon treatment with ethyl 3-amino crotanoate results in compound 9. Compound 9 is cyclized to compound 10 by treatment with an organic or inorganic base. In one embodiment the organic or inorganic base is a strong base. In one embodiment, the strong base is a tertiary organic base. In another embodiment, the strong base is aqueous $Et_3N$. The dichloro pyrimidine 11 is obtained by treating compound 10 with a chlorinating agent. In one embodiment, the chlorinating agent is $POCl_3$. In another embodiment, this transformation can also be carried out by using other chlorinating agents such as $PCl_5$, $SOCl_2$ in the presence of an organic base such as TEA, tributyl amine, and N,N-dimethylaniline. The 4-position of dichloropyrimidine 11 is then substituted by reaction with an optionally substituted ($R^2$) aniline to afford compound 12. The 2-position of pyrimidine 12 is then $R^1$-substituted using coupling agents such as boronic acids or boronic ester reagents to provide compound 13. The methyl group at position 4 of pyrimidine 13 is then oxidized using an oxidizing agent such as $SeO_2$ to provide compound 14. The resulting pyrimidine aldehyde 14 is converted to pyrimido-pyridazinone 1C using hydrazine hydrate.

Scheme 4

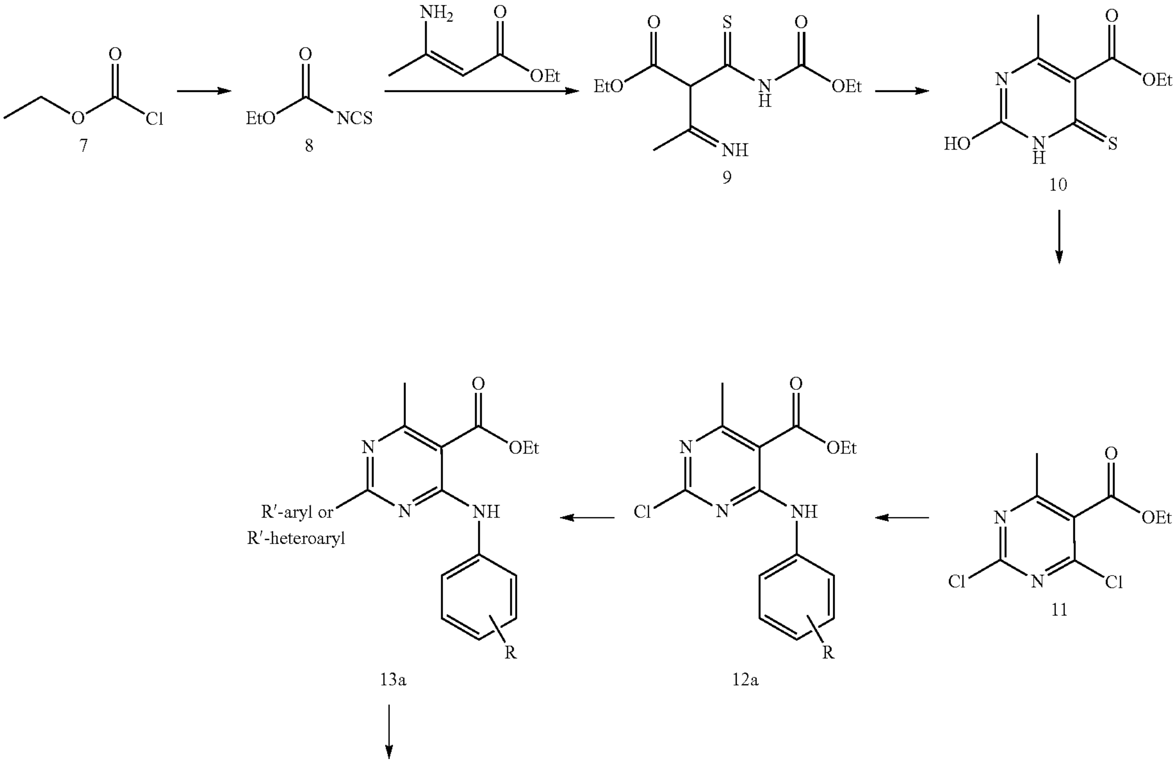

7 8 9 10

13a 12a 11

-continued

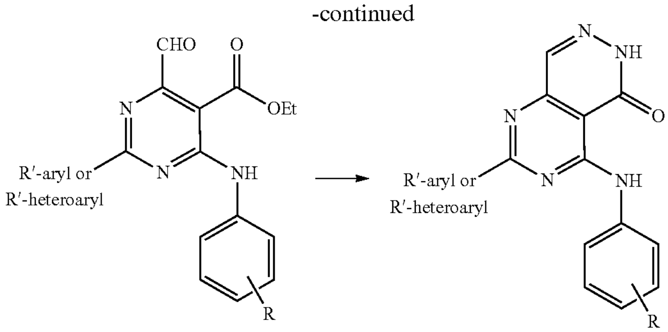

14a ID

Scheme 4 provides the synthesis of compounds ID which are encompassed by the structure of Formula (I). Treatment of ethyl chloroformate 7 with ammonium thiocyanate results in ethyl thiocyanato formate 8 which upon treatment with ethyl 3-amino crotanoate results in compound 9. Compound 9 is cyclized to compound 10 as described in Scheme 3, i.e., by treatment with aqueous $Et_3N$. The dichloro pyrimidine compound 11 is obtained by treating compound 10 with $POCl_3$. The 4-position of dichloropyrimidine 11 is then substituted by reaction with an optionally R-substituted aniline to afford compound 12a. The 2-position of pyrimidine compound 12a is then substituted with an R'-substituted aryl or heteroaryl group using a boronic acid or an boronic ester reagent to provide compound 13a. In one embodiment, the boronic acid is (R'-aryl)-$B(OH)_2$ or (R'-heteroaryl)-B $(OH)_2$. The methyl at position-4 on pyrimidine 13a is then oxidized using $SeO_2$. The resulting pyrimidine aldehyde 14a is converted to pyrimido-pyridazinone 1D using hydrazine hydrate.

Scheme 5

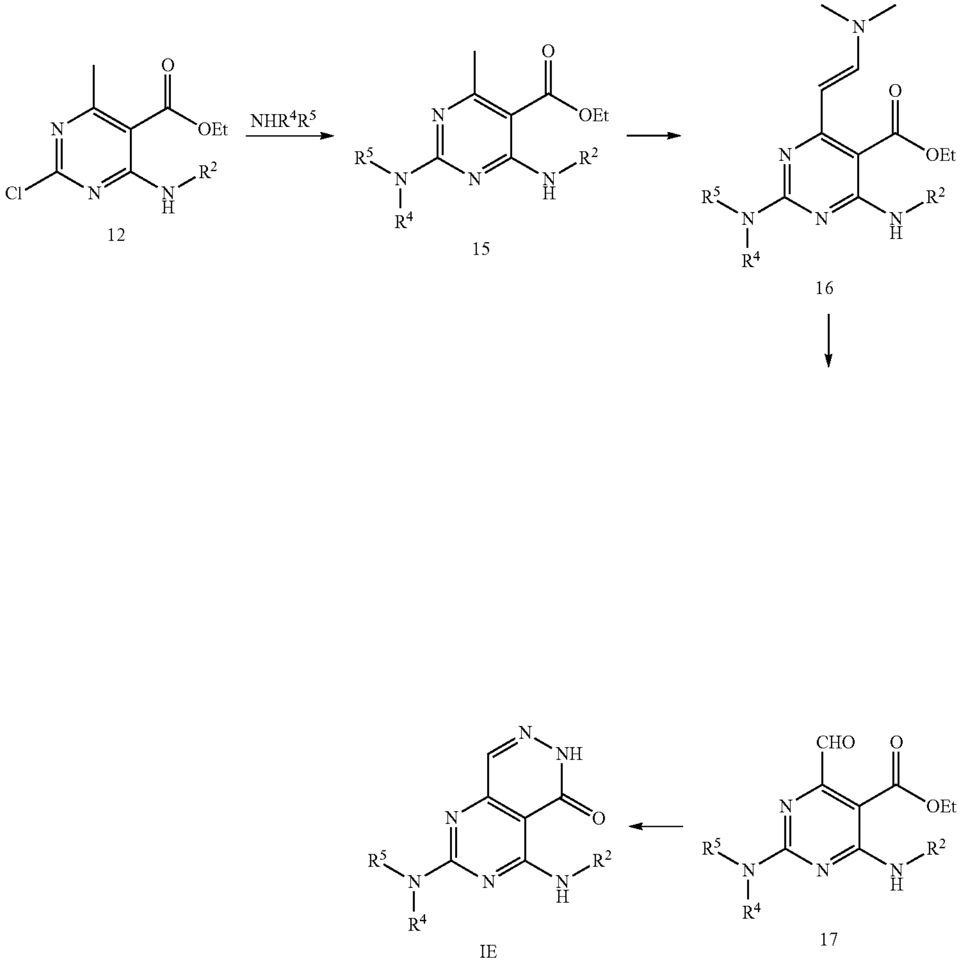

12 15 16 17 IE

Scheme 5 provides the synthesis of compound IE which are encompassed by the structure of Formula (I). Compound 12 is reacted with an optionally substituted amine ($NHR^4R^5$) to provide compound 15. The methyl group at the 4-position of compound 15 is reacted with DMF.DMA to provide compound 16. Compound 17 is obtained by oxidative cleavage of the olefin of compound 16. In one embodiment, oxidative cleavage is performed using $NaIO_4$. Finally, pyrimido-pyridazinone IE is obtained by cyclizing the aldehyde 17. In one embodiment, the cyclizaton is performed using hydrazine, hydrazine hydrate or hydrazine hydrochloride, as described previously.

Scheme 6 provides the synthesis of compounds 1F which are encompassed by the structure of Formula (I). Compound 12a is reacted with optionally substituted amines to result in 15a. The methyl group of 15a is reacted with DMF.DMA to give compound 16a. The aldehyde 17a is obtained by the oxidative cleavage of the olefin in 16a. In one embodiment, the oxidative cleavage is performed with $NaIO_4$. Finally, the pyrimido-pyridazinone 1F is obtained by cyclizing aldehyde 17a. In one embodiment, cyclization is performed using with hydrazine.

Scheme 6

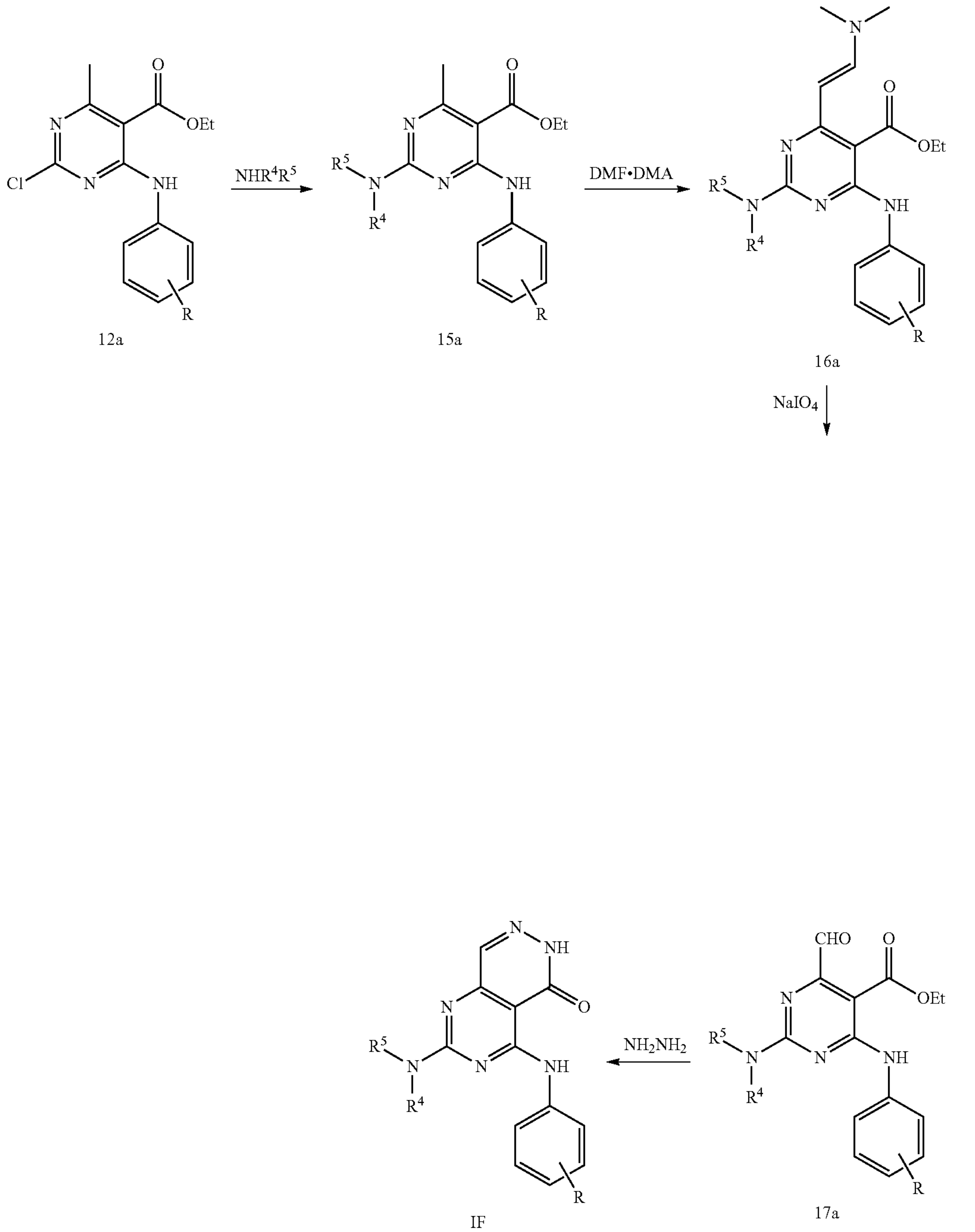

12a 15a 16a IF 17a

Scheme 7

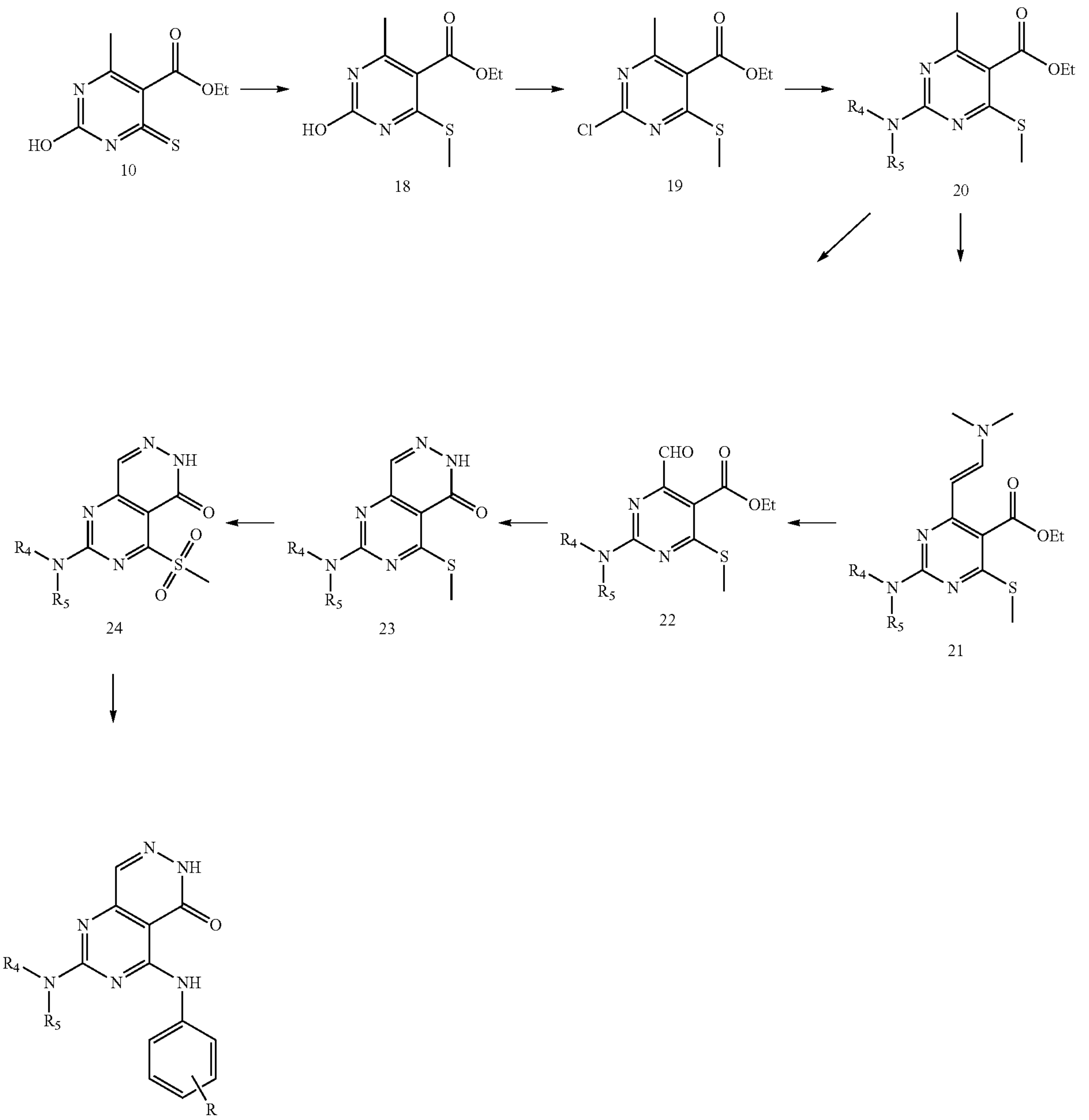

1G

Scheme 7 provides the synthesis of compound 1G which are encompassed by the structure of Formula (I). Compound 10 is reacted with an alkylating agent to the S-methyl compound 18. In one embodiment, the reacted is performed under basic conditions. In another embodiment, the alkylating agent is methyl iodide, ethyl iodide, propyl iodide, dimethylsulfate, among others. Compound 19 is obtained by chlorinating compound 18. In one embodiment, compound 18 is chlorinated using $POCl_3$. Compound 19 is then $NR^4R^5$ substituted with an optionally substituted amine to provide compound 20 [using $NHR^4R^5$?]. The methyl group of compound 20 is reacted with DMF.DMA to give compound 21. The aldehyde 22 is obtained by the oxidative cleavage of the olefin group in compound 21. In one embodiment, the oxidative cleavage is performed with $NaIO_4$. Alternatively, compound 20 may directly converted to the pyrimidine aldehyde 22 by oxidizing the methyl group using $SeO_2$ or a combination of $CO_2$, t-butyl hydroperoxide, and an alcohol such as $C_1$ to $C_6$ alkyl)$H_2OH$. The resulting pyrimidine aldehyde 22 is converted to pyrimido-pyridazinone 23 using hydrazine hydrate or hydrazine hydrochloride. The methyl thio group in compound 23 is oxidized to a methane sulfonyl group. In one embodiment compound 23 is reacted with meta-chloroperoxybenzoic acid (mCPBA) or hydrogen peroxide/acetic acid. Finally, the methane sulfonyl group of compound 24 is replaced with suitably substituted aniline to provide compound 1G.

Scheme 8

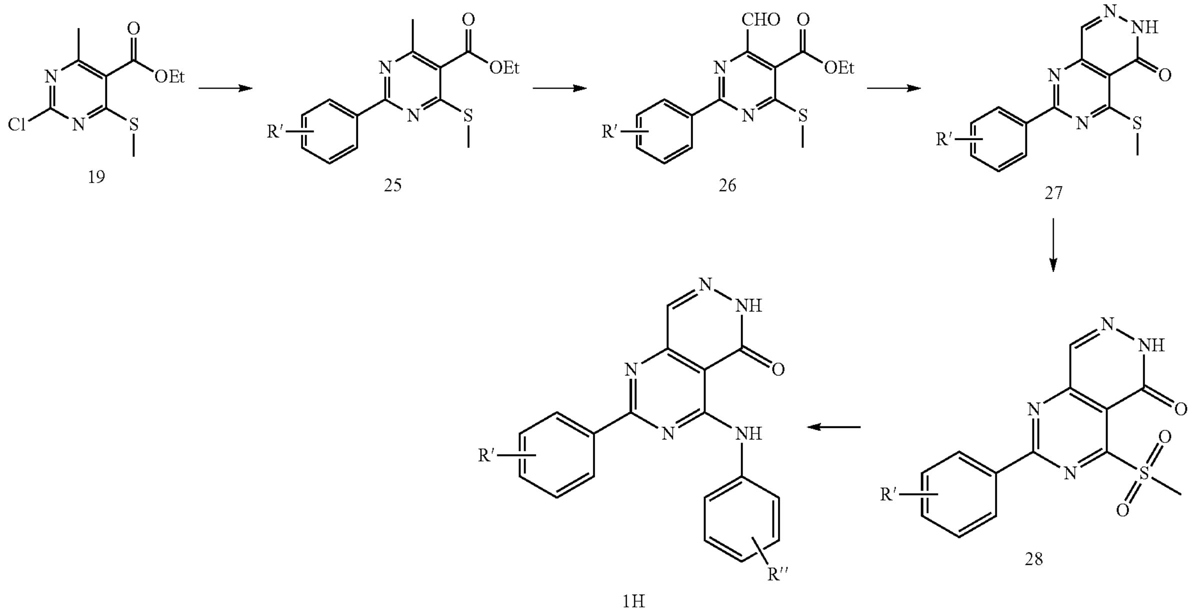

Scheme 8 provides the synthesis of compound 1H which is encompassed by the structure of Formula (I). In this scheme, compound 19 is coupled with an optionally substituted boronic acid or boronic ester to give compound 25. In one embodiment, the coupling is performed in the presence of a coupling agent such as $Pd(PPh_3)_4$ or $PdCl_2(PPh_3)_2$. The methyl group in compound 25 is then oxidized to the corresponding aldehyde. In one embodiment, the oxidation is performed using $SeO_2$ or a combination of $CO_2$, t-butyl hydroperoxide, and an alcohol such as $C_1$ to $C_6$ alkyl)$H_2OH$ to give compound 26. Compound 26 is converted to pyrimido-pyridazinone 27 using hydrazine hydrate or hydrazine hydrochloride. The methyl thio group in compound 27 is then oxidized to a methane sulfonyl group. In one embodiment, the oxidation is performed using mCPBA or hydrogen peroxide/acetic acid. Finally, the methane sulfonyl group of compound 28 is replaced with suitably substituted aniline to provide compound 1H.

Pharmaceutical compositions of the invention comprise a compound of Formula (I) optionally with other pharmaceutically inert or inactive ingredients. In one embodiment, the pharmaceutically inert or inactive ingredient is one or more pharmaceutically acceptable carrier or excipient. The present invention also contemplates combining the compound of Formula (I) with one or more therapeutic agents, i.e., active ingredients, as described below. In a further embodiment, a compound of Formula (I) is combined with one or more inert/inactive ingredients and one or more therapeutic agents.

The pharmaceutical compositions of the invention contain an amount of a compound of Formula (I) that is effective for treating inflammation in a subject. Specifically, the dosage of the compound of Formula (I) to achieve a therapeutic effect will depend on factors such as the formulation, pharmacological potency of the drug, age, weight and sex of the patient, condition being treated, severity of the patient's symptoms, specific compound of Formula (I), route of delivery, and response pattern of the patient. It is also contemplated that the treatment and dosage of the compound of Formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect.

In one embodiment, the therapeutically effective amount is about 0.0001% to about 25% w/w. In another embodiment, the therapeutically effective amount is less than about 20% w/w, about 15% w/w, about 10% w/w, about 5% w/w, or about 1% w/w. In another embodiment, the therapeutically effective amount is about 0.0001% to about 10% w/w. In a further embodiment, the therapeutically effective amount is about 0.005 to about 5% w/w. In yet another embodiment, the therapeutically effective amount is about 0.01 to about 5% w/w. In still a further embodiment, the therapeutically effective amount is about 0.01% w/w, about 0.05% w/w, about 0.1% w/w, about 0.2% w/w, about 0.3% w/w, about 0.4% w/w, about 0.5% w/w, about 0.6% w/w, about 0.7% w/w, about 0.8% w/w, about 0.8% w/w, about 0.9% w/w, about 1% w/w, about 2% w/w, about 3% w/w, about 4% w/w, or about 5% w/w.

The therapeutically effective amounts may be provided on regular schedule, i.e., on a less than daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner. The therapeutically effective amounts described herein refer to total amounts administered for a given time period; that is, if more than one compound of Formula (I) is administered, the therapeutically effective amounts correspond to the total amount administered.

The compound of Formula (I) may be administered by any route, taking into consideration the specific condition for which it has been selected. The compounds of Formula (I) may be delivered orally, by injection (including intravascularly, e.g, intravenously or intra-arterially), inhalation (intranasally and intratracheally), ocularly, transdermally (via simple passive diffusion formulations or via facilitated delivery using, for example, iontophoresis, microporation with microneedles, radio-frequency ablation or the like), intravascularly, subcutaneously, intramuscularly, sublingually, intracranially, epidurally, rectally, and vaginally, among others. Desirably, the compound of Formula (I) may be administered by injection, transdermally or topically.

In one embodiment, the compound of Formula (I) may be administered topically to the eye, e.g., as solutions, suspensions or ointments. Examples of ophthalmically compatible carriers which may be used include, without limitation, an aqueous solution, such as saline solution, oil solution or ointments containing ophthalmically compatible preservatives, surfactants, buffers, and viscosity regulators. These compositions may also contain stabilizing agents, antibacterial agents, and may be manufactured in different dosage units, suitable for ocular administration. Drug inserts, either soluble or insoluble, may also be used.

In another embodiment, the compound of Formula (I) may be administered by injection. Solutions for injection or infusion may be prepared as aqueous solutions. Desirably, the compound of Formula (I) is present in a concentration of about 0.001 μg/mL to 1 mg/mL, or this amount may be adjusted higher or lower as needed. These solutions may also contain stabilizing agents, antibacterial agents, buffers and may be manufactured in different dosage unit ampoules or bottles.

In a further embodiment, the compound of Formula (I) may be administered rectally. Dosage units for rectal administration may be prepared in the form of ointments or suppositories, which contain the compound of Formula (I) in a mixture with a neutral fat base, or they may be prepared in the form of gelatin-rectal capsules that contain the compound of Formula (I) in a mixture with, e.g., a vegetable oil or paraffin oil. Ointments, suppositories or creams containing at least one compound of Formula (I) are useful for the treatment of hemorrhoids.

In yet another embodiment, the compound of Formula (I) may be administered orally. Dosage units for oral administration include, without limitation, tablets, caplets, capsules, powders, suspensions, microcapsules, dispersible powder, granules, suspensions, syrups, elixirs, and aerosols, which contain the compound of Formula (I) optionally with one or more excipient. In one embodiment, the compositions are compressed into a tablet or caplet. In another embodiment, the tablet or caplet may be administered to the subject. In another embodiment, the tablet or caplet may be added to a capsule. In a further embodiment, the composition containing the compound of Formula (I) is added directly to a capsule. In one embodiment, the capsule includes hydroxypropyl methylcellulose, hypromellose capsule, or a hard shell gelatin capsule. In yet another embodiment the tablets or caplets are optionally film-coated using film-coatings known to those of skill in the art. In one embodiment, the film-coating is selected from among polymers such as, without limitation, hydroxypropylmethylcellulose, ethyl cellulose, polyvinyl alcohols, and combinations thereof.

Although the compound of Formula (I) may be administered alone, i.e., neat, it may also be administered in the presence of one or more pharmaceutical carriers that are physiologically compatible. The amount of the pharmaceutical carrier(s) is determined by the solubility and chemical nature of the compound of Formula (I), chosen route of administration, and standard pharmacological practice. The carriers may be in dry (solid) or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. In one embodiment, the compound of Formula (I) is dissolved a liquid carrier. In another embodiment, the compound of Formula (I) is suspended in a liquid carrier. One of skill in the art of formulations would be able to select a suitable liquid carrier, depending on the route of administration. The compound of Formula (I) may alternatively be formulated in a solid carrier of which a variety of solid carriers and excipients are known to those of skill in the art. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of Formula (I). For example, the unit dosage can be packaged compositions, e.g., packeted powders, vials, ampoules, prefilled syringes or sachets containing liquids.

Examples of excipients which may be combined with one or more compound of Formula (I) include, without limitation, adjuvants, antioxidants, binders, buffers, coatings, coloring agents, compression aids, diluents, disintegrants, emulsifiers (e g., polyoxyethylene fatty acid esters), emollients, encapsulating materials, fillers, flavoring agents, glidants, granulating agents, lubricants, metal chelators, osmoregulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc) or viscosity regulators (such as polymers to increase viscosity). See, for example, the excipients described in the "Handbook of Pharmaceutical Excipients", 5th Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of Formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a modified-release delivery device. "Modified-release" as used herein refers to delivery of a compound of Formula (I) which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices. For use in such modified-release delivery devices, the compound of Formula (I) is formulated as described herein.

Also contemplated is the administration of the compounds of Formula (I) with other medication(s) or therapeutic agent(s). In one embodiment, the compounds of Formula (I) are combined with other medications or therapeutic agents in a single composition. However, the present invention is not so limited. In other embodiments, the compounds of Formula (I) may be administered in one or more separate formulations from other compounds of Formula (I), or other medications or therapeutic agents as described below.

Additionally, one or more agents typically used to treat inflammation may be used in conjunction with a combination of the invention in the methods, compositions, and kits described herein. Such agents include, but are not limited to, non-steroidal anti-inflammatory drugs.

The compound of Formula (I) may be combined with glucose or dextrose when utilized for infusion or as a regional analgesic or anti-pruritic.

Further, the compound of Formula (I) may be combined with thickening agents to form a jelly, or may also contain penetration enhancers, for use in topical or dermal applications such as for urogenital topical procedures.

Finally, the compound of Formula (I) may be formulated as an ointment for administration to accessible mucous membranes.

Also provided herein are kits or packages of pharmaceutical formulations containing the compounds of Formula (I) or compositions described herein. The kits may be organized to indicate a single formulation or combination of formulations to be taken at each desired time.

Suitably, the kit contains packaging or a container with the compound of Formula (I) formulated for the desired delivery route. Suitably, the kit contains instructions on dosing and an insert regarding the compound of Formula (I).

Optionally, the kit may further contain instructions for monitoring local or circulating levels of product and materials for performing such assays including, e.g., reagents, well plates, containers, markers or labels, and the like. Such kits are readily packaged in a manner suitable for treatment of a desired indication. For example, the kit may also contain instructions for use of an oral dosage form such as a pill, capsule, patch, spray pump or other delivery device. Other suitable components to include in such kits will be readily apparent to one of skill in the art, taking into consideration the desired indication and the delivery route.

The compounds of Formula (I) or compositions described herein can be a single dose or for continuous or periodic discontinuous administration. For continuous administration, a package or kit can include the compound of Formula (I) in each dosage unit (e.g., solution, lotion, tablet, pill, drug-eluting patch or other unit described above or utilized in drug delivery), and optionally instructions for administering the doses less-than-daily, daily, weekly, or monthly, for a predetermined length of time or as prescribed. When the compound of Formula (I) is to be delivered periodically in a discontinuous fashion, a package or kit can include placebos during periods when the compound of Formula (I) is not delivered. When varying concentrations of a composition, of the components of the composition, or the relative ratios of the compounds of Formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period.

In another embodiment, the package is a foil or blister package, labeled ampoule, vial or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials or other suitable packaging means in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forceps, measuring spoon, eye dropper or any such medically approved delivery means.

In one embodiment, a kit is provided and contains a compound of Formula (I). The compound of Formula (I) may be in the presence or absence of one or more of the carriers or excipients described above. The kit may optionally contain instructions for administering the compound of Formula (I) to a subject having inflammation.

In a further embodiment, a kit is provided and contains a compound of Formula (I) in a second dosage unit, and one or more of the carriers or excipients described above in a third dosage unit. The kit may optionally contain instructions for administering the compound of Formula (I) to a subject having inflammation.

As discussed above, the methods, compositions, and kits of the invention can be used to treat inflammation resulting from a number of conditions. The term "inflammation" as used herein includes all types of inflammation. In one embodiment, the inflammation may be acute or chronic. In another embodiment, the inflammation may be nociceptive, dysfunctional, idiopathic, neuropathic, somatic, visceral, and/or procedural. For example, the inflammation may be from a migraine, gynecological condition, pre-labor or labor, stroke, surgery, neuralgia, sickle cell, interstitial cystitis, urological condition (such as urethritis), dental work/injury, or headache, among other. Inflammation may also occur in patients with cancer, which may be due to multiple causes, such as nerve compression and mechanical forces resulting from tissue distension as a consequence of invasion by a tumor and tumor metastasis into bone or other tissues.

In one embodiment, inflammation results from neuropathy, such as post-herpetic neuralgia. In still another embodiment, the inflammation results from a surgery or procedure.

In yet a further embodiment, the inflammation results from an infection, cancer, colitis, cystitis, irritable bowel syndrome, or idiopathic neuropathy.

"Somatic inflammation" includes inflammation in bone, joint, muscle, skin, or connective tissue.

"Central inflammation" includes inflammation arising as a consequence of brain trauma, stroke, or spinal cord injury.

"Visceral inflammation" includes inflammation in visceral organs, such as the respiratory or gastrointestinal tract and pancreas, the urinary tract and reproductive organs. In one embodiment, visceral inflammation results from tumor involvement of the organ capsule. In another embodiment, visceral inflammation from obstruction of hollow viscus.

"Idiopathic inflammation" refers to inflammation which has no underlying cause or refers to inflammation caused by condition which remains undiagnosed.

"Dysfunctional inflammation" refers to inflammation which occurs in the absence of a noxious stimulus, tissue damage or a lesion to the nervous system. In one embodiment, dysfunctional inflammation results from rheumatologic conditions such as arthritis and fibromyalgia, tension type headache, irritable bowel disorders and erythermalgia.

"Nociceptive inflammation" includes inflammation caused by noxious stimuli that threaten to or actually injure body tissues. In one embodiment, nociceptive inflammation results from a cut, bruise, bone fracture, crush injury, burn, trauma, surgery, labor, sprain, bump, injection, dental procedure, skin biopsy, or obstruction. In another embodiment, nociceptive inflammation is located in the skin, musculoskeletal system, or internal organs.

"Neuropathic inflammation" is inflammation due to abnormal processing of sensory input by the peripheral or central nervous system consequent on a lesion to these systems. In one embodiment, neuropathic inflammation is chronic and non-malignant. In one embodiment, neuropathic inflammation is due to trauma, surgery, herniation of an intervertebral disk, spinal cord injury, diabetes, infection with herpes zoster (shingles), HIV/AIDS, late-stage cancer, amputation (such as mastectomy), carpal tunnel syndrome, chronic alcohol use, exposure to radiation, and as an unintended side-effect of neurotoxic treatment agents, such as certain anti-HIV and chemotherapeutic drugs.

"Procedural inflammation" includes refers to inflammation arising from a medical procedure. The medical procedure may include any type of medical, dental or surgical procedure. In one embodiment, the procedural inflammation is postoperative. In another embodiment, the inflammation is associated with an injection, draining an abscess, surgery, dermatological, dental procedure, ophthalmic procedure, arthroscopy and use of other medical instrumentation, and/or cosmetic surgery.

A "migraine" is a type of headache, typically defined clinically as being caused by activation of sensory fibers innervating the meninges of the brain.

The term "treat", "treating", or any variation thereof is meant to include therapy utilized to remedy a health problem or condition in a patient or subject. In one embodiment, the health problem or condition may be eliminated permanently or for a short period of time. In a further embodiment, the health problem or condition may be prevented. In another embodiment, the severity of the health problem or condition, or of one or more symptoms characteristic of the health problem or condition, may be lessened permanently, or for a short period of time. The effectiveness of a treatment of inflammation can be determined using any standard inflammation index, such as those described herein, or can be determined based on the patient's subjective inflammation assessment. A patient is considered "treated" if there is a reported reduction in inflammation, or a reduced reaction to stimuli that should cause inflammation.

In one embodiment, the treatment methods described herein include administering a compound of Formula (I) to a patient. Additional, optional agents, such as those described above for use in the combination, may be administered to the patient prior to, concurrently with, or subsequent to the compound of Formula (I).

The present invention is further exemplified, but not limited, by the following examples that illustrate the preparation of compounds of Formula (I) according to the invention

EXAMPLES

Example 1: 4-(4-morpholinophenylamino)-2-phenylpyrimido[5,4-d]pyridazin-5(6H)-one

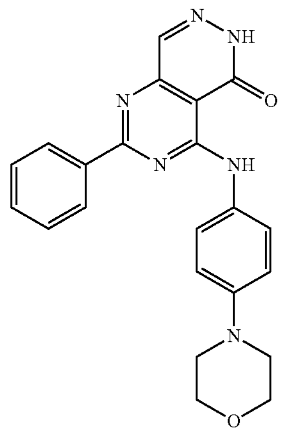 [SMILES: O=c1[nH]ncc2nc(-c3ccccc3)nc(Nc3ccc(N4CCOCC4)cc3)c12]

a: Ethyl 2-(bis(methylthio)methylene)-3-oxobutanoate

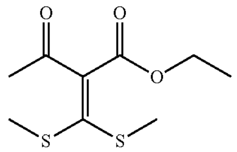

To a solution of ethyl acetoacetate (10 g, 76.9 mmol) in DMF (40 mL) was added $K_2CO_3$ (10.6 g, 76.9 mmol) and the reaction mixture was stirred at RT for 2 hours. Carbon disulfide (8.8 g, 230 mmol) was added, stirring was continued. After 2 hours, methyl iodide was added and stirring was continued for additional 10 hours. The reaction mixture was partitioned between ethyl acetate and water, the organic layer washed with water and dried over $Na_2SO_4$ and the solvent evaporated in vacuum. The crude product was purified by column chromatography over silica gel using ethyl acetate and petroleum ether as eluent to give the desired product (8.8 g). $^1$H-NMR 400 Hz ($CDCl_3$): δ 4.29 (q, J=7.2 Hz, 2H), 2.44 (s, 6H), 2.34 (s, 3H), 1.33 (t, J=7.2 Hz, 3H); MS m/z 235 (M+1).

b: Ethyl 4-methyl-6-(methylthio)-2-phenylpyrimidine-5-carboxylate

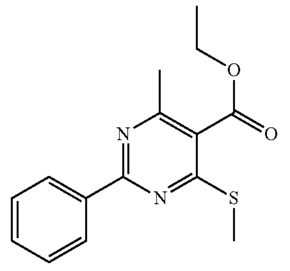 [SMILES: CCOC(=O)c1c(C)nc(-c2ccccc2)nc1SC]

To a solution of ethyl 2-(bis(methylthio)methylene)-3-oxobutanoate (500 mg, 2 mmol) in ethanol was added benzamidine acetate (732 mg, 6 mmol) and triethyl amine (1.41 mL) and the reaction mixture was refluxed overnight. The reaction mixture was concentrated and partitioned between ethyl acetate and water and the organic layer washed with water and dried over $Na_2SO_4$ and the solvent evaporated in vacuum. The crude product was purified by column chromatography over silica gel using 1% ethyl acetate in petroleum ether as eluent to give the desired product (350 mg). $^1$H-NMR 400 Hz ($CDCl_3$): δ 8.50 (d, J=7.6 Hz, 2H), 7.50-7.46 (m, 3H), 4.45 (q, J=7.2 Hz, 2H), 2.67 (s, 3H), 2.65 (s, 3H), 1.44 (t, J=7.2 Hz, 3H); MS m/z 288.7 (M+1).

c: Ethyl 4-formyl-6-(methylthio)-2-phenylpyrimidine-5-carboxylate

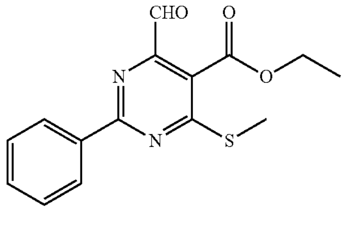 [SMILES: CCOC(=O)c1c(C=O)nc(-c2ccccc2)nc1SC]

To a solution of ethyl 4-methyl-6-(methylthio)-2-phenylpyrimidine-5-carboxylate (5 g 17.4 mmol) in 1.4-dioxane (50 mL) was added selenium dioxide (9.6 g, 86.5 mmol) and water (1.5 mL) and the reaction mixture was refluxed for 12 hours. Dioxane was removed in a vacuum and the crude solid suspended in ethyl acetate and filtered. The filtrate was concentrated and purified by column chromatography over silica gel using 10% ethyl acetate in petroleum ether as eluent to give the desired product (3.1 g). $^1$H-NMR (400 Hz, $CDCl_3$): δ 10.10 (s, 1H), 8.54 (d, J=7.2 Hz, 2H), 7.56-7.43 (m, 3H), 4.47 (q, J=7.2 Hz, 2H), 2.67 (s, 3H), 2.64 (s, 3H), 1.42 (t, J=7.2 Hz, 3H); MS m/z 303.1 (M+1).

d: 4-(methylthio)-2-phenylpyrimido[4,5-d]pyridazin-5(6H)-one

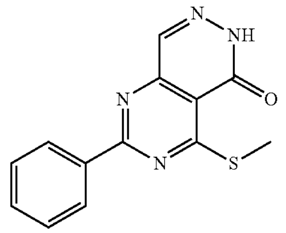 [SMILES: CSc1nc(-c2ccccc2)nc2cn[nH]c(=O)c12]

To a solution of ethyl 4-formyl-6-(methylthio)-2-phenylpyrimidine-5-carboxylate (600 mg, 1.98 mmol) in ethanol (15 mL) was added hydrazine dihydrochloride (0.2 g, 1.98 mmol) and the mixture refluxed for 1 hour. The precipitated solid was filtered and dried in vacuum. The desired product (520 mg) was obtained by column chromatography over silica gel using methanol/dichloromethane as eluent. $^1$H-NMR (400 Hz, DMSO-$d_6$): δ 13.19 (s, 1H), 8.54 (d, J=8.0 Hz, 2H), 8.36 (s, 1H), 7.64-7.58 (m, 3H), 2.67 (s, 3H); MS m/z 271.1 (M+1).

e: 4-(4-Morpholinophenylamino)-2-phenylpyrimido[5,4-d]pyridazin-5(6H)-one 4-(Methylthio)-2-phenylpyrimido[4,5-d]pyridazin-5(6H)-one (0.1 g, 0.37 mmol) was dissolved in dichloromethane, m-chloro perbenzoic acid (0.19 g) was added and the reaction mixture was stirred room temperature for 10-12 hours. The solid precipitate was filtered and dried under vacuum. The crude product was dissolved in NMP, 4-(morpholinomethyl)aniline (45 mg, 0.25 mmol) was added and the reaction mixture was heated to 60° C. for 30 minutes. The reaction mixture was cooled and ice water was added. The solid precipitate was filtered and dried under vacuum to yield the desired product (38 mg).

Example 2: Methyl 4-(5-oxo-4-(4-(piperazin-1-ylmethyl)phenylamino)-5,6-dihydropyrimido[4,5-d]pyridazin-2-yl)benzoate hydrochloride

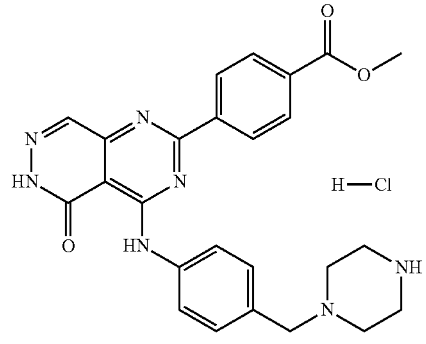 [SMILES: COC(=O)c1ccc(-c2nc(Nc3ccc(CN4CCNCC4)cc3)c3c(=O)[nH]ncc3n2)cc1 ; Cl]

a: (Z)-Ethyl 3-amino-2-(ethoxycarbonylcarbamothioyl)but-2-enoate

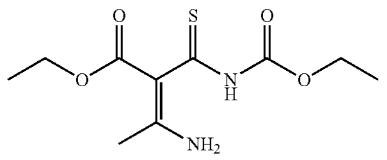 [SMILES: CCOC(=O)NC(=S)/C(C(=O)OCC)=C(/C)N]

To a solution of ethyl chloroformate (1 g, 9.2 mmol) in 1,4-dioxane cooled to 0° C. was added ammonium thiocyanate (0.771 g, 10 mmol) and pyridine (0.726 g, 9.2 mmol) and the mixture was stirred at 0° C. for 2 hours. The reaction mixture was extracted with diethyl ether, dried over $Na_2SO_4$ and concentrated in vacuum to give crude ethyl isothiocyanatoformate. This crude product was added dropwise over a period of 2-3 hours to a solution of ethyl 3-aminocrotanoate (1.19 g, 9.2 mmol) in dioxane at 0-10° C. The reaction mixture was quenched with ice water and the resulting solid filtered and dried to get the desired crude product, which is used without further purification. $^1H$ NMR (400 MHz, $CDCl_3$): δ 10.52 (s, 1H), 9.51 (s, 1H), 5.25 (s, 1H), 4.21-4.12 (m, 4H), 2.26 (s, 3H), 1.29-1.21 (m, 6H); MS m/z 261.1 (M+1).

b: Ethyl 2-hydroxy-4-mercapto-6-methylpyrimidine-5-carboxylate

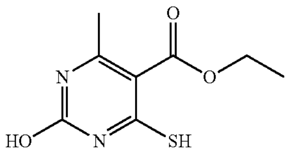

(Z)-ethyl 3-amino-2-(ethoxycarbonylcarbamothioyl)but-2-enoate was dissolved in 30% aqueous triethyl amine and the reaction mixture stirred at 70° C. After 2 hours, the reaction mixture was cooled and neutralized with glacial acetic acid and the aqueous mixture extracted with EtOAc. The organic layer was washed with water, dried over $Na_2SO_4$ and concentrated under vacuum to give the desired product. $^1H$ NMR (400 MHz, DMSO-$d_6$): δ 12.54 (s, 1H), 11.85 (s, 1H), 4.21 (q, J=7.6 Hz, 2H), 2.03 (s, 3H), 1.24 (t. J=7.6 Hz, 3H); MS m/z 213.1 (M-1).

c: Ethyl 2,4-dichloro-6-methylpyrimidine-5-carboxylate

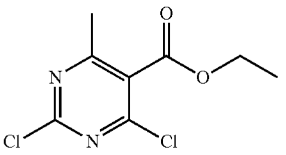

Ethyl 2-hydroxy-4-mercapto-6-methylpyrimidine-5-carboxylate (1.4 g, 6.54 mmol) was taken up in $POCl_3$ (13.67 mL) at 0° C., tri-n-butylamine was added and the mixture heated to 90° C. for 5 hours. The mixture was cooled, poured slowly on to crushed ice and extracted with dichloromethane. The organic layer was washed with water, dried over $Na_2SO_4$ and concentrated under vacuum. The pure product was obtained by column purification over silica gel using 3% EtOAc/hexane as eluent. $^1H$ NMR (400 MHz, $CDCl_3$): δ 4.47 (q, J=6.8 Hz, 2H), 2.57 (s, 3H), 1.42 (t. J=6.8 Hz, 3H); MS m/z 235.1 (M+1).

d: Ethyl 4-(4-((4-(tert-butoxycarbonyl)piperazin-1-yl)methyl)phenylamino)-2-chloro-6-methylpyrimidine-5-carboxylate

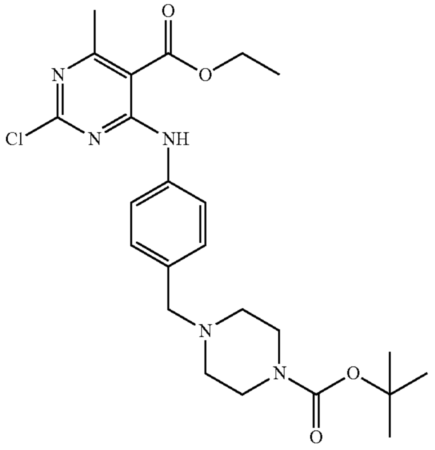 [SMILES: CCOC(=O)c1c(C)nc(Cl)nc1Nc1ccc(CN2CCN(C(=O)OC(C)(C)C)CC2)cc1]

Ethyl 2,4-dichloro-6-methylpyrimidine-5-carboxylate (0.5 g, 2.1 mmol) and tert-butyl 4-(4-aminobenzyl)piperazine-1-carboxylate (0.6 g, 2.06 mmol) were dissolved in NMP and stirred at 0° C. for 2 hour. The reaction mixture was poured onto water and extracted with EtOAc. The organic layer was washed with water, dried over $Na_2SO_4$ and evaporated under vacuum to get the desired compound (0.62 g). $^1H$ NMR (400 MHz, $CDCl_3$): δ 10.58 (s, 1H), 7.58 (d, J=6.4 Hz, 2H), 7.31 (d, J=6.4 Hz, 2H), 4.45 (q, J=6.8 Hz, 2H), 3.56 (s, 2H), 3.41 (m, 4H), 2.69 (s, 3H), 2.47 (m, 4H), 1.45 (s, 9H), 1.43 (t, J=6.8 Hz, 3H); MS m/z 490.0 (M+1).

e: Ethyl 4-(4-((4-(tert-butoxycarbonyl)piperazin-1-yl)methyl)phenylamino)-2-(4-(methoxycarbonyl)phenyl)-6-methylpyrimidine-5-carboxylate

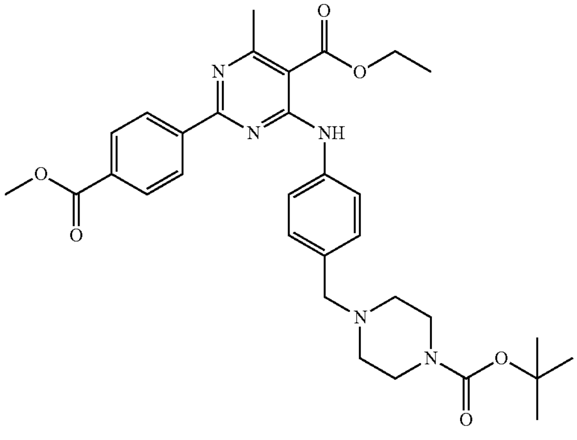 [SMILES: CCOC(=O)c1c(C)nc(-c2ccc(C(=O)OC)cc2)nc1Nc1ccc(CN2CCN(C(=O)OC(C)(C)C)CC2)cc1]

Ethyl 4-(4-((4-(tert-butoxycarbonyl)piperazin-1-yl)methyl)phenylamino)-2-chloro-6-methylpyrimidine-5-carboxylate (0.8 g, 1.63 mmol), $K_2CO_3$ (0.56 g, 4 mmol), $Pd(PPh_3)_4$(0.28 g, 0.24 mmol) were dissolved in dioxane/water (20:1), 4-(methoxycarbonyl)phenylboronic acid (0.38 g, 2.1 mmol) was added the mixture was heated to 100° C. for 3 hours. The mixture was diluted with water and extracted with EtOAc. The organic layer was concentrated and purified by column chromatography over silica gel using 30% EtOAc/hexanes as eluent to give the desired product (0.7 g). $^1$H NMR (400 MHz, DMSO-$d_6$): δ 9.88 (s, 1H), 8.43 (d, J=8.0 Hz, 2H), 8.10 (d, J=8.0 Hz, 2H), 7.68 (d, J=8.4 Hz, 2H), 7.35 (d, J=8.4 Hz, 2H), 4.39 (q, J=6.8 Hz, 2H), 3.89 (s, 3H), 3.49 (s, 2H), 2.68 (m, 4H), 2.50 (s, 3H), 2.33 (m, 4H), 1.91 (t, J=6.8 Hz, 3H), 1.39 (s, 9H); MS m/z 590.2 (M+1).

f: Ethyl 4-(4-((4-(tert-butoxycarbonyl)piperazin-1-yl)methyl)phenylamino)-6-formyl-2-(4-(methoxycarbonyl)phenyl)pyrimidine-5-carboxylate

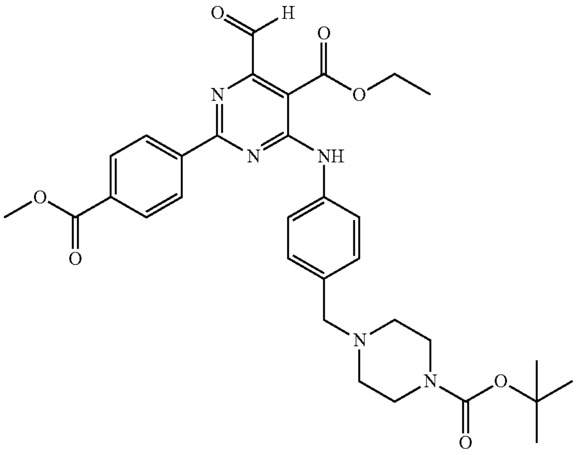 [SMILES: CCOC(=O)c1c(C=O)nc(-c2ccc(C(=O)OC)cc2)nc1Nc1ccc(CN2CCN(C(=O)OC(C)(C)C)CC2)cc1]

Ethyl 4-(4-((4-(tert-butoxycarbonyl)piperazin-1-yl)methyl)phenylamino)-2-(4-(methoxycarbonyl)phenyl)-6-methylpyrimidine-5-carboxylate (0.63 g, 1.06 mmol) was dissolved in dioxane (10 mL), $SeO_2$ (0.6 g, 5.4 mmol) and water (0.096 mL) were added and the reaction mixture heated at 100° C. for 3.5 hours. The reaction mixture was concentrated in vacuum and the mixture loaded on to a column of silica gel and eluted with MeOH, dichloromethane as eluent, to give the desired compound (0.52 g). $^1$H NMR (400 MHz, DMSO-$d_6$): δ 10.18 (s, 1H), 9.53 (s, 1H), 8.56 (d, J=8.4 Hz, 2H), 8.08 (d, J=8.4 Hz, 2H), 7.71 (d, J=8.4 Hz, 2H), 7.37 (d, J=8.4 Hz, 2H), 4.39 (q, J=6.8 Hz, 2H), 3.89 (s, 3H), 3.41 (s, 2H), 3.26 (m, 4H), 2.35 (m, 4H)), 1.39 (s, 9H), 1.36 (t, J=6.8 Hz, 3H); MS m/z 636.5 (M+1).

g: tert-butyl 4-(4-(2-(4-(methoxycarbonyl)phenyl)-5-oxo-5,6-dihydropyrimido[4,5-d]pyridazin-4-ylamino)benzyl)piperazine-1-carboxylate

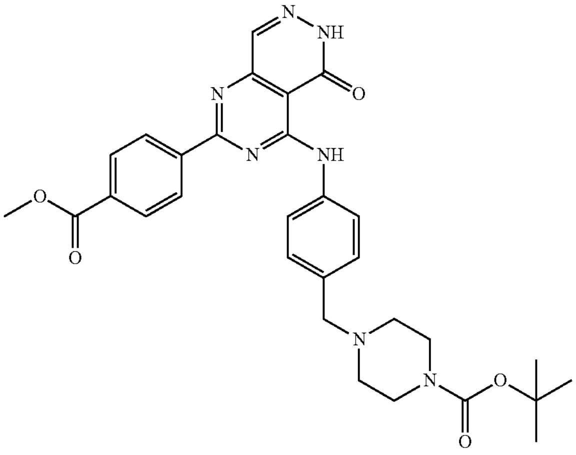 [SMILES: COC(=O)c1ccc(-c2nc(Nc3ccc(CN4CCN(C(=O)OC(C)(C)C)CC4)cc3)c3c(=O)[nH]ncc3n2)cc1]

Ethyl 4-(4-((4-(tert-butoxycarbonyl)piperazin-1-yl)methyl)phenylamino)-6-formyl-2-(4-(methoxycarbonyl)phenyl)pyrimidine-5-carboxylate (0.5 g, 0.82 mmol) was dissolved in ethanol (5 mL), hydrazine hydrate (60 μL, 1.24 mmol) was added and the mixture is refluxed for 2.5 hours. The reaction mixture was cooled to obtain a solid precipitate. The precipitate was filtered and the solid dried under vacuum (0.4 g). $^1$H NMR (400 MHz, DMSO-$d_6$): δ 13.41 (s, 1H), 11.52 (s, 1H), 8.52 (d, J=8.4 Hz, 2H), 8.34 (s, 1H), 8.13 (d, J=8.8 Hz, 2H), 7.86 (d, J=8.8 Hz, 2H), 7.42 (d, J=8.4 Hz, 2H), 3.90 (s, 3H), 3.51 (s, 2H), 3.29 (t, J=4.4 Hz, 4H), 2.34 (t, J=4.4 Hz, 4H), 1.39 (s, 9H); MS m/z 572.3 (M+1).

h: Methyl 4-(5-oxo-4-(4-(piperazin-1-ylmethyl)phenylamino)-5,6-dihydropyrimido[4,5-d]pyridazin-2-yl)benzoate hydrochloride Tert-butyl 4-(4-(2-(4-(methoxycarbonyl)phenyl)-5-oxo-5,6-dihydropyrimido[4,5-d]pyridazin-4-ylamino)benzyl)piperazine-1-carboxylate (0.1 g, 0.175 mmol) was dissolved in dioxane.HCl (5 mL) and stirred at room temperature for 1.5 hours. The solid obtained was filtered and the residue washed with EtOAc and dried to give the desired product (40 mg).

Example 3: 2-morpholino-4-(4-(piperazin-1-ylmethyl)phenylamino)pyrimido[4,5-d]pyridazin-5(6H)-one hydrochloride

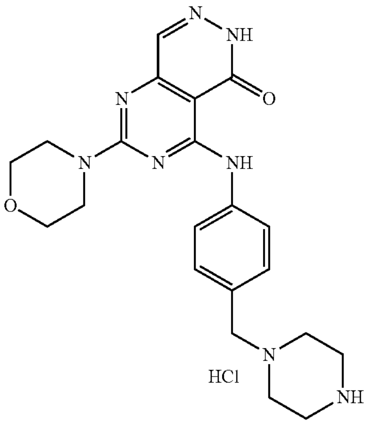 [SMILES: O=c1[nH]ncc2nc(N3CCOCC3)nc(Nc3ccc(CN4CCNCC4)cc3)c12 ; Cl]

a: Ethyl 4-(4-((4-(tert-butoxycarbonyl)piperazin-1-yl)methyl)phenylamino)-6-methyl-2-morpholinopyrimidine-5-carboxylate

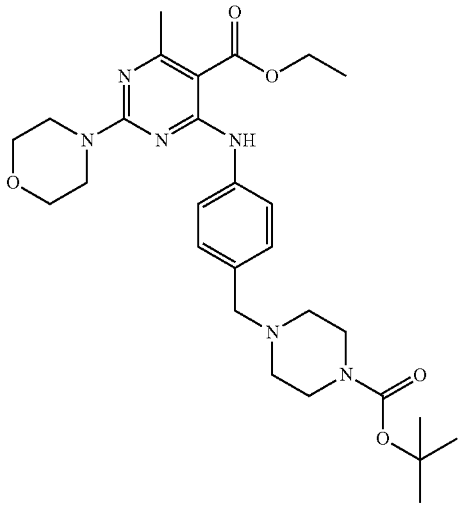 [SMILES: CCOC(=O)c1c(C)nc(N2CCOCC2)nc1Nc1ccc(CN2CCN(C(=O)OC(C)(C)C)CC2)cc1]

Ethyl 4-(4-((4-(tert-butoxycarbonyl)piperazin-1-yl)methyl)phenylamino)-2-chloro-6-methylpyrimidine-5-carboxylate (0.6 g, 1.23 mmol) was dissolved in NMP (5 mL), morpholine (0.14 mL) was added and the mixture was stirred at room temperature for 45 minutes. The reaction mixture was poured into water and extracted with EtOAc. The organic layer was washed with water, dried over $Na_2SO_4$ and evaporated to give the desired product (0.53 g). $^1$H NMR (400 MHz, DMSO-$d_6$): δ 10.48 (s, 1H), 7.56 (d, J=8.4 Hz, 2H), 7.26 (d, J=8.4 Hz, 2H), 4.30 (q, J=6.8 Hz, 2H), 3.75 (s, 2H), 3.64 (m, 4H), 3.46-3.21 (m, 8H), 2.69 (s, 3H), 2.41 (m, 4H), 1.38 (s, 9H), 1.33 (t, J=6.8 Hz, 3H); MS m/z 541.1 (M+1).

b: (E)-ethyl 4-(4-((4-(tert-butoxycarbonyl)piperazin-1-yl)methyl)phenylamino)-6-(2-(dimethylamino)vinyl)-2-morpholinopyrimidine-5-carboxylate

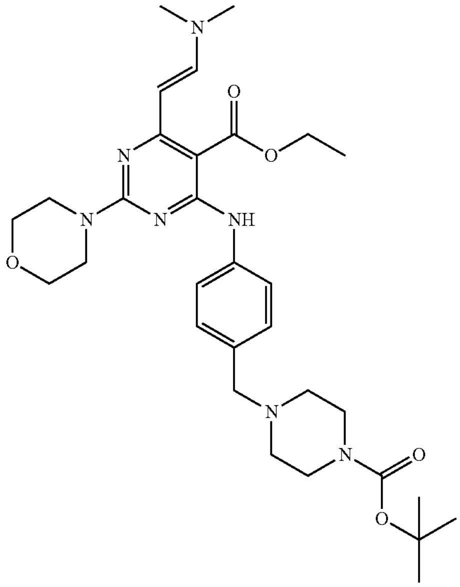 [SMILES: CCOC(=O)c1c(/C=C/N(C)C)nc(N2CCOCC2)nc1Nc1ccc(CN2CCN(C(=O)OC(C)(C)C)CC2)cc1]

Ethyl 4-(4-((4-(tert-butoxycarbonyl)piperazin-1-yl)methyl)phenylamino)-6-methyl-2-morpholinopyrimidine-5-carboxylate (350 mg, 0.64 mmol) was dissolved in DMF (5 mL), dimethyl formamide dimethyl acetal (0.26 mL) was added and the mixture was heated to 130° C. for 12 hours. The reaction mixture was poured into water and extracted with EtOAc. The organic layer was washed with water, dried over $Na_2SO_4$ and evaporated to give the desired product (0.23 g). $^1$H NMR (400 MHz, DMSO-$d_6$): δ 10.44 (s, 1H), 7.94 (d, J=12.2 Hz, 1H), 7.55 (d, J=8.8 Hz, 2H), 7.22 (d, J=8.8 Hz, 2H), 5.89 (d, J=12.2 Hz, 1H), 4.30 (q, J=6.8 Hz, 2H), 3.80 (s, 2H), 3.75-3.65 (m, 8H), 3.33 (m, 4H), 3.32 (m, 6H), 2.41 (m, 4H), 1.38 (s, 9H), 1.32 (t, J=6.8 Hz, 3H); MS m/z 596.4 (M+1).

c: Ethyl 4-(4-((4-(tert-butoxycarbonyl)piperazin-1-yl)methyl)phenylamino)-6-formyl-2-morpholinopyrimidine-5-carboxylate

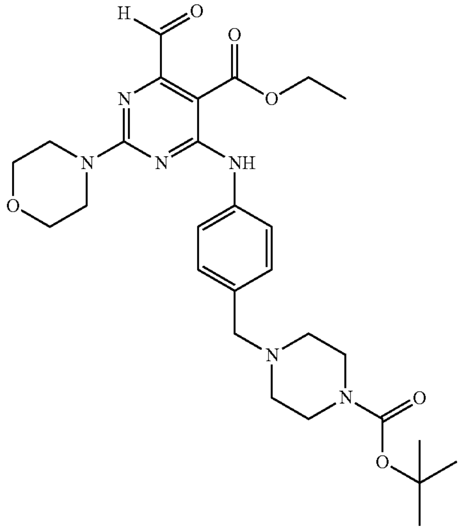 [SMILES: CCOC(=O)c1c(C=O)nc(N2CCOCC2)nc1Nc1ccc(CN2CCN(C(=O)OC(C)(C)C)CC2)cc1]

(E)-ethyl 4-(4-((4-(tert-butoxycarbonyl)piperazin-1-yl)methyl)phenylamino)-6-(2-(dimethylamino)vinyl)-2-morpholinopyrimidine-5-carboxylate (0.2 g, 0.336 mmol) was dissolved in methanol (4 mL) and to this mixture at room temperature was added a solution of sodium periodate (0.21 g, 1 mmol) in methanol (4 mL). The mixture was stirred at room temperature for 3 hours and the precipitate filtered. The filtrate was evaporated, diluted with water and extracted with EtOAc. The organic layer was dried over $Na_2SO_4$ and evaporated in vacuum. The crude product was purified by column chromatography over silica gel using acetone/dichloromethane as eluent. (0.11 g). $^1$H NMR (400 MHz, DMSO-$d_6$): δ 10.07 (s, 1H), 10.02 (s, 1H), 7.59 (d, J=8.4 Hz, 2H), 7.30 (d, J=8.4 Hz, 2H), 4.31 (q, J=6.8 Hz, 2H), 3.83 (s, 2H), 3.75-3.65 (m, 8H), 3.33 (m, 4H), 2.32 (m, 4H), 1.38 (s, 9H), 1.31 (t, J=6.8 Hz, 3H); MS m/z 555.5 (M+1).

d: 2-morpholino-4-(4-(piperazin-1-ylmethyl)phenylamino)pyrimido[4,5-d]pyridazin-5(6H)-one hydrochloride Ethyl 4-(4-((4-(tert-butoxycarbonyl)piperazin-1-yl)methyl)phenylamino)-6-formyl-2-morpholinopyrimidine-5-carboxylate (100 mg, 0.18 mmol) was dissolved in ethanol, hydrazine dihydrochloride (28 mg, 26 mmol) was added and the mixture was refluxed for 3 hours. The solid precipitated was filtered and dried in vacuum to give the desired product (49 mg).

By repeating the procedures described in the above examples, using appropriate starting materials, the following compounds of Formula I, as identified in Table 1, are obtained, together with their spectroscopic data in Table 2.

TABLE 1

| Ex | Structure | IUPAC Name | Synthetic Scheme |
|---|---|---|---|
| 1 | 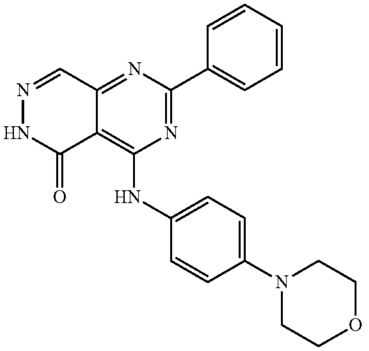 [SMILES: O=c1[nH]ncc2nc(-c3ccccc3)nc(Nc3ccc(N4CCOCC4)cc3)c12] | 4-(4-morpholinophenylamino)-2-phenylpyrimido[4,5-d]-pyridazin-5(6H)-one | 1 |
| 2 | 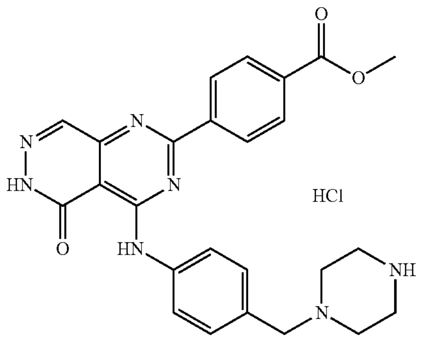 [SMILES: COC(=O)c1ccc(-c2nc(Nc3ccc(CN4CCNCC4)cc3)c3c(=O)[nH]ncc3n2)cc1 ; Cl] HCl | methyl 4-(5-oxo-4-(4-(piperazin-1-ylmethyl)phenylamino)-5,6-dihydropyrimido[4,5-d]-pyridazin-2-yl)benzoate hydrochloride | 3 |

TABLE 1-continued

| Ex | Structure | IUPAC Name | Synthetic Scheme |
|---|---|---|---|
| 3 | 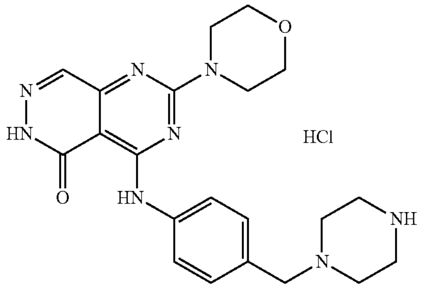 [SMILES: O=c1[nH]ncc2nc(N3CCOCC3)nc(Nc3ccc(CN4CCNCC4)cc3)c12 ; Cl] | 2-morpholino-4-(4-(piperazin-1-ylmethyl)phenylamino)-pyrimido[4,5-d]pyridazin-5(6H)-one hydrochloride | 5 |
| 4 | 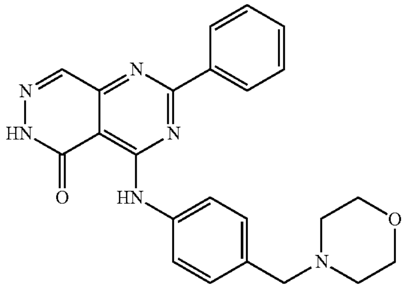 [SMILES: O=c1[nH]ncc2nc(-c3ccccc3)nc(Nc3ccc(CN4CCOCC4)cc3)c12] | 4-(4-(morpholinomethyl)-phenylamino)-2-phenyl-pyrimido[4,5-d]pyridazin-5(6H)-one | 1 |
| 5 | 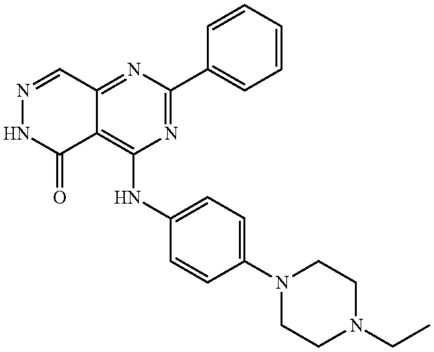 [SMILES: CCN1CCN(c2ccc(Nc3nc(-c4ccccc4)nc4cn[nH]c(=O)c34)cc2)CC1] | 4-(4-(4-ethylpiperazin-1-yl)-phenylamino)-2-phenyl-pyrimido-[4,5-d]pyridazin-5(6H)-one | 1 |
| 6 | 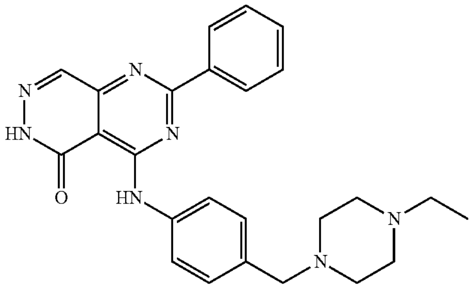 [SMILES: CCN1CCN(Cc2ccc(Nc3nc(-c4ccccc4)nc4cn[nH]c(=O)c34)cc2)CC1] | 4-(4-((4-ethylpiperazin-1-yl)-methyl)phenylamino)-2-phenyl-pyrimido[4,5-d]pyridazin-5(6H)-one | 1 |
| 7 | 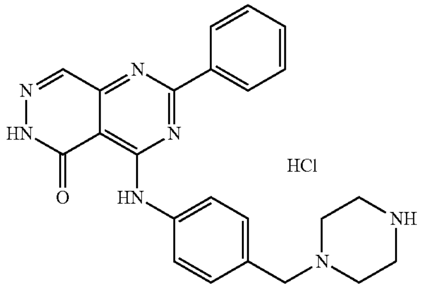 [SMILES: O=c1[nH]ncc2nc(-c3ccccc3)nc(Nc3ccc(CN4CCNCC4)cc3)c12 ; Cl] | 2-phenyl-4-(4-(piperazin-1-yl-methyl)phenylamino)pyrimido-[4,5-d]pyridazin-5(6H)-one hydrochloride | 1 |

TABLE 1-continued
| Ex | Structure | IUPAC Name | Synthetic Scheme |
|---|---|---|---|
| 8 | 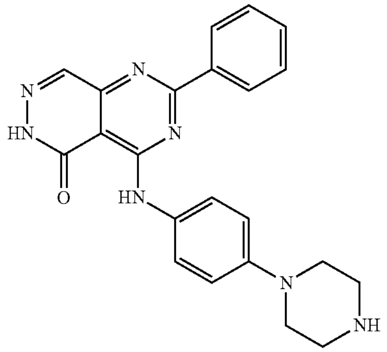 [SMILES: O=c1[nH]ncc2nc(-c3ccccc3)nc(Nc3ccc(N4CCNCC4)cc3)c12] | 2-phenyl-4-(4-(piperazin-1-yl)-phenylamino)pyrimido[4,5-d]-pyridazin-5(6H)-one | 1 |
| 9 | 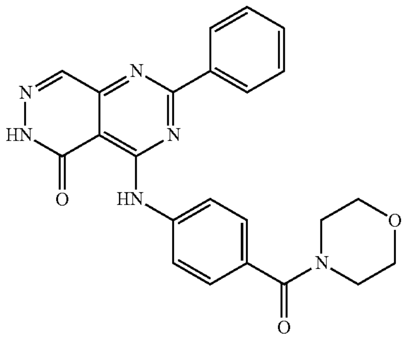 [SMILES: O=C(c1ccc(Nc2nc(-c3ccccc3)nc3cn[nH]c(=O)c23)cc1)N1CCOCC1] | 4-(4-(morpholine-4-carbonyl)-phenylamino)-2-phenyl-pyrimido-[4,5-d]pyridazin-5(6H)-one | 1 |
| 10 | 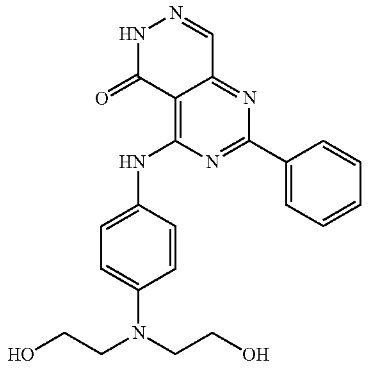 [SMILES: O=c1[nH]ncc2nc(-c3ccccc3)nc(Nc3ccc(N(CCO)CCO)cc3)c12] | 4-(4-(bis(2-hydroxyethyl)-amino)phenylamino)-2-phenyl-pyrimido[4,5-d]pyridazin-5(6H)-one | 1 |
| 11 | 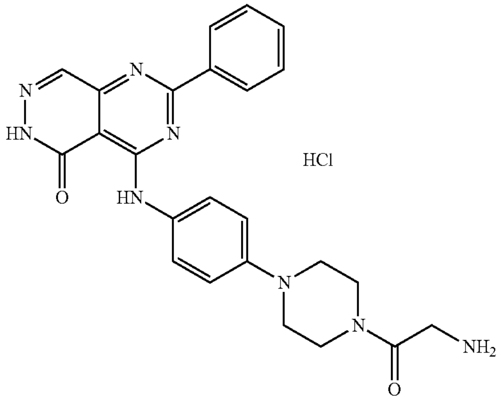 [SMILES: NCC(=O)N1CCN(c2ccc(Nc3nc(-c4ccccc4)nc4cn[nH]c(=O)c34)cc2)CC1 ; Cl] | 4-(4-(4-(2-aminoacetyl)-piperazin-1-yl)phenylamino)-2-phenylpyrimido[4,5-d]-pyridazin-5(6H)-one hydrochloride | 1 |

TABLE 1-continued

| Ex | Structure | IUPAC Name | Synthetic Scheme |
| --- | --- | --- | --- |
| 12 | 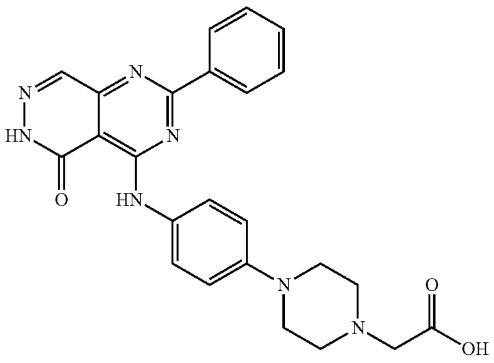 | 2-(4-(4-(5-oxo-2-phenyl-5,6-dihydropyrimido[4,5-d]-pyridazin-4-ylamino)phenyl)-piperazin-1-yl)acetic acid | 1 |
| 13 | 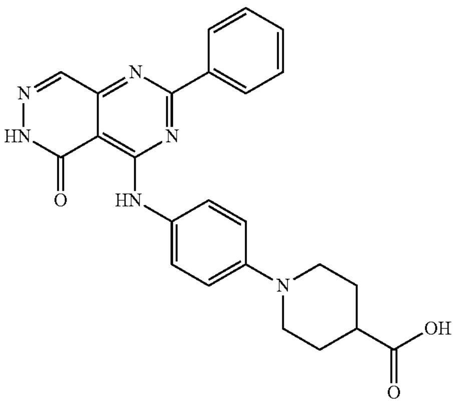 [SMILES: O=C(O)C1CCN(c2ccc(Nc3nc(-c4ccccc4)nc4cn[nH]c(=O)c34)cc2)CC1] | 1-(4-(5-oxo-2-phenyl-5,6-dihydropyrimido[4,5-d]-pyridazin-4-ylamino)phenyl)-piperidine-4-carboxylic acid | 1 |
| 14 | 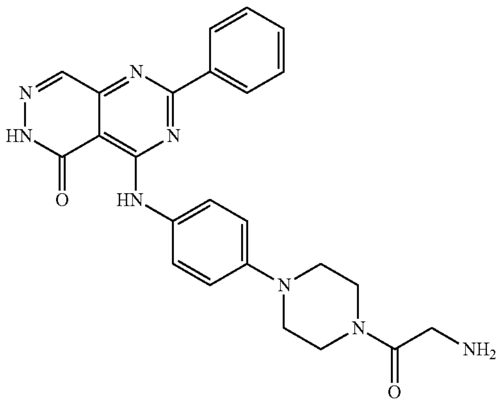 [SMILES: NCC(=O)N1CCN(c2ccc(Nc3nc(-c4ccccc4)nc4cn[nH]c(=O)c34)cc2)CC1] | 4-(4-(4-(2-aminoacetyl)-piperazin-1-yl)phenylamino)-2-phenylpyrimido[4,5-d]-pyridazin-5(6H)-one | 1 |
| 15 | 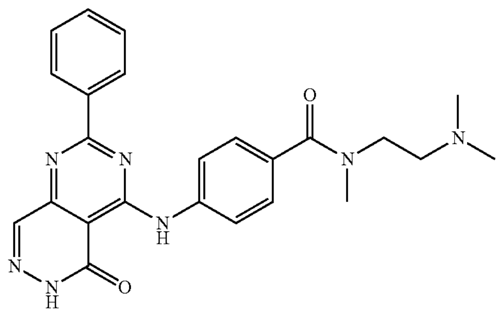 [SMILES: CN(C)CCN(C)C(=O)c1ccc(Nc2nc(-c3ccccc3)nc3cn[nH]c(=O)c23)cc1] | N-(2-(dimethylamino)ethyl)-N-methyl-4-(5-oxo-2-phenyl-5,6-dihydropyrimido[4,5-d]-pyridazin-4-ylamino)benzamide | 1 |

TABLE 1-continued
| Ex | Structure | IUPAC Name | Synthetic Scheme |
|---|---|---|---|
| 16 | 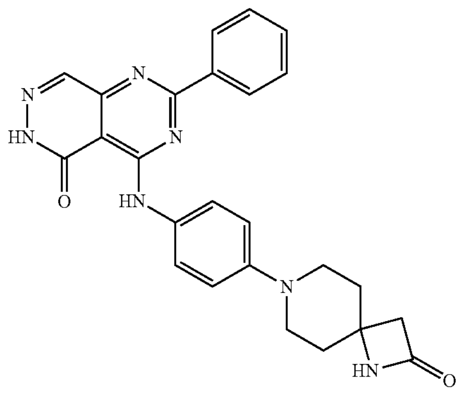 [SMILES: O=C1CC2(CCN(c3ccc(Nc4nc(-c5ccccc5)nc5cn[nH]c(=O)c45)cc3)CC2)N1] | 4-(4-(2-oxo-1,7-diazaspiro-[3.5]nonan-7-yl)phenylamino)-2-phenylpyrimido[4,5-d]-pyridazin-5(6H)-one | 1 |
| 17 | 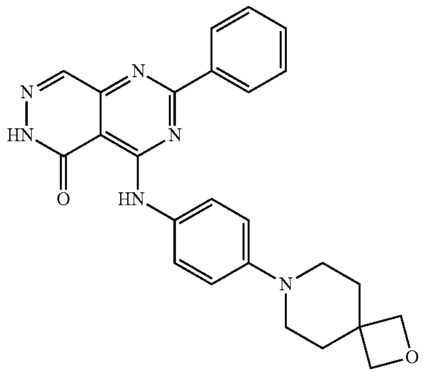 [SMILES: O=c1[nH]ncc2nc(-c3ccccc3)nc(Nc3ccc(N4CCC5(CC4)COC5)cc3)c12] | 4-(4-(2-oxa-7-azaspiro[3.5]-nonan-7-yl)phenylamino)-2-phenylpyrimido[4,5-d]-pyridazin-5(6H)-one | 1 |
| 18 | 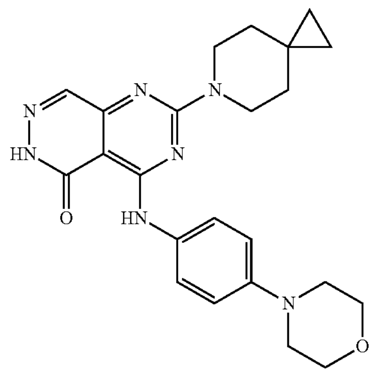 | 4-(4-morpholinophenylamino)-2-(6-azaspiro[2.5]octan-6-yl)-pyrimido[4,5-d]pyridazin-5(6H)-one | 5 |
| 19 | 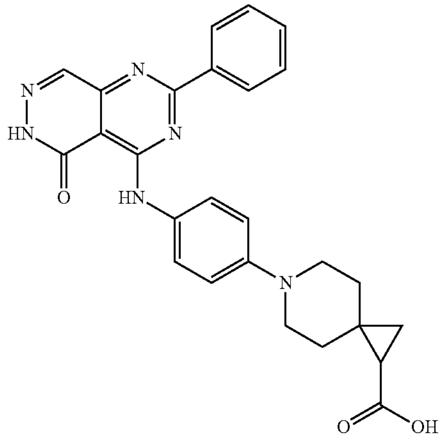 [SMILES: O=C(O)C1CC12CCN(c1ccc(Nc3nc(-c4ccccc4)nc4cn[nH]c(=O)c34)cc1)CC2] | 6-(4-(5-oxo-2-phenyl-5,6-dihydropyrimido[4,5-d]-pyridazin-4-ylamino)phenyl)-6-azaspiro[2.5]octane-1-carboxylic acid | 1 |

TABLE 1-continued
| Ex | Structure | IUPAC Name | Synthetic Scheme |
|---|---|---|---|
| 20 | 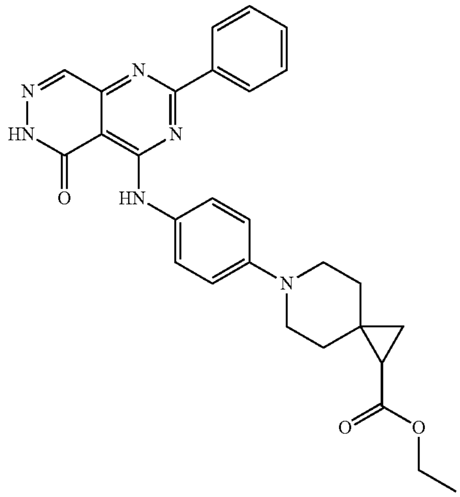 [SMILES: CCOC(=O)C1CC12CCN(c1ccc(Nc3nc(-c4ccccc4)nc4cn[nH]c(=O)c34)cc1)CC2] | ethyl 6-(4-(5-oxo-2-phenyl-5,6-dihydropyrimido[4,5-d]-pyridazin-4-ylamino)phenyl)-6-azaspiro[2.5]octane-1-carboxylate | 1 |
| 21 | 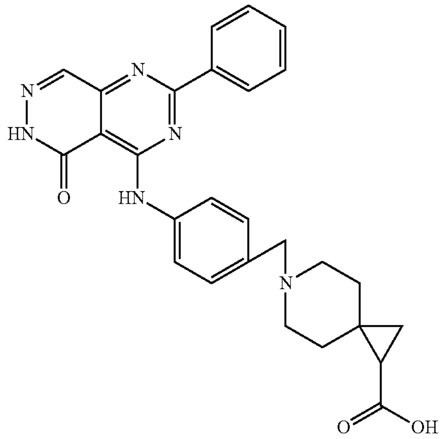 [SMILES: O=C(O)C1CC12CCN(Cc1ccc(Nc3nc(-c4ccccc4)nc4cn[nH]c(=O)c34)cc1)CC2] | 6-(4-(5-oxo-2-phenyl-5,6-dihydropyrimido[4,5-d]-pyridazin-4-ylamino)benzyl)-6-azaspiro[2.5]octane-1-carboxylic acid | 1 |
| 22 | 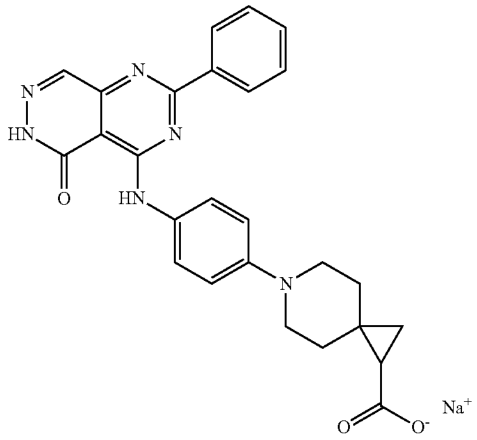 [SMILES: O=C([O-])C1CC12CCN(c1ccc(Nc3nc(-c4ccccc4)nc4cn[nH]c(=O)c34)cc1)CC2 ; [Na+]] | sodium 6-(4-(5-oxo-2-phenyl-5,6-dihydropyrimido[4,5-d]-pyridazin-4-ylamino)phenyl)-6-azaspiro[2.5]octane-1-carboxylate | 1 |

TABLE 1-continued

| Ex | Structure | IUPAC Name | Synthetic Scheme |
|---|---|---|---|
| 23 | 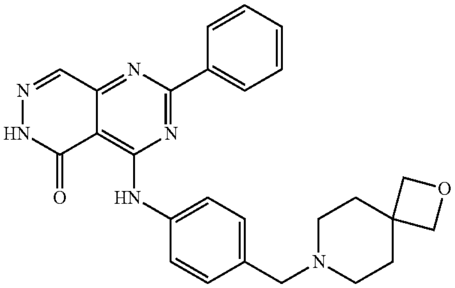 [SMILES: O=c1[nH]ncc2nc(-c3ccccc3)nc(Nc3ccc(CN4CCC5(CC4)COC5)cc3)c12] | 4-(4-(2-oxa-7-azaspiro[3.5]-nonan-7-ylmethyl)phenyl-amino)-2-phenylpyrimido[4,5-d]pyridazin-5(6H)-one | 1 |
| 24 | 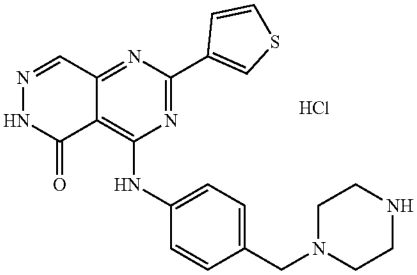 [SMILES: O=c1[nH]ncc2nc(-c3ccsc3)nc(Nc3ccc(CN4CCNCC4)cc3)c12 ; Cl] HCl | 4-(4-(piperazin-1-ylmethyl)-phenylamino)-2-(thiophen-3-yl)pyrimido[4,5-d]pyridazin-5(6H)-one hydrochloride | 3 |
| 25 | 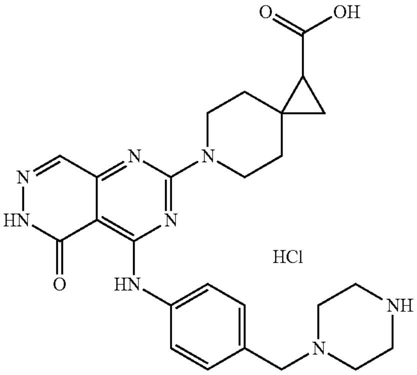 [SMILES: O=C(O)C1CC12CCN(c1nc(Nc3ccc(CN4CCNCC4)cc3)c3c(=O)[nH]ncc3n1)CC2 ; Cl] HCl | 6-(5-oxo-4-(4-(piperazin-1-ylmethyl)phenylamino)-5,6-dihydropyrimido[4,5-d]-pyridazin-2-yl)-6-azaspiro-[2.5]octane-1-carboxylic acid hydrochloride | 5 |
| 26 | 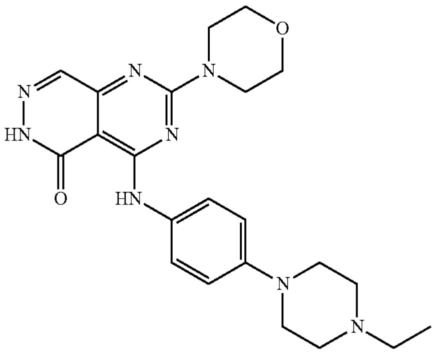 [SMILES: CCN1CCN(c2ccc(Nc3nc(N4CCOCC4)nc4cn[nH]c(=O)c34)cc2)CC1] | 4-(4-(4-ethylpiperazin-1-yl)-phenylamino)-2-morpholino-pyrimido[4,5-d]pyridazin-5(6H)-one | 5 |

TABLE 1-continued

| Ex | Structure | IUPAC Name | Synthetic Scheme |
| --- | --- | --- | --- |
| 27 | 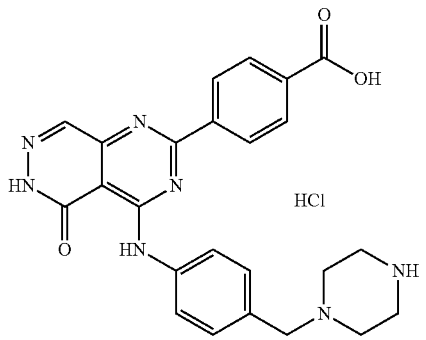 [SMILES: O=C(O)c1ccc(-c2nc(Nc3ccc(CN4CCNCC4)cc3)c3c(=O)[nH]ncc3n2)cc1 ; Cl] | 4-(5-oxo-4-(4-(piperazin-1-ylmethyl)phenylamino)-5,6-dihydropyrimido[4,5-d]-pyridazin-2-yl)benzoic acid hydrochloride | 3 |
| 28 | 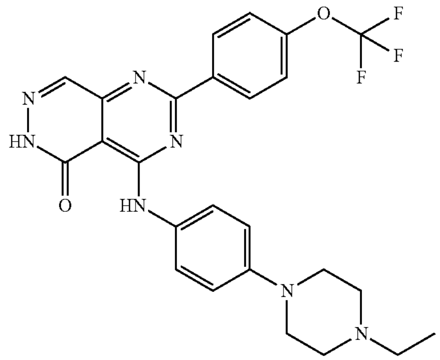 [SMILES: CCN1CCN(c2ccc(Nc3nc(-c4ccc(OC(F)(F)F)cc4)nc4cn[nH]c(=O)c34)cc2)CC1] | 4-(4-(4-ethylpiperazin-1-yl)-phenylamino)-2-(4-(trifluoro-methoxy)phenyl)pyrimido-[4,5-d]pyridazin-5(6H)-one | 3 |
| 29 | 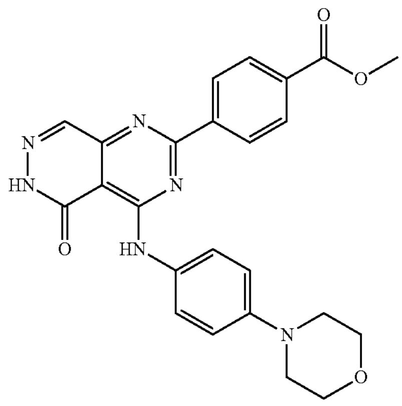 [SMILES: COC(=O)c1ccc(-c2nc(Nc3ccc(N4CCOCC4)cc3)c3c(=O)[nH]ncc3n2)cc1] | methyl 4-(4-(4-morpholino-phenylamino)-5-oxo-5,6-dihydropyrimido[4,5-d]-pyridazin-2-yl)benzoate | 3 |
| 30 | 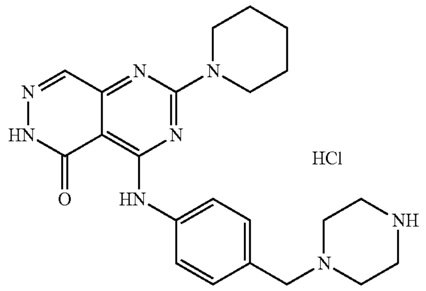 [SMILES: O=c1[nH]ncc2nc(N3CCCCC3)nc(Nc3ccc(CN4CCNCC4)cc3)c12 ; Cl] | 4-(4-(piperazin-1-ylmethyl)-phenylamino)-2-(piperidin-1-yl)pyrimido[4,5-d]pyridazin-5(6H)-one hydrochloride | 5 |

TABLE 1-continued

| Ex | Structure | IUPAC Name | Synthetic Scheme |
|---|---|---|---|
| 31 | 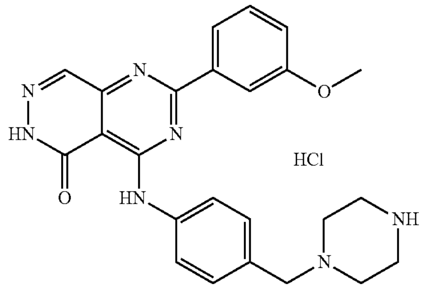 [SMILES: COc1cccc(-c2nc(Nc3ccc(CN4CCNCC4)cc3)c3c(=O)[nH]ncc3n2)c1 ; Cl] HCl | 2-(3-methoxyphenyl)-4-(4-(piperazin-1-ylmethyl)phenyl-amino)pyrimido[4,5-d]-pyridazin-5(6H)-one hydrochloride | 3 |
| 32 | 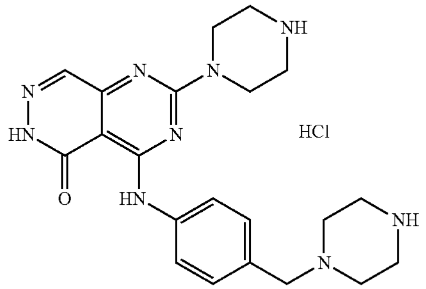 [SMILES: O=c1[nH]ncc2nc(N3CCNCC3)nc(Nc3ccc(CN4CCNCC4)cc3)c12 ; Cl] HCl | 2-(piperazin-1-yl)-4-(4-(piperazin-1-ylmethyl)phenyl-amino)pyrimido[4,5-d]-pyridazin-5(6H)-one dihydrochloride | 5 |
| 33 | 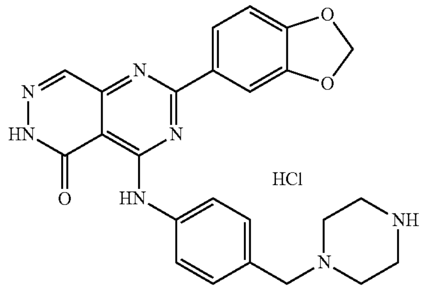 [SMILES: O=c1[nH]ncc2nc(-c3ccc4c(c3)OCO4)nc(Nc3ccc(CN4CCNCC4)cc3)c12 ; Cl] HCl | 2-(benzo[d][1,3]dioxol-5-yl)-4-(4-(piperazin-1-ylmethyl)-phenylamino)pyrimido[4,5-d]-pyridazin-5(6H)-one hydrochloride | 3 |
| 34 | 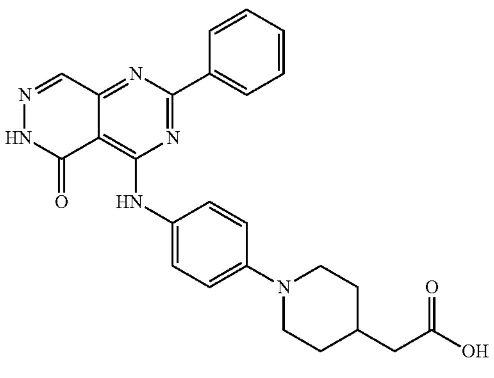 [SMILES: O=C(O)CC1CCN(c2ccc(Nc3nc(-c4ccccc4)nc4cn[nH]c(=O)c34)cc2)CC1] | 2-(1-(4-(5-oxo-2-phenyl-5,6-dihydropyrimido[4,5-d]-pyridazin-4-ylamino)phenyl)-piperidin-4-yl)acetic acid | 1 |

TABLE 1-continued

| Ex | Structure | IUPAC Name | Synthetic Scheme |
|---|---|---|---|
| 35 | 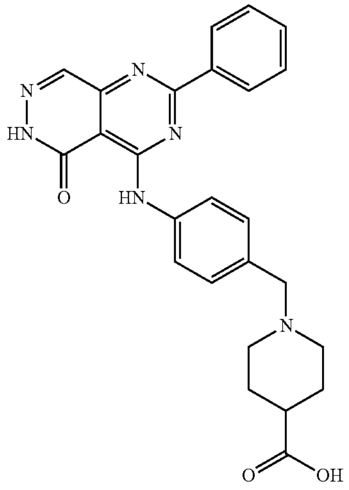 [SMILES: O=C(O)C1CCN(Cc2ccc(Nc3nc(-c4ccccc4)nc4cn[nH]c(=O)c34)cc2)CC1] | 1-(4-(5-oxo-2-phenyl-5,6-dihydropyrimido[4,5-d]-pyridazin-4-ylamino)benzyl)-piperidine-4-carboxylic acid | 1 |
| 36 | 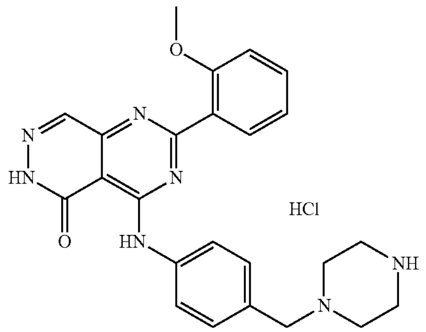 [SMILES: COc1ccccc1-c1nc(Nc2ccc(CN3CCNCC3)cc2)c2c(=O)[nH]ncc2n1 ; Cl] | 2-(2-methoxyphenyl)-4-(4-(piperazin-1-ylmethyl)phenyl-amino)pyrimido[4,5-d]-pyridazin-5(6H)-one hydrochloride | 3 |
| 37 | 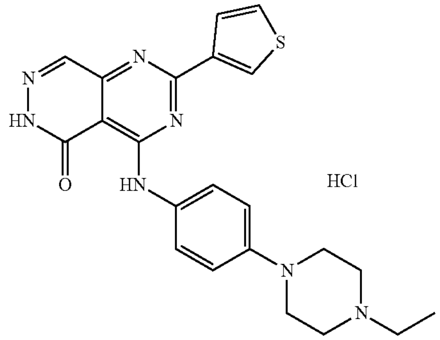 [SMILES: CCN1CCN(c2ccc(Nc3nc(-c4ccsc4)nc4cn[nH]c(=O)c34)cc2)CC1 ; Cl] | 4-(4-(4-ethylpiperazin-1-yl)-phenylamino)-2-(thiophen-3-yl)pyrimido[4,5-d]pyridazin-5(6H)-one hydrochloride | 3 |
| 38 | 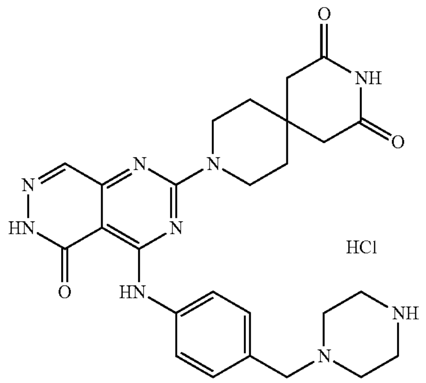 [SMILES: O=C1CC2(CCN(c3nc(Nc4ccc(CN5CCNCC5)cc4)c4c(=O)[nH]ncc4n3)CC2)CC(=O)N1 ; Cl] | 9-(5-oxo-4-(4-(piperazin-1-ylmethyl)phenylamino)-5,6-dihydropyrimido[4,5-d]-pyridazin-2-yl)-3,9-diazaspiro-[5.5]undecane-2,4-dione hydrochloride | 5 |

TABLE 1-continued

| Ex | Structure | IUPAC Name | Synthetic Scheme |
|---|---|---|---|
| 39 | 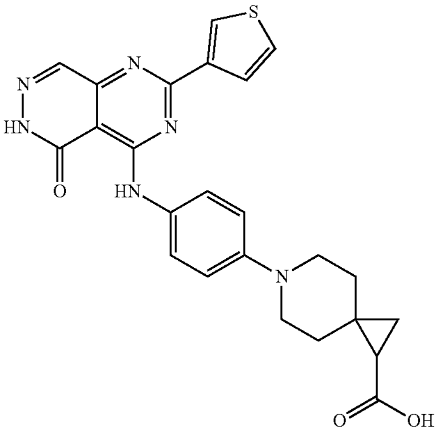 [SMILES: O=C(O)C1CC12CCN(c1ccc(Nc3nc(-c4ccsc4)nc4cn[nH]c(=O)c34)cc1)CC2] | 6-(4-(5-oxo-2-(thiophen-3-yl)-5,6-dihydropyrimido[4,5-d]-pyridazin-4-ylamino)phenyl)-6-azaspiro[2.5]octane-1-carboxylic acid | 3 |
| 40 | 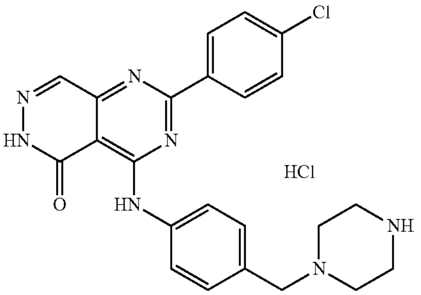 [SMILES: O=c1[nH]ncc2nc(-c3ccc(Cl)cc3)nc(Nc3ccc(CN4CCNCC4)cc3)c12 ; Cl] HCl | 2-(4-chlorophenyl)-4-(4-(piperazin-1-ylmethyl)phenyl-amino)pyrimido[4,5-d]-pyridazin-5(6H)-one hydrochloride | 3 |
| 41 | 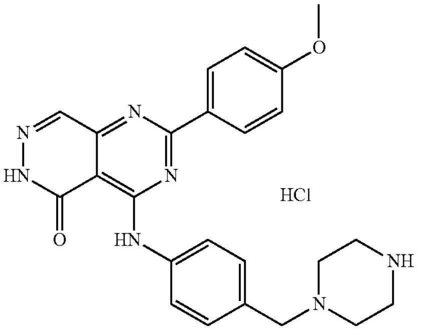 [SMILES: COc1ccc(-c2nc(Nc3ccc(CN4CCNCC4)cc3)c3c(=O)[nH]ncc3n2)cc1 ; Cl] HCl | 2-(4-methoxyphenyl)-4-(4-(piperazin-1-ylmethyl)-phenylamino)pyrimido[4,5-d]-pyridazin-5(6H)-one hydrochloride | 3 |
| 42 | 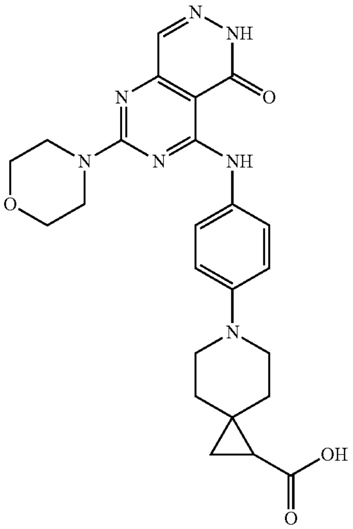 [SMILES: O=C(O)C1CC12CCN(c1ccc(Nc3nc(N4CCOCC4)nc4cn[nH]c(=O)c34)cc1)CC2] | 6-(4-((2-morpholino-5-oxo-5,6-dihydropyrimido[4,5-d]-pyridazin-4-yl)amino)phenyl)-6-azaspiro[2.5]octane-1-carboxylic acid | 5 |

TABLE 1-continued

| Ex | Structure | IUPAC Name | Synthetic Scheme |
| --- | --- | --- | --- |
| 43 | 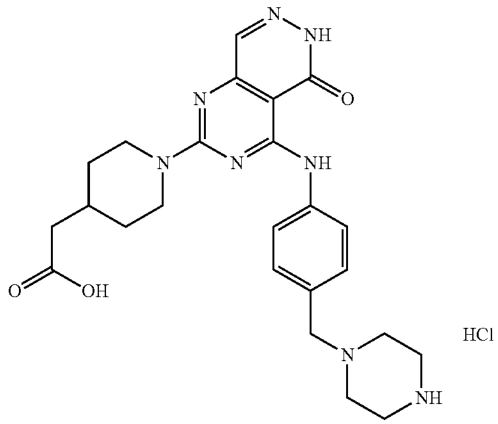 [SMILES: O=C(O)CC1CCN(c2nc(Nc3ccc(CN4CCNCC4)cc3)c3c(=O)[nH]ncc3n2)CC1 ; Cl] | 2-(1-(5-oxo-4-((4-(piperazin-1-ylmethyl)phenyl)amino)-5,6-dihydropyrimido[4,5-d]-pyridazin-2-yl)piperidin-4-yl)acetic acid hydrochloride | 5 |
| 44 | 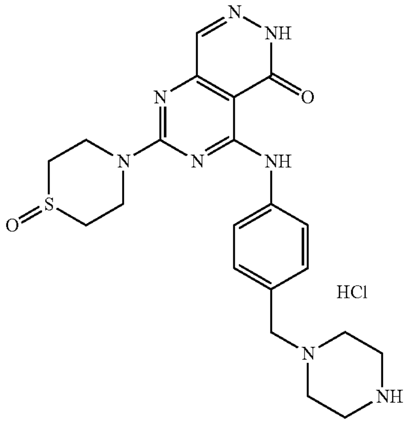 [SMILES: O=c1[nH]ncc2nc(N3CCS(=O)CC3)nc(Nc3ccc(CN4CCNCC4)cc3)c12 ; Cl] | 2-(1-oxidothiomorpholino)-4-((4-(piperazin-1-ylmethyl)-phenyl)amino)pyrimido[4,5-d]-pyridazin-5(6H)-one hydrochloride | 5 |
| 45 | 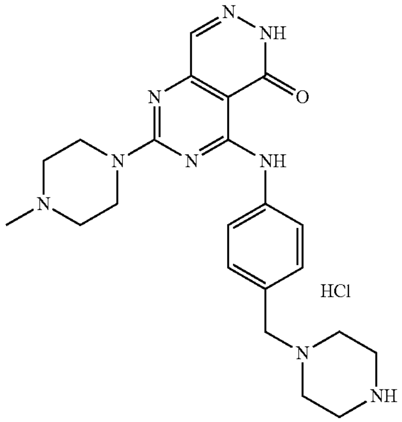 [SMILES: CN1CCN(c2nc(Nc3ccc(CN4CCNCC4)cc3)c3c(=O)[nH]ncc3n2)CC1 ; Cl] | 2-(4-methylpiperazin-1-yl)-4-((4-(piperazin-1-ylmethyl)-phenyl)amino)pyrimido[4,5-d]-pyridazin-5(6H)-one hydrochloride | 5 |

TABLE 1-continued
| Ex | Structure | IUPAC Name | Synthetic Scheme |
|---|---|---|---|
| 46 | 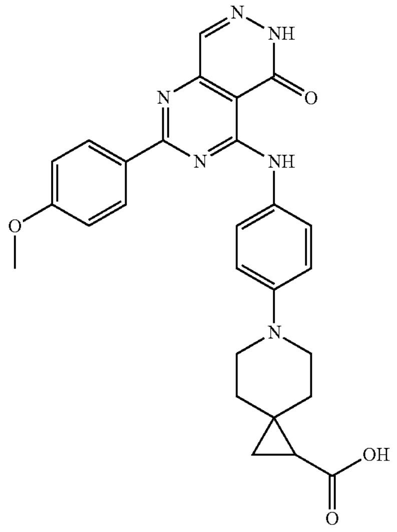 [SMILES: COc1ccc(-c2nc(Nc3ccc(N4CCC5(CC4)CC5C(=O)O)cc3)c3c(=O)[nH]ncc3n2)cc1] | 6-(4-((2-(4-methoxyphenyl)-5-oxo-5,6-dihydropyrimido-[4,5-d]pyridazin-4-yl)amino)-phenyl)-6-azaspiro[2.5]octane-1-carboxylic acid | 3 |
| 47 | 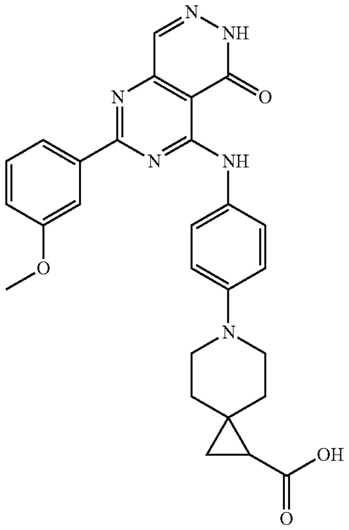 [SMILES: COc1cccc(-c2nc(Nc3ccc(N4CCC5(CC4)CC5C(=O)O)cc3)c3c(=O)[nH]ncc3n2)c1] | 6-(4-((2-(3-methoxyphenyl)-5-oxo-5,6-dihydropyrimido-[4,5-d]pyridazin-4-yl)amino)-phenyl)-6-azaspiro[2.5]octane-1-carboxylic acid | 3 |
| 48 | 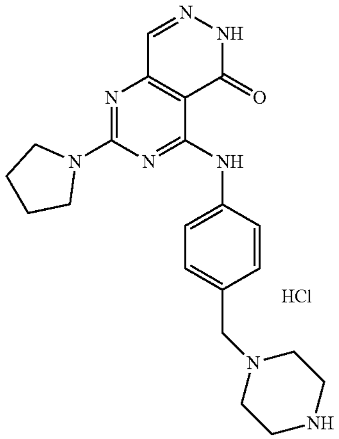 [SMILES: O=c1[nH]ncc2nc(N3CCCC3)nc(Nc3ccc(CN4CCNCC4)cc3)c12 ; Cl] | 4-((4-(piperazin-1-ylmethyl)-phenyl)amino)-2-(pyrrolidin-1-yl)pyrimido[4,5-d]pyridazin-5(6H)-one hydrochloride | 5 |

TABLE 1-continued
| Ex | Structure | IUPAC Name | Synthetic Scheme |
|---|---|---|---|
| 49 | 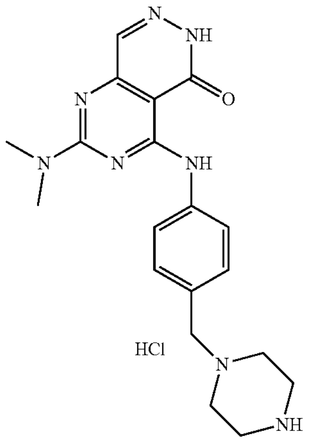 [SMILES: CN(C)c1nc(Nc2ccc(CN3CCNCC3)cc2)c2c(=O)[nH]ncc2n1 ; Cl] | 2-(dimethylamino)-4-((4-(piperazin-1-ylmethyl)phenyl)-amino)pyrimido[4,5-d]-pyridazin-5(6H)-one hydrochloride | 5 |
| 50 | 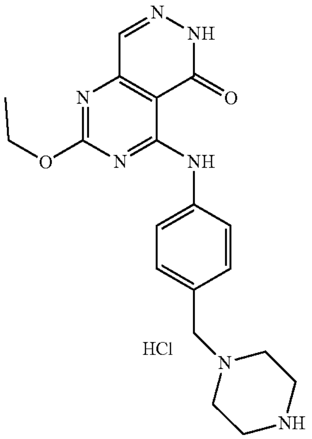 [SMILES: CCOc1nc(Nc2ccc(CN3CCNCC3)cc2)c2c(=O)[nH]ncc2n1 ; Cl] | 2-ethoxy-4-((4-(piperazin-1-ylmethyl)phenyl)amino)-pyrimido[4,5-d]pyridazin-5(6H)-one hydrochloride | 5 |
| 51 | 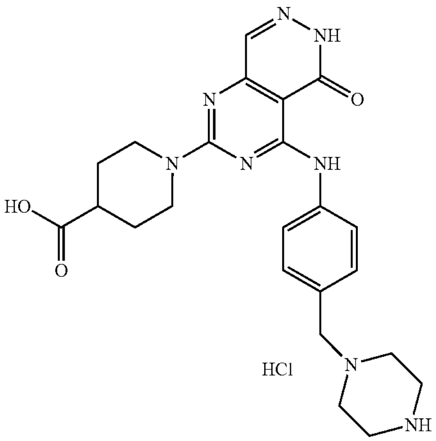 [SMILES: O=C(O)C1CCN(c2nc(Nc3ccc(CN4CCNCC4)cc3)c3c(=O)[nH]ncc3n2)CC1 ; Cl] | 1-(5-oxo-4-((4-(piperazin-1-ylmethyl)phenyl)amino)-5,6-dihydropyrimido[4,5-d]-pyridazin-2-yl)piperidine-4-carboxylic acid hydrochloride | 5 |

TABLE 1-continued
| Ex | Structure | IUPAC Name | Synthetic Scheme |
|---|---|---|---|
| 52 | 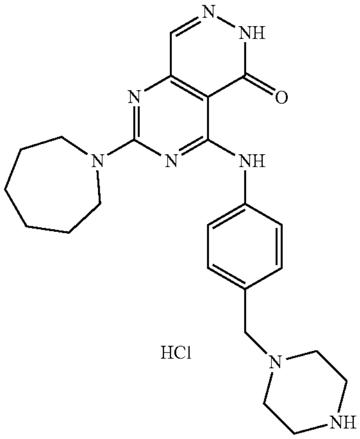 [SMILES: O=c1[nH]ncc2nc(N3CCCCCC3)nc(Nc3ccc(CN4CCNCC4)cc3)c12 ; Cl] | 2-(azepan-1-yl)-4-((4-(piperazin-1-ylmethyl)phenyl)amino)-pyrimido[4,5-d]pyridazin-5(6H)-one hydrochloride | 5 |
| 53 | 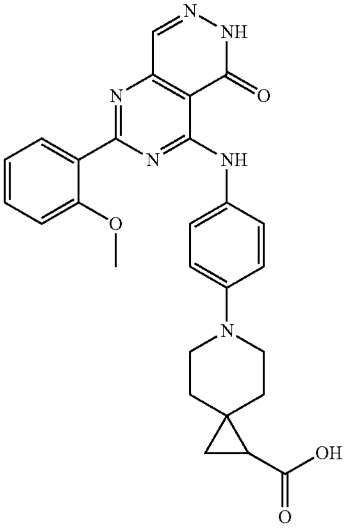 [SMILES: COc1ccccc1-c1nc(Nc2ccc(N3CCC4(CC3)CC4C(=O)O)cc2)c2c(=O)[nH]ncc2n1] | 6-(4-((2-(2-methoxyphenyl)-5-oxo-5,6-dihydropyrimido-[4,5-d]pyridazin-4-yl)amino)-phenyl)-6-azaspiro[2.5]octane-1-carboxylic acid | 3 |
| 54 | 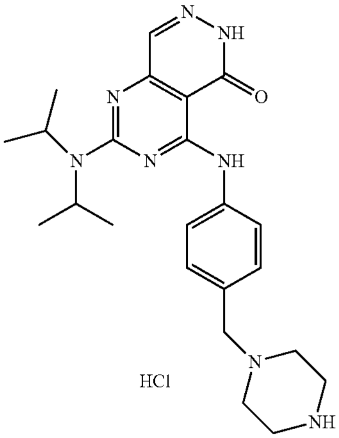 [SMILES: CC(C)N(c1nc(Nc2ccc(CN3CCNCC3)cc2)c2c(=O)[nH]ncc2n1)C(C)C ; Cl] | 2-(diisopropylamino)-4-((4-(piperazin-1-ylmethyl)phenyl)-amino)pyrimido[4,5-d]pyridazin-5(6H)-one hydrochloride | 5 |

TABLE 1-continued

| Ex | Structure | IUPAC Name | Synthetic Scheme |
|---|---|---|---|
| 55 | 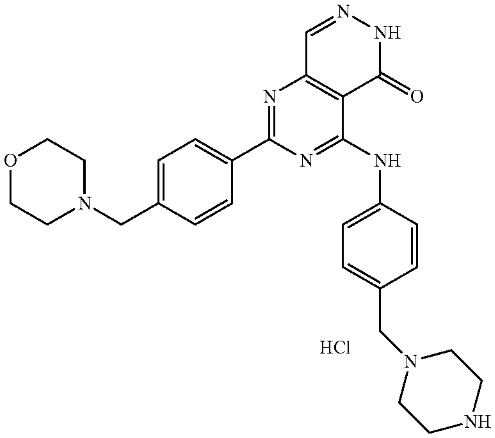 [SMILES: O=c1[nH]ncc2nc(-c3ccc(CN4CCOCC4)cc3)nc(Nc3ccc(CN4CCNCC4)cc3)c12 ; Cl] | 2-(4-(morpholinomethyl)-phenyl)-4-((4-(piperazin-1-ylmethyl)phenyl)amino)-pyrimido[4,5-d]pyridazin-5(6H)-one hydrochloride | 3 |
| 56 | 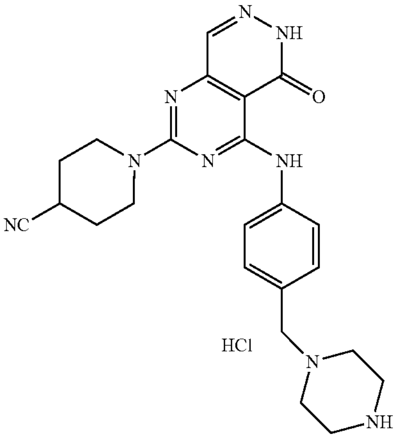 [SMILES: N#CC1CCN(c2nc(Nc3ccc(CN4CCNCC4)cc3)c3c(=O)[nH]ncc3n2)CC1 ; Cl] | 1-(5-oxo-4-((4-(piperazin-1-ylmethyl)phenyl)amino)-5,6-dihydropyrimido[4,5-d]-pyridazin-2-yl)piperidine-4-carbonitrile hydrochloride | 5 |
| 57 | 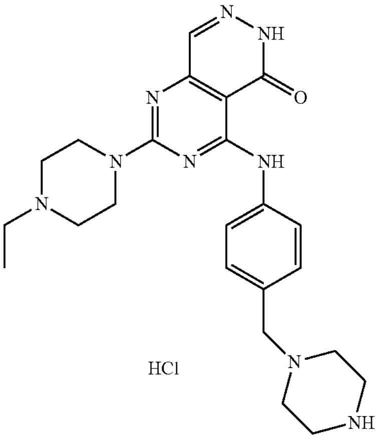 [SMILES: CCN1CCN(c2nc(Nc3ccc(CN4CCNCC4)cc3)c3c(=O)[nH]ncc3n2)CC1 ; Cl] | 2-(4-ethylpiperazin-1-yl)-4-((4-(piperazin-1-ylmethyl)-phenyl)amino)pyrimido[4,5-d]-pyridazin-5(6H)-one hydrochloride | 5 |

TABLE 1-continued
| Ex | Structure | IUPAC Name | Synthetic Scheme |
|---|---|---|---|
| 58 | 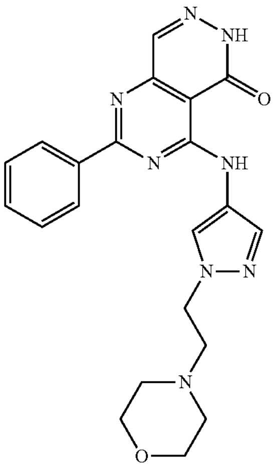 [SMILES: O=c1[nH]ncc2nc(-c3ccccc3)nc(Nc3cnn(CCN4CCOCC4)c3)c12] | 4-((1-(2-morpholinoethyl)-1H-pyrazol-4-yl)amino)-2-phenylpyrimido[4,5-d]-pyridazin-5(6H)-one | 1 |
| 59 | 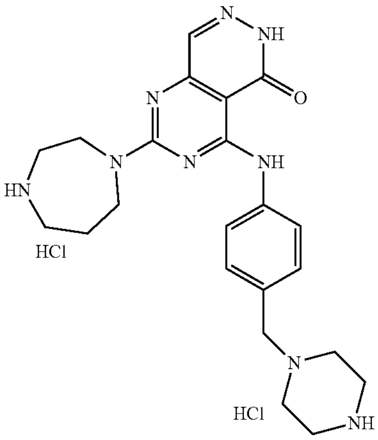 [SMILES: O=c1[nH]ncc2nc(N3CCCNCC3)nc(Nc3ccc(CN4CCNCC4)cc3)c12 ; Cl ; Cl] | 2-(1,4-diazepan-1-yl)-4-((4-(piperazin-1-ylmethyl)phenyl)-amino)pyrimido[4,5-d]-pyridazin-5(6H)-one dihydrochloride | 5 |
| 60 | 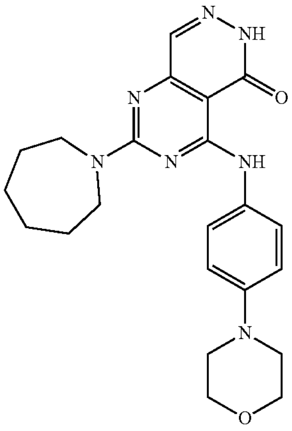 [SMILES: O=c1[nH]ncc2nc(N3CCCCCC3)nc(Nc3ccc(N4CCOCC4)cc3)c12] | 2-(azepan-1-yl)-4-((4-morpholinophenyl)amino)-pyrimido[4,5-d]pyridazin-5(6H)-one | 5 |

TABLE 1-continued
| Ex | Structure | IUPAC Name | Synthetic Scheme |
|---|---|---|---|
| 61 | 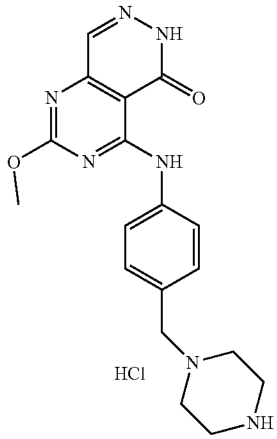 [SMILES: COc1nc(Nc2ccc(CN3CCNCC3)cc2)c2c(=O)[nH]ncc2n1 ; Cl] | 2-methoxy-4-((4-(piperazin-1-ylmethyl)phenyl)amino)-pyrimido[4,5-d]pyridazin-5(6H)-one hydrochloride | 5 |
| 62 | 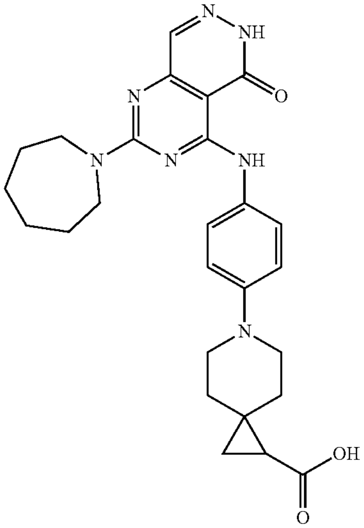 | 6-(4-((2-(azepan-1-yl)-5-oxo-5,6-dihydropyrimido[4,5-d]-pyridazin-4-yl)amino)phenyl)-6-azaspiro[2.5]octane-1-carboxylic acid | 5 |
| 63 | 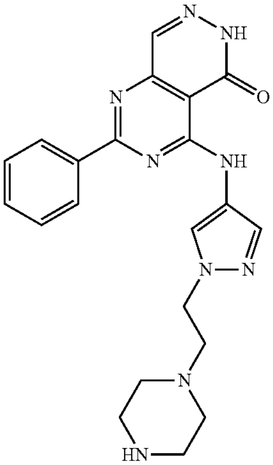 [SMILES: O=c1[nH]ncc2nc(-c3ccccc3)nc(Nc3cnn(CCN4CCNCC4)c3)c12] | 2-phenyl-4-((1-(2-(piperazin-1-yl)ethyl)-1H-pyrazol-4-yl)amino)pyrimido[4,5-d]-pyridazin-5(6H)-one hydrochloride | 1 |

TABLE 1-continued
| Ex | Structure | IUPAC Name | Synthetic Scheme |
|---|---|---|---|
| 64 | 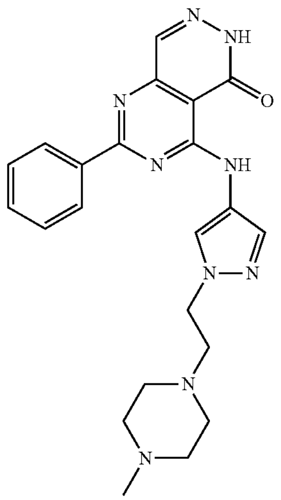 [SMILES: CN1CCN(CCn2cc(Nc3nc(-c4ccccc4)nc4cn[nH]c(=O)c34)cn2)CC1] | 4-((1-(2-(4-methylpiperazin-1-yl)ethyl)-1H-pyrazol-4-yl)amino)-2-phenylpyrimido-[4,5-d]pyridazin-5(6H)-one | 1 |
| 65 | 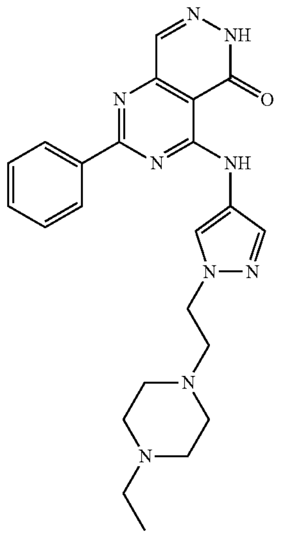 [SMILES: CCN1CCN(CCn2cc(Nc3nc(-c4ccccc4)nc4cn[nH]c(=O)c34)cn2)CC1] | 4-((1-(2-(4-ethylpiperazin-1-yl)ethyl)-1H-pyrazol-4-yl)-amino)-2-phenylpyrimido-[4,5-d]pyridazin-5(6H)-one | 1 |
| 66 | 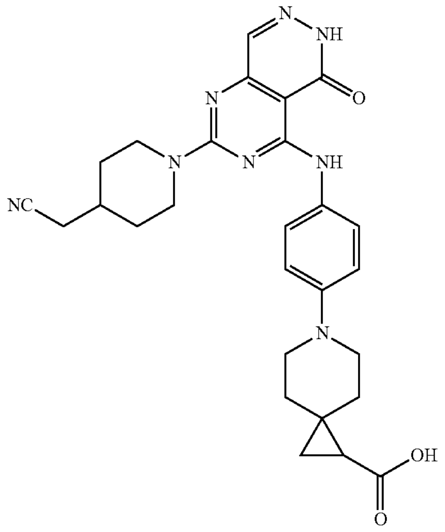 | 6-(4-((2-(4-(cyanomethyl)-piperidin-1-yl)-5-oxo-5,6-dihydropyrimido[4,5-d]-pyridazin-4-yl)amino)phenyl)-6-azaspiro[2.5]octane-1-carboxylic acid | 5 |

TABLE 1-continued
| Ex | Structure | IUPAC Name | Synthetic Scheme |
|---|---|---|---|
| 67 | 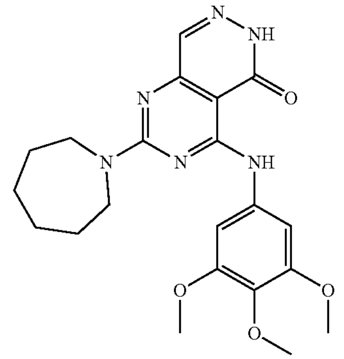 [SMILES: COc1cc(Nc2nc(N3CCCCCC3)nc3cn[nH]c(=O)c23)cc(OC)c1OC] | 2-(azepan-1-yl)-4-((3,4,5-trimethoxyphenyl)amino)-pyrimido[4,5-d]pyridazin-5(6H)-one | 5 |
| 68 | 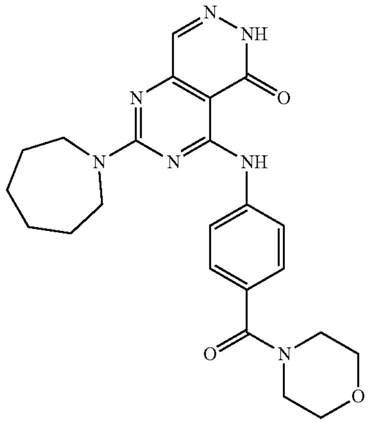 [SMILES: O=C(c1ccc(Nc2nc(N3CCCCCC3)nc3cn[nH]c(=O)c23)cc1)N1CCOCC1] | 2-(azepan-1-yl)-4-((4-(morpholine-4-carbonyl)-phenyl)amino)pyrimido-[4,5-d]pyridazin-5(6H)-one | 5 |
| 69 | 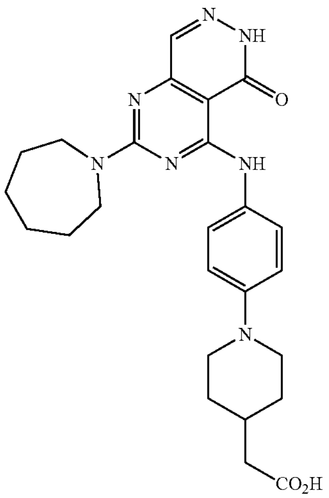 [SMILES: O=C(O)CC1CCN(c2ccc(Nc3nc(N4CCCCCC4)nc4cn[nH]c(=O)c34)cc2)CC1] | 2-(1-(4-((2-(azepan-1-yl)-5-oxo-5,6-dihydropyrimido[4,5-d]-pyridazin-4-yl)amino)phenyl)-piperidin-4-yl)acetic acid | 5 |

TABLE 1-continued

| Ex | Structure | IUPAC Name | Synthetic Scheme |
|---|---|---|---|
| 70 | 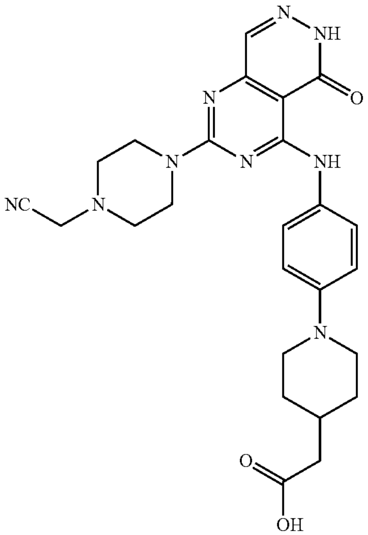 [SMILES: N#CCN1CCN(c2nc(Nc3ccc(N4CCC(CC(=O)O)CC4)cc3)c3c(=O)[nH]ncc3n2)CC1] | 2-(1-(4-((2-(4-(cyanomethyl)-piperazin-1-yl)-5-oxo-5,6-dihydropyrimido[4,5-d]-pyridazin-4-yl)amino)phenyl)-piperidin-4-yl)acetic acid | 5 |
| 71 | 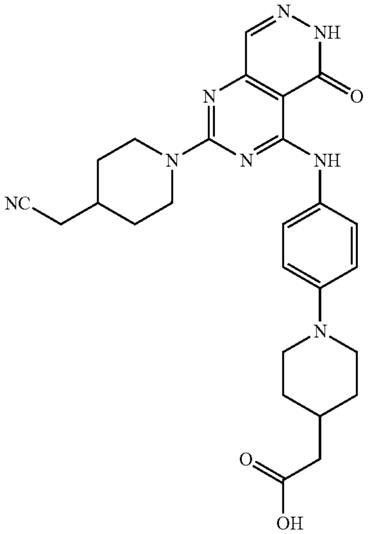 | 2-(1-((4-((2-(4-(cyanomethyl)-piperidin-1-yl)-5-oxo-5,6-dihydropyrimido[4,5-d]-pyridazin-4-yl)amino)phenyl)-piperidin-4-yl)acetic acid | 5 |
| 72 | 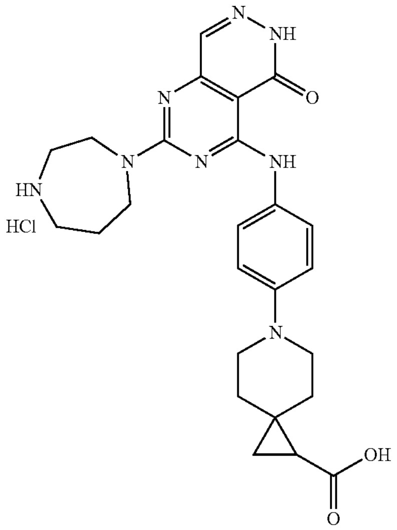 [SMILES: Cl ; O=C(O)C1CC12CCN(c1ccc(Nc3nc(N4CCCNCC4)nc4cn[nH]c(=O)c34)cc1)CC2] | 6-(4-((2-(1,4-diazepan-1-yl)-5-oxo-5,6-dihydropyrimido-[4,5-d]pyridazin-4-yl)amino)-phenyl)-6-azaspiro[2.5]octane-1-carboxylic acid hydrochloride | 5 |

TABLE 1-continued
| Ex | Structure | IUPAC Name | Synthetic Scheme |
| --- | --- | --- | --- |
| 73 | 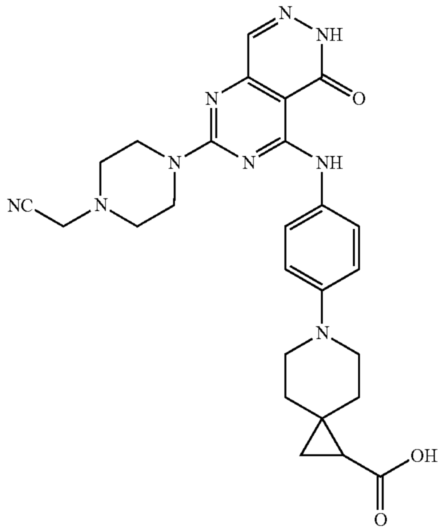 | 6-(4-((2-(4-(cyanomethyl)-piperazin-1-yl)-5-oxo-5,6-dihydropyrimido[4,5-d]-pyridazin-4-yl)amino)phenyl)-6-azaspiro[2.5]octane-1-carboxylic acid | 5 |
| 74 | 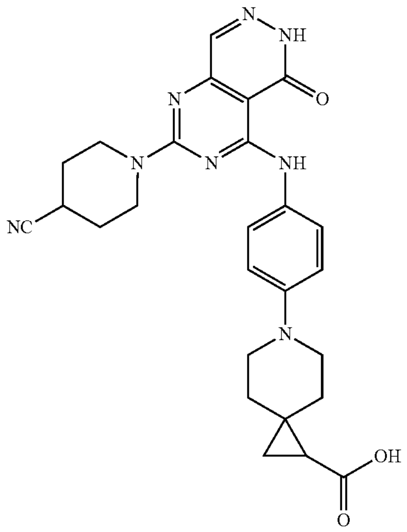 [SMILES: N#CC1CCN(c2nc(Nc3ccc(N4CCC5(CC4)CC5C(=O)O)cc3)c3c(=O)[nH]ncc3n2)CC1] | 6-(4-((2-(4-cyanopiperidin-1-yl)-5-oxo-5,6-dihydropyrimido-[4,5-d]pyridazin-4-yl)amino)-phenyl)-6-azaspiro[2.5]octane-1-carboxylic acid | 5 |

TABLE 1-continued
| Ex | Structure | IUPAC Name | Synthetic Scheme |
|---|---|---|---|
| 75 | 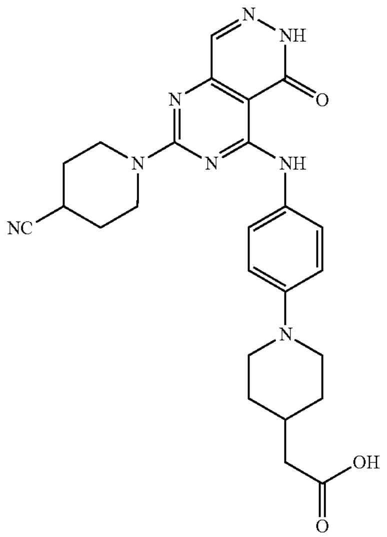 [SMILES: N#CC1CCN(c2nc(Nc3ccc(N4CCC(CC(=O)O)CC4)cc3)c3c(=O)[nH]ncc3n2)CC1] | 2-(1-(4-((2-(4-cyanopiperidin-1-yl)-5-oxo-5,6-dihydro-pyrimido[4,5-d]pyridazin-4-yl)amino)phenyl)piperidin-4-yl)acetic acid | 5 |
| 76 | 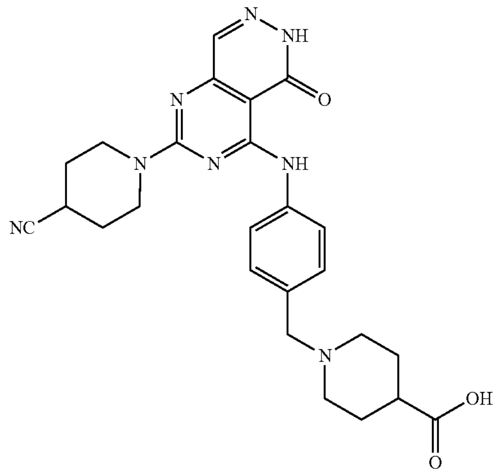 [SMILES: N#CC1CCN(c2nc(Nc3ccc(CN4CCC(C(=O)O)CC4)cc3)c3c(=O)[nH]ncc3n2)CC1] | 1-(4-((2-(4-cyanopiperidin-1-yl)-5-oxo-5,6-dihydropyrimido-[4,5-d]pyridazin-4-yl)amino)-benzyl)piperidine-4-carboxylic acid | 5 |
| 77 | 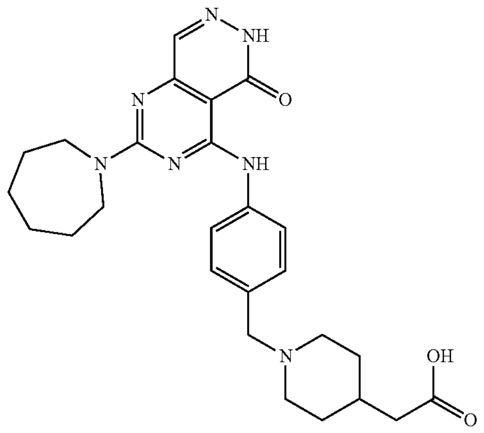 | 2-(1-(4-((2-(azepan-1-yl)-5-oxo-5,6-dihydropyrimido[4,5-d]pyridazin-4-yl)amino)benzyl)-piperidin-4-yl)acetic acid | 5 |

TABLE 1-continued
| Ex | Structure | IUPAC Name | Synthetic Scheme |
|---|---|---|---|
| 78 | 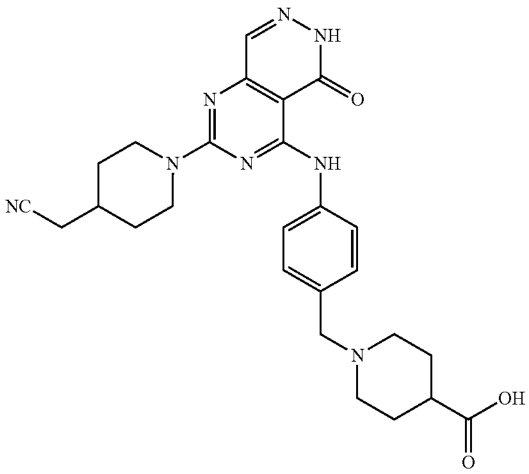 [SMILES: N#CCC1CCN(c2nc(Nc3ccc(CN4CCC(C(=O)O)CC4)cc3)c3c(=O)[nH]ncc3n2)CC1] | 1-(4-((2-(4-(cyanomethyl)-piperidin-1-yl)-5-oxo-5,6-dihydropyrimido[4,5-d]-pyridazin-4-yl)amino)benzyl)-piperidine-4-carboxylic acid | 5 |
| 79 | 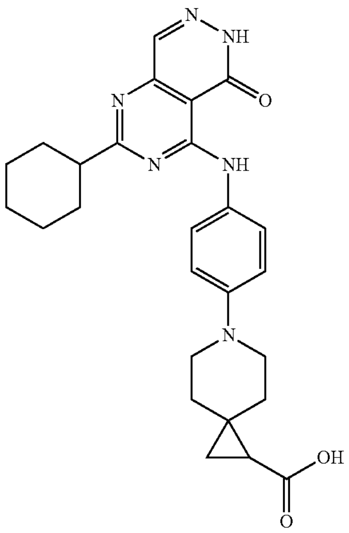 [SMILES: O=C(O)C1CC12CCN(c1ccc(Nc3nc(C4CCCCC4)nc4cn[nH]c(=O)c34)cc1)CC2] | 6-(4-((2-cyclohexyl-5-oxo-5,6-dihydropyrimido[4,5-d]-pyridazin-4-yl)amino)phenyl)-6-azaspiro[2.5]octane-1-carboxylic acid | 3 |
| 80 | 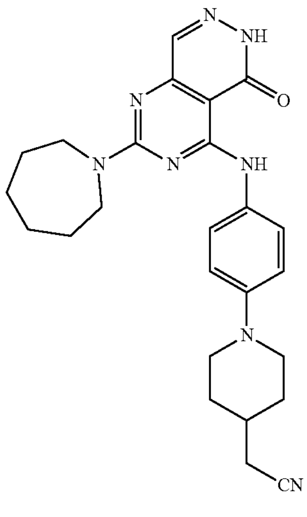 | 2-(1-(4-((2-(azepan-1-yl)-5-oxo-5,6-dihydropyrimido[4,5-d]-pyridazin-4-yl)amino)phenyl)-piperidin-4-yl)acetonitrile | 5 |

TABLE 1-continued
| Ex | Structure | IUPAC Name | Synthetic Scheme |
|---|---|---|---|
| 81 | 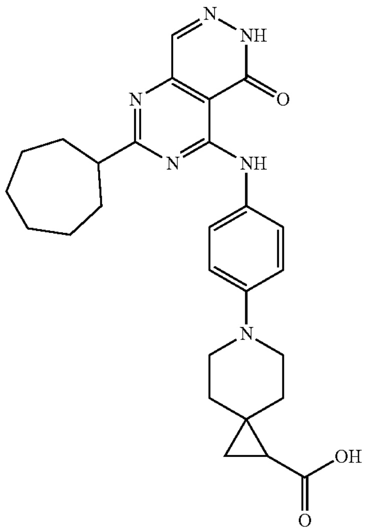 | 6-(4-((2-cycloheptyl-5-oxo-5,6-dihydropyrimido[4,5-d]-pyridazin-4-yl)amino)phenyl)-6-azaspiro[2.5]octane-1-carboxylic acid | 3 |
| 82 | 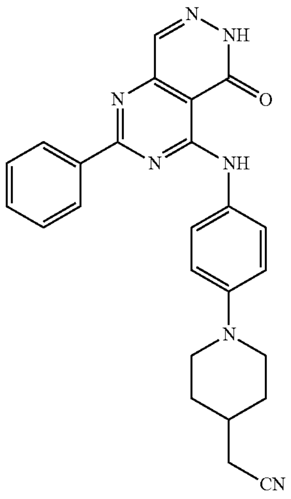 [SMILES: N#CCC1CCN(c2ccc(Nc3nc(-c4ccccc4)nc4cn[nH]c(=O)c34)cc2)CC1] | 2-(1-(4-((5-oxo-2-phenyl-5,6-dihydropyrimido[4,5-d]-pyridazin-4-yl)amino)phenyl)-piperidin-4-yl)acetonitrile | 1 |
| 83 | 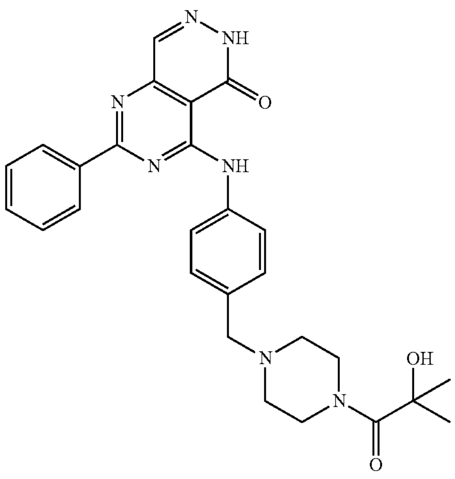 [SMILES: CC(C)(O)C(=O)N1CCN(Cc2ccc(Nc3nc(-c4ccccc4)nc4cn[nH]c(=O)c34)cc2)CC1] | 4-((4-((4-(2-hydroxy-2-methylpropanoyl)piperazin-1-yl)methyl)phenyl)amino)-2-phenylpyrimido[4,5-d]-pyridazin-5(6H)-one | 1 |

TABLE 1-continued
| Ex | Structure | IUPAC Name | Synthetic Scheme |
|---|---|---|---|
| 84 | 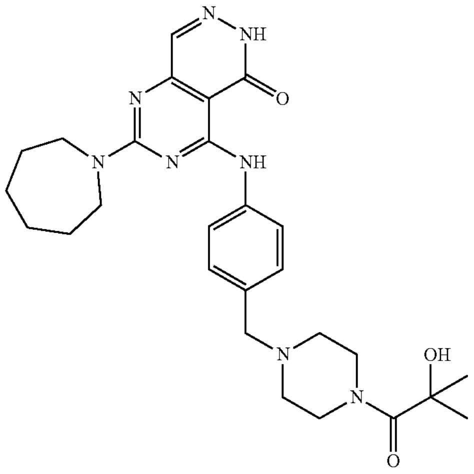 [SMILES: CC(C)(O)C(=O)N1CCN(Cc2ccc(Nc3nc(N4CCCCCC4)nc4cn[nH]c(=O)c34)cc2)CC1] | 2-(azepan-1-yl)-4-((4-((4-(2-hydroxy-2-methylpropanoyl)-piperazin-1-yl)methyl)phenyl)-amino)pyrimido[4,5-d]-pyridazin-5(6H)-one | 3 |
| 85 | 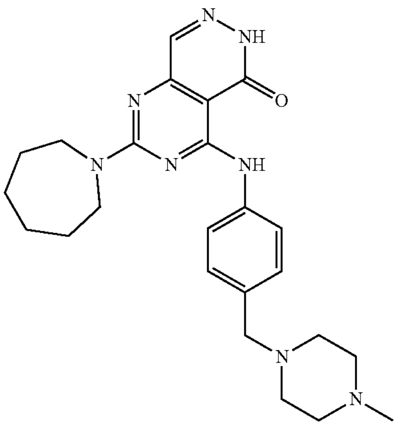 [SMILES: CN1CCN(Cc2ccc(Nc3nc(N4CCCCCC4)nc4cn[nH]c(=O)c34)cc2)CC1] | 2-(azepan-1-yl)-4-((4-((4-methylpiperazin-1-yl)methyl)-phenyl)amino)pyrimido[4,5-d]-pyridazin-5(6H)-one | 3 |
| 86 | 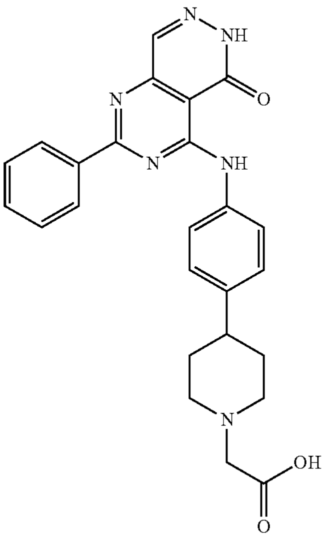 [SMILES: O=C(O)CN1CCC(c2ccc(Nc3nc(-c4ccccc4)nc4cn[nH]c(=O)c34)cc2)CC1] | 2-(4-(4-((5-oxo-2-phenyl-5,6-dihydropyrimido[4,5-d]-pyridazin-4-yl)amino)phenyl)-piperidin-1-yl)acetic acid | 1 |

TABLE 1-continued
| Ex | Structure | IUPAC Name | Synthetic Scheme |
|---|---|---|---|
| 87 | 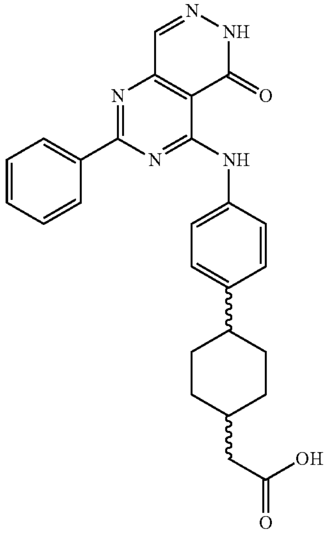 [SMILES: O=C(O)CC1CCC(c2ccc(Nc3nc(-c4ccccc4)nc4cn[nH]c(=O)c34)cc2)CC1] | 2-(4-(4-((5-oxo-2-phenyl-5,6-dihydropyrimido[4,5-d]-pyridazin-4-yl)amino)phenyl)-cyclohexyl)acetic acid | 3 |
| 88 | 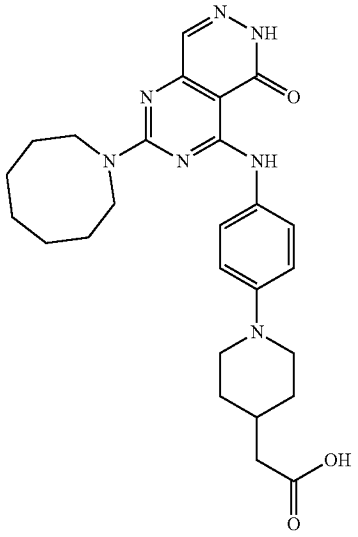 [SMILES: O=C(O)CC1CCN(c2ccc(Nc3nc(N4CCCCCCC4)nc4cn[nH]c(=O)c34)cc2)CC1] | 2-(1-(4-((2-(azocan-1-yl)-5-oxo-5,6-dihydropyrimido[4,5-d]-pyridazin-4-yl)amino)phenyl)-piperidin-4-yl)acetic acid | 5 |
| 89 | 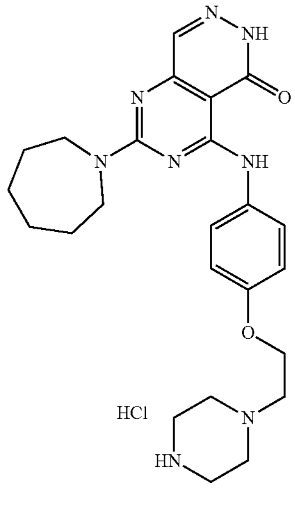 [SMILES: O=c1[nH]ncc2nc(N3CCCCCC3)nc(Nc3ccc(OCCN4CCNCC4)cc3)c12 ; Cl] | 2-(azepan-1-yl)-4-((4-(2-(piperazin-1-yl)ethoxy)phenyl)-amino)pyrimido[4,5-d]-pyridazin-5(6H)-one hydrochloride | 5 |

TABLE 1-continued
| Ex | Structure | IUPAC Name | Synthetic Scheme |
|---|---|---|---|
| 90 | 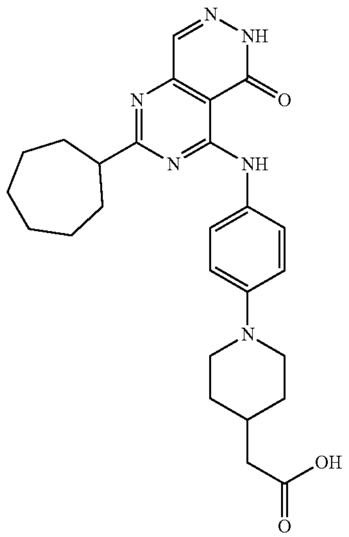 | 2-(1-(4-((2-cycloheptyl-5-oxo-5,6-dihydropyrimido[4,5-d]-pyridazin-4-yl)amino)phenyl)-piperidin-4-yl)acetic acid | 3 |
| 91 | 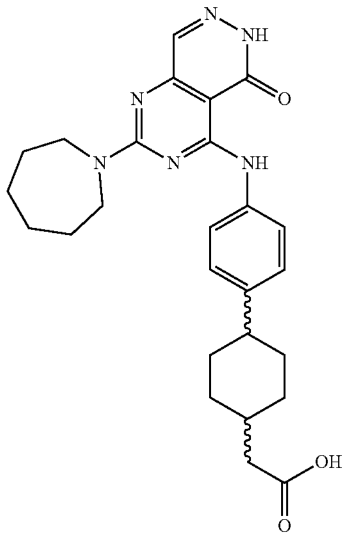 [SMILES: O=C(O)CC1CCC(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]-pyridazin-4-yl)amino)phenyl)-cyclohexyl)acetic acid | 5 |
| 92 | 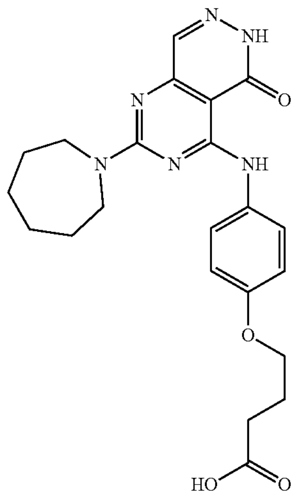 [SMILES: O=C(O)CCCOc1ccc(Nc2nc(N3CCCCCC3)nc3cn[nH]c(=O)c23)cc1] | 4-(4-((2-(azepan-1-yl)-5-oxo-5,6-dihydropyrimido[4,5-d]-pyridazin-4-yl)amino)phenoxy)-butanoic acid | 5 |

TABLE 1-continued
| Ex | Structure | IUPAC Name | Synthetic Scheme |
|---|---|---|---|
| 93 | 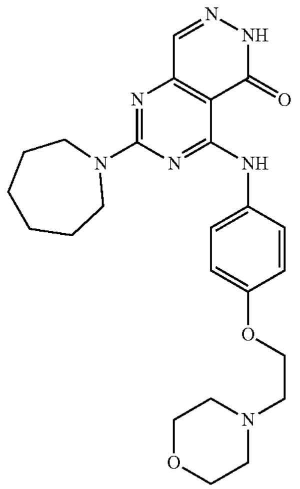 [SMILES: O=c1[nH]ncc2nc(N3CCCCCC3)nc(Nc3ccc(OCCN4CCOCC4)cc3)c12] | 2-(azepan-1-yl)-4-((4-(2-morpholinoethoxy)phenyl)-amino)pyrimido[4,5-d]-pyridazin-5(6H)-one | 5 |
| 94 | 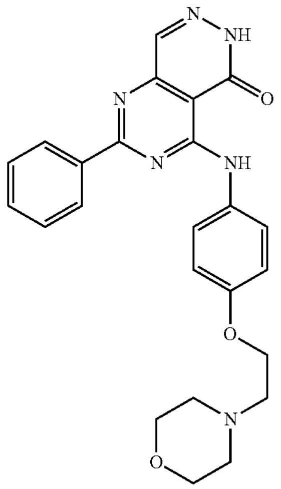 [SMILES: O=c1[nH]ncc2nc(-c3ccccc3)nc(Nc3ccc(OCCN4CCOCC4)cc3)c12] | 4-((4-(2-morpholinoethoxy)-phenyl)amino)-2-phenyl-pyrimido[4,5-d]pyridazin-5(6H)-one | 3 |
| 95 | 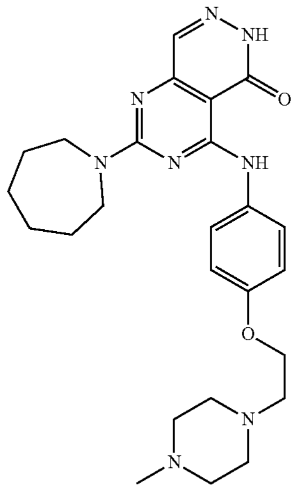 [SMILES: CN1CCN(CCOc2ccc(Nc3nc(N4CCCCCC4)nc4cn[nH]c(=O)c34)cc2)CC1] | 2-(azepan-1-yl)-4-((4-(2-(4-methylpiperazin-1-yl)ethoxy)-phenyl)amino)pyrimido[4,5-d]-pyridazin-5(6H)-one | 5 |

TABLE 1-continued
| Ex | Structure | IUPAC Name | Synthetic Scheme |
|---|---|---|---|
| 96 | 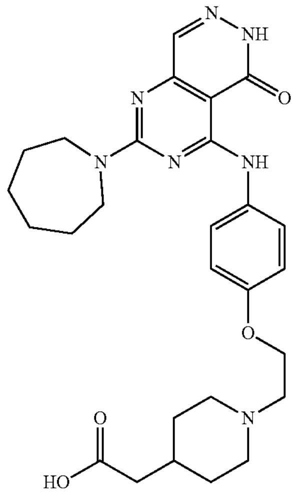 [SMILES: O=C(O)CC1CCN(CCOc2ccc(Nc3nc(N4CCCCCC4)nc4cn[nH]c(=O)c34)cc2)CC1] | 2-(1-(2-(4-((2-(azepan-1-yl)-5-oxo-5,6-dihydropyrimido-[4,5-d]pyridazin-4-yl)amino)-phenoxy)ethyl)piperidin-4-yl)acetic acid | 5 |
| 97 | 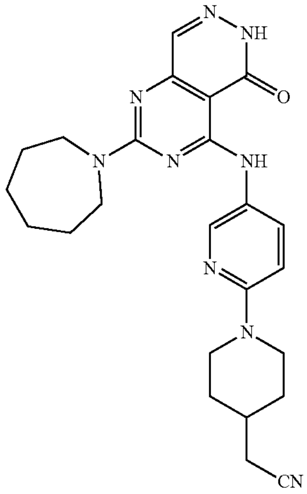 | 2-(1-(5-((2-(azepan-1-yl)-5-oxo-5,6-dihydropyrimido[4,5-d]-pyridazin-4-yl)amino)pyridin-2-yl)piperidin-4-yl)acetonitrile | 5 |
| 98 | 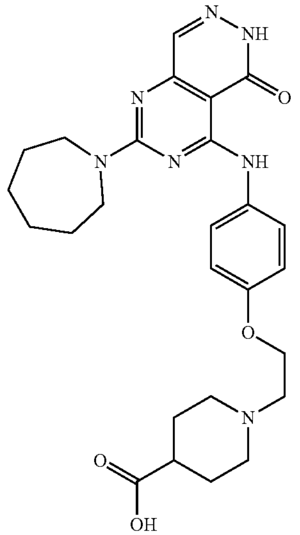 [SMILES: O=C(O)C1CCN(CCOc2ccc(Nc3nc(N4CCCCCC4)nc4cn[nH]c(=O)c34)cc2)CC1] | 1-(2-(4-((2-(azepan-1-yl)-5-oxo-5,6-dihydropyrimido[4,5-d]-pyridazin-4-yl)amino)phenoxy)-ethyl)piperidine-4-carboxylic acid | 5 |

TABLE 1-continued
| Ex | Structure | IUPAC Name | Synthetic Scheme |
| --- | --- | --- | --- |
| 99 | 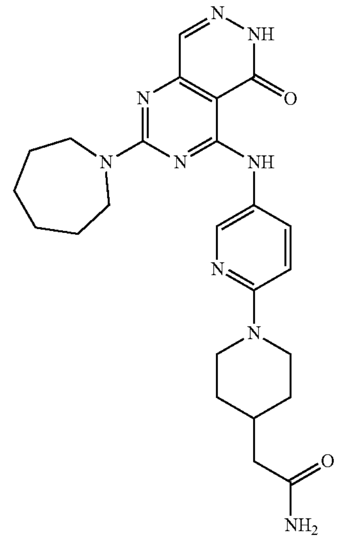 | 2-(1-(5-((2-(azepan-1-yl)-5-oxo-5,6-dihydropyrimido[4,5-d]-pyridazin-4-yl)amino)pyridin-2-yl)piperidin-4-yl)acetamide | 5 |
| 100 | 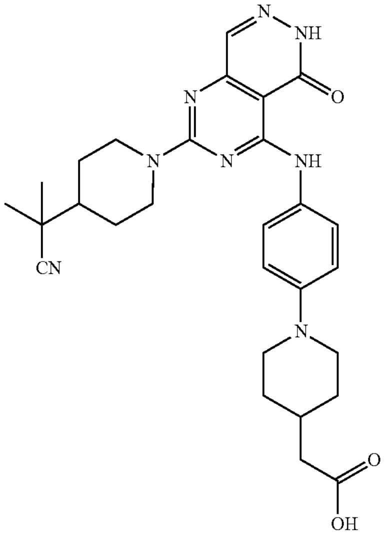 [SMILES: CC(C)(C#N)C1CCN(c2nc(Nc3ccc(N4CCC(CC(=O)O)CC4)cc3)c3c(=O)[nH]ncc3n2)CC1] | 2-(1-(4-((2-(4-(2-cyanopropan-2-yl)piperidin-1-yl)-5-oxo-5,6-dihydropyrimido[4,5-d]-pyridazin-4-yl)amino)phenyl)-piperidin-4-yl)acetic acid | 5 |
| 101 | 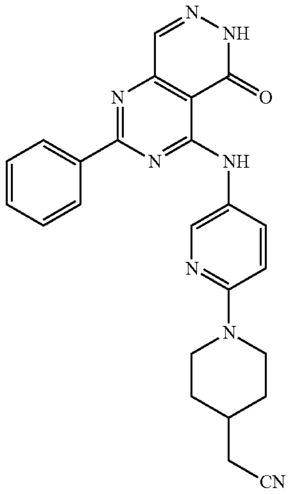 [SMILES: N#CCC1CCN(c2ccc(Nc3nc(-c4ccccc4)nc4cn[nH]c(=O)c34)cn2)CC1] | 2-(1-(5-((5-oxo-2-phenyl-5,6-dihydropyrimido[4,5-d]-pyridazin-4-yl)amino)pyridin-2-yl)piperidin-4-yl)acetonitrile | 3 |

TABLE 1-continued
| Ex | Structure | IUPAC Name | Synthetic Scheme |
|---|---|---|---|
| 102 | 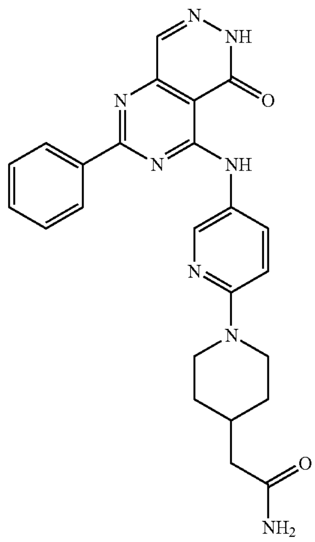 [SMILES: NC(=O)CC1CCN(c2ccc(Nc3nc(-c4ccccc4)nc4cn[nH]c(=O)c34)cn2)CC1] | 2-(1-(5-((5-oxo-2-phenyl-5,6-dihydropyrimido[4,5-d]-pyridazin-4-yl)amino)pyridin-2-yl)piperidin-4-yl)acetamide | 3 |
| 103 | 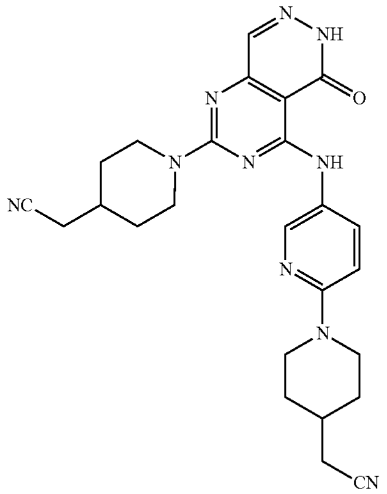 [SMILES: N#CCC1CCN(c2ccc(Nc3nc(N4CCC(CC#N)CC4)nc4cn[nH]c(=O)c34)cn2)CC1] | 2-(1-(5-((2-(4-(cyanomethyl)-piperidin-1-yl)-5-oxo-5,6-dihydropyrimido[4,5-d]-pyridazin-4-yl)amino)pyridin-2-yl)piperidin-4-yl)acetonitrile | 5 |
| 104 | 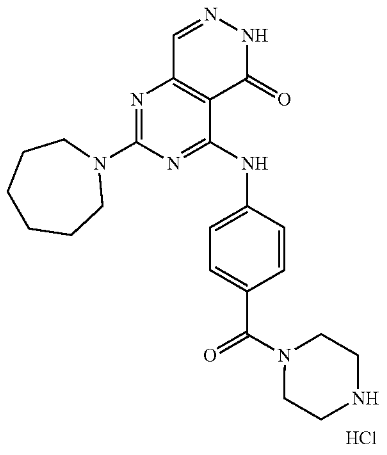 [SMILES: O=C(c1ccc(Nc2nc(N3CCCCCC3)nc3cn[nH]c(=O)c23)cc1)N1CCNCC1 ; Cl] | 2-(azepan-1-yl)-4-((4-(piperazine-1-carbonyl)-phenyl)amino)pyrimido-[4,5-d]pyridazin-5(6H)-one hydrochloride | 5 |

TABLE 1-continued
| Ex | Structure | IUPAC Name | Synthetic Scheme |
|---|---|---|---|
| 105 | 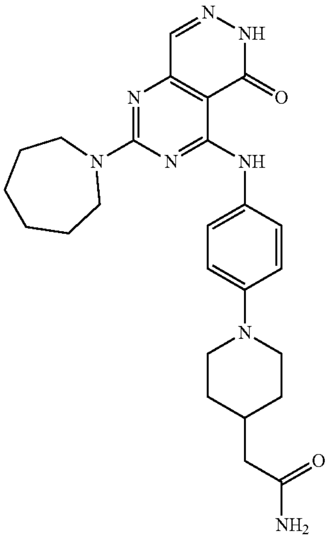 | 2-(1-(4-((2-(azepan-1-yl)-5-oxo-5,6-dihydropyrimido[4,5-d]pyridazin-4-yl)amino)-phenyl)piperidin-4-yl)-acetamide | 5 |
| 106 | 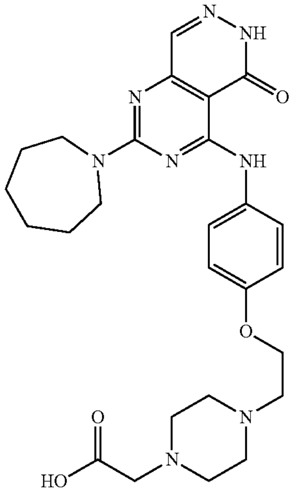 [SMILES: O=C(O)CN1CCN(CCOc2ccc(Nc3nc(N4CCCCCC4)nc4cn[nH]c(=O)c34)cc2)CC1] | 2-(4-(2-(4-((2-(azepan-1-yl)-5-oxo-5,6-dihydropyrimido-[4,5-d]pyridazin-4-yl)amino)-phenoxy)ethyl)piperazin-1-yl)acetic acid | 3 |
| 107 | 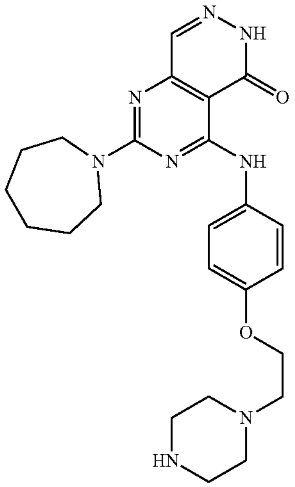 [SMILES: O=c1[nH]ncc2nc(N3CCCCCC3)nc(Nc3ccc(OCCN4CCNCC4)cc3)c12] | 2-(azepan-1-yl)-4-((4-(2-(piperazin-1-yl)ethoxy)-phenyl)amino)pyrimido-[4,5-d]pyridazin-5(6H)-one | 5 |

TABLE 1-continued
| Ex | Structure | IUPAC Name | Synthetic Scheme |
| --- | --- | --- | --- |
| 108 | 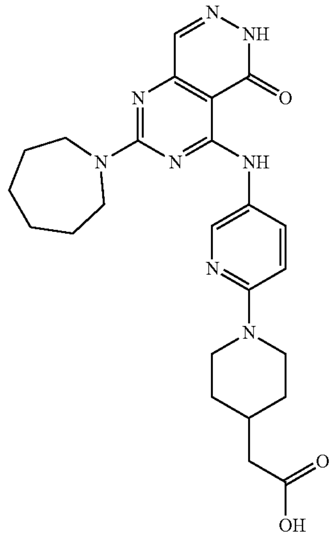 [SMILES: O=C(O)CC1CCN(c2ccc(Nc3nc(N4CCCCCC4)nc4cn[nH]c(=O)c34)cn2)CC1] | 2-(1-(5-((2-(azepan-1-yl)-5-oxo-5,6-dihydropyrimido[4,5-d]-pyridazin-4-yl)amino)pyridin-2-yl)piperidin-4-yl)acetic acid | 5 |
| 109 | 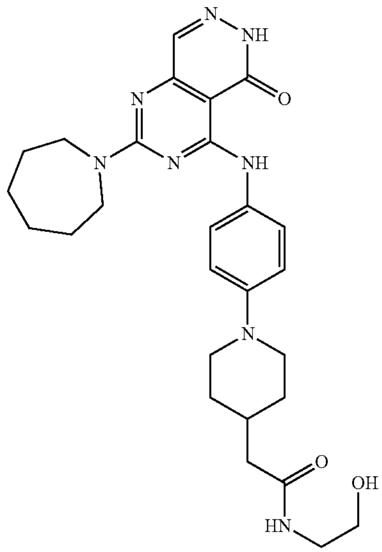 [SMILES: O=C(CC1CCN(c2ccc(Nc3nc(N4CCCCCC4)nc4cn[nH]c(=O)c34)cc2)CC1)NCCO] | 2-(1-(4-((2-(azepan-1-yl)-5-oxo-5,6-dihydropyrimido[4,5-d]pyridazin-4-yl)amino)-phenyl)piperidin-4-yl)-N-(2-hydroxyethyl)acetamide | 5 |

TABLE 1-continued
| Ex | Structure | IUPAC Name | Synthetic Scheme |
|---|---|---|---|
| 110 | 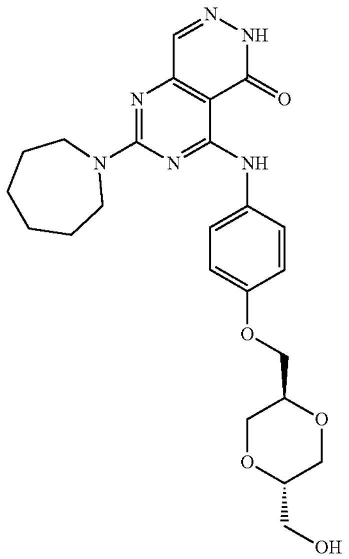 [SMILES: O=c1[nH]ncc2nc(N3CCCCCC3)nc(Nc3ccc(OC[C@@H]4CO[C@@H](CO)CO4)cc3)c12] | 2-(azepan-1-yl)-4-((4-(((2S,5S)-5-(hydroxymethyl)-1,4-dioxan-2-yl)methoxy)phenyl)amino)-pyrimido[4,5-d]pyridazin-5(6H)-one | 5 |
| 111 | 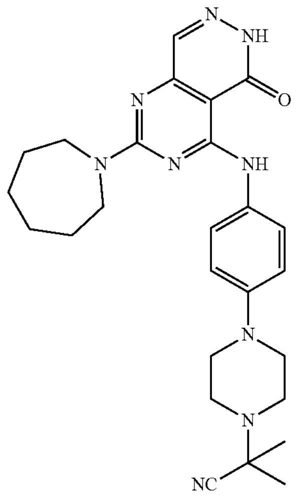 [SMILES: CC(C)(C#N)N1CCN(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]pyridazin-4-yl)amino)-phenyl)piperazin-1-yl)-2-methylpropanenitrile | 5 |
| 112 | 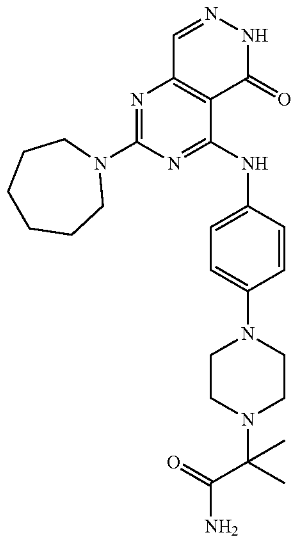 [SMILES: CC(C)(C(N)=O)N1CCN(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]-pyridazin-4-yl)amino)phenyl)-piperazin-1-yl)-2-methyl-propanamide | 5 |

TABLE 1-continued
| Ex | Structure | IUPAC Name | Synthetic Scheme |
|---|---|---|---|
| 113 | 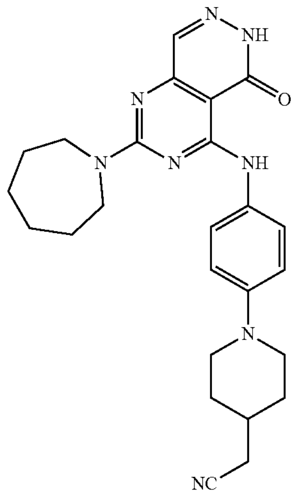 [SMILES: N#CCC1CCN(c2ccc(Nc3nc(N4CCCCCC4)nc4cn[nH]c(=O)c34)cc2)CC1] | 2-(1-(4-((2-(azepan-1-yl)-5-oxo-5,6-dihydropyrimido[4,5-d]-pyridazin-4-yl)amino)phenyl)-piperidin-4-yl)acetonitrile | 5 |
| 114 | 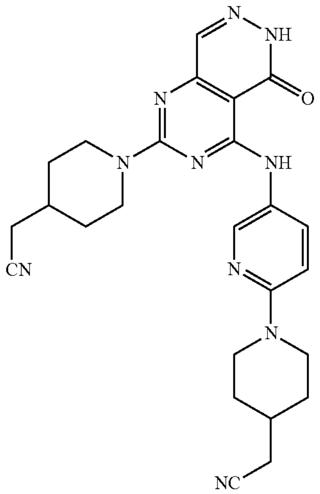 [SMILES: N#CCC1CCN(c2ccc(Nc3nc(N4CCC(CC#N)CC4)nc4cn[nH]c(=O)c34)cn2)CC1] | 2-(1-(5-((2-(4-(cyanomethyl)-piperidin-1-yl)-5-oxo-5,6-dihydropyrimido[4,5-d]-pyridazin-4-yl)amino)pyridin-2-yl)piperidin-4-yl)acetonitrile | 5 |
| 115 | 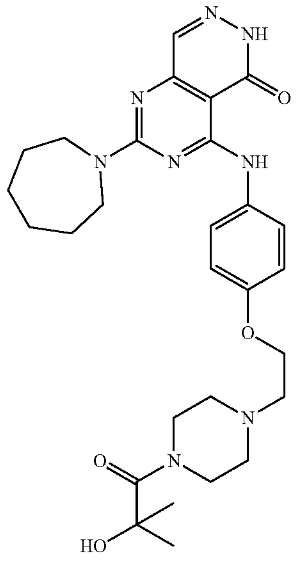 [SMILES: CC(C)(O)C(=O)N1CCN(CCOc2ccc(Nc3nc(N4CCCCCC4)nc4cn[nH]c(=O)c34)cc2)CC1] | 2-(azepan-1-yl)-4-((4-(2-(4-(2-hydroxy-2-methylpropanoyl)-piperazin-1-yl)ethoxy)phenyl)-amino)pyrimido[4,5-d]-pyridazin-5(6H)-one | 5 |

TABLE 1-continued

| Ex | Structure | IUPAC Name | Synthetic Scheme |
|---|---|---|---|
| 116 | 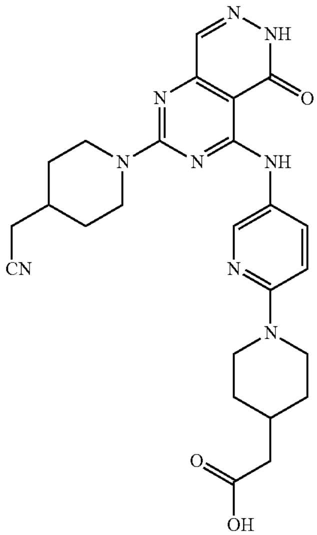 [SMILES: N#CCC1CCN(c2nc(Nc3ccc(N4CCC(CC(=O)O)CC4)nc3)c3c(=O)[nH]ncc3n2)CC1] | 2-(1-(5-((2-(4-(cyanomethyl)-piperidin-1-yl)-5-oxo-5,6-dihydropyrimido[4,5-d]-pyridazin-4-yl)amino)pyridin-2-yl)piperidin-4-yl)acetic acid | 5 |
| 117 | 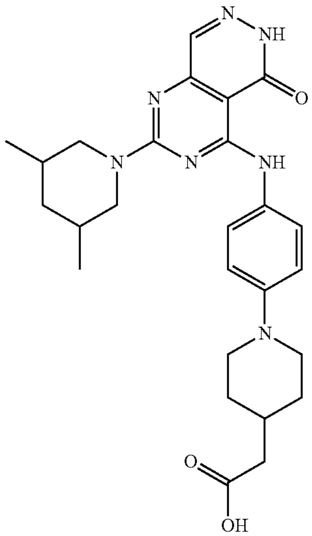 [SMILES: CC1CC(C)CN(c2nc(Nc3ccc(N4CCC(CC(=O)O)CC4)cc3)c3c(=O)[nH]ncc3n2)C1] | 2-(1-(4-((2-(3,5-dimethyl-piperidin-1-yl)-5-oxo-5,6-dihydropyrimido[4,5-d]-pyridazin-4-yl)amino)phenyl)-piperidin-4-yl)acetic acid | 5 |
| 118 | 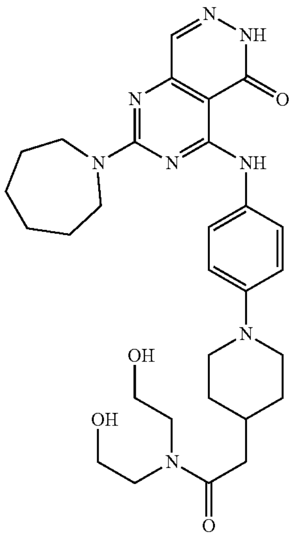 [SMILES: O=C(CC1CCN(c2ccc(Nc3nc(N4CCCCCC4)nc4cn[nH]c(=O)c34)cc2)CC1)N(CCO)CCO] | 2-(1-(4-((2-(azepan-1-yl)-5-oxo-5,6-dihydropyrimido[4,5-d]pyridazin-4-yl)amino)-phenyl)piperidin-4-yl)-N,N-bis(2-hydroxyethyl)acetamide | 5 |

TABLE 1-continued
| Ex | Structure | IUPAC Name | Synthetic Scheme |
|---|---|---|---|
| 119 | 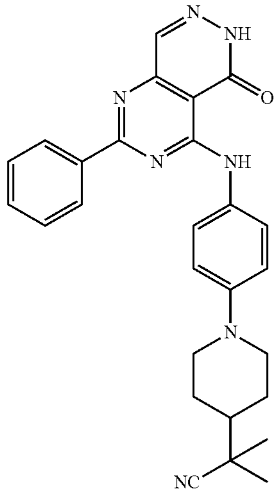 [SMILES: CC(C)(C#N)C1CCN(c2ccc(Nc3nc(-c4ccccc4)nc4cn[nH]c(=O)c34)cc2)CC1] | 2-methyl-2-(1-(4-((5-oxo-2-phenyl-5,6-dihydropyrimido-[4,5-d]pyridazin-4-yl)amino)-phenyl)piperidin-4-yl)-propanenitrile | 3 |
| 120 | 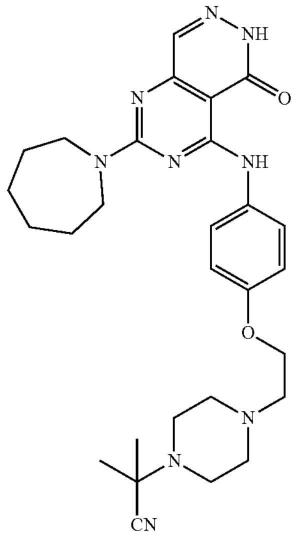 [SMILES: CC(C)(C#N)N1CCN(CCOc2ccc(Nc3nc(N4CCCCCC4)nc4cn[nH]c(=O)c34)cc2)CC1] | 2-(4-(2-(4-((2-(azepan-1-yl)-5-oxo-5,6-dihydropyrimido-[4,5-d]pyridazin-4-yl)amino)-phenoxy)ethyl)piperazin-1-yl)-2-methylpropanenitrile | 5 |
| 121 | 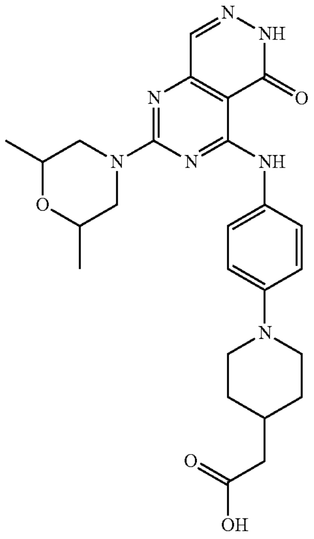 | 2-(1-(4-((2-(2,6-dimethyl-morpholino)-5-oxo-5,6-dihydropyrimido[4,5-d]-pyridazin-4-yl)amino)phenyl)-piperidin-4-yl)acetic acid | 3 |

TABLE 1-continued
| Ex | Structure | IUPAC Name | Synthetic Scheme |
|---|---|---|---|
| 122 | 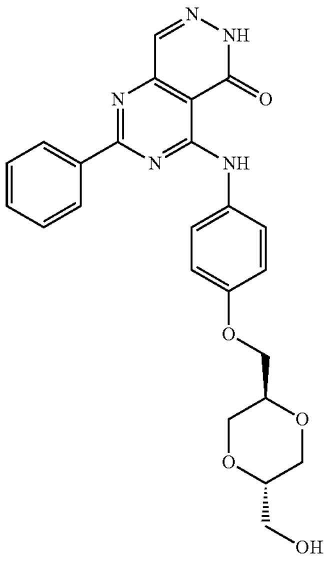 [SMILES: O=c1[nH]ncc2nc(-c3ccccc3)nc(Nc3ccc(OC[C@@H]4CO[C@@H](CO)CO4)cc3)c12] | 4-((4-(((2S,5S)-5-(hydroxy-methyl)-1,4-dioxan-2-yl)-methoxy)phenyl)amino)-2-phenylpyrimido[4,5-d]-pyridazin-5(6H)-one | 3 |
| 123 | 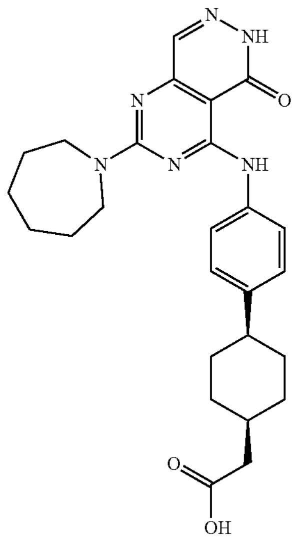 [SMILES: O=C(O)C[C@H]1CC[C@@H](c2ccc(Nc3nc(N4CCCCCC4)nc4cn[nH]c(=O)c34)cc2)CC1] | 2-((1S,4S)-4-(4-((2-(azepan-1-yl)-5-oxo-5,6-dihydro-pyrimido[4,5-d]pyridazin-4-yl)amino)phenyl)cyclohexyl)-acetic acid | 5 |

TABLE 1-continued
| Ex | Structure | IUPAC Name | Synthetic Scheme |
|---|---|---|---|
| 124 | 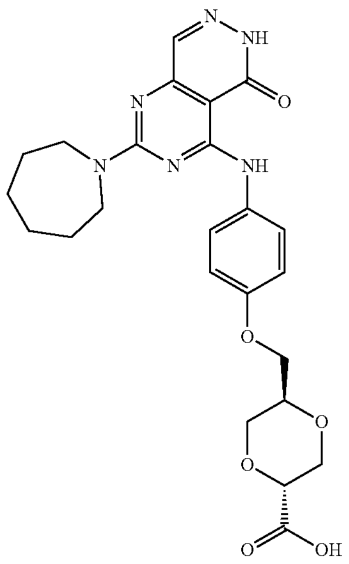 [SMILES: O=C(O)[C@H]1CO[C@H](COc2ccc(Nc3nc(N4CCCCCC4)nc4cn[nH]c(=O)c34)cc2)CO1] | (2R,5S)-5-((4-((2-(azepan-1-yl)-5-oxo-5,6-dihydro-pyrimido[4,5-d]pyridazin-4-yl)amino)phenoxy)methyl)-1,4-dioxane-2-carboxylic acid | 5 |
| 125 | 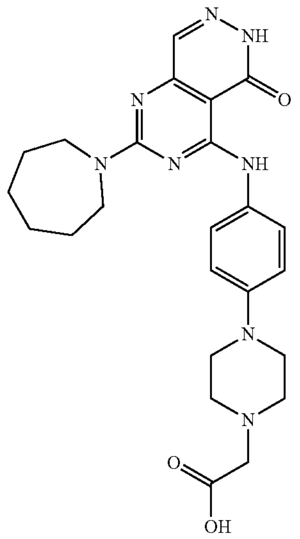 [SMILES: O=C(O)CN1CCN(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]pyridazin-4-yl)amino)-phenyl)piperazin-1-yl)acetic acid | 5 |

TABLE 1-continued
| Ex | Structure | IUPAC Name | Synthetic Scheme |
|---|---|---|---|
| 126 | 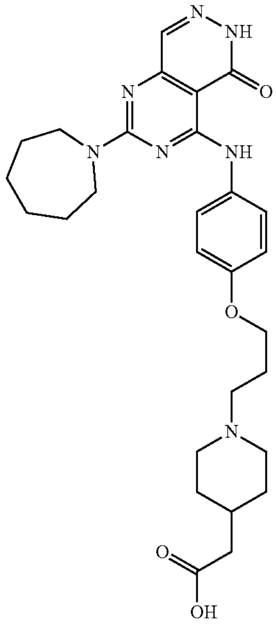 [SMILES: O=C(O)CC1CCN(CCCOc2ccc(Nc3nc(N4CCCCCC4)nc4cn[nH]c(=O)c34)cc2)CC1] | 2-(1-(3-(4-((2-(azepan-1-yl)-5-oxo-5,6-dihydropyrimido-[4,5-d]pyridazin-4-yl)amino)-phenoxy)propyl)piperidin-4-yl)acetic acid | 5 |
| 127 | 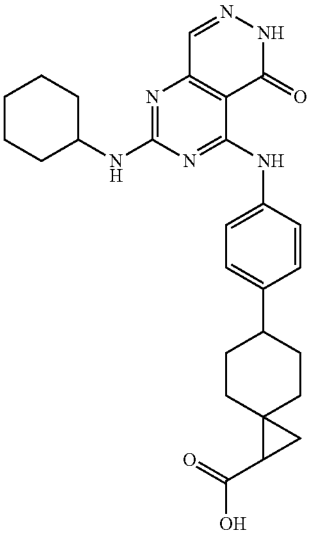 [SMILES: O=C(O)C1CC12CCC(c1ccc(Nc3nc(NC4CCCCC4)nc4cn[nH]c(=O)c34)cc1)CC2] | 6-(4-((2-(cyclohexylamino)-5-oxo-5,6-dihydropyrimido[4,5-d]pyridazin-4-yl)amino)-phenyl)spiro[2.5]octane-1-carboxylic acid | 5 |

TABLE 1-continued
| Ex | Structure | IUPAC Name | Synthetic Scheme |
|---|---|---|---|
| 128 | 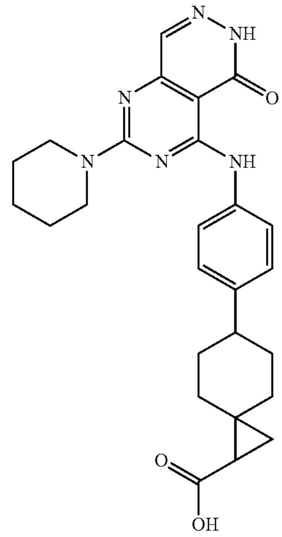 [SMILES: O=C(O)C1CC12CCC(c1ccc(Nc3nc(N4CCCCC4)nc4cn[nH]c(=O)c34)cc1)CC2] | 6-(4-((5-oxo-2-(piperidin-1-yl)-5,6-dihydropyrimido[4,5-d]pyridazin-4-yl)amino)-phenyl)spiro[2.5]octane-1-carboxylic acid | 5 |
| 129 | 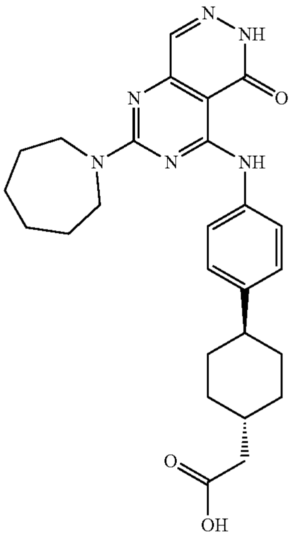 [SMILES: O=C(O)C[C@H]1CC[C@H](c2ccc(Nc3nc(N4CCCCCC4)nc4cn[nH]c(=O)c34)cc2)CC1] | 2-((1R,4R)-4-(4-((2-(azepan-1-yl)-5-oxo-5,6-dihydro-pyrimido[4,5-d]pyridazin-4-yl)amino)phenyl)cyclohexyl)-acetic acid | 5 |
| 130 | 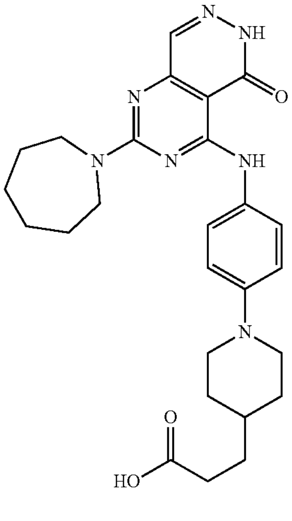 [SMILES: O=C(O)CCC1CCN(c2ccc(Nc3nc(N4CCCCCC4)nc4cn[nH]c(=O)c34)cc2)CC1] | 3-(1-(4-((2-(azepan-1-yl)-5-oxo-5,6-dihydropyrimido[4,5-d]pyridazin-4-yl)amino)-phenyl)piperidin-4-yl)-propanoic acid | 5 |

TABLE 1-continued
| Ex | Structure | IUPAC Name | Synthetic Scheme |
|---|---|---|---|
| 131 | 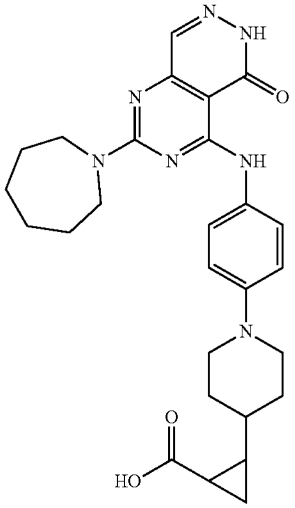 [SMILES: O=C(O)C1CC1C1CCN(c2ccc(Nc3nc(N4CCCCCC4)nc4cn[nH]c(=O)c34)cc2)CC1] | 2-(1-(4-((2-(azepan-1-yl)-5-oxo-5,6-dihydropyrimido[4,5-d]pyridazin-4-yl)amino)-phenyl)piperidin-4-yl)-cyclopropanecarboxylic acid | 5 |
| 132 | 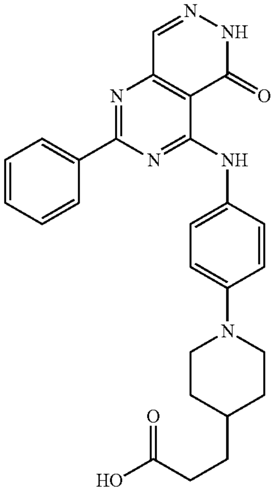 [SMILES: O=C(O)CCC1CCN(c2ccc(Nc3nc(-c4ccccc4)nc4cn[nH]c(=O)c34)cc2)CC1] | 3-(1-(4-((5-oxo-2-phenyl-5,6-dihydropyrimido[4,5-d]-pyridazin-4-yl)amino)phenyl)-piperidin-4-yl)propanoic acid | 3 |
| 133 | 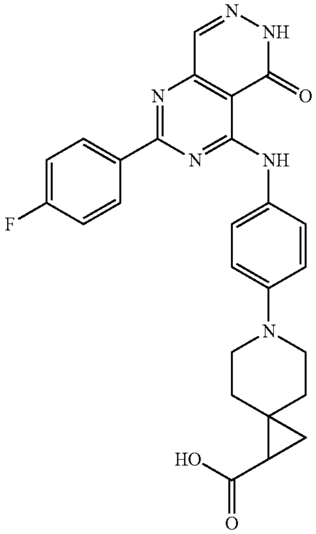 [SMILES: O=C(O)C1CC12CCN(c1ccc(Nc3nc(-c4ccc(F)cc4)nc4cn[nH]c(=O)c34)cc1)CC2] | 6-(4-((2-(4-fluorophenyl)-5-oxo-5,6-dihydropyrimido[4,5-d]pyridazin-4-yl)amino)phenyl)-6-azaspiro[2.5]octane-1-carboxylic acid | 3 |

TABLE 1-continued
| Ex | Structure | IUPAC Name | Synthetic Scheme |
|---|---|---|---|
| 134 | 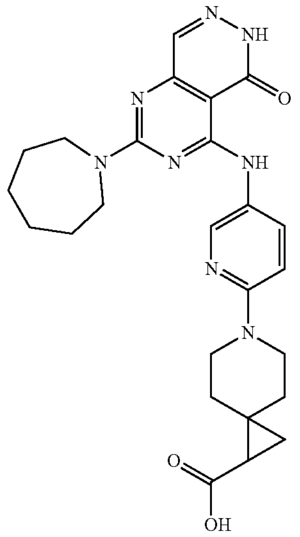 [SMILES: O=C(O)C1CC12CCN(c1ccc(Nc3nc(N4CCCCCC4)nc4cn[nH]c(=O)c34)cn1)CC2] | 6-(5-((2-(azepan-1-yl)-5-oxo-5,6-dihydropyrimido[4,5-d]-pyridazin-4-yl)amino)pyridin-2-yl)-6-azaspiro[2.5]octane-1-carboxylic acid | 5 |
| 135 | 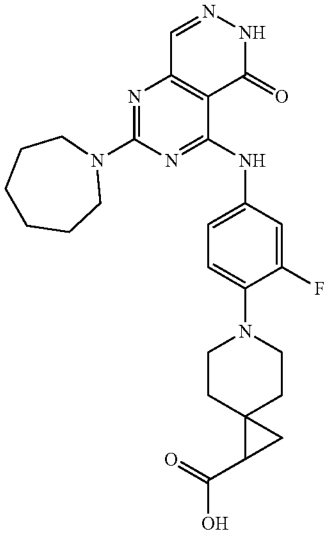 [SMILES: O=C(O)C1CC12CCN(c1ccc(Nc3nc(N4CCCCCC4)nc4cn[nH]c(=O)c34)cc1F)CC2] | 6-(4-((2-(azepan-1-yl)-5-oxo-5,6-dihydropyrimido[4,5-d]-pyridazin-4-yl)amino)-2-fluorophenyl)-6-azaspiro-[2.5]octane-1-carboxylic acid | 5 |

TABLE 1-continued
| Ex | Structure | IUPAC Name | Synthetic Scheme |
|---|---|---|---|
| 136 | 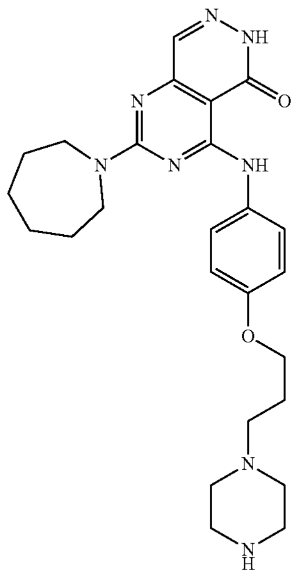 [SMILES: O=c1[nH]ncc2nc(N3CCCCCC3)nc(Nc3ccc(OCCCN4CCNCC4)cc3)c12] | 2-(azepan-1-yl)-4-((4-(3-(piperazin-1-yl)propoxy)-phenyl)amino)pyrimido[4,5-d]-pyridazin-5(6H)-one | 5 |
| 137 | 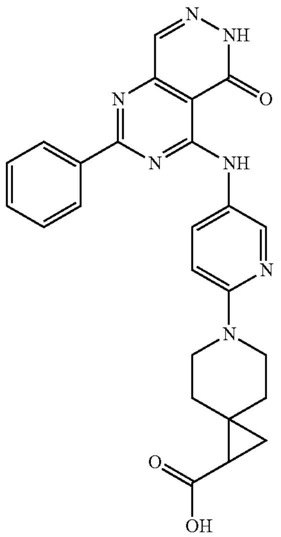 [SMILES: O=C(O)C1CC12CCN(c1ccc(Nc3nc(-c4ccccc4)nc4cn[nH]c(=O)c34)cn1)CC2] | 6-(5-((5-oxo-2-phenyl-5,6-dihydropyrimido[4,5-d]-pyridazin-4-yl)amino)pyridin-2-yl)-6-azaspiro[2.5]octane-1-carboxylic acid | 3 |

TABLE 1-continued
| Ex | Structure | IUPAC Name | Synthetic Scheme |
|---|---|---|---|
| 138 | 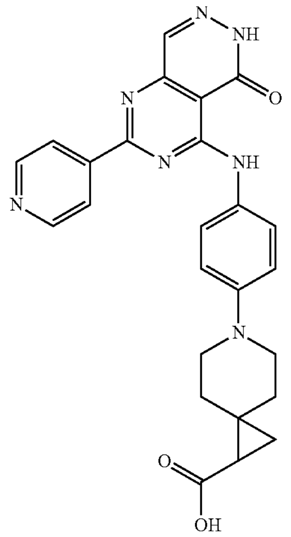 [SMILES: O=C(O)C1CC12CCN(c1ccc(Nc3nc(-c4ccncc4)nc4cn[nH]c(=O)c34)cc1)CC2] | 6-(4-((5-oxo-2-(pyridin-4-yl)-5,6-dihydropyrimido[4,5-d]-pyridazin-4-yl)amino)phenyl)-6-azaspiro[2.5]octane-1-carboxylic acid | 3 |
| 139 | 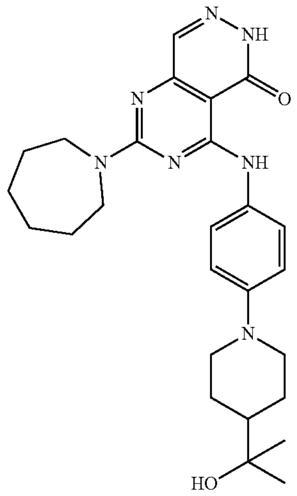 | 2-(azepan-1-yl)-4-((4-(4-(2-hydroxypropan-2-yl)piperidin-1-yl)phenyl)amino)pyrimido-[4,5-d]pyridazin-5(6H)-one | 5 |
| 140 | 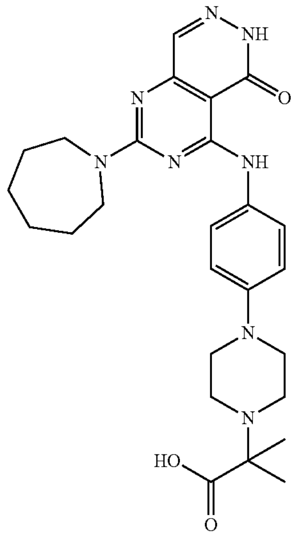 [SMILES: CC(C)(C(=O)O)N1CCN(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]pyridazin-4-yl)amino)-phenyl)piperazin-1-yl)-2-methylpropanoic acid | 5 |

TABLE 1-continued
| Ex | Structure | IUPAC Name | Synthetic Scheme |
|---|---|---|---|
| 141 | 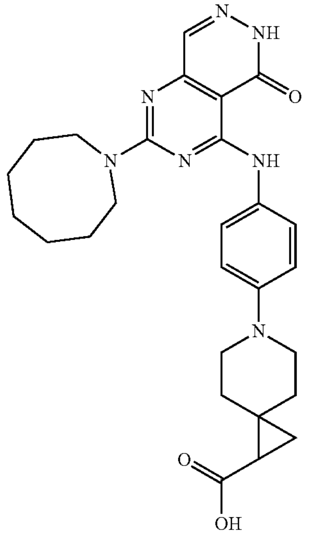 [SMILES: O=C(O)C1CC12CCN(c1ccc(Nc3nc(N4CCCCCCC4)nc4cn[nH]c(=O)c34)cc1)CC2] | 6-(4-((2-(azocan-1-yl)-5-oxo-5,6-dihydropyrimido[4,5-d]-pyridazin-4-yl)amino)phenyl)-6-azaspiro[2.5]octane-1-carboxylic acid | 5 |
| 142 | 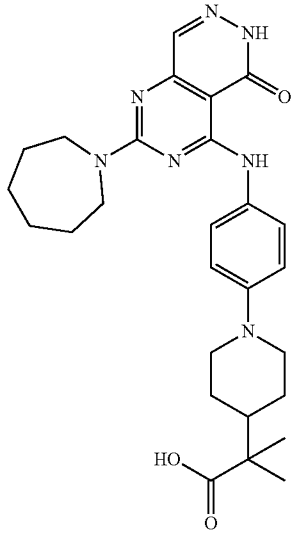 [SMILES: CC(C)(C(=O)O)C1CCN(c2ccc(Nc3nc(N4CCCCCC4)nc4cn[nH]c(=O)c34)cc2)CC1] | 2-(1-(4-((2-(azepan-1-yl)-5-oxo-5,6-dihydropyrimido[4,5-d]pyridazin-4-yl)amino)-phenyl)piperidin-4-yl)-2-methylpropanoic acid | 5 |
| 143 | 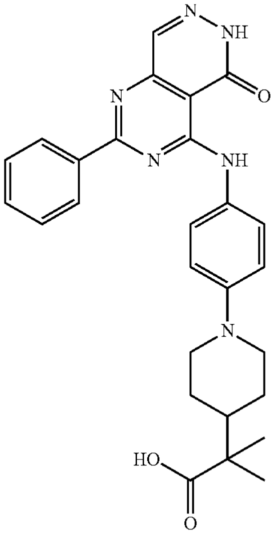 [SMILES: CC(C)(C(=O)O)C1CCN(c2ccc(Nc3nc(-c4ccccc4)nc4cn[nH]c(=O)c34)cc2)CC1] | 2-methyl-2-(1-(4-((5-oxo-2-phenyl-5,6-dihydropyrimido-[4,5-d]pyridazin-4-yl)amino)-phenyl)piperidin-4-yl)-propanoic acid | 2 |

TABLE 1-continued
| Ex | Structure | IUPAC Name | Synthetic Scheme |
|---|---|---|---|
| 144 | 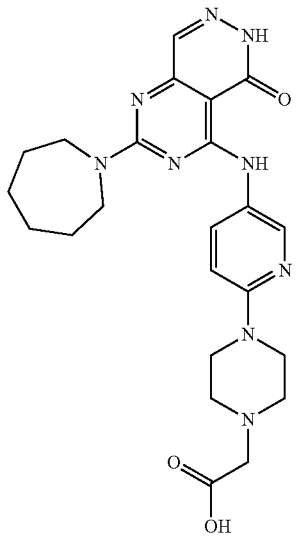 [SMILES: O=C(O)CN1CCN(c2ccc(Nc3nc(N4CCCCCC4)nc4cn[nH]c(=O)c34)cn2)CC1] | 2-(4-(5-((2-(azepan-1-yl)-5-oxo-5,6-dihydropyrimido[4,5-d]pyridazin-4-yl)amino)-pyridin-2-yl)piperazin-1-yl)-acetic acid | 7 |
| 145 | 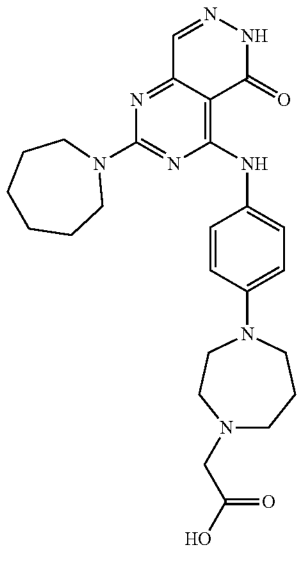 [SMILES: O=C(O)CN1CCCN(c2ccc(Nc3nc(N4CCCCCC4)nc4cn[nH]c(=O)c34)cc2)CC1] | 2-(4-(4-((2-(azepan-1-yl)-5-oxo-5,6-dihydropyrimido[4,5-d]pyridazin-4-yl)amino)-phenyl)1,4-diazepan-1-yl)-acetic acid | 7 |

TABLE 1-continued

| Ex | Structure | IUPAC Name | Synthetic Scheme |
|---|---|---|---|
| 146 | 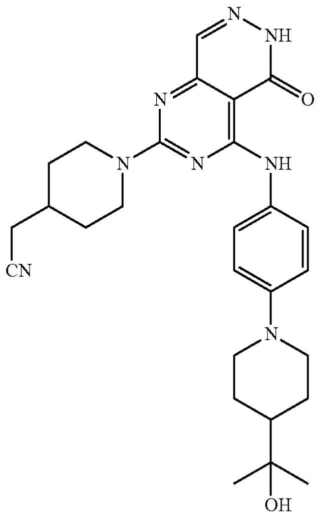 [SMILES: CC(C)(O)C1CCN(c2ccc(Nc3nc(N4CCC(CC#N)CC4)nc4cn[nH]c(=O)c34)cc2)CC1] | 2-(1-(4-((4-(4-(2-hydroxy-propan-2-yl)piperidin-1-yl)-phenyl)amino)-5-oxo-5,6-dihydropyrimido[4,5-d]-pyridazin-2-yl)piperidin-4-yl)acetonitrile | 7 |
| 147 | 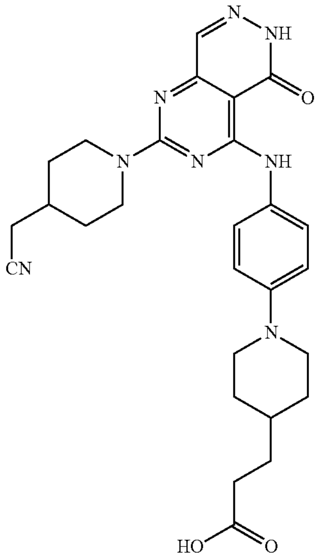 [SMILES: N#CCC1CCN(c2nc(Nc3ccc(N4CCC(CCC(=O)O)CC4)cc3)c3c(=O)[nH]ncc3n2)CC1] | 3-(1-(4-((2-(4-(cyanomethyl)-piperidin-1-yl)-5-oxo-5,6-dihydropyrimido[4,5-d]-pyridazin-4-yl)amino)phenyl)-piperidin-4-yl)propanoic acid | 7 |
| 148 | 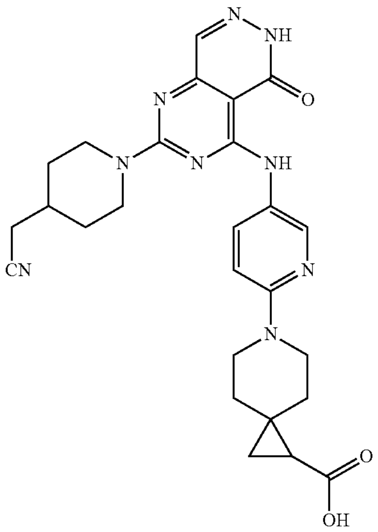 [SMILES: N#CCC1CCN(c2nc(Nc3ccc(N4CCC5(CC4)CC5C(=O)O)nc3)c3c(=O)[nH]ncc3n2)CC1] | 6-(5-((2-(4-(cyanomethyl)-piperidin-1-yl)-5-oxo-5,6-dihydropyrimido[4,5-d]-pyridazin-4-yl)amino)pyridin-2-yl)-6-azaspiro[2.5]octane-1-carboxylic acid | 7 |

TABLE 1-continued
| Ex | Structure | IUPAC Name | Synthetic Scheme |
|---|---|---|---|
| 149 | 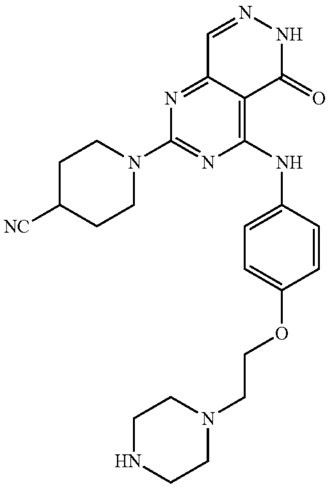 [SMILES: N#CC1CCN(c2nc(Nc3ccc(OCCN4CCNCC4)cc3)c3c(=O)[nH]ncc3n2)CC1] | 1-(5-oxo-4-((4-(2-(piperazin-1-yl)ethoxy)phenyl)amino)-5,6-dihydropyrimido[4,5-d]-pyridazin-2-yl)piperidine-4-carbonitrile | 7 |
| 150 | 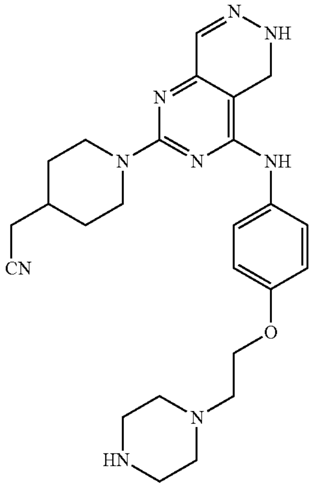 [SMILES: N#CCC1CCN(c2nc3c(c(Nc4ccc(OCCN5CCNCC5)cc4)n2)CNN=C3)CC1] | 2-(1-(5-oxo-4-((4-(2-(piperazin-1-yl)ethoxy)phenyl)amino)-5,6-dihydropyrimido-[4,5-d]-pyridazin-2-yl)piperidin-4-yl)acetonitrile | 7 |
| 151 | 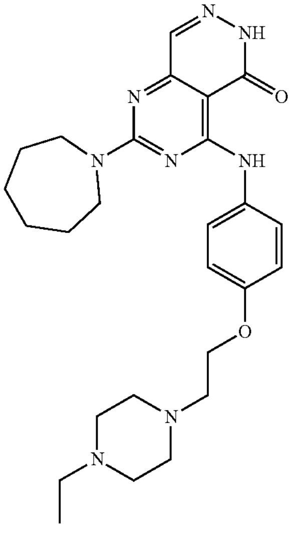 [SMILES: CCN1CCN(CCOc2ccc(Nc3nc(N4CCCCCC4)nc4cn[nH]c(=O)c34)cc2)CC1] | 2-(azepan-1-yl)-4-((4-(2-(4-ethylpiperazin-1-yl)ethoxy)-phenyl)amino)pyrimido[4,5-d]-pyridazin-5(6H)-one | 7 |

TABLE 1-continued
| Ex | Structure | IUPAC Name | Synthetic Scheme |
|---|---|---|---|
| 152 | 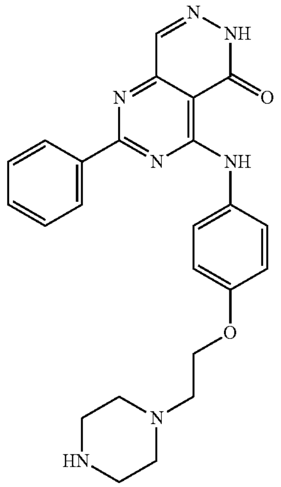 [SMILES: O=c1[nH]ncc2nc(-c3ccccc3)nc(Nc3ccc(OCCN4CCNCC4)cc3)c12] | 2-phenyl-4-((4-(2-(piperazin-1-yl)ethoxy)phenyl)amino)-pyrimido[4,5-d]pyridazin-5(6H)-one | 8 |
| 153 | 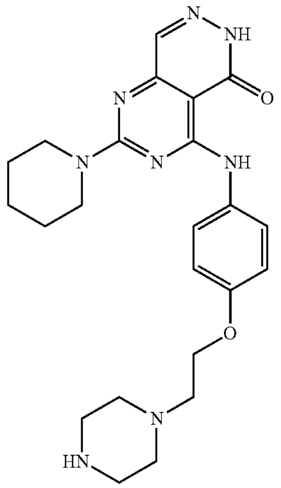 [SMILES: O=c1[nH]ncc2nc(N3CCCCC3)nc(Nc3ccc(OCCN4CCNCC4)cc3)c12] | 4-((4-(2-(piperazin-1-yl)-ethoxy)phenyl)amino)-2-(piperidin-1-yl)pyrimido-[4,5-d]pyridazin-5(6H)-one | 7 |
| 154 | 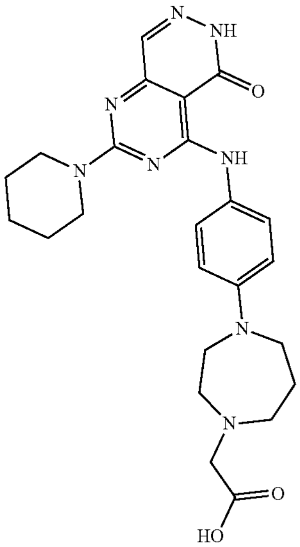 [SMILES: O=C(O)CN1CCCN(c2ccc(Nc3nc(N4CCCCC4)nc4cn[nH]c(=O)c34)cc2)CC1] | 2-(4-(4-((5-oxo-2-(piperidin-1-yl)-5,6-dihydropyrimido-[4,5-d]pyridazin-4-yl)-amino)phenyl)-1,4-diazepan-1-yl)acetic acid | 7 |

TABLE 1-continued
| Ex | Structure | IUPAC Name | Synthetic Scheme |
|---|---|---|---|
| 155 | 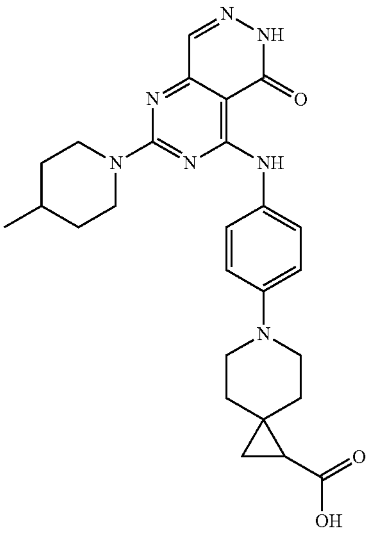 [SMILES: CC1CCN(c2nc(Nc3ccc(N4CCC5(CC4)CC5C(=O)O)cc3)c3c(=O)[nH]ncc3n2)CC1] | 6-(4-((2-(4-methylpiperidin-1-yl)-5-oxo-5,6-dihydro-pyrimido[4,5-d]pyridazin-4-yl)amino)phenyl)-6-azaspiro-[2.5]octane-1-carboxylic acid | 7 |
| 156 | 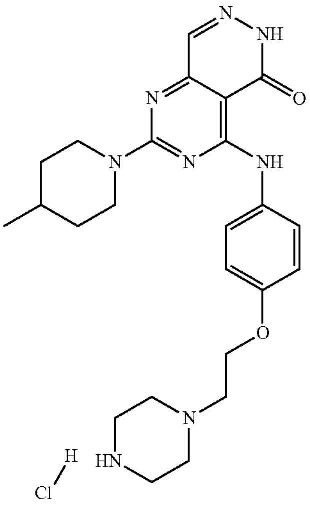 | 2-(4-methylpiperidin-1-yl)-4-((4-(2-(piperazin-1-yl)ethoxy)-phenyl)amino)pyrimido[4,5-d]-pyridazin-5(6H)-one hydrochloride | 7 |
| 157 | 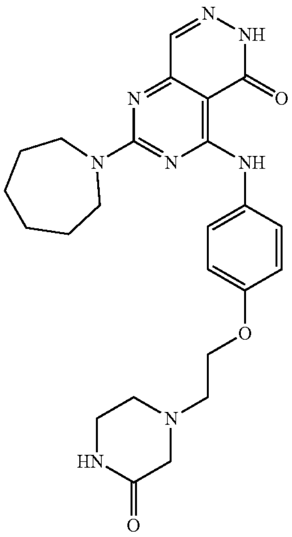 [SMILES: O=C1CN(CCOc2ccc(Nc3nc(N4CCCCCC4)nc4cn[nH]c(=O)c34)cc2)CCN1] | 2-(azepan-1-yl)-4-((4-(2-(3-oxopiperazin-1-yl)ethoxy)-phenyl)amino)pyrimido[4,5-d]-pyridazin-5(6H)-one | 7 |

TABLE 1-continued
| Ex | Structure | IUPAC Name | Synthetic Scheme |
| --- | --- | --- | --- |
| 158 | 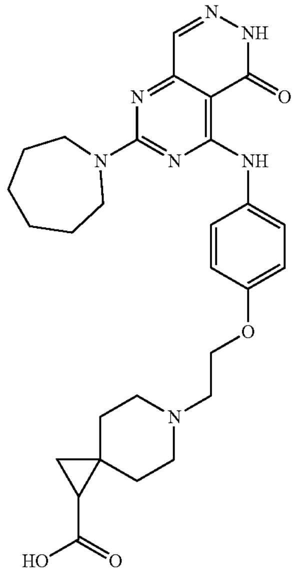 [SMILES: O=C(O)C1CC12CCN(CCOc1ccc(Nc3nc(N4CCCCCC4)nc4cn[nH]c(=O)c34)cc1)CC2] | 6-(2-(4-((2-(azepan-1-yl)-5-oxo-5,6-dihydropyrimido[4,5-d]pyridazin-4-yl)amino)-phenoxy)ethyl)-6-azaspiro-[2.5]octane-1-carboxylic acid | 7 |
| 159 | 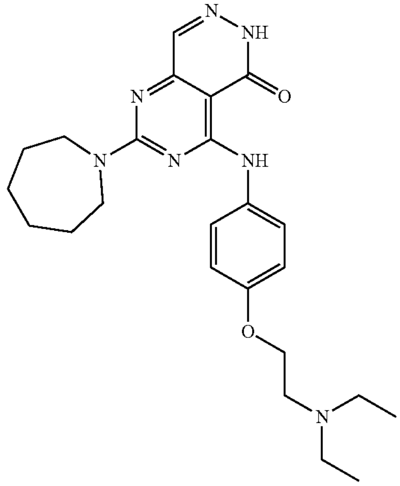 [SMILES: CCN(CC)CCOc1ccc(Nc2nc(N3CCCCCC3)nc3cn[nH]c(=O)c23)cc1] | 2-(azepan-1-yl)-4-((4-(2-(diethylamino)ethoxy)phenyl)-amino)pyrimido[4,5-d]-pyridazin-5(6H)-one | 7 |
| 160 | 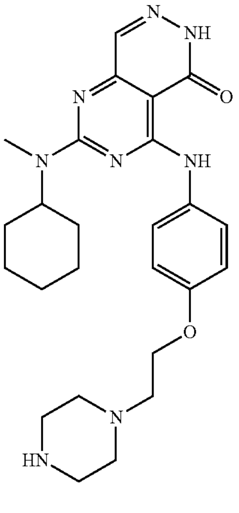 [SMILES: CN(c1nc(Nc2ccc(OCCN3CCNCC3)cc2)c2c(=O)[nH]ncc2n1)C1CCCCC1] | 2-(cyclohexyl(methyl)amino)-4-((4-(2-(piperazin-1-yl)-ethoxy)phenyl)amino)pyrimido-[4,5-d]pyridazin-5(6H)-one | 7 |

TABLE 1-continued
| Ex | Structure | IUPAC Name | Synthetic Scheme |
|---|---|---|---|
| 161 | 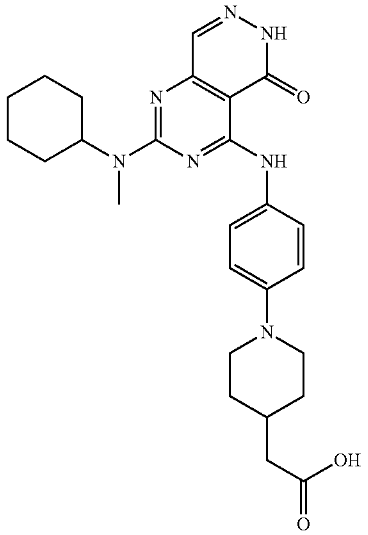 [SMILES: CN(c1nc(Nc2ccc(N3CCC(CC(=O)O)CC3)cc2)c2c(=O)[nH]ncc2n1)C1CCCCC1] | 2-(1-(4-((2-(cyclohexyl-(methyl)amino)-5-oxo-5,6-dihydropyrimido[4,5-d]-pyridazin-4-yl)amino)-phenyl)piperidin-4-yl)acetic acid | 7 |
| 162 | 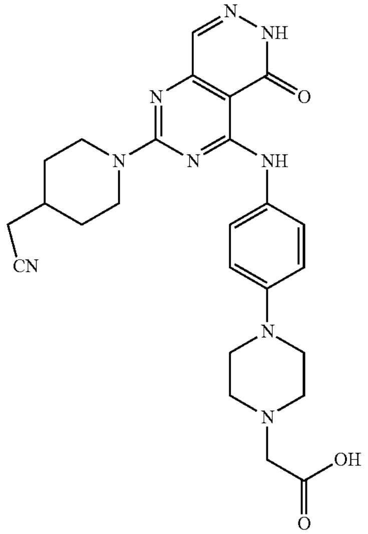 [SMILES: N#CCC1CCN(c2nc(Nc3ccc(N4CCN(CC(=O)O)CC4)cc3)c3c(=O)[nH]ncc3n2)CC1] | 2-(4-(4-((2-(4-(cyanomethyl)-piperidin-1-yl)-5-oxo-5,6-dihydropyrimido[4,5-d]-pyridazin-4-yl)amino)phenyl)-piperazin-1-yl)acetic acid | 7 |
| 163 | 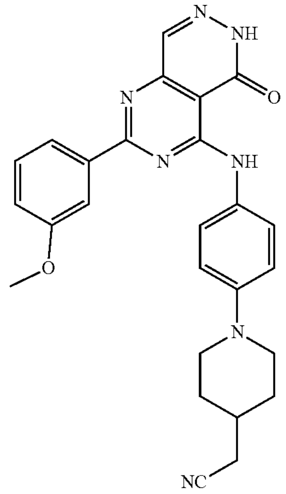 [SMILES: COc1cccc(-c2nc(Nc3ccc(N4CCC(CC#N)CC4)cc3)c3c(=O)[nH]ncc3n2)c1] | 2-(1-(4-((2-(3-methoxyphenyl)-5-oxo-5,6-dihydropyrimido-[4,5-d]pyridazin-4-yl)amino)-phenyl)piperidin-4-yl)-acetonitrile | 8 |

TABLE 1-continued
| Ex | Structure | IUPAC Name | Synthetic Scheme |
| --- | --- | --- | --- |
| 164 | 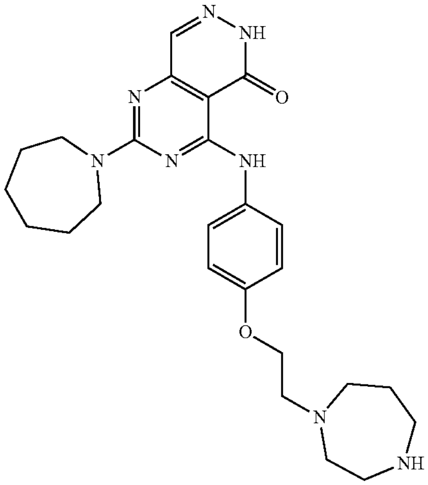 [SMILES: O=c1[nH]ncc2nc(N3CCCCCC3)nc(Nc3ccc(OCCN4CCCNCC4)cc3)c12] | 4-((4-(2-(1,4-diazepan-1-yl)-ethoxy)phenyl)amino)-2-(azepan-1-yl)pyrimido[4,5-d]-pyridazin-5(6H)-one | 7 |
| 165 | 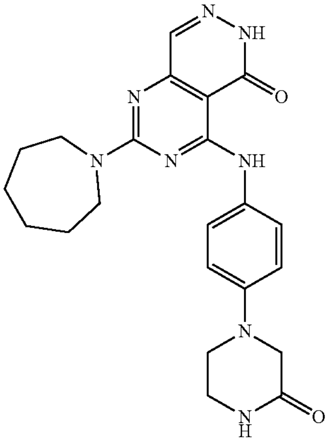 [SMILES: O=C1CN(c2ccc(Nc3nc(N4CCCCCC4)nc4cn[nH]c(=O)c34)cc2)CCN1] | 2-(azepan-1-yl)-4-((4-(3-oxopiperazin-1-yl)phenyl)-amino)pyrimido[4,5-d]-pyridazin-5(6H)-one | 7 |
| 166 | 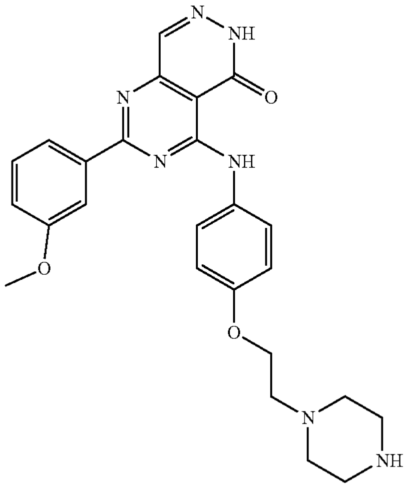 [SMILES: COc1cccc(-c2nc(Nc3ccc(OCCN4CCNCC4)cc3)c3c(=O)[nH]ncc3n2)c1] | 2-(3-methoxyphenyl)-4-((4-(2-(piperazin-1-yl)ethoxy)-phenyl)amino)pyrimido-[4,5-d]pyridazin-5(6H)-one | 8 |

TABLE 1-continued
| Ex | Structure | IUPAC Name | Synthetic Scheme |
|---|---|---|---|
| 167 | 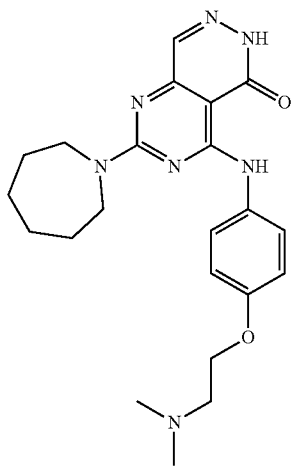 [SMILES: CN(C)CCOc1ccc(Nc2nc(N3CCCCCC3)nc3cn[nH]c(=O)c23)cc1] | 2-(azepan-1-yl)-4-((4-(2-(dimethylamino)ethoxy)phenyl)-amino)pyrimido[4,5-d]-pyridazin-5(6H)-one | 7 |
| 168 | 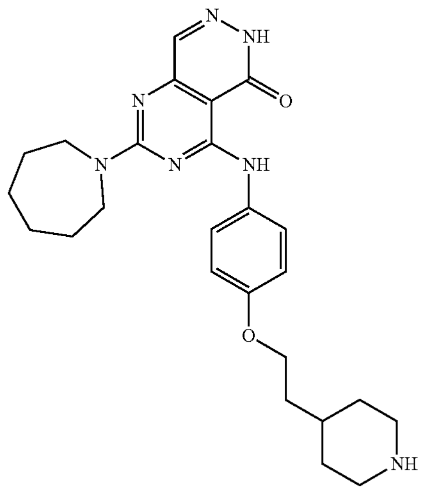 [SMILES: O=c1[nH]ncc2nc(N3CCCCCC3)nc(Nc3ccc(OCCC4CCNCC4)cc3)c12] | 2-(azepan-1-yl)4-((4-(2-(piperidin-4-yl)ethoxy)phenyl)-amino)pyrimido[4,5-d]-pyridazin-5(6H)-one | 7 |
| 169 | 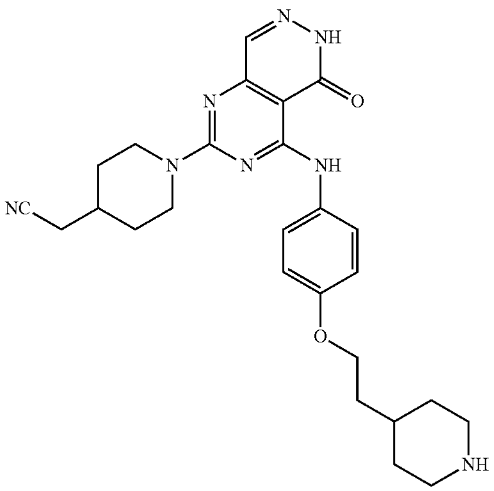 [SMILES: N#CCC1CCN(c2nc(Nc3ccc(OCCC4CCNCC4)cc3)c3c(=O)[nH]ncc3n2)CC1] | 2-(1-(5-oxo-4-((4-(2-(piperidin-4-yl)ethoxy)phenyl)amino)-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 170 | 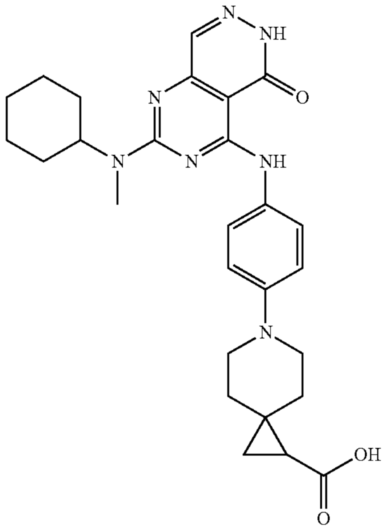 [SMILES: CN(c1nc(Nc2ccc(N3CCC4(CC3)CC4C(=O)O)cc2)c2c(=O)[nH]ncc2n1)C1CCCCC1] | 6-(4-((2-(cyclohexyl(methyl)-amino)-5-oxo-5,6-dihydro-pyrimido[4,5-d]pyridazin-4-yl)amino)phenyl)-6-azaspiro-[2.5]octane-1-carboxylic acid | 7 |
| 171 | 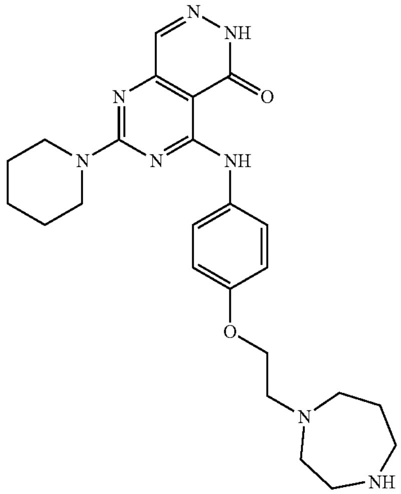 [SMILES: O=c1[nH]ncc2nc(N3CCCCC3)nc(Nc3ccc(OCCN4CCCNCC4)cc3)c12] | 4-((4-(2-(1,4-diazepan-1-yl)-ethoxy)phenyl)amino)-2-(piperidin-1-yl)pyrimido-[4,5-d]pyridazin-5(6H)-one | 7 |
| 172 | 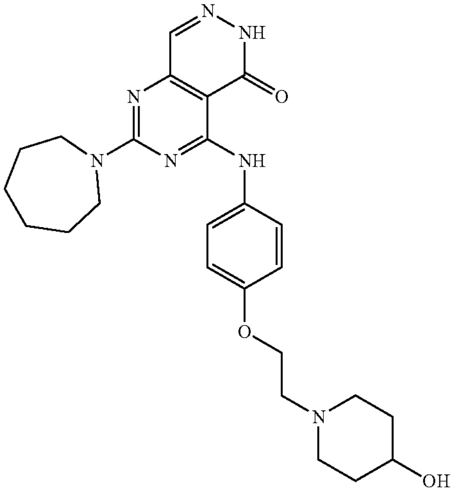 [SMILES: O=c1[nH]ncc2nc(N3CCCCCC3)nc(Nc3ccc(OCCN4CCC(O)CC4)cc3)c12] | 2-(azepan-1-yl)-4-((4-(2-(4-hydroxypiperidin-1-yl)ethoxy)-phenyl)amino)pyrimido[4,5-d]-pyridazin-5(6H)-one | 7 |

TABLE 1-continued
| Ex | Structure | IUPAC Name | Synthetic Scheme |
| --- | --- | --- | --- |
| 173 | 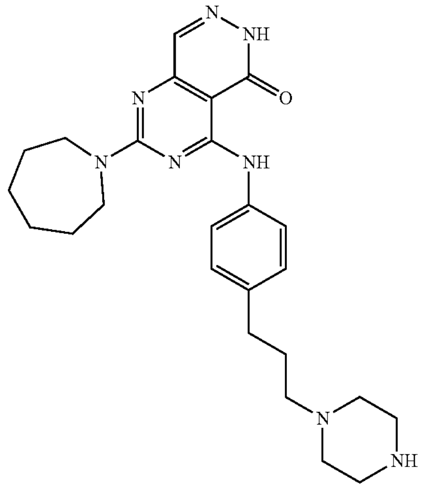 [SMILES: O=c1[nH]ncc2nc(N3CCCCCC3)nc(Nc3ccc(CCCN4CCNCC4)cc3)c12] | 2-(azepan-1-yl)-4-((4-(3-(piperazin-1-yl)propyl)phenyl)-amino)pyrimido[4,5-d]-pyridazin-5(6H)-one | 7 |
| 174 | 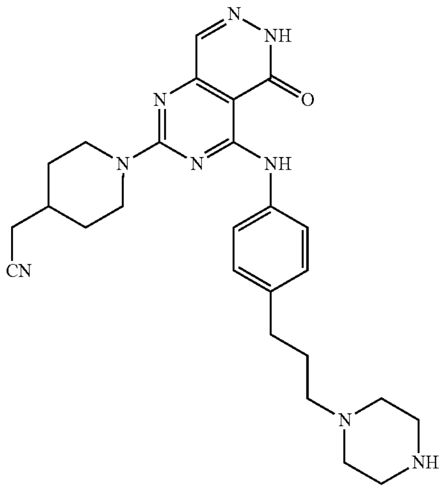 [SMILES: N#CCC1CCN(c2nc(Nc3ccc(CCCN4CCNCC4)cc3)c3c(=O)[nH]ncc3n2)CC1] | 2-(1-(5-oxo-4-((4-(3-(piperazin-1-yl)propyl)phenyl)amino)-5,6-dihydropyrimido[4,5-d]-pyridazin-2-yl)piperidin-4-yl)acetonitrile | 7 |
| 175 | 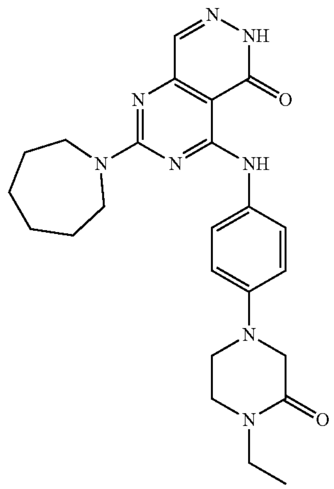 [SMILES: CCN1CCN(c2ccc(Nc3nc(N4CCCCCC4)nc4cn[nH]c(=O)c34)cc2)CC1=O] | 2-(azepan-1-yl)-4-((4-(4-ethyl-3-oxopiperazin-1-yl)phenyl)-amino)pyrimido[4,5-d]-pyridazin-5(6H)-one | 7 |

TABLE 1-continued
| Ex | Structure | IUPAC Name | Synthetic Scheme |
|---|---|---|---|
| 176 | 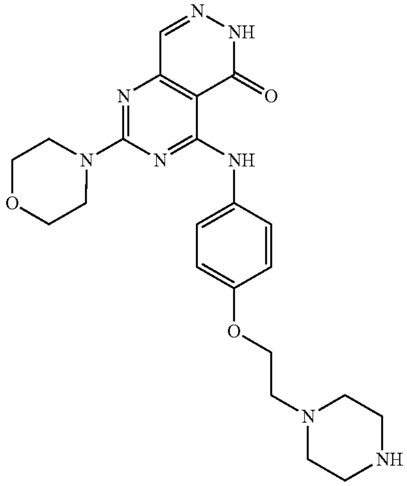 [SMILES: O=c1[nH]ncc2nc(N3CCOCC3)nc(Nc3ccc(OCCN4CCNCC4)cc3)c12] | 2-morpholino-4-((4-(2-(piperazin-1-yl)ethoxy)phenyl)-amino)pyrimido[4,5-d]-pyridazin-5(6H)-one | 5 |
| 177 | 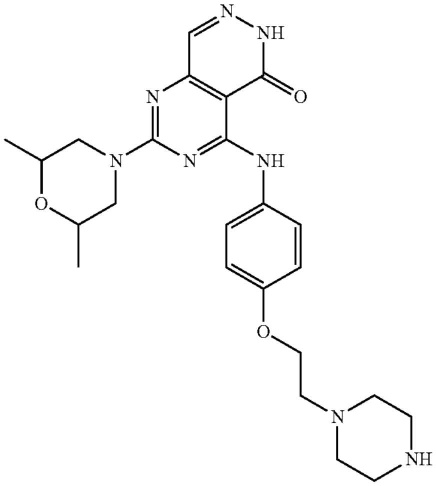 [SMILES: CC1CN(c2nc(Nc3ccc(OCCN4CCNCC4)cc3)c3c(=O)[nH]ncc3n2)CC(C)O1] | 2-(2,6-dimethylmorpholino)-4-((4-(2-(piperazin-1-yl)-ethoxy)phenyl)amino)pyrimido-[4,5-d]pyridazin-5(6H)-one | 5 |
| 178 | 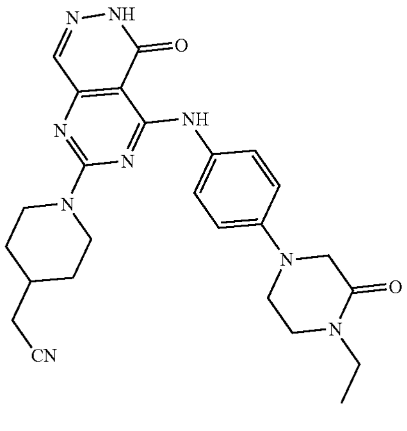 [SMILES: CCN1CCN(c2ccc(Nc3nc(N4CCC(CC#N)CC4)nc4cn[nH]c(=O)c34)cc2)CC1=O] | 2-(1-(4-((4-(4-ethyl-3-oxo-piperazin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 179 | 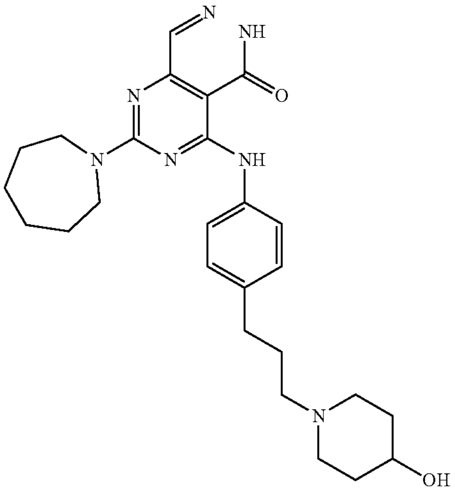 [SMILES: N=Cc1nc(N2CCCCCC2)nc(Nc2ccc(CCCN3CCC(O)CC3)cc2)c1C(N)=O] | 2-(azepan-1-yl)-4-((4-(3-(4-hydroxypiperidin-1-yl)propyl)-phenyl)amino)pyrimido[4,5-d]-pyridazin-5(6H)-one | 7 |
| 180 | 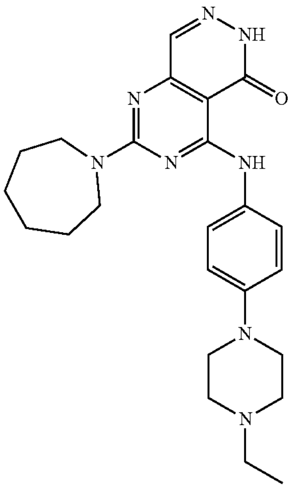 [SMILES: CCN1CCN(c2ccc(Nc3nc(N4CCCCCC4)nc4cn[nH]c(=O)c34)cc2)CC1] | 2-(azepan-1-yl)-4-((4-(4-ethylpiperazin-1-yl)phenyl)-amino)pyrimido[4,5-d]-pyridazin-5(6H)-one | 7 |
| 181 | 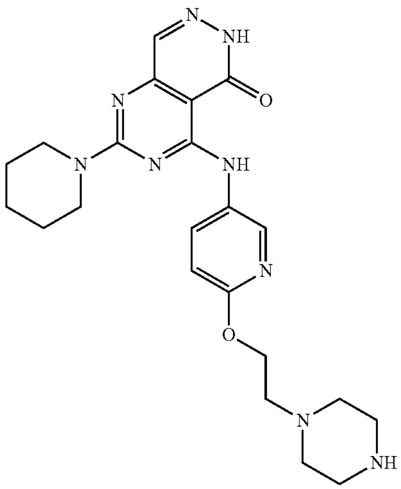 [SMILES: O=c1[nH]ncc2nc(N3CCCCC3)nc(Nc3ccc(OCCN4CCNCC4)nc3)c12] | 4-((6-(2-(piperazin-1-yl)-ethoxy)pyridin-3-yl)amino)-2-(piperidin-1-yl)pyrimido-[4,5-d]pyridazin-5(6H)-one | 7 |

TABLE 1-continued
| Ex | Structure | IUPAC Name | Synthetic Scheme |
|---|---|---|---|
| 182 | 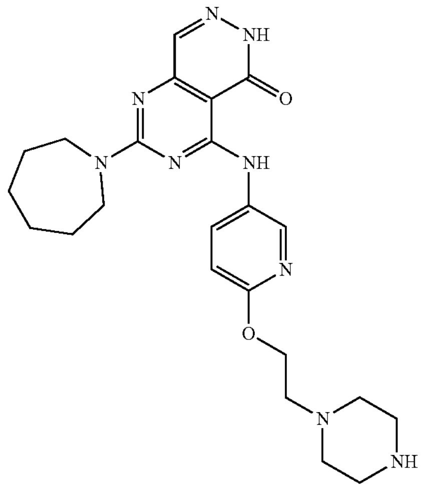 [SMILES: O=c1[nH]ncc2nc(N3CCCCCC3)nc(Nc3ccc(OCCN4CCNCC4)nc3)c12] | 2-(azepan-1-yl)-4-((6-(2-(piperazin-1-yl)ethoxy)pyridin-3-yl)amino)pyrimido[4,5-d]-pyridazin-5(6H)-one | 7 |
| 183 | 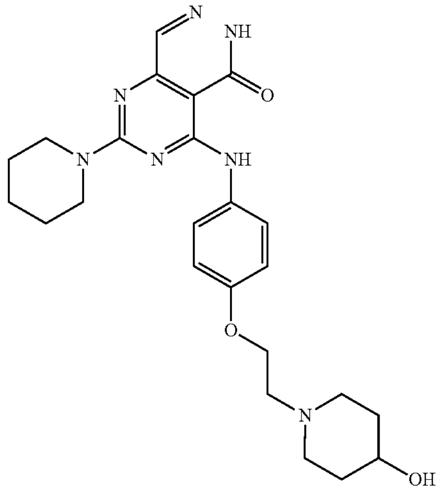 [SMILES: N=Cc1nc(N2CCCCC2)nc(Nc2ccc(OCCN3CCC(O)CC3)cc2)c1C(N)=O] | 4-((4-(2-(4-hydroxypiperidin-1-yl)ethoxy)phenyl)amino)-2-(piperidin-1-yl)pyrimido[4,5-d]-pyridazin-5(6H)-one | 7 |
| 184 | 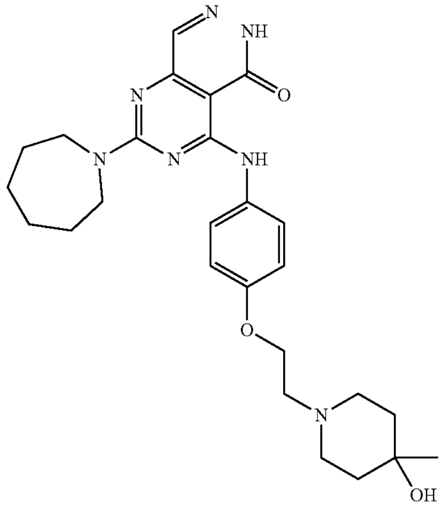 [SMILES: CC1(O)CCN(CCOc2ccc(Nc3nc(N4CCCCCC4)nc(C=N)c3C(N)=O)cc2)CC1] | 2-(azepan-1-yl)-4-((4-(2-(4-hydroxy-4-methylpiperidin-1-yl)ethoxy)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 185 | 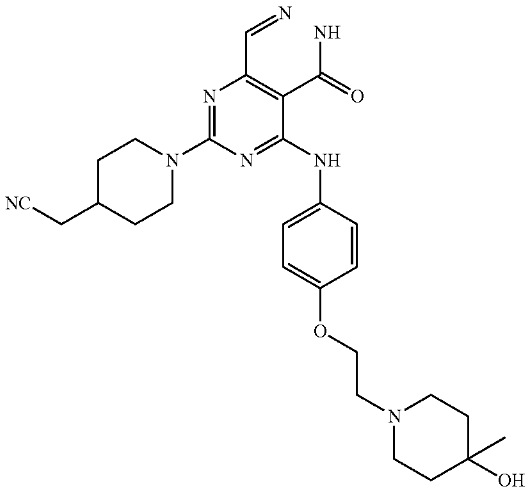 [SMILES: CC1(O)CCN(CCOc2ccc(Nc3nc(N4CCC(CC#N)CC4)nc(C=N)c3C(N)=O)cc2)CC1] | 2-(1-(4-((4-(2-(4-hydroxy-4-methylpiperidin-1-yl)ethoxy)-phenyl)amino)-5-oxo-5,6-dihydropyrimido[4,5-d]-pyridazin-2-yl)piperidin-4-yl)acetonitrile | 7 |
| 186 | 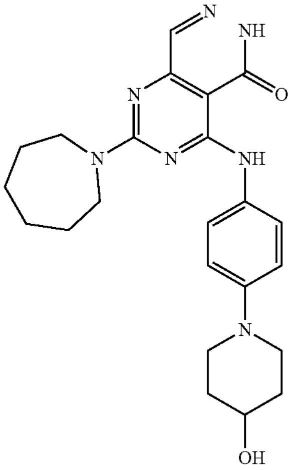 [SMILES: N=Cc1nc(N2CCCCCC2)nc(Nc2ccc(N3CCC(O)CC3)cc2)c1C(N)=O] | 2-(azepan-1-yl)-4-((4-(4-hydroxypiperidin-1-yl)phenyl)-amino)pyrimido[4,5-d]-pyridazin-5(6H)-one | 7 |
| 187 | 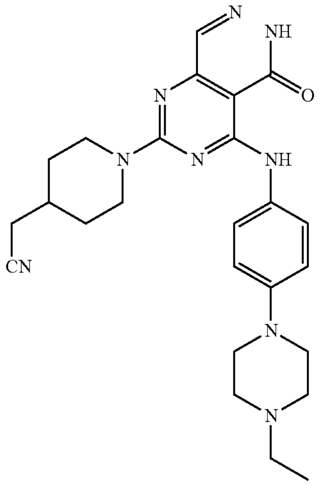 [SMILES: CCN1CCN(c2ccc(Nc3nc(N4CCC(CC#N)CC4)nc(C=N)c3C(N)=O)cc2)CC1] | 2-(1-(4-((4-(4-ethylpiperazin-1-yl)phenyl)amino)-5-oxo-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 188 | 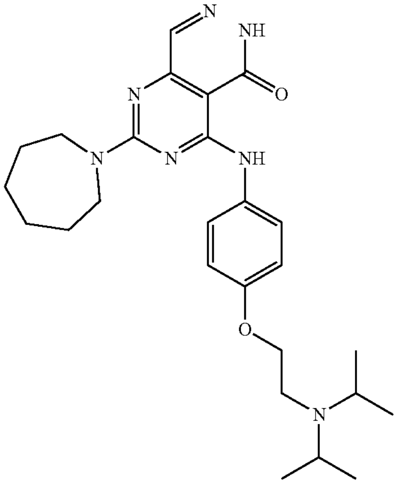 [SMILES: CC(C)N(CCOc1ccc(Nc2nc(N3CCCCCC3)nc(C=N)c2C(N)=O)cc1)C(C)C] | 2-(azepan-1-yl)-4-((4-(2-(diisopropylamino)ethoxy)-phenyl)amino)pyrimido[4,5-d]-pyridazin-5(6H)-one | 7 |
| 189 | 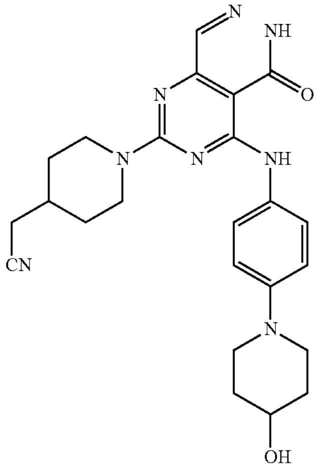 [SMILES: N#CCC1CCN(c2nc(C=N)c(C(N)=O)c(Nc3ccc(N4CCC(O)CC4)cc3)n2)CC1] | 2-(1-(4-((4-(4-hydroxypiperidin-1-yl)phenyl)amino)-5-oxo-5,6-dihydropyrimido[4,5-d]-pyridazin-2-yl)piperidin-4-yl)acetonitrile | 7 |
| 190 | 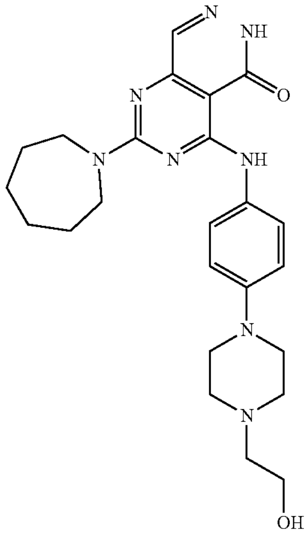 | 2-(azepan-1-yl)-4-((4-(4-(2-hydroxyethyl)piperazin-1-yl)-phenyl)amino)pyrimido[4,5-d]-pyridazin-5(6H)-one | 7 |

TABLE 1-continued
| Ex | Structure | IUPAC Name | Synthetic Scheme |
|---|---|---|---|
| 191 | 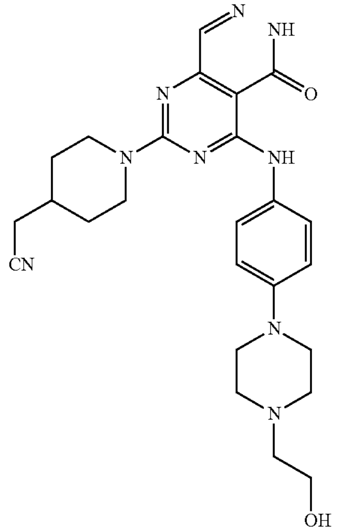 | 2-(1-(4-((4-(4-(2-hydroxy-ethyl)piperazin-1-yl)phenyl)-amino)-5-oxo-5,6-dihydro-pyrimido[4,5-d]pyridazin-2-yl)piperidin-4-yl)acetonitrile | 7 |
| 192 | 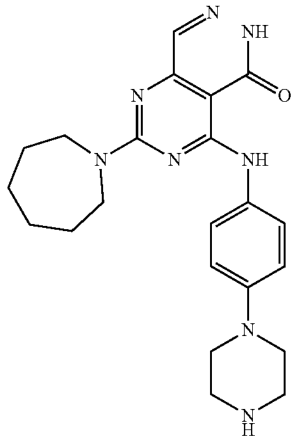 [SMILES: N=Cc1nc(N2CCCCCC2)nc(Nc2ccc(N3CCNCC3)cc2)c1C(N)=O] | 2-(azepan-1-yl)-4-((4-(piperazin-1-yl)phenyl)amino)pyrimido-[4,5-d]pyridazin-5(6H)-one | 7 |
| 193 | 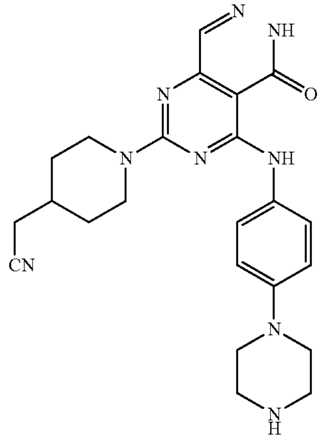 [SMILES: N#CCC1CCN(c2nc(C=N)c(C(N)=O)c(Nc3ccc(N4CCNCC4)cc3)n2)CC1] | 2-(1-(5-oxo-4-((4-(piperazin-1-yl)phenyl)amino)-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 194 | 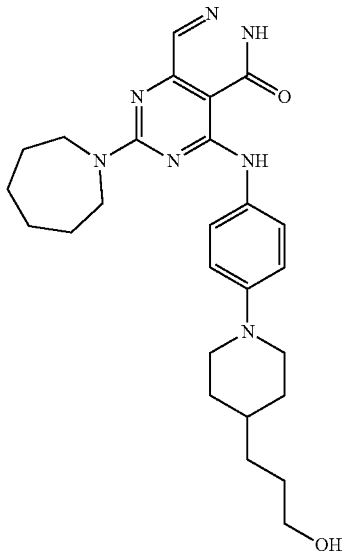 | 2-(azepan-1-yl)-4-((4-(4-(3-hydroxypropyl)piperidin-1-yl)phenyl)amino)pyrimido[4,5-d]pyridazin-5(6H)-one | 7 |
| 195 | 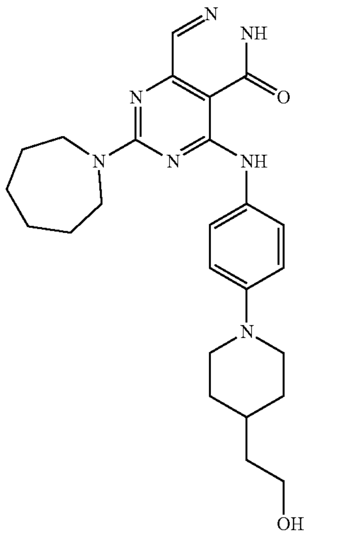 [SMILES: N=Cc1nc(N2CCCCCC2)nc(Nc2ccc(N3CCC(CCO)CC3)cc2)c1C(N)=O] | 2-(azepan-1-yl)-4-((4-(4-(2-hydroxyethyl)piperidin-1-yl)phenyl)amino)pyrimido[4,5-d]pyridazin-5(6H)-one | 7 |

TABLE 1-continued
| Ex | Structure | IUPAC Name | Synthetic Scheme |
| --- | --- | --- | --- |
| 196 | 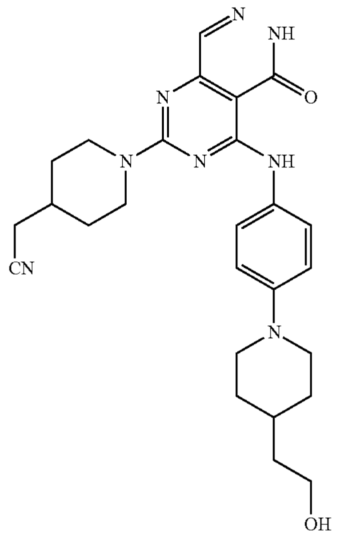 | 2-(1-(4-((4-(4-(2-hydroxy-ethyl)piperidin-1-yl)phenyl)-amino)-5-oxo-5,6-dihydro-pyrimido[4,5-d]pyridazin-2-yl)piperidin-4-yl)acetonitrile | 7 |
| 197 | 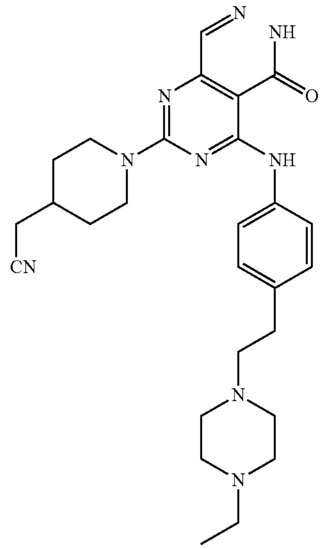 [SMILES: CCN1CCN(CCc2ccc(Nc3nc(N4CCC(CC#N)CC4)nc(C=N)c3C(N)=O)cc2)CC1] | 2-(1-(4-((4-(2-(4-ethylpiperazin-1-yl)ethyl)phenyl)amino)-5-oxo-5,6-dihydropyrimido[4,5-d]pyridazin-2-yl)piperidin-4-yl)acetonitrile | 7 |
| 198 | 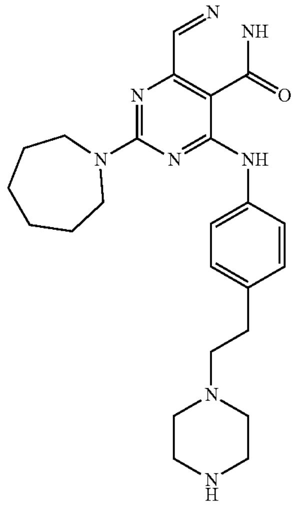 [SMILES: N=Cc1nc(N2CCCCCC2)nc(Nc2ccc(CCN3CCNCC3)cc2)c1C(N)=O] | 2-(azepan-1-yl)-4-((4-(2-(piperazin-1-yl)ethyl)phenyl)-amino)pyrimido[4,5-d]-pyridazin-5(6H)-one | 7 |

TABLE 1-continued
| Ex | Structure | IUPAC Name | Synthetic Scheme |
|---|---|---|---|
| 199 | 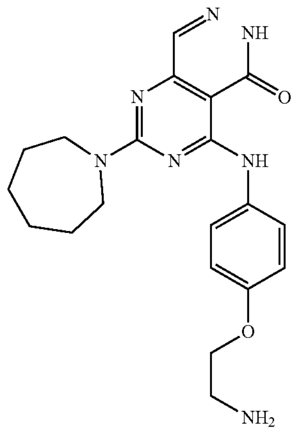 [SMILES: N=Cc1nc(N2CCCCCC2)nc(Nc2ccc(OCCN)cc2)c1C(N)=O] | 4-((4-(2-aminoethoxy)phenyl)-amino)-2-(azepan-1-yl)pyrimido-[4,5-d]pyridazin-5(6H)-one | 7 |
| 200 | 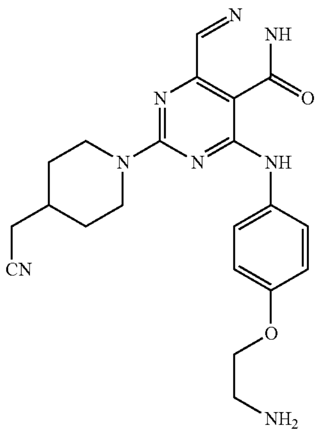 [SMILES: N#CCC1CCN(c2nc(C=N)c(C(N)=O)c(Nc3ccc(OCCN)cc3)n2)CC1] | 2-(1-(4-((4-(2-aminoethoxy)-phenyl)amino)-5-oxo-5,6-dihydropyrimido[4,5-d]-pyridazin-2-yl)piperidin-4-yl)acetonitrile | 7 |
| 201 | 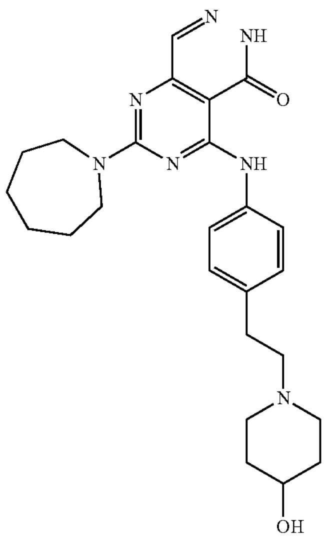 [SMILES: N=Cc1nc(N2CCCCCC2)nc(Nc2ccc(CCN3CCC(O)CC3)cc2)c1C(N)=O] | 2-(azepan-1-yl)-4-((4-(2-(4-hydroxypiperidin-1-yl)ethyl)-phenyl)amino)pyrimido[4,5-d]-pyridazin-5(6H)-one | 7 |

TABLE 1-continued
| Ex | Structure | IUPAC Name | Synthetic Scheme |
|---|---|---|---|
| 202 | 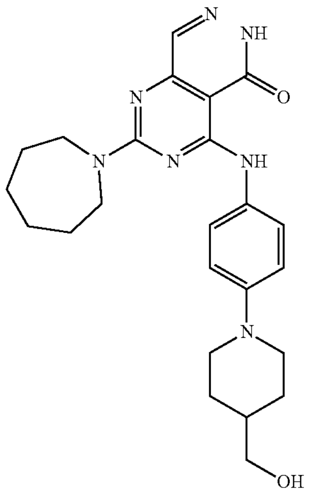 [SMILES: N=Cc1nc(N2CCCCCC2)nc(Nc2ccc(N3CCC(CO)CC3)cc2)c1C(N)=O] | 2-(azepan-1-yl)-4-((4-(4-(hydroxymethyl)piperidin-1-yl)phenyl)amino)pyrimido[4,5-d]pyridazin-5(6H)-one | 7 |
| 203 | 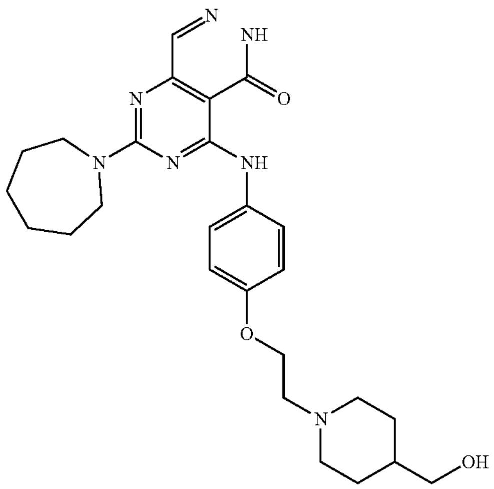 [SMILES: N=Cc1nc(N2CCCCCC2)nc(Nc2ccc(OCCN3CCC(CO)CC3)cc2)c1C(N)=O] | 2-(azepan-1-yl)-4-((4-(2-(4-(hydroxymethyl)piperidin-1-yl)ethoxy)phenyl)amino)-pyrimido[4,5-d]pyridazin-5(6H)-one | 7 |
| 204 | 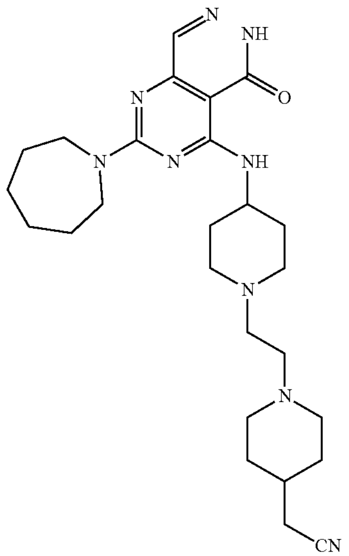 [SMILES: N#CCC1CCN(CCN2CCC(Nc3nc(N4CCCCCC4)nc(C=N)c3C(N)=O)CC2)CC1] | 2-(1-(2-(4-((2-(azepan-1-yl)-5-oxo-5,6-dihydropyrimido-[4,5-d]pyridazin-4-yl)amino)-piperidin-1-yl)ethyl)piperidin-4-yl)acetonitrile | 7 |

TABLE 1-continued
| Ex | Structure | IUPAC Name | Synthetic Scheme |
|---|---|---|---|
| 205 | 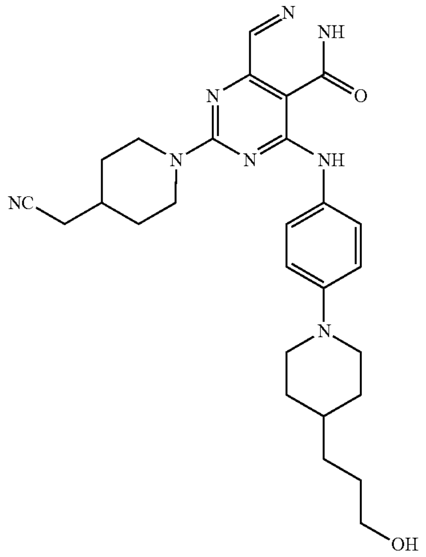 [SMILES: N#CCC1CCN(c2nc(C=N)c(C(N)=O)c(Nc3ccc(N4CCC(CCCO)CC4)cc3)n2)CC1] | 2-(1-(4-((4-(4-(3-hydroxy-propyl)piperidin-1-yl)phenyl)-amino)-5-oxo-5,6-dihydro-pyrimido[4,5-d]pyridazin-2-yl)piperidin-4-yl)acetonitrile | 7 |
| 206 | 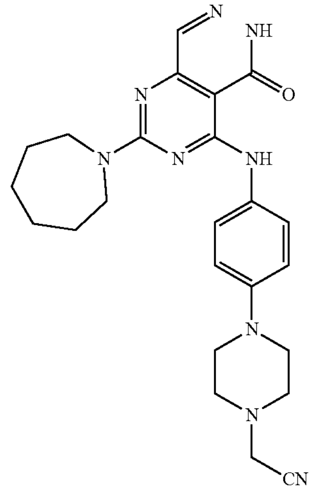 [SMILES: N#CCN1CCN(c2ccc(Nc3nc(N4CCCCCC4)nc(C=N)c3C(N)=O)cc2)CC1] | 2-(4-(4-((2-(azepan-1-yl)-5-oxo-5,6-dihydropyrimido[4,5-d]-pyridazin-4-yl)amino)phenyl)-piperazin-1-yl)acetonitrile | 7 |
| 207 | 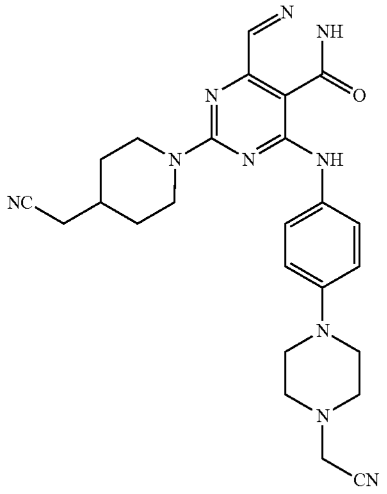 [SMILES: N#CCC1CCN(c2nc(C=N)c(C(N)=O)c(Nc3ccc(N4CCN(CC#N)CC4)cc3)n2)CC1] | 2-(1-(4-((4-(4-(cyanomethyl)-piperazin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 208 | 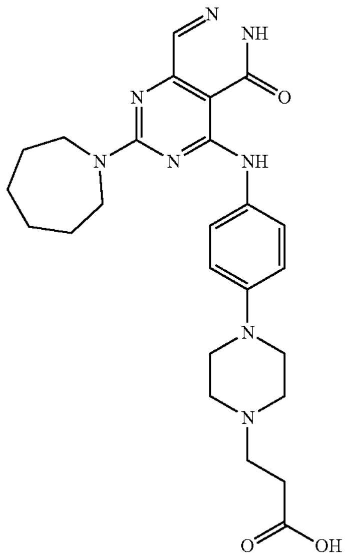 [SMILES: N=Cc1nc(N2CCCCCC2)nc(Nc2ccc(N3CCN(CCC(=O)O)CC3)cc2)c1C(N)=O] | 3-(4-(4-((2-(azepan-1-yl)-5-oxo-5,6-dihydropyrimido-[4,5-d]pyridazin-4-yl)amino)-phenyl)piperazin-1-yl)-propanoic acid | 7 |
| 209 | 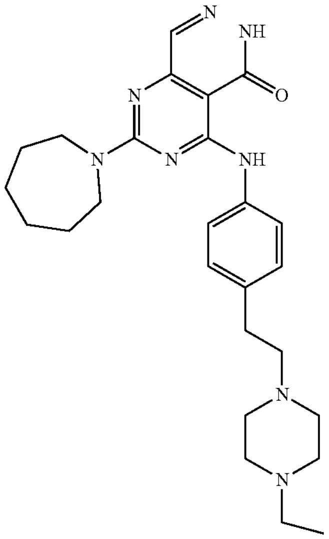 [SMILES: CCN1CCN(CCc2ccc(Nc3nc(N4CCCCCC4)nc(C=N)c3C(N)=O)cc2)CC1] | 2-(azepan-1-yl)-4-((4-(2-(4-ethylpiperazin-1-yl)ethyl)-phenyl)amino)pyrimido[4,5-d]-pyridazin-5(6H)-one | 7 |

TABLE 1-continued
| Ex | Structure | IUPAC Name | Synthetic Scheme |
|---|---|---|---|
| 210 | 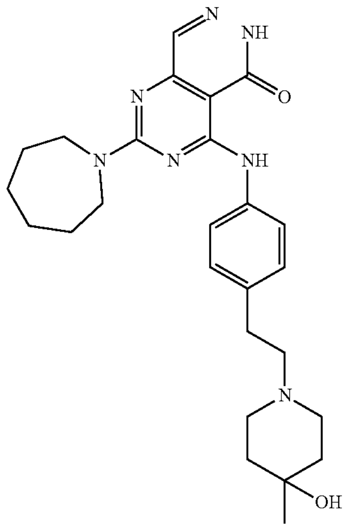 [SMILES: CC1(O)CCN(CCc2ccc(Nc3nc(N4CCCCCC4)nc(C=N)c3C(N)=O)cc2)CC1] | 2-(azepan-1-yl)-4-((4-(2-(4-hydroxy-4-methylpiperidin-1-yl)ethyl)phenyl)amino)-pyrimido[4,5-d]pyridazin-5(6H)-one | 7 |
| 211 | 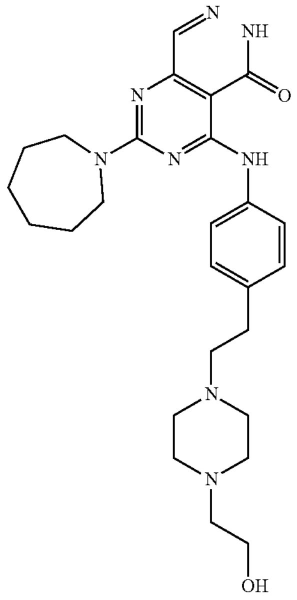 [SMILES: N=Cc1nc(N2CCCCCC2)nc(Nc2ccc(CCN3CCN(CCO)CC3)cc2)c1C(N)=O] | 2-(azepan-1-yl)-4-((4-(2-(4-(2-hydroxyethyl)piperazin-1-yl)ethyl)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 212 | 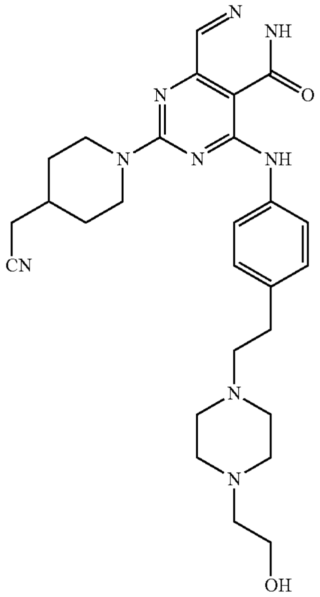 [SMILES: N#CCC1CCN(c2nc(C=N)c(C(N)=O)c(Nc3ccc(CCN4CCN(CCO)CC4)cc3)n2)CC1] | 2-(1-(4-((4-(2-(4-(2-hydroxyethyl)piperazin-1-yl)ethyl)phenyl)amino)-5-oxo-5,6-dihydropyrimido-[4,5-d]pyridazin-2-yl)-piperidin-4-yl)acetonitrile | 7 |
| 213 | 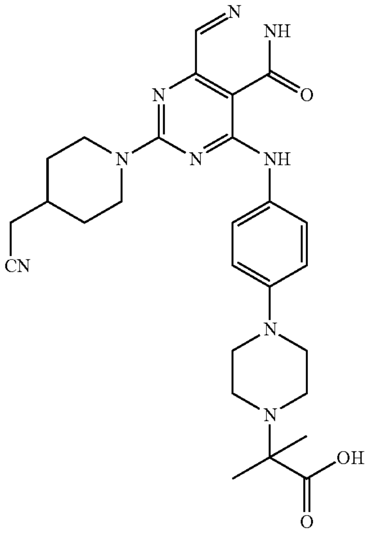 [SMILES: CC(C)(C(=O)O)N1CCN(c2ccc(Nc3nc(N4CCC(CC#N)CC4)nc(C=N)c3C(N)=O)cc2)CC1] | 2-(4-(4-((2-(4-(cyanomethyl)-piperidin-1-yl)-5-oxo-5,6-dihydropyrimido[4,5-d]-pyridazin-4-yl)amino)phenyl)-piperazin-1-yl)-2-methyl-propanoic acid | 7 |

TABLE 1-continued
| Ex | Structure | IUPAC Name | Synthetic Scheme |
|---|---|---|---|
| 214 | 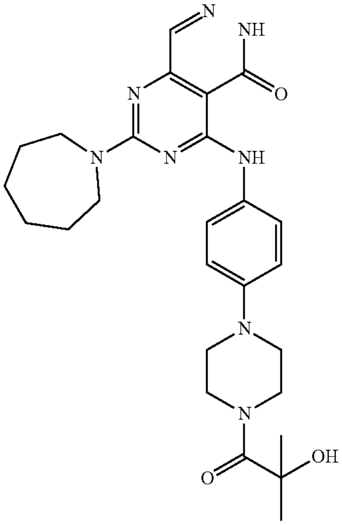 [SMILES: CC(C)(O)C(=O)N1CCN(c2ccc(Nc3nc(N4CCCCCC4)nc(C=N)c3C(N)=O)cc2)CC1] | 2-(azepan-1-yl)-4-((4-(4-(2-hydroxy-2-methylpropanoyl)-piperazin-1-yl)phenyl)amino)-pyrimido[4,5-d]pyridazin-5(6H)-one | 7 |
| 215 | 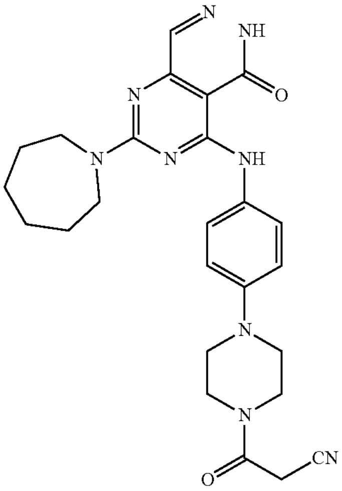 [SMILES: N#CCC(=O)N1CCN(c2ccc(Nc3nc(N4CCCCCC4)nc(C=N)c3C(N)=O)cc2)CC1] | 3-(4-(4-((2-(azepan-1-yl)-5-oxo-5,6-dihydropyrimido[4,5-d]pyridazin-4-yl)amino)-phenyl)piperazin-1-yl)-3-oxopropanenitrile | 7 |
| 216 | 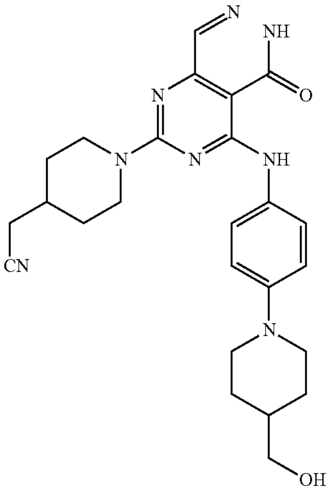 [SMILES: N#CCC1CCN(c2nc(C=N)c(C(N)=O)c(Nc3ccc(N4CCC(CO)CC4)cc3)n2)CC1] | 2-(1-(4-((4-(4-(hydroxymethyl)-piperidin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 217 | 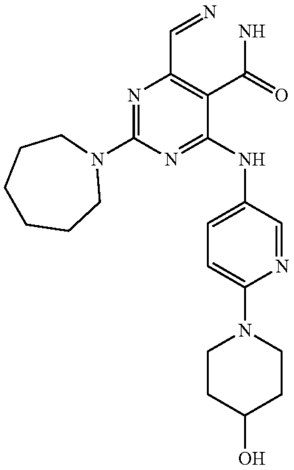 [SMILES: N=Cc1nc(N2CCCCCC2)nc(Nc2ccc(N3CCC(O)CC3)nc2)c1C(N)=O] | 2-(azepan-1-yl)-4-((6-(4-hydroxypiperidin-1-yl)pyridin-3-yl)amino)pyrimido[4,5-d]-pyridazin-5(6H)-one | 7 |
| 218 | 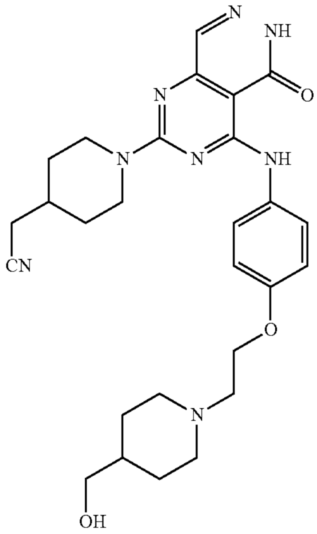 [SMILES: N#CCC1CCN(c2nc(C=N)c(C(N)=O)c(Nc3ccc(OCCN4CCC(CO)CC4)cc3)n2)CC1] | 2-(1-(4-((4-(2-(4-(hydroxy-methyl)piperidin-1-yl)ethoxy)-phenyl)amino)-5-oxo-5,6-dihydropyrimido[4,5-d]-pyridazin-2-yl)piperidin-4-yl)acetonitrile | 7 |
| 219 | 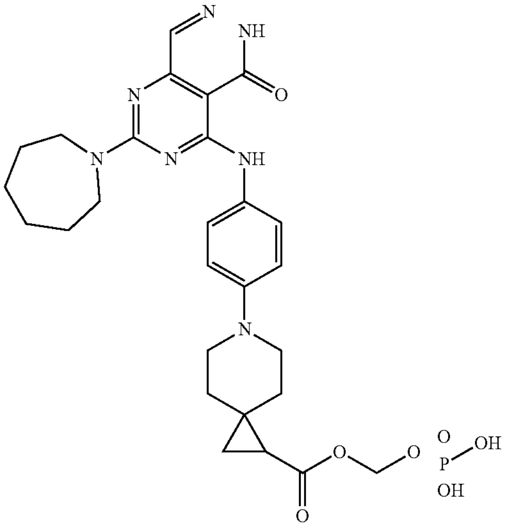 | (phosphonooxy)methyl 6-(4-((2-(azepan-1-yl)-5-oxo-5,6-dihydropyrimido[4,5-d]-pyridazin-4-yl)amino)phenyl)-6-azaspiro[2.5]octane-1-carboxylate | 7 |

TABLE 1-continued
| Ex | Structure | IUPAC Name | Synthetic Scheme |
|---|---|---|---|
| 220 | 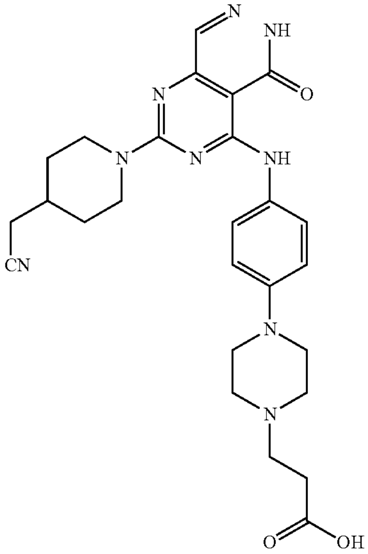 [SMILES: N#CCC1CCN(c2nc(C=N)c(C(N)=O)c(Nc3ccc(N4CCN(CCC(=O)O)CC4)cc3)n2)CC1] | 3-(4-(4-((2-(4-(cyanomethyl)-piperidin-1-yl)-5-oxo-5,6-dihydropyrimido[4,5-d]-pyridazin-4-yl)amino)phenyl)-piperazin-1-yl)propanoic acid | 7 |
| 221 | 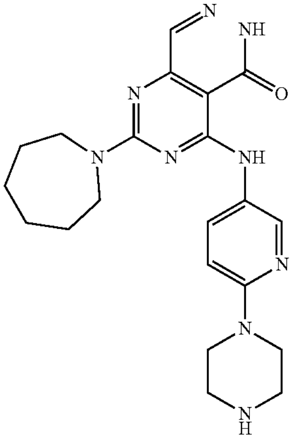 [SMILES: N=Cc1nc(N2CCCCCC2)nc(Nc2ccc(N3CCNCC3)nc2)c1C(N)=O] | 2-(azepan-1-yl)-4-((6-(piperazin-1-yl)pyridin-3-yl)amino)-pyrimido[4,5-d]pyridazin-5(6H)-one | 7 |
| 222 | 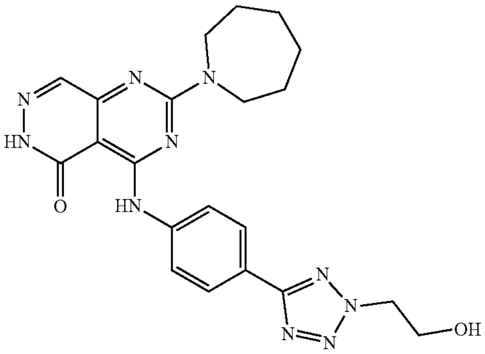 [SMILES: O=c1[nH]ncc2nc(N3CCCCCC3)nc(Nc3ccc(-c4nnn(CCO)n4)cc3)c12] | 2-(azepan-1-yl)-4-((4-(2-(2-hydroxyethyl)-2H-tetrazol-5-yl)phenyl)amino)pyrimido[4,5-d]pyridazin-5(6H)-one | 7 |

TABLE 1-continued
| Ex | Structure | IUPAC Name | Synthetic Scheme |
|---|---|---|---|
| 223 | 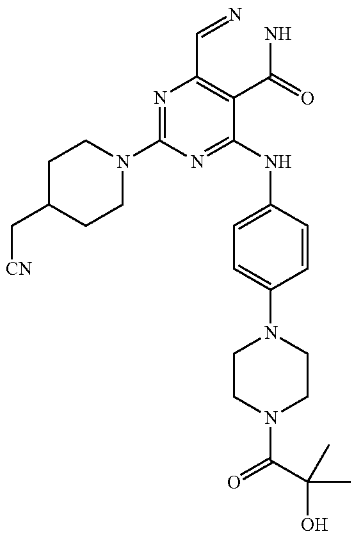 [SMILES: CC(C)(O)C(=O)N1CCN(c2ccc(Nc3nc(N4CCC(CC#N)CC4)nc(C=N)c3C(N)=O)cc2)CC1] | 2-(1-(4-((4-(4-(2-hydroxy-2-methylpropanoyl)piperazin-1-yl)phenyl)amino)-5-oxo-5,6-dihydropyrimido[4,5-d]-pyridazin-2-yl)piperidin-4-yl)acetonitrile | 7 |
| 224 | 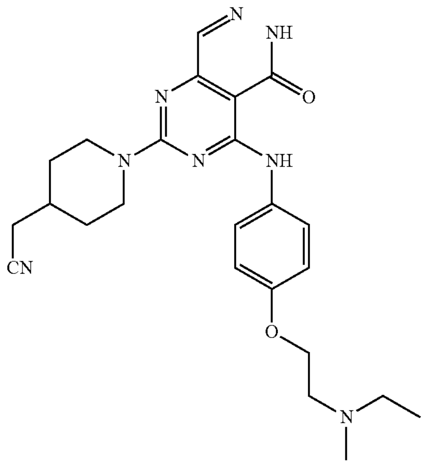 [SMILES: CCN(C)CCOc1ccc(Nc2nc(N3CCC(CC#N)CC3)nc(C=N)c2C(N)=O)cc1] | 2-(1-(4-((4-(2-(diethylamino)-ethoxy)phenyl)amino)-5-oxo-5,6-dihydropyrimido[4,5-d]-pyridazin-2-yl)piperidin-4-yl)acetonitrile | 7 |
| 225 | 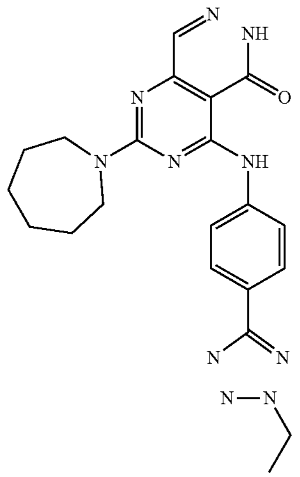 | 2-(azepan-1-yl)-4-((4-(2-ethyl-2H-tetrazol-5-yl)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 226 | 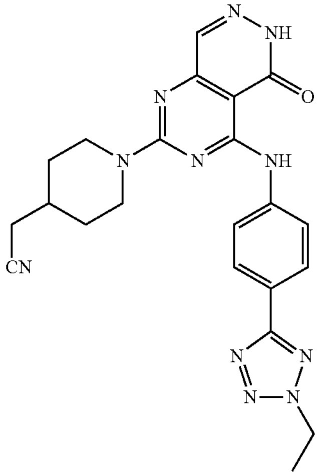 [SMILES: CCn1nnc(-c2ccc(Nc3nc(N4CCC(CC#N)CC4)nc4cn[nH]c(=O)c34)cc2)n1] | 2-(1-(4-((4-(2-ethyl-2H-tetrazol-5-yl)phenyl)amino)-5-oxo-5,6-dihydropyrimido-[4,5-d]pyridazin-2-yl)piperidin-4-yl)acetonitrile | 7 |
| 227 | 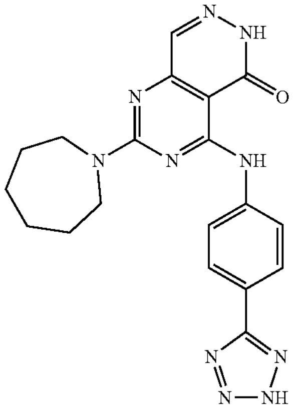 [SMILES: O=c1[nH]ncc2nc(N3CCCCCC3)nc(Nc3ccc(-c4nn[nH]n4)cc3)c12] | 4-((4-(2H-tetrazol-5-yl)phenyl)-amino)-2-(azepan-1-yl)-pyrimido[4,5-d]pyridazin-5(6H)-one | 7 |
| 228 | 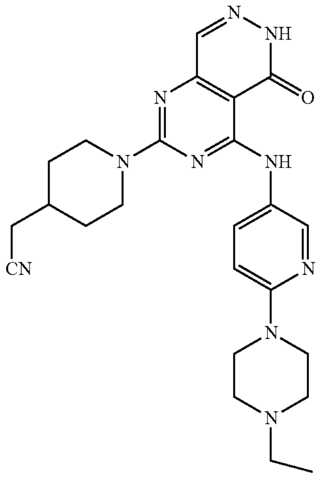 [SMILES: CCN1CCN(c2ccc(Nc3nc(N4CCC(CC#N)CC4)nc4cn[nH]c(=O)c34)cn2)CC1] | 2-(1-(4-((6-(4-ethylpiperazin-1-yl)pyridin-3-yl)amino)-5-oxo-5,6-dihydropyrimido[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 229 | 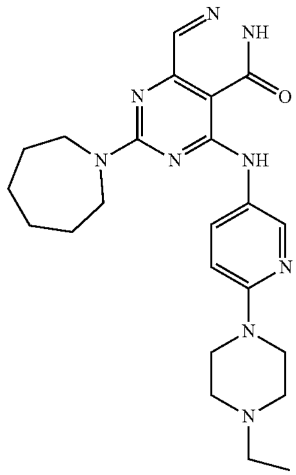 [SMILES: CCN1CCN(c2ccc(Nc3nc(N4CCCCCC4)nc(C=N)c3C(N)=O)cn2)CC1] | 2-(azepan-1-yl)-4-((6-(4-ethylpiperazin-1-yl)pyridin-3-yl)amino)pyrimido[4,5-d]-pyridazin-5(6H)-one | 7 |
| 230 | 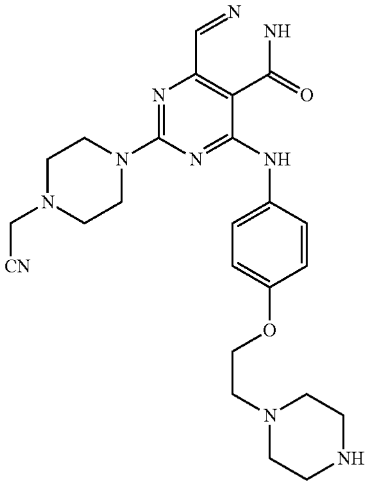 [SMILES: N#CCN1CCN(c2nc(C=N)c(C(N)=O)c(Nc3ccc(OCCN4CCNCC4)cc3)n2)CC1] | 2-(4-(5-oxo-4-((4-(2-(piperazin-1-yl)ethoxy)-phenyl)amino)-5,6-dihydropyrimido[4,5-d]-pyridazin-2-yl)piperazin-1-yl)acetonitrile | 7 |
| 231 | 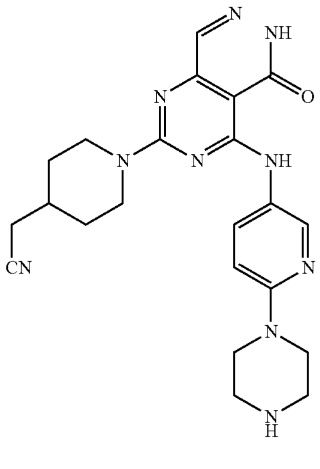 [SMILES: N#CCC1CCN(c2nc(C=N)c(C(N)=O)c(Nc3ccc(N4CCNCC4)nc3)n2)CC1] | 2-(1-(5-oxo-4-((6-(piperazin-1-yl)pyridin-3-yl)amino)-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
| --- | --- | --- | --- |
| 232 | 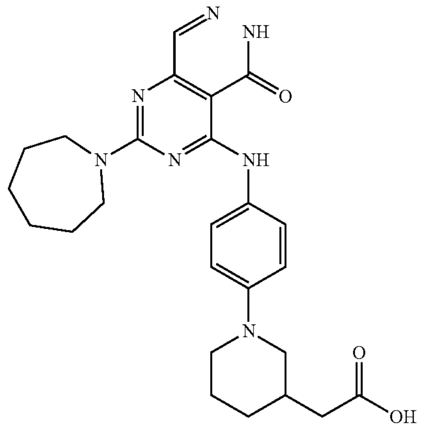 [SMILES: N=Cc1nc(N2CCCCCC2)nc(Nc2ccc(N3CCCC(CC(=O)O)C3)cc2)c1C(N)=O] | 2-(1-(4-((2-(azepan-1-yl)-5-oxo-5,6-dihydropyrimido[4,5-d]-pyridazin-4-yl)amino)phenyl)-piperidin-3-yl)acetic acid | 7 |
| 233 | 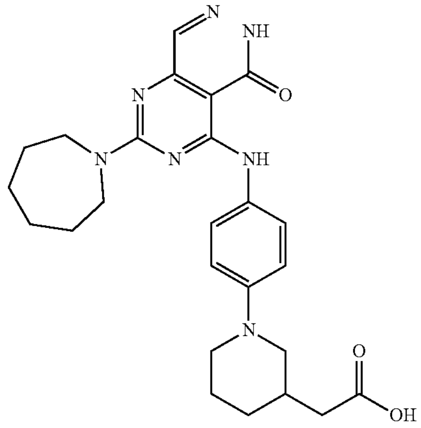 [SMILES: N=Cc1nc(N2CCCCCC2)nc(Nc2ccc(N3CCCC(CC(=O)O)C3)cc2)c1C(N)=O] | 2-(1-(4-((2-(azepan-1-yl)-5-oxo-5,6-dihydropyrimido[4,5-d]-pyridazin-4-yl)amino)phenyl)-piperidin-3-yl)acetic acid | 7 |
| 234 | 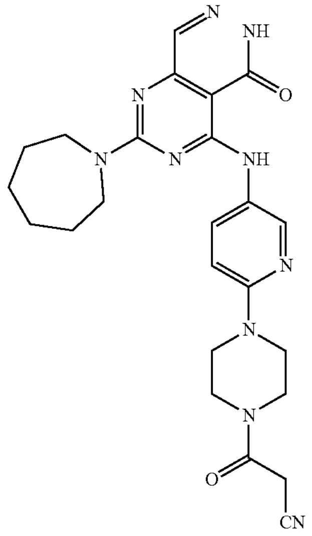 [SMILES: N#CCC(=O)N1CCN(c2ccc(Nc3nc(N4CCCCCC4)nc(C=N)c3C(N)=O)cn2)CC1] | 3-(4-(5-((2-(azepan-1-yl)-5-oxo-5,6-dihydropyrimido-[4,5-d]pyridazin-4-yl)amino)-pyridin-2-yl)piperazin-1-yl)-3-oxopropanenitrile | 7 |

TABLE 1-continued
| Ex | Structure | IUPAC Name | Synthetic Scheme |
| --- | --- | --- | --- |
| 235 | 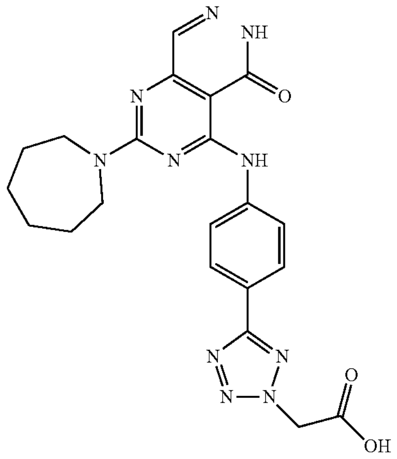 [SMILES: N=Cc1nc(N2CCCCCC2)nc(Nc2ccc(-c3nnn(CC(=O)O)n3)cc2)c1C(N)=O] | 2-(5-(4-((2-(azepan-1-yl)-5-oxo-5,6-dihydropyrimido-[4,5-d]pyridazin-4-yl)amino)-phenyl)-2H-tetrazol-2-yl)acetic acid | 7 |
| 236 | 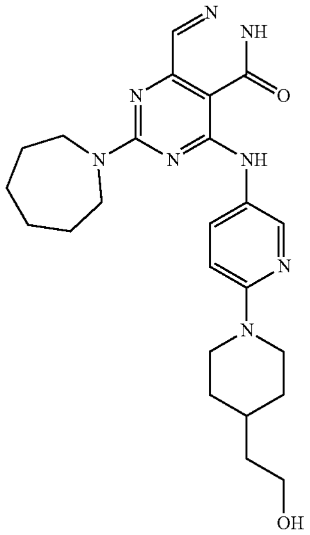 [SMILES: N=Cc1nc(N2CCCCCC2)nc(Nc2ccc(N3CCC(CCO)CC3)nc2)c1C(N)=O] | 2-(azepan-1-yl)-4-((6-(4-(2-hydroxyethyl)piperidin-1-yl)pyridin-3-yl)amino)-pyrimido[4,5-d]pyridazin-5(6H)-one | 7 |
| 237 | 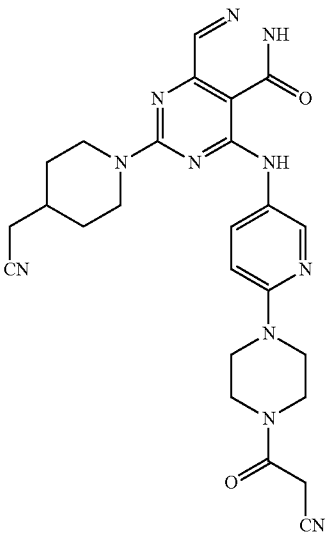 | 3-(4-(5-((2-(4-(cyanomethyl)-piperidin-1-yl)-5-oxo-5,6-dihydropyrimido[4,5-d]-pyridazin-4-yl)amino)pyridin-2-yl)piperazin-1-yl)-3-oxo-propanenitrile | 7 |

TABLE 1-continued
| Ex | Structure | IUPAC Name | Synthetic Scheme |
|---|---|---|---|
| 238 | 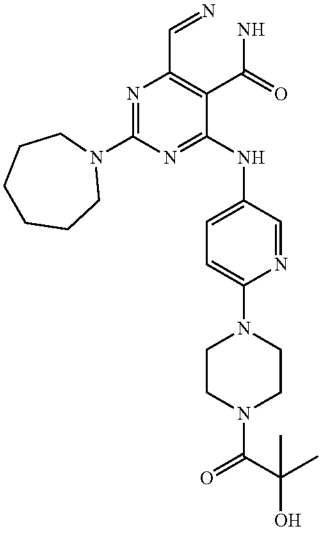 [SMILES: CC(C)(O)C(=O)N1CCN(c2ccc(Nc3nc(N4CCCCCC4)nc(C=N)c3C(N)=O)cn2)CC1] | 2-(azepan-1-yl)-4-((6-(4-(2-hydroxy-2-methylpropanoyl)-piperazin-1-yl)pyridin-3-yl)-amino)pyrimido[4,5-d]-pyridazin-5(6H)-one | 7 |
| 239 | 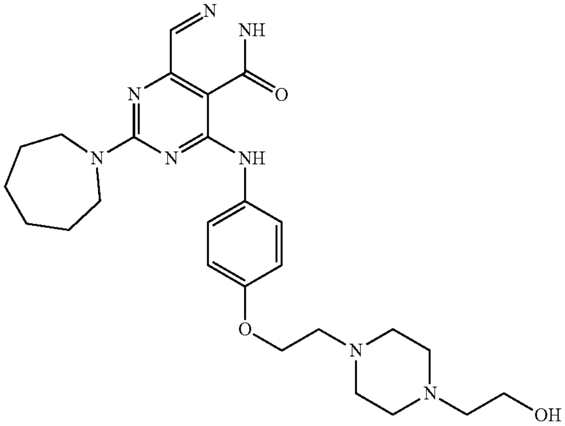 [SMILES: N=Cc1nc(N2CCCCCC2)nc(Nc2ccc(OCCN3CCN(CCO)CC3)cc2)c1C(N)=O] | 2-(azepan-1-yl)-4-((4-(2-(4-(2-hydroxyethyl)piperazin-1-yl)ethoxy)phenyl)amino)-pyrimido[4,5-d]pyridazin-5(6H)-one | 7 |
| 240 | 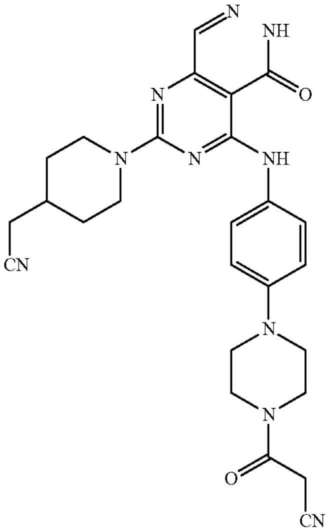 | 3-(4-(4-((2-(4-(cyanomethyl)-piperidin-1-yl)-5-oxo-5,6-dihydropyrimido[4,5-d]-pyridazin-4-yl)amino)phenyl)-piperazin-1-yl)-3-oxopropane-nitrile | 7 |

TABLE 1-continued
| Ex | Structure | IUPAC Name | Synthetic Scheme |
| --- | --- | --- | --- |
| 241 | 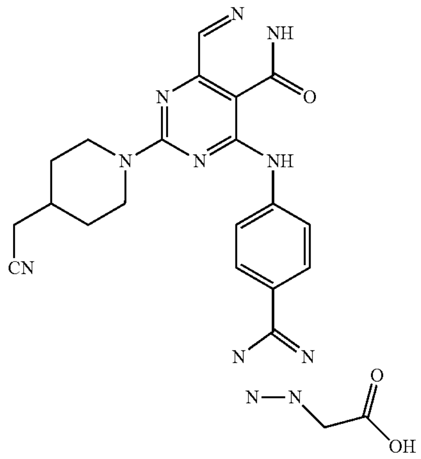 | 2-(5-(4-((2-(4-(cyanomethyl)-piperidin-1-yl)-5-oxo-5,6-dihydropyrimido[4,5-d]-pyridazin-4-yl)amino)phenyl)-2H-tetrazol-2-yl)acetic acid | 7 |
| 242 | 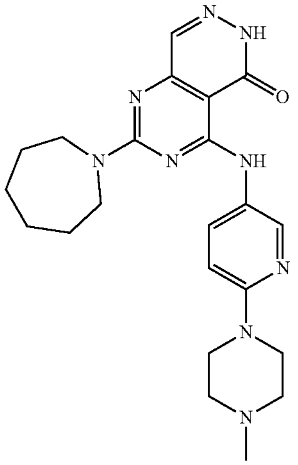 [SMILES: CN1CCN(c2ccc(Nc3nc(N4CCCCCC4)nc4cn[nH]c(=O)c34)cn2)CC1] | 2-(azepan-1-yl)-4-((6-(4-methylpiperazin-1-yl)pyridin-3-yl)amino)pyrimido[4,5-d]-pyridazin-5(6H)-one | 7 |
| 243 | 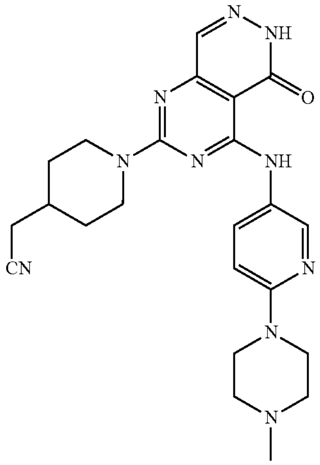 [SMILES: CN1CCN(c2ccc(Nc3nc(N4CCC(CC#N)CC4)nc4cn[nH]c(=O)c34)cn2)CC1] | 2-(1-(4-((6-(4-methylpiperazin-1-yl)pyridin-3-yl)amino)-5-oxo-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
| --- | --- | --- | --- |
| 244 | 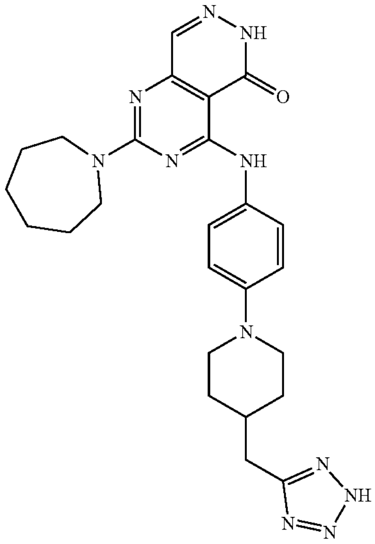 [SMILES: O=c1[nH]ncc2nc(N3CCCCCC3)nc(Nc3ccc(N4CCC(Cc5nn[nH]n5)CC4)cc3)c12] | 4-((4-(4-((2H-tetrazol-5-yl)-methyl)piperidin-1-yl)phenyl)-amino)-2-(azepan-1-yl)-pyrimido-[4,5-d]pyridazin-5(6H)-one | 7 |
| 245 | 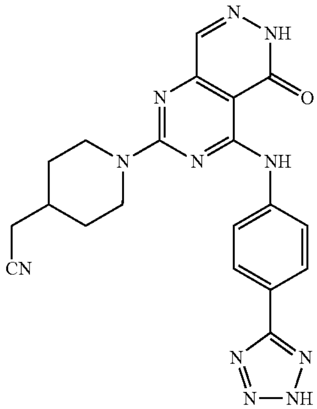 [SMILES: N#CCC1CCN(c2nc(Nc3ccc(-c4nn[nH]n4)cc3)c3c(=O)[nH]ncc3n2)CC1] | 2-(1-(4-((4-(2H-tetrazol-5-yl)phenyl)amino)-5-oxo-5,6-dihydropyrimido[4,5-d]-pyridazin-2-yl)piperidin-4-yl)acetonitrile | 7 |
| 246 | 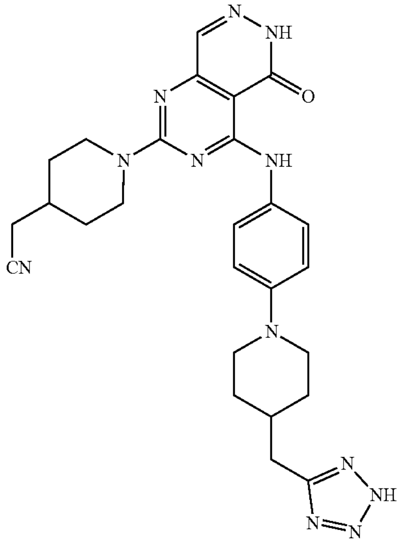 [SMILES: N#CCC1CCN(c2nc(Nc3ccc(N4CCC(Cc5nn[nH]n5)CC4)cc3)c3c(=O)[nH]ncc3n2)CC1] | 2-(1-(4-((4-(4-((2H-tetrazol-5-yl)methyl)piperidin-1-yl)-phenyl)amino)-5-oxo-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 247 | 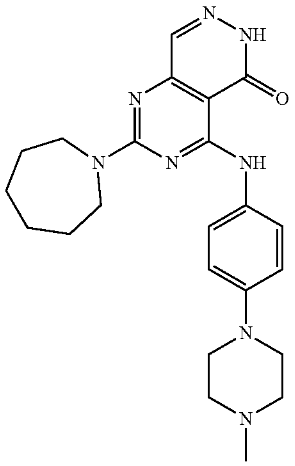 [SMILES: CN1CCN(c2ccc(Nc3nc(N4CCCCCC4)nc4cn[nH]c(=O)c34)cc2)CC1] | 2-(azepan-1-yl)-4-((4-(4-methylpiperazin-1-yl)phenyl)-amino)pyrimido[4,5-d]-pyridazin-5(6H)-one | 7 |
| 248 | 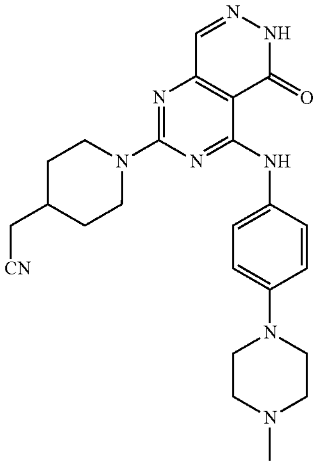 [SMILES: CN1CCN(c2ccc(Nc3nc(N4CCC(CC#N)CC4)nc4cn[nH]c(=O)c34)cc2)CC1] | 2-(1-(4-((4-(4-methylpiperazin-1-yl)phenyl)amino)-5-oxo-5,6-dihydropyrimido[4,5-d]-pyridazin-2-yl)piperidin-4-yl)acetonitrile | 7 |
| 249 | 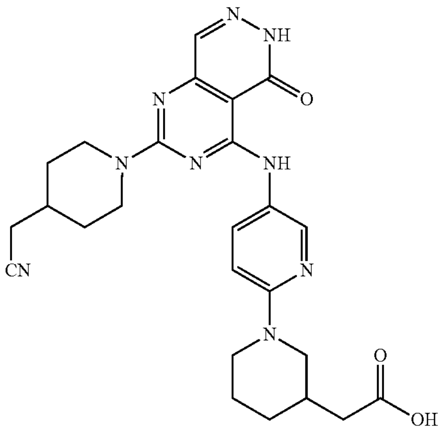 | 2-(1-(5-((2-(4-(cyanomethyl)-piperidin-1-yl)-5-oxo-5,6-dihydropyrimido[4,5-d]-pyridazin-4-yl)amino)pyridin-2-yl)piperidin-3-yl)acetic acid | 7 |

TABLE 1-continued

| Ex | Structure | IUPAC Name | Synthetic Scheme |
|---|---|---|---|
| 250 | 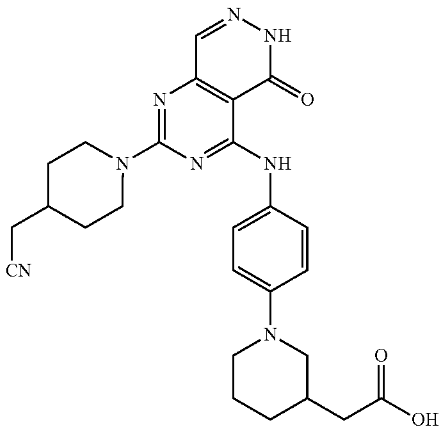 | 2-(1-(4-((2-(4-(cyanomethyl)-piperidin-1-yl)-5-oxo-5,6-dihydropyrimido[4,5-d]-pyridazin-4-yl))amino)phenyl)-piperidin-3-yl)acetic acid | 7 |
| 251 | 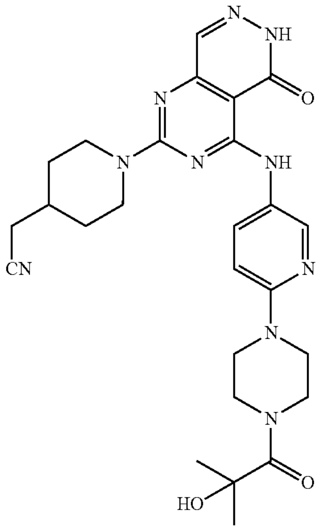 [SMILES: CC(C)(O)C(=O)N1CCN(c2ccc(Nc3nc(N4CCC(CC#N)CC4)nc4cn[nH]c(=O)c34)cn2)CC1] | 2-(1-(4-((6-(4-(2-hydroxy-2-methylpropanoyl)piperazin-1-yl)pyridin-3-yl)amino)-5-oxo-5,6-dihydropyrimido[4,5-d]-pyridazin-2-yl)piperidin-4-yl)acetonitrile | 7 |
| 252 | 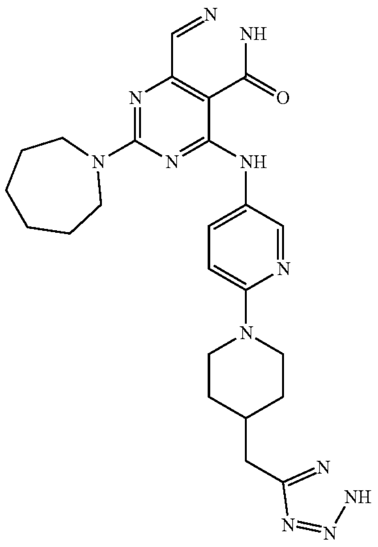 [SMILES: N=Cc1nc(N2CCCCCC2)nc(Nc2ccc(N3CCC(CC(=N)/N=N\N)CC3)nc2)c1C(N)=O] | 4-((6-(4-((2H-tetrazol-5-yl)-methyl)piperidin-1-yl)pyridin-3-yl)amino)-2-(azepan-1-yl)-pyrimido[4,5-d]pyridazin-5(6H)-one | 7 |

TABLE 1-continued
| Ex | Structure | IUPAC Name | Synthetic Scheme |
|---|---|---|---|
| 253 | 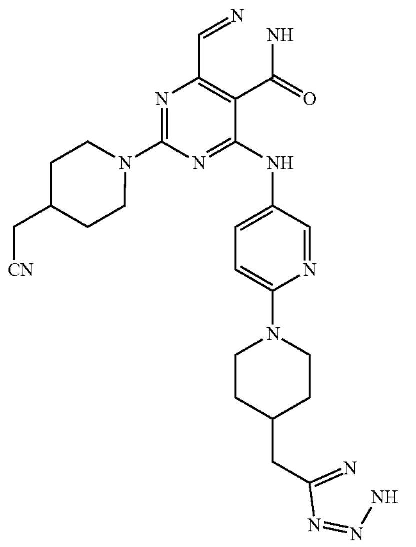 [SMILES: N#CCC1CCN(c2nc(C=N)c(C(N)=O)c(Nc3ccc(N4CCC(CC(=N)/N=N\N)CC4)nc3)n2)CC1] | 2-(1-(4-((6-(4-((2H-tetrazol-5-yl)methyl)piperidin-1-yl)-pyridin-3-yl)amino)-5-oxo-5,6-dihydropyrimido[4,5-d]-pyridazin-2-yl)piperidin-4-yl)acetonitrile | 7 |
| 254 | 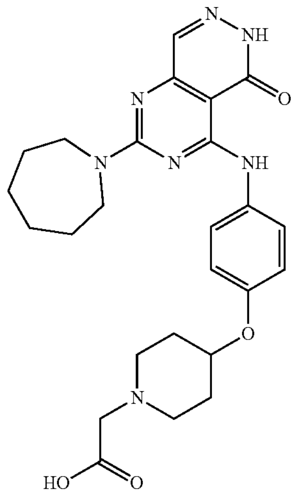 [SMILES: O=C(O)CN1CCC(Oc2ccc(Nc3nc(N4CCCCCC4)nc4cn[nH]c(=O)c34)cc2)CC1] | 2-(4-(4-((2-(azepan-1-yl)-5-oxo-5,6-dihydropyrimido-[4,5-d]pyridazin-4-yl)amino)-phenoxy)piperidin-1-yl)acetic acid | 7 |
| 255 | 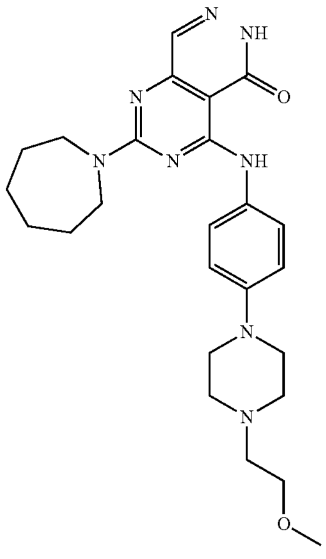 [SMILES: COCCN1CCN(c2ccc(Nc3nc(N4CCCCCC4)nc(C=N)c3C(N)=O)cc2)CC1] | 2-(azepan-1-yl)-4-((4-(4-(2-methoxyethyl)piperazin-1-yl)phenyl)amino)pyrimido-[4,5-d]pyridazin-5(6H)-one | 7 |

TABLE 1-continued
| Ex | Structure | IUPAC Name | Synthetic Scheme |
|---|---|---|---|
| 256 | 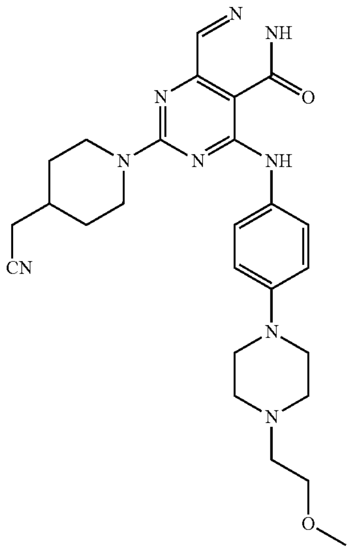 [SMILES: COCCN1CCN(c2ccc(Nc3nc(N4CCC(CC#N)CC4)nc(C=N)c3C(N)=O)cc2)CC1] | 2-(1-(4-((4-(4-(2-methoxyethyl)-piperazin-1-yl)phenyl)amino)-5-oxo-5,6-dihydropyrimido-[4,5-d]pyridazin-2-yl)piperidin-4-yl)acetonitrile | 7 |
| 257 | 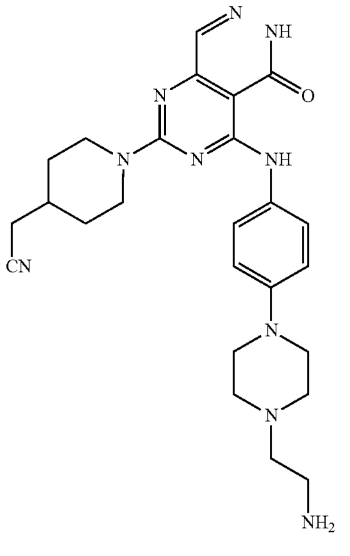 [SMILES: N#CCC1CCN(c2nc(C=N)c(C(N)=O)c(Nc3ccc(N4CCN(CCN)CC4)cc3)n2)CC1] | 2-(1-(4-((4-(4-(2-aminoethyl)-piperazin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 258 | 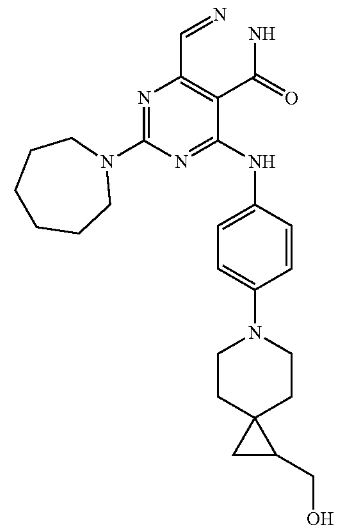 [SMILES: N=Cc1nc(N2CCCCCC2)nc(Nc2ccc(N3CCC4(CC3)CC4CO)cc2)c1C(N)=O] | 2-(azepan-1-yl)-4-((4-(1-(hydroxymethyl)-6-azaspiro-[2.5]octan-6-yl)phenyl)amino)-pyrimido[4,5-d]pyridazin-5(6H)-one | 7 |
| 259 | 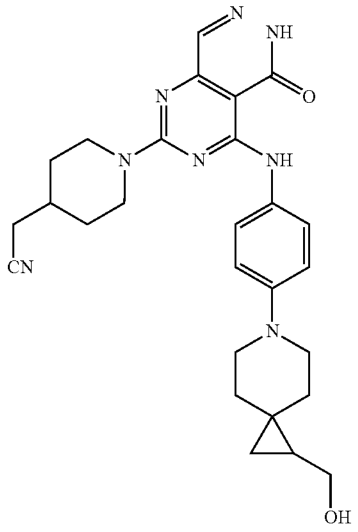 [SMILES: N#CCC1CCN(c2nc(C=N)c(C(N)=O)c(Nc3ccc(N4CCC5(CC4)CC5CO)cc3)n2)CC1] | 2-(1-(4-((4-(1-(hydroxymethyl)-6-azaspiro[2.5]octan-6-yl)-phenyl)amino)-5-oxo-5,6-dihydropyrimido[4,5-d]-pyridazin-2-yl)piperidin-4-yl)acetonitrile | 7 |
| 260 | 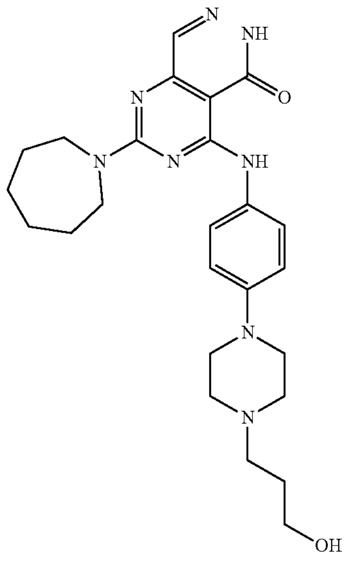 | 2-(azepan-1-yl)-4-((4-(4-(3-hydroxypropyl)piperazin-1-yl)phenyl)amino)pyrimido-[4,5-d]pyridazin-5(6H)-one | 7 |

TABLE 1-continued
| Ex | Structure | IUPAC Name | Synthetic Scheme |
|---|---|---|---|
| 261 | 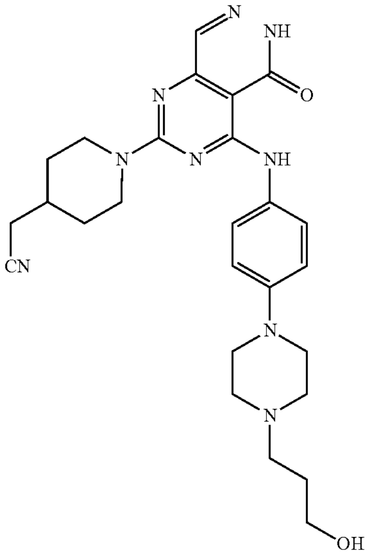 [SMILES: N#CCC1CCN(c2nc(C=N)c(C(N)=O)c(Nc3ccc(N4CCN(CCCO)CC4)cc3)n2)CC1] | 2-(1-(4-((4-(4-(3-hydroxy-propyl)piperazin-1-yl)phenyl)-amino)-5-oxo-5,6-dihydro-pyrimido[4,5-d]pyridazin-2-yl)piperidin-4-yl)acetonitrile | 7 |
| 262 | 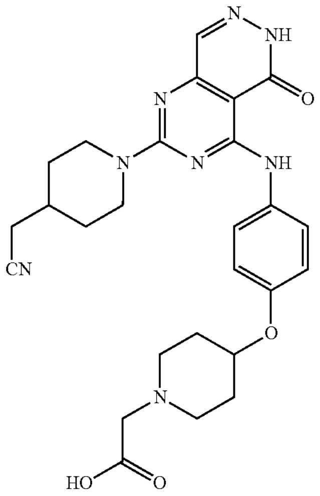 [SMILES: N#CCC1CCN(c2nc(Nc3ccc(OC4CCN(CC(=O)O)CC4)cc3)c3c(=O)[nH]ncc3n2)CC1] | 2-(4-(4-((2-(4-(cyanomethyl)-piperidin-1-yl)-5-oxo-5,6-dihydropyrimido[4,5-d]-pyridazin-4-yl)amino)phenoxy)-piperidin-1-yl)acetic acid | 7 |
| 263 | 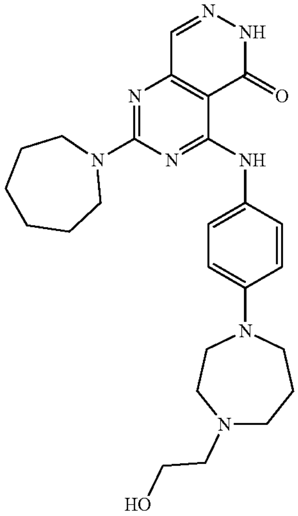 [SMILES: O=c1[nH]ncc2nc(N3CCCCCC3)nc(Nc3ccc(N4CCCN(CCO)CC4)cc3)c12] | 2-(azepan-1-yl)-4-((4-(4-(2-hydroxyethyl)-1,4-diazepan-1-yl)phenyl)amino)pyrimido-[4,5-d]pyridazin-5(6H)-one | 7 |

TABLE 1-continued

| Ex | Structure | IUPAC Name | Synthetic Scheme |
|---|---|---|---|
| 264 | 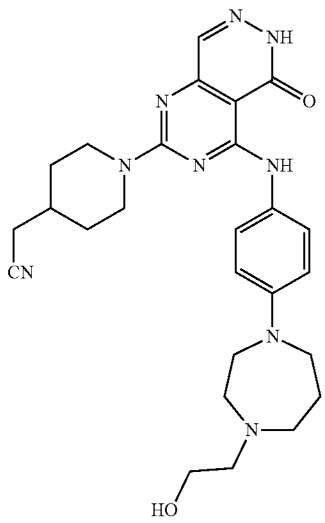 [SMILES: N#CCC1CCN(c2nc(Nc3ccc(N4CCCN(CCO)CC4)cc3)c3c(=O)[nH]ncc3n2)CC1] | 2-(1-(4-((4-(4-(2-hydroxyethyl)-1,4-diazepan-1-yl)phenyl)-amino)-5-oxo-5,6-dihydro-pyrimido[4,5-d]pyridazin-2-yl)piperidin-4-yl)acetonitrile | 7 |
| 265 | 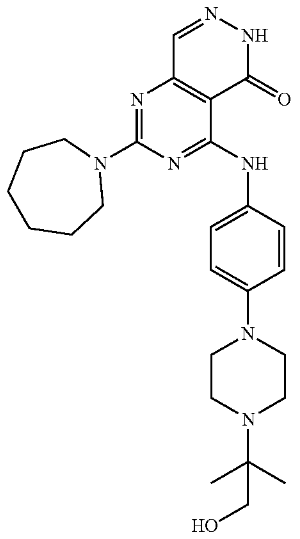 [SMILES: CC(C)(CO)N1CCN(c2ccc(Nc3nc(N4CCCCCC4)nc4cn[nH]c(=O)c34)cc2)CC1] | 2-(azepan-1-yl)-4-((4-(4-(1-hydroxy-2-methylpropan-2-yl)piperazin-1-yl)phenyl)-amino)pyrimido[4,5-d]-pyridazin-5(6H)-one | 7 |
| 266 | 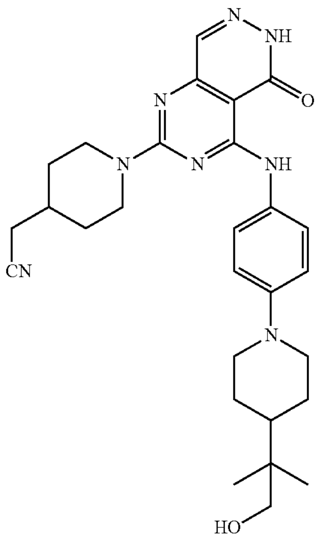 [SMILES: CC(C)(CO)C1CCN(c2ccc(Nc3nc(N4CCC(CC#N)CC4)nc4cn[nH]c(=O)c34)cc2)CC1] | 2-(1-(4-((4-(4-(1-hydroxy-2-methylpropan-2-yl)piperazin-1-yl)phenyl)amino)-5-oxo-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 267 | 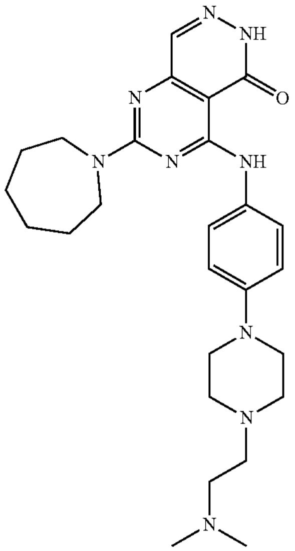 [SMILES: CN(C)CCN1CCN(c2ccc(Nc3nc(N4CCCCCC4)nc4cn[nH]c(=O)c34)cc2)CC1] | 2-(azepan-1-yl)-4-((4-(4-(2-(dimethylamino)ethyl)piperazin-1-yl)phenyl)amino)pyrimido-[4,5-d]pyridazin-5(6H)-one | 7 |
| 268 | 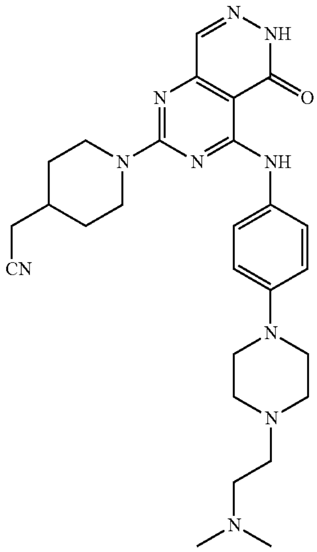 [SMILES: CN(C)CCN1CCN(c2ccc(Nc3nc(N4CCC(CC#N)CC4)nc4cn[nH]c(=O)c34)cc2)CC1] | 2-(1-(4-((4-(4-(2-(dimethyl-amino)ethyl)piperazin-1-yl)phenyl)amino)-5-oxo-5,6-dihydropyrimido[4,5-d]-pyridazin-2-yl)piperidin-4-yl)acetonitrile | 7 |
| 269 | 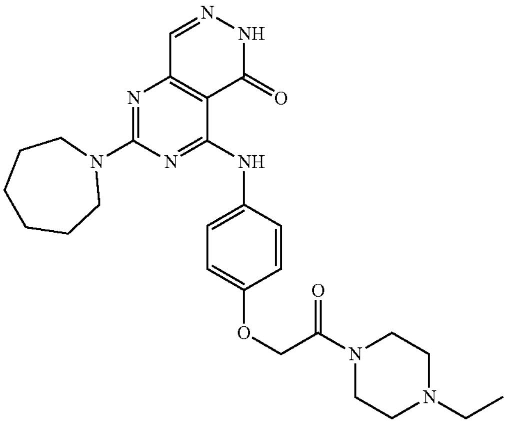 [SMILES: CCN1CCN(C(=O)COc2ccc(Nc3nc(N4CCCCCC4)nc4cn[nH]c(=O)c34)cc2)CC1] | 2-(azepan-1-yl)-4-((4-(2-(4-ethylpiperazin-1-yl)-2-oxoethoxy)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 270 | 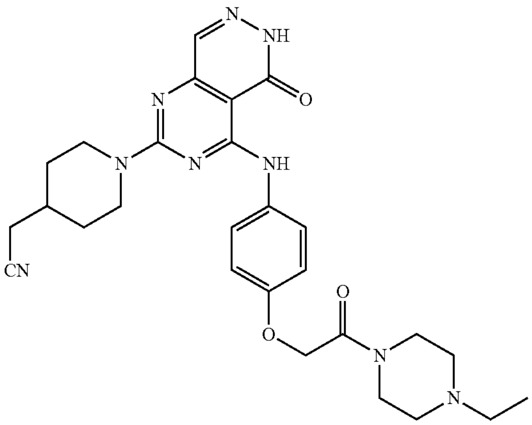 [SMILES: CCN1CCN(C(=O)COc2ccc(Nc3nc(N4CCC(CC#N)CC4)nc4cn[nH]c(=O)c34)cc2)CC1] | 2-(1-(4-((4-(2-(4-ethylpiperazin-1-yl)-2-oxoethoxy)phenyl)-amino)-5-oxo-5,6-dihydro-pyrimido[4,5-d]pyridazin-2-yl)piperidin-4-yl)acetonitrile | 7 |
| 271 | 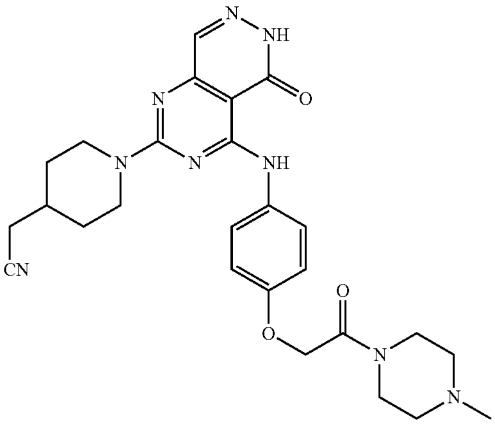 [SMILES: CN1CCN(C(=O)COc2ccc(Nc3nc(N4CCC(CC#N)CC4)nc4cn[nH]c(=O)c34)cc2)CC1] | 2-(1-(4-((4-(2-(4-methyl-piperazin-1-yl)-2-oxoethoxy)-phenyl)amino)-5-oxo-5,6-dihydropyrimido[4,5-d]-pyridazin-2-yl)piperidin-4-yl)acetonitrile | 7 |
| 272 | 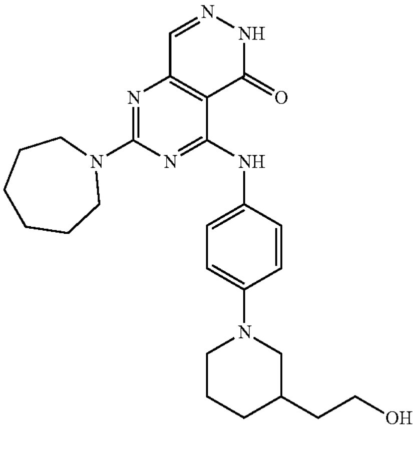 [SMILES: O=c1[nH]ncc2nc(N3CCCCCC3)nc(Nc3ccc(N4CCCC(CCO)C4)cc3)c12] | 2-(azepan-1-yl)-4-((4-(3-(2-hydroxyethyl)piperidin-1-yl)phenyl)amino)pyrimido-[4,5-d]pyridazin-5(6H)-one | 7 |

TABLE 1-continued
| Ex | Structure | IUPAC Name | Synthetic Scheme |
|---|---|---|---|
| 273 | 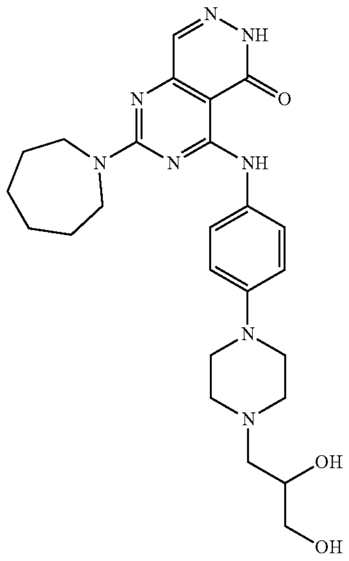 [SMILES: O=c1[nH]ncc2nc(N3CCCCCC3)nc(Nc3ccc(N4CCN(CC(O)CO)CC4)cc3)c12] | 2-(azepan-1-yl)-4-((4-(4-(2,3-dihydroxypropyl)piperazin-1-yl)phenyl)amino)pyrimido-[4,5-d]pyridazin-5(6H)-one | 7 |
| 274 | 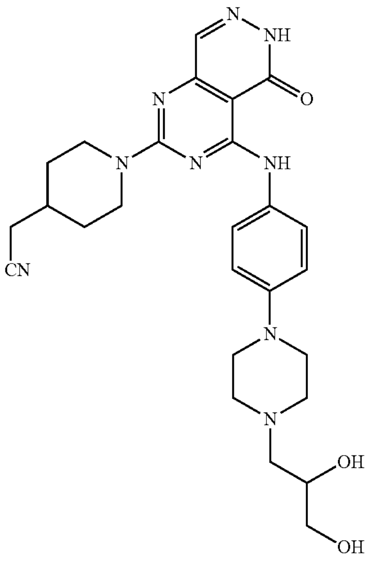 [SMILES: N#CCC1CCN(c2nc(Nc3ccc(N4CCN(CC(O)CO)CC4)cc3)c3c(=O)[nH]ncc3n2)CC1] | 2-(1-(4-((4-(4-(2,3-dihydroxy-propyl)piperazin-1-yl)phenyl)-amino)-5-oxo-5,6-dihydro-pyrimido[4,5-d]pyridazin-2-yl)piperidin-4-yl)acetonitrile | 7 |

TABLE 1-continued
| Ex | Structure | IUPAC Name | Synthetic Scheme |
| --- | --- | --- | --- |
| 275 | 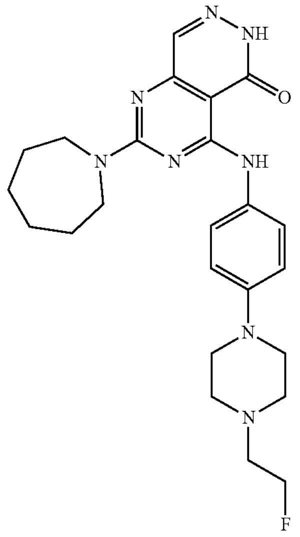 [SMILES: O=c1[nH]ncc2nc(N3CCCCCC3)nc(Nc3ccc(N4CCN(CCF)CC4)cc3)c12] | 2-(azepan-1-yl)-4-((4-(4-(2-fluoroethyl)piperazin-1-yl)phenyl)amino)pyrimido-[4,5-d]pyridazin-5(6H)-one | 7 |
| 276 | 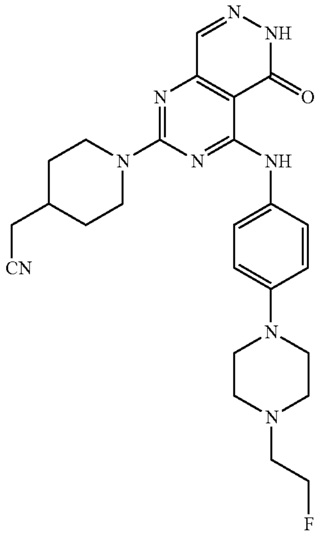 [SMILES: N#CCC1CCN(c2nc(Nc3ccc(N4CCN(CCF)CC4)cc3)c3c(=O)[nH]ncc3n2)CC1] | 2-(1-(4-((4-(4-(2-fluoroethyl)-piperazin-1-yl)phenyl)amino)-5-oxo-5,6-dihydropyrimido-[4,5-d]pyridazin-2-yl)piperidin-4-yl)acetonitrile | 7 |
| 277 | 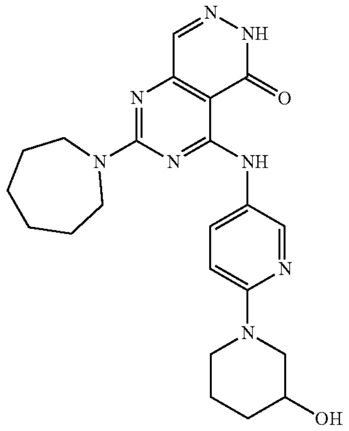 [SMILES: O=c1[nH]ncc2nc(N3CCCCCC3)nc(Nc3ccc(N4CCCC(O)C4)nc3)c12] | 2-(azepan-1-yl)-4-((6-(3-hydro-piperidin-1-yl)pyridin-3-yl)-amino)pyrimido[4,5-d]-pyridazin-5(6H)-one | 7 |

TABLE 1-continued
| Ex | Structure | IUPAC Name | Synthetic Scheme |
|---|---|---|---|
| 278 | 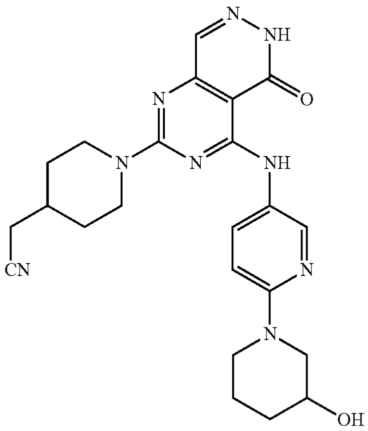 [SMILES: N#CCC1CCN(c2nc(Nc3ccc(N4CCCC(O)C4)nc3)c3c(=O)[nH]ncc3n2)CC1] | 2-(1-(4-((6-(3-hydroxypiperidin-1-yl)pyridin-3-yl)amino)-5-oxo-5,6-dihydropyrimido[4,5-d]-pyridazin-2-yl)piperidin-4-yl)acetonitrile | 7 |
| 279 | 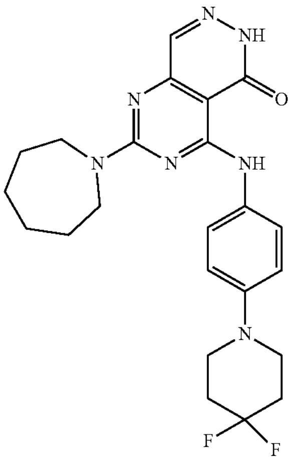 [SMILES: O=c1[nH]ncc2nc(N3CCCCCC3)nc(Nc3ccc(N4CCC(F)(F)CC4)cc3)c12] | 2-(azepan-1-yl)-4-((4-(4,4-difluoropiperidin-1-yl)phenyl)-amino)pyrimido[4,5-d]-pyridazin-5(6H)-one | 7 |
| 280 | 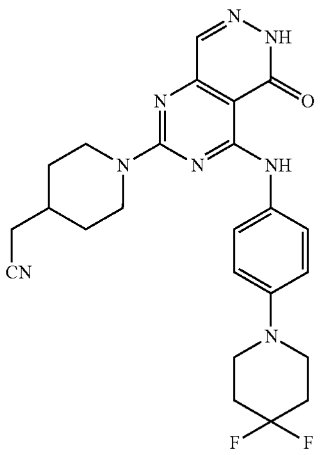 [SMILES: N#CCC1CCN(c2nc(Nc3ccc(N4CCC(F)(F)CC4)cc3)c3c(=O)[nH]ncc3n2)CC1] | 2-(1-(4-((4-(4,4-difluoro-piperidin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 281 | 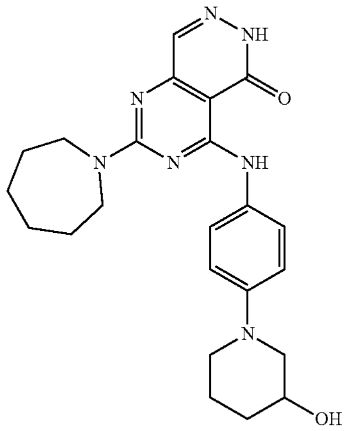 | 2-(azepan-1-yl)-4-((4-(3-hydroxypiperidin-1-yl)phenyl)-amino)pyrimido[4,5-d]-pyridazin-5(6H)-one | 7 |
| 282 | 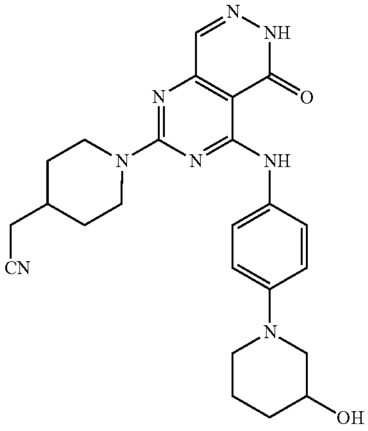 | 2-(1-(4-((4-(3-hydroxypiperidin-1-yl)phenyl)amino)-5-oxo-5,6-dihydropyrimido[4,5-d]-pyridazin-2-yl)piperidin-4-yl)acetonitrile | 7 |
| 283 | 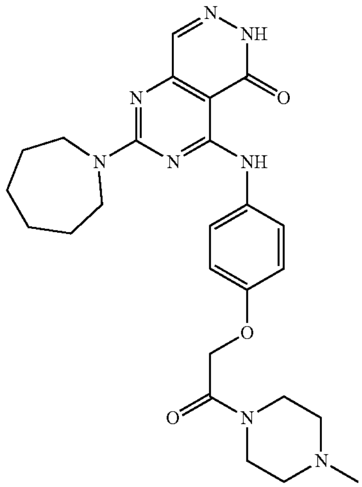 [SMILES: CN1CCN(C(=O)COc2ccc(Nc3nc(N4CCCCCC4)nc4cn[nH]c(=O)c34)cc2)CC1] | 2-(azepan-1-yl)-4-((4-(2-(4-methylpiperazin-1-yl)-2-oxoethoxy)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 284 | 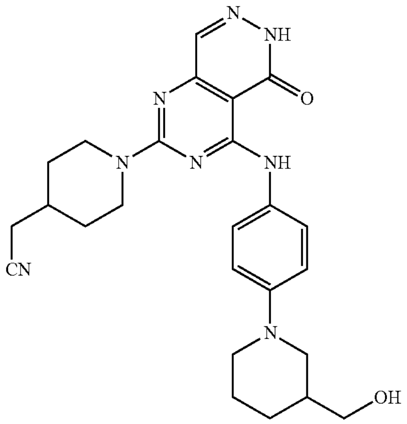 [SMILES: N#CCC1CCN(c2nc(Nc3ccc(N4CCCC(CO)C4)cc3)c3c(=O)[nH]ncc3n2)CC1] | 2-(1-(4-((4-(3-(hydroxymethyl)-piperidin-1-yl)phenyl)amino)-5-oxo-5,6-dihydropyrimido-[4,5-d]pyridazin-2-yl)piperidin-4-yl)acetonitrile | 7 |
| 285 | 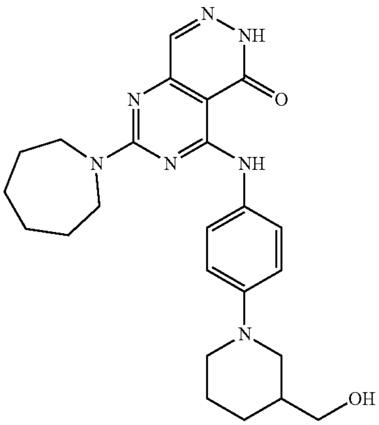 [SMILES: O=c1[nH]ncc2nc(N3CCCCCC3)nc(Nc3ccc(N4CCCC(CO)C4)cc3)c12] | 2-(azepan-1-yl)-4-((4-(3-(hydroxymethyl)piperidin-1-yl)phenyl)amino)pyrimido-[4,5-d]pyridazin-5(6H)-one | 7 |
| 286 | 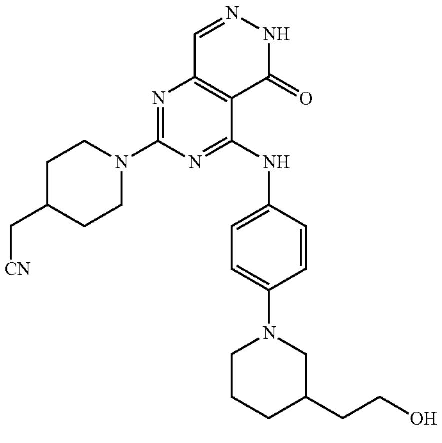 [SMILES: N#CCC1CCN(c2nc(Nc3ccc(N4CCCC(CCO)C4)cc3)c3c(=O)[nH]ncc3n2)CC1] | 2-(1-(4-((4-(3-(2-hydroxyethyl)-piperidin-1-yl)phenyl)amino)-5-oxo-5,6-dihydropyrimido-[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 287 | 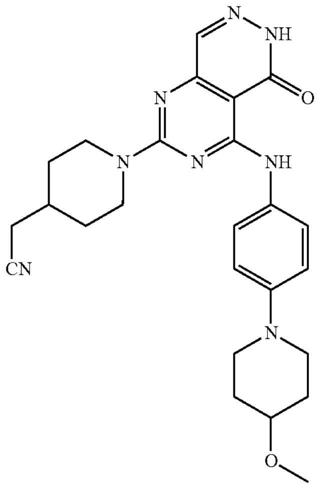 [SMILES: COC1CCN(c2ccc(Nc3nc(N4CCC(CC#N)CC4)nc4cn[nH]c(=O)c34)cc2)CC1] | 2-(1-(4-((4-(4-methoxypiperidin-1-yl)phenyl)amino)-5-oxo-5,6-dihydropyrimido[4,5-d]-pyridazin-2-yl)piperidin-4-yl)acetonitrile | 7 |
| 288 | 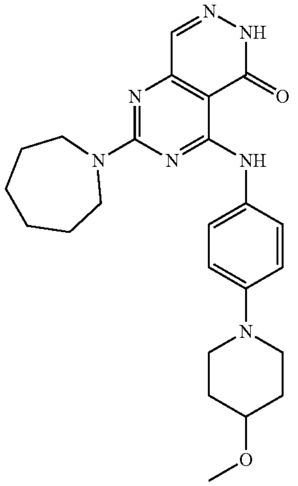 [SMILES: COC1CCN(c2ccc(Nc3nc(N4CCCCCC4)nc4cn[nH]c(=O)c34)cc2)CC1] | 2-(azepan-1-yl)-4-((4-(4-methoxypiperidin-1-yl)phenyl)-amino)pyrimido[4,5-d]-pyridazin-5(6H)-one | 7 |
| 289 | 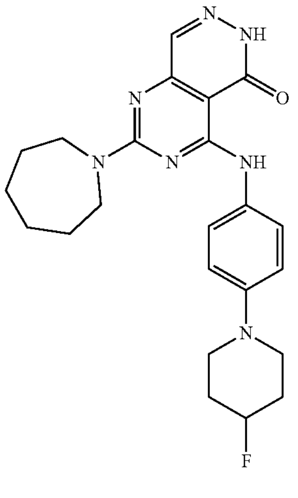 [SMILES: O=c1[nH]ncc2nc(N3CCCCCC3)nc(Nc3ccc(N4CCC(F)CC4)cc3)c12] | 2-(azepan-1-yl)-4-((4-(4-fluoropiperidin-1-yl)phenyl)-amino)pyrimido[4,5-d]-pyridazin-5(6H)-one | 7 |

TABLE 1-continued
| Ex | Structure | IUPAC Name | Synthetic Scheme |
|---|---|---|---|
| 290 | 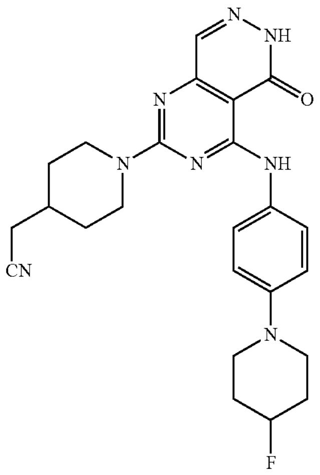 [SMILES: N#CCC1CCN(c2nc(Nc3ccc(N4CCC(F)CC4)cc3)c3c(=O)[nH]ncc3n2)CC1] | 2-(1-(4-((4-(4-fluoropiperidin-1-yl)phenyl)amino)-5-oxo-5,6-dihydropyrimido[4,5-d]-pyridazin-2-yl)piperidin-4-yl)acetonitrile | 7 |
| 291 | 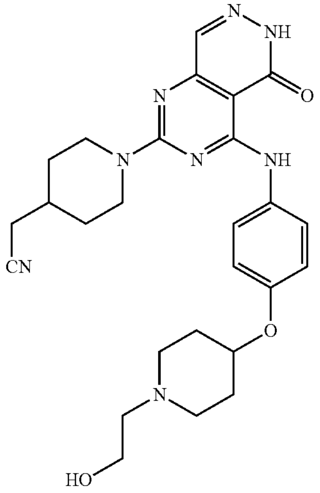 [SMILES: N#CCC1CCN(c2nc(Nc3ccc(OC4CCN(CCO)CC4)cc3)c3c(=O)[nH]ncc3n2)CC1] | 2-(1-(4-((4-((1-(2-hydroxy-ethyl)piperidin-4-yl)oxy)-phenyl)amino)-5-oxo-5,6-dihydropyrimido[4,5-d]-pyridazin-2-yl)piperidin-4-yl)acetonitrile | 7 |
| 292 | 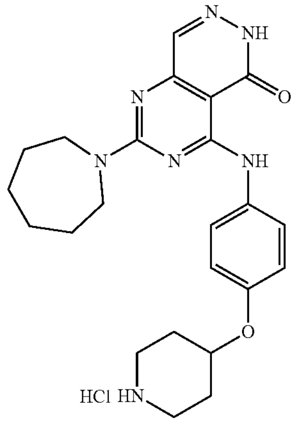 | 2-(azepan-1-yl)-4-((4-(piperidin-4-yloxy)phenyl)amino)pyrimido-[4,5-d]pyridazin-5(6H)-one hydrochloride | 7 |

TABLE 1-continued

| Ex | Structure | IUPAC Name | Synthetic Scheme |
|---|---|---|---|
| 293 | 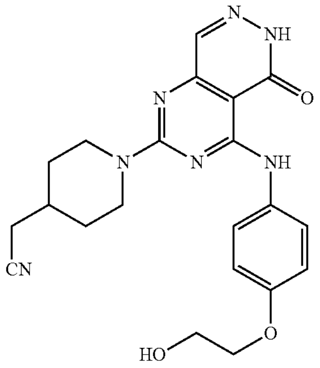 [SMILES: N#CCC1CCN(c2nc(Nc3ccc(OCCO)cc3)c3c(=O)[nH]ncc3n2)CC1] | 2-(1-(4-((4-(2-hydroxyethoxy)-phenyl)amino)-5-oxo-5,6-dihydropyrimido[4,5-d]-pyridazin-2-yl)piperidin-4-yl)acetonitrile | 7 |
| 294 | 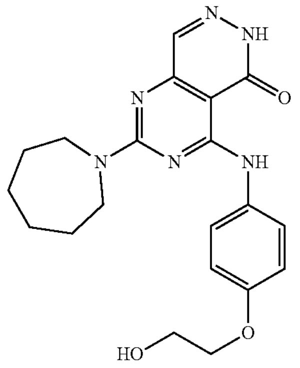 [SMILES: O=c1[nH]ncc2nc(N3CCCCCC3)nc(Nc3ccc(OCCO)cc3)c12] | 2-(azepan-1-yl)-4-((4-(2-hydroxyethoxy)phenyl)amino)-pyrimido[4,5-d]pyridazin-5(6H)-one | 7 |
| 295 | 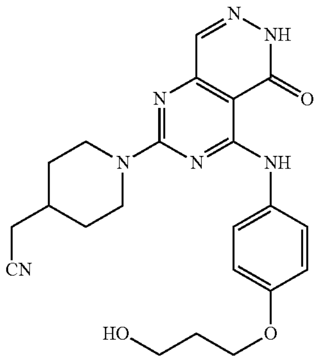 [SMILES: N#CCC1CCN(c2nc(Nc3ccc(OCCCO)cc3)c3c(=O)[nH]ncc3n2)CC1] | 2-(1-(4-((4-(3-hydroxypropoxy)-phenyl)amino)-5-oxo-5,6-dihydropyrimido[4,5-d]-pyridazin-2-yl)piperidin-4-yl)acetonitrile | 7 |
| 296 | 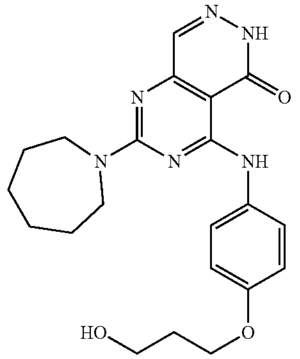 [SMILES: O=c1[nH]ncc2nc(N3CCCCCC3)nc(Nc3ccc(OCCCO)cc3)c12] | 2-(azepan-1-yl)-4-((4-(3-hydroxypropoxy)phenyl)-amino)pyrimido[4,5-d]-pyridazin-5(6H)-one | 7 |

TABLE 1-continued
| Ex | Structure | IUPAC Name | Synthetic Scheme |
|---|---|---|---|
| 297 | 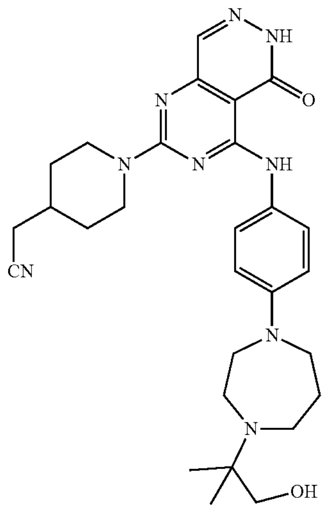 [SMILES: CC(C)(CO)N1CCCN(c2ccc(Nc3nc(N4CCC(CC#N)CC4)nc4cn[nH]c(=O)c34)cc2)CC1] | 2-(1-(4-((4-(4-(1-hydroxy-2-methylpropan-2-yl)-1,4-diazepan-1-yl)phenyl)amino)-5-oxo-5,6-dihydropyrimido-[4,5-d]pyridazin-2-yl)piperidin-4-yl)acetonitrile | 7 |
| 298 | 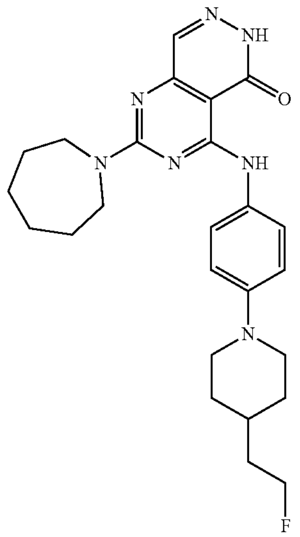 [SMILES: O=c1[nH]ncc2nc(N3CCCCCC3)nc(Nc3ccc(N4CCC(CCF)CC4)cc3)c12] | 2-(azepan-1-yl)-4-((4-(4-(2-fluoroethyl)piperidin-1-yl)phenyl)amino)pyrimido-[4,5-d]pyridazin-5(6H)-one | 7 |
| 299 | 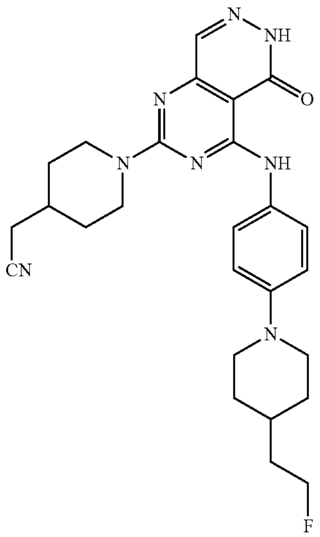 | 2-(1-(4-((4-(4-(2-fluoroethyl)-piperidin-1-yl)phenyl)amino)-5-oxo-5,6-dihydropyrimido-[4,5-d]pyridazin-2-yl)piperidin-4-yl)acetonilrile | 7 |

TABLE 1-continued

| Ex | Structure | IUPAC Name | Synthetic Scheme |
|---|---|---|---|
| 300 | 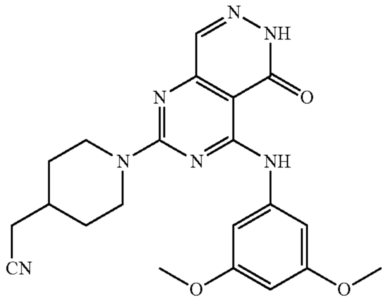 [SMILES: COc1cc(Nc2nc(N3CCC(CC#N)CC3)nc3cn[nH]c(=O)c23)cc(OC)c1] | 2-(1-(4-((3,5-dimethoxyphenyl)-amino)-5-oxo-5,6-dihydro-pyrimido[4,5-d]pyridazin-2-yl)piperidin-4-yl)acetonitrile | 7 |
| 301 | 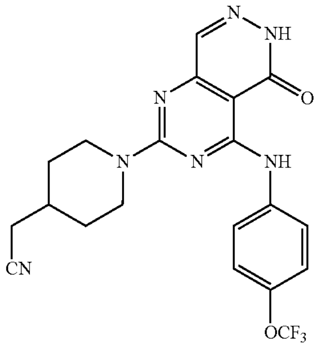 [SMILES: N#CCC1CCN(c2nc(Nc3ccc(OC(F)(F)F)cc3)c3c(=O)[nH]ncc3n2)CC1] | 2-(1-(5-oxo-4-((4-(trifluoro-methoxy)phenyl)amino)-5,6-dihydropyrimido[4,5-d]-pyridazin-2-yl)piperidin-4-yl)acetonitrile | 7 |
| 302 | 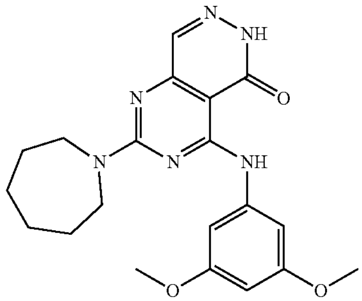 [SMILES: COc1cc(Nc2nc(N3CCCCCC3)nc3cn[nH]c(=O)c23)cc(OC)c1] | 2-(azepan-1-yl)-4-((3,5-dimethoxyphenyl)amino)-pyrimido[4,5-d]pyridazin-5(6H)-one | 7 |
| 303 | 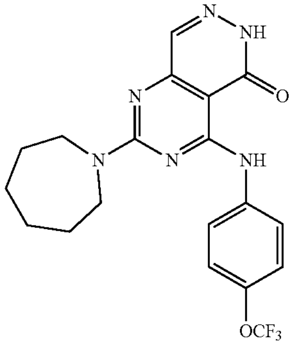 [SMILES: O=c1[nH]ncc2nc(N3CCCCCC3)nc(Nc3ccc(OC(F)(F)F)cc3)c12] | 2-(azepan-1-yl)-4-((4-(trifluoro-methoxy)phenyl)amino)-pyrimido[4,5-d]pyridazin-5(6H)-one | 7 |

TABLE 1-continued
| Ex | Structure | IUPAC Name | Synthetic Scheme |
|---|---|---|---|
| 304 | 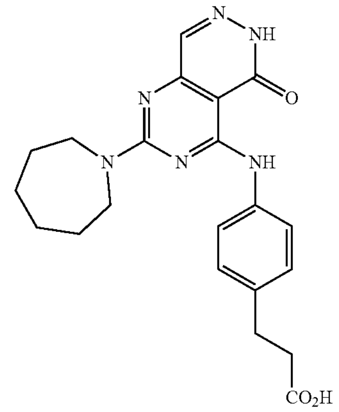 [SMILES: O=C(O)CCc1ccc(Nc2nc(N3CCCCCC3)nc3cn[nH]c(=O)c23)cc1] | 3-(4-((2-(azepan-1-yl)-5-oxo-5,6-dihydropyrimido[4,5-d]-pyridazin-4-yl)amino)phenyl)-propanoic acid | 7 |
| 305 | 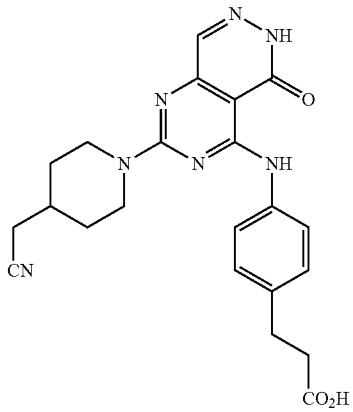 [SMILES: N#CCC1CCN(c2nc(Nc3ccc(CCC(=O)O)cc3)c3c(=O)[nH]ncc3n2)CC1] | 3-(4-((2-(4-(cyanomethyl)-piperidin-1-yl)-5-oxo-5,6-dihydropyrimido[4,5-d]-pyridazin-4-yl)amino)phenyl)-propanoic acid | 7 |
| 306 | 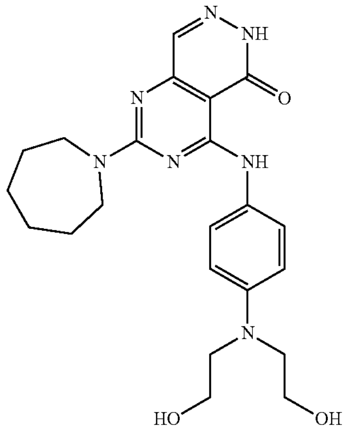 [SMILES: O=c1[nH]ncc2nc(N3CCCCCC3)nc(Nc3ccc(N(CCO)CCO)cc3)c12] | 2-(azepan-1-yl)-4-((4-(bis(2-hydroxyethyl)amino)phenyl)-amino)pyrimido[4,5-d]-pyridazin-5(6H)-one | 7 |

TABLE 1-continued

| Ex | Structure | IUPAC Name | Synthetic Scheme |
|---|---|---|---|
| 307 | 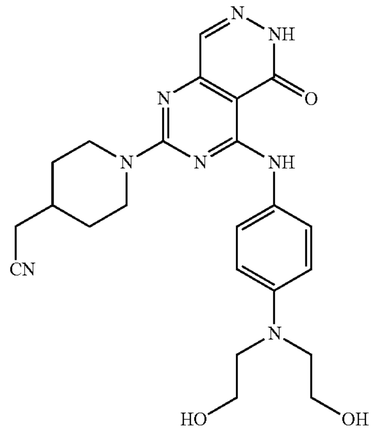 [SMILES: N#CCC1CCN(c2nc(Nc3ccc(N(CCO)CCO)cc3)c3c(=O)[nH]ncc3n2)CC1] | 2-(1-(4-((4-(bis(2-hydroxyethyl)-amino)phenyl)amino)-5-oxo-5,6-dihydropyrimido[4,5-d]-pyridazin-2-yl)piperidin-4-yl)acetonitrile | 7 |
| 308 | 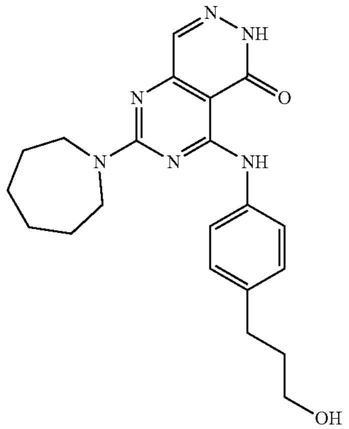 [SMILES: O=c1[nH]ncc2nc(N3CCCCCC3)nc(Nc3ccc(CCCO)cc3)c12] | 2-(azepan-1-yl)-4-((4-(3-hydroxypropyl)phenyl)amino)-pyrimido[4,5-d]pyridazin-5(6H)-one | 7 |
| 309 | 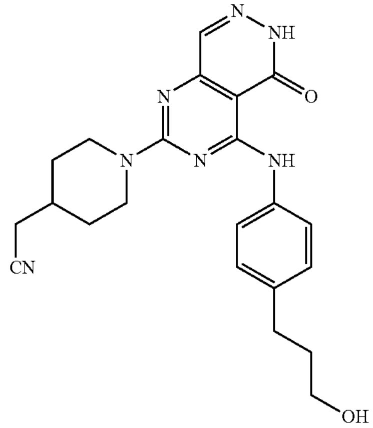 [SMILES: N#CCC1CCN(c2nc(Nc3ccc(CCCO)cc3)c3c(=O)[nH]ncc3n2)CC1] | 2-(1-(4-((4-(3-hydroxypropyl)-phenyl)amino)-5-oxo-5,6-dihydropyrimido[4,5-d]-pyridazin-2-yl)piperidin-4-yl)acetonitrile | 7 |
| 310 | 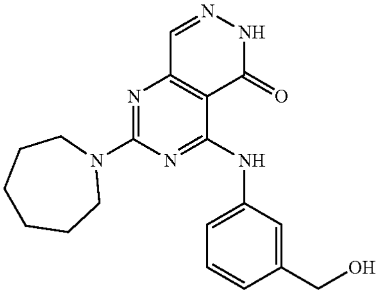 [SMILES: O=c1[nH]ncc2nc(N3CCCCCC3)nc(Nc3cccc(CO)c3)c12] | 2-(azepan-1-yl)-4-((3-(hydroxy-methyl)phenyl)amino)pyrimido-[4,5-d]pyridazin-5(6H)-one | 7 |

TABLE 1-continued

| Ex | Structure | IUPAC Name | Synthetic Scheme |
|---|---|---|---|
| 311 | 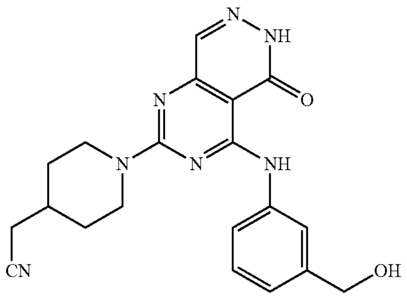 [SMILES: N#CCC1CCN(c2nc(Nc3cccc(CO)c3)c3c(=O)[nH]ncc3n2)CC1] | 2-(1-(4-((3-(hydroxymethyl)-phenyl)amino)-5-oxo-5,6-dihydropyrimido[4,5-d]-pyridazin-2-yl)piperidin-4-yl)acetonitrile | 7 |
| 312 | 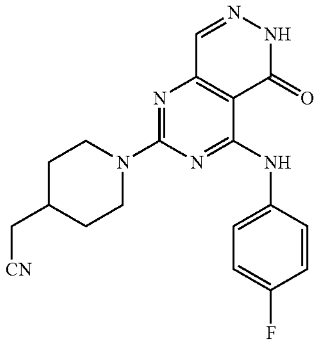 [SMILES: N#CCC1CCN(c2nc(Nc3ccc(F)cc3)c3c(=O)[nH]ncc3n2)CC1] | 2-(1-(4-((4-fluorophenyl)amino)-5-oxo-5,6-dihydropyrimido-[4,5-d]pyridazin-2-yl)piperidin-4-yl)acetonitrile | 7 |
| 313 | 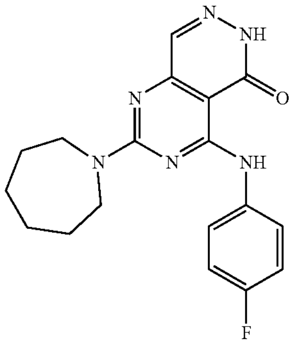 [SMILES: O=c1[nH]ncc2nc(N3CCCCCC3)nc(Nc3ccc(F)cc3)c12] | 2-(azepan-1-yl)-4-((4-fluoro-phenyl)amino)pyrimido-[4,5-d]pyridazin-5(6H)-one | 7 |
| 314 | 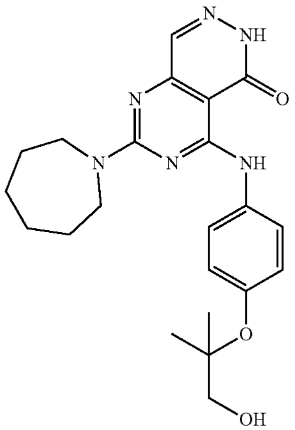 [SMILES: CC(C)(CO)Oc1ccc(Nc2nc(N3CCCCCC3)nc3cn[nH]c(=O)c23)cc1] | 2-(azepan-1-yl)-4-((4-((1-hydroxy-2-methylpropan-2-yl)oxy)phenyl)amino)pyrimido-[4,5-d]pyridazin-5(6H)-one | 7 |

TABLE 1-continued
| Ex | Structure | IUPAC Name | Synthetic Scheme |
|---|---|---|---|
| 315 | 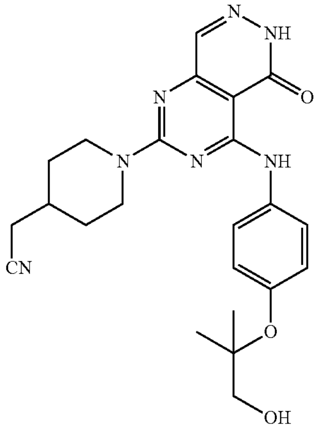 [SMILES: CC(C)(CO)Oc1ccc(Nc2nc(N3CCC(CC#N)CC3)nc3cn[nH]c(=O)c23)cc1] | 2-(1-(4-((4-((1-hydroxy-2-methylpropan-2-yl)oxy)-phenyl)amino)-5-oxo-5,6-dihydropyrimido[4,5-d]-pyridazin-2-yl)piperidin-4-yl)acetonitrile | 7 |
| 316 | 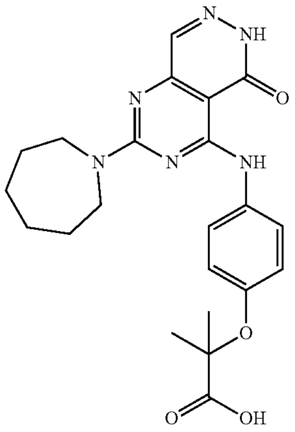 [SMILES: CC(C)(Oc1ccc(Nc2nc(N3CCCCCC3)nc3cn[nH]c(=O)c23)cc1)C(=O)O] | 2-(4-((2-(azepan-1-yl)-5-oxo-5,6-dihydropyrimido[4,5-d]-pyridazin-4-yl)amino)phenoxy)-2-methylpropanoic acid | 7 |
| 317 | 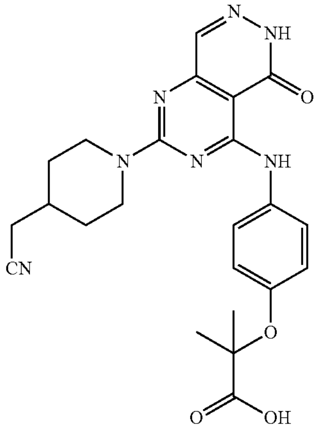 [SMILES: CC(C)(Oc1ccc(Nc2nc(N3CCC(CC#N)CC3)nc3cn[nH]c(=O)c23)cc1)C(=O)O] | 2-(4-((2-(4-(cyanomethyl)-piperidin-1-yl)-5-oxo-5,6-dihydropyrimido[4,5-d]-pyridazin-4-yl)amino)phenoxy)-2-methylpropanoic acid | 7 |

TABLE 1-continued
| Ex | Structure | IUPAC Name | Synthetic Scheme |
|---|---|---|---|
| 318 | 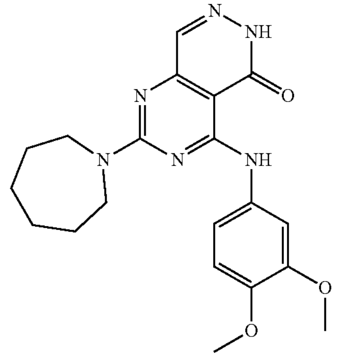 [SMILES: COc1ccc(Nc2nc(N3CCCCCC3)nc3cn[nH]c(=O)c23)cc1OC] | 2-(azepan-1-yl)-4-((3,4-dimethoxyphenyl)amino)-pyrimido[4,5-d]pyridazin-5(6H)-one | 7 |
| 319 | 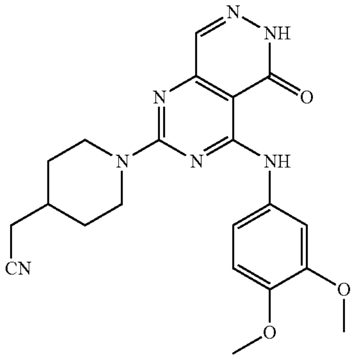 [SMILES: COc1ccc(Nc2nc(N3CCC(CC#N)CC3)nc3cn[nH]c(=O)c23)cc1OC] | 2-(1-(4-((3,4-dimethoxyphenyl)-amino)-5-oxo-5,6-dihydro-pyrimido[4,5-d]pyridazin-2-yl)piperidin-4-yl)acetonitrile | 7 |
| 320 | 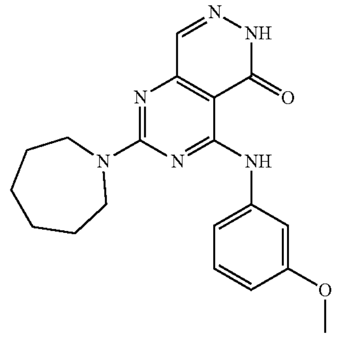 [SMILES: COc1cccc(Nc2nc(N3CCCCCC3)nc3cn[nH]c(=O)c23)c1] | 2-(azepan-1-yl)-4-((3-methoxy-phenyl)amino)pyrimido[4,5-d]-pyridazin-5(6H)-one | 7 |
| 321 | 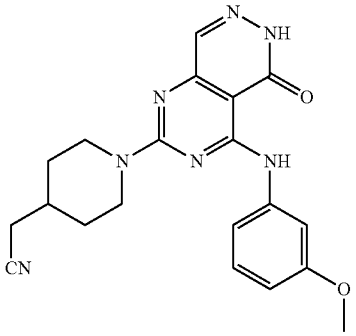 [SMILES: COc1cccc(Nc2nc(N3CCC(CC#N)CC3)nc3cn[nH]c(=O)c23)c1] | 2-(1-(4-((3-methoxyphenyl)-amino)-5-oxo-5,6-dihydro-pyrimido[4,5-d]pyridazin-2-yl)piperidin-4-yl)acetonitrile | 7 |

TABLE 1-continued
| Ex | Structure | IUPAC Name | Synthetic Scheme |
|---|---|---|---|
| 322 | 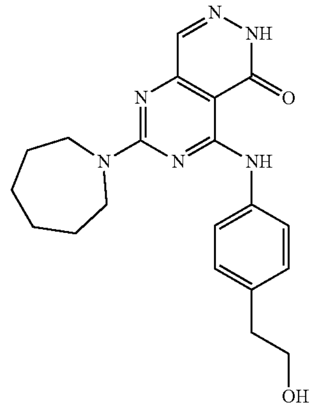 [SMILES: O=c1[nH]ncc2nc(N3CCCCCC3)nc(Nc3ccc(CCO)cc3)c12] | 2-(azepan-1-yl)-4-((4-(2-hydroxyethyl)phenyl)amino)-pyrimido[4,5-d]pyridazin-5(6H)-one | 7 |
| 323 | 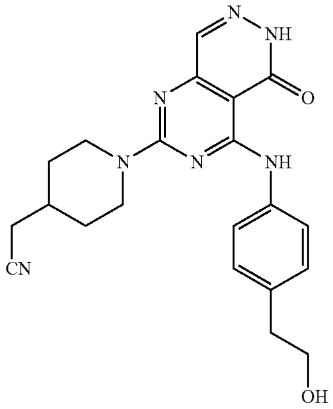 [SMILES: N#CCC1CCN(c2nc(Nc3ccc(CCO)cc3)c3c(=O)[nH]ncc3n2)CC1] | 2-(1-(4-((4-(2-hydroxyethyl)-phenyl)amino)-5-oxo-5,6-dihydropyrimido[4,5-d]-pyridazin-2-yl)piperidin-4-yl)acetonitrile | 7 |
| 324 | 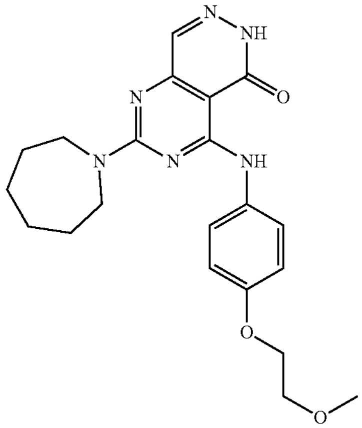 [SMILES: COCCOc1ccc(Nc2nc(N3CCCCCC3)nc3cn[nH]c(=O)c23)cc1] | 2-(azepan-1-yl)-4-((4-(2-methoxyethoxy)phenyl)amino)-pyrimido[4,5-d]pyridazin-5(6H)-one | 7 |

TABLE 1-continued

| Ex | Structure | IUPAC Name | Synthetic Scheme |
|---|---|---|---|
| 325 | 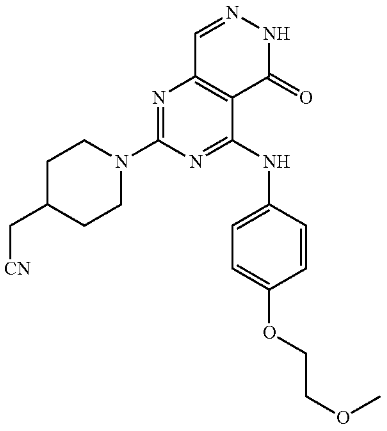 [SMILES: COCCOc1ccc(Nc2nc(N3CCC(CC#N)CC3)nc3cn[nH]c(=O)c23)cc1] | 2-(1-(4-((4-(2-methoxyethoxy)-phenyl)amino)-5-oxo-5,6-dihydropyrimido[4,5-d]-pyridazin-2-yl)piperidin-4-yl)acetonitrile | 7 |
| 326 | 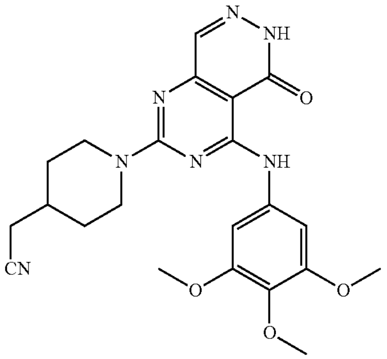 [SMILES: COc1cc(Nc2nc(N3CCC(CC#N)CC3)nc3cn[nH]c(=O)c23)cc(OC)c1OC] | 2-(1-(5-oxo-4-((3,4,5-trimethoxyphenyl)amino)-5,6-dihydropyrimido[4,5-d]-pyridazin-2-yl)piperidin-4-yl)acetonilrile | 7 |
| 327 | 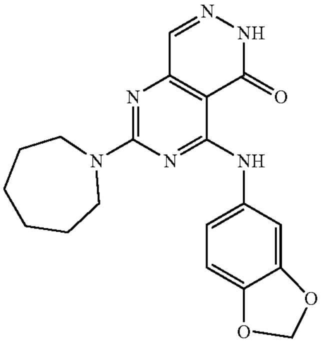 [SMILES: O=c1[nH]ncc2nc(N3CCCCCC3)nc(Nc3ccc4c(c3)OCO4)c12] | 2-(azepan-1-yl)-4-(benzo[d]-[1,3]dioxol-5-ylamino)pyrimido-[4,5-d]pyridazin-5(6H)-one | 7 |
| 328 | 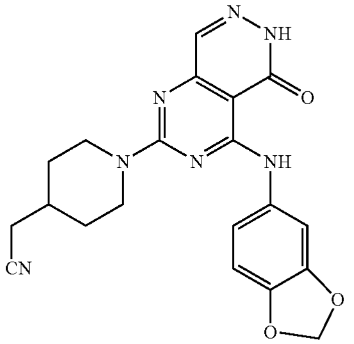 [SMILES: N#CCC1CCN(c2nc(Nc3ccc4c(c3)OCO4)c3c(=O)[nH]ncc3n2)CC1] | 2-(1(4-(benzo[d][1,3]dioxol-5-ylamino)-5-oxo-5,6-dihydropyrimido[4,5-d]-pyridazin-2-yl)piperidin-4-yl)acetonitrile | 7 |

TABLE 1-continued
| Ex | Structure | IUPAC Name | Synthetic Scheme |
|---|---|---|---|
| 329 | 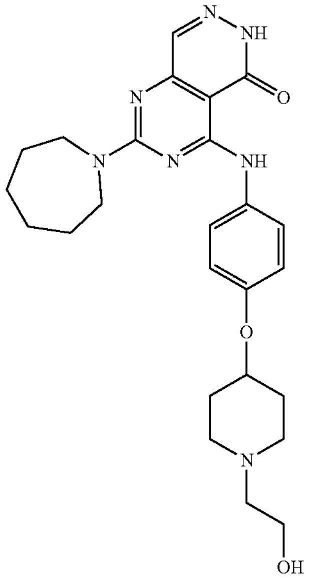 [SMILES: O=c1[nH]ncc2nc(N3CCCCCC3)nc(Nc3ccc(OC4CCN(CCO)CC4)cc3)c12] | 2-(azepan-1-yl)-4-((4-((1-(2-hydroxyethyl)piperidin-4-yl)oxy)phenyl)amino)pyrimido-[4,5-d]pyridazin-5(6H)-one | 7 |
| 330 | 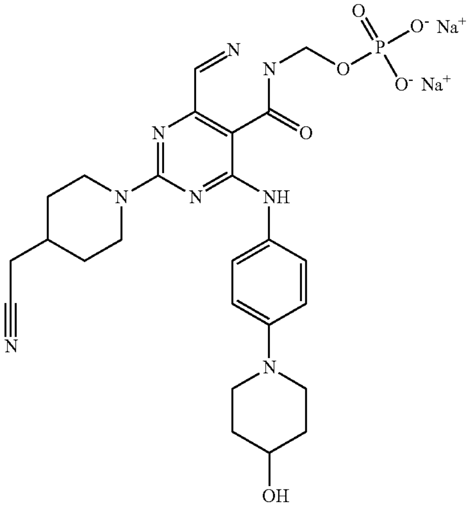 [SMILES: N#CCC1CCN(c2nc(C=N)c(C(=O)NCOP(=O)([O-])[O-])c(Nc3ccc(N4CCC(O)CC4)cc3)n2)CC1 ; [Na+] ; [Na+]] | sodium (2-(4-(cyanomethyl)-piperidin-1-yl)-4-((4-(4-hydroxypiperidin-1-yl)phenyl)-amino)-5-oxopyrimido[4,5-d]-pyridazin-6(5H)-yl)methyl phosphate | 7 |
| 331 | 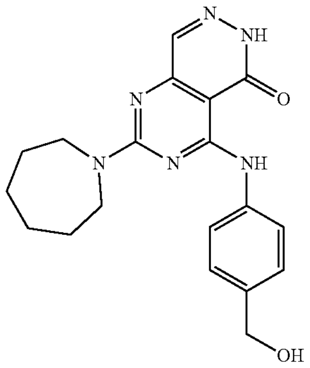 [SMILES: O=c1[nH]ncc2nc(N3CCCCCC3)nc(Nc3ccc(CO)cc3)c12] | 2-(azepan-1-yl)-4-((4-(hydroxy-methyl)phenyl)amino)pyrimido-[4,5-d]pyridazin-5(6H)-one | 7 |

TABLE 1-continued

| Ex | Structure | IUPAC Name | Synthetic Scheme |
|---|---|---|---|
| 332 | 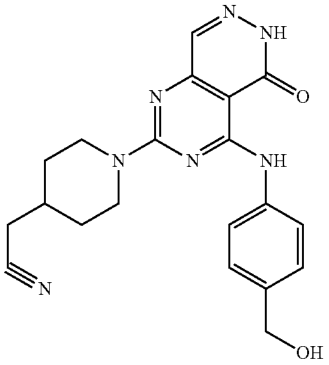 [SMILES: N#CCC1CCN(c2nc(Nc3ccc(CO)cc3)c3c(=O)[nH]ncc3n2)CC1] | 2-(1-(4-((4-(hydroxymethyl)-phenyl)amino)-5-oxo-5,6-dihydropyrimido[4,5-d]-pyridazin-2-yl)piperidin-4-yl)acetonitrile | 7 |
| 333 | 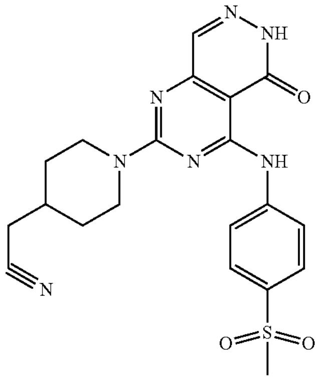 [SMILES: CS(=O)(=O)c1ccc(Nc2nc(N3CCC(CC#N)CC3)nc3cn[nH]c(=O)c23)cc1] | 2-(1-(4-((4-(methylsulfonyl)-phenyl)amino)-5-oxo-5,6-dihydropyrimido[4,5-d]-pyridazin-2-yl)piperidin-4-yl)acetonitrile | 7 |
| 334 | 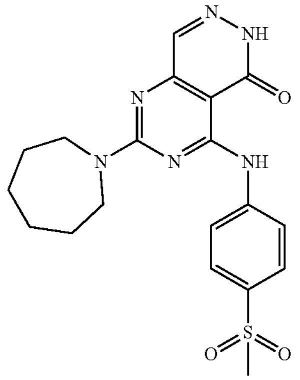 [SMILES: CS(=O)(=O)c1ccc(Nc2nc(N3CCCCCC3)nc3cn[nH]c(=O)c23)cc1] | 2-(azepan-1-yl)-4-((4-(methyl-sulfonyl)phenyl)amino)pyrimido-[4,5-d]pyridazin-5(6H)-one | 7 |
| 335 | 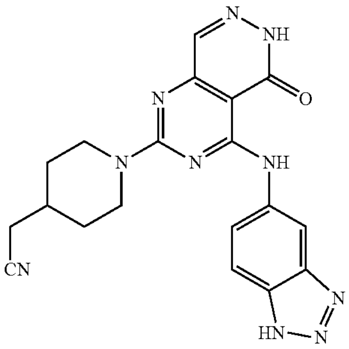 [SMILES: N#CCC1CCN(c2nc(Nc3ccc4[nH]nnc4c3)c3c(=O)[nH]ncc3n2)CC1] | 2-(1-(4-((1H-benzo[d][1,2,3]-triazol-5-yl)amino)-5-oxo-5,6-dihydropyrimido[4,5-d]-pyridazin-2-yl)piperidin-4-yl)acetonitrile | 7 |

TABLE 1-continued

| Ex | Structure | IUPAC Name | Synthetic Scheme |
| --- | --- | --- | --- |
| 336 | 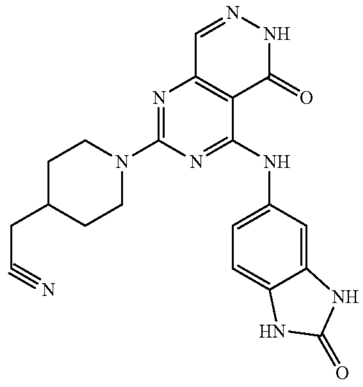 [SMILES: N#CCC1CCN(c2nc(Nc3ccc4[nH]c(=O)[nH]c4c3)c3c(=O)[nH]ncc3n2)CC1] | 2-(1-(5-oxo-4-((2-oxo-2,3-dihydro-1H-benzo[d]imidazol-5-yl)amino)-5,6-dihydro-pyrimido[4,5-d]pyridazin-2-yl)piperidin-4-yl)acetonitrile | 7 |
| 337 | 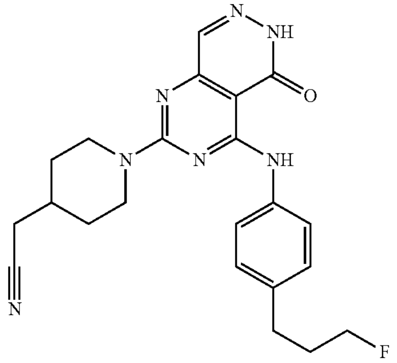 [SMILES: N#CCC1CCN(c2nc(Nc3ccc(CCCF)cc3)c3c(=O)[nH]ncc3n2)CC1] | 2-(1-(4-((4-(3-fluoropropyl)-phenyl)amino)-5-oxo-5,6-dihydropyrimido[4,5-d]-pyridazin-2-yl)piperidin-4-yl)acetonitrile | 7 |
| 338 | 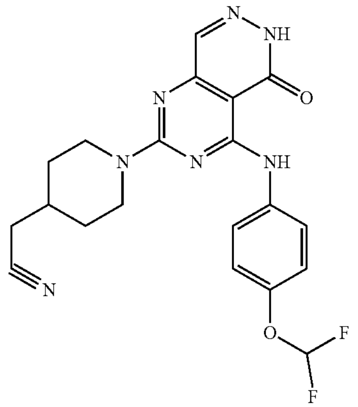 [SMILES: N#CCC1CCN(c2nc(Nc3ccc(OC(F)F)cc3)c3c(=O)[nH]ncc3n2)CC1] | 2-(1-(4-((4-(difluoromethoxy)-phenyl)amino)-5-oxo-5,6-dihydropyrimido[4,5-d]-pyridazin-2-yl)piperidin-4-yl)acetonitrile | 7 |
| 339 | 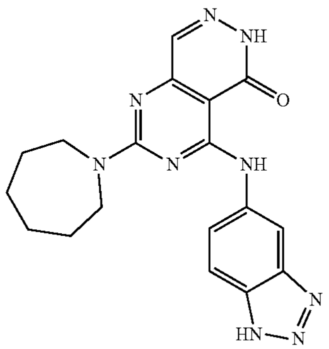 [SMILES: O=c1[nH]ncc2nc(N3CCCCCC3)nc(Nc3ccc4[nH]nnc4c3)c12] | 4-((1H-benzo[d][1,2,3]triazol-5-yl)amino)-2-(azepan-1-yl)-pyrimido[4,5-d]pyridazin-5(6H)-one | 7 |

The following compounds in Table A are prepared by one of skill in the art using the above-noted Schemes, descriptions, and Examples 1-339.

TABLE A

| Structure | IUPAC Name |
|---|---|
| 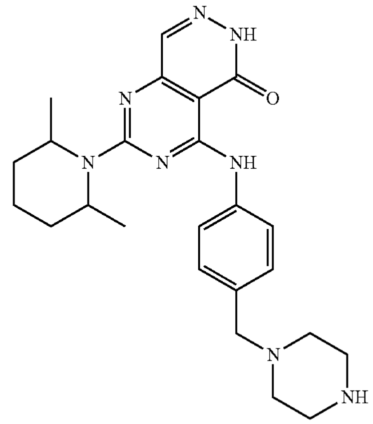 [SMILES: CC1CCCC(C)N1c1nc(Nc2ccc(CN3CCNCC3)cc2)c2c(=O)[nH]ncc2n1] | 2-(2,6-dimethylpiperidin-1-yl)-4-((4-(piperazin-1-ylmethyl)phenyl)amino)pyrimido[4,5-d]pyridazin-5(6H)-one |
| 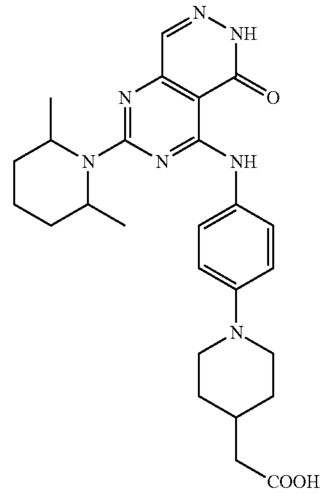 [SMILES: CC1CCCC(C)N1c1nc(Nc2ccc(N3CCC(CC(=O)O)CC3)cc2)c2c(=O)[nH]ncc2n1] | 2-(1-(4-((2-(2,6-dimethylpiperidin-1-yl)-5-oxo-5,6-dihydropyrimido[4,5-d]pyridazin-4-yl)amino)phenyl)piperidin-4-yl)acetic acid |
| 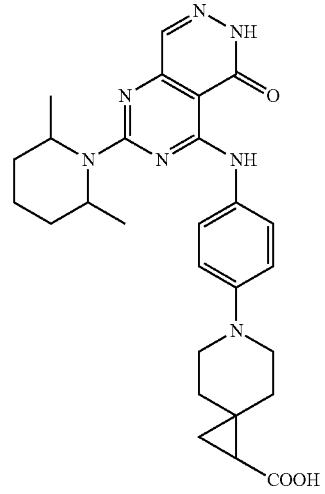 [SMILES: CC1CCCC(C)N1c1nc(Nc2ccc(N3CCC4(CC3)CC4C(=O)O)cc2)c2c(=O)[nH]ncc2n1] | 6-(4-((2-(2,6-dimethylpiperidin-1-yl)-5-oxo-5,6-dihydropyrimido [4,5-d]pyridazin-4-yl)amino)phenyl)-6-azaspiro[2.5]octane-1-carboxylic acid |

TABLE A-continued
| Structure | IUPAC Name |
| --- | --- |
| 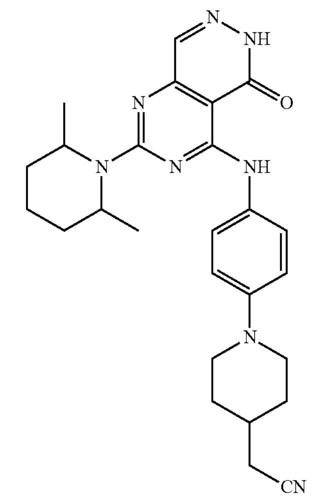 [SMILES: CC1CCCC(C)N1c1nc(Nc2ccc(N3CCC(CC#N)CC3)cc2)c2c(=O)[nH]ncc2n1] | 2-(1-(4-((2-(2,6-dimethylpiperidin-1-yl)-5-oxo-5,6-dihydropyrimido[4,5-d]pyridazin-4-yl)amino)phenyl)piperidin-4-yl)acetonitrile |
| 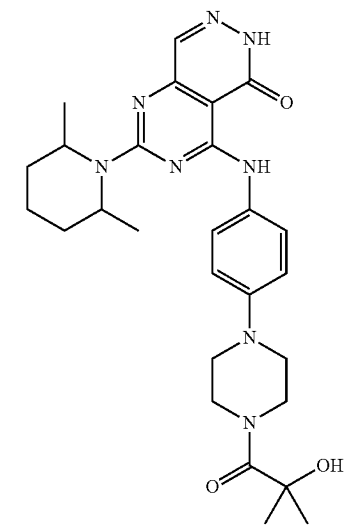 [SMILES: CC1CCCC(C)N1c1nc(Nc2ccc(N3CCN(C(=O)C(C)(C)O)CC3)cc2)c2c(=O)[nH]ncc2n1] | 2-(2,6-dimethylpiperidin-1-yl)-4-((4-(4-(2-hydroxy-2-methylpropanoyl)piperazin-1-yl)phenyl)amino)pyrimido[4,5-d]pyridazin-5(6H)-one |
| 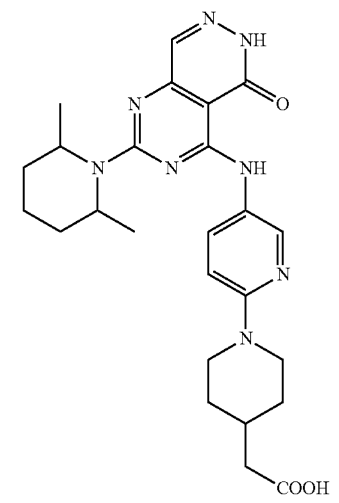 [SMILES: CC1CCCC(C)N1c1nc(Nc2ccc(N3CCC(CC(=O)O)CC3)nc2)c2c(=O)[nH]ncc2n1] | 2-(1-(5-((2-(2,6-dimethylpiperidin-1-yl)-5-oxo-5,6-dihydropyrimido[4,5-d]pyridazin-4-yl)amino)pyridin-2-yl)piperidin-4-yl)acetic acid |

TABLE A-continued
| Structure | IUPAC Name |
| --- | --- |
| 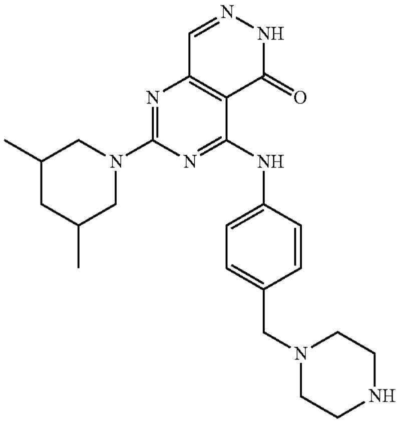 [SMILES: CC1CC(C)CN(c2nc(Nc3ccc(CN4CCNCC4)cc3)c3c(=O)[nH]ncc3n2)C1] | 2-(3,5-dimethylpiperidin-1-yl)-4-((4-(piperazin-1-ylmethyl)phenyl)amino)pyrimido[4,5-d]pyridazin-5(6H)-one |
| 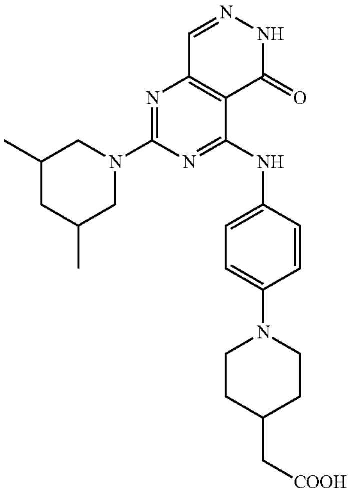 [SMILES: CC1CC(C)CN(c2nc(Nc3ccc(N4CCC(CC(=O)O)CC4)cc3)c3c(=O)[nH]ncc3n2)C1] | 2-(1-(4-((2-(3,5-dimethylpiperidin-1-yl)-5-oxo-5,6-dihydropyrimido[4,5-d]pyridazin-4-yl)amino)phenyl)piperidin-4-yl)acetic acid |
| 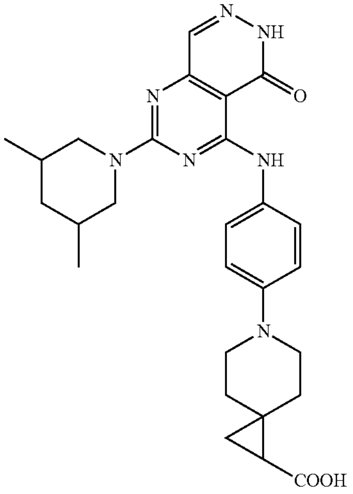 [SMILES: CC1CC(C)CN(c2nc(Nc3ccc(N4CCC5(CC4)CC5C(=O)O)cc3)c3c(=O)[nH]ncc3n2)C1] | 6-(4-((2-(3,5-dimethylpiperidin-1-yl)-5-oxo-5,6-dihydropyrimido[4,5-d]pyridazin-4-yl)amino)phenyl)-6-azaspiro[2.5]octane-1-carboxylic acid |

TABLE A-continued
| Structure | IUPAC Name |
|---|---|
| 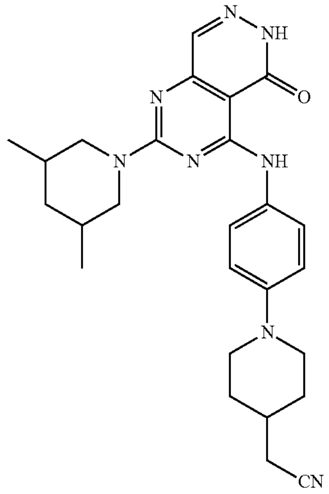 [SMILES: CC1CC(C)CN(c2nc(Nc3ccc(N4CCC(CC#N)CC4)cc3)c3c(=O)[nH]ncc3n2)C1] | 2-(1-(4-((2-(3,5-dimethylpiperidin-1-yl)-5-oxo-5,6-dihydropyrimido[4,5-d]pyridazin-4-yl)amino)phenyl)piperidin-4-yl)acetonitrile |
| 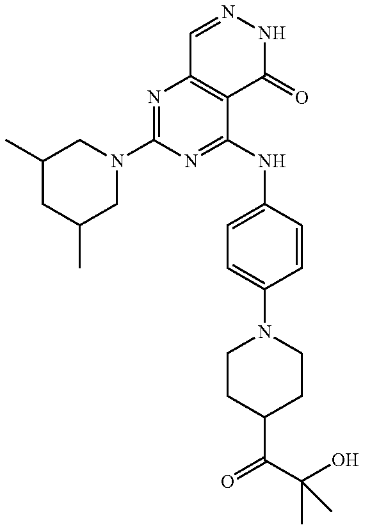 [SMILES: CC1CC(C)CN(c2nc(Nc3ccc(N4CCC(C(=O)C(C)(C)O)CC4)cc3)c3c(=O)[nH]ncc3n2)C1] | 2-(3,5-dimethylpiperidin-1-yl)-4-((4-(4-(2-hydroxy-2-methylpropanoyl)piperidin-1-yl)phenyl)amino)pyrimido[4,5-d]pyridazin-5(6H)-one |
| 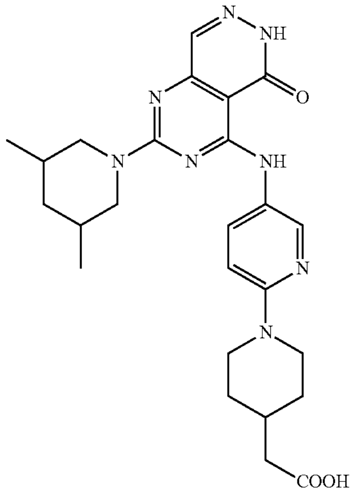 [SMILES: CC1CC(C)CN(c2nc(Nc3ccc(N4CCC(CC(=O)O)CC4)nc3)c3c(=O)[nH]ncc3n2)C1] | 2-(1-(5-((2-(3,5-dimethylpiperidin-1-yl)-5-oxo-5,6-dihydropyrimido[4,5-d]pyridazin-4-yl)amino)pyridin-2-yl)piperidin-4-yl)acetic acid |

TABLE A-continued
| Structure | IUPAC Name |
|---|---|
| 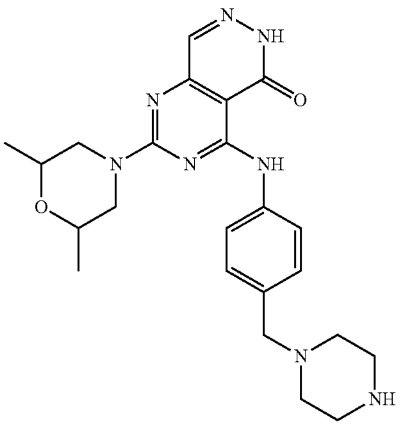 [SMILES: CC1CN(c2nc(Nc3ccc(CN4CCNCC4)cc3)c3c(=O)[nH]ncc3n2)CC(C)O1] | 2-(2,6-dimethylmorpholino)-4-((4-(piperazin-1-ylmethyl)phenyl)amino)pyrimido[4,5-d]pyridazin-5(6H)-one |
| 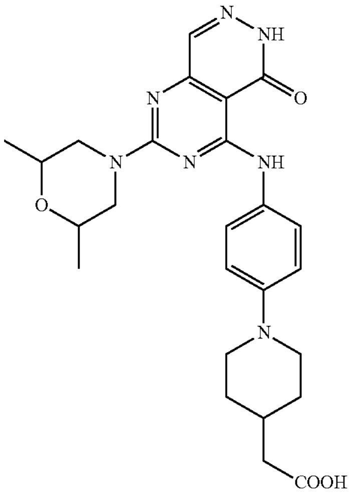 [SMILES: CC1CN(c2nc(Nc3ccc(N4CCC(CC(=O)O)CC4)cc3)c3c(=O)[nH]ncc3n2)CC(C)O1] | 2-(1-(4-((2-(2,6-dimethylmorpholino)-5-oxo-5,6-dihydropyrimido[4,5-d]pyridazin-4-yl)amino)phenyl)piperidin-4-yl)acetic acid |
| 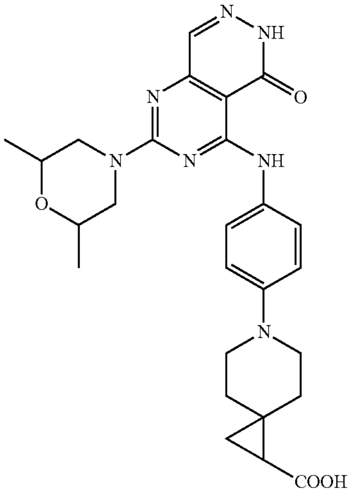 [SMILES: CC1CN(c2nc(Nc3ccc(N4CCC5(CC4)CC5C(=O)O)cc3)c3c(=O)[nH]ncc3n2)CC(C)O1] | 6-(4-((2-(2,6-dimethylmorpholino)-5-oxo-5,6-dihydropyrimido[4,5-d]pyridazin-4-yl)amino)phenyl)-6-azaspiro[2.5]octane-1-carboxylic acid |

TABLE A-continued
| Structure | IUPAC Name |
| --- | --- |
| 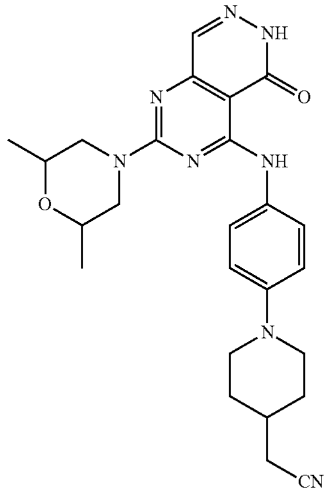 [SMILES: CC1CN(c2nc(Nc3ccc(N4CCC(CC#N)CC4)cc3)c3c(=O)[nH]ncc3n2)CC(C)O1] | 2-(1-(4-((2-(2,6-dimethylmorpholino)-5-oxo-5,6-dihydropyrimido[4,5-d]pyridazin-4-yl)amino)phenyl)piperidin-4-yl)acetonitrile |
| 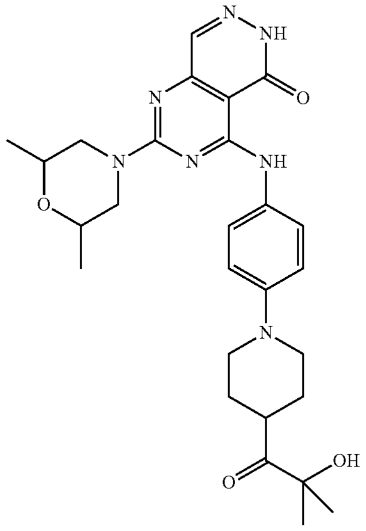 [SMILES: CC1CN(c2nc(Nc3ccc(N4CCC(C(=O)C(C)(C)O)CC4)cc3)c3c(=O)[nH]ncc3n2)CC(C)O1] | 2-(2,6-dimethylmorpholino)-4-((4-(4-(2-hydroxy-2-methylpropanoyl)piperidin-1-yl)phenyl)amino)pyrimido[4,5-d]pyridazin-5(6H)-one |
| 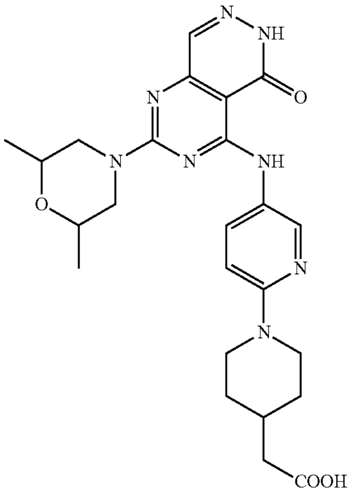 [SMILES: CC1CN(c2nc(Nc3ccc(N4CCC(CC(=O)O)CC4)nc3)c3c(=O)[nH]ncc3n2)CC(C)O1] | 2-(1-(5-((2-(2,6-dimethylmorpholino)-5-oxo-5,6-dihydropyrimido[4,5-d]pyridazin-4-yl)amino)pyridin-2-yl)piperidin-4-yl)acetic acid |

TABLE A-continued
| Structure | IUPAC Name |
|---|---|
| 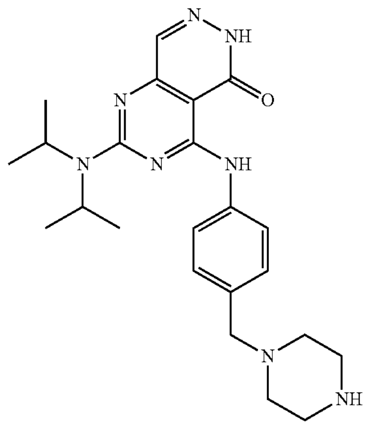 [SMILES: CC(C)N(c1nc(Nc2ccc(CN3CCNCC3)cc2)c2c(=O)[nH]ncc2n1)C(C)C] | 2-(diisopropylamino)-4-((4-(piperazin-1-ylmethyl)phenyl)amino)pyrimido[4,5-d]pyridazin-5(6H)-one |
| 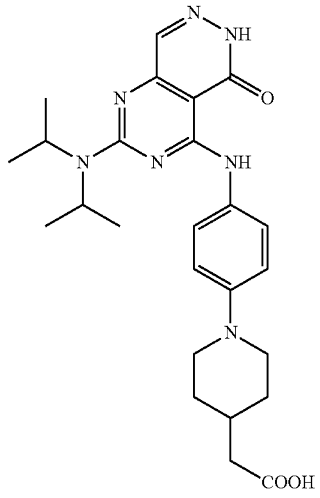 [SMILES: CC(C)N(c1nc(Nc2ccc(N3CCC(CC(=O)O)CC3)cc2)c2c(=O)[nH]ncc2n1)C(C)C] | 2-(1-(4-((2-(diisopropylamino)-5-oxo-5,6-dihydropyrimido[4,5-d]pyridazin-4-yl)amino)phenyl)piperidin-4-yl)acetic acid |
| 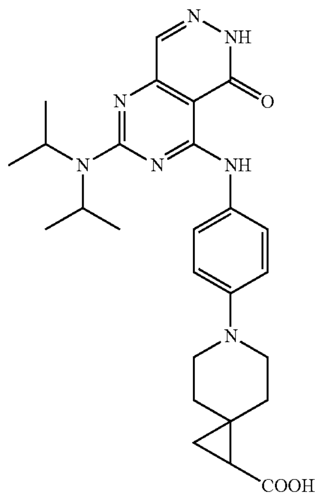 [SMILES: CC(C)N(c1nc(Nc2ccc(N3CCC4(CC3)CC4C(=O)O)cc2)c2c(=O)[nH]ncc2n1)C(C)C] | 6-(4-((2-(diisopropylamino)-5-oxo-5,6-dihydropyrimido[4,5-d]pyridazin-4-yl)amino)phenyl)-6-azaspiro[2.5]octane-1-carboxylic acid |

TABLE A-continued
| Structure | IUPAC Name |
|---|---|
| 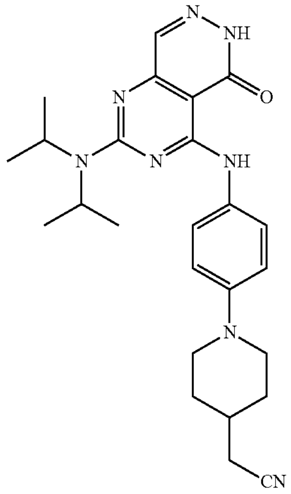 [SMILES: CC(C)N(c1nc(Nc2ccc(N3CCC(CC#N)CC3)cc2)c2c(=O)[nH]ncc2n1)C(C)C] | 2-(1-(4-((2-(diisopropylamino)-5-oxo-5,6-dihydropyrimido[4,5-d]pyridazin-4-yl)amino)phenyl)piperidin-4-yl)acetonitrile |
| 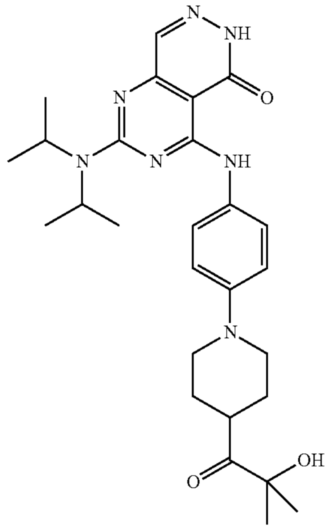 [SMILES: CC(C)N(c1nc(Nc2ccc(N3CCC(C(=O)C(C)(C)O)CC3)cc2)c2c(=O)[nH]ncc2n1)C(C)C] | 2-(diisopropylamino)-4-((4-(4-(2-hydroxy-2-methylpropanoyl)piperidin-1-yl)phenyl)amino)pyrimido[4,5-d]pyridazin-5(6H)-one |
| 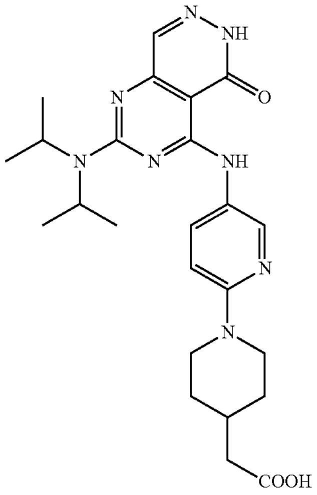 [SMILES: CC(C)N(c1nc(Nc2ccc(N3CCC(CC(=O)O)CC3)nc2)c2c(=O)[nH]ncc2n1)C(C)C] | 2-(1-(5-((2-(diisopropylamino)-5-oxo-5,6-dihydropyrimido[4,5-d]pyridazin-4-yl)amino)pyridin-2-yl)piperidin-4-yl)acetic acid |

TABLE A-continued
| Structure | IUPAC Name |
| --- | --- |
| 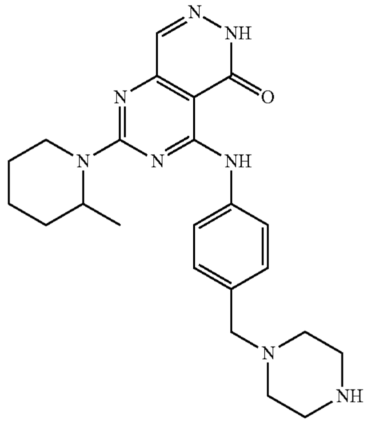 [SMILES: CC1CCCCN1c1nc(Nc2ccc(CN3CCNCC3)cc2)c2c(=O)[nH]ncc2n1] | 2-(2-methylpiperidin-1-yl)-4-((4-(piperazin-1-ylmethyl)phenyl)amino)pyrimido[4,5-d]pyridazin-5(6H)-one |
| 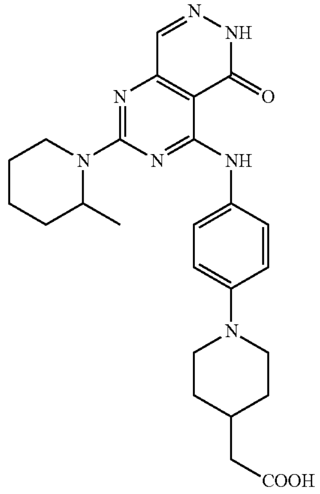 [SMILES: CC1CCCCN1c1nc(Nc2ccc(N3CCC(CC(=O)O)CC3)cc2)c2c(=O)[nH]ncc2n1] | 2-(1-(4-((2-(2-methylpiperidin-1-yl)-5-oxo-5,6-dihydropyrimido[4,5-d]pyridazin-4-yl)amino)phenyl)piperidin-4-yl)acetic acid |
| 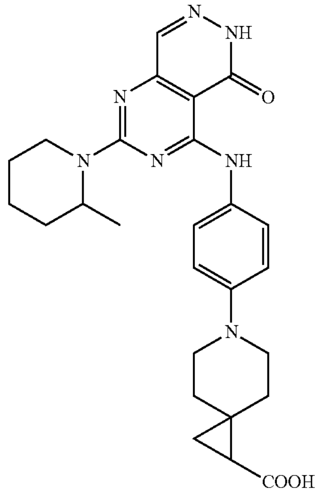 [SMILES: CC1CCCCN1c1nc(Nc2ccc(N3CCC4(CC3)CC4C(=O)O)cc2)c2c(=O)[nH]ncc2n1] | 6-(4-((2-(2-methylpiperidin-1-yl)-5-oxo-5,6-dihydropyrimido[4,5-d]pyridazin-4-yl)amino)phenyl)-6-azaspiro[2.5]octane-1-carboxylic acid |

TABLE A-continued
| Structure | IUPAC Name |
|---|---|
| 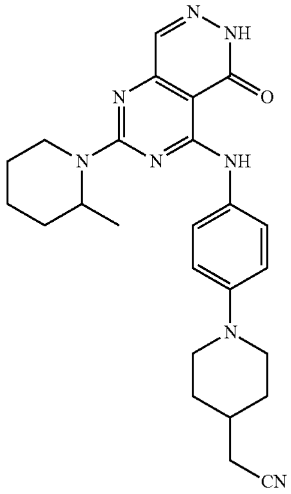 [SMILES: CC1CCCCN1c1nc(Nc2ccc(N3CCC(CC#N)CC3)cc2)c2c(=O)[nH]ncc2n1] | 2-(1-(4-((2-(2-methylpiperidin-1-yl)-5-oxo-5,6-dihydropyrimido[4,5-d]pyridazin-4-yl)amino)phenyl)piperidin-4-yl)acetonitrile |
| 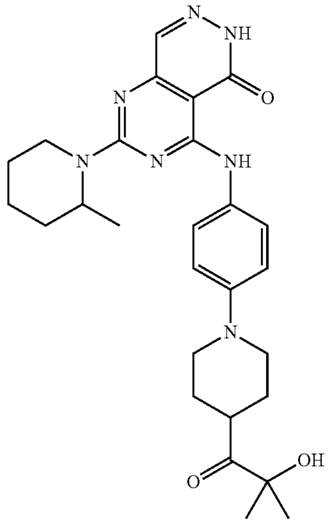 [SMILES: CC1CCCCN1c1nc(Nc2ccc(N3CCC(C(=O)C(C)(C)O)CC3)cc2)c2c(=O)[nH]ncc2n1] | 4-((4-(4-(2-hydroxy-2-methylpropanoyl)piperidin-1-yl)phenyl)amino)-2-(2-methylpiperidin-1-yl)pyrimido[4,5-d]pyridazin-5(6H)-one |
| 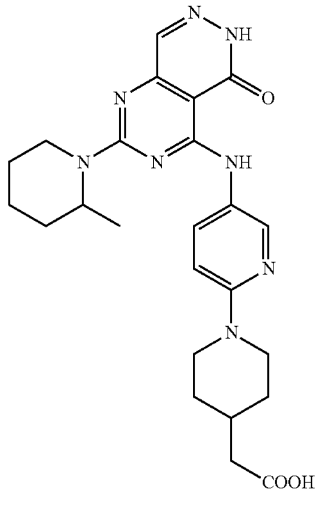 [SMILES: CC1CCCCN1c1nc(Nc2ccc(N3CCC(CC(=O)O)CC3)nc2)c2c(=O)[nH]ncc2n1] | 2-(1-(5-((2-(2-methylpiperidin-1-yl)-5-oxo-5,6-dihydropyrimido[4,5-d]pyridazin-4-yl)amino)pyridin-2-yl)piperidin-4-yl)acetic acid |

TABLE A-continued
| Structure | IUPAC Name |
| --- | --- |
| 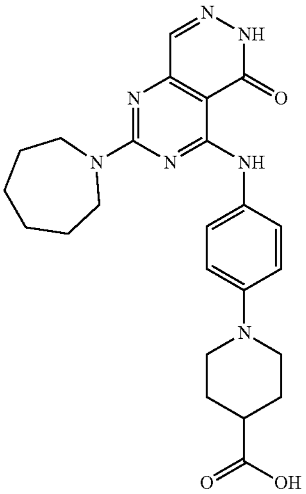 [SMILES: O=C(O)C1CCN(c2ccc(Nc3nc(N4CCCCCC4)nc4cn[nH]c(=O)c34)cc2)CC1] | 1-(4-((2-(azepan-1-yl)-5-oxo-5,6-dihydropyrimido[4,5-d]pyridazin-4-yl)amino)phenyl)piperidine-4-carboxylic acid |
| 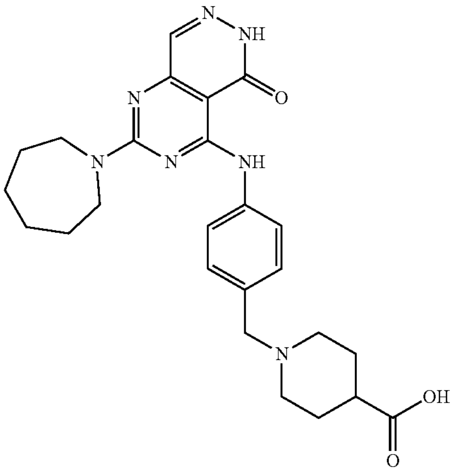 [SMILES: O=C(O)C1CCN(Cc2ccc(Nc3nc(N4CCCCCC4)nc4cn[nH]c(=O)c34)cc2)CC1] | 1-(4-((2-(azepan-1-yl)-5-oxo-5,6-dihydropyrimido[4,5-d]pyridazin-4-yl)amino)benzyl)piperidine-4-carboxylic acid |
| 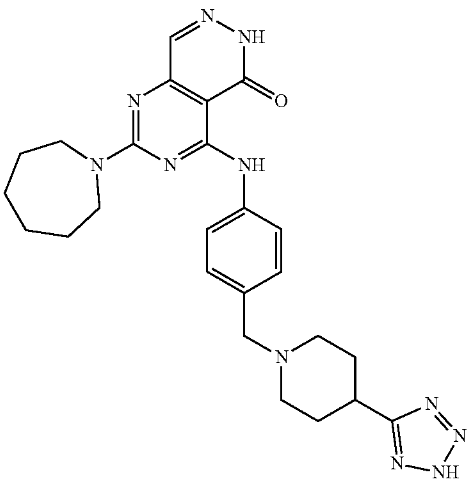 [SMILES: O=c1[nH]ncc2nc(N3CCCCCC3)nc(Nc3ccc(CN4CCC(c5nn[nH]n5)CC4)cc3)c12] | 4-((4-((4-(2H-tetrazol-5-yl)piperidin-1-yl)methyl)phenyl)amino)-2-(azepan-1-yl)pyrimido[4,5-d]pyridazin-5(6H)-one |

TABLE A-continued
| Structure | IUPAC Name |
| --- | --- |
| 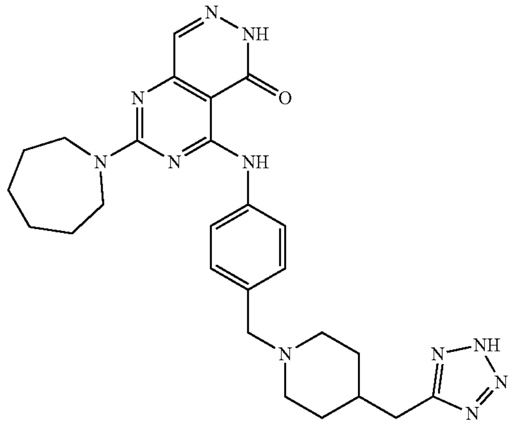 [SMILES: O=c1[nH]ncc2nc(N3CCCCCC3)nc(Nc3ccc(CN4CCC(Cc5nn[nH]n5)CC4)cc3)c12] | 4-((4-((4-((2H-tetrazol-5-yl)methyl)piperidin-1-yl)methyl)phenyl)amino)-2-(azepan-1-yl)pyrimido[4,5-d]pyridazin-5(6H)-one |
| 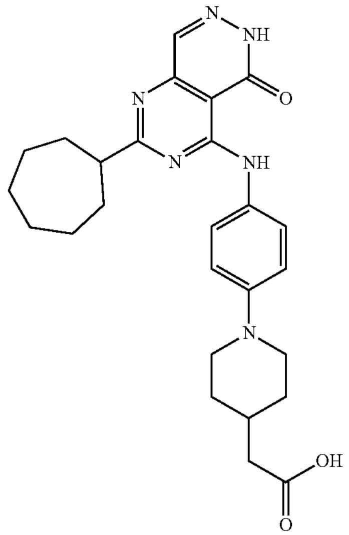 [SMILES: O=C(O)CC1CCN(c2ccc(Nc3nc(C4CCCCCC4)nc4cn[nH]c(=O)c34)cc2)CC1] | 2-(1-(4-((2-cycloheptyl-5-oxo-5,6-dihydropyrimido[4,5-d]pyridazin-4-yl)amino)phenyl)piperidin-4-yl)acetic acid |
| 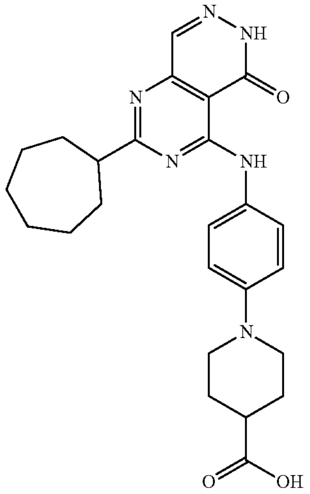 [SMILES: O=C(O)C1CCN(c2ccc(Nc3nc(C4CCCCCC4)nc4cn[nH]c(=O)c34)cc2)CC1] | 1-(4-((2-cycloheptyl-5-oxo-5,6-dihydropyrimido[4,5-d]pyridazin-4-yl)amino)phenyl)piperidine-4-carboxylic acid |

TABLE A-continued
| Structure | IUPAC Name |
|---|---|
| 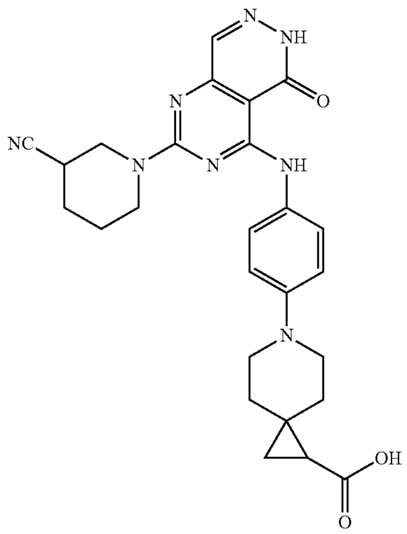 [SMILES: N#CC1CCCN(c2nc(Nc3ccc(N4CCC5(CC4)CC5C(=O)O)cc3)c3c(=O)[nH]ncc3n2)C1] | 6-(4-((2-(3-cyanopiperidin-1-yl)-5-oxo-5,6-dihydropyrimido[4,5-d]pyridazin-4-yl)amino)phenyl)-6-azaspiro[2.5]octane-1-carboxylic acid |
| 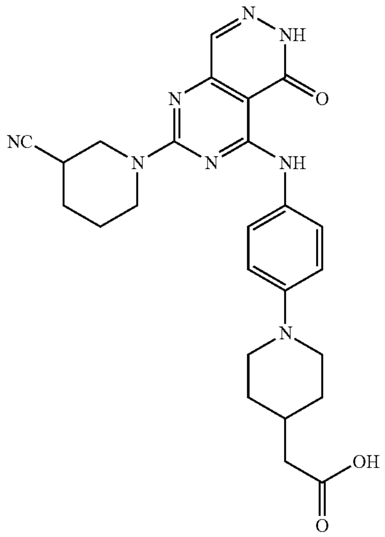 [SMILES: N#CC1CCCN(c2nc(Nc3ccc(N4CCC(CC(=O)O)CC4)cc3)c3c(=O)[nH]ncc3n2)C1] | 2-(1-(4-((2-(3-cyanopiperidin-1-yl)-5-oxo-5,6-dihydropyrimido[4,5-d]pyridazin-4-yl)amino)phenyl)piperidin-4-yl)acetic acid |
| 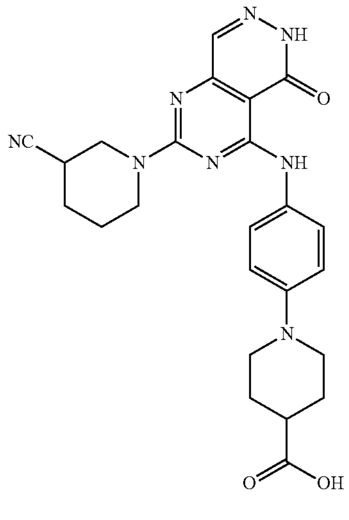 [SMILES: N#CC1CCCN(c2nc(Nc3ccc(N4CCC(C(=O)O)CC4)cc3)c3c(=O)[nH]ncc3n2)C1] | 1-(4-((2-(3-cyanopiperidin-1-yl)-5-oxo-5,6-dihydropyrimido[4,5-d]pyridazin-4-yl)amino)phenyl)piperidine-4-carboxylic acid |

TABLE A-continued
| Structure | IUPAC Name |
|---|---|
| 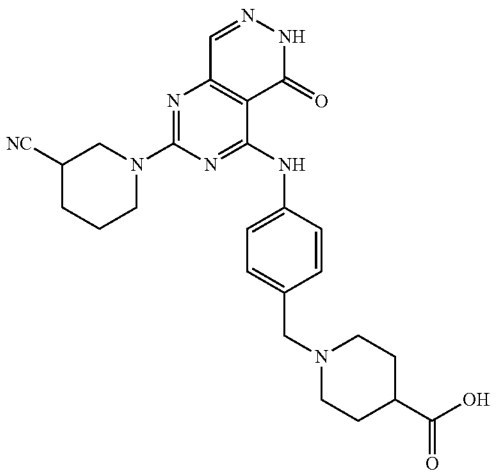 [SMILES: N#CC1CCCN(c2nc(Nc3ccc(CN4CCC(C(=O)O)CC4)cc3)c3c(=O)[nH]ncc3n2)C1] | 1-(4-((2-(3-cyanopiperidin-1-yl)-5-oxo-5,6-dihydropyrimido[4,5-d]pyridazin-4-yl)amino)benzyl)piperidine-4-carboxylic acid |
| 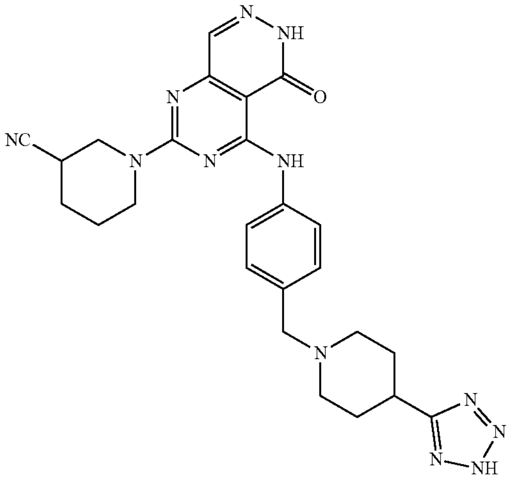 [SMILES: N#CC1CCCN(c2nc(Nc3ccc(CN4CCC(c5nn[nH]n5)CC4)cc3)c3c(=O)[nH]ncc3n2)C1] | 1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-3-carbonitrile |
| 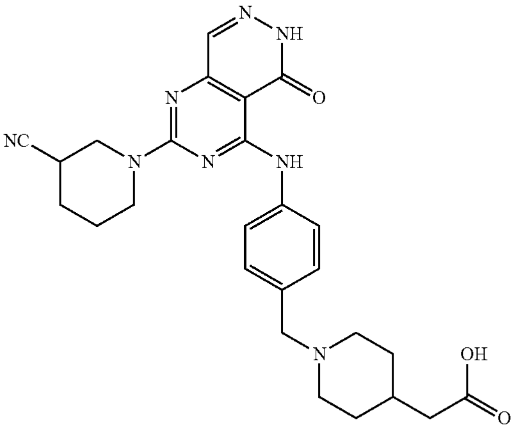 [SMILES: N#CC1CCCN(c2nc(Nc3ccc(CN4CCC(CC(=O)O)CC4)cc3)c3c(=O)[nH]ncc3n2)C1] | 2-(1-(4-((2-(3-cyanopiperidin-1-yl)-5-oxo-5,6-dihydropyrimido[4,5-d]pyridazin-4-yl)amino)benzyl)piperidin-4-yl)acetic acid |

TABLE A-continued
| Structure | IUPAC Name |
|---|---|
| 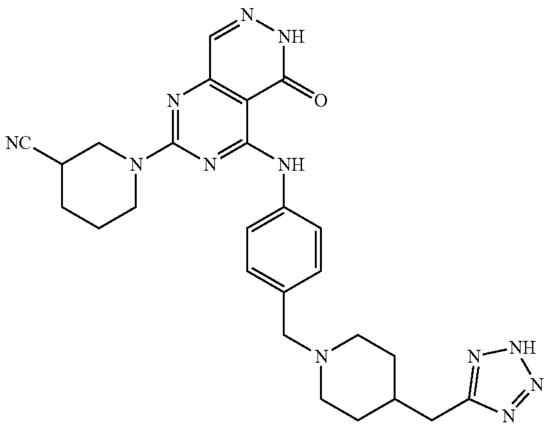 [SMILES: N#CC1CCCN(c2nc(Nc3ccc(CN4CCC(Cc5nn[nH]n5)CC4)cc3)c3c(=O)[nH]ncc3n2)C1] | 1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-3-carbonitrile |
| 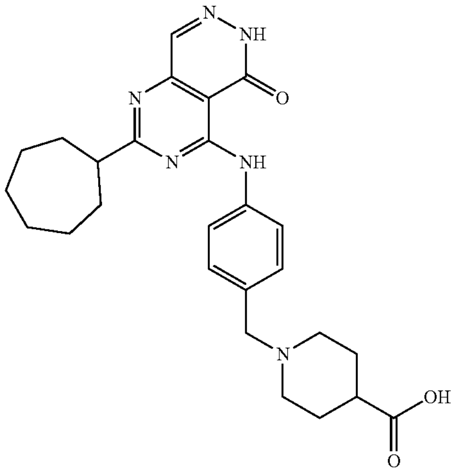 [SMILES: O=C(O)C1CCN(Cc2ccc(Nc3nc(C4CCCCCC4)nc4cn[nH]c(=O)c34)cc2)CC1] | 1-(4-((2-cycloheptyl-5-oxo-5,6-dihydropyrimido[4,5-d]pyridazin-4-yl)amino)benzyl)piperidine-4-carboxylic acid |
| 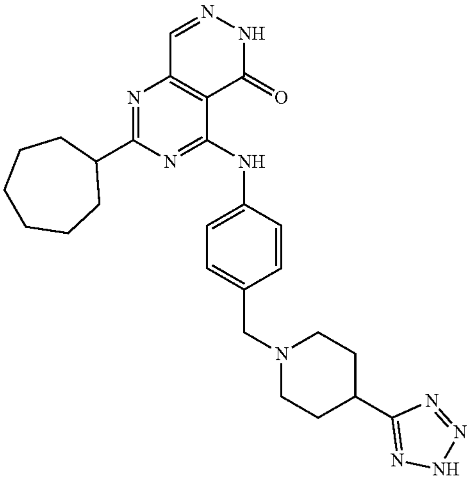 | 4-((4-((4-(2H-tetrazol-5-yl)piperidin-1-yl)methyl)phenyl)amino)-2-cycloheptylpyrimido[4,5-d]pyridazin-5(6H)-one |

TABLE A-continued
| Structure | IUPAC Name |
|---|---|
| 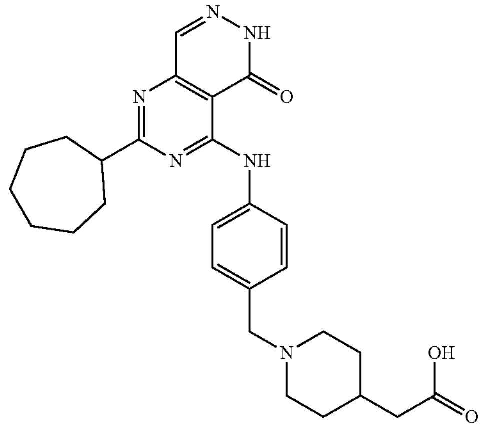 | 2-(1-(4-((2-cycloheptyl-5-oxo-5,6-dihydropyrimido[4,5-d]pyridazin-4-yl)amino)benzyl)piperidin-4-yl)acetic acid |
| 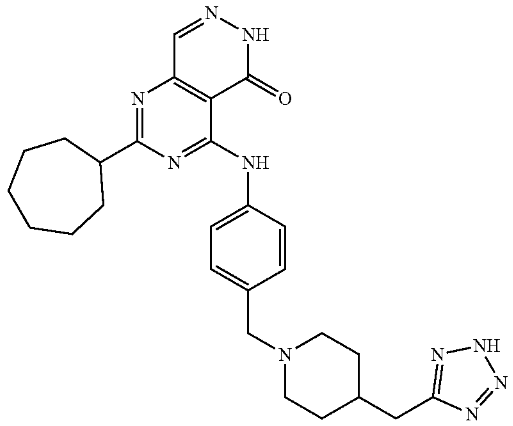 | 4-((4-((4-((2H-tetrazol-5-yl)methyl)piperidin-1-yl)methyl)phenyl)amino)-2-cycloheptylpyrimido[4,5-d]pyridazin-5(6H)-one |
| 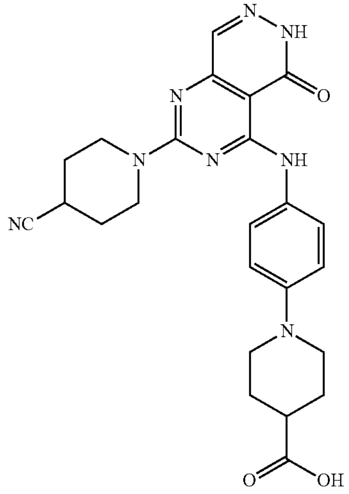 [SMILES: N#CC1CCN(c2nc(Nc3ccc(N4CCC(C(=O)O)CC4)cc3)c3c(=O)[nH]ncc3n2)CC1] | 1-(4-((2-(4-cyanopiperidin-1-yl)-5-oxo-5,6-dihydropyrimido[4,5-d]pyridazin-4-yl)amino)phenyl)piperidine-4-carboxylic acid |

TABLE A-continued

| Structure | IUPAC Name |
| --- | --- |
| 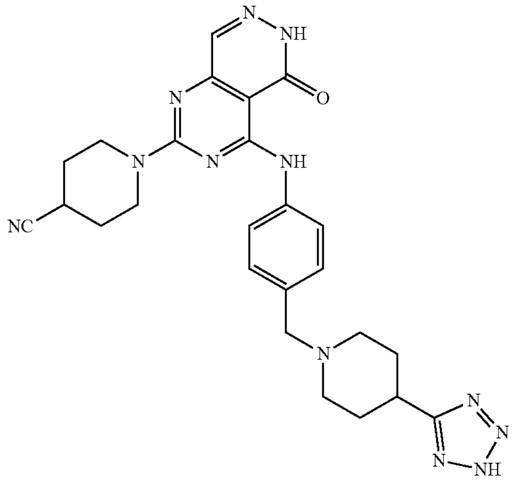 [SMILES: N#CC1CCN(c2nc(Nc3ccc(CN4CCC(c5nn[nH]n5)CC4)cc3)c3c(=O)[nH]ncc3n2)CC1] | 1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-4-carbonitrile |
| 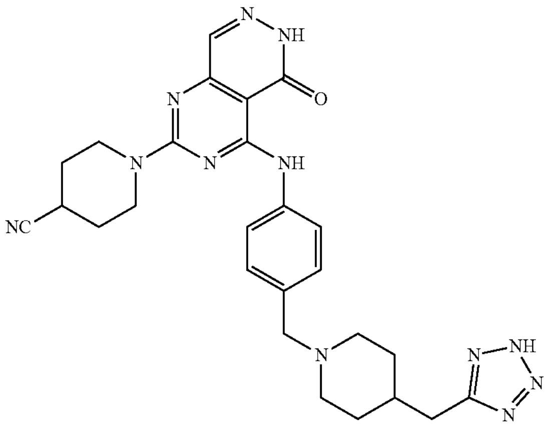 [SMILES: N#CC1CCN(c2nc(Nc3ccc(CN4CCC(Cc5nn[nH]n5)CC4)cc3)c3c(=O)[nH]ncc3n2)CC1] | 1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-4-carbonitrile |
| 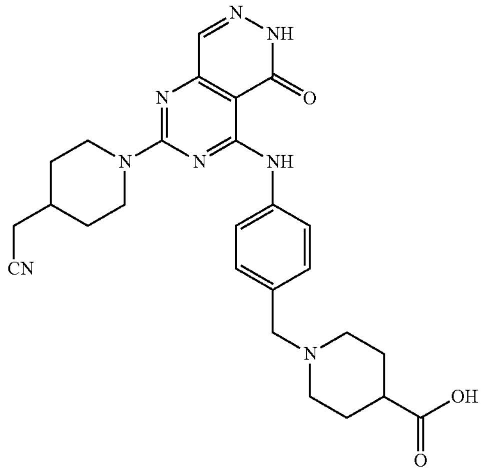 | 1-(4-((2-(4-(cyanomethyl)piperidin-1-yl)-5-oxo-5,6-dihydropyrimido[4,5-d]pyridazin-4-yl)amino)benzyl)piperidine-4-carboxylic acid |

TABLE A-continued

| Structure | IUPAC Name |
| --- | --- |
| 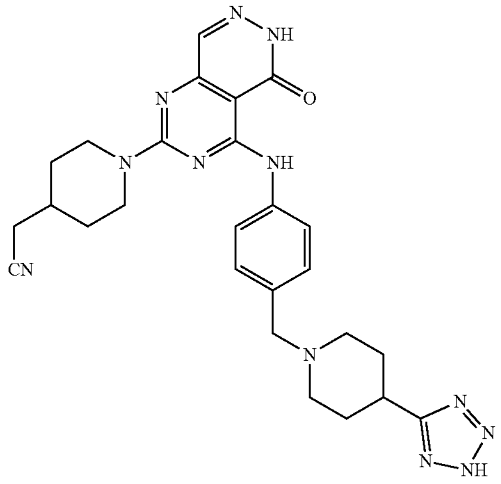 | 2-(1-(4-((4-((4-(2H-tetrazol-5-yl)piperidin-1-yl)methyl)phenyl)amino)-5-oxo-5,6-dihydropyrimido[4,5-d]pyridazin-2-yl)piperidin-4-yl)acetonitrile |
| 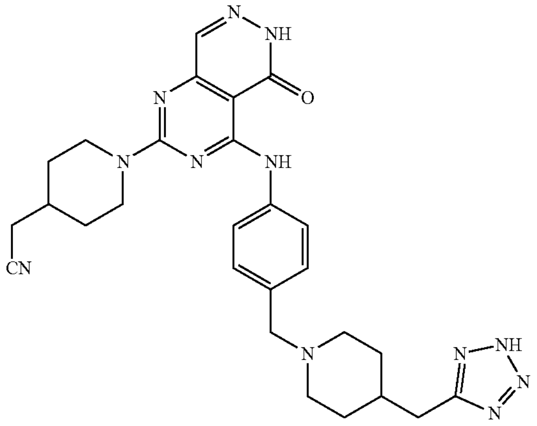 [SMILES: N#CCC1CCN(c2nc(Nc3ccc(CN4CCC(Cc5nn[nH]n5)CC4)cc3)c3c(=O)[nH]ncc3n2)CC1] | 2-(1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidin-4-yl)acetonitrile |
| 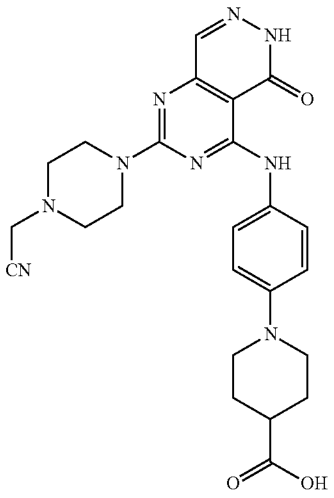 [SMILES: N#CCN1CCN(c2nc(Nc3ccc(N4CCC(C(=O)O)CC4)cc3)c3c(=O)[nH]ncc3n2)CC1] | 1-(4-((2-(4-(cyanomethyl)piperazin-1-yl)-5-oxo-5,6-dihydropyrimido[4,5-d]pyridazin-4-yl)amino)phenyl)piperidine-4-carboxylic acid |

TABLE A-continued
| Structure | IUPAC Name |
| --- | --- |
| 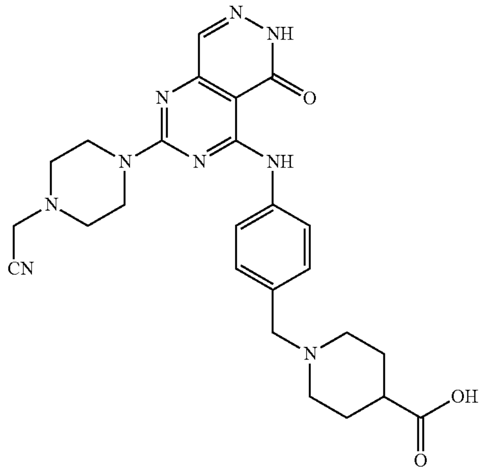 | 1-(4-((2-(4-(cyanomethyl)piperazin-1-yl)-5-oxo-5,6-dihydropyrimido[4,5-d]pyridazin-4-yl)amino)benzyl)piperidine-4-carboxylic acid |
| 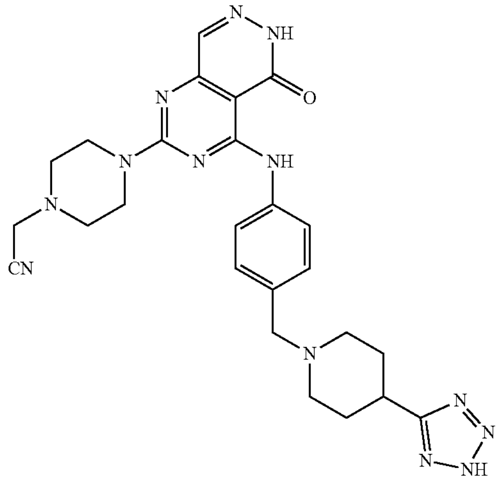 | 2-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)acetonitrile |
| 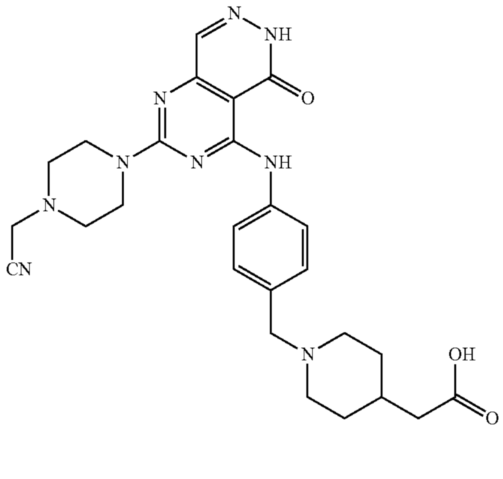 [SMILES: N#CCN1CCN(c2nc(Nc3ccc(CN4CCC(CC(=O)O)CC4)cc3)c3c(=O)[nH]ncc3n2)CC1] | 2-(1-(4-((2-(4-(cyanomethyl)piperazin-1-yl)-5-oxo-5,6-dihydropyrimido[4,5-d]pyridazin-4-yl)amino)benzyl)piperidin-4-yl)acetic acid |

TABLE A-continued
| Structure | IUPAC Name |
| --- | --- |
| 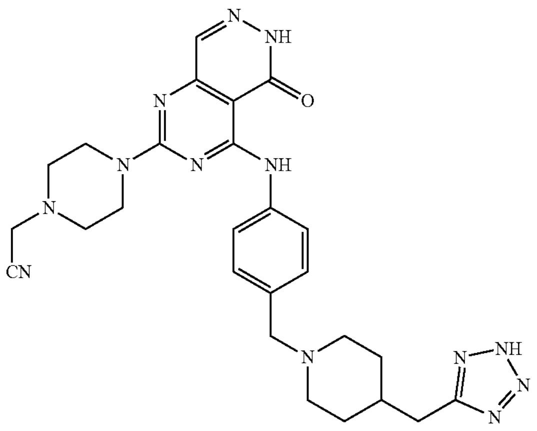 [SMILES: N#CCN1CCN(c2nc(Nc3ccc(CN4CCC(Cc5nn[nH]n5)CC4)cc3)c3c(=O)[nH]ncc3n2)CC1] | 2-(4-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperazin-1-yl)acetonitrile |
| 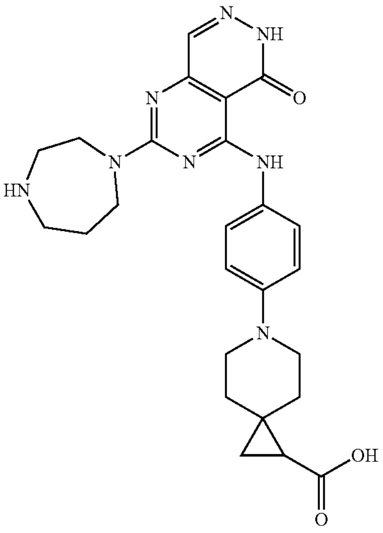 [SMILES: O=C(O)C1CC12CCN(c1ccc(Nc3nc(N4CCCNCC4)nc4cn[nH]c(=O)c34)cc1)CC2] | 6-(4-((2-(1,4-diazepan-1-yl)-5-oxo-5,6-dihydropyrimido[4,5-d]pyridazin-4-yl)amino)phenyl)-6-azaspiro[2.5]octane-1-carboxylic acid |
| 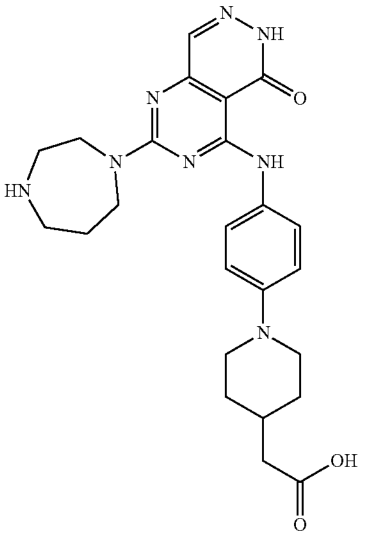 [SMILES: O=C(O)CC1CCN(c2ccc(Nc3nc(N4CCCNCC4)nc4cn[nH]c(=O)c34)cc2)CC1] | 2-(1-(4-((2-(1,4-diazepan-1-yl)-5-oxo-5,6-dihydropyrimido[4,5-d]pyridazin-4-yl)amino)phenyl)piperidin-4-yl)acetic acid |

TABLE A-continued
| Structure | IUPAC Name |
| --- | --- |
| 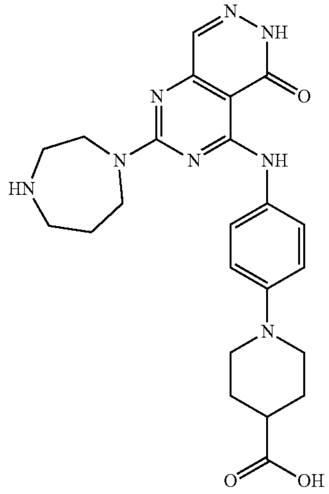 [SMILES: O=C(O)C1CCN(c2ccc(Nc3nc(N4CCCNCC4)nc4cn[nH]c(=O)c34)cc2)CC1] | 1-(4-((2-(1,4-diazepan-1-yl)-5-oxo-5,6-dihydropyrimido[4,5-d]pyridazin-4-yl)amino)phenyl)piperidine-4-carboxylic acid |
| 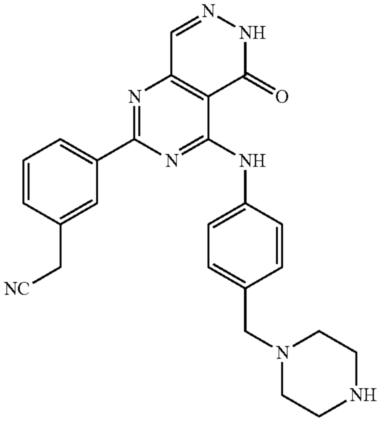 [SMILES: N#CCc1cccc(-c2nc(Nc3ccc(CN4CCNCC4)cc3)c3c(=O)[nH]ncc3n2)c1] | 1-(4-((2-(1,4-diazepan-1-yl)-5-oxo-5,6-dihydropyrimido[4,5-d]pyridazin-4-yl)amino)benzyl)piperidine-4-carboxylic acid |
| 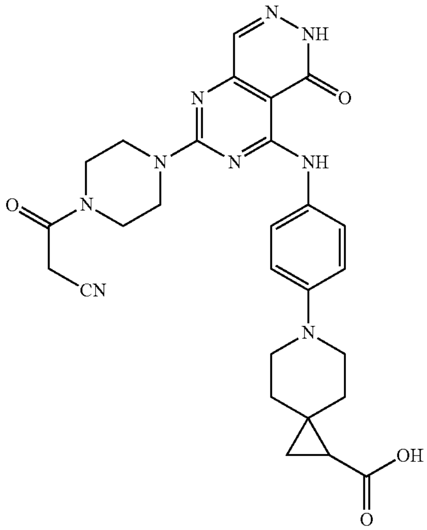 | 6-(4-((2-(4-(2-cyanoacetyl)piperazin-1-yl)-5-oxo-5,6-dihydropyrimido[4,5-d]pyridazin-4-yl)amino)phenyl)-6-azaspiro[2.5]octane-1-carboxylic acid |

TABLE A-continued
| Structure | IUPAC Name |
| --- | --- |
| 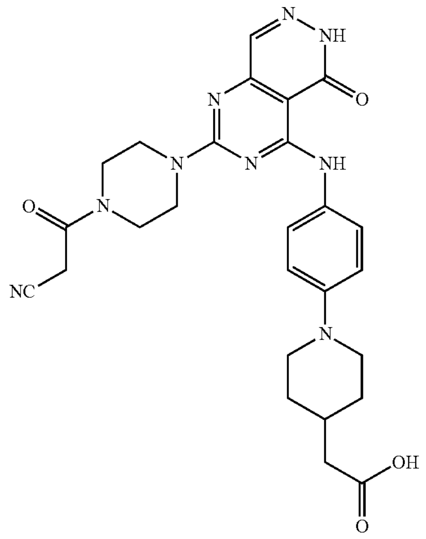 | 2-(1-(4-((2-(4-(2-cyanoacetyl)piperazin-1-yl)-5-oxo-5,6-dihydropyrimido[4,5-d]pyridazin-4-yl)amino)phenyl)piperidin-4-yl)acetic acid |
| 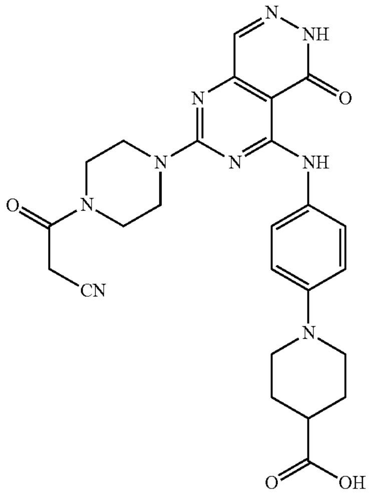 | 1-(4-((2-(4-(2-cyanoacetyl)piperazin-1-yl)-5-oxo-5,6-dihydropyrimido[4,5-d]pyridazin-4-yl)amino)phenyl)piperidine-4-carboxylic acid |
| 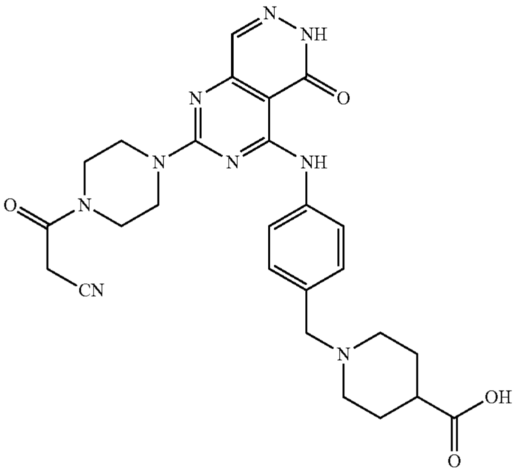 | 1-(4-((2-(4-(2-cyanoacetyl)piperazin-1-yl)-5-oxo-5,6-dihydropyrimido[4,5-d]pyridazin-4-yl)amino)benzyl)piperidine-4-carboxylic acid |

TABLE A-continued

| Structure | IUPAC Name |
|---|---|
| 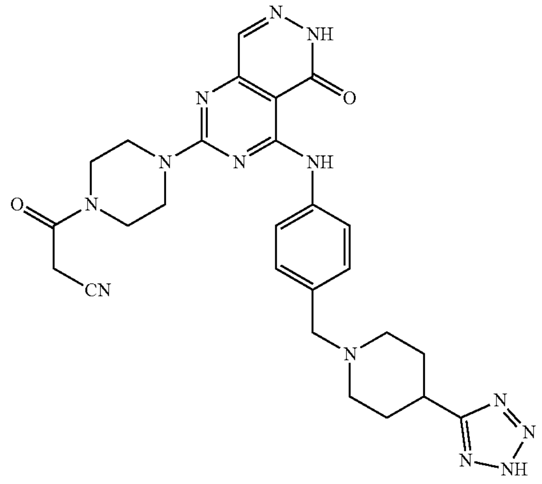 | 3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)-3-oxopropanenitrile |
| 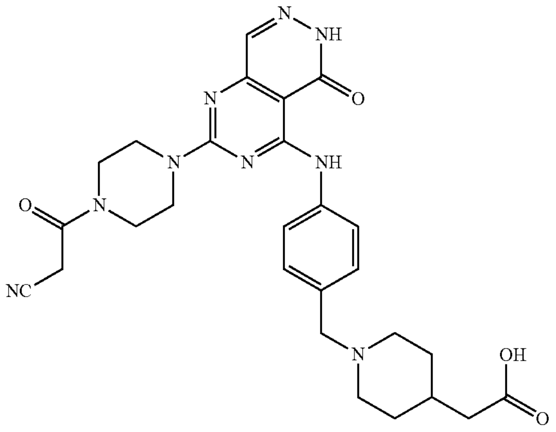 [SMILES: N#CCC(=O)N1CCN(c2nc(Nc3ccc(CN4CCC(CC(=O)O)CC4)cc3)c3c(=O)[nH]ncc3n2)CC1] | 2-(1-(4-((2-(4-(2-cyanoacetyl)piperazin-1-yl)-5-oxo-5,6-dihydropyrimido[4,5-d]pyridazin-4-yl)amino)benzyl)piperidin-4-yl)acetic acid |
| 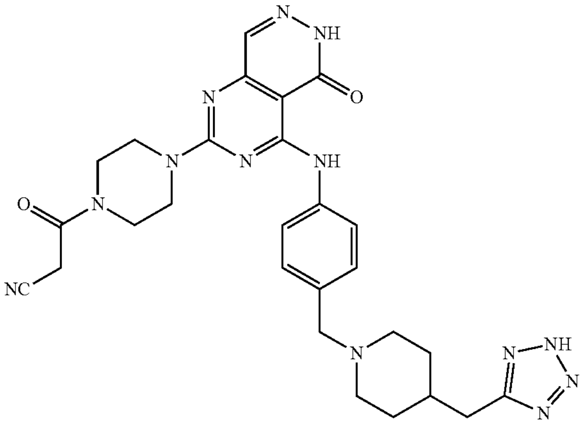 [SMILES: N#CCC(=O)N1CCN(c2nc(Nc3ccc(CN4CCC(Cc5nn[nH]n5)CC4)cc3)c3c(=O)[nH]ncc3n2)CC1] | 4-((4-((4-((2H-tetrazol-5-yl)methyl)piperidin-1-yl)methyl)phenyl)amino)-2-(4-(2-isocyanoacetyl)piperazin-1-yl)pyrimido[4,5-d]pyridazin-5(6H)-one |

TABLE A-continued
| Structure | IUPAC Name |
| --- | --- |
| 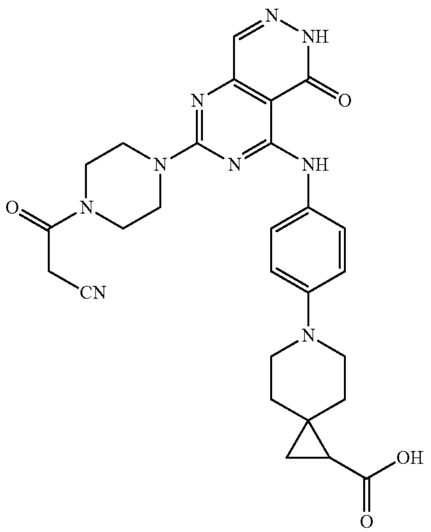 | 6-(4-((2-(1-(2-cyanoacetyl)piperidin-4-yl)-5-oxo-5,6-dihydropyrimido[4,5-d]pyridazin-4-yl)amino)phenyl)-6-azaspiro[2.5]octane-1-carboxylic acid |
| 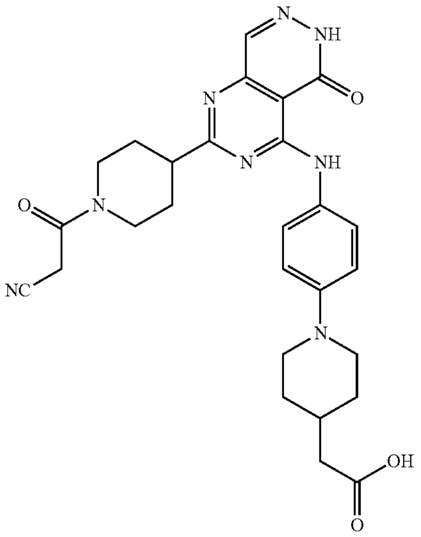 [SMILES: N#CCC(=O)N1CCC(c2nc(Nc3ccc(N4CCC(CC(=O)O)CC4)cc3)c3c(=O)[nH]ncc3n2)CC1] | 2-(1-(4-((2-(1-(2-cyanoacetyl)piperidin-4-yl)-5-oxo-5,6-dihydropyrimido[4,5-d]pyridazin-4-yl)amino)phenyl)piperidin-4-yl)acetic acid |
| 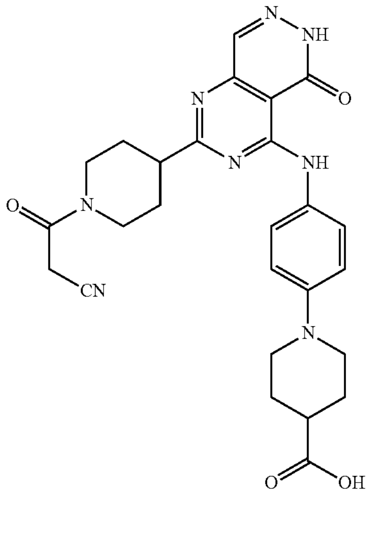 | 1-(4-((2-(1-(2-cyanoacetyl)piperidin-4-yl)-5-oxo-5,6-dihydropyrimido[4,5-d]pyridazin-4-yl)amino)phenyl)piperidine-4-carboxylic acid |

TABLE A-continued

| Structure | IUPAC Name |
| --- | --- |
| 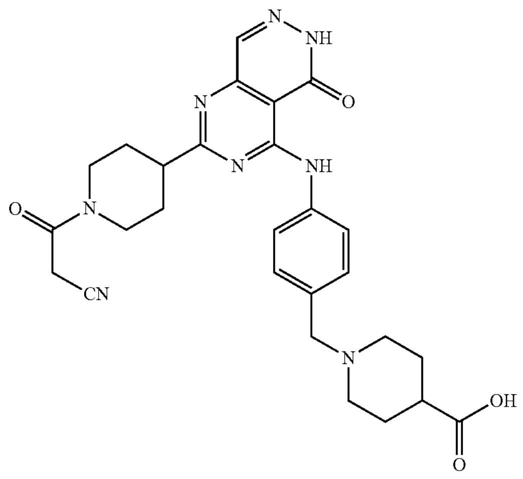 | 1-(4-((2-(1-(2-cyanoacetyl)piperidin-4-yl)-5-oxo-5,6-dihydropyrimido[4,5-d]pyridazin-4-yl)amino)benzyl)piperidine-4-carboxylic acid |
| 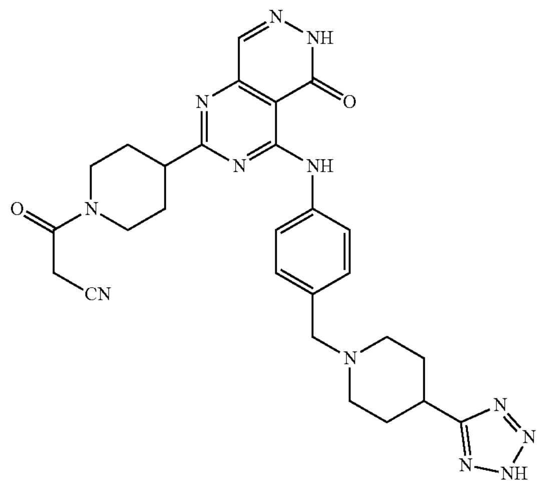 | 3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperidin-1-yl)-3-oxopropanenitrile |
| 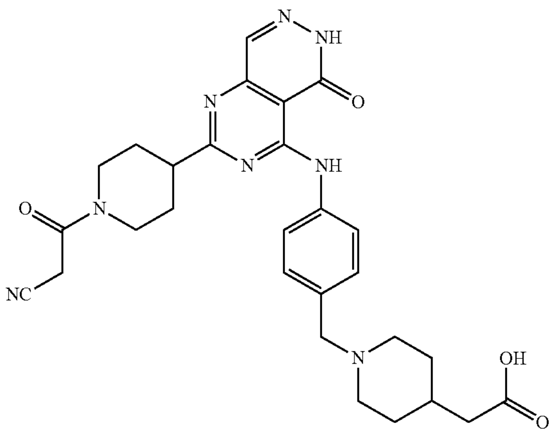 [SMILES: N#CCC(=O)N1CCC(c2nc(Nc3ccc(CN4CCC(CC(=O)O)CC4)cc3)c3c(=O)[nH]ncc3n2)CC1] | 2-(1-(4-((2-(1-(2-cyanoacetyl)piperidin-4-yl)-5-oxo-5,6-dihydropyrimido[4,5-d]pyridazin-4-yl)amino)benzyl)piperidin-4-yl)acetic acid |

TABLE A-continued
| Structure | IUPAC Name |
|---|---|
| 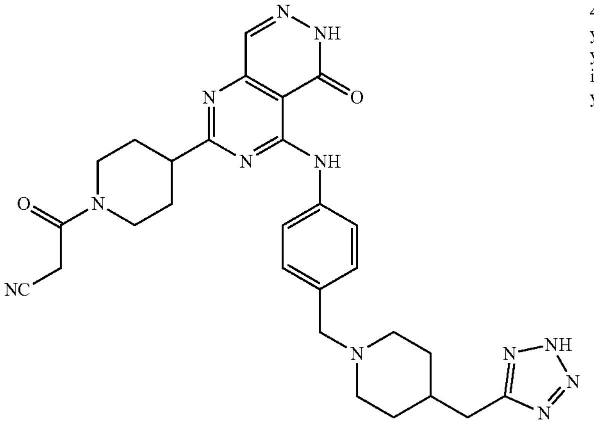 | 4-((4-((4-((2H-tetrazol-5-yl)methyl)piperidin-1-yl)methyl)phenyl)amino)-2-(1-(2-isocyanoacetyl)piperidin-4-yl)pyrimido[4,5-d]pyridazin-5(6H)-one |
TABLE 2
| | | Physical Data | |
|---|---|---|---|
| Ex # | Structure | $^1$H-NMR in DMSO-$d_6$ at 400 Hz (δ) | MS m/z |
| 1 | 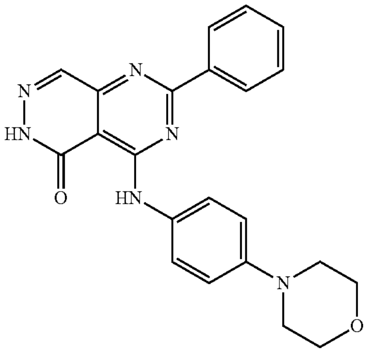 [SMILES: O=c1[nH]ncc2nc(-c3ccccc3)nc(Nc3ccc(N4CCOCC4)cc3)c12] | 13.32 (s, 1H), 11.32 (s, 1H), 8.42 (d, J = 6.7 Hz, 2H), 8.29 (s, 1H), 7.76 (d, J = 8.6 Hz, 2H), 7.6-7.55 (m, 3H), 7.07 (d, J = 9.2 Hz, 2H), 3.77 (t, J = 4.9 Hz, 4H), 3.15 (t, J = 4.6 Hz, 4H) | 401.3 (M + 1) |
| 2 | 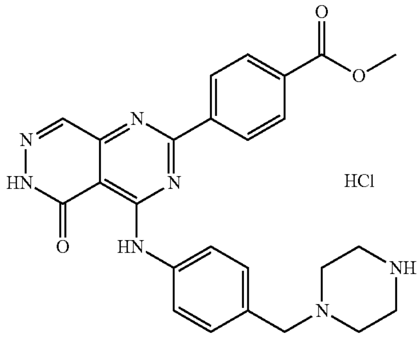 [SMILES: COC(=O)c1ccc(-c2nc(Nc3ccc(CN4CCNCC4)cc3)c3c(=O)[nH]ncc3n2)cc1 ; Cl] HCl | 13.47 (s, 1H), 11.62 (s, 1H), 9.75 (br, 2H), 8.51 (d, J = 8.3 Hz, 2H), 8.37 (s, 1H), 8.13 (d, J = 8.3 Hz, 2H), 8.0 (d, J = 8.3 Hz, 2H), 7.76 (d, J = 8.3 HZ, 2H), 4.4 (s, 2H), 3.91 (s, 3H), 3.57-3.51 (m, 8H) | 472.1 (M + 1) |
| 3 | 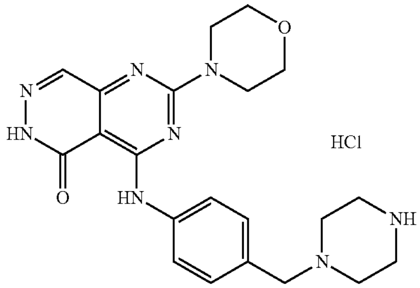 [SMILES: O=c1[nH]ncc2nc(N3CCOCC3)nc(Nc3ccc(CN4CCNCC4)cc3)c12 ; Cl] HCl | 12.9 (s, 1H), 11.52 (s, 1H), 9.4 (s, 2H), 7.94 (s, 1H), 7.81 (d, J = 7.0 Hz, 2H), 7.61 (br, 2H), 4.3 (br, 2H), 3.84 (m, 4H), 3.7 (m, 4H), 3.47 (m, 8H) | 423.0 (M + 1) |

TABLE 2-continued
| Ex # | Structure | Physical Data $^1$H-NMR in DMSO-$d_6$ at 400 Hz (δ) | MS m/z |
|---|---|---|---|
| 4 | 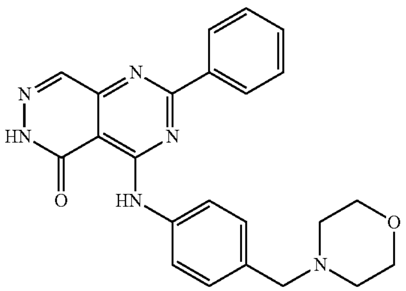 [SMILES: O=c1[nH]ncc2nc(-c3ccccc3)nc(Nc3ccc(CN4CCOCC4)cc3)c12] | 13.37 (s, 1H), 11.51 (s, 1H), 8.45 (d, J = 5.9 Hz, 2H), 8.39 (s, 1H), 7.89 (d, J = 8.1 Hz, 2H), 7.6 (d, J = 7.0 Hz, 3H), 7.44 (d, J = 8.6 Hz, 2H), 4.03 (s, 4H), 3.59-3.58 (m, 4H), 3.5 (s, 2H) | 415.4 (M + 1) |
| 5 | 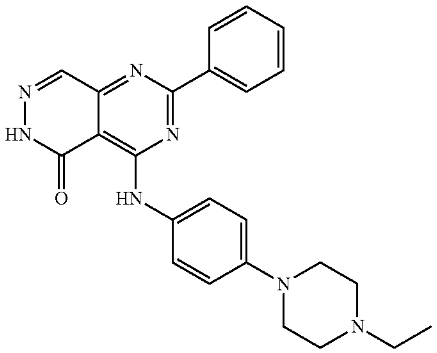 [SMILES: CCN1CCN(c2ccc(Nc3nc(-c4ccccc4)nc4cn[nH]c(=O)c34)cc2)CC1] | 13.31 (s, 1H), 11.33 (s, 1H), 8.42 (d, J = 6.7 Hz, 2H), 8.3 (s, 1H), 7.75 (d, J = 8.9 Hz, 2H), 7.62-7.56 (m, 3H), 7.06 (d, J = 8.9 Hz, 2H), 3.18 (t, J = 4.4 Hz, 4H), 2.39 (q, J = 7.2 Hz, 2), 1.24 (m, 4H), 1.05 (t, J = 7.2 Hz, 3H) | 428.2 (M + 1) |
| 6 | 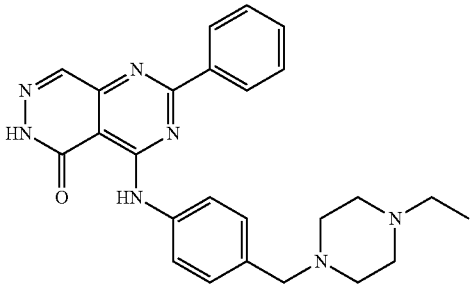 [SMILES: CCN1CCN(Cc2ccc(Nc3nc(-c4ccccc4)nc4cn[nH]c(=O)c34)cc2)CC1] | 13.37 (s, 2H), 11.5 (s, 1H), 8.44 (d, J = 5.9 Hz, 2H), 8.34 (s, 1H), 7.87 (d, J = 8.3 Hz, 2H), 7.60 (d, J = 7.0 Hz, 3H), 7.41 (d, J = 8.3 Hz, 2H), 3.48 (s, 2H), 2.40-2.31 (m, 10H), 0.98 (t, J = 7.1 Hz, 3H) | 442.3 (M + 1) |
| 7 | 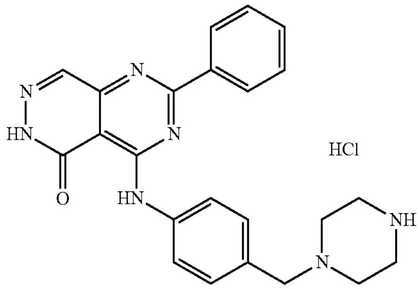 [SMILES: O=c1[nH]ncc2nc(-c3ccccc3)nc(Nc3ccc(CN4CCNCC4)cc3)c12 ; Cl] HCl | 13.42 (s, 1H), 11.62 (s, 1H), 8.45 (d, J = 6.8 Hz, 2H), 8.37 (s, 1H), 8.03 (d, J = 7.3 Hz, 2H), 7.69-7.58 (m, 5H), 3.43 (m, 10H) | 414.0 (M + 1) |

TABLE 2-continued
| Ex # | Structure | Physical Data<br>$^1$H-NMR in DMSO-$d_6$ at 400 Hz (δ) | MS m/z |
|---|---|---|---|
| 8 | 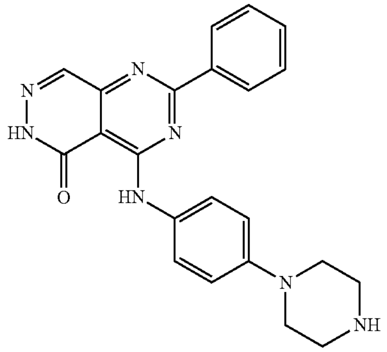 [SMILES: O=c1[nH]ncc2nc(-c3ccccc3)nc(Nc3ccc(N4CCNCC4)cc3)c12] | 11.68 (s, 1H), 8.42 (d, J = 6.2 Hz, 2H), 8.30 (s 1H), 7.75 (d, J = 8.9 Hz, 2H), 7.57 (d, J = 8.9 Hz, 2H), 7.04 (d, J = 8.9 Hz, 2H), 3.08-3.07 (m, 4H), 2.86-2.85 (m, 4H) | 400.3 (M + 1) |
| 9 | 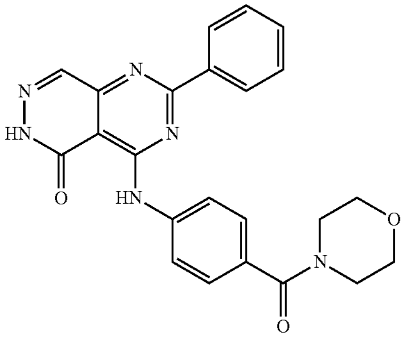 [SMILES: O=C(c1ccc(Nc2nc(-c3ccccc3)nc3cn[nH]c(=O)c23)cc1)N1CCOCC1] | 13.42 (s, 1H), 11.63 (s, 1H), 8.47-8.45 (m, 2H), 8.37 (s, 1H), 8.01 (d, J = 8.3 Hz, 2H), 7.63-7.57 (m, 5H), 3.63-3.55 (m, 8H) | 429.2 (M + 1) |
| 10 | 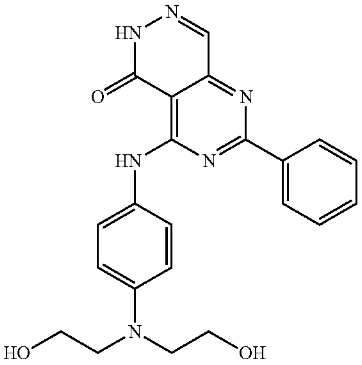 [SMILES: O=c1[nH]ncc2nc(-c3ccccc3)nc(Nc3ccc(N(CCO)CCO)cc3)c12] | 13.28 (s, 1H), 11.23 (s, 1H), 8.42-8.4 (d, J = 9.2 Hz, 2H), 8.27 (s, 1H), 7.66 (d, J = 9.2 Hz, 2H), 7.59-7.55 (m, 3H), 6.80 (d, J = 8.8 Hz, 2H), 4.77 (t, J = 5.4 Hz, 2H), 3.58 (dd, J = 5.9 Hz, 11.7 Hz, 4H), 3.47-3.44 (m, 4H) | 419.3 (M + 1) |
| 11 | 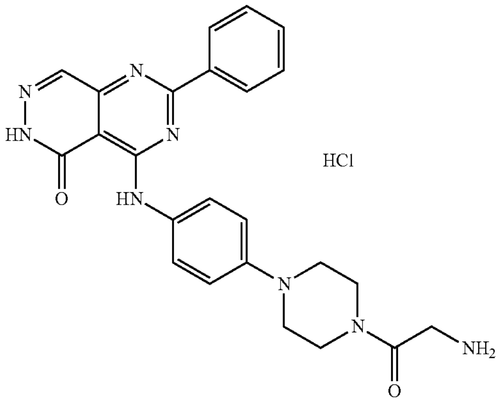 [SMILES: NCC(=O)N1CCN(c2ccc(Nc3nc(-c4ccccc4)nc4cn[nH]c(=O)c34)cc2)CC1 ; Cl] HCl | 13.34 (s, 1H), 11.35 (s, 1H), 8.45-8.42 (m, 2H), 8.3 (s, 1H), 8.11 (s, 2H), 7.80 (d, J = 8.8 Hz, 2H), 7.61-7.56 (m, 3H), 7.15 (d, J = 7.3 Hz, 2H), 3.7 (m, 2H), 3.27-3.22 (m, 4H) | 457.2 (M + 1) |

TABLE 2-continued
| Ex # | Structure | Physical Data $^1$H-NMR in DMSO-$d_6$ at 400 Hz (δ) | MS m/z |
|---|---|---|---|
| 12 | 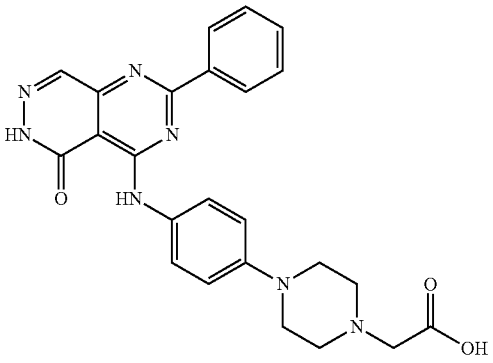 [SMILES: O=C(O)CN1CCN(c2ccc(Nc3nc(-c4ccccc4)nc4cn[nH]c(=O)c34)cc2)CC1] | 13.32 (s, 1H), 11.31 (s, 1H), 8.42 (d, J = 7.0 Hz, 2H), 8.3 (s, 1H), 7.76 (d, J = 9.2 Hz, 2H), 7.62-7.55 (m, 3H), 7.07 (d, J = 9.2 Hz, 2H), 3.35-3.29 (m, 8H), 2.79 (s, 2H) | 458.1 (M + 1) |
| 13 | 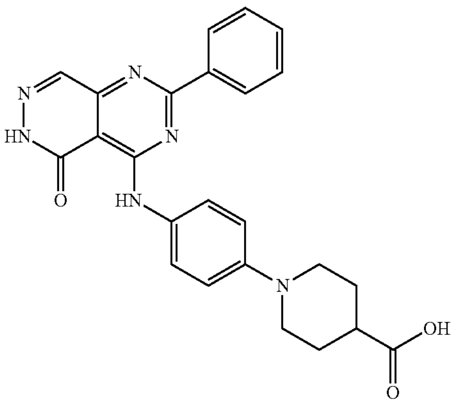 [SMILES: O=C(O)C1CCN(c2ccc(Nc3nc(-c4ccccc4)nc4cn[nH]c(=O)c34)cc2)CC1] | 13.31 (s, 1H), 12.3 (s, 1H), 11.31 (s, 1H), 8.43-8.41 (m, 2H), 8.3 (s, 1H), 7.74 (d, J = 9.3 Hz, 2H), 7.6-7.55 (m, 3H), 7.07 (d, J = 8.8 Hz, 2H), 3.69-3.66 (m, 2H), 2.79 (t, J = 10.8 Hz, 2H), 2.43-2.39 (m, 1H), 1.94-1.91 (m, 2H), 1.72-1.66 (m, 2H) | 443.0 (M + 1) |
| 14 | 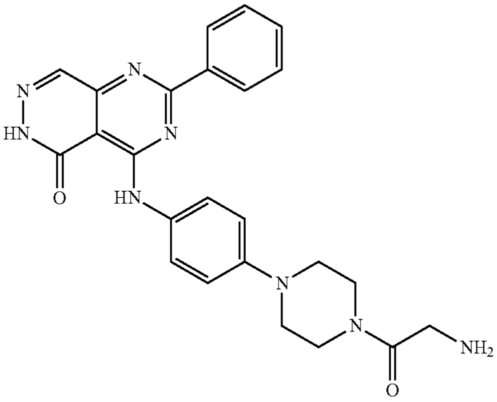 [SMILES: NCC(=O)N1CCN(c2ccc(Nc3nc(-c4ccccc4)nc4cn[nH]c(=O)c34)cc2)CC1] | 11.5 (s, 1H), 8.42-8.41 (m, 2H), 8.31 (s, 1H), 7.78 (d, J = 8.8 Hz, 2H), 7.57 (d, J = 7.4 Hz, 3H), 7.09 (d, J = 9.3 Hz, 2H), 3.39 (m, 4H), 3.17 (m, 8H) | 457.3 (M + 1) |
| 15 | 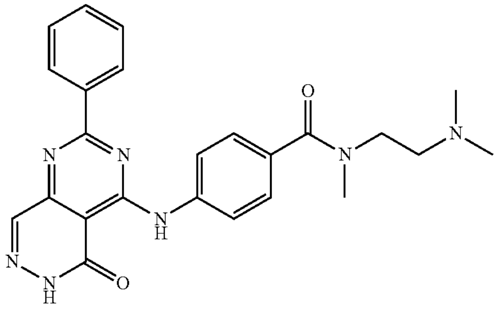 [SMILES: CN(C)CCN(C)C(=O)c1ccc(Nc2nc(-c3ccccc3)nc3cn[nH]c(=O)c23)cc1] | 13.1 (s, 1H), 11.6 (s, 1H), 8.45 (d, J = 6.4 Hz, 2H), 8.36 (s, 1H), 7.97 (d, J = 7.4 Hz, 2H), 7.59 (m, 3H), 7.53 (d, J = 7.9 Hz, 2H), 3.36 (br, 2H), 2.99 (s, 3H), 2.2-2.0 (m, 6H), 1.85 (s, 2H) | 444.4 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 16 | 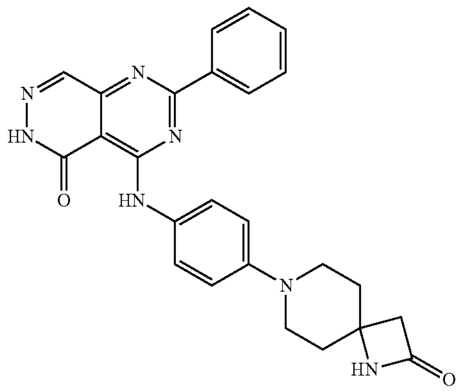 [SMILES: O=C1CC2(CCN(c3ccc(Nc4nc(-c5ccccc5)nc5cn[nH]c(=O)c45)cc3)CC2)N1] | 13.31 (s, 1H), 11.31 (s, 1H), 8.42 (dd, J = 1.4, 7.8 Hz, 2H) 8.31 (d, J = 9.2 Hz, 2H), 7.74 (d, J = 9.2 Hz, 2H), 7.61-7.57 (m, 3H), 7.09 (d, J = 9.2 Hz, 2H), 3.22-3.2 (m, 4H), 2.66-2.65 (m, 2H), 1.84-1.78 (m, 24H) | 454.1 (M + 1) |
| 17 | 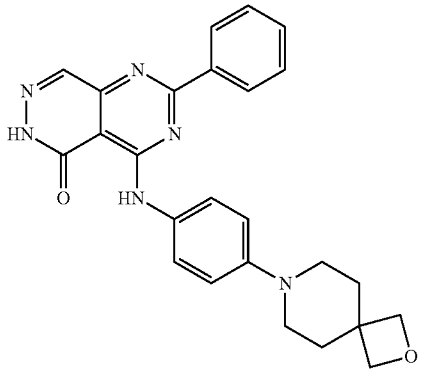 [SMILES: O=c1[nH]ncc2nc(-c3ccccc3)nc(Nc3ccc(N4CCC5(CC4)COC5)cc3)c12] | 13.31 (s, 1H), 11.29 (s, 1H), 8.43-8.40 (m, 2H), 8.29 (s, 1H), 7.73 (d, J = 8.7 Hz, 2H), 7.6-7.64 (m, 3H), 7.07 (d, J = 9.2 Hz, 2H), 4.36 (s, 4H), 3.13 (t, J = 5.4 Hz, 4H), 1.91 (t, J = 5.4 Hz, 4H) | 441.4 (M + 1) |
| 18 | 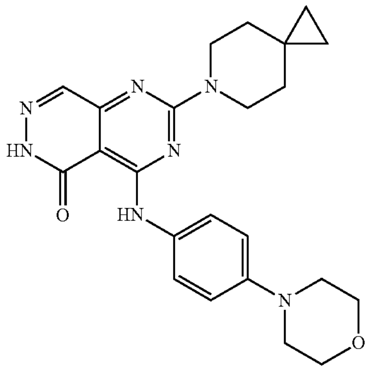 [SMILES: O=c1[nH]ncc2nc(N3CCC4(CC3)CC4)nc(Nc3ccc(N4CCOCC4)cc3)c12] | 12.73 (s, 1H), 11.13 (s, 1H), 7.87 (s, 1H), 7.58 (d, J = 8.7 Hz, 2H), 6.97 (d, J = 9.2 Hz, 2H), 3.89 (br, 4H), 3.73 (t, J = 4.9 Hz, 4H), 3.09 (t, J = 4.9 Hz, 4H), 1.4 (d, J = 4.6 Hz, 4H), 0.38 (s, 4H) | 434.0 (M + 1) |

TABLE 2-continued
| Ex # | Structure | Physical Data $^1H$-NMR in DMSO-$d_6$ at 400 Hz (δ) | MS m/z |
|---|---|---|---|
| 19 | 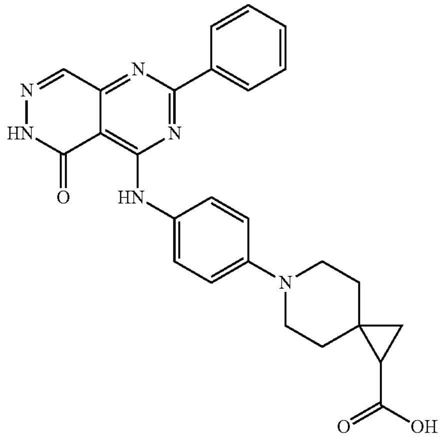 [SMILES: O=C(O)C1CC12CCN(c1ccc(Nc3nc(-c4ccccc4)nc4cn[nH]c(=O)c34)cc1)CC2] | 13.3 (s, 1H), 12.02 (s, 1H), 11.30 (s, 1H), 8.42 (d, J = 6.7 Hz, 2H), 8.28 (s, 1H), 7.73 (d, J = 8.9 Hz, 2H), 7.6-7.55 (m, 3H), 7.07 (d, J = 9.2 Hz, 2H), 3.28-3.27 (m, 2H), 3.1-3.05 (m, 1H), 2.5 (t, J = 1.6 Hz, 2H), 1.8-1.5 (m, 4H), 0.99-0.96 (m, 2H) | 469.3 (M + 1) |
| 20 | 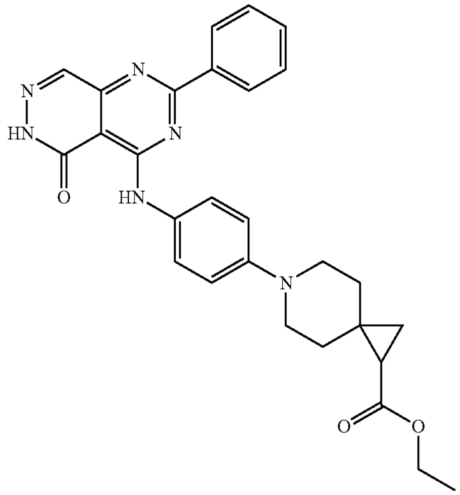 [SMILES: CCOC(=O)C1CC12CCN(c1ccc(Nc3nc(-c4ccccc4)nc4cn[nH]c(=O)c34)cc1)CC2] | 13.31 (s, 1H), 11.31 (s, 1H), 8.43-8.41 (m, 2H), 8.39 (s, 1H), 7.74 (d, J = 8.8 Hz, 2H), 7.62-7.54 (m, 3H), 7.08 (d, J = 9.3 Hz, 2H), 4.11-4.06 (m, 2H), 3.26-3.19 (m, 2H), 3.07-3.02 (m, 1H), 2.42 (t, J = 2.0 Hz, 2H), 1.84-1.5 (m, 4H), 1.19 (t, J = 7.1 Hz, 3H), 1.06-1.02 (m, 2H) | 497.0 (M + 1) |
| 21 | 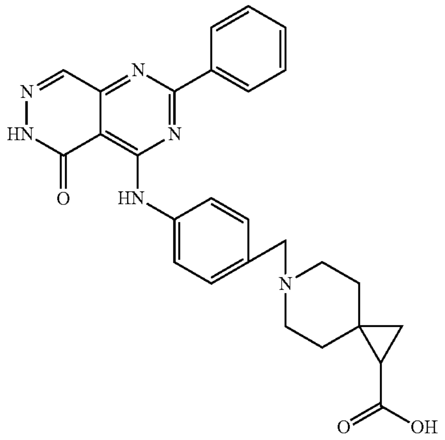 [SMILES: O=C(O)C1CC12CCN(Cc1ccc(Nc3nc(-c4ccccc4)nc4cn[nH]c(=O)c34)cc1)CC2] | 13.4 (s, 1H), 11.55 (s, 1H), 8.45 (d, J = 7.8 Hz, 2H), 8.35 (s, 1H), 7.93 (d, J = 7.8 Hz, 2H), 7.63-7.58 (m, 3H), 7.5 (d, J = 8.3 Hz, 2H), 1.75 (m, 2H), 1.54-1.50 (m, 2H), 0.93 (m, 2H) | 483.0 (M + 1) |

TABLE 2-continued
| Ex # | Structure | Physical Data $^1$H-NMR in DMSO-$d_6$ at 400 Hz (δ) | MS m/z |
|---|---|---|---|
| 22 | 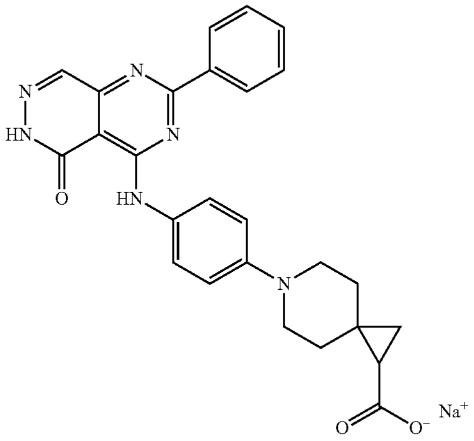 [SMILES: O=C([O-])C1CC12CCN(c1ccc(Nc3nc(-c4ccccc4)nc4cn[nH]c(=O)c34)cc1)CC2 ; [Na+]] | 8.47 (s, 1H), 8.39 (dd, J = 3.2, 6.6 Hz, 2H), 7.82 (d, J = 8.8 Hz, 2H), 7.58-7.57 (m, 3H), 7.08 (d, J = 9.3 Hz, 2H), 3.14 (t, J = 5.4 Hz, 2H), 2.56 (t, J = 2.0 Hz, 2H), 1.86-1.76 (m, 2H), 1.69-1.47 (m, 2H), 1.34-1.31 (m, 1H), 0.85-0.83 (m, 1H), 0.55-0.52 (m, 1H) | 469 (M + 1) |
| 23 | 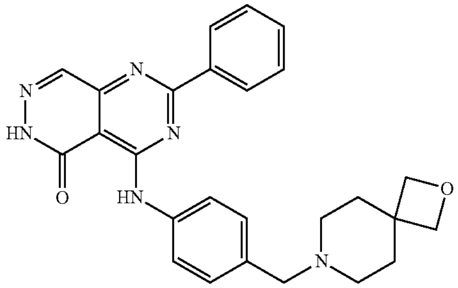 [SMILES: O=c1[nH]ncc2nc(-c3ccccc3)nc(Nc3ccc(CN4CCC5(CC4)COC5)cc3)c12] | 13.39 (s, 1H), 11.5 (s, 1H), 8.44 (d, J = 6.3 Hz, 2H), 8.34 (s, 1H), 7.86 (t, J = 8.1 Hz, 2H), 7.62 (d, J = 7.4 Hz, 2H), 7.48 (d, J = 6.8 Hz, 1H), 7.40 (d, J = 6.9 Hz, 2H), 4.27 (s, 4H), 3.44 (s, 2H), 2.33-2.28 (m, 4H), 1.76 (m, 4H) | 455.0 (M + 1) |
| 24 | 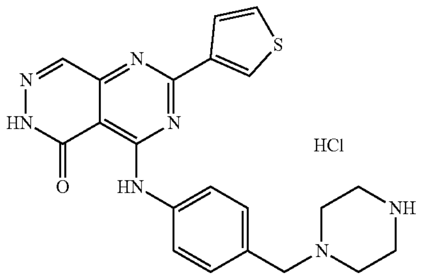 [SMILES: O=c1[nH]ncc2nc(-c3ccsc3)nc(Nc3ccc(CN4CCNCC4)cc3)c12 ; Cl] | 13.39 (s, 1H), 11.61 (s, 1H), 9.61 (br 2H), 8.52 (d, J = 1.9 Hz, 1H), 8.31 (s, 1H), 8.02 (d, J = 9.3 Hz, 2H), 7.85-7.84 (m, 1H), 7.75-7.72 (m, 3H), 4.40 (s, 2H), 3.49-3.42 (m, 4H), 2.50 (t, J = 2.0 Hz, 4H) | 420 (M + 1) |
| 25 | 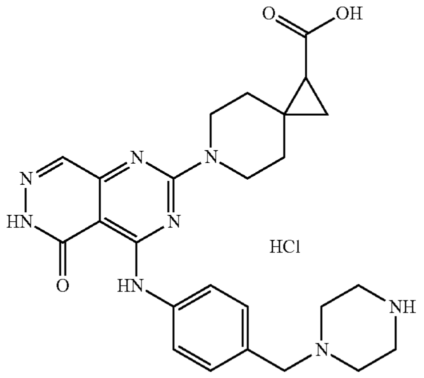 [SMILES: O=C(O)C1CC12CCN(c1nc(Nc3ccc(CN4CCNCC4)cc3)c3c(=O)[nH]ncc3n1)CC2 ; Cl] | 12.86 (s, 1H), 11.51 (s, 1H), 9.67 (s, 2H), 7.95 (s, 1H), 7.82 (d, J = 7.8 Hz, 2H), 7.66 (d, J = 8.3 Hz, 2H), 4.36 (br, 2H), 4.12-3.92 (m, 4H), 3.5-3.37 (m, 5H), 3.35-3.23 (m, 2H), 1.74-1.52 (m, 6H), 1.06-1.02 (m, 2H) | 491.3 (M + 1) |

TABLE 2-continued
| Ex # | Structure | Physical Data | |
|---|---|---|---|
| | | $^1$H-NMR in DMSO-$d_6$ at 400 Hz (δ) | MS m/z |
| 26 | 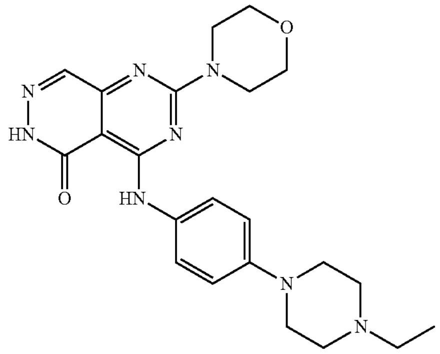 [SMILES: CCN1CCN(c2ccc(Nc3nc(N4CCOCC4)nc4cn[nH]c(=O)c34)cc2)CC1] | 12.8 (s, 1H), 11.17 (s, 1H), 7.88 (s, 1H), 7.55 (d, J = 8.8 Hz, 2H), 6.96 (d, J = 8.8 Hz, 2H), 3.8 (m, 4H), 3.67 (m, 4H), 3.29 (m, 4H), 3.13-3.11 (m, 4H), 2.37-2.35 (m, 2H), 1.03 (t, J = 7.1 Hz, 3H) | 437.3 (M + 1) |
| 27 | 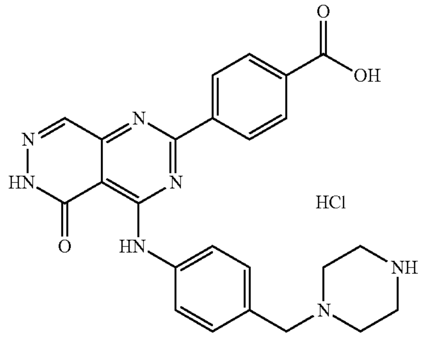 [SMILES: O=C(O)c1ccc(-c2nc(Nc3ccc(CN4CCNCC4)cc3)c3c(=O)[nH]ncc3n2)cc1 ; Cl] HCl | 13.48 (s, 1H), 11.64 (s, 1H), 9.42 (br, 2H), 8.53 (d, J = 8.3 Hz, 2H), 8.4 (s, 1H), 8.14 (d, J = 8.3 Hz, 2H), 8.02 (d, J = 7.8 Hz, 2H), 7.73 (br, 2H), 4.40 (br, 2H), 3.63 (m, 4H), 3.51-3.39 (m, 4H) | 458.0 (M + 1) |
| 28 | 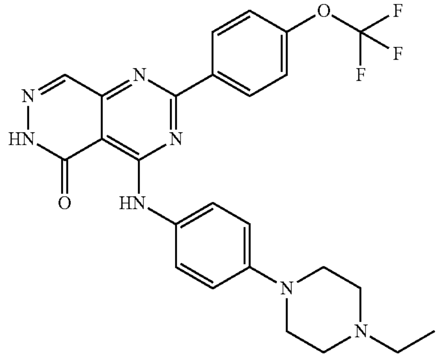 [SMILES: CCN1CCN(c2ccc(Nc3nc(-c4ccc(OC(F)(F)F)cc4)nc4cn[nH]c(=O)c34)cc2)CC1] | 13.36 (s, 1H), 11.33 (s, 1H), 8.51 (d, J = 8.8 Hz, 2H), 8.31 (s, 1H), 7.73 (d, J = 8.7 Hz, 2H), 7.56 (d, J = 8.3 Hz, 2H), 7.06 (d, J = 9.3 Hz, 2H), 3.30 (m, 4H), 3.19-3.16 (m, 4H), 2.39-2.33 (m, 4H), 1.05 (t, J = 7.1 Hz, 3H) | 512.2 (M + 1) |
| 29 | 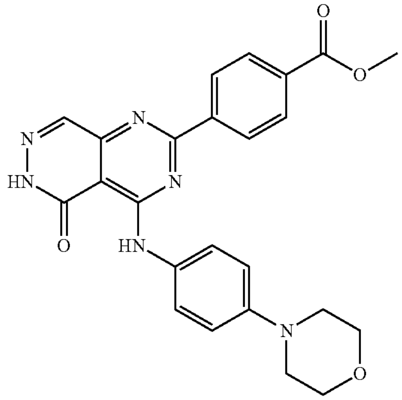 [SMILES: COC(=O)c1ccc(-c2nc(Nc3ccc(N4CCOCC4)cc3)c3c(=O)[nH]ncc3n2)cc1] | 13.4 (br, 1H), 11.6 (br, 1H), 8.52 (d, J = 8.3 Hz, 2H), 8.33 (s, 1H), 8.14 (d, J = 8.3 Hz, 2J), 7.77 (d, J = 8.8 Hz, 2H), 7.08 (d, J = 8.8 Hz, 2H), 3.91 (s, 3H), 3.77 (t, J = 4.7 Hz, 4H), 3.15 (t, J = 4.7 Hz, 4H) | 459.2 (M + 1) |

TABLE 2-continued
| | | Physical Data | |
| --- | --- | --- | --- |
| Ex # | Structure | $^1$H-NMR in DMSO-$d_6$ at 400 Hz (δ) | MS m/z |
| 30 | 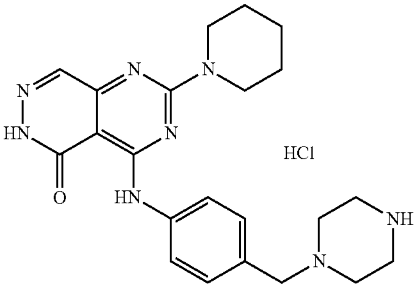 [SMILES: O=c1[nH]ncc2nc(N3CCCCC3)nc(Nc3ccc(CN4CCNCC4)cc3)c12 ; Cl] HCl | 12.87 (s, 1H), 11.51 (s, 1H), 9.8 (br, 2H), 7.96 (s, 1H), 7.82 (d, J = 7.8 Hz, 2H), 6.68 (d, J = 8.3 Hz, 2H), 4.82 (m, 6H), 4.38 (s, 2H), 3.86 (m, 4H), 3.48 (m, 4H), 1.66 (m, 2H), 1.09 (m, 2H) | 421.1 (M + 1) |
| 31 | 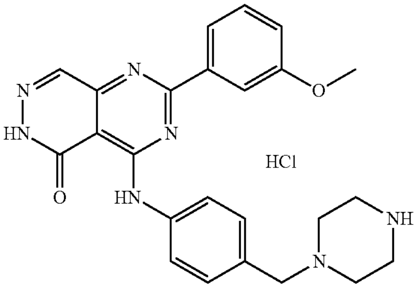 [SMILES: COc1cccc(-c2nc(Nc3ccc(CN4CCNCC4)cc3)c3c(=O)[nH]ncc3n2)c1 ; Cl] HCl | 13.43 (s, 1H), 11.59 (s, 1H), 9.47 (br, 2H), 8.37 (s, 1H), 8.05-8.03 (m, 3H), 7.98 (s, 1H), 7.74 (d, J = 7.8 Hz, 2H), 7.51 (t, J = 8.1 Hz, 1H), 7.2 (dd, J = 4.0, 8.3 Hz, 1H), 4.41 (br, 2H), 3.89 (s, 3H), 3.45 (t, J = 4.9 Hz, 4H), 3.23 (m, 4H) | 443.9 (M + 1) |
| 32 | 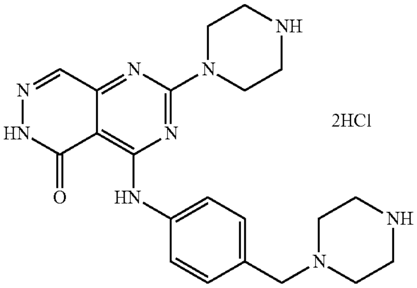 [SMILES: O=c1[nH]ncc2nc(N3CCNCC3)nc(Nc3ccc(CN4CCNCC4)cc3)c12 ; "2HCl"] 2HCl | 12.99 (s, 1H), 11.53 (s, 1H), 9.6 (br, 2H), 9.35 (br, 2H), 7.98 (s, 1H), 7.9 (d, J = 8.3 Hz, 2H), 7.65 (d, J = 7.8 Hz, 2H), 4.36 (br, 2H), 4.08 (m, 4H), 3.44 (m, 4H), 3.39 (m, 8H) | 422.2 (M + 1) |
| 33 | 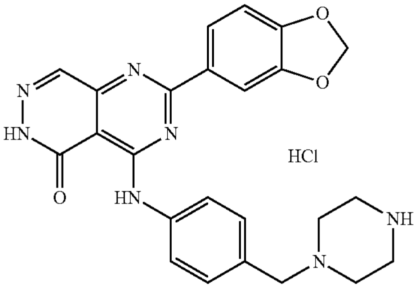 [SMILES: O=c1[nH]ncc2nc(-c3ccc4c(c3)OCO4)nc(Nc3ccc(CN4CCNCC4)cc3)c12 ; Cl] HCl | 13.37 (s, 1H), 11.59 (s, 1H), 9.4 (br, 2H), 8.32 (s, 1H), 8.09 (dd, J = 1.5, 8.5 Hz, 1H), 8.0 (d, J = 8.3 Hz, 1H), 7.86 (d, J = 1.5 Hz, 1H), 7.71 (d, J = 6.4 Hz, 2H), 7.12 (d, J = 8.3 Hz, 1H), 6.17 (s, 2H), 4.4 (br, 2H), 3.65-3.49 (m, 4H), 2.51-2.5 (m, 4H) | 458.1 (M + 1) |
| 34 | 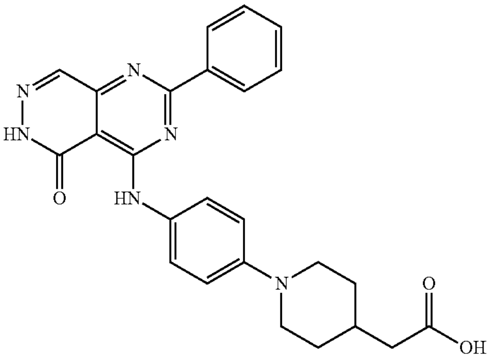 [SMILES: O=C(O)CC1CCN(c2ccc(Nc3nc(-c4ccccc4)nc4cn[nH]c(=O)c34)cc2)CC1] | 13.2 (s, 1H), 11.29 (s, 1H), 8.42-8.4 (m, 2H), 8.28 (s, 1H), 7.72 (d, J = 9.3 Hz, 2H), 7.6-7.54 (m, 3H), 7.04 (d, J = 8.8 Hz, 2H), 3.72-3.69 (m, 2H), 2.71-2.66 (m, 2H), 2.47-2.41 (m, 1H), 2.2-2.18 (m, 2H), 1.84-1.76 (m, 2H), 1.35-1.27 (m, 2H) | 455 (M − 1) |

TABLE 2-continued
| Ex # | Structure | Physical Data ¹H-NMR in DMSO-$d_6$ at 400 Hz (δ) | MS m/z |
|---|---|---|---|
| 35 | 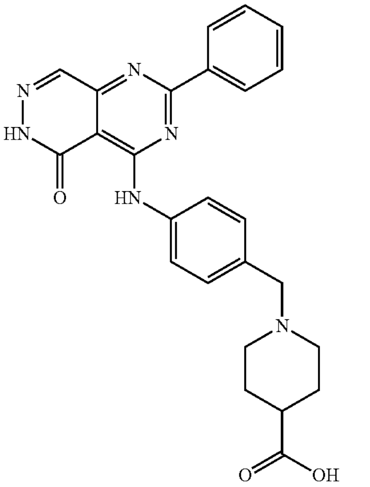 [SMILES: O=C(O)C1CCN(Cc2ccc(Nc3nc(-c4ccccc4)nc4cn[nH]c(=O)c34)cc2)CC1] | 13.37 (s, 1H), 11.51 (s, 1H), 8.45-8.43 (m, 2H), 8.33 (s, 1H), 7.89 (d, J = 8.3 Hz, 2H), 7.62-7.56 (m, 3H), 7.44 (d, J = 8.3 Hz, 2H), 3.58 (m, 2H), 2.85 (m, 2H), 2.49-2.14 (m, 3H), 1.84-1.81 (m, 2H), 1.64-1.59 (m, 2H) | 457 (M + 1) |
| 36 | 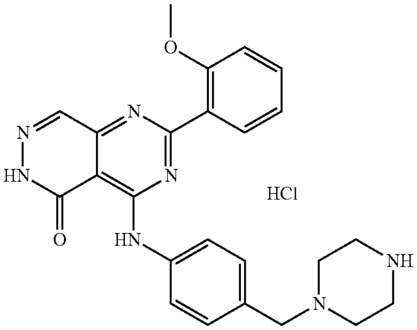 [SMILES: COc1ccccc1-c1nc(Nc2ccc(CN3CCNCC3)cc2)c2c(=O)[nH]ncc2n1 ; Cl] HCl | 13.42 (s, 1H), 11.56 (s, 1H), 9.63 (br, 2H), 8.34 (s, 1H), 8.10 (d, J = 8.8 Hz, 2H), 7.84 (dd, J = 1.7, 7.6 Hz, 1H), 7.71 (d, J = 8.3 Hz, 2H), 5.56-7.52 (m, 1H), 7.26 (d, J = 8.3 Hz, 2H), 7.10 (t, J = 7.1 Hz, 1H), 4.39 (s, 2H), 3.94 (s, 3H), 3.64 (m, 4H), 3.47-3.37 (m, 4H) | 444.1 (M + 1) |
| 37 | 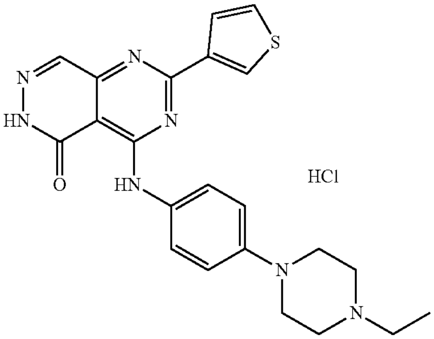 [SMILES: CCN1CCN(c2ccc(Nc3nc(-c4ccsc4)nc4cn[nH]c(=O)c34)cc2)CC1 ; Cl] HCl | 13.28 (s, 1H), 11.30 (s, 1H), 8.46 (d, J = 1.9 Hz, 1H), 8.24 (s, 1H), 7.81-7.80 (m, 1H), 7.75 (d, J = 8.8 Hz, 2H), 7.69 (dd, J = 3.2, 5.2 Hz, 1H), 7.05 (d, J = 8.8 Hz, 2H), 3.32-3.3 (m, 8H), 2.39-2.33 (m, 2H), 1.05 (t, J = 7.3 Hz, 3H) | 434.0 (M + 1) |
| 38 | 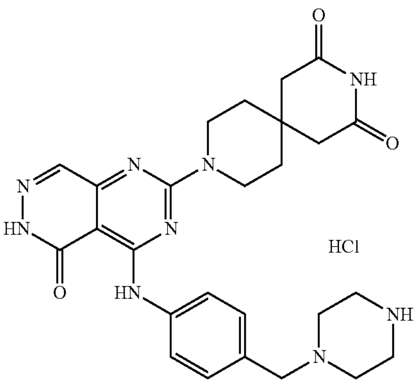 [SMILES: O=C1CC2(CCN(c3nc(Nc4ccc(CN5CCNCC5)cc4)c4c(=O)[nH]ncc4n3)CC2)CC(=O)N1 ; Cl] HCl | 13.11 (b, 1H), 12.87 (s, 1H), 11.56 (s, 1h), 9.61 (b, 2H), 7.95 (s, 1h), 7.88 (d, J = 8.3 Hz, 2H), 7.67 (d, J = 8.8 Hz, 2H), 5.05 (s, 2H), 3.89 (m, 4H), 3.54 (m, 4H), 3.01 (s, 4H), 2.75 (m, 4H), 1.60 (m, 4H) | 475.0 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 39 | 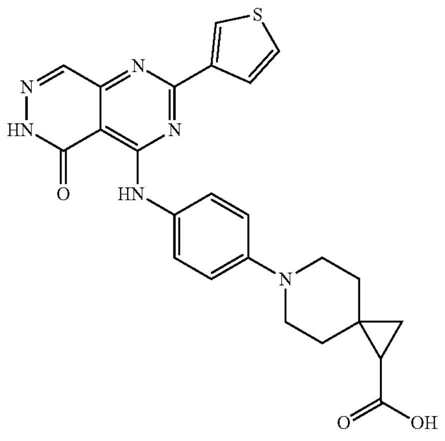 [SMILES: O=C(O)C1CC12CCN(c1ccc(Nc3nc(-c4ccsc4)nc4cn[nH]c(=O)c34)cc1)CC2] | 12.0 (br, 1H), 8.46-8.45 (m, 1H), 8.23 (s, 1H), 7.81 (dd, J = 1.0, 4.9 Hz, 1H), 7.74 (d, J = 9.3 Hz, 2H), 7.69 (dd, J = 3.0, 4.9 Hz, 1H), 7.07 (d, J = 9.3 Hz, 2H), 3.27-3.2 (m, 2H), 3.19-3.08 (m, 1H), 2.61-2.53 (m, 2H), 1.81-1.77 (m, 2H), 1.60-1.55 (m, 2H), 1.01-0.95 (m, 2H) | 475.0 (M + 1) |
| 40 | 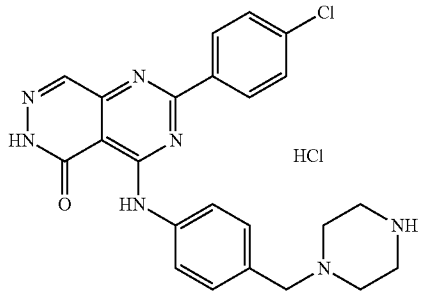 [SMILES: O=c1[nH]ncc2nc(-c3ccc(Cl)cc3)nc(Nc3ccc(CN4CCNCC4)cc3)c12 ; Cl] | 13.44 (s, 1H), 11.62 (s, 1H), 9.5 (b, 2H), 8.42 (d, J = 8.8 Hz, 2H), 8.35 (s, 1H), 7.98 (d, J = 7.8 Hz, 2H), 7.71 (b, 2H), 7.66 (d, J = 8.3 Hz, 2H), 4.4 (b, 2H), 3.95 (m, 4H), 3.41 (m, 4H) | 448.0 (M + 1) |
| 41 | 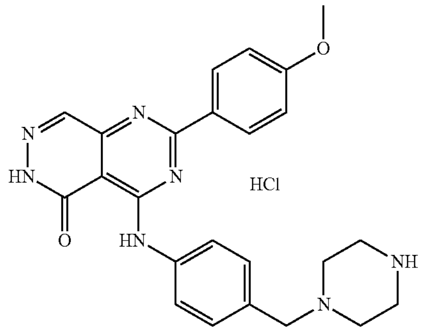 [SMILES: COc1ccc(-c2nc(Nc3ccc(CN4CCNCC4)cc3)c3c(=O)[nH]ncc3n2)cc1 ; Cl] | 13.36 (s, 1H), 11.60 (s, 1H), 9.68 (b, 2H), 8.40 (d, J = 8.8 Hz, 2H), 8.31 (s, 1H), 8.01 (d, J = 8.3 Hz, 2H), 7.75 (d, J = 8.8 Hz, 2H), 7.13 (d, J = 8.8 Hz, 2H), 4.41 (s, 2H), 3.87-3.75 (m, 7H), 3.49-3.45 (m, 4H) | 444.0 (M + 1) |

TABLE 2-continued
| Ex # | Structure | Physical Data<br>$^1$H-NMR in DMSO-$d_6$ at 400 Hz (δ) | MS m/z |
|---|---|---|---|
| 42 | 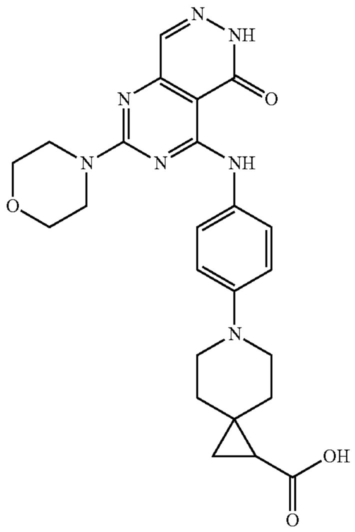 [SMILES: O=C(O)C1CC12CCN(c1ccc(Nc3nc(N4CCOCC4)nc4cn[nH]c(=O)c34)cc1)CC2] | 12.80 (s, 1H), 11.95 (br, 1H), 11.17 (s, 1H), 7.88 (s, 1H), 7.55 (d, J = 8.8 Hz, 2H), 6.99 (d, J = 8.7 Hz, 2H), 3.81 (m, 4H), 3.67 (m, 4H), 3.23-3.16 (m, 4H), 3.06-3.03 (m, 1H), 1.77-1.76 (m, 2H), 1.56-1.53 (m, 2H), 0.98-0.94 (m, 2H) | 478 (M + 1) |
| 43 | 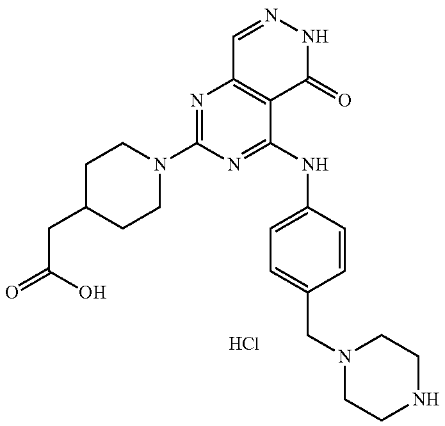 [SMILES: O=C(O)CC1CCN(c2nc(Nc3ccc(CN4CCNCC4)cc3)c3c(=O)[nH]ncc3n2)CC1 ; Cl] HCl | 12.84 (s, 1H), 11.95 (br, 1H), 11.49 (s, 1H), 9.62 (br, 2H), 7.93 (s, 1H), 7.83 (d, J = 8.3 Hz, 2H), 7.65 (d, J = 8.3 Hz, 2H), 4.8-4.6 (m, 2H), 4.36 (br, 2H), 3.65 (br, 4H), 3.46 (br, 4H), 3.1-4.04 (m, 1H), 2.2-2.09 (m, 2H), 2.02 (br, 2H), 1.82-1.79 (m, 2H), 1.23-1.19 (m, 2H) | 479 (M + 1) |
| 44 | 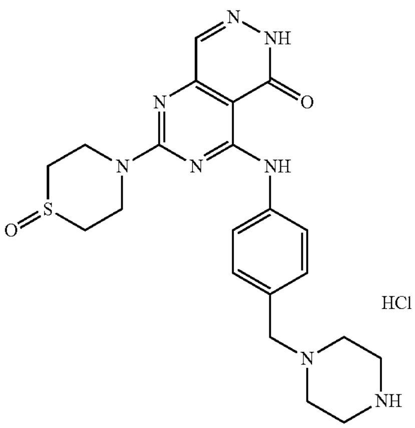 [SMILES: O=c1[nH]ncc2nc(N3CCS(=O)CC3)nc(Nc3ccc(CN4CCNCC4)cc3)c12 ; Cl] HCl | 12.93 (s, 1H), 11.41 (s, 1H), 8.72 (br, 2H), 7.98 (s, 1H), 7.75 (d, J = 7.3 Hz, 2H), 7.43 (d, J = 7.3 Hz, 2H), 4.62-4.53 (m, 2H), 4.0-3.94 (m, 2H), 3.82 (br, 2H), 3.19 (br, 4H), 2.95-2.83 (m, 8H) | 455 (M + 1) |

TABLE 2-continued
| Ex # | Structure | Physical Data $^1$H-NMR in DMSO-$d_6$ at 400 Hz (δ) | MS m/z |
|---|---|---|---|
| 45 | 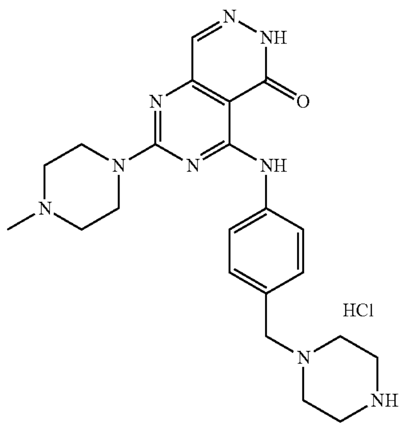 [SMILES: CN1CCN(c2nc(Nc3ccc(CN4CCNCC4)cc3)c3c(=O)[nH]ncc3n2)CC1 ; Cl] | 13.02 (s, 1H), 11.55 (s, 1H), 11.18 (br, 1H), 9.67 (br, 2H), 7.99 (s, 1H), 7.81 (d, J = 8.8 Hz, 2H), 7.67 (d, J = 7.4 Hz, 2H), 4.71 (br, 2H), 4.39 (s, 2H), 3.36 (br, 6H), 3.30-3.09 (m, 8H), 2.80 (s, 3H) | 436.2 (M + 1_ |
| 46 | 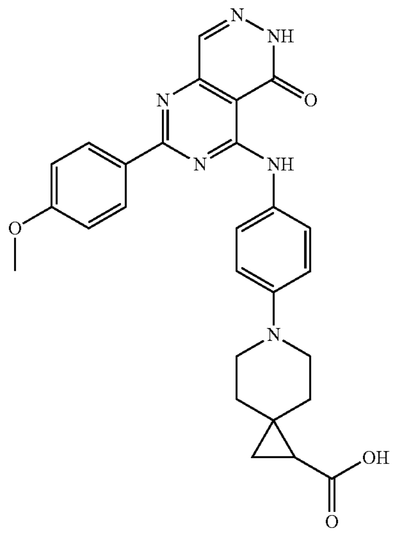 [SMILES: COc1ccc(-c2nc(Nc3ccc(N4CCC5(CC4)CC5C(=O)O)cc3)c3c(=O)[nH]ncc3n2)cc1] | 11.23 (s, 1H), 8.34 (d, J = 8.8 Hz, 2H), 8.2 (s, 1H), 7.69 (d, J = 8.8 Hz, 2H), 7.07 (d, J = 8.8 Hz, 2H), 7.03 (d, J = 9.2 Hz, 2H), 3.85 (s, 3H), 3.27-3.22 (m, 8H), 3.09-3.06 (m, 1H), 1.55-1.49 (m, 2H) | 479.73 (M − 1) |
| 47 | 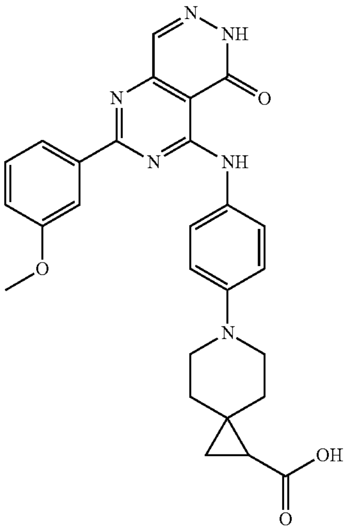 [SMILES: COc1cccc(-c2nc(Nc3ccc(N4CCC5(CC4)CC5C(=O)O)cc3)c3c(=O)[nH]ncc3n2)c1] | 11.35 (s, 1H), 8.27 (s, 1H), 7.98 (d, J = 7.4 Hz, 2H), 7.93 (s, 1H), 7.69 (d, J = 7.8 Hz, 2H), 7.45 (t, J = 7.4 Hz, 1H), 7.14 (d, J = 7.8 Hz, 1H), 7.02 (d, J = 7.8 Hz, 2H), 3.84 (s, 3H), 3.11 (br peak, 5H), 1.85 (br, 2H), 1.51-1.16 (m, 4H) | 499.3 (M + 1) |

TABLE 2-continued
| | | Physical Data | |
|---|---|---|---|
| Ex # | Structure | $^{1}$H-NMR in DMSO-$d_6$ at 400 Hz (δ) | MS m/z |
| 48 | 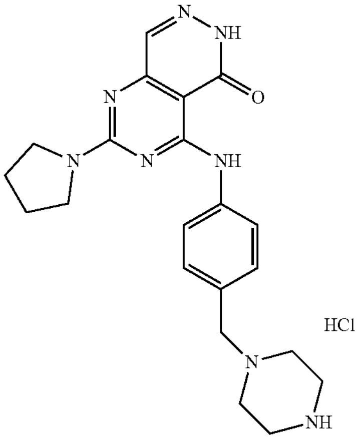 [SMILES: O=c1[nH]ncc2nc(N3CCCC3)nc(Nc3ccc(CN4CCNCC4)cc3)c12 ; Cl] HCl | 12.86 (s, 1H), 11.57 (s, 1H), 9.42 (br, 2H), 7.96 (s, 1H), 7.94 (d, J = 7.3 Hz, 2H), 7.61 (d, J = 6.9 Hz, 2H), 4.35 (br, 2H), 3.64-3.57 (m, 4H), 3.46-3.38 (m, 4H), 3.26-3.23 (m, 4H), 1.99 (m, 4H) | 407.5 (M + 1) |
| 49 | 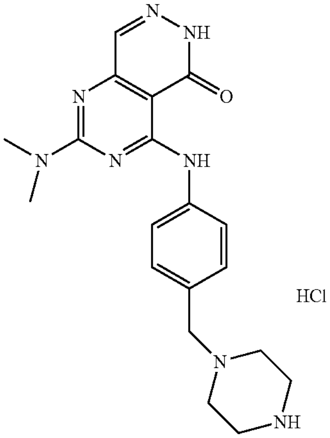 [SMILES: CN(C)c1nc(Nc2ccc(CN3CCNCC3)cc2)c2c(=O)[nH]ncc2n1 ; Cl] HCl | 12.84 (s, 1H), 11.53 (s, 1H), 7.94 (s, 1H), 7.90 (d, J = 7.9 Hz, 2H), 7.62 (d, J = 6.9 Hz, 2H), 4.3 (br, 2H), 3.42 (m, 4H), 3.24 (s, 6H), 2.51 (m, 4H) | 381.3 (M + 1) |
| 50 | 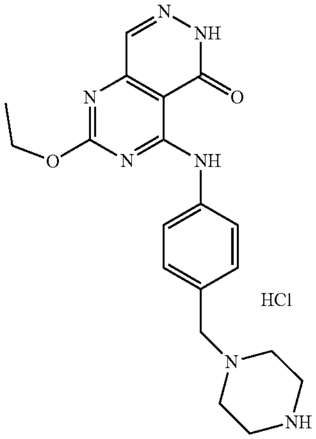 [SMILES: CCOc1nc(Nc2ccc(CN3CCNCC3)cc2)c2c(=O)[nH]ncc2n1 ; Cl] HCl | 13.28 (s, 1H), 11.8 (br, 1H), 11.58 (s, 1H), 9.41 (br, 2H), 8.15 (s, 1H), 7.9 (d, J = 8.3 Hz, 2H), 7.78 (d, J = 7.8 Hz, 2H), 4.45 (q, J = 7.1 Hz, 2H), 4.37 (br, 2H), 3.47 (m, 4H), 3.39 (m, 4H), 1.38 (t, J = 7.1 Hz, 3H) | 382.4 (M + 1) |

TABLE 2-continued
| Ex # | Structure | Physical Data $^1$H-NMR in DMSO-$d_6$ at 400 Hz (δ) | MS m/z |
|---|---|---|---|
| 51 | 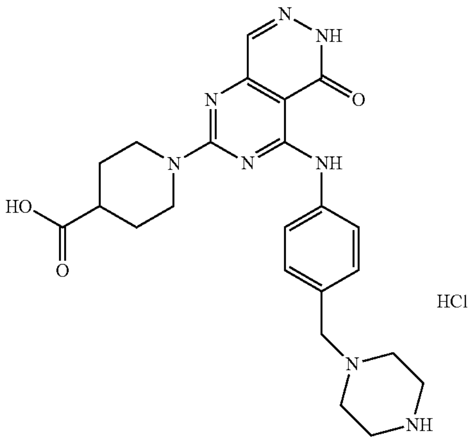 [SMILES: O=C(O)C1CCN(c2nc(Nc3ccc(CN4CCNCC4)cc3)c3c(=O)[nH]ncc3n2)CC1 ; Cl] HCl | 12.87 (s, 1H), 11.50 (s, 1H), 9.60 (br, 2H), 7.95 (s, 1H), 7.83 (d, J = 8.3 Hz, 2H), 7.66 (d, J = 8.3 Hz, 2H), 4.65-4.50 (m, 2H), 4.38 (s, 2H), 2.64-2.59 (m, 1H), 1.97-1.94 (m, 2H), 1.6 (s, 2H), 1.56-1.54 (m, 2H) | 465.3 (M + 1) |
| 52 | 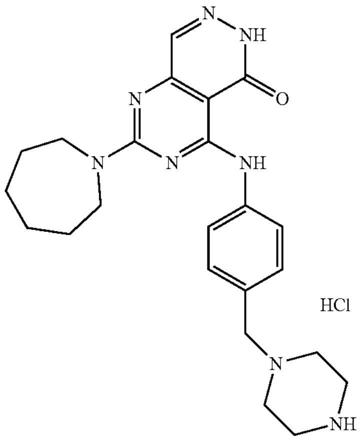 [SMILES: O=c1[nH]ncc2nc(N3CCCCCC3)nc(Nc3ccc(CN4CCNCC4)cc3)c12 ; Cl] HCl | 12.84 (s, 1H), 11.54 (s, 1H), 9.56 (br, 2H), 7.95 (s, 1H), 7.88 (d, J = 8.8 Hz, 2H), 7.65 (d, J = 8.8 Hz, 2H), 4.37 (s, 2H), 3.84-3.79 (m, 8H), 2.51-2.50 (m, 4H), 1.81-1.77 (m, 4H), 1.53 (s, 4H) | 433.1 (M − 1) |
| 53 | 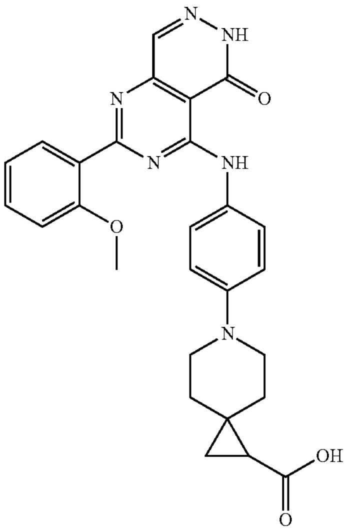 [SMILES: COc1ccccc1-c1nc(Nc2ccc(N3CCC4(CC3)CC4C(=O)O)cc2)c2c(=O)[nH]ncc2n1] | 13.29 (s, 1H), 11.95 (br, 1H), 11.26 (s, 1H), 8.25 (s, 1H), 7.78 (d, J = 9.2 Hz, 2H), 7.74 (dd, J = 1.7 Hz, J = 7.6 Hz, 1H), 7.52-7.48 (m, 1H), 7.2 (d, J = 7.8 Hz, 1H), 7.07 (t, J = 7.1 Hz, 1H), 6.99 (d, J = 9.3 Hz, 2H), 3.88 (s, 3H), 3.27-2.15 (m, 4H), 3.05-3.03 (m, 1H), 1.79-1.75 (m, 2H), 1.58-1.50 (m, 2H), 0.98-0.92 (m, 2H) | 499.3 (M + 1) |

TABLE 2-continued
| Ex # | Structure | Physical Data<br>$^1$H-NMR in DMSO-$d_6$ at 400 Hz (δ) | MS m/z |
|---|---|---|---|
| 54 | 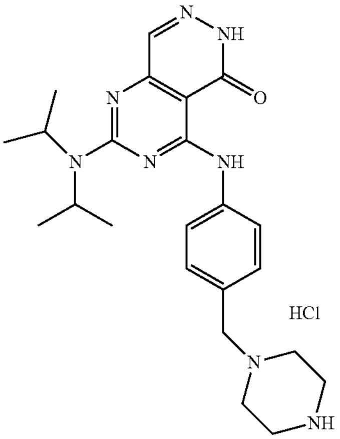 [SMILES: CC(C)N(c1nc(Nc2ccc(CN3CCNCC3)cc2)c2c(=O)[nH]ncc2n1)C(C)C ; Cl] HCl | 12.81 (s, 1H), 11.53 (s, 1H), 9.35 (br, 2H), 7.93 (s, 1H), 7.89 (d, J = 8.3 Hz, 2H), 7.62 (d, J = 7.8 Hz, 2H), 4.33 (br, 2H), 3.7-3.66 (m, 6H), 3.29 (m, 4H), 1.19-1.18 (m, 12H) | 437.2 (M + 1) |
| 55 | 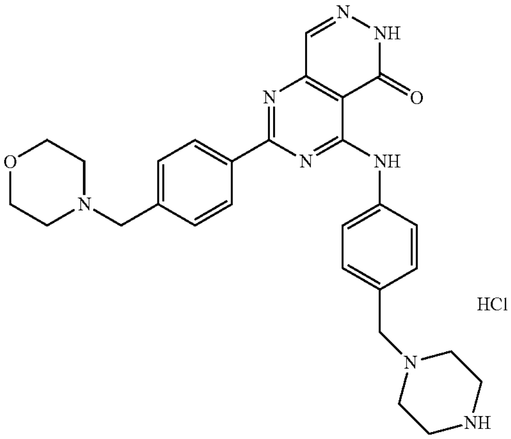 [SMILES: O=c1[nH]ncc2nc(-c3ccc(CN4CCOCC4)cc3)nc(Nc3ccc(CN4CCNCC4)cc3)c12 ; Cl] HCl | 13.4 (s, 1H), 11.58 (br, 1H), 9.70 (br, 2H), 8.45 (d, J = 8.3 Hz, 2H), 8.34 (s, 1H), 8.01 (d, J = 8.3 Hz, 2H), 7.86 (d, J = 8.3 Hz, 2H), 7.76 (d, J = 8.3 Hz, 2H), 4.45 (m, 4H), 3.94-3.65 (m, 4H), 3.5 (m, 4H), 3.38-3.16 (m, 6H), 1.6 (s, 2H) | 513.2 (M + 1) |
| 56 | 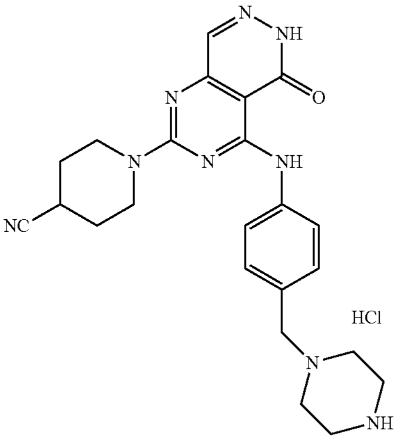 [SMILES: N#CC1CCN(c2nc(Nc3ccc(CN4CCNCC4)cc3)c3c(=O)[nH]ncc3n2)CC1 ; Cl] HCl | 12.80 (s, 1H), 11.95 (br, 1H), 11.50 (s, 1H), 9.62 (br, 2H), 7.95 (s, 1H), 7.81 (d, J = 8.3 Hz, 2H), 7.66 (d, J = 8.3 Hz, 2H), 4.37 (s. 2H), 4.17 (br, 2H), 3.75-3.63 (m, 4H), 3.47 (br, 6H), 3.36-3.18 (m, 3H), 1.79-1.76 (m, 2H) | 446.3 (M + 1) |

TABLE 2-continued
| Ex # | Structure | Physical Data ^1H-NMR in DMSO-$d_6$ at 400 Hz (δ) | MS m/z |
|---|---|---|---|
| 57 | 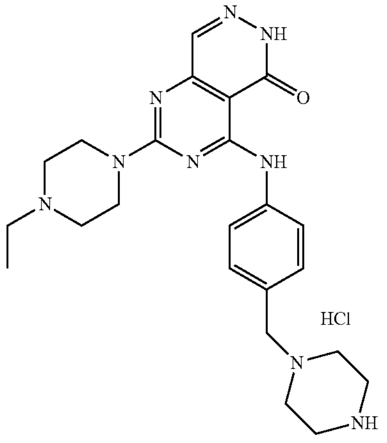 [SMILES: CCN1CCN(c2nc(Nc3ccc(CN4CCNCC4)cc3)c3c(=O)[nH]ncc3n2)CC1 ; Cl] | 13.01 (s, 1H), 11.95 (br, 1H), 11.02 (s, 1H), 9.59 (br, 2H), 8.0 (s, 1H), 7.81 (d, J = 8.8 Hz, 2H), 7.65 (d, J = 7.8 Hz, 2H), 4.8 (br, 2H), 4.37 (br, 2H), 3.65-3.61 (m, 8H), 3.39-3.04 (m, 8H), 1.29 (t, J = 7.4 Hz, 3H) | 450.4 (M + 1) |
| 58 | 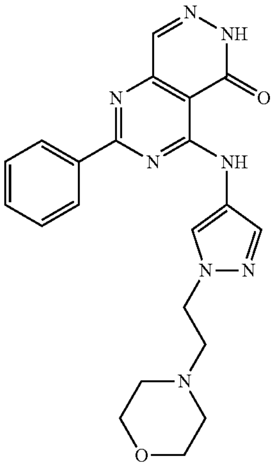 [SMILES: O=c1[nH]ncc2nc(-c3ccccc3)nc(Nc3cnn(CCN4CCOCC4)c3)c12] | 13.31 (s, 1H), 11.24 (s, 1H), 8.46-8.44 (m, 2H), 8.34 (s, 1H), 8.3 (s, 1H), 7.93 (s, 1H), 7.62-7.56 (m, 3H), 4.31 (t, J = 6.3 Hz, 2H), 3.54 (t, J = 4.4 Hz, 4H), 2.75 (t, J = 6.4 Hz, 2H), 2.5-2.44 (m, 4H) | 419.2 (M + 1) |
| 59 | 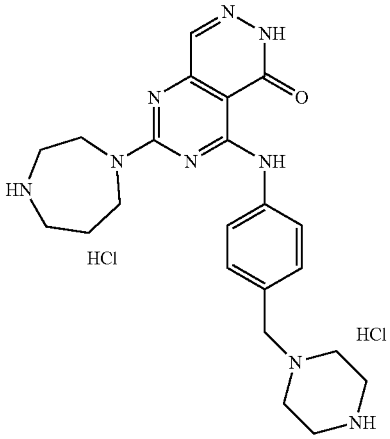 [SMILES: O=c1[nH]ncc2nc(N3CCCNCC3)nc(Nc3ccc(CN4CCNCC4)cc3)c12 ; Cl ; Cl] | 12.95 (s, 1H), 11.53 (s, 1H), 9.65 (br, 2H), 9.28-9.22 (m, 2H), 7.97 (s, 1H), 7.87-7.80 (m, 2H), 7.67 (d, J = 8.9 Hz, 2H), 4.37 (br, 2H), 4.09-4.04 (m, 2H), 3.96-3.90 (m, 2H), 3.52-3.20 (m, 10H), 2.12-2.09 (m, 2H), 1.6 (s, 2H) | 436.3 (M + 1) |

TABLE 2-continued
| Ex # | Structure | Physical Data $^1$H-NMR in DMSO-$d_6$ at 400 Hz (δ) | MS m/z |
|---|---|---|---|
| 60 | 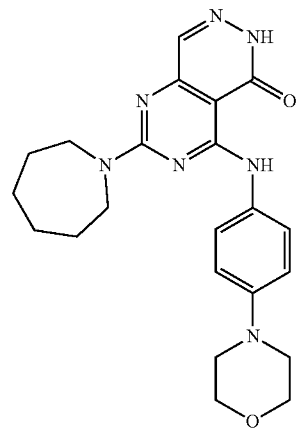 [SMILES: O=c1[nH]ncc2nc(N3CCCCCC3)nc(Nc3ccc(N4CCOCC4)cc3)c12] | 12.70 (s, 1H), 11.17 (s, 1H), 7.86 (s, 1H), 7.64 (d, J = 9.3 Hz, 2H), 6.97 (d, J = 8.8 Hz, 2H), 3.81-3.76 (m, 4H), 3.75-3.72 (m, 4H), 3.09 (t, J = 4.7 Hz, 4H), 1.76 (t, J = 4.4 Hz, 4H), 1.51 (m, 4H) | 422.3 (M + 1) |
| 61 | 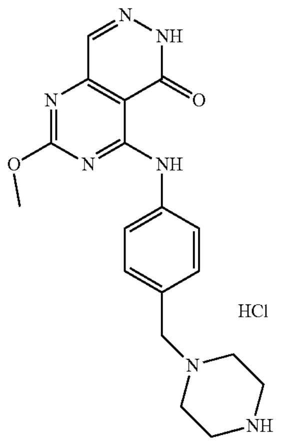 [SMILES: COc1nc(Nc2ccc(CN3CCNCC3)cc2)c2c(=O)[nH]ncc2n1 ; Cl] HCl | 13.28 (s, 1H), 11.71 (s, 1H), 9.68 (br, 2H), 8.1 (s, 1H), 7.97 (d, J = 7.8 Hz, 2H), 7.68 (d, J = 6.8 Hz, 2H), 4.37 (br, 2H) | 368.3 (M + 1) |
| 62 | 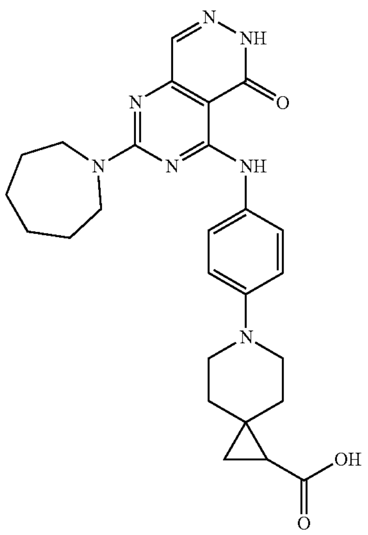 [SMILES: O=C(O)C1CC12CCN(c1ccc(Nc3nc(N4CCCCCC4)nc4cn[nH]c(=O)c34)cc1)CC2] | 12.7 (s, 1H), 11.16 (s, 1H), 7.86 (s, 1H), 7.61 (d, J = 9.3 Hz, 2H), 6.98 (d, J = 9.3 Hz, 2H), 3.81 (t, J = 5.9 Hz, 2H), 3.75 (t, J = 5.9 Hz, 2H), 3.26-3.01 (m, 5H), 1.79-1.75 (m, 6H), 1.55-1.51 (m, 6H), 0.95-0.92 (m, 2H), 3.65 (s, 3H), 3.53-3.29 (m, 10H) | 490.4 (M + 1) |

TABLE 2-continued
| | | Physical Data | |
|---|---|---|---|
| Ex # | Structure | $^{1}$H-NMR in DMSO-$d_6$ at 400 Hz (δ) | MS m/z |
| 63 | 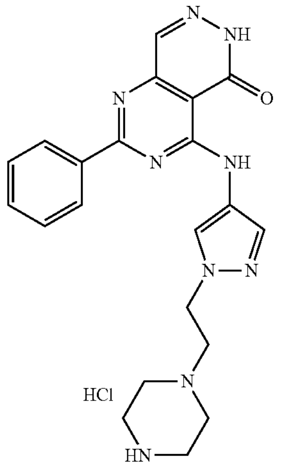 [SMILES: O=c1[nH]ncc2nc(-c3ccccc3)nc(Nc3cnn(CCN4CCNCC4)c3)c12 ; Cl] | 13.35 (s, 1H), 11.19 (s, 1H), 9.5 (br, 2H), 8.49-8.47 (m, 2H), 8.43 (s, 1H), 8.32 (s, 1H), 8.06 (s, 1H), 7.63-7.60 (m, 3H), 4.68 (br, 2H), 4.06-3.95 (m, 8H), 3.65 (m, 2H) | 418.1 (M + 1) |
| 64 | 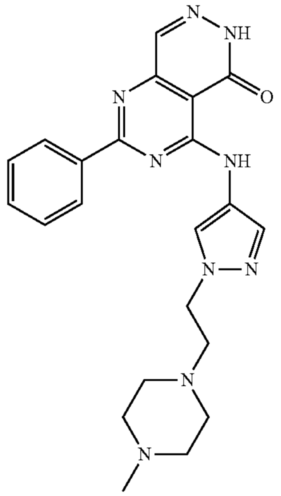 [SMILES: CN1CCN(CCn2cc(Nc3nc(-c4ccccc4)nc4cn[nH]c(=O)c34)cn2)CC1] | 13.31 (s, 1H), 11.14 (s, 1H), 8.46 (d, J = 6.4 Hz, 2H), 8.31 (d, J = 8.3 Hz, 2H), 7.92 (s, 1H), 7.62-7.58 (m, 3H), 4.29 (t, J = 6.1 Hz, 2H), 2.74 (t, J = 6.2 Hz, 2H), 2.45 (m, 4H), 2.28 (m, 4H), 2.09 (s, 3H) | 432.2 (M + 1) |
| 65 | 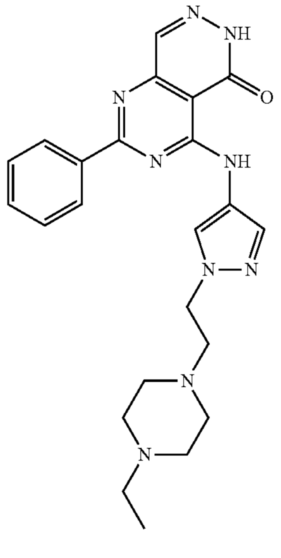 [SMILES: CCN1CCN(CCn2cc(Nc3nc(-c4ccccc4)nc4cn[nH]c(=O)c34)cn2)CC1] | 13.31 (s, 1H), 11.14 (s, 1H), 8.32 (d, J = 10.7 Hz, 2H), 7.92 (s, 1H), 7.64-7.54 (m, 3H), 4.29 (t, J = 6.4 Hz, 2H), 2.74 (t, J = 6.4 Hz, 2H), 2.45-2.31 (m, 8H), 2.23 (q, J = 7.1 Hz, 2H) | 446.1 (M + 1) |

TABLE 2-continued
| Ex # | Structure | Physical Data $^1$H-NMR in DMSO-$d_6$ at 400 Hz (δ) | MS m/z |
|---|---|---|---|
| 66 | 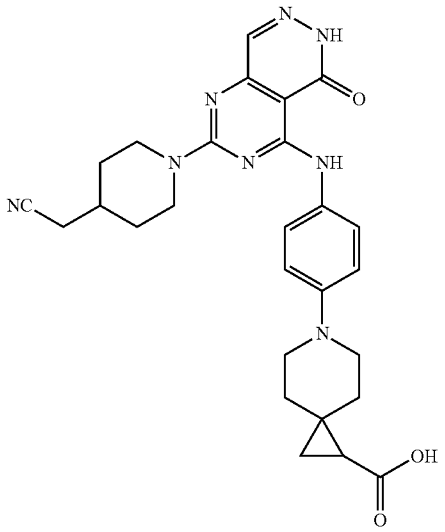 | 12.75 (s, 1H), 12.0 (br, 1H), 11.14 (s, 1H), 7.88 (s, 1H), 7.56 (d, J = 9.3 Hz, 2H), 7.0 (d, J = 8.8 Hz, 2H), 4.72 (br, 2H), 3.27-3.14 (m, 4H), 3.06-2.96 (m, 4H), 1.97-1.91 (m, 1H), 1.84-1.75 (m, 4H), 1.60-1.52 (m, 2H), 1.34-1.17 (m, 3H), 0.99-0.94 (m, 2H) | 515.6 (M + 1) |
| 67 | 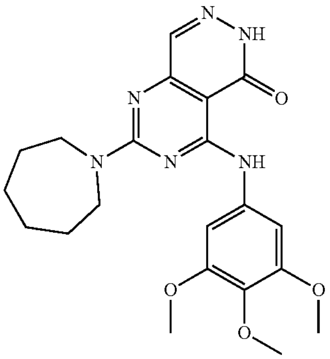 [SMILES: COc1cc(Nc2nc(N3CCCCCC3)nc3cn[nH]c(=O)c23)cc(OC)c1OC] | 12.76 (s, 1H), 11.40 (s, 1H), 7.89 (s, 1H), 7.22 (s, 2H), 3.81 (m, 10H), 3.65 (s, 3H), 1.75 (m, 4H), 1.51 (m, 4H) | 427.3 (M + 1) |
| 68 | 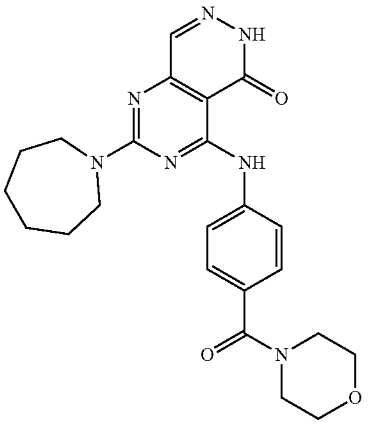 [SMILES: O=C(c1ccc(Nc2nc(N3CCCCCC3)nc3cn[nH]c(=O)c23)cc1)N1CCOCC1] | 12.79 (s, 1H), 11.51 (s, 1H), 7.91 (s, 1H), 7.85 (d, J = 8.3 Hz, 2H), 7.47 (d, J = 8.4 Hz, 2H), 3.84-3.77 (m, 4H), 3.61 (m, 4H), 3.51 (m, 4H), 1.81-1.76 (m, 4H), 1.52 (m, 4H) | 450.3 (M + 1) |

TABLE 2-continued
| Ex # | Structure | Physical Data $^1$H-NMR in DMSO-$d_6$ at 400 Hz (δ) | MS m/z |
|---|---|---|---|
| 69 | 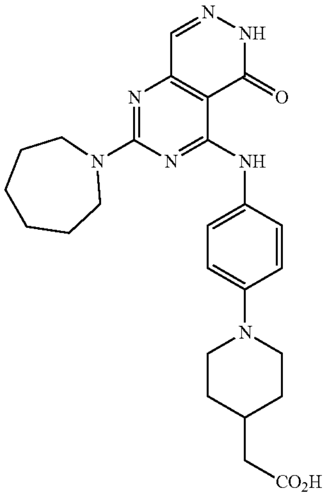 [SMILES: O=C(O)CC1CCN(c2ccc(Nc3nc(N4CCCCCC4)nc4cn[nH]c(=O)c34)cc2)CC1] | 12.7 (s, 1H), 12.1 (s, 1H), 7.86 (s, 1H), 7.61 (d, J = 8.8 Hz, 2H), 6.95 (d, J = 9.3 Hz, 2H), 3.8 (t, J = 6.1 Hz, 2H), 3.75 (t, J = 5.9 Hz, 2H), 3.66-3.63 (m, 2H), 2.63 (m, 3H), 2.19 (d, J = 6.8 Hz, 2H), 1.77-1.74 (m, 6H), 1.51 (m, 4H), 1.4-1.2 (m, 2H) | 478.3 (M + 1) |
| 70 | 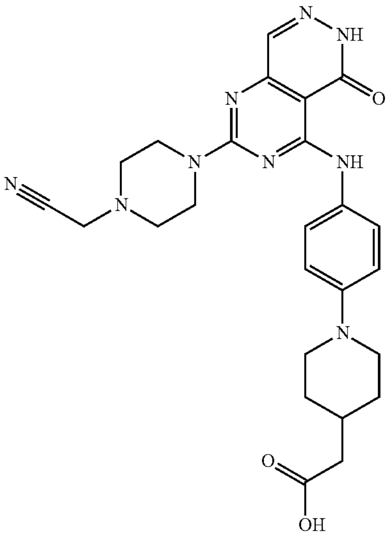 | 12.80 (s, 1H), 12.10 (br, 1H), 11.15 (s, 1H), 7.89 (s, 1H), 7.55 (d, J = 8.3 Hz, 2H), 6.97 (s, 1H), 3.88 (m, 4H), 3.67 (s, 2H), 3.65-3.64 (m, 2H), 2.68-2.62 (m, 2H), 2.55 (m, 4H), 2.19 (d, J = 6.4 Hz, 2H), 1.99 (m, 1H), 1.77-1.75 (m, 2H), 1.34 (t, J = 7.8 Hz, 4H) | 504.3 (M + 1) |
| 71 | 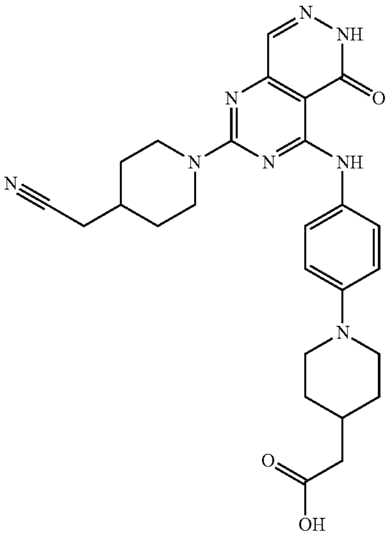 | 12.75 (s, 1H), 11.13 (s, 1H), 7.87 (s, 1H), 7.55 (d, J = 9.3 Hz, 2H), 6.97 (d, J = 8.8 Hz, 2H), 4.72 (m, 2H), 3.66 (d, J = 11.7 Hz, 2H), 3.02-2.95 (m, 2H), 2.19 (d, J = 6.8 Hz, 2H), 2.00-1.97 (m, 1H), 1.84-1.74 (m, 5H), 1.34-1.21 (m, 4H) | 503.4 (M + 1) |

TABLE 2-continued
| Ex # | Structure | Physical Data ¹H-NMR in DMSO-$d_6$ at 400 Hz (δ) | MS m/z |
|---|---|---|---|
| 72 | 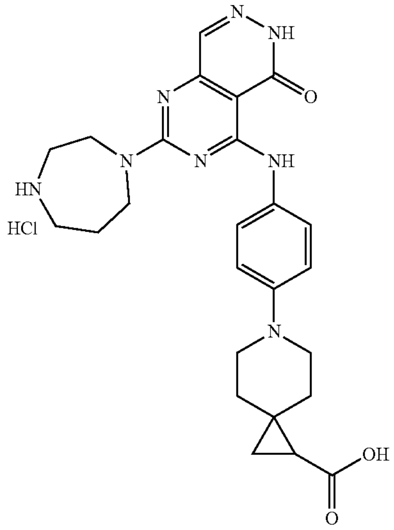 [SMILES: Cl ; O=C(O)C1CC12CCN(c1ccc(Nc3nc(N4CCCNCC4)nc4cn[nH]c(=O)c34)cc1)CC2] | 12.95 (s, 1H), 11.51 (s, 1H), 9.33-9.29 (m, 2H), 7.98 (s, 1H), 7.9-7.85 (m, 4H), 4.09-4.04 (m, 6H), 3.55 (m, 4H), 3.32-3.17 (m, 6H), 2.2-2.11 (m, 4H), 1.73-1.70 (m, 1H), 1.24-1.05 (m, 4H) | 491.1 (M + 1) |
| 73 | 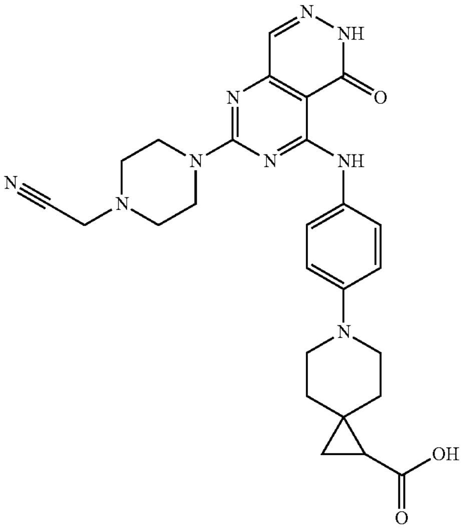 [SMILES: N#CCN1CCN(c2nc(Nc3ccc(N4CCC5(CC4)CC5C(=O)O)cc3)c3c(=O)[nH]ncc3n2)CC1] | 12.8 (s, 1H), 12.05 (br, 1H), 11.16 (s, 1H), 7.89 (s, 1H), 7.56 (d, J = 8.8 Hz, 2H), 7.01 (d, J = 7.9 Hz, 2H), 3.87-3.81 (m, 6H), 3.27-3.16 (m, 4H), 3.04-3.03 (m, 2H), 1.82-1.77 (m, 4H), 1.57-1.53 (m, 4H), 0.98-0.96 (m, 2H) | 516.3 (M + 1) |

TABLE 2-continued
| Ex # | Structure | Physical Data $^1$H-NMR in DMSO-$d_6$ at 400 Hz (δ) | MS m/z |
|---|---|---|---|
| 74 | 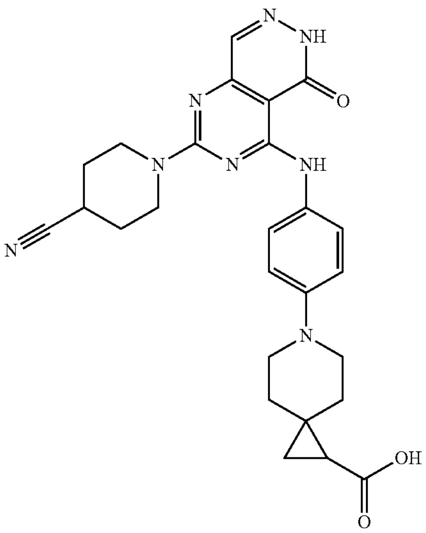 [SMILES: N#CC1CCN(c2nc(Nc3ccc(N4CCC5(CC4)CC5C(=O)O)cc3)c3c(=O)[nH]ncc3n2)CC1] | 12.79 (s, 1H), 12.06 (s, 1H), 11.14 (s, 1H), 7.89 (s, 1H), 7.55 (d, J = 8.8 Hz, 2H), 7.00 (d, J = 8.8 Hz, 2H), 4.14 (m, 2H), 3.64-3.59 (m, 2H), 3.27-3.16 (m, 4H), 3.07-3.02 (m, 1H), 2.01-1.91 (m, 2H), 1.82-1.73 (m, 4H), 1.61-1.52 (m, 4H), 0.99-0.93 (m, 2H) | 501.4 (M + 1) |
| 75 | 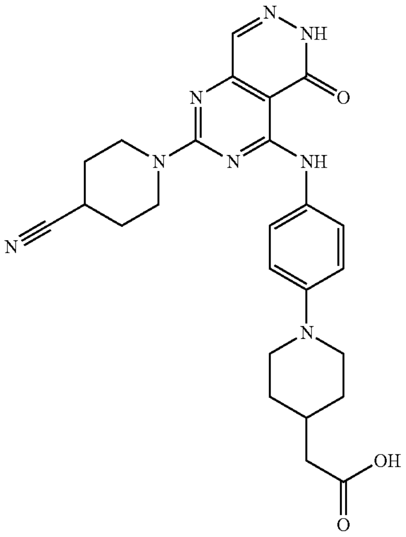 [SMILES: N#CC1CCN(c2nc(Nc3ccc(N4CCC(CC(=O)O)CC4)cc3)c3c(=O)[nH]ncc3n2)CC1] | 12.79 (s, 1H), 12.05 (s, 1H), 11.13 (s, 1H), 7.89 (s, 1H), 7.54 (d, J = 8.8 Hz, 2H), 6.97 (d, J = 8.8 Hz, 2H), 4.15 (m, 2H), 3.67-3.59 (m, 4H), 3.2-3.16 (m, 2H), 2.65 (t, J = 11.8 Hz, 2H), 2.20 (d, J = 6.9 Hz, 2H), 1.95 (m, 2H), 1.78-1.75 (m, 5H), 1.31-1.24 (m, 2H) | 489.2 (M + 1) |
| 76 | 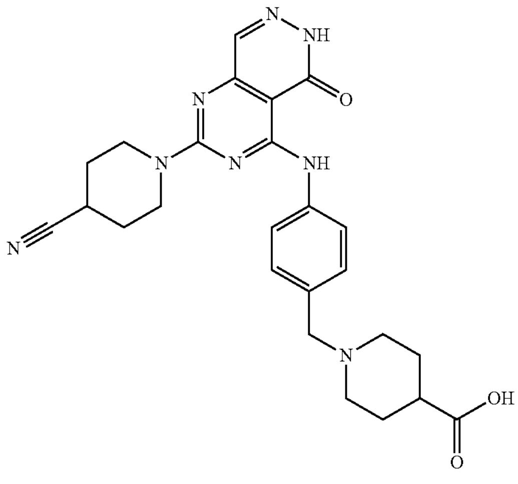 [SMILES: N#CC1CCN(c2nc(Nc3ccc(CN4CCC(C(=O)O)CC4)cc3)c3c(=O)[nH]ncc3n2)CC1] | 12.84 (s, 1H), 12.05 (s, 1H), 11.35 (s, 1H), 7.91 (s, 1H), 7.66 (d, J = 8.8 Hz, 2H), 7.32 (d, J = 8.8 Hz, 2H), 4.16 (br, 2H), 3.42 (s, 2H), 3.22-3.17 (m, 2H), 2.75 (d, J = 11.3 Hz, 2H), 2.44 (t, J = 3.9 Hz, 1H), 2.18-2.15 (m, 1H), 1.99-1.95 (m, 4H), 1.79-1.76 (m, 4H), 1.58-1.50 (m, 2H) | 489.3 (M + 1) |

TABLE 2-continued
| Ex # | Structure | Physical Data ¹H-NMR in DMSO-$d_6$ at 400 Hz (δ) | MS m/z |
|---|---|---|---|
| 77 | 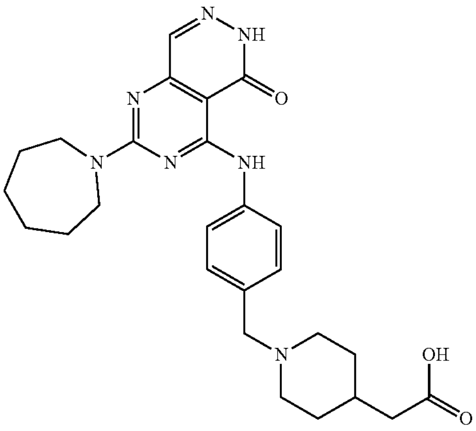 [SMILES: O=C(O)CC1CCN(Cc2ccc(Nc3nc(N4CCCCCC4)nc4cn[nH]c(=O)c34)cc2)CC1] | 12.76 (s, 1H), 12.0 (s, 1H), 11.39 (s, 1H), 7.90 (s, 1H), 7.76 (d, J = 7.4 Hz, 2H), 7.34 (m, 2H), 3.82-3.78 (m, 4H), 2.86 (m, 2H), 2.14 (m, 2H), 1.99 (m, 1H), 1.76-1.68 (m, 8H), 1.52 (m, 4H), 1.24-1.18 (m, 4H) | 492.4 (M + 1) |
| 78 | 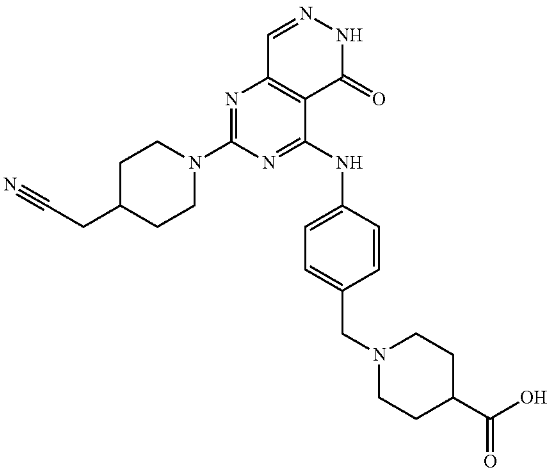 [SMILES: N#CCC1CCN(c2nc(Nc3ccc(CN4CCC(C(=O)O)CC4)cc3)c3c(=O)[nH]ncc3n2)CC1] | [1] 12.81 (s, 1H), 12.0 (s, 1H), 11.39 (s, 1H), 7.91 (s, 1H), 7.72 (d, J = 7.3 Hz, 2H), 7.38 (d, J = 6.9 Hz, 2H), 4.8-4.71 (m, 2H), 3.65 (br, 2H), 3.02-2.90 (m, 4H), 2.33-2.29 (m, 4H), 2.01 (m, 2H), 1.86-1.83 (m, 4H), 1.62 (m, 2H), 1.23 (m, 2H) | 503.3 (M + 1) |
| 79 | 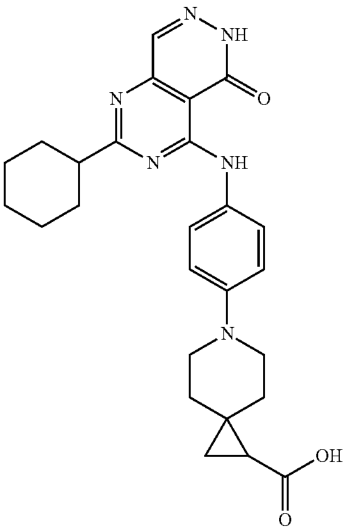 [SMILES: O=C(O)C1CC12CCN(c1ccc(Nc3nc(C4CCCCC4)nc4cn[nH]c(=O)c34)cc1)CC2] | 13.23 (s, 1H), 12.09 (s, 1H), 11.21 (s, 1H), 8.16 (s, 1H), 7.68 (d, J = 8.8 Hz, 2H), 7.01 (d, J = 8.8 Hz, 2H), 3.32-3.21 (m, 2H), 3.06 (m, 1H), 2.77-2.63 (m, 1H), 1.97 (m, 2H), 1.78-1.67 (m, 5H), 1.59-1.54 (m, 5H), 1.42-1.23 (m, 4H), 0.98-0.95 (m, 2H) | 475.4 (M + 1) |

TABLE 2-continued
| | | Physical Data | |
|---|---|---|---|
| Ex # | Structure | $^1$H-NMR in DMSO-$d_6$ at 400 Hz (δ) | MS m/z |
| 80 | 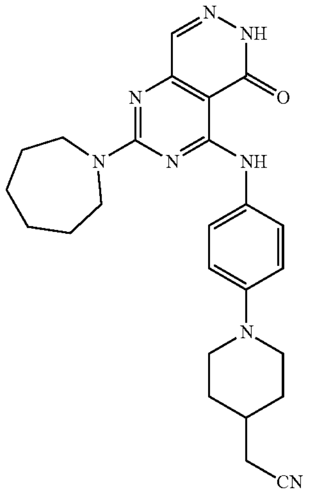 [SMILES: N#CCC1CCN(c2ccc(Nc3nc(N4CCCCCC4)nc4cn[nH]c(=O)c34)cc2)CC1] | 12.7 (s, 1H), 11.61 (s, 1H), 7.86 (s, 1H), 7.62 (d, J = 9.2 Hz, 2H), 6.97 (d, J = 8.8 Hz, 2H), 3.81-3.67 (m, 6H), 2.69-2.54 (m, 4H), 1.80-1.74 (m, 7H), 1.51 (m, 4H), 1.43-1.36 (m, 2H) | 459.3 (M + 1) |
| 81 | 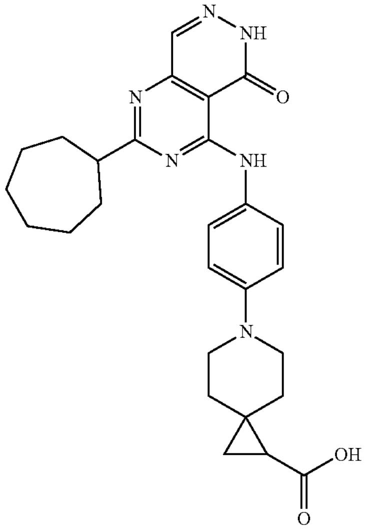 | 13.23 (s, 1H), 12.05 (brs, 1H), 11.20 (s, 1H), 8.16 (s, 1H), 7.69 (d, J = 8.8 Hz, 2H), 7.01 (d, J = 8.8 Hz, 2H), 3.26-3.20 (m, 4H), 3.19-3.13 (m, 1H), 2.93-2.90 (m, 1H), 2.02-1.91 (m, 2H), 1.82-1.76 (m, 6H), 1.63-1.52 (m, 9H), 0.99-0.97 (m, 2H) | 489.4 (M + 1) |
| 82 | 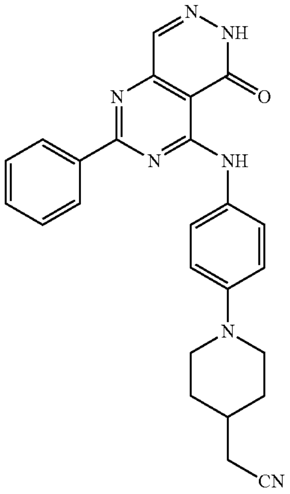 [SMILES: N#CCC1CCN(c2ccc(Nc3nc(-c4ccccc4)nc4cn[nH]c(=O)c34)cc2)CC1] | 13.31 (s, 1H), 11.31 (s, 1H), 8.43-8.41 (m, 2H), 8.29 (s, 1H), 7.74 (d, J = 9.3 Hz, 2H), 7.76-7.54 (m, 3H), 7.07 (d, J = 8.8 Hz, 2H), 3.76 (m, 2H), 2.72 (m, 2H), 2.57 (d, J = 6.3 Hz, 2H), 1.83-1.80 (m, 3H), 1.45-1.42 (m, 2H) | 438.4 (M + 1) |

TABLE 2-continued
| Ex # | Structure | Physical Data $^1$H-NMR in DMSO-$d_6$ at 400 Hz (δ) | MS m/z |
|---|---|---|---|
| 83 | 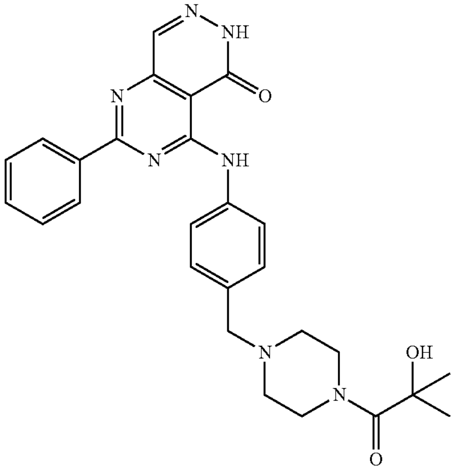 [SMILES: CC(C)(O)C(=O)N1CCN(Cc2ccc(Nc3nc(-c4ccccc4)nc4cn[nH]c(=O)c34)cc2)CC1] | 13.37 (s, 1H), 11.51 (s, 1H), 8.44 (dd, J = 1.7 Hz, 7.6 Hz, 2H), 8.33 (s, 1H), 7.89 (d, J = 8.3 Hz, 2H), 7.62-7.57 (m, 3H), 7.44 (d, J = 8.3 Hz, 2H), 5.37 (s, 1H), 3.9 (br, 1H), 3.52 (m, 4H), 2.39 (m, 4H), 1.30 (s, 6H) | 500.3 (M + 1) |
| 84 | 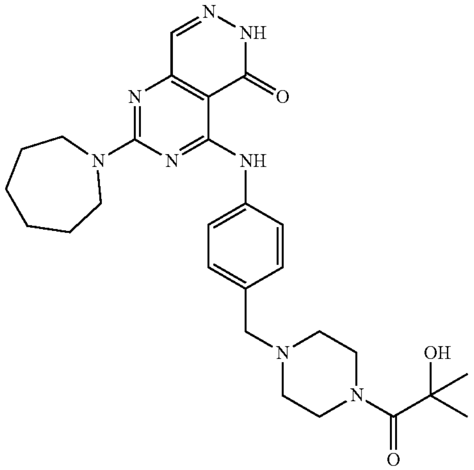 [SMILES: CC(C)(O)C(=O)N1CCN(Cc2ccc(Nc3nc(N4CCCCCC4)nc4cn[nH]c(=O)c34)cc2)CC1] | 12.75 (s, 1H), 11.38 (s, 1H), 7.90 (s, 1H), 7.75 (d, J = 8.3 Hz, 2H), 7.33 (d, J = 7.9 Hz, 2H), 5.37 (s, 1H), 3.83-3.76 (m, 4H), 3.38 (s, 2H), 3.13-3.08 (m, 4H), 2.36 (m, 4H), 1.8-1.76 (m, 4H), 1.52 (m, 4H), 1.29 (s, 6H) | 521.4 (M + 1) |
| 85 | 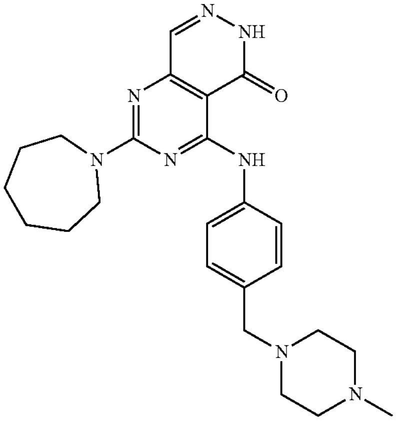 [SMILES: CN1CCN(Cc2ccc(Nc3nc(N4CCCCCC4)nc4cn[nH]c(=O)c34)cc2)CC1] | 12.74 (s, 1H), 11.35 (s, 1H), 7.89 (s, 1H), 7.72 (d, J = 8.3 Hz, 2H), 7.30 (d, J = 7.8 Hz, 2H), 4.12-4.11 (m, 4H), 3.81-3.77 (m, 6H), 2.35 (m, 4H), 2.16 (s, 1H), 1.85-1.75 (m, 4H), 1.51 (m, 4H) | 449.3 (M + 1) |

TABLE 2-continued
| Ex # | Structure | Physical Data<br>$^1$H-NMR in DMSO-$d_6$ at 400 Hz (δ) | MS m/z |
|---|---|---|---|
| 86 | 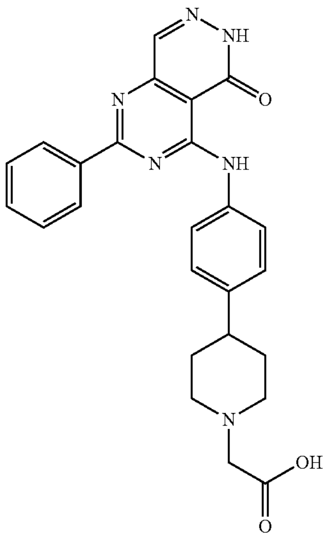 [SMILES: O=C(O)CN1CCC(c2ccc(Nc3nc(-c4ccccc4)nc4cn[nH]c(=O)c34)cc2)CC1] | 13.35 (s, 1H), 11.48 (s, 1H), 8.45-8.30 (m, 2H), 8.28 (s, 1H), 7.86 (d, J = 8.3 Hz, 2H), 7.59-7.57 (m, 3H), 7.38 (d, J = 7.8 Hz, 2H), 3.50 (m, 6H), 2.73-2.68 (m, 2H), 1.91-1.90 (m, 3H) | 457.3 (M + 1) |
| 87 | 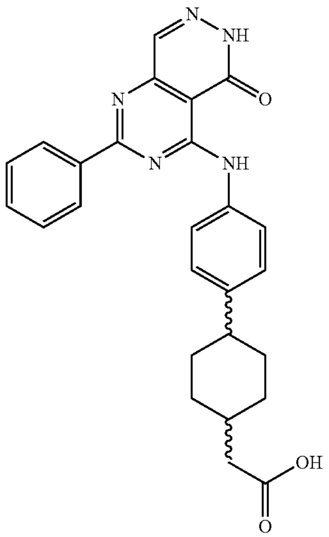 [SMILES: O=C(O)CC1CCC(c2ccc(Nc3nc(-c4ccccc4)nc4cn[nH]c(=O)c34)cc2)CC1] | 13.21 (s, 1H), 11.45 (s, 1H), 8.43-8.31 (m, 2H), 8.30 (s, 1H), 7.82-7.79 (m, 2H), 7.60-7.56 (m, 3H), 7.39-7.33 (m, 2H), 3.31 (s, 1H), 2.67 (m, 1H), 2.36 (m, 1H), 2.14 (d, J = 6.8 Hz, 2H), 1.85 (m, 2H), 1.64 (m, 4H), 1.48 (m, 1H) | 454.2 (M − 1) |

TABLE 2-continued
| Ex # | Structure | Physical Data ¹H-NMR in DMSO-$d_6$ at 400 Hz (δ) | MS m/z |
|---|---|---|---|
| 88 | 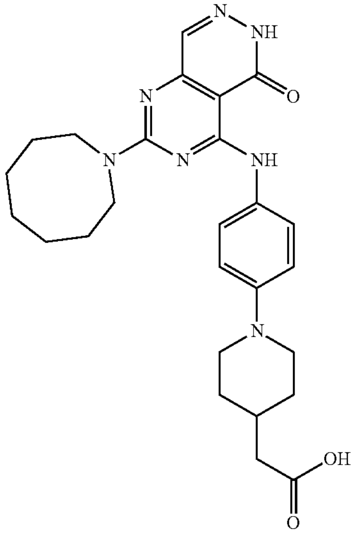 [SMILES: O=C(O)CC1CCN(c2ccc(Nc3nc(N4CCCCCCC4)nc4cn[nH]c(=O)c34)cc2)CC1] | 12.69 (s, 1H), 12.01 (s, 1H), 11.15 (s, 1H), 7.85 (s, 1H), 7.60 (d, J = 8.8 Hz, 2H), 6.94 (d, J = 8.8 Hz, 2H), 3.70 (m, 6H), 2.67 (m, 2H), 2.18 (d, J = 5.8 Hz, 2H), 1.79 (m, 7H), 1.21-1.51 (m, 8H) | 492.3 (M + 1) |
| 89 | 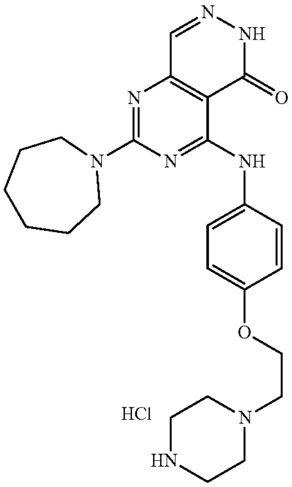 [SMILES: O=c1[nH]ncc2nc(N3CCCCCC3)nc(Nc3ccc(OCCN4CCNCC4)cc3)c12 ; Cl] | 12.89 (s, 1H), 1H), 12.28 (s, 1H), 1H), 11.30 (s, 1H), 9.78 (s, 2H), 8.02 (s, 1H), 7.73 (d, J = 9.2 Hz, 2H), 7.06 (d, J = 9.2 Hz, 2H), 4.43 (t, J = 4.8 Hz, 2H), 3.82 (t, J = 6 Hz, 2H), 3.75 (t, J = 6 Hz, 2H), 3.64-3.37 (m, 10H), 1.77 (m, 4H), 1.59 (m, 4H) | 464.7 (M + 1) |
| 90 | 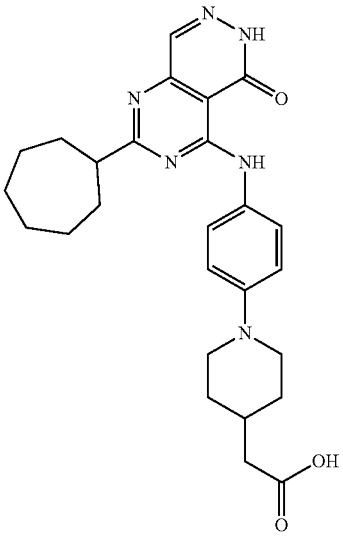 [SMILES: O=C(O)CC1CCN(c2ccc(Nc3nc(C4CCCCCC4)nc4cn[nH]c(=O)c34)cc2)CC1] | 13.02 (s, 1H), 11.19 (s, 1H), 8.15 (s, 1H), 7.67 (d, J = 8.8 Hz, 2H), 6.97 (d, J = 8.8 Hz, 2H), 3.67 (d, J = 6.4 Hz, 2H), 2.92 (m, 1H), 2.65 (m, 2H), 2.18 (d, J = 6.4 Hz, 2H), 2.08 (m, 2H), 1.99-1.54 (m, 14H), 1.33-1.28 (m, 2H) | 477.2 (M + 1) |

TABLE 2-continued
| Ex # | Structure | Physical Data ¹H-NMR in DMSO-$d_6$ at 400 Hz (δ) | MS m/z |
|---|---|---|---|
| 91 | 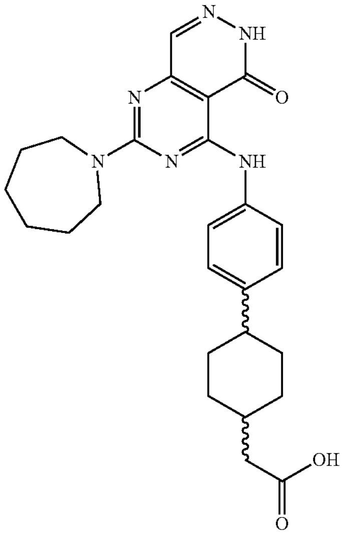 [SMILES: O=C(O)CC1CCC(c2ccc(Nc3nc(N4CCCCCC4)nc4cn[nH]c(=O)c34)cc2)CC1] | 12.73 (s, 1H), 12.01 (s, 1H), 11.32 (s, 1H), 7.88 (s, 1H), 7.68 (m, 2H), 7.27 (m, 2H), 3.77 (m, 4H), 2.37 (m, 1H), 2.15 (d, J = 6.8 Hz, 2H), 1.80-1.60 (m, 9H), 1.57 (m, 4H), 1.51 (m, 4H) | 477.3 (M + 1) |
| 92 | 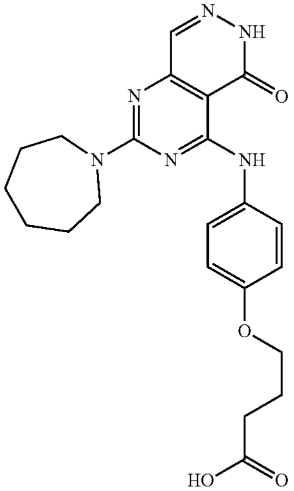 [SMILES: O=C(O)CCCOc1ccc(Nc2nc(N3CCCCCC3)nc3cn[nH]c(=O)c23)cc1] | 12.71 (s, 1H), 11.16 (s, 1H), 7.85 (s, 1H), 7.65 (d, J = 8.8 Hz, 2H), 6.94 (d, J = 8.8 Hz, 2H), 3.96 (t, J = 6 Hz, 2H), 3.79 (t, J = 6 Hz, 2H), 3.72 (t, J = 6 Hz, 2H), 2.35 (t, J = 7.2 Hz, 2H), 1.92 (m, 2H), 1.74 (m, 4H), 1.50 (m, 4H) | 439.1 (M + 1) |
| 93 | 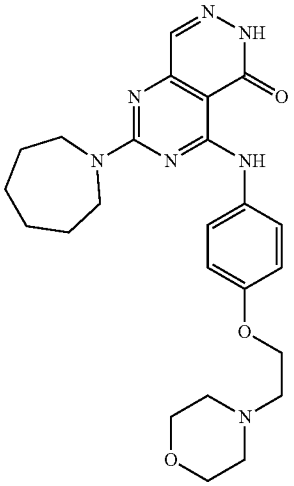 [SMILES: O=c1[nH]ncc2nc(N3CCCCCC3)nc(Nc3ccc(OCCN4CCOCC4)cc3)c12] | 12.71 (s, 1H), 11.17 (s, 1H), 7.86 (s, 1H), 7.67 (d, J = 8.8 Hz, 2H), 6.96 (d, J = 8.8 Hz, 2H), 4.08 (t, J = 5.4 Hz, 2H), 3.79 (t, J = 6.4 Hz, 2H), 3.73 (t, J = 6 Hz, 2H), 3.57 (t, J = 4.4 Hz, 4H), 2.68 (t, J = 5.4 Hz, 2H), 2.50 (m, 4H), 1.75 (m, 4H), 1.50 (m, 4H) | 466 (M + 1) |

TABLE 2-continued
| Ex # | Structure | Physical Data $^1$H-NMR in DMSO-$d_6$ at 400 Hz (δ) | MS m/z |
|---|---|---|---|
| 94 | 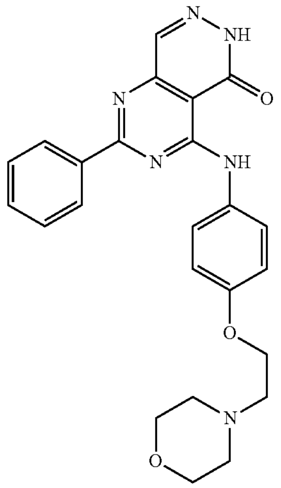 [SMILES: O=c1[nH]ncc2nc(-c3ccccc3)nc(Nc3ccc(OCCN4CCOCC4)cc3)c12] | 13.32 (s, 1H), 11.30 (s, 1H), 8.40 (d, J = 6.0 Hz, 2H), 8.30 (s, 1H), 7.78 (d, J = 7.2 Hz, 2H), 7.55 (m, 3H), 7.08 (d, J = 7.2 Hz, 2H), 4.13 (t, J = 5.4 Hz, 2H), 3.57 (t, J = 4.4 Hz, 4H), 2.68 (t, J = 5.4 Hz, 2H), 2.50 (m, 4H) | 445.1 (M + 1) |
| 95 | 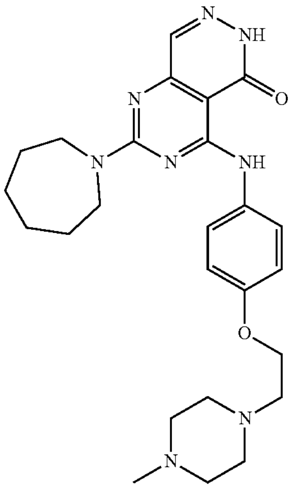 [SMILES: CN1CCN(CCOc2ccc(Nc3nc(N4CCCCCC4)nc4cn[nH]c(=O)c34)cc2)CC1] | 12.71 (s, 1H), 11.18 (s, 1H), 7.87 (s, 1H), 7.68 (d, J = 8.4 Hz, 2H), 6.97 (d, J = 8.4 Hz, 2H), 4.09 (t, J = 5.4 Hz, 2H), 3.80-3.74 (m, 4H), 2.68 (t, J = 5.4 Hz, 2H), 2.62 (s, 3H), 2.50 (m, 8H), 1.74 (m, 4H), 1.50 (m, 4H) | 479 (M + 1) |
| 96 | 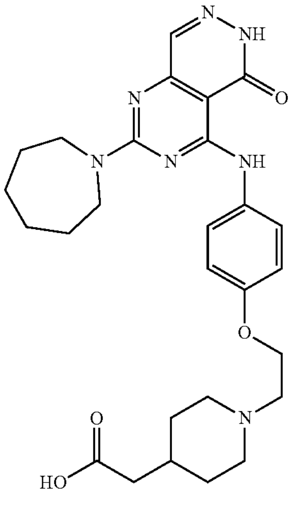 [SMILES: O=C(O)CC1CCN(CCOc2ccc(Nc3nc(N4CCCCCC4)nc4cn[nH]c(=O)c34)cc2)CC1] | 12.71 (s, 1H), 12.01 (s, 1H), 11.17 (s, 1H), 7.86 (s, 1H), 7.67 (d, J = 8.8 Hz, 2H), 6.97 (d, J = 8.8 Hz, 2H), 4.08 (t, J = 5.4 Hz, 2H), 3.79-3.74 (m, 4H), 2.96 (m, 2H), 2.75 (m, 2H), 2.13 (m, 4H), 1.75-1.65 (m, 11H), 1.20 (m, 2H) | 522.1 (M + 1) |

TABLE 2-continued
| Ex # | Structure | Physical Data $^1$H-NMR in DMSO-$d_6$ at 400 Hz (δ) | MS m/z |
|---|---|---|---|
| 97 | 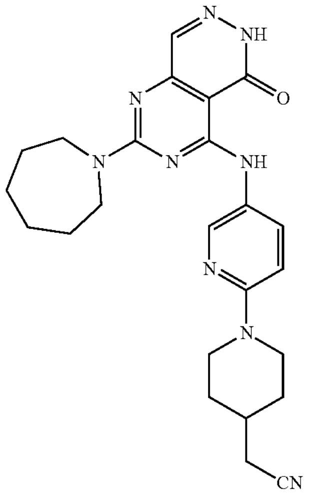 [SMILES: N#CCC1CCN(c2ccc(Nc3nc(N4CCCCCC4)nc4cn[nH]c(=O)c34)cn2)CC1] | 12.70 (s, 1H), 10.98 (s, 1H), 8.44 (d, J = 2.8 Hz, 1H), 7.95 (dd, $J^1$ = 9.6 Hz, $J^2$ = 2.8 Hz, 1H), 7.86 (s, 1H), 6.90 (d, J = 9.6 Hz, 1H), 4.3 (d, J = 13.2 Hz, 2H), 3.79 (t, J = 6.4 Hz, 2H), 3.70 (t, J = 6.0 Hz, 2H), 2.8 (m, 2H), 2.50 (m, 2H), 1.88 (m, 1H), 1.87-1.74 (m, 6H), 1.50-1.29 (m, 4H), 1.23 (m, 2H) | 460.1 (M + 1) |
| 98 | 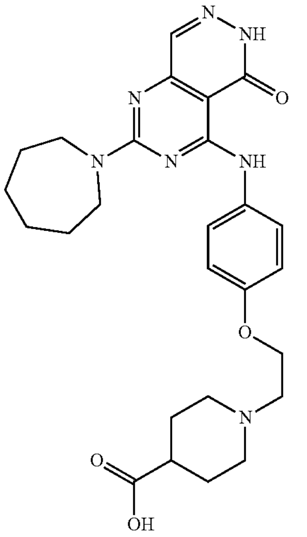 [SMILES: O=C(O)C1CCN(CCOc2ccc(Nc3nc(N4CCCCCC4)nc4cn[nH]c(=O)c34)cc2)CC1] | 12.71 (s, 1H), 11.17 (s, 1H), 7.86 (s, 1H), 7.66 (d, J = 8.8 Hz, 2H), 6.97 (d, J = 8.8 Hz, 2H), 4.07 (t, J = 5.2 Hz, 2H), 3.80 (t, J = 5.6 Hz, 2H), 3.73 (t, J = 5.6 Hz, 2H), 2.87 (m, 2H), 2.45 (m, 2H), 2.19 (m, 3H), 1.80-1.77 (m, 6H), 1.59 (m, 6H) | 508.4 (M + 1) |
| 99 | 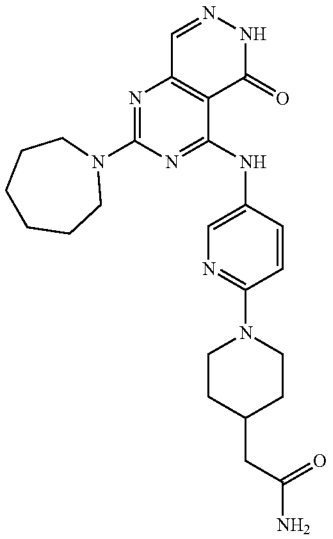 | 12.70 (s, 1H), 10.97 (s, 1H), 8.43 (d, J = 2.8 Hz, 1H), 7.92 (dd, $J^1$ = 9.6 Hz, $J^2$ = 2.8 Hz, 1H), 7.86 (s, 1H), 7.26 (s, br, 1H), 6.87 (d, J = 9.6 Hz, 1H), 6.75 (s, br, 1H), 4.22 (d, J = 13.2 Hz, 2H), 3.79 (t, J = 6.4 Hz, 2H), 3.70 (t, J = 6.0 Hz, 2H), 2.79 (m, 2H), 2.00 (d, J = 6.8 Hz, 2H), 1.91 (m, 1H), 1.89-168 (m, 6H), 1.50-1.19 (m, 4H), 1.15 (m, 2H) | 478 (M + 1) |

TABLE 2-continued
| Ex # | Structure | Physical Data $^1$H-NMR in DMSO-$d_6$ at 400 Hz (δ) | MS m/z |
|---|---|---|---|
| 100 | 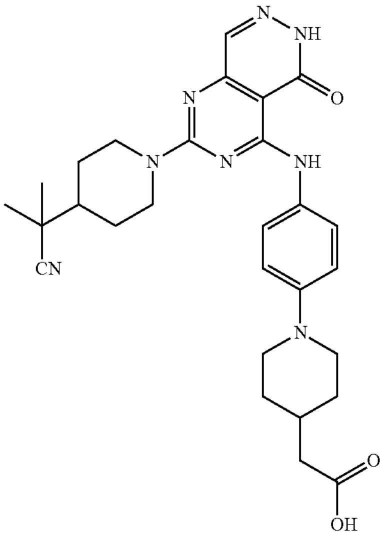 [SMILES: CC(C)(C#N)C1CCN(c2nc(Nc3ccc(N4CCC(CC(=O)O)CC4)cc3)c3c(=O)[nH]ncc3n2)CC1] | 12.75 (s, 1H), 12.01 (s, br, 1H), 11.12 (s, 1H), 7.87 (s, 1H), 7.56 (d, J = 8.8 Hz, 2H), 6.97 (d, J = 8.8 Hz, 2H), 4.89 (m, 2H), 3.65 (m, 2H), 2.9 (m, 2H), 2.64 (m, 2H), 2.18 (d, J = 6.0 Hz, 2H), 1.92-1.74 (m, 7H), 1.30 (s, 6H), 1.23 (m, 3H) | 531.1 (M + 1) |
| 101 | 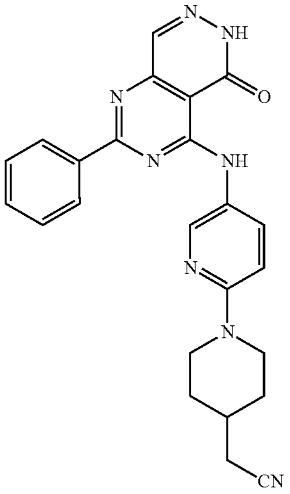 [SMILES: N#CCC1CCN(c2ccc(Nc3nc(-c4ccccc4)nc4cn[nH]c(=O)c34)cn2)CC1] | 13.31 (s, 1H), 11.11 (s, 1H), 8.55 (d, J = 2.8 Hz, 1H), 8.36 (m, 2H), 8.29 (s, 1H), 8.04 (dd, $J^1$ = 9.2 Hz, $J^2$ = 2.8 Hz, 1H), 7.55 (m, 3H), 6.98 (d, J = 9.2 Hz, 1H), 4.35 (d, J = 12.8 Hz, 2H), 2.85 (t, J = 11.2 Hz, 2H), 2.50 (m, 2H), 1.90 (m, 1H), 1.89 (m, 2H), 1.27 (m, 2H) | 439.1 (M + 1) |
| 102 | 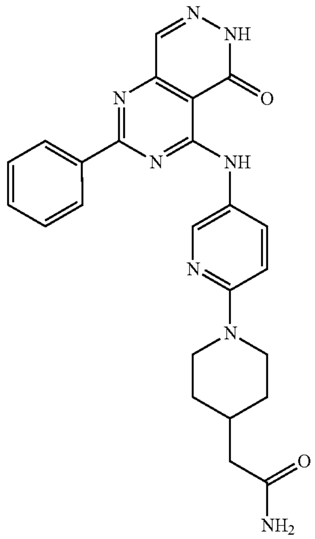 [SMILES: NC(=O)CC1CCN(c2ccc(Nc3nc(-c4ccccc4)nc4cn[nH]c(=O)c34)cn2)CC1] | 13.31 (s, 1H), 11.11 (s, 1H), 8.54 (d, J = 2.4 Hz, 1H), 8.36 (d, J = 6.8 Hz, 2H), 8.30 (s, 1H), 8.04 (dd, $J^1$ = 9.2 Hz, $J^2$ = 2.4 Hz, 1H), 7.57 (m, 3H), 7.27 (s, br, 1H), 6.97 (d, J = 9.2 Hz, 1H), 6.76 (s, br, 1H), 4.30 (d, J = 12.8 Hz, 2H), 2.83 (t, J = 12.4 Hz, 2H), 2.02 (d, J = 7.2 Hz, 2H), 1.74 (m, 3H), 1.19 (m, 2H) | 457.2 (M + 1) |

TABLE 2-continued
| Ex # | Structure | Physical Data | |
|---|---|---|---|
| | | $^1$H-NMR in DMSO-$d_6$ at 400 Hz (δ) | MS m/z |
| 103 | 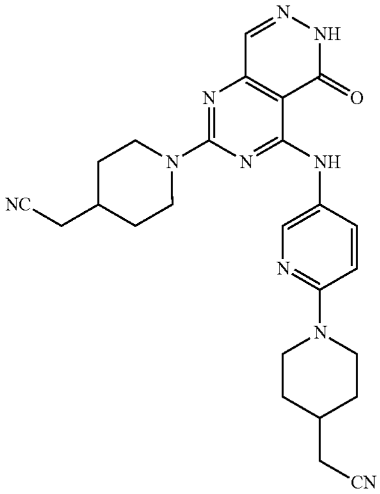 [SMILES: N#CCC1CCN(c2ccc(Nc3nc(N4CCC(CC#N)CC4)nc4cn[nH]c(=O)c34)cn2)CC1] | 12.75 (s, 1H), 11.13 (s, 1H), 7.87 (s, 1H), 7.55 (d, J = 8.8 Hz, 2H), 6.98 (d, J = 8.8 Hz, 2H), 4.89 (m, 2H), 3.7 (d, J = 12.8 Hz, 2H), 2.98 (t, J = 11.2 Hz, 2H), 2.69-2.60 (m, 8H), 1.97-1.80 (m, 6H), 1.39 (m, 2H) | 484.3 (M + 1) |
| 104 | 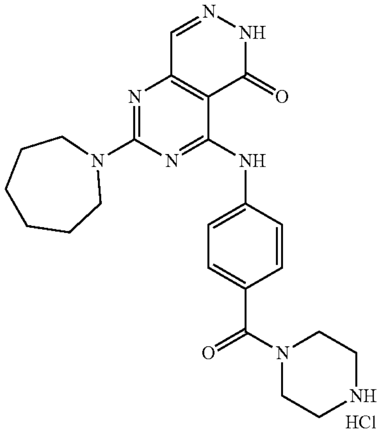 [SMILES: O=C(c1ccc(Nc2nc(N3CCCCCC3)nc3cn[nH]c(=O)c23)cc1)N1CCNCC1 ; Cl] | 12.83 (s, 1H), 11.55 (s, 1H), 9.32 (s, br, 2H), 7.95 (s, 1H), 7.87 (d, J = 8.8 Hz, 2H), 7.52 (d, J = 8.8 Hz, 2H), 3.84-3.73 (m, 8H), 3.15 (m, 4H), 1.81-1.76 (m, 4H), 1.52-1.23 (m, 4H) | 449.2 (M + 1) |
| 105 | 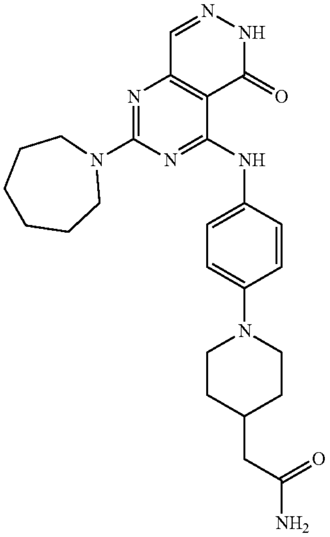 [SMILES: NC(=O)CC1CCN(c2ccc(Nc3nc(N4CCCCCC4)nc4cn[nH]c(=O)c34)cc2)CC1] | 12.69 (s, 1H), 11.14 (s, 1H), 7.85 (s, 1H), 7.69 (d, J = 8.8 Hz, 2H), 7.27 (s, 1H), 6.94 (d, J = 8.8 Hz, 2H), 6.75 (s, 1H), 3.79-3.74 (m, 4H), 3.63 (d, J = 11.6 Hz, 2H), 2.62 (t, J = 12.0 Hz, 2H), 2.02 (d, J = 6.8 Hz, 2H), 1.76-1.71 (m, 7H), 1.50 (m, 4H), 1.30 (m, 2H) | 477.5 (M + 1) |

TABLE 2-continued
| Ex # | Structure | Physical Data<br>$^1$H-NMR in DMSO-$d_6$ at 400 Hz (δ) | MS m/z |
|---|---|---|---|
| 106 | 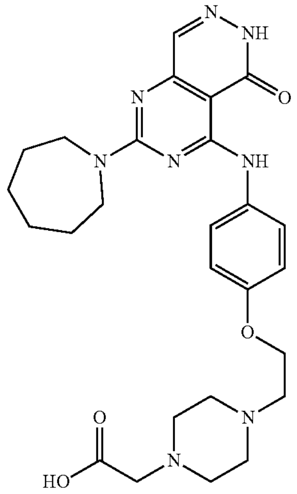 [SMILES: O=C(O)CN1CCN(CCOc2ccc(Nc3nc(N4CCCCCC4)nc4cn[nH]c(=O)c34)cc2)CC1] | 12.72 (s, 1H), 11.17 (s, 1H), 7.87 (s, 1H), 7.66 (d, J = 8.8 Hz, 2H), 6.97 (d, J = 8.8 Hz, 2H), 4.07 (s, br, 2H), 3.80 (s, br, 2H), 3.73 (s, br, 2H), 2.71-2.57 (m, 6H), 2.50-2.32 (m, 6H), 1.99-1.62 (m, 4H), 1.50-1.32 (m, 4H) | 523.3 (M + 1) |
| 107 | 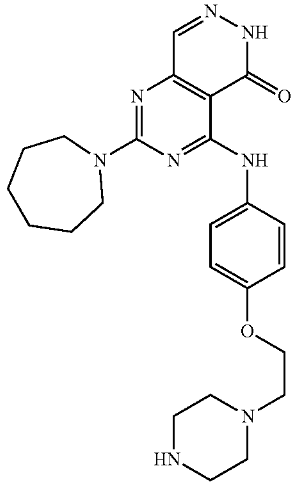 [SMILES: O=c1[nH]ncc2nc(N3CCCCCC3)nc(Nc3ccc(OCCN4CCNCC4)cc3)c12] | 12.69 (s, 1H), 11.17 (s, 1H), 7.87 (s, 1H), 7.66 (d, J = 8.8 Hz, 2H), 6.97 (d, J = 8.8 Hz, 2H), 4.06 (t, J = 5.6 Hz, 2H), 3.80 (t, J = 6.0 Hz, 2H), 3.73 (t, J = 6.0 Hz, 2H), 2.69-2.63 m, 6H), 2.39 (m, 4H), 1.98 (m, 4H), 1.50 (m, 4H) | 465.2 (M + 1) |
| 108 | 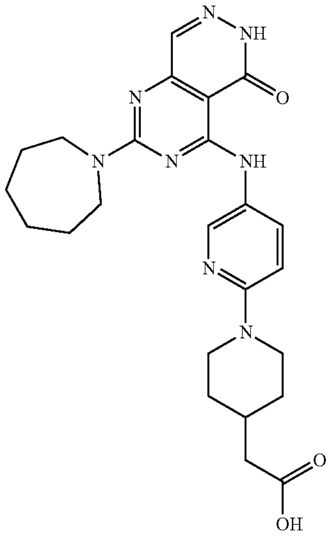 [SMILES: O=C(O)CC1CCN(c2ccc(Nc3nc(N4CCCCCC4)nc4cn[nH]c(=O)c34)cn2)CC1] | 12.70 (s, 1H), 12.15 (s, br, 1H), 10.97 (s, 1H), 8.43 (d, J = 2.4 Hz, 1H), 7.92 (dd, $J^1$ = 8.8 Hz, $J^2$ = 2.4 Hz, 1H), 7.86 (s, 1H), 6.87 (d, J = 8.8 Hz, 1H), 4.23 (d, J = 12.8 Hz, 2H), 3.78 (t, J = 6 Hz, 2H), 3.70 (t, J = 6 Hz, 2H), 2.77 (t, J = 11.2 Hz, 2H), 2.17 (d, J = 6.8 Hz, 2H), 1.88 (m, 1H), 1.73 (m, 6H), 1.49 (m, 4H), 1.29 (m, 2H) | 479.2 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 109 | 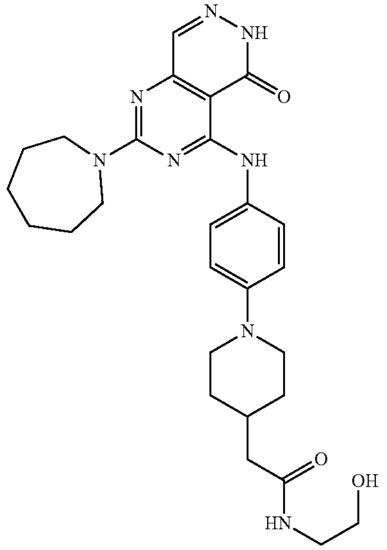 [SMILES: O=C(CC1CCN(c2ccc(Nc3nc(N4CCCCCC4)nc4cn[nH]c(=O)c34)cc2)CC1)NCCO] | 12.69 (s, 1H), 11.14 (s, 1H), 7.85 (s, 1H), 7.60 (d, J = 8.8 Hz, 2H), 6.94 (d, J = 8.8 Hz, 2H), 4.63 (t, J = 6 Hz, 1H), 3.79 (t, J = 6.0 Hz, 2H), 3.75 (t, J = 6.0 Hz, 2H), 3.63 (d, J = 12.4 Hz, 2H), 3.39 (m, 2H), 3.12 (m, 2H), 2.67 (m, 2H), 2.04 (m, 3H), 1.73 (m, 4H), 1.49 (m, 4H), 1.21 (m, 5H) | 521.4 (M + 1) |
| 110 | 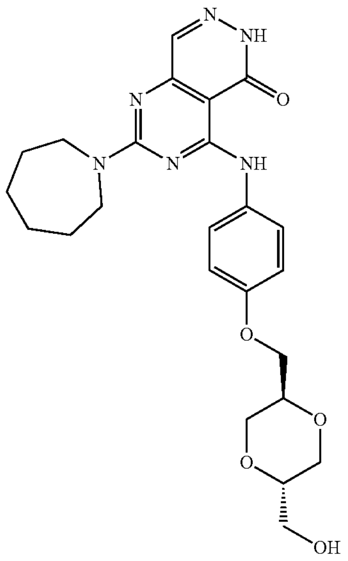 [SMILES: O=c1[nH]ncc2nc(N3CCCCCC3)nc(Nc3ccc(OC[C@@H]4CO[C@@H](CO)CO4)cc3)c12] | 12.71 (s, 1H), 11.17 (s, 1H), 7.86 (s, 1H), 7.66 (d, J = 8.8 Hz, 2H), 6.97 (d, J = 8.8 Hz, 2H), 4.72 (t, J = 6.0 Hz, 1H), 3.95-3.73 (m, 9H), 3.50-3.38 (m, 5H), 1.75 (m, 4H), 1.50 (m, 4H) | 483.2 (M + 1) |

TABLE 2-continued
| Ex # | Structure | Physical Data $^1$H-NMR in DMSO-$d_6$ at 400 Hz (δ) | MS m/z |
|---|---|---|---|
| 111 | 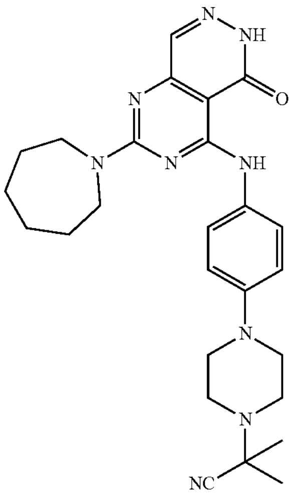 [SMILES: CC(C)(C#N)N1CCN(c2ccc(Nc3nc(N4CCCCCC4)nc4cn[nH]c(=O)c34)cc2)CC1] | 12.69 (s, 1H), 11.16 (s, 1H), 7.86 (s, 1H), 7.62 (d, J = 8.8 Hz, 2H), 6.97 (d, J = 8.8 Hz, 2H), 3.79 (t, J = 6.0 Hz, 2H), 3.77 (m, 2H), 3.75 (t, J = 6.0 Hz, 2H), 2.60 (t, J = 11.2 Hz, 2H), 1.88 (m, 7H), 1.48 (m, 6H), 1.31 (s, 6H) | 487.4 (M + 1) |
| 112 | 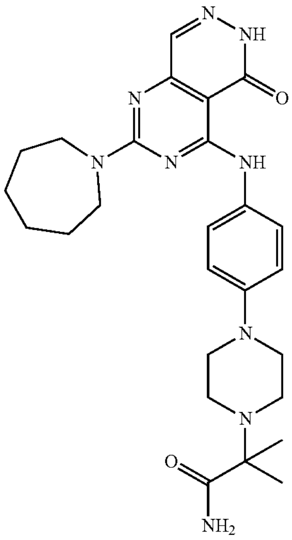 [SMILES: CC(C)(C(N)=O)N1CCN(c2ccc(Nc3nc(N4CCCCCC4)nc4cn[nH]c(=O)c34)cc2)CC1] | 12.69 (s, 1H), 11.14 (s, 1H), 7.85 (s, 1H), 7.85 (s, 1H), 7.60 (d, J = 8.8 Hz, 2H), 7.01 (s, 1H), 6.94 (d, J = 8.8 Hz, 2H), 6.79 (s, 1H), 3.79 (m, 6H), 1.70-1.50 (m, 12H), 1.3 (m, 2H), 1.01 (s, 6H) | 505.2 (M + 1) |
| 113 | 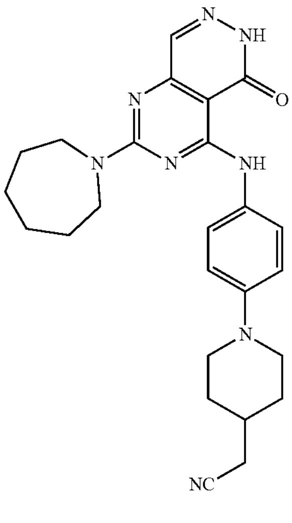 [SMILES: N#CCC1CCN(c2ccc(Nc3nc(N4CCCCCC4)nc4cn[nH]c(=O)c34)cc2)CC1] | 12.69 (s, 1H), 11.15 (s, 1H), 7.86 (s, 1H), 7.61 (d, J = 8.8 Hz, 2H), 6.96 (d, J = 8.8 Hz, 2H), 3.80 (t, J = 6.0 Hz, 2H), 3.75 (t, J = 6.0 Hz, 2H), 3.69 (d, J = 12.4 Hz, 2H), 2.68-2.54 (m, 6H), 1.79 (m, 5H), 1.51 (m, 4H), 1.35 (m, 2H) | 459.2 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 114 | 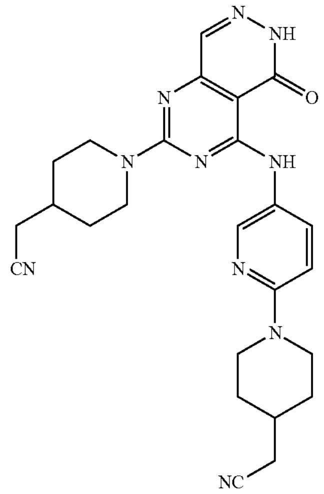 [SMILES: N#CCC1CCN(c2ccc(Nc3nc(N4CCC(CC#N)CC4)nc4cn[nH]c(=O)c34)cn2)CC1] | 12.75 (s, 1H), 10.95 (s, 1H), 8.4 (s, 1H), 7.88 (s, 1H), 7.86 (s, 1H), 6.91 (d, J = 8.8 Hz, 1H), 5.75 (s, br, 2H), 4.30 (d, J = 12.4 Hz, 2H), 2.96 (t, J = 11.6 Hz, 2H), 2.80 (t, J = 12 Hz, 2H), 2.50 (m, 4H), 1.96-1.75 (m, 6H), 1.26 (m, 4H) | 485.0 (M + 1) |
| 115 | 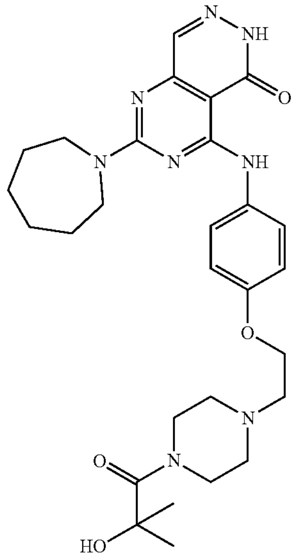 [SMILES: CC(C)(O)C(=O)N1CCN(CCOc2ccc(Nc3nc(N4CCCCCC4)nc4cn[nH]c(=O)c34)cc2)CC1] | 12.71 (s, 1H), 11.17 (s, 1H), 7.87 (s, 1H), 7.67 (d, J = 8.8 Hz, 2H), 6.97 (d, J = 8.8 Hz, 2H), 5.37 (s, 1H), 4.09 (t, J = 5.6 Hz, 2H), 3.80 (t, J = 5.6 Hz, 2H), 3.73 (t, J = 6.0 Hz, 2H), 2.70 (t, J = 5.2 Hz, 2H), 2.50 (m, 8H), 1.75 (m, 4H), 1.50 (m, 4H), 1.30 (s, 6H) | 551.1 (M + 1) |
| 116 | 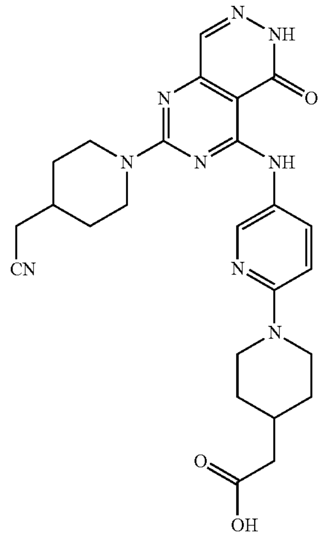 [SMILES: N#CCC1CCN(c2nc(Nc3ccc(N4CCC(CC(=O)O)CC4)nc3)c3c(=O)[nH]ncc3n2)CC1] | 12.75 (s, 1H), 12.07 (s, 1H), 10.95 (s, 1H), 8.39 (d, J = 2.4 Hz, 1H), 7.88 (s, 1H), 7.85 (dd, $J^1$ = 9.2 Hz, $J^2$ = 2.4 Hz, 1H), 6.90 (d, J = 9.2 Hz, 1H), 4.56 (m, 2H), 4.24 (d, J = 12.8 Hz, 2H), 3.80 (t, J = 5.6 Hz, 2H), 3.73 (t, J = 6.1 Hz, 2H), 2.18 (d, J = 7.6 Hz, 2H), 1.96-1.72 (m, 8H), 1.19-1.14 (m, 4H) | 504.1 (M + 1) |

TABLE 2-continued
| Ex # | Structure | Physical Data ¹H-NMR in DMSO-d$_6$ at 400 Hz (δ) | MS m/z |
|---|---|---|---|
| 117 | 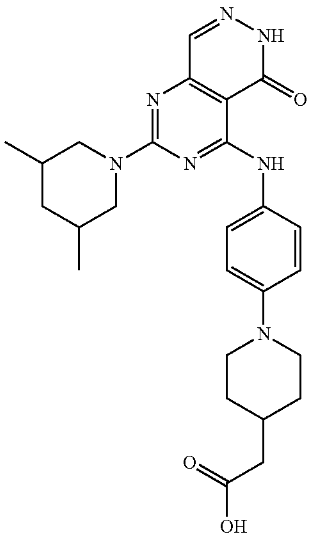 [SMILES: CC1CC(C)CN(c2nc(Nc3ccc(N4CCC(CC(=O)O)CC4)cc3)c3c(=O)[nH]ncc3n2)C1] | 12.73 (s, 1H), 12.01 (s, br, 1H), 11.19 (s, br, 1H), 7.88 (s, 1H), 7.67 (d, J = 8.8 Hz, 2H), 6.97 (d, J = 8.8 Hz, 2H), 4.67 (m, 2H), 3.65 (d, J = 12.4 Hz, 2H), 2.56 (m, 5H), 2.21 (d, J = 6 Hz, 2H), 1.79 (m, 4H), 1.57 (m, 4H), 0.92 (s, 6H) | 491.4 (M + 1) |
| 118 | 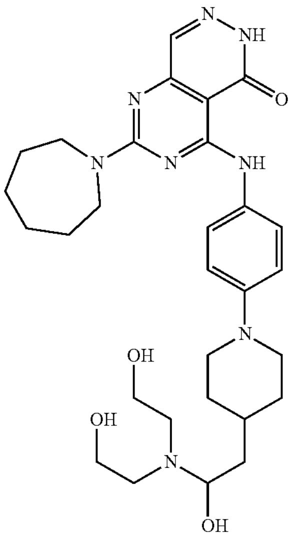 [SMILES: O=c1[nH]ncc2nc(N3CCCCCC3)nc(Nc3ccc(N4CCC(CC(O)N(CCO)CCO)CC4)cc3)c12] | 12.69 (s, 1H), 11.14 (s, 1H), 7.85 (s, 1H), 7.69 (d, J = 8.8 Hz, 2H), 6.95 (d, J = 8.8 Hz, 2H), 4.81 (t, J = 5.6 Hz, 1H), 4.64 (t, J = 5.6 Hz, 1H), 4.13 (d, J = 2 Hz, 2H), 3.81-3.75 (m, 6H), 3.51-3.44 (m, 6H), 2.50 (m, 4H), 2.30 (m, 5H), 1.75 (m, 4H), 1.50 (m, 4H) | 565.1 (M + 1) |
| 119 | 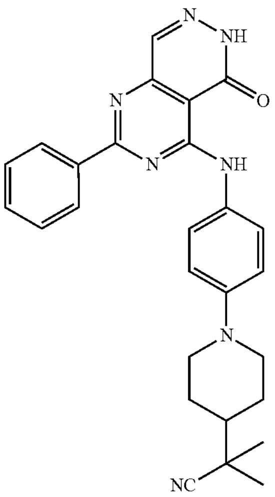 [SMILES: CC(C)(C#N)C1CCN(c2ccc(Nc3nc(-c4ccccc4)nc4cn[nH]c(=O)c34)cc2)CC1] | 13.30 (s, 1H), 11.30 (s, 1H), 8.41 (d, J = 6.4 Hz, 2H), 8.28 (s, 1H), 7.73 (d, J = 8.8 Hz, 2H), 7.58 (m, 3H), 7.06 (d, J = 8.8 Hz, 2H), 3.85 (d, J = 12.0 Hz, 2H), 2.65 (t, J = 10.8 Hz, 2H), 1.88 (d, J = 11.6 Hz, 2H), 1.49 (m, 3H), 1.36 (s, 6H) | 466.2 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 120 | 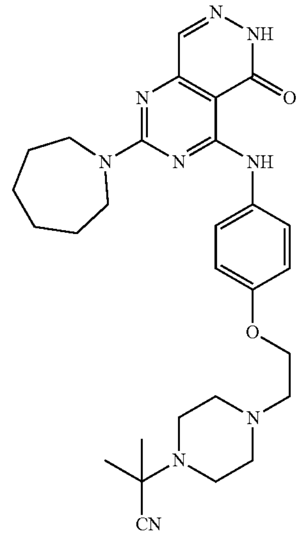 [SMILES: CC(C)(C#N)N1CCN(CCOc2ccc(Nc3nc(N4CCCCCC4)nc4cn[nH]c(=O)c34)cc2)CC1] | 12.70 (s, 1H), 11.17 (s, 1H), 7.87 (s, 1H), 7.66 (d, J = 8.8 Hz, 2H), 6.97 (d, J = 8.8 Hz, 2H), 4.07 (t, J = 5.4 Hz, 2H), 3.80 (t, J = 5.6 Hz, 2H), 3.73 (t, J = 6 Hz, 2H), 3.03 (d, J = 10 Hz, 2H), 2.67 (d, J = 1.6 Hz, 2H), 1.98 (m, 11H), 1.50 (m, 4H), 1.27 (s, 6H) | 531.0 (M + 1) |
| 121 | 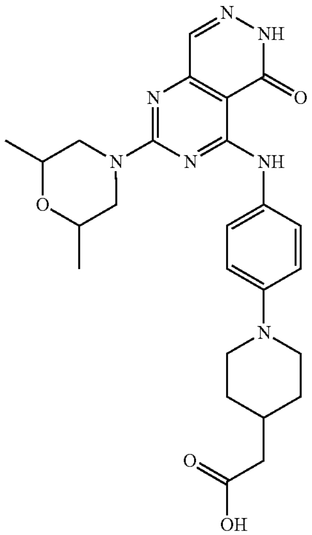 [SMILES: CC1CN(c2nc(Nc3ccc(N4CCC(CC(=O)O)CC4)cc3)c3c(=O)[nH]ncc3n2)CC(C)O1] | 12.70 (s, 1H), 12.21 (s, 1H), 11.14 (s, 1H), 7.88 (s, 1H), 7.53 (d, J = 8.8 Hz, 2H), 6.97 (d, J = 8.8 Hz, 2H), 4.56 (m, 2H), 3.62 (m, 4H), 2.64 (t, J = 11.4 Hz, 4H), 2.19 (d, J = 6.8 Hz, 2H), 1.75 (m, 3H), 1.33 (m, 2H), 1.17 (d, J = 6.0 Hz, 6H) | 494.1 (M + 1) |

TABLE 2-continued
| Ex # | Structure | Physical Data<br>$^1$H-NMR in DMSO-$d_6$ at 400 Hz (δ) | MS m/z |
|---|---|---|---|
| 122 | 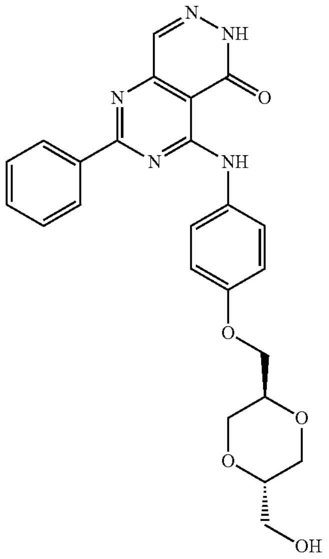 [SMILES: O=c1[nH]ncc2nc(-c3ccccc3)nc(Nc3ccc(OC[C@@H]4CO[C@@H](CO)CO4)cc3)c12] | 11.32 (s, 1H), 11.30 (s, 1H), 8.40 (d, J = 6.4 Hz, 2H), 8.30 (s, 1H), 7.78 (d, J = 8.8 Hz, 2H), 7.57 (m, 3H), 7.08 (d, J = 8.8 Hz, 2H), 4.73 (t, J = 6 Hz, 1H), 4.00 (d, J = 4.8 Hz, 2H), 3.92-3.80 (m, 3H), 3.50-3.39 (m, 5H) | 462 (M + 1) |
| 123 | 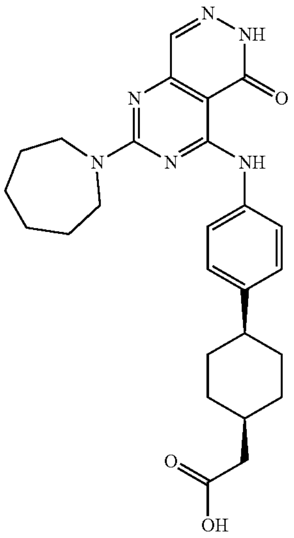 [SMILES: O=C(O)C[C@H]1CC[C@@H](c2ccc(Nc3nc(N4CCCCCC4)nc4cn[nH]c(=O)c34)cc2)CC1] | 12.73 (s, 1H), 12.01 (s, br, 1H), 11.32 (s, 1H), 7.88 (s, 1H), 7.70 (d, J = 8.8 Hz, 2H), 7.28 (d, J = 8.8 Hz, 2H), 4.52 (s, br, 1H), 3.81-3.77 (m, 4H), 2.35 (m, 3H), 1.80-1.51 (m, 16H) | 477.2 (M + 1) |

TABLE 2-continued
| Ex # | Structure | Physical Data $^1$H-NMR in DMSO-$d_6$ at 400 Hz (δ) | MS m/z |
|---|---|---|---|
| 124 | 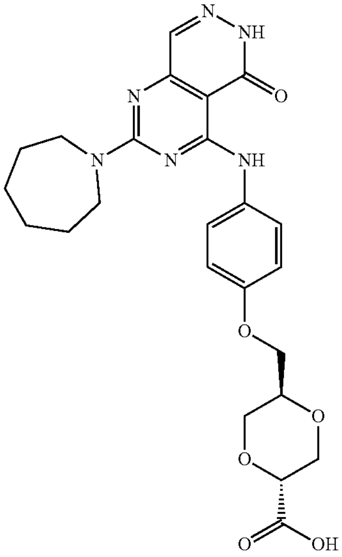 [SMILES: O=C(O)[C@H]1CO[C@H](COc2ccc(Nc3nc(N4CCCCCC4)nc4cn[nH]c(=O)c34)cc2)CO1] | 12.71 (s, 1H), 11.17 (s, 1H), 7.86 (s, 1H), 7.67 (d, J = 8.8 Hz, 2H), 6.96 (d, J = 8.8 Hz, 2H), 3.99-3.71 (m, 10H), 3.43 (m, 2H), 1.75 (m, 4H), 1.50 (m, 4H) | 495.4 (M − 1) |
| 125 | 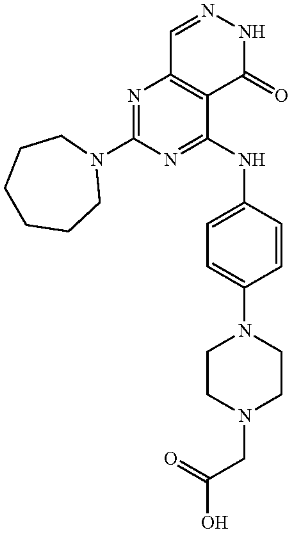 [SMILES: O=C(O)CN1CCN(c2ccc(Nc3nc(N4CCCCCC4)nc4cn[nH]c(=O)c34)cc2)CC1] | 12.70 (s, 1H), 11.16 (s, 1H), 7.86 (s, 1H), 7.64 (d, J = 8.8 Hz, 2H), 6.96 (d, J = 8.8 Hz, 2H), 3.80 (t, J = 5.6 Hz, 2H), 3.75 (t, J = 5.6 Hz, 2H), 3.65-3.16 (m, 7H), 2.71-2.66 (m, 4H), 1.75 (m, 4H), 1.51 (m, 4H) | 499.3 (M + 1) |

TABLE 2-continued
| Ex # | Structure | Physical Data $^1$H-NMR in DMSO-$d_6$ at 400 Hz (δ) | MS m/z |
|---|---|---|---|
| 126 | 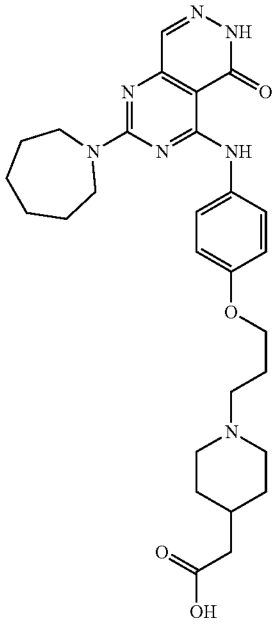 [SMILES: O=C(O)CC1CCN(CCCOc2ccc(Nc3nc(N4CCCCCC4)nc4cn[nH]c(=O)c34)cc2)CC1] | 12.71 (s, 1H), 11.17 (s, 1H), 7.87 (s, 1H), 7.66 (d, J = 8.8 Hz, 2H), 6.4 (d, J = 8.8 Hz, H), 3.98 (t, J = 6.4 Hz, 2H), 3.80 (t, J = 6.0 Hz, 2H), 3.73 (t, J = 6.0 Hz, 2H), 2.84 (m, 2H), 2.45 (m, 2H), 2.12 (d, J = 6.4 Hz, 2H), 1.88 (m, 7H), 1.75 (m, 4H), 1.50 (m, 4H), 1.19 (m, 2H) | 536.0 (M + 1) |
| 127 | 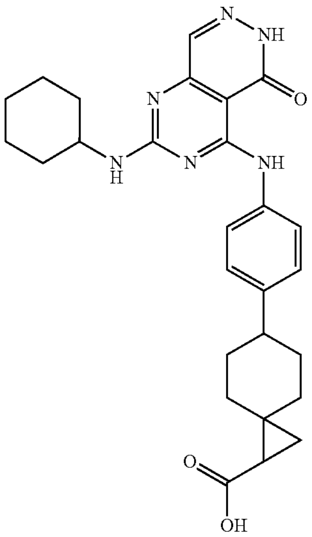 [SMILES: O=C(O)C1CC12CCC(c1ccc(Nc3nc(NC4CCCCC4)nc4cn[nH]c(=O)c34)cc1)CC2] | 12.63 (s, 1H), 12.08 (s, 1H), 11.17 (s, 1H), 7.86 (s, 1H), 7.65 (d, J = 8.8 Hz, 2H), 6.97 (d, J = 8.8 Hz, 2H), 3.42-3.10 (m, 4H), 1.99 (m, 4H), 1.39-1.22 (m, 11H), 0.97-0.92 (m, 2H) | 490.2 (M + 1) |

TABLE 2-continued
| Ex # | Structure | Physical Data $^1$H-NMR in DMSO-$d_6$ at 400 Hz (δ) | MS m/z |
|---|---|---|---|
| 128 | 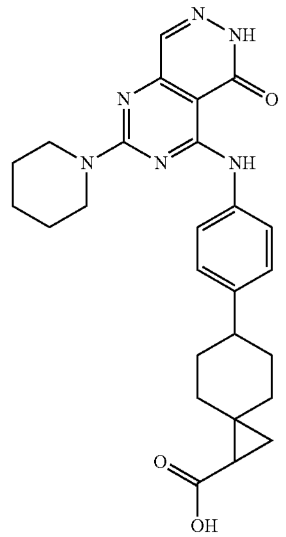 [SMILES: O=C(O)C1CC12CCC(c1ccc(Nc3nc(N4CCCCC4)nc4cn[nH]c(=O)c34)cc1)CC2] | 12.71 (s, 1H), 12.04 (s, 1H), 11.12 (s, 1H), 7.86 (s, 1H), 7.55 (d, J = 8.8 Hz, 2H), 6.98 (d, J = 8.8 Hz, 2H), 3.82 (m, 4H), 3.33-3.05 (m, 4H), 1.78 (m, 2H), 1.65-1.53 (m, 9H), 0.98-0.92 (m, 2H) | 476.2 (M + 1) |
| 129 | 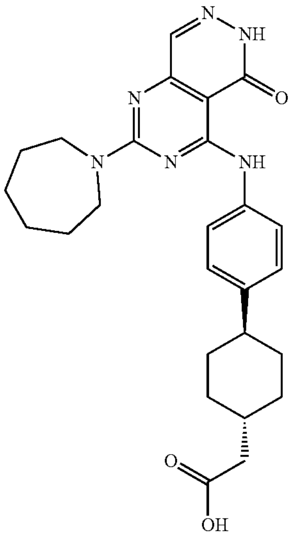 [SMILES: O=C(O)C[C@H]1CC[C@H](c2ccc(Nc3nc(N4CCCCCC4)nc4cn[nH]c(=O)c34)cc2)CC1] | 12.73 (s, 1H), 12.06 (s, 1H), 11.30 (s, 1H), 7.87 (s, 1H), 7.68 (d, J = 8.8 Hz, 2H), 7.23 (d, J = 8.8 Hz, 2H), 3.80 (t, J = 6.0 Hz, 2H), 3.76 (t, J = 5.2 Hz, 2H), 2.44 (m, 1H), 2.13 (d, J = 6.8 Hz, 2H), 1.79-1.51 (m, 9H), 1.47-1.23 (m, 6H), 1.15 (m, 2H) | 475.4 (M − 1) |
| 130 | 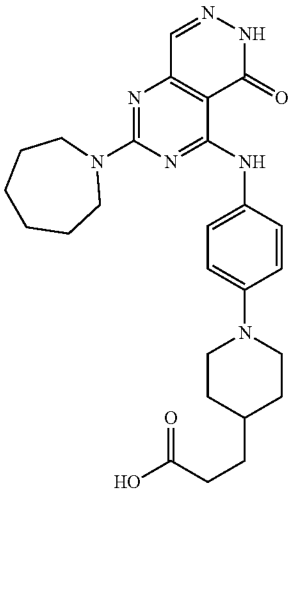 [SMILES: O=C(O)CCC1CCN(c2ccc(Nc3nc(N4CCCCCC4)nc4cn[nH]c(=O)c34)cc2)CC1] | 12.69 (s, 1H), 12.03 (s, 1H), 11.14 (s, 1H), 7.85 (s, 1H), 7.60 (d, J = 8.8 Hz, 2H), 6.94 (d, J = 8.8 Hz, 2H), 3.79 (t, J = 5.6 Hz, 2H), 3.74 (t, J = 5.6 Hz, 2H), 3.64 (d, J = 12.8 Hz, 2H), 2.59 (t, J = 10.4 Hz, 2H), 2.25 (t, J = 7.6 Hz, 2H), 1.75 (m, 6H), 1.50 (m, 6H), 1.30 (m, 1H), 1.23 (m, 2H) | 492.3 (M + 1) |

TABLE 2-continued
| Ex # | Structure | Physical Data $^1$H-NMR in DMSO-$d_6$ at 400 Hz (δ) | MS m/z |
|---|---|---|---|
| 131 | 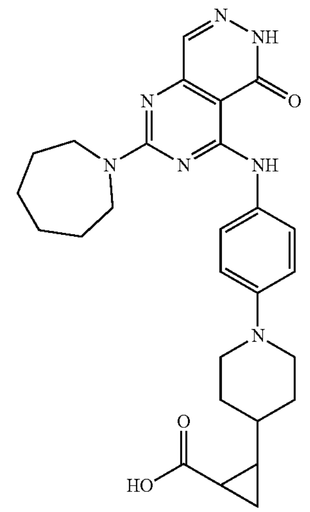 [SMILES: O=C(O)C1CC1C1CCN(c2ccc(Nc3nc(N4CCCCCC4)nc4cn[nH]c(=O)c34)cc2)CC1] | 12.69 (s, 1H), 12.03 (s, 1H), 11.14 (s, 1H), 7.85 (s, 1H), 7.60 (d, J = 8.8 Hz, 2H), 6.95 (d, J = 8.8 Hz, 2H), 3.79 (t, J = 5.6 Hz, 2H), 3.74 (t, J = 5.6 Hz, 2H), 3.65 (d, J = 12.8 Hz, 2H), 2.59 (t, J = 10.4 Hz, 2H), 1.76 (m, 2H), 1.74 (m, 4H), 1.50 (m, 4H), 1.45 (m, 2H), 1.23 (m, 2H), 0.95-0.92 (m, 3H) | 504.1 (M + 1) |
| 132 | 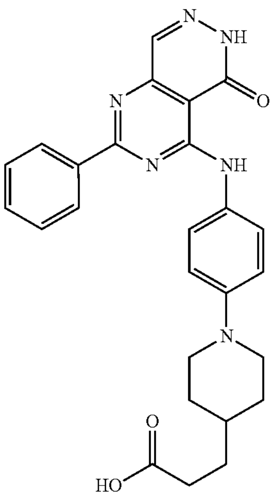 [SMILES: O=C(O)CCC1CCN(c2ccc(Nc3nc(-c4ccccc4)nc4cn[nH]c(=O)c34)cc2)CC1] | 12.59 (s, 2H), 11.28 (s, 1H), 8.40 (d, J = 6 Hz, 2H), 8.27 (s, 1H), 7.71 (d, J = 8.8 Hz, 2H), 7.56 (m, 3H), 7.04 (d, J = 8.8 Hz, 2H), 3.73 (d, J = 12.4 Hz, 2H), 2.64 (t, J = 12 Hz, 2H), 2.25 (t, J = 7.2 Hz, 2H), 1.76 (d, J = 11.6 Hz, 2H), 1.50 (d, J = 6.8 Hz, 2H), 1.38 (m, 1H), 1.25 (m, 2H) | 471.3 (M + 1) |
| 133 | 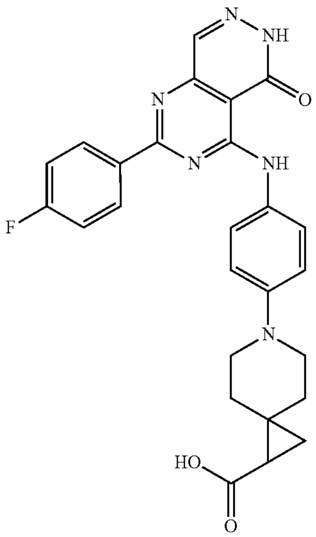 [SMILES: O=C(O)C1CC12CCN(c1ccc(Nc3nc(-c4ccc(F)cc4)nc4cn[nH]c(=O)c34)cc1)CC2] | 13.01 (s, 2H), 11.26 (s, 1H), 8.39 (m, 2H), 8.23 (s, 1H), 7.65 (d, J = 8.8 Hz, 2H), 7.34 (t, J = 8.8 Hz, 2H), 7.01 (d, J = 8.8 Hz, 2H), 3.29-3.15 (m, 4H), 1.80 (t, J = 5.8 Hz, 2H), 1.60-1.52 (m, 3H), 0.94-0.80 (m, 2H) | 471.3 (M + 1) |

TABLE 2-continued
| Ex # | Structure | Physical Data ¹H-NMR in DMSO-$d_6$ at 400 Hz (δ) | MS m/z |
|---|---|---|---|
| 134 | 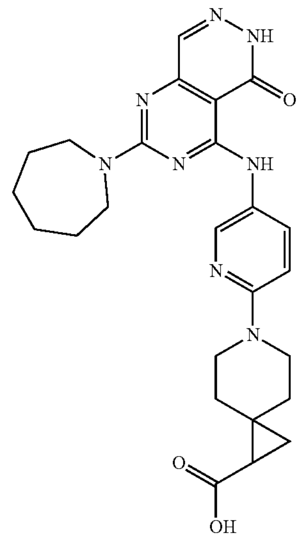 [SMILES: O=C(O)C1CC12CCN(c1ccc(Nc3nc(N4CCCCCC4)nc4cn[nH]c(=O)c34)cn1)CC2] | 12.70 (s, 1H), 12.0 (s, 1H), 10.98 (s, 1H), 8.44 (d, J = 2.4 Hz, 1H), 7.94 (dd, $J^1$ = 9.2 Hz, $J^2$ = 2.4 Hz, 1H), 7.86 (s, 1H), 6.90 (d, J = 9.2 Hz, 1H), 3.79 (t, J = 5.2 Hz, 2H), 3.70 (t, J = 5.2 Hz, 2H), 3.61 (m, 2H), 1.73 (m, 7H), 1.49 (m, 8H), 0.98-0.94 (m, 2H) | 491.4 (M + 1) |
| 135 | 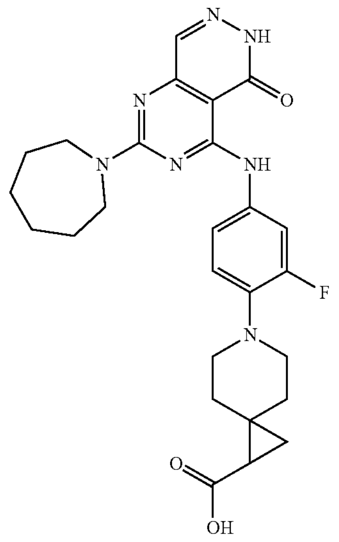 [SMILES: O=C(O)C1CC12CCN(c1ccc(Nc3nc(N4CCCCCC4)nc4cn[nH]c(=O)c34)cc1F)CC2] | 12.75 (s, 1H), 12.06 (s, 1H), 11.30 (s, 1H), 7.90 (d, J = 2.4 Hz, 1H), 7.88 (s, 1H), 7.29 (dd, $J^1$ = 9.6 Hz, $J^2$ = 2.4 Hz, 1H), 7.07 (t, J = 9.6 Hz, 1H), 3.81 (t, J = 6.4 Hz, 2H), 3.76 (t, J = 5.6 Hz, 2H), 3.02-2.99 (m, 4H), 1.79 (m, 6H), 1.54 (m, 7H), 0.98-0.92 (m, 2H) | 508.4 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 136 | 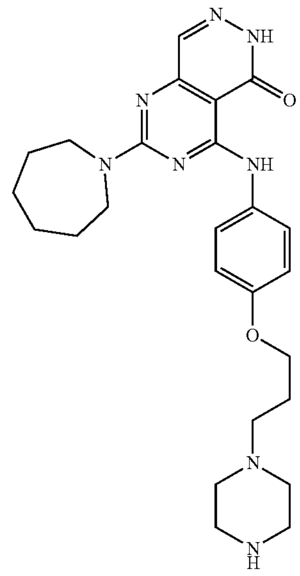 [SMILES: O=c1[nH]ncc2nc(N3CCCCCC3)nc(Nc3ccc(OCCCN4CCNCC4)cc3)c12] | 12.89 (s, 1H), 11.17 (s, 1H), 7.87 (s, 1H), 7.66 (d, J = 8.8 Hz, 2H), 6.95 (d, J = 8.8 Hz, 2H), 3.99 (t, J = 6.4 Hz, 2H), 3.80 (t, J = 6.4 Hz, 2H), 3.73 (t, J = 6 Hz, 2H), 3.58 (s, 1H), 2.67 (m, 4H), 2.46-2.33 (m, 4H), 1.75 (m, 4H), 1.50 (m, 4H) | 479.3 (M + 1) |
| 137 | 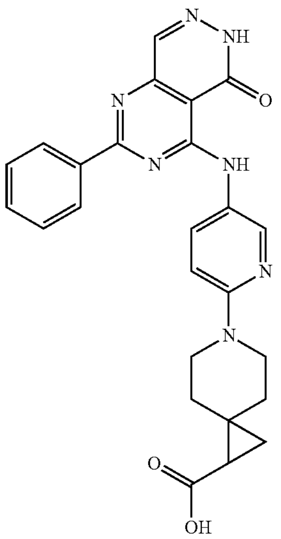 [SMILES: O=C(O)C1CC12CCN(c1ccc(Nc3nc(-c4ccccc4)nc4cn[nH]c(=O)c34)cn1)CC2] | 13.33 (s, 1H), 12.01 (s, 1H), 11.12 (s, 1H), 8.56 (d, J = 2.4 Hz, 1H), 8.37 (d, J = 8 Hz, 2H), 8.30 (s, 1H), 8.19 (dd, $J^1$ = 9.6 Hz, $J^2$ = 2.4 Hz, 1H), 7.57 (m, 3H), 7.02 (d, J = 9.6 Hz, 1H), 3.33-3.30 (m, 4H), 1.73 (m, 2H), 1.58 (m, 3H), 1.00 (m, H) | 470.2 (M + 1) |

TABLE 2-continued
| Ex # | Structure | Physical Data $^1$H-NMR in DMSO-$d_6$ at 400 Hz (δ) | MS m/z |
|---|---|---|---|
| 138 | 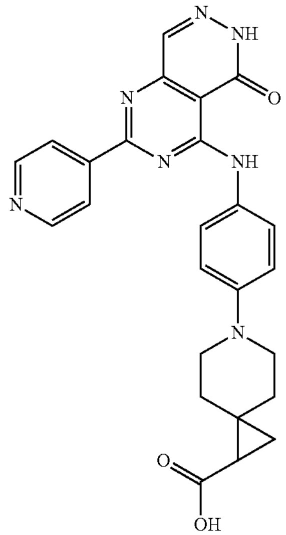 [SMILES: O=C(O)C1CC12CCN(c1ccc(Nc3nc(-c4ccncc4)nc4cn[nH]c(=O)c34)cc1)CC2] | 13.05 (s, 2H), 11.35 (s, 1H), 8.80 (d, J = 3.6 Hz, 2H), 8.31 (s, 1H), 8.21 (d, J = 3.6 Hz, 2H), 7.70 (d, J = 7.6 Hz, 2H), 7.06 (d, J = 7.6 Hz, 2H), 3.10 (m, 4H), 1.80 (m, 2H), 1.57 (m, 3H), 0.98-0.93 (m, 2H) | 470.1 (M + 1) |
| 139 | 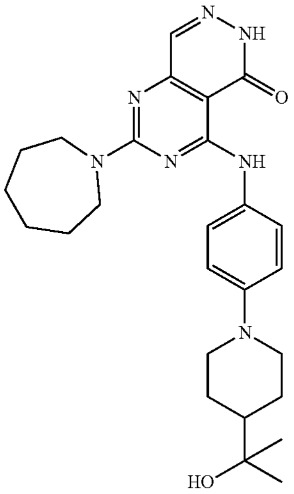 | 12.69 (s, 2H), 11.14 (s, 1H), 7.85 (s, 1H), 7.60 (d, J = 8.8 Hz, 2H), 6.95 (d, J = 8.8 Hz, 2H), 4.11 (s, 1H), 3.79 (t, J = 6 Hz, 2H), 3.75 (t, J = 5.6 Hz, 2H), 3.72 (m, 2H), 2.50 (m, 2H), 1.78 (m, 6H), 1.50 (m, 4H), 1.34 (m, 3H), 1.06 (s, 6H) | 478.2 (M + 1) |
| 140 | 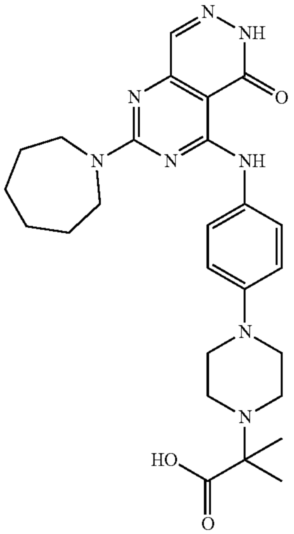 | 12.70 (s, 2H), 11.16 (s, 1H), 7.86 (s, 1H), 7.62 (d, J = 8.8 Hz, 2H), 6.95 (d, J = 8.8 Hz, 2H), 3.80 (t, J = 6 Hz, 2H), 3.75 (t, J = 6 Hz, 2H), 3.16 (m, 4H), 2.76 (m, 4H), 1.75 (m, 4H), 1.50 (m, 4H), 1.25 (s, 6H) | 507.2 (M + 1) |

TABLE 2-continued
| Ex # | Structure | Physical Data: $^1$H-NMR in DMSO-$d_6$ at 400 Hz (δ) | Physical Data: MS m/z |
|---|---|---|---|
| 141 | 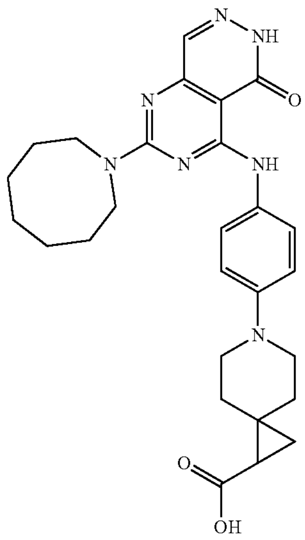 [SMILES: O=C(O)C1CC12CCN(c1ccc(Nc3nc(N4CCCCCCC4)nc4cn[nH]c(=O)c34)cc1)CC2] | 12.75 (s, 1H), 12.0 (s, 1H), 11.14 (s, 1H), 7.84 (s, 1H), 7.60 (d, J = 8.8 Hz, 2H), 6.94 (d, J = 8.8 Hz, 2H), 3.75 (t, J = 6 Hz, 2H), 3.70 (t, J = 5.6 Hz, 2H), 3.21 (m, 3H), 1.79 (m, 8H), 1.51-1.41 (m, 8H), 0.84 (m, 4H), 0.66 (m, 1H) | 504.2 (M + 1) |
| 142 | 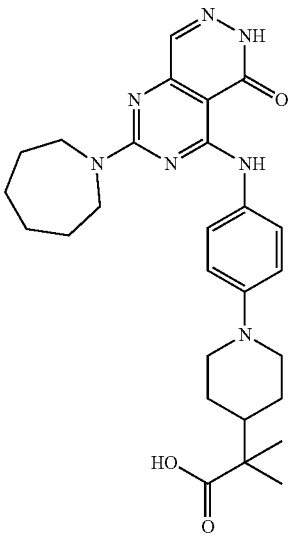 [SMILES: CC(C)(C(=O)O)C1CCN(c2ccc(Nc3nc(N4CCCCCC4)nc4cn[nH]c(=O)c34)cc2)CC1] | 12.69 (s, 1H), 12.02 (s, 1H), 11.14 (s, 1H), 7.85 (s, 1H), 7.60 (d, J = 8.8 Hz, 2H), 6.94 (d, J = 8.8 Hz, 2H), 3.79 (t, J = 5.6 Hz, 2H), 3.74 (t, J = 5.2 Hz, 2H), 3.70 (m, 2H), 2.5 (m, 2H), 1.76 (m, 4H), 1.60-1.50 (m, 7H), 1.37 (m, 2H), 1.05 (s, 6H) | 506.2 (M + 1) |

TABLE 2-continued
| Ex # | Structure | Physical Data $^1$H-NMR in DMSO-$d_6$ at 400 Hz (δ) | MS m/z |
|---|---|---|---|
| 143 | 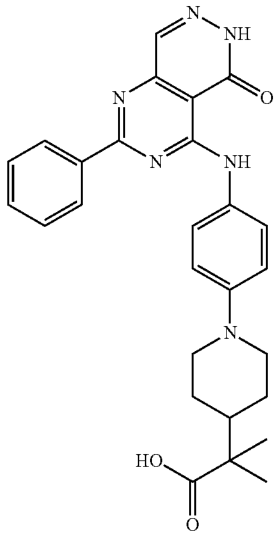 [SMILES: CC(C)(C(=O)O)C1CCN(c2ccc(Nc3nc(-c4ccccc4)nc4cn[nH]c(=O)c34)cc2)CC1] | 13.30 (s, 1H), 12.4 (s, 1H), 11.30 (s, 1H), 8.41 (d, J = 6 Hz, 2H), 8.29 (s, 1H), 7.70 (d, J = 8.8 Hz, 2H), 7.58 (m, 3H), 7.05 (d, J = 8.8 Hz, 2H), 3.80 (d, J = 12 Hz, 2H), 2.61 (t, J = 11.2 Hz, 2H), 1.65-1.62 (m, 3H), 1.43-1.37 (m, 2H), 1.07 (s, 6H) | 485.0 (M + 1) |
| 144 | 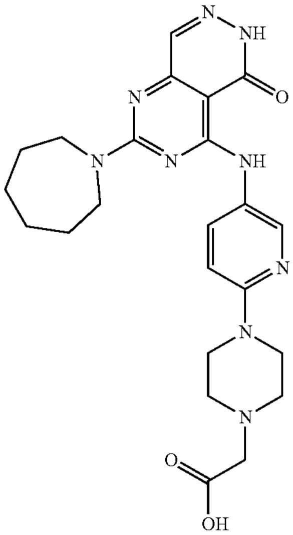 [SMILES: O=C(O)CN1CCN(c2ccc(Nc3nc(N4CCCCCC4)nc4cn[nH]c(=O)c34)cn2)CC1] | 12.71 (bs, 1H), 11.00 (bs, 1H), 8.46 (bs, 1H), 7.96-7.86 (m, 2H), 6.88 (bs, 1H), 3.78-3.70 (m, 4H), 3.49 (m, 4H), 3.19 (m, 4H), 2.66 (bs, 2H), 1.73-1.50 (m, 8H) | 480.0 |

TABLE 2-continued
| Ex # | Structure | Physical Data $^1$H-NMR in DMSO-$d_6$ at 400 Hz (δ) | MS m/z |
|---|---|---|---|
| 145 | 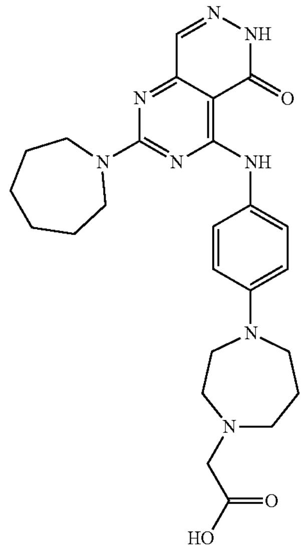 [SMILES: O=C(O)CN1CCCN(c2ccc(Nc3nc(N4CCCCCC4)nc4cn[nH]c(=O)c34)cc2)CC1] | 12.67 (s, 1H), 11.09 (s, 1H), 7.84 (s, 1H), 7.57 (d, J = 9.3 Hz, 2H), 6.73 (d, J = 8.8 Hz, 2H), 3.81-3.73 (m, 6H), 3.57-3.43 (m, 4H), 2.98 (t, J = 4.4 Hz, 2H), 2.82 (t, J = 5.2 Hz, 2H), 1.96-1.94 (m, 2H), 1.78-1.74 (m, 4H), 1.51 (m, 4H) | 493.3 |
| 146 | 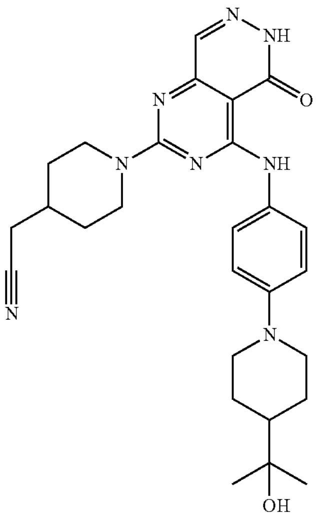 [SMILES: CC(C)(O)C1CCN(c2ccc(Nc3nc(N4CCC(CC#N)CC4)nc4cn[nH]c(=O)c34)cc2)CC1] | 12.75 (s, 1H), 11.13 (s, 1H), 7.84 (s, 1H), 7.54 (d, J = 8.8 Hz, 2H), 6.97 (d, J = 8.8 Hz, 2H), 4.12 (s, 1H), 4.65 (m, 2H), 3.76-3.74 (m, 2H), 3.01-2.95 (m, 2H), 2.55-2.53 (m, 4H), 1.97 (m, 1H), 1.84-1.77 (m, 4H), 1.35-1.21 (m, 4H), 1.06 (s, 6H) | 503.4 |

TABLE 2-continued
| Ex # | Structure | Physical Data ¹H-NMR in DMSO-$d_6$ at 400 Hz (δ) | MS m/z |
|---|---|---|---|
| 147 | 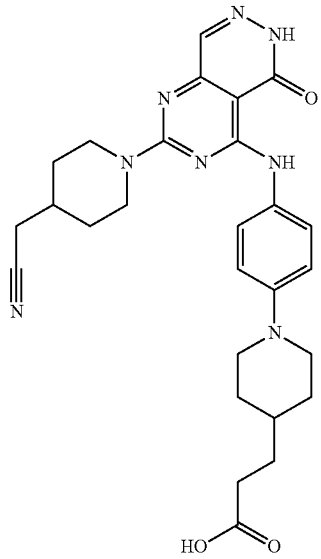 [SMILES: N#CCC1CCN(c2nc(Nc3ccc(N4CCC(CCC(=O)O)CC4)cc3)c3c(=O)[nH]ncc3n2)CC1] | 12.75 (s, 1H), 12.01 (s, 1H), 11.12 (s, 1H), 7.87 (s, 1H), 7.54 (d, J = 7.3 Hz, 2H), 6.97 (d, J = 7.4 Hz, 2H), 4.77 (m, 2H), 3.66 (m, 2H), 2.98 (m, 2H), 2.60 (m, 4H), 2.26 (m, 2H), 1.97 (m, 1H), 1.83-1.82 (m, 2H), 1.75-1.72 (m, 2H), 1.50-1.37 (m, 3H), 1.23 (m, 4H) | 517.3 |
| 148 | 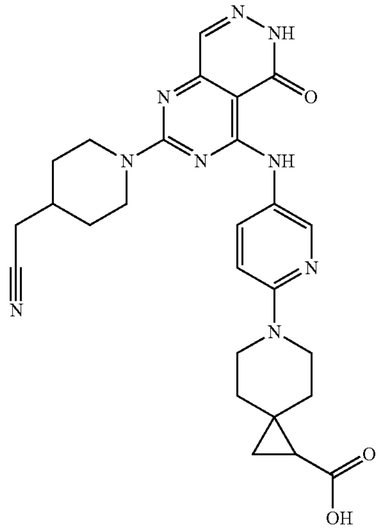 [SMILES: N#CCC1CCN(c2nc(Nc3ccc(N4CCC5(CC4)CC5C(=O)O)nc3)c3c(=O)[nH]ncc3n2)CC1] | 12.76 (s, 1H), 12.05 (s, 1H), 10.96 (s, 1H), 8.40 (s, 1H), 7.88 (s, 2H), 6.93 (s, 1H), 4.61-4.51 (m, 3H), 3.55-3.52 (m, 4H), 2.66-2.96 (m, 3H), 1.56-1.46 (m, 10H), 1.48-1.23 (m, 4H), 0.85-0.97 (m, 3H) | 516.3 |
| 149 | 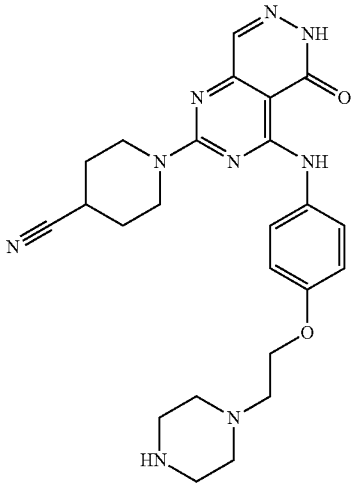 [SMILES: N#CC1CCN(c2nc(Nc3ccc(OCCN4CCNCC4)cc3)c3c(=O)[nH]ncc3n2)CC1] | 12.80 (bs, 1H), 11.15 (s, 1H), 7.90 (s, 1H), 7.60 (d, J = 8.8 Hz, 2H), 6.98 (d, J = 8.8 Hz, 2H), 4.13 (m, 2H), 4.08 (t, J = 5.7 Hz, 4H), 3.64-3.59 (m, 2H), 3.39-3.37 (m, 2H), 3.18 (t, J = 4.2 Hz, 2H), 2.79 (m, 4H), 2.68 (t, J = 5.9 Hz, 2H), 1.95 (q, J = 3.4 Hz, 2H), 1.76-1.73 (m, 2H) | 476.1 |

TABLE 2-continued
| Ex # | Structure | Physical Data $^{1}$H-NMR in DMSO-$d_6$ at 400 Hz (δ) | MS m/z |
|---|---|---|---|
| 150 | 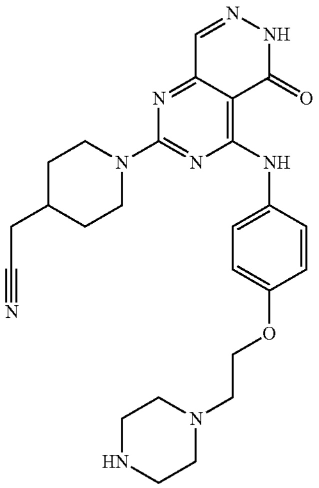 [SMILES: N#CCC1CCN(c2nc(Nc3ccc(OCCN4CCNCC4)cc3)c3c(=O)[nH]ncc3n2)CC1] | 12.80 (bs, 1H), 11.15 (s, 1H), 7.89 (s, 1H), 7.61 (d, J = 9.3 Hz, 2H), 6.99 (d, J = 9.3 Hz, 2H), 4.80-4.60 (m, 3H), 4.07 (t, J = 5.9 Hz, 2H), 3.01-2.95 (m, 3H), 2.72-2.53 (m, 6H), 2.41-2.32 (m, 4H), 1.98-1.81 (m, 4H), 1.24-1.21 (m, 2H) | 490.3 |
| 151 | 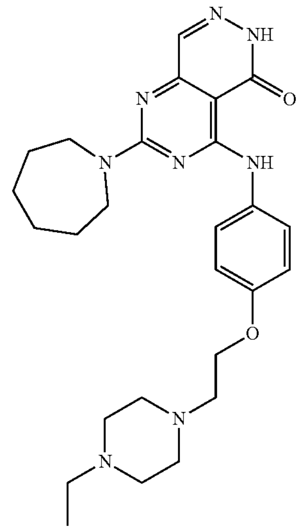 [SMILES: CCN1CCN(CCOc2ccc(Nc3nc(N4CCCCCC4)nc4cn[nH]c(=O)c34)cc2)CC1] | 12.72 (s, 1H), 11.18 (s, 1H), 7.87 (s, 1H), 7.67 (d, J = 9.3 Hz, 2H), 6.97 (d, J = 9.3 Hz, 2H), 4.07 (t, J = 5.7 Hz, 2H), 3.80 (t, J = 6.1 Hz, 2H), 3.74 (t, J = 5.9 Hz, 2H) | 493.4 |
| 152 | 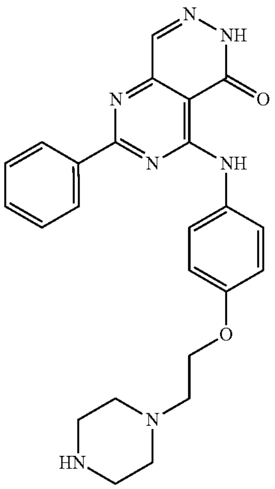 [SMILES: O=c1[nH]ncc2nc(-c3ccccc3)nc(Nc3ccc(OCCN4CCNCC4)cc3)c12] | 11.31 (s, 1H), 8.40 (d, J = 6.3 Hz, 2H), 8.30 (s, 1H), 7.78 (d, J = 8.8 Hz, 2H), 7.61-7.54 (m, 3H), 7.06 (d, J = 8.8 Hz, 2H), 4.11 (t, J = 5.9 Hz, 2H), 2.70-2.66 (m, 6H), 2.42 (m, 4H) | 444.2 |

TABLE 2-continued
| Ex # | Structure | Physical Data <br> $^1$H-NMR in DMSO-$d_6$ at 400 Hz (δ) | MS m/z |
|---|---|---|---|
| 153 | 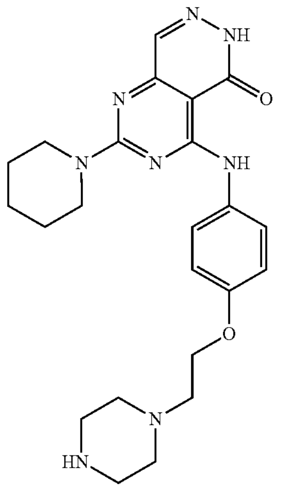 [SMILES: O=c1[nH]ncc2nc(N3CCCCC3)nc(Nc3ccc(OCCN4CCNCC4)cc3)c12] | 12.65 (bs, 1H), 11.1 (s, 1H), 7.87 (s, 1H), 7.60 (d, J = 9.3 Hz, 2H), 6.97 (d, J = 8.8 Hz, 2H), 4.07 (t, J = 5.7 Hz, 2H), 3.81 (m, 4H), 2.68 (m, 4H), 2.64 (t, J = 5.9 Hz, 2H), 2.39 (m, 4H), 1.65-1.64 (m, 2H), 1.55 (m, 4H) | 451.3 |
| 154 | 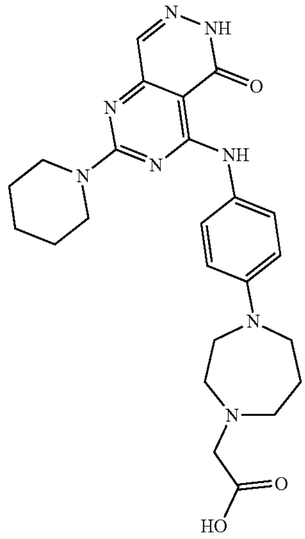 [SMILES: O=C(O)CN1CCCN(c2ccc(Nc3nc(N4CCCCC4)nc4cn[nH]c(=O)c34)cc2)CC1] | 12.69 (s, 1H), 11.06 (s, 1H), 7.84 (s, 1H), 7.51 (d, J = 9.2 Hz, 2H), 6.73 (d, J = 8.8 Hz, 2H), 3.81 (m, 4H), 3.64-3.54 (m, 4H), 3.45 (t, J = 6.1 Hz, 2H), 2.97 (t, J = 4.4 Hz, 2H), 2.81 (t, J = 5.2 Hz, 2H), 1.93 (t, J = 5.1 Hz, 2H), 1.65-1.64 (m, 2H), 1.54 (m, 4H) | 479.2 |
| 155 | 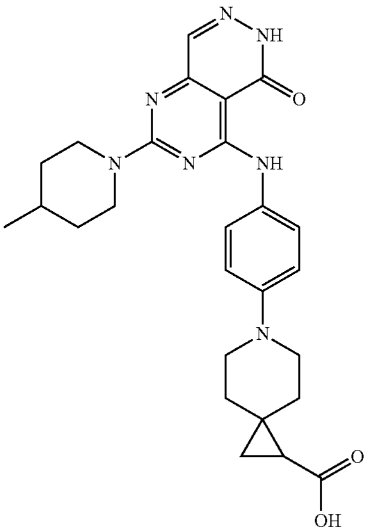 [SMILES: CC1CCN(c2nc(Nc3ccc(N4CCC5(CC4)CC5C(=O)O)cc3)c3c(=O)[nH]ncc3n2)CC1] | 12.79 (s, 1H), 11.30 (s, 1H), 7.90 (s, 1H), 7.72 (m, 2H), 7.38 (m, 2H), 4.74-4.65 (m, 2H), 3.17-2.98 (m, 4H), 1.99-1.91 (m, 3H), 1.74-1.62 (m, 8H), 1.23-1.01 (m, 4H), 0.93 (d, J = 5.9 Hz, 3H) | 490.3 |

TABLE 2-continued
| Ex # | Structure | Physical Data: $^1$H-NMR in DMSO-$d_6$ at 400 Hz (δ) | Physical Data: MS m/z |
|---|---|---|---|
| 156 | 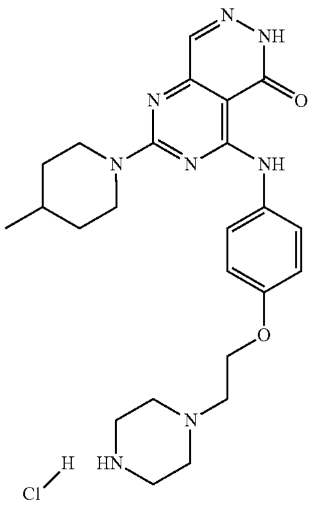 | 12.82 (s, 1H), 11.22 (s, 1H), 9.65 (s, 2H), 7.93 (s, 1H), 7.67 (d, J = 9.3 Hz, 2H), 7.07 (d, J = 8.8 Hz, 2H), 4.75-4.63 (m, 2H), 4.43 (d, J = 4.4 Hz, 2H), 3.83-3.50 (m, 8H), 2.97 (m, 2H), 1.73-1.70 (m, 4H), 1.11-1.07 (m, 3H), 0.93 (d, J = 6.4 Hz, 3H) | 465.3 |
| 157 | 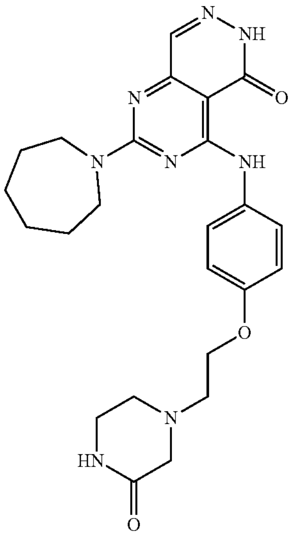 [SMILES: O=C1CN(CCOc2ccc(Nc3nc(N4CCCCCC4)nc4cn[nH]c(=O)c34)cc2)CCN1] | 12.72 (s, 1H), 11.18 (s, 1H), 7.87 (s, 1H), 7.67 (d, J = 7.8 Hz, 2H), 6.98 (d, J = 7.8 Hz, 2H), 4.12 (s, 2H), 3.80-3.74 (m, 4H), 3.17-3.07 (m, 4H), 2.78-2.69 (m, 4H), 1.76 (m, 4H), 1.51 (m, 4H) | 479.0 |

TABLE 2-continued
| Ex # | Structure | Physical Data $^1$H-NMR in DMSO-$d_6$ at 400 Hz (δ) | MS m/z |
|---|---|---|---|
| 158 | 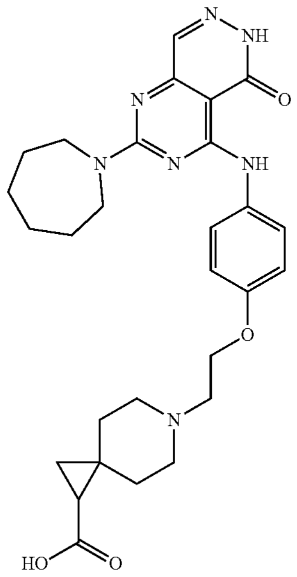 [SMILES: O=C(O)C1CC12CCN(CCOc1ccc(Nc3nc(N4CCCCCC4)nc4cn[nH]c(=O)c34)cc1)CC2] | 12.71 (s, 1H), 11.17 (s, 1H), 7.87 (s, 1H), 7.66 (d, J = 9.3 Hz, 2H), 6.97 (d, J = 8.8 Hz, 2H), 4.07 (t, J = 5.9 Hz, 2H), 3.80 (t, J = 6.1 Hz, 2H), 3.73 (t, J = 5.9 Hz, 2H), 2.69 (t, J = 5.9 Hz, 2H), 2.33-2.31 (m, 2H), 1.75-1.65 (m, 7H), 1.50-1.41 (m, 8H), 0.88-0.78 (m, 2H) | 534.0 |
| 159 | 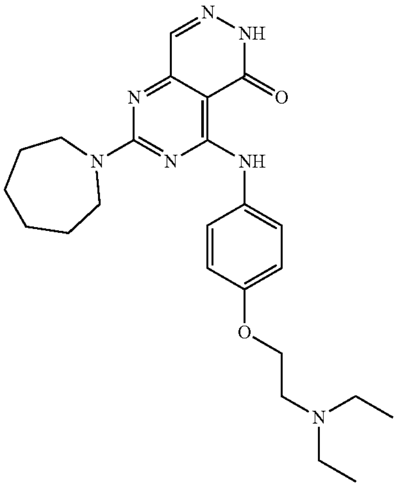 [SMILES: CCN(CC)CCOc1ccc(Nc2nc(N3CCCCCC3)nc3cn[nH]c(=O)c23)cc1] | 12.72 (s, 1H), 11.19 (s, 1H), 7.87 (s, 1H), 7.69 (d, J = 8.8 Hz, 2H), 6.98 (d, J = 8.8 Hz, 2H), 4.07 (m, 2H), 3.80 (t, J = 6.1 Hz, 2H), 3.74 (t, J = 5.8 Hz, 2H), 3.0-2.80 (m, 2H), 2.68-2.53 (m, 4H), 1.76 (m, 4H), 1.51 (m, 4H), 1.03 (m, 6H) | 452.4 |
| 160 | 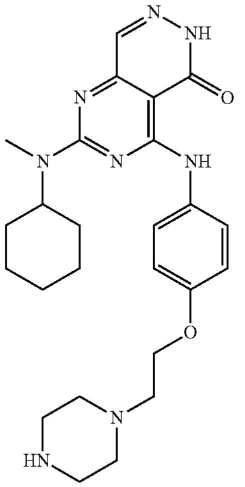 [SMILES: CN(c1nc(Nc2ccc(OCCN3CCNCC3)cc2)c2c(=O)[nH]ncc2n1)C1CCCCC1] | 12.67 (s, 1H), 11.18-11.11 (m, 1H), 7.87 (s, 1H), 7.65 (d, J = 8.8 Hz, 2H), 6.96 (d, J = 8.8 Hz, 2H), 4.08 (t, J = 5.9 Hz, 2H), 3.07-3.02 (m, 3H), 2.69-2.63 (m, 6H), 2.39 (m, 4H), 1.86-1.70 (m, 2H), 1.67-1.53 (m, 6H), 1.40-1.14 (m, 4H) | 479.0 |

TABLE 2-continued
| Ex # | Structure | Physical Data: $^1$H-NMR in DMSO-$d_6$ at 400 Hz (δ) | Physical Data: MS m/z |
|---|---|---|---|
| 161 | 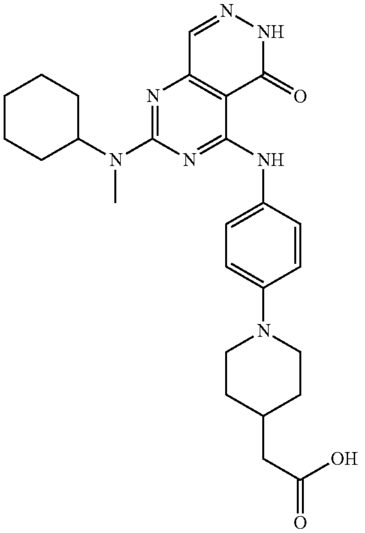 [SMILES: CN(c1nc(Nc2ccc(N3CCC(CC(=O)O)CC3)cc2)c2c(=O)[nH]ncc2n1)C1CCCCC1] | 12.71 (s, 1H), 12.10 (bs, 1H), 11.15-11.08 (m, 1H), 7.86 (s, 1H), 7.59 (d, J = 8.3 Hz, 2H), 6.95 (d, J = 8.4 Hz, 2H), 3.65-3.60 (m, 2H), 3.06-3.03 (m, 3H), 2.67-2.61 (m, 2H), 2.19 (d, J = 6.3 Hz, 2H), 1.82-1.52 (m, 10H), 1.50-1.14 (m, 6H) | 492.1 |
| 162 | 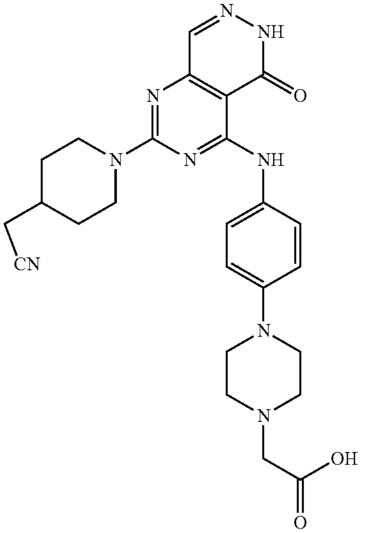 [SMILES: N#CCC1CCN(c2nc(Nc3ccc(N4CCN(CC(=O)O)CC4)cc3)c3c(=O)[nH]ncc3n2)CC1] | 12.76 (s, 1H), 11.14 (s, 1H), 7.88 (s, 1H), 7.57 (d, J = 8.9 Hz, 2H), 6.99 (d, J = 8.8 Hz, 2H), 4.95-4.60 (m, 2H), 3.20-3.15 (m, 6H), 3.02-2.99 (m, 2H), 2.72-2.67 (m, 4H), 2.55-2.53 (m, 4H), 2.1-1.95 (m, 1H), 1.84-1.81 (m, 2H), 1.24-1.21 (m, 2H) | 504.2 |
| 163 | 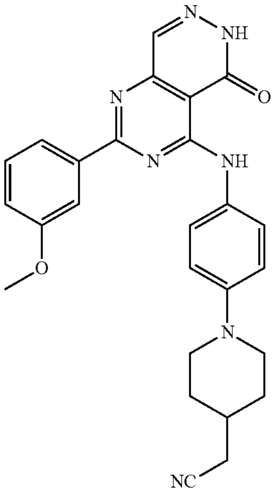 [SMILES: COc1cccc(-c2nc(Nc3ccc(N4CCC(CC#N)CC4)cc3)c3c(=O)[nH]ncc3n2)c1] | 13.31 (s, 1H), 11.26 (s, 1H), 8.29 (s, 1H), 8.00 (d, J = 7.8 Hz, 2H), 7.95 (d, J = 2.5 Hz, 1H), 7.72 (d, J = 8.8 Hz, 2H), 7.48 (t, J = 7.6 Hz, 1H), 7.17 (dd, $J_1$ = 2.4 Hz, $J_2$ = 7.8 Hz, 1H), 7.05 (d, J = 9.3 Hz, 2H), 3.86 (s, 3H), 3.76 (m, 2H), 2.74-2.56 (m, 4H), 1.83-1.80 (m, 3H), 1.42-1.38 (m, 2H) | 466 (M − 1) |

TABLE 2-continued
| Ex # | Structure | Physical Data $^1$H-NMR in DMSO-$d_6$ at 400 Hz (δ) | MS m/z |
|---|---|---|---|
| 164 | 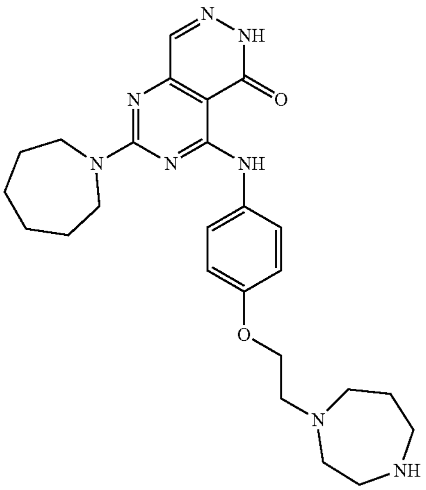 [SMILES: O=c1[nH]ncc2nc(N3CCCCCC3)nc(Nc3ccc(OCCN4CCCNCC4)cc3)c12] | 11.17 (s, 1H), 7.87 (s, 1H), 7.66 (d, J = 9.2 Hz, 2H), 6.96 (d, J = 8.8 Hz, 2H), 4.04 (t, J = 6.1 Hz, 2H), 3.80 (t, J = 6.1 Hz, 2H), 3.74 (t, J = 5.9 Hz, 2H), 2.86 (t, J = 6.2 Hz, 2H), 2.79-2.67 (m, 7H), 1.75 (m, 4H), 1.69-1.63 (m, 2H), 1.50 (m, 4H) | 491.4 |
| 165 | 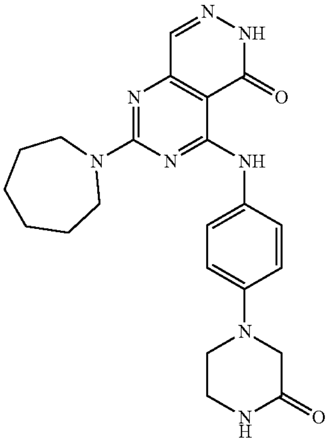 [SMILES: O=C1CN(c2ccc(Nc3nc(N4CCCCCC4)nc4cn[nH]c(=O)c34)cc2)CCN1] | 12.70 (s, 1H), 11.17 (s, 1H), 8.03 (s, 1H), 7.86 (s, 1H), 7.65 (d, J = 9.3 Hz, 2H), 6.97 (d, J = 9.2 Hz, 2H), 3.80 (t, J = 5.9 Hz, 2H), 3.75 (t, J = 5.9 Hz, 2H), 3.70 (s, 2H), 3.40-3.38 (m, 2H), 3.30-3.29 (m, 2H), 1.79-1.75 (m, 4H), 1.15 (m, 4H) | 435.3 |
| 166 | 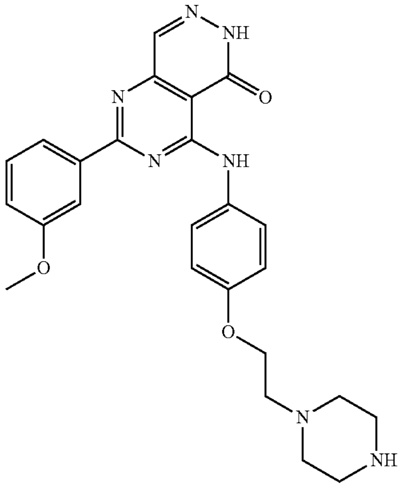 [SMILES: COc1cccc(-c2nc(Nc3ccc(OCCN4CCNCC4)cc3)c3c(=O)[nH]ncc3n2)c1] | 11.27 (s, 1H), 8.03 (s, 1H), 8.01 (d, J = 7.3 Hz, 1H), 7.94 (s, 1H), 7.78 (d, J = 8.8 Hz, 2H), 7.47 (t, J = 7.6 Hz, 2H), 7.16 (d, J = 7.3 Hz, 2H), 7.06 (d, J = 8.30 Hz, 2H), 4.11 (m, 2H), 3.86 (s, 3H), 2.71-2.67 (m, 6H), 2.42 (m, 4H) | 474.2 |

TABLE 2-continued
| Ex # | Structure | Physical Data: $^1$H-NMR in DMSO-$d_6$ at 400 Hz (δ) | Physical Data: MS m/z |
|---|---|---|---|
| 167 | 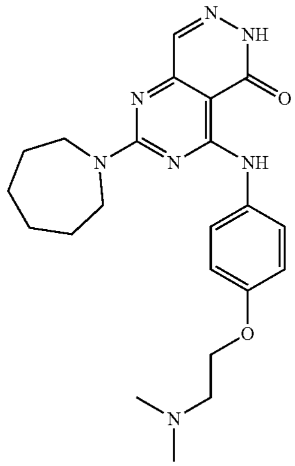 [SMILES: CN(C)CCOc1ccc(Nc2nc(N3CCCCCC3)nc3cn[nH]c(=O)c23)cc1] | 12.71 (s, 1H), 11.18 (s, 1H), 7.87 (s, 1H), 7.67 (d, J = 8.8 Hz, 2H), 6.97 (d, J = 8.8 Hz, 2H), 4.05 (t, J = 5.6 Hz, 2H), 3.80 (t, J = 6.2 Hz, 2H), 3.74 (t, J = 5.9 Hz, 2H), 2.65 (t, 5.6 Hz, 2H), 2.24 (s, 6H), 1.76 (m, 4H), 1.51 (m, 4H) | 424.1 |
| 168 | 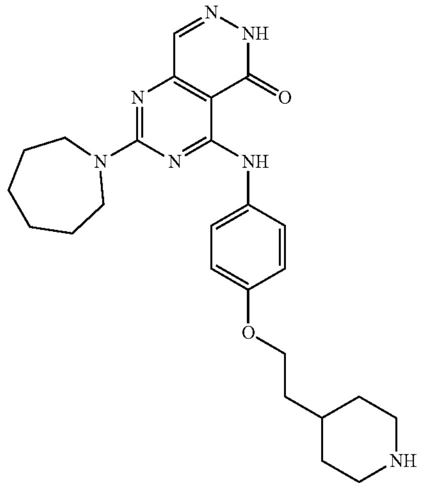 [SMILES: O=c1[nH]ncc2nc(N3CCCCCC3)nc(Nc3ccc(OCCC4CCNCC4)cc3)c12] | 11.17 (s, 1H), 7.87 (s, 1H), 7.66 (d, J = 8.8 Hz, 2H), 6.95 (d, J = 8.8 Hz, 2H), 4.00 (t, J = 6.6 Hz, 2H), 3.80 (t, J = 6.2 Hz, 2H), 3.74 (t, J = 5.9 Hz, 2H), 2.91-2.89 (m, 2H), 2.43 (m, 2H), 1.76 (m, 4H), 1.65-1.60 (m, 4H), 1.51 (m, 4H), 1.09-1.01 (m, 2H) | 464.1 |
| 169 | 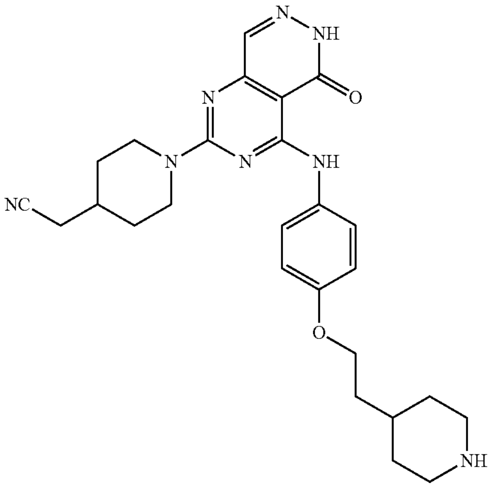 [SMILES: N#CCC1CCN(c2nc(Nc3ccc(OCCC4CCNCC4)cc3)c3c(=O)[nH]ncc3n2)CC1] | 11.15 (s, 1H), 7.94 (s, 1H), 7.75 (d, J = 9.0 Hz, 2H), 6.97 (d, J = 8.8 Hz, 2H), 4.79-4.68 (m, 4H), 4.00 (t, J = 6.4 Hz, 2H), 3.02-2.90 (m, 4H), 2.45-2.42 (m, 2H), 1.97 (m, 1H), 1.84-1.81 (m, 2H), 1.64-1.54 (m, 4H), 1.34-1.23 (m, 2H), 1.12-1.06 (m, 2H) | 489.1 |

TABLE 2-continued
| Ex # | Structure | Physical Data $^1H$-NMR in DMSO-$d_6$ at 400 Hz (δ) | MS m/z |
|---|---|---|---|
| 170 | 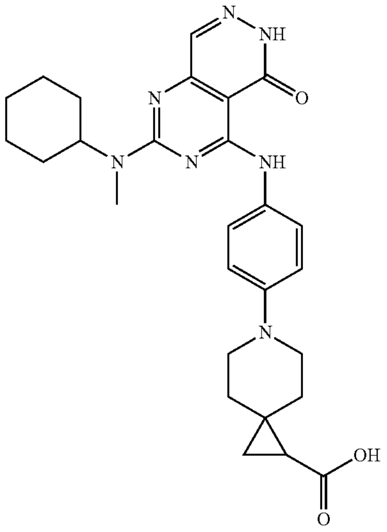 [SMILES: CN(c1nc(Nc2ccc(N3CCC4(CC3)CC4C(=O)O)cc2)c2c(=O)[nH]ncc2n1)C1CCCCC1] | 12.70 (bs, 1H), 11.15-11.09 (m, 1H), 7.86 (s, 1H), 7.60 (d, J = 8.3 Hz, 2H), 6.97 (d, J = 8.8 Hz, 2H), 4.80-4.49 (m, 2H), 3.22-3.03 (m, 4H), 1.83-1.52 (m, 13H), 1.40-1.34 (m, 2H), 1.31-1.14 (m, 2H), 0.96-0.91 (m, 2H) | 502.3 |
| 171 | 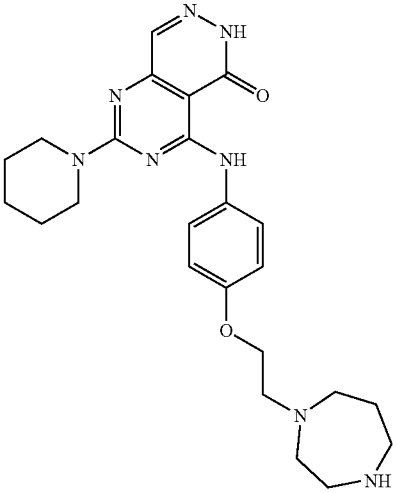 [SMILES: O=c1[nH]ncc2nc(N3CCCCC3)nc(Nc3ccc(OCCN4CCCNCC4)cc3)c12] | 11.14 (s, 1H), 7.86 (s, 1H), 7.60 (d, J = 9.3 Hz, 2H), 6.97 (d, J = 8.8 Hz, 2H), 4.04 (t, J = 6.1 Hz, 2H), 3.81 (m, 4H), 2.86 (t, J = 6.2 Hz, 2H), 2.79-2.67 (m, 6H), 1.67-1.63 (m, 4H), 1.54 (m, 4H) | 477.2 |
| 172 | 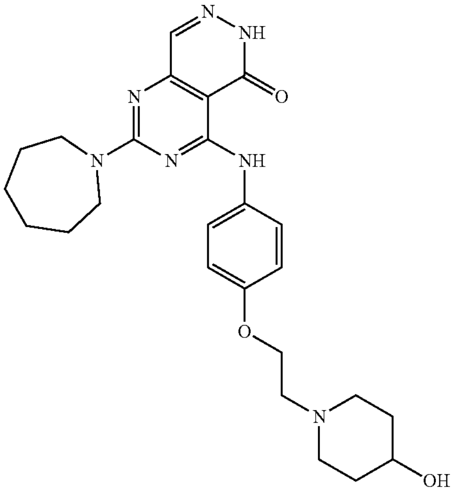 [SMILES: O=c1[nH]ncc2nc(N3CCCCCC3)nc(Nc3ccc(OCCN4CCC(O)CC4)cc3)c12] | 12.71 (bs, 1H), 11.18 (s, 1H), 7.87 (s, 1H), 7.67 (d, J = 8.8 Hz, 2H), 6.97 (d, J= 8.8 Hz, 2H), 4.56 (bs, 1H), 4.07 (m, 2H), 3.80 (t, J = 5.7 Hz, 2H), 3.74 (t, J = 5.9 Hz, 2H), 3.46 (m, 1H) 2.8-2.67 (m, 4H), 1.75-1.74 (m, 6H), 2.33-2.16 (m, 2H), 1.51-1.40 (m, 4H), 1.30-1.17 (m, 2H) | 480.1 |

TABLE 2-continued
| Ex # | Structure | Physical Data $^1$H-NMR in DMSO-$d_6$ at 400 Hz (δ) | MS m/z |
|---|---|---|---|
| 173 | 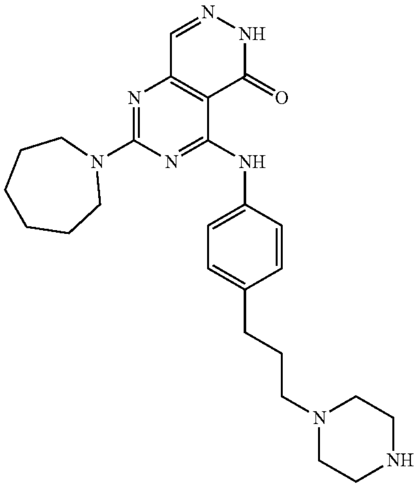 [SMILES: O=c1[nH]ncc2nc(N3CCCCCC3)nc(Nc3ccc(CCCN4CCNCC4)cc3)c12] | 12.65 (bs, 1H), 11.29 (s, 1H), 7.88 (s, 1H), 7.67 (d, J = 8.3 Hz, 2H), 7.21 (d, J = 8.3 Hz, 2H), 3.80 (t, J = 5.7 Hz, 2H), 3.74 (t, J = 5.9 Hz, 2H), 2.68 (m, 4H) 2.56-2.54 (m, 2H), 2.25-2.20 (m, 6H), 1.74-1.67 (m, 6H), 1.51 (m, 4H) | 463.4 |
| 174 | 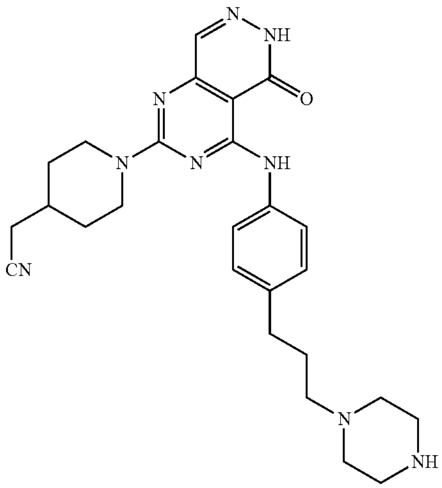 [SMILES: N#CCC1CCN(c2nc(Nc3ccc(CCCN4CCNCC4)cc3)c3c(=O)[nH]ncc3n2)CC1] | 12.70 (bs, 1H), 11.27 (s, 1H), 7.90 (s, 1H), 7.61 (d, J = 8.3 Hz, 2H), 7.24 (d, J = 8.3 Hz, 2H), 4.78-4.71 (m, 2H), 3.00 (m, 2H), 2.68 (m, 4H), 2.59-2.54 (m, 4H), 2.25-2.21 (m, 6H), 1.98 (m, 2H), 1.85-1.82 (m, 2H), 1.75-1.68 (m, 2H), 1.23-1.22 (m, 2H) | 488.2 |
| 175 | 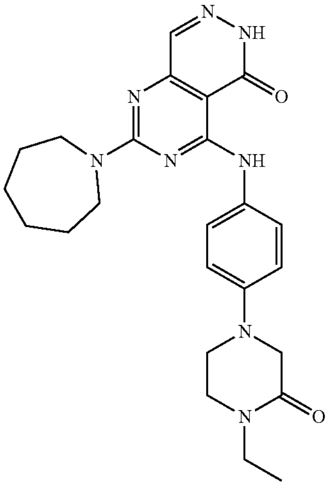 [SMILES: CCN1CCN(c2ccc(Nc3nc(N4CCCCCC4)nc4cn[nH]c(=O)c34)cc2)CC1=O] | 12.70 (bs, 1H), 11.17 (s, 1H), 7.86 (s, 1H), 7.65 (d, J = 8.8 Hz, 2H), 6.98 (d, J = 8.3 Hz, 2H), 3.80 (t, J = 6.2 Hz, 2H), 3.77-3.74 (m, 4H), 3.46-3.41 (m, 4H), 3.39-3.35 (m, 2H), 1.79-1.75 (m, 4H), 1.51 (m, 4H), 1.07 (t, J = 7.1 Hz, 3H) | 463.2 |

TABLE 2-continued
| Ex # | Structure | Physical Data $^1$H-NMR in DMSO-$d_6$ at 400 Hz (δ) | MS m/z |
|---|---|---|---|
| 176 | 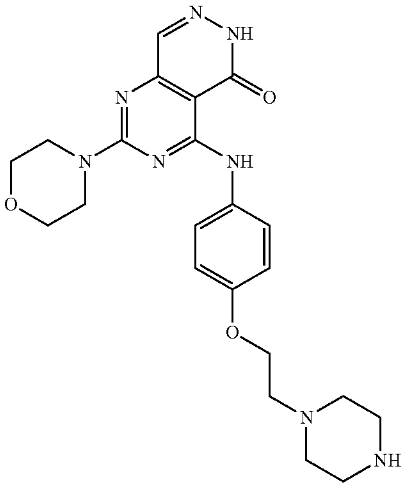 [SMILES: O=c1[nH]ncc2nc(N3CCOCC3)nc(Nc3ccc(OCCN4CCNCC4)cc3)c12] | 12.82 (s, 1H), 11.18 (s, 1H), 7.90 (s, 1H), 7.61 (d, J = 8.8 Hz, 2H), 6.98 (d, J = 8.8 Hz, 2H), 4.07 (t, J = 5.9 Hz, 2H), 3.80 (m, 4H), 3.68-3.67 (m, 4H), 2.72 (t, J = 4.7 Hz, 4H), 2.68-2.66 (m, 2H), 2.42-2.32 (m, 4H) | 453.2 |
| 177 | 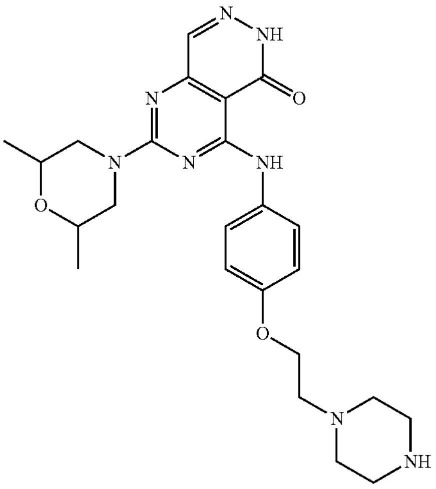 [SMILES: CC1CN(c2nc(Nc3ccc(OCCN4CCNCC4)cc3)c3c(=O)[nH]ncc3n2)CC(C)O1] | 12.82 (s, 1H), 11.50 (bs, 1H), 7.92 (s, 1H), 7.60 (d, J = 8.8 Hz, H), 6.99 (d, J = 9.3 Hz, 2H), 4.55 (m, 2H), 4.07 (t, J = 5.9 Hz, 2H), 3.57-3.55 (m, 2H), 3.27-3.20 (m, 2H), 2.69-2.66 (m, 4H), 2.39-2.30 (m, 6H), 1.16 (d, J = 5.8 Hz, 6H) | 481.0 |
| 178 | 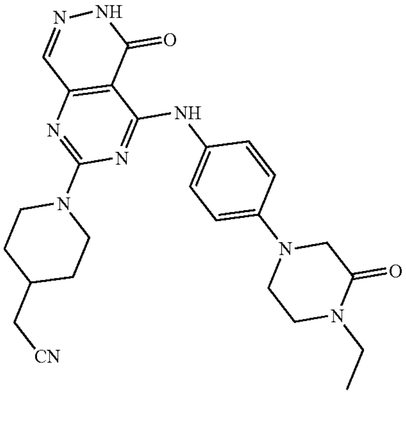 [SMILES: CCN1CCN(c2ccc(Nc3nc(N4CCC(CC#N)CC4)nc4cn[nH]c(=O)c34)cc2)CC1=O] | 12.76 (s, 1H), 11.15 (s, 1H), 7.88 (s, 1H), 7.59 (d, J = 8.8 Hz, 2H), 7.00 (d, J = 9.3 Hz, 2H), 4.78-4.71 (m, 2H), 3.75 (s, 2H), 3.48-3.43 (m, 4H), 3.38 (q, J = 7.1 Hz, 2H), 3.02-2.96 (m, 2H), 2.55-2.54 (m, 2H), 2.55-2.54 (m, 2H), 1.98-1.97 (m, 1H), 1.84-1.81 (m, 2H), 1.23-1.21 (m, 4H), 1.07 (t, J = 7.1 Hz, 3H); MS m/z | 488.3 |

TABLE 2-continued
| Ex # | Structure | Physical Data <br> $^{1}$H-NMR in DMSO-$d_6$ at 400 Hz (δ) | MS m/z |
|---|---|---|---|
| 179 | 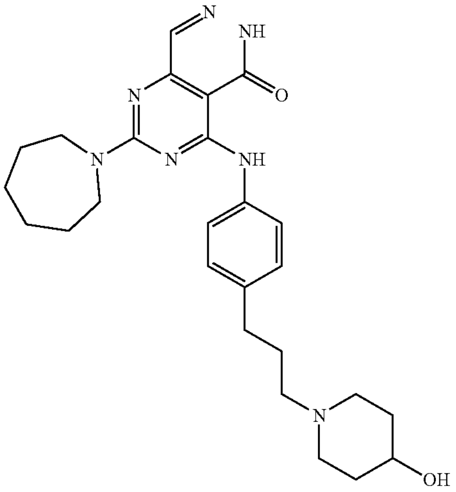 [SMILES: N=Cc1nc(N2CCCCCC2)nc(Nc2ccc(CCCN3CCC(O)CC3)cc2)c1C(N)=O] | 12.73 (s, 1H), 11.29 (s, 1H), 7.88 (s, 1H), 7.67 (d, J = 8.4 Hz, 2H), 7.21 (d, J = 8.4 Hz, 2H), 4.51 (d, J = 3.9 Hz, 1H), 3.81 (t, J = 6.1 Hz, 2H), 3.75 (t, J = 5.9 Hz, 2H), 3.4 (m, 1H), 2.67 (m, 2H), 2.56 (t, J = 7.6 Hz, 2H), 2.23 (t, J = 6.9 Hz, 2H), 1.97-1.92 (m, 2H), 1.76-1.68 (m, 8H), 1.51 (m, 4H), 1.38-1.21 (m, 2H) | 478.3 |
| 180 | 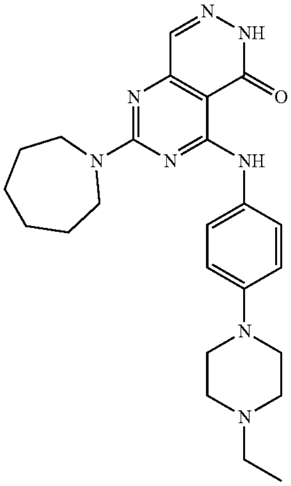 [SMILES: CCN1CCN(c2ccc(Nc3nc(N4CCCCCC4)nc4cn[nH]c(=O)c34)cc2)CC1] | 12.7 (s, 1H), 11.16 (s, 1H), 7.86 (s, 1H), 7.63 (d, J = 8.8 Hz, 2H), 6.96 (d, J = 9.3 Hz, 2H), 3.51 (t, J = 6.2 Hz, 2H), 3.75 (t, J = 5.9 Hz, 2H), 3.27-3.14 (m, 4H), 2.45 (m, 6H), 1.77-1.75 (m, 4H), 1.51 (m, 4H), 1.05 (t, J = 7.1 Hz, 3H) | 449.1 |
| 181 | 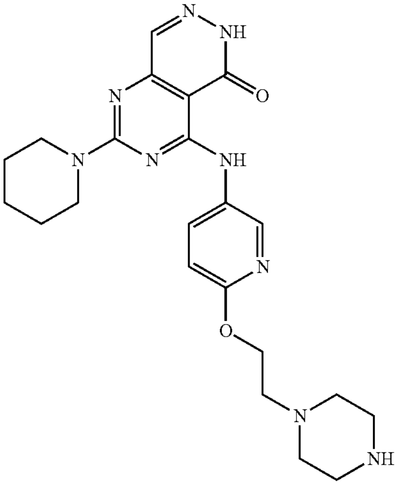 [SMILES: O=c1[nH]ncc2nc(N3CCCCC3)nc(Nc3ccc(OCCN4CCNCC4)nc3)c12] | 12.70 (bs, 1H), 11.03 (s, 1H), 8.47 (d, J = 1.4 Hz, 1H), 7.98 (dd, $J_1$ = 2.2 Hz, $J_2$ = 8.6 Hz, 1H), 7.88 (s, 1H), 6.86 (d, J = 8.8 Hz, 1H), 4.34 (t, J = 5.9 Hz, 2H), 3.79 (m, 4H), 2.67-2.62 (m, 7H), 2.38-2.33 (m, 4H), 1.63 (m, 2H), 1.54 (m, 4H) | 452.1 |

TABLE 2-continued
| Ex # | Structure | Physical Data $^1$H-NMR in DMSO-$d_6$ at 400 Hz (δ) | MS m/z |
|---|---|---|---|
| 182 | 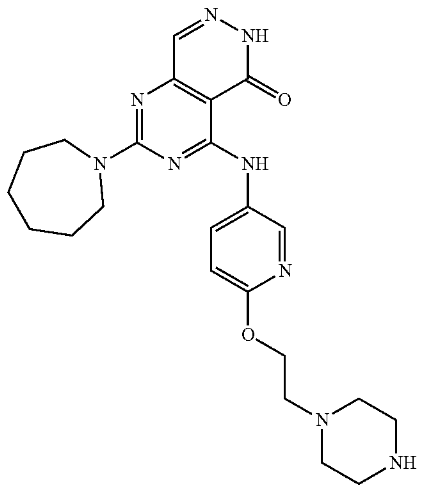 [SMILES: O=c1[nH]ncc2nc(N3CCCCCC3)nc(Nc3ccc(OCCN4CCNCC4)nc3)c12] | 12.70 (bs, 1H), 11.06 (s, 1H), 8.49 (d, J = 2.5 Hz, 1H), 8.05 (dd, $J_1$ = 2.8 Hz, $J_2$ = 9.1 Hz, 1H), 7.88 (s, 1H), 6.85 (d, J = 9.3 Hz, 1H), 4.34 (t, J = 6.2 Hz, 2H), 3.79 (t, J = 6.1 Hz, 2H), 3.69 (t, J = 5.9 Hz, 2H), 2.68-2.67 (m, 4H), 2.63 (t, J = 5.9 Hz, 2H), 2.38 (m, 4H), 1.72 (m, 4H), 1.50 (m, 4H) | 466.4 |
| 183 | 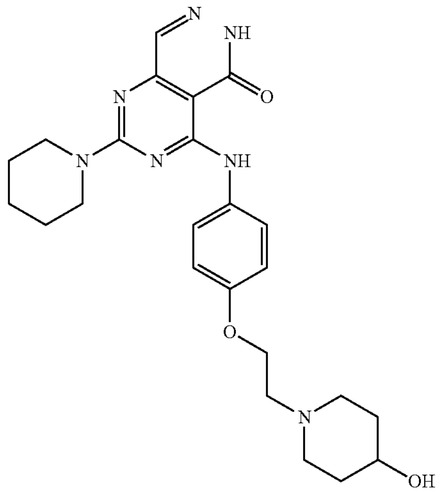 [SMILES: N=Cc1nc(N2CCCCC2)nc(Nc2ccc(OCCN3CCC(O)CC3)cc2)c1C(N)=O] | 12.73 (s, 1H), 11.14 (s, 1H), 7.87 (s, 1H), 7.61 (d, J = 8.8 Hz, 2H), 6.98 (d, J = 8.8 Hz, 2H), 4.57 (bs, 1H), 4.08 (m, 2H), 3.81 (m, 4H), 3.46 (m, 1H), 2.82-2.53 (m, 4H), 2.33-2.18 (m, 2H), 1.73-1.37 (m, 10H) | 466.4 |
| 184 | 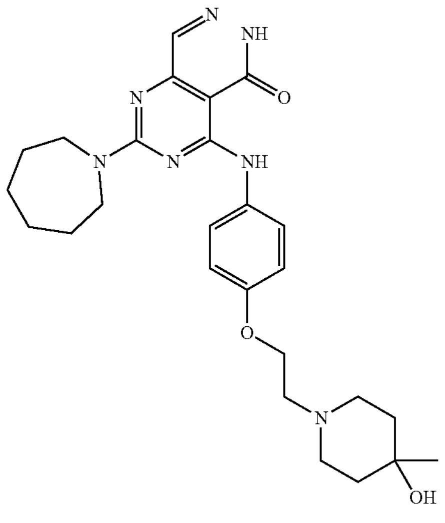 [SMILES: CC1(O)CCN(CCOc2ccc(Nc3nc(N4CCCCCC4)nc(C=N)c3C(N)=O)cc2)CC1] | 12.72 (s, 1H), 11.19 (s, 1H), 7.87 (s, 1H), 7.68 (d, J = 8.8 Hz, 2H), 6.99 (d, J = 8.8 Hz, 2H), 4.14-4.07 (m, 3H), 3.80 (t, J = 6.1 Hz, 2H), 3.74 (t, J = 5.9 Hz, 2H), 3.18-3.16 (m, 6H), 1.91 (m, 4H), 1.76 (m, 8H), 1.13 (s, 3H) | 494.4 |

TABLE 2-continued
| Ex # | Structure | Physical Data: $^1$H-NMR in DMSO-$d_6$ at 400 Hz (δ) | MS m/z |
|---|---|---|---|
| 185 | 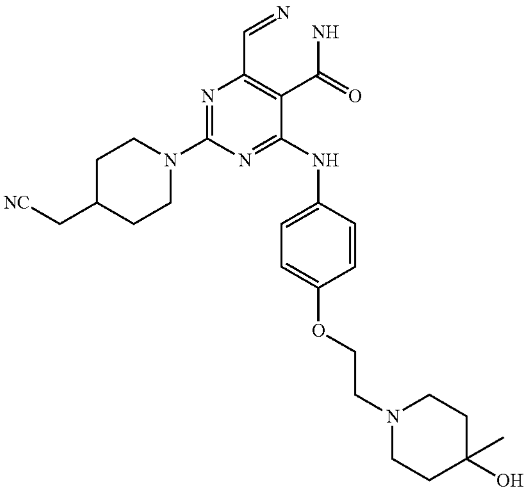 [SMILES: CC1(O)CCN(CCOc2ccc(Nc3nc(N4CCC(CC#N)CC4)nc(C=N)c3C(N)=O)cc2)CC1] | 12.77 (s, 1H), 11.16 (s, 1H), 7.87 (s, 1H), 7.61 (d, J = 8.8 Hz, 2H), 6.99 (d, J = 8.8 Hz, 2H), 4.80-4.68 (m, 3H), 4.10 (m, 3H), 3.02-2.95 (m, 2H), 2.70-2.53 (m, 6H), 1.98-1.95 (m, 1H), 1.84-1.81 (m, 2H), 1.49 (m, 4H), 1.26-1.21 (m, 4H), 1.11 (s, 3H) | 519.3 |
| 186 | 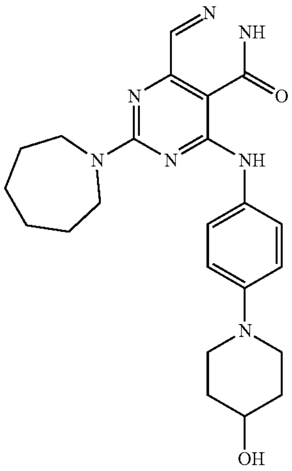 | 12.69 (s, 1H), 11.14 (s, 1H), 7.86 (s, 1H), 7.60 (d, J = 9.3 Hz, 2H), 6.95 (d, J = 8.8 Hz, 2H), 4.66 (d, J = 3.9 Hz, 1H), 3.80 (t, J = 6.2 Hz, 2H), 3.75 (d, J = 5.9 Hz, 2H), 3.62-3.60 (m, 1H), 3.52-3.49 (m, 2H), 2.84-2.79 (m, 2H), 1.82-1.76 (m, 6H), 1.48-1.46 (m, 6H) | 436.2 |
| 187 | 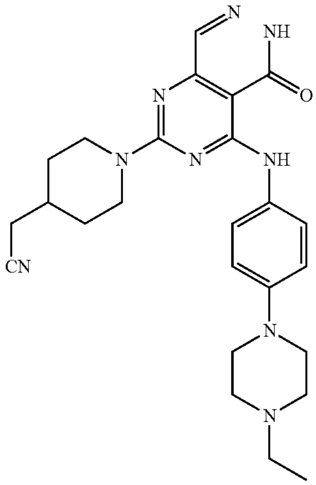 [SMILES: CCN1CCN(c2ccc(Nc3nc(N4CCC(CC#N)CC4)nc(C=N)c3C(N)=O)cc2)CC1] | 12.75 (s, 1H), 11.14 (s, 1H), 7.88 (s, 1H), 7.57 (d, J = 7.4 Hz, 2H), 6.98 (d, J = 9.3 Hz, 2H), 4.80-4.60 (m, 2H), 3.15 (m, 4H), 3.02-2.96 (m, 2H), 2.57-2.53 (m, 6H), 2.45-2.44 (m, 2H), 1.91 (m, 1H), 1.83 (m, 2H), 1.24 (m, 2H), 1.06 (t, J = 7.4 Hz, 3H) | 474.3 |

TABLE 2-continued
| Ex # | Structure | Physical Data: $^1$H-NMR in DMSO-$d_6$ at 400 Hz (δ) | MS m/z |
|---|---|---|---|
| 188 | 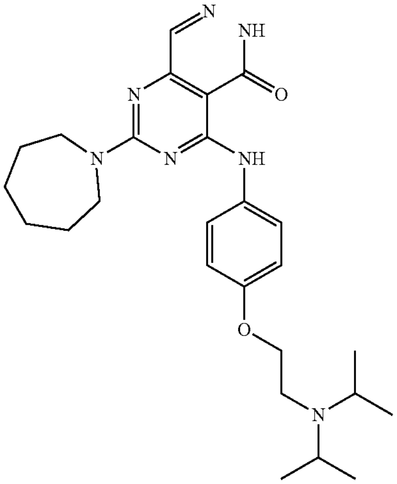 [SMILES: CC(C)N(CCOc1ccc(Nc2nc(N3CCCCCC3)nc(C=N)c2C(N)=O)cc1)C(C)C] | 12.72 (s, 1H), 11.18 (s, 1H), 7.87 (s, 1H), 7.67 (d, J = 9.3 Hz, 2H), 6.95 (d, J = 8.8 Hz, 2H), 3.92 (m, 2H), 3.80 (d, J = 6.1 Hz, 2H), 3.74 (d, J = 6.0 Hz, 2H), 3.05 (m, 2H), 2.87-2.76 (m, 2H), 1.76 (m, 4H), 1.51 (, 4H), 1.02 (m, 12H) | 480.3 |
| 189 | 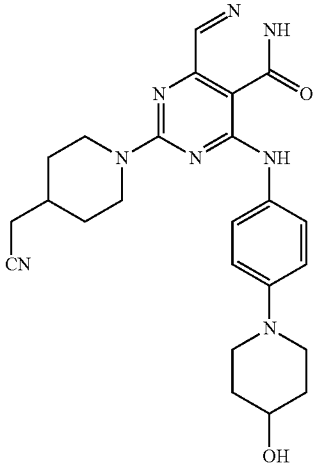 [SMILES: N#CCC1CCN(c2nc(C=N)c(C(N)=O)c(Nc3ccc(N4CCC(O)CC4)cc3)n2)CC1] | 12.75 (s, 1H), 11.12 (s, 1H), 7.87 (s, 1H), 7.53 (d, J = 9.3 Hz, 2H), 6.97 (d, J = 9.3 Hz, 2H), 4.76-4.71 (m, 2H), 6.66 (d, J = 4.4 Hz, 1H), 3.64-3.59 (m, 1H), 3.53-3.50 (m, 2H), 3.02-2.95 (m, 2H), 2.86-2.80 (m, 2H), 1.97-1.91 (m, 1H), 1.84-1.80 (m, 4H), 1.49-1.46 (m, 2H), 1.27-1.21 (m, 4H) | 461.1 |
| 190 | 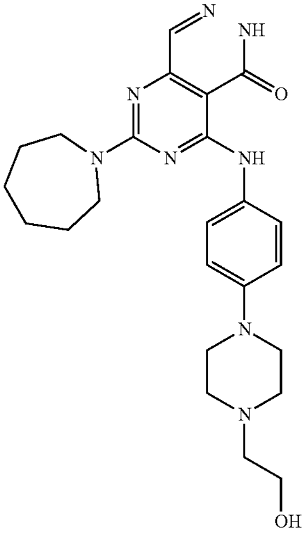 | 12.70 (s, 1H), 11.16 (s, 1H), 7.86 (s, 1H), 7.62 (d, J = 8.8 Hz, 2H), 6.95 (d, J = 9.3 Hz, 2H), 4.44 (m, 1H), 3.80 (t, J = 6.2 Hz, 2H), 3.65 (t, J = 5.9 Hz, 2H), 3.54 (m, 2H), 3.12 (t, J = 4.9 Hz, 4H), 2.57 (t, J = 4.9 Hz, 4H), 2.45 (t, J = 6.1 Hz, 2H), 1.91-1.75 (m, 4H), 1.51 (m, 4H); MS m/z | 465.3 |

TABLE 2-continued
| Ex # | Structure | Physical Data <br> $^1$H-NMR in DMSO-$d_6$ at 400 Hz (δ) | MS m/z |
|---|---|---|---|
| 191 | 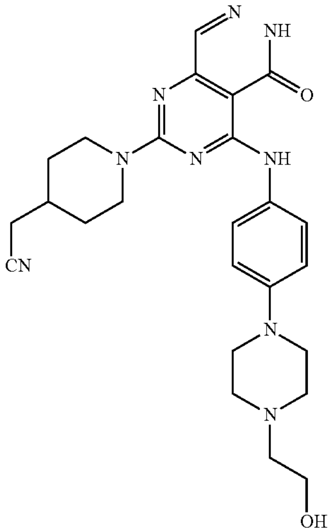 [SMILES: N#CCC1CCN(c2nc(C=N)c(C(N)=O)c(Nc3ccc(N4CCN(CCO)CC4)cc3)n2)CC1] | 12.75 (s, 1H), 11.14 (s, 1H), 7.87 (s, 1H), 7.56 (d, J = 8.8 Hz, 2H), 6.97 (d, J = 9.3 Hz, 2H), 4.77 (m, 2H), 4.44 (m, 1H), 3.56-3.52 (m, 2H), 3.13-3.11 (m, 4H), 3.02-2.95 (m, 2H), 2.56-2.52 (m, 4H), 2.46-2.45 (m, 2H), 2.01-1.95 (m, 1H), 1.84-1.81 (m, 2H), 1.23-1.21 (m, 4H); MS m/z | 490.1 |
| 192 | 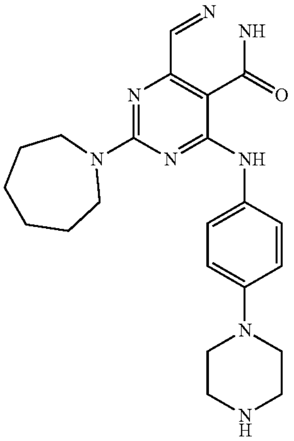 | 12.70 (s, 1H), 11.15 (s, 1H), 7.86 (s, 1H), 7.62 (d, J = 8.8 Hz, 2H), 6.94 (d, J = 9.3 Hz, 2H), 3.80 (t, J = 6.2 Hz, 2H), 3.75 (t, J = 5.9 Hz, 2H), 3.05-3.03 (m, 4H), 2.85 (t, J = 4.4 Hz, 4H), 1.76 (m, 4H), 1.51 (m, 4H); MS m/z | 421.1 |
| 193 | 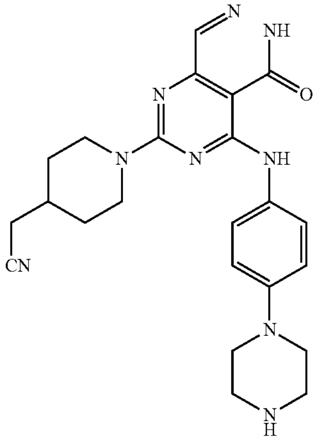 | 12.73 (s, 1H), 11.13 (s, 1H), 7.87 (s, 1H), 7.55 (d, J = 8.8 Hz, 2H), 6.96 (d, J = 8.8 Hz, 2H), 4.77-4.71 (m, 2H), 3.04 (m, 4H), 2.83 (m, 4H), 2.55-2.53 (m, 4H), 1.97-1.94 (m, 1H), 1.84-1.81 (m, 2H), 1.23-1.21 (m, 2H) | 446.1 |

TABLE 2-continued
| Ex # | Structure | Physical Data $^1$H-NMR in DMSO-$d_6$ at 400 Hz (δ) | MS m/z |
|---|---|---|---|
| 194 | 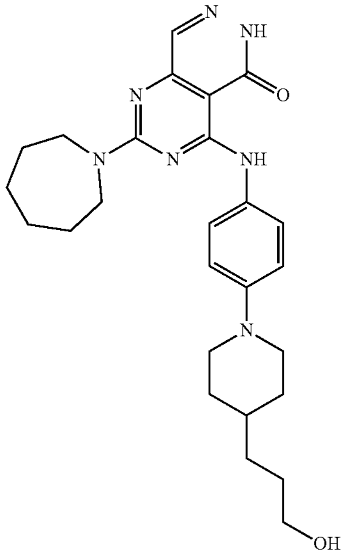 [SMILES: N=Cc1nc(N2CCCCCC2)nc(Nc2ccc(N3CCC(CCCO)CC3)cc2)c1C(N)=O] | 12.69 (s, 1H), 11.14 (s, 1H), 7.86 (s, 1H), 7.60 (d, J = 8.8 Hz, 2H), 6.94 (d, J = 9.3 Hz, 2H), 4.36 (t, J = 5.1 Hz, 1H), 3.80 (t, J = 6.1 Hz, 2H), 3.75 (t, J = 5.9 Hz, 2H), 3.66-3.63 (m, 2H), 3.39 (q, J = 5.1 Hz, 2H), 2.63-2.57 (m, 2H), 1.75-1.73 (m, 6H), 1.51-1.42 (m, 6H), 1.35-1.30 (m, 1H), 1.28-1.19 (m, 4H) | 478.2 |
| 195 | 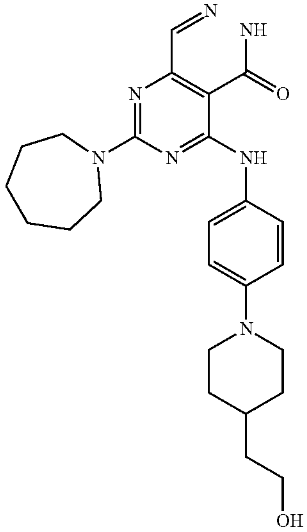 | 12.69 (s, 1H), 11.15 (s, 1H), 7.86 (s, 1H), 7.60 (d, J = 8.8 Hz, 2H), 6.95 (d, J = 9.3 Hz, 2H), 4.36 (t, J = 5.2 Hz, 1H), 3.80 (t, J = 6.2 Hz, 2H), 3.75 (t, J = 5.9 Hz, 2H), 3.66-3.63 (m, 2H), 3.47 (q, J = 5.9 Hz, 2H), 2.63-2.57 (m, 2H), 1.75-1.73 (m, 6H), 1.51 (m, 5H), 1.40 (q, J = 6.9 Hz, 2H), 1.26-1.22 (m, 2H) | 464.2 |

TABLE 2-continued
| Ex # | Structure | Physical Data: $^1$H-NMR in DMSO-$d_6$ at 400 Hz (δ) | MS m/z |
|---|---|---|---|
| 196 | 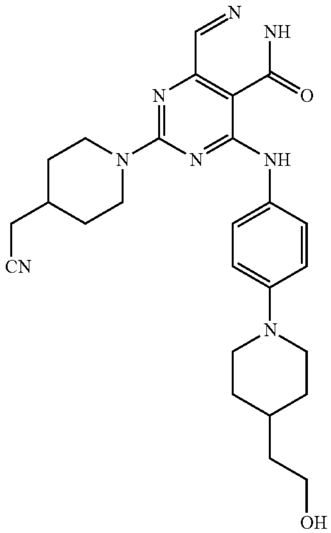 [SMILES: N#CCC1CCN(c2nc(C=N)c(C(N)=O)c(Nc3ccc(N4CCC(CCO)CC4)cc3)n2)CC1] | 12.75 (s, 1H), 11.12 (s, 1H), 7.87 (s, 1H), 7.54 (d, J = 9.3 Hz, 2H), 6.97 (d, J = 9.3 Hz, 2H), 4.76 (m, 2H), 4.36 (t, J = 5.2 Hz, 1H), 3.01-2.95 (m, 2H), 3.47 (q, J = 6.4 Hz, 2H), 3.01-2.95 (m, 2H), 2.64-2.58 (m, 2H), 2.55-2.52 (m, 2H), 1.98-1.94 (m, 1H), 1.84-1.81 (m, 2H), 1.76-1.72 (m, 2H), 1.56-1.51 (m, 1H), 1.40 (q, J = 6.4 Hz, 2H), 1.29-1.20 (m, 2H) | 489.1 |
| 197 | 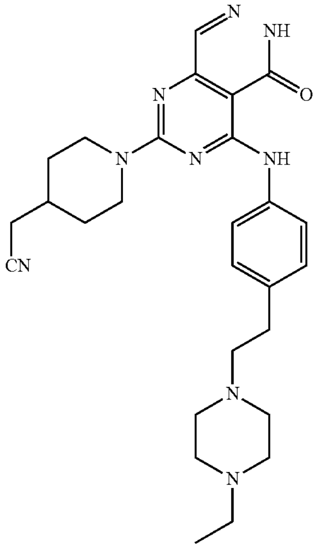 | 12.79 (s, 1H), 11.28 (s, 1H), 7.90 (s, 1H), 7.62 (d, J = 8.3 Hz, 2H), 7.26 (d, J = 8.3 Hz, 2H), 4.79-4.71 (m, 2H), 3.01 (m, 2H), 2.75-2.71 (m, 2H), 2.55-2.54 (m, 6H), 2.33-2.28 (m, 6H), 1.98-1.97 (m, 1H), 1.85-1.82 (m, 2H), 1.23-1.22 (m, 2H), 1.02 (t, J = 6.9 Hz, 3H) | 502.3 |
| 198 | 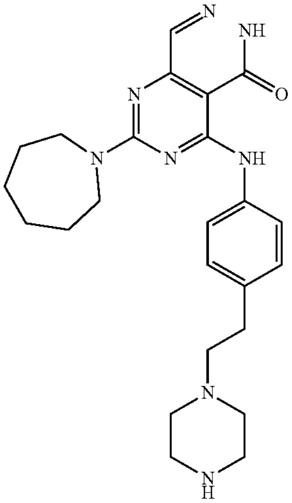 [SMILES: N=Cc1nc(N2CCCCCC2)nc(Nc2ccc(CCN3CCNCC3)cc2)c1C(N)=O] | 12.70 (bs, 1H), 11.30 (s, 1H), 7.88 (s, 1H), 7.67 (d, J = 8.3 Hz, 2H), 7.23 (d, J = 8.3 Hz, 2H), 3.81 (t, J = 6.1 Hz, 2H), 3.76 (t, J = 5.9 Hz, 2H), 2.72-2.68 (m, 6H), 2.48-2.44 (m, 2H), 2.36 (m, 4H), 1.78-1.75 (m, 4H), 1.51 (m, 4H) | 449.2 |

TABLE 2-continued
| Ex # | Structure | Physical Data $^{1}H$-NMR in DMSO-$d_6$ at 400 Hz (δ) | MS m/z |
|---|---|---|---|
| 199 | 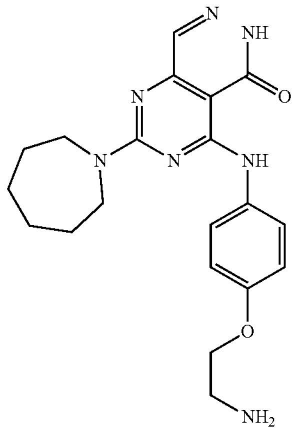 [SMILES: N=Cc1nc(N2CCCCCC2)nc(Nc2ccc(OCCN)cc2)c1C(N)=O] | 11.17 (s, 1H), 7.87 (s, 1H), 7.67 (d, J = 9.3 Hz, 2H), 6.97 (d, J = 9.3 Hz, 2H), 3.96 (t, J = 5.6 Hz, 2H), 3.80 (t, J = 6.2 Hz, 2H), 3.74 (t, J = 6.1 Hz, 2H), 2.90 (t, J = 5.6 Hz, 2H), 1.75 (m, 4H), 1.51 (m, 4H) | 396.2 |
| 200 | 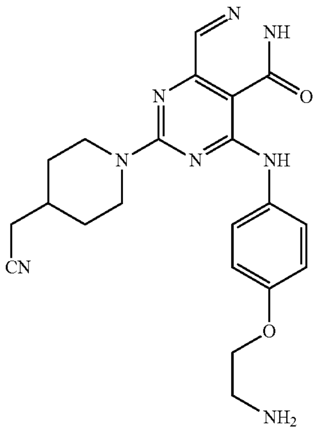 | 11.15 (s, 1H), 7.89 (s, 1H), 7.62 (d, J = 9.3 Hz, 2H), 7.00 (d, J = 8.8 Hz, 2H), 4.78-4.68 (m, 2H), 3.98 (t, J = 5.4 Hz, 2H), 3.02-2.94 (m, 4H), 2.55-2.53 (m, 4H), 1.97-1.94 (m, 1H), 1.84-1.81 (m, 2H), 1.23-1.18 (m, 2H) | 421.2 |
| 201 | 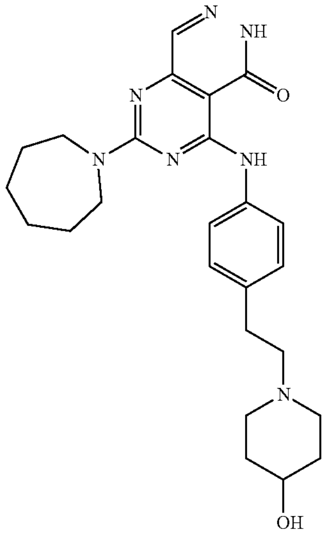 [SMILES: N=Cc1nc(N2CCCCCC2)nc(Nc2ccc(CCN3CCC(O)CC3)cc2)c1C(N)=O] | 12.75 (s, 1H), 11.35 (s, 1H), 7.89 (s, 1H), 7.74 (d, J = 8.3 Hz, 2H), 7.28 (d, J = 8.3 Hz, 2H), 4.90 (m, 1H), 3.81 (t, J = 5.9 Hz, 2H), 3.77 (t, J = 5.6 Hz, 2H), 3.6 (m, 2H), 3.16-3.13 (m, 2H), 2.92 (m, 4H), 1.85-1.77 (m, 5H), 1.52 (m, 6H) | 464.2 |

TABLE 2-continued
| Ex # | Structure | Physical Data<br>$^1$H-NMR in DMSO-$d_6$ at 400 Hz (δ) | MS m/z |
|---|---|---|---|
| 202 | 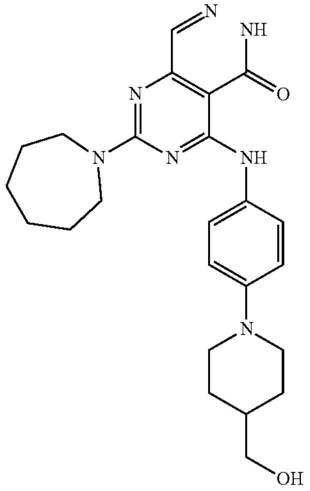 | 12.70 (s, 1H), 11.15 (s, 1H), 7.86 (s, 1H), 7.61 (d, J = 9.2 Hz, 2H), 6.95 (d, J = 9.3 Hz, 2H), 4.47 (t, J = 5.4 Hz, 1H), 4.34 (m, 2H), 3.80 (t, J = 6.2 Hz, 2H), 3.75 (t, J = 5.9 Hz, 2H), 3.69-3.66 (m, 2H), 3.29 (t, J = 5.9 Hz, 2H), 2.64-2.58 (m, 2H), 2.4-2.26 (m, 3H), 1.76-1.73 (m, 4H), 1.51 (m, 4H) | 450.2 |
| 203 | 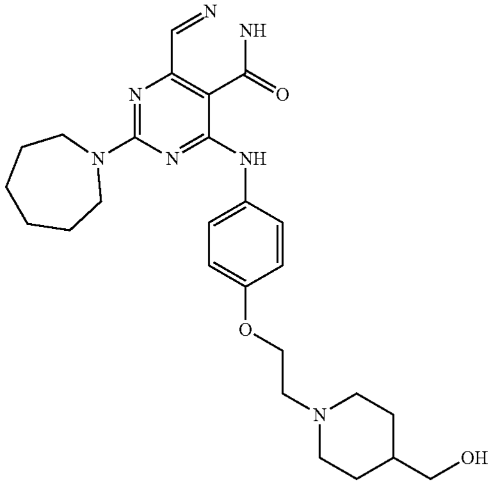 [SMILES: N=Cc1nc(N2CCCCCC2)nc(Nc2ccc(OCCN3CCC(CO)CC3)cc2)c1C(N)=O] | 12.71 (s, 1H), 11.17 (s, 1H), 7.87 (s, 1H), 7.66 (d, J = 8.8 Hz, 2H), 6.97 (d, J = 9.3 Hz, 2H), 4.40 (t, J = 5.4 Hz, 1H), 4.07 (t, J = 5.7 Hz, 2H), 3.80 (t, J = 6.1 Hz, 2H), 3.74 (t, J = 5.9 Hz, 2H), 3.24 (t, J = 5.6 Hz, 2H), 2.96-2.94 (m, 2H), 2.68-2.67 (m, 2H), 2.02 (m, 2H)H, 1.76 (m, 2044H), 1.65-1.62 (m, 2H), 1.51 (m, 4H), 1.43 (m, 1H), 1.15-1.07 (m, 2H) | 494.4 |
| 204 | 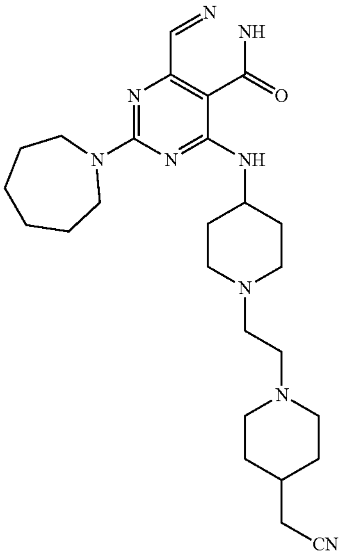 [SMILES: N#CCC1CCN(CCN2CCC(Nc3nc(N4CCCCCC4)nc(C=N)c3C(N)=O)CC2)CC1] | 12.52 (s, 1H), 8.90 (d, J = 6.9 Hz, 1H), 7.79 (s, 1H), 4.48-4.46 (m, 2H), 3.91-3.87 (m, 2H), 3.76 (t, J = 5.9 Hz, 2H), 3.71 (t, J = 5.8 Hz, 2H), 2.93-2.91 (m, 2H), 2.78 (m, 2H), 2.47-2.45 (m, 4H), 2.37-2.20 (m, 1H), 1.97-1.91 (m, 5H), 1.71-1.48 (m, 12H) | 494.4 |

TABLE 2-continued
| Ex # | Structure | Physical Data $^1$H-NMR in DMSO-$d_6$ at 400 Hz (δ) | MS m/z |
|---|---|---|---|
| 205 | 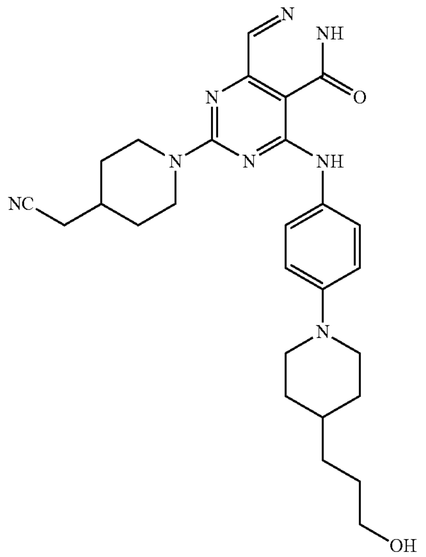 [SMILES: N#CCC1CCN(c2nc(C=N)c(C(N)=O)c(Nc3ccc(N4CCC(CCCO)CC4)cc3)n2)CC1] | 12.75 (s, 1H), 11.12 (s, 1H), 7.87 (s, 1H) 7.54 (d, J = 8.8 Hz, 1H), 6.97 (d, J = 9.3 Hz, 2H), 4.76 (m, 2H), 4.36 (t, J = 5.1 Hz, 1H), 3.68-3.65 (m, 2H), 3.39 (q, J = 6.3 Hz, 2H) (, 3.01-2.95 (m, 2H), 2.64-2.58 (m, 2H), 2.55-2.52 (m, 2H), 1.97-1.94 (m, 1H), 1.84-1.81 (m, 2H), 1.75-1.73 (m, 2H), 1.50-1.44 (m, 2H), 1.43-1.31 (m, 1H), 1.28-1.20 (m, 6H) | 503.5 |
| 206 | 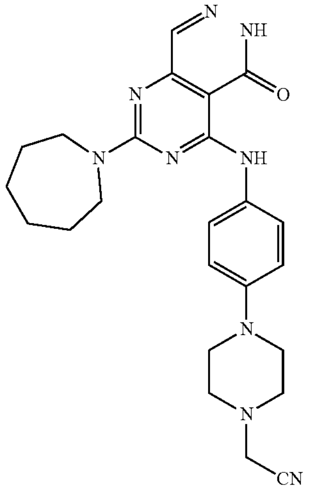 [SMILES: N#CCN1CCN(c2ccc(Nc3nc(N4CCCCCC4)nc(C=N)c3C(N)=O)cc2)CC1] | 12.70 (s, 1H), 11.17 (s, 1H), 7.86 (s, 1H), 7.64 (d, J = 9.3 Hz, 2H), 6.98 (d, J = 8.8 Hz, 2H), 3.82-3.78 (m, 4H), 3.75 (t, J = 5.9 Hz, 2H), 3.17 (t, J = 4.7 Hz, 4H) 2.63 (t, J = 4.7 Hz, 4H), 1.78-1.75 (m, 4H), 1.51 (m, 4H) | 460.3 |
| 207 | 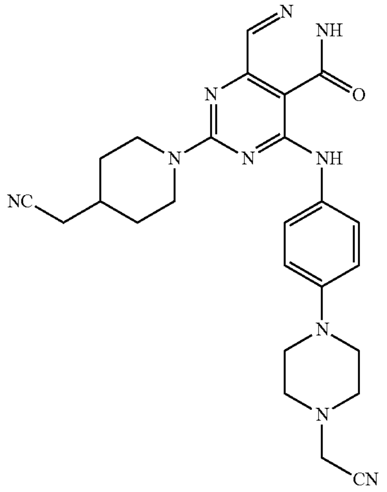 [SMILES: N#CCC1CCN(c2nc(C=N)c(C(N)=O)c(Nc3ccc(N4CCN(CC#N)CC4)cc3)n2)CC1] | 12.76 (s, 1H), 11.15 (s, 1H), 7.88 (s, 1H) 7.58 (d, J = 8.8 Hz, 2H), 7.00 (d, J = 8.8 Hz, 2H), 4.78-4.72 (m, 2H), 3.80 (s, 2H), 3.18 (t, J = 4.9 Hz, 4H), 2.63 (t, J = 4.9 Hz, 4H), 2.55-2.53 (m, 2H), 1.98-1.95 (m, 1H), 1.84-1.81 (m, 2H), 1.26-1.18 (m, 2H) | 485.3 |

TABLE 2-continued
| Ex # | Structure | Physical Data $^1$H-NMR in DMSO-$d_6$ at 400 Hz (δ) | MS m/z |
|---|---|---|---|
| 208 | 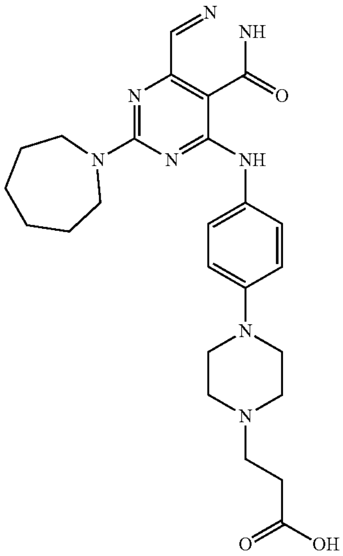 [SMILES: N=Cc1nc(N2CCCCCC2)nc(Nc2ccc(N3CCN(CCC(=O)O)CC3)cc2)c1C(N)=O] | 12.70 (s, 1H), 11.16 (s, 1H), 7.86 (s, 1H), 7.62 (d, J = 9.3 Hz, 2H), 6.96 (d, J = 8.8 Hz, 2H), 3.80 (t, J = 6.1 Hz, 2H), 3.75 (t, J = 5.9 Hz, 2H), 3.11-3.10 (m, 4H), 2.61-2.60 (m, 2H), 2.55-2.54 (m, 4H), 2.44-2.40 (m, 2H), 1.77-1.75 (m, 4H), 1.51 (m, 4H) | 493.4 |
| 209 | 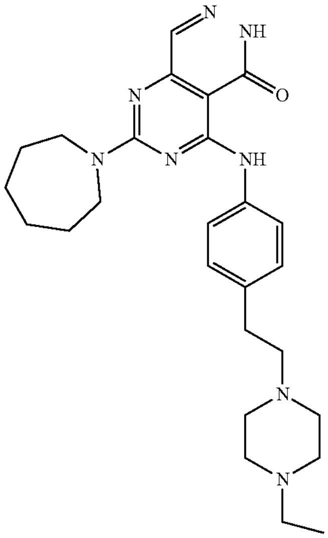 [SMILES: CCN1CCN(CCc2ccc(Nc3nc(N4CCCCCC4)nc(C=N)c3C(N)=O)cc2)CC1] | 12.70 (s, 1H), 11.90 (s, 1H), 7.86 (s, 1H), 7.91 (s, 1H), 7.68 (d, J = 8.3 Hz, 2H), 7.22 (d, J = 8.3 Hz, 2H), 3.78 (m, 4H), 2.72-2.55 (m, 4H), 2.33-2.26 (m, 10H), 1.76 (m, 4H), 1.51 (m, 4H), 0.98 (t, J = 7.1 Hz, 3H) | 477.3 |

TABLE 2-continued
| Ex # | Structure | Physical Data $^1$H-NMR in DMSO-$d_6$ at 400 Hz (δ) | MS m/z |
|---|---|---|---|
| 210 | 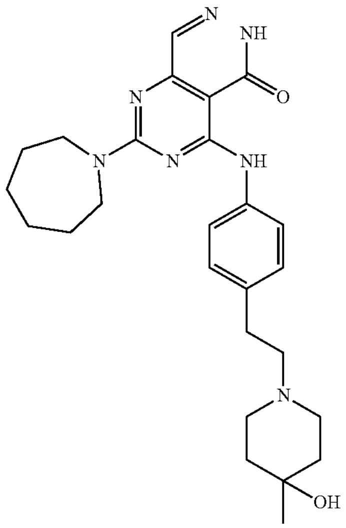 [SMILES: CC1(O)CCN(CCc2ccc(Nc3nc(N4CCCCCC4)nc(C=N)c3C(N)=O)cc2)CC1] | 12.73 (s, 1H), 11.30 (s, 1H), 7.88 (s, 1H), 7.67 (d, J = 8.3 Hz, 2H), 7.23 (d, J = 8.3 Hz, 2H), 4.08 (s, 1H), 3.81 (t, J = 5.9 Hz, 2H), 3.76 (t, J = 5.9 Hz, 2H), 2.72-2.68 (m, 2H), 2.43-2.33 (m, 4H), 1.79-1.75 (m, 4H), 1.51 (m, 4H), 1.47-1.44 (m, 4H), 1.09 (s, 3H) | 478.0 |
| 211 | 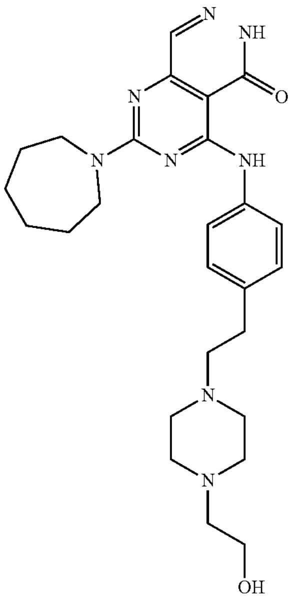 [SMILES: N=Cc1nc(N2CCCCCC2)nc(Nc2ccc(CCN3CCN(CCO)CC3)cc2)c1C(N)=O] | 12.74 (s, 1H), 11.30 (s, 1H), 7.88 (s, 1H), 7.68 (d, J = 8.8 Hz, 2H), 7.23 (d, J = 8.7 Hz, 2H), 4.51-4.44 (m, 1H), 3.81 (t, J = 6.2 Hz, 2H), 3.76 (t, J = 5.9 Hz, 2H), 3.49 (q, J = 6.2 Hz, 2H), 2.73-2.68 (m, 2H), 2.45-2.32 (m, 6H), 2.28-2.24 (m, 6H), 1.79-1.75 (m, 4H) | 493.4 |

TABLE 2-continued
| Ex # | Structure | Physical Data <br> $^1$H-NMR in DMSO-$d_6$ at 400 Hz (δ) | MS m/z |
|---|---|---|---|
| 212 | 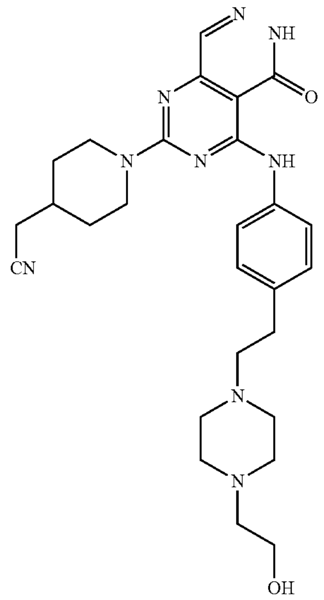 | 12.79 (s, 1H), 11.28 (s, 1H), 7.90 (s, 1H), 7.62 (d, J = 7.8 Hz, 2H), 7.26 (d, J = 7.9 Hz, 2H), 4.80-4.70 (m, 2H), 4.41 (m, 1H), 3.49 (m, 2H), 3.27-3.01 (m, 2H), 2.72-2.67 (m, 2H), 2.60 (m, 8H), 2.45-2.33 (m, 8H), 1.98 (m, 1H), 1.85-1.82 (m, 2H) | 518.3 |
| 213 | 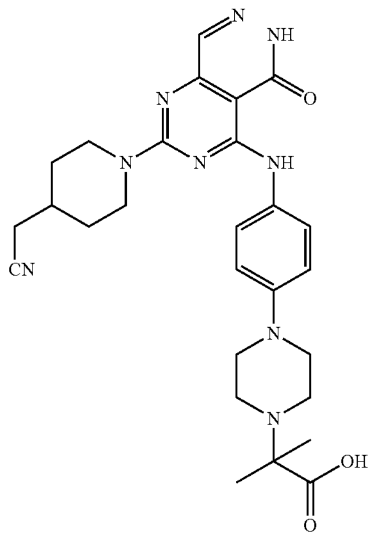 [SMILES: CC(C)(C(=O)O)N1CCN(c2ccc(Nc3nc(N4CCC(CC#N)CC4)nc(C=N)c3C(N)=O)cc2)CC1] | 12.77 (s, 1H), 11.19 (s, 1H), 7.89 (s, 1H), 7.63 (d, J = 6.8 Hz, 2H), 7.06 (m, 2H), 4.72 (m, 2H), 3.59 (m, 8H), 3.00 (m, 2H), 1.98 (m, 1H), 1.84-1.82 (m, 2H), 1.55 (s, 6H), 1.24 (m, 4H) | 532.4 |

TABLE 2-continued
| Ex # | Structure | Physical Data $^1$H-NMR in DMSO-$d_6$ at 400 Hz (δ) | MS m/z |
|---|---|---|---|
| 214 | 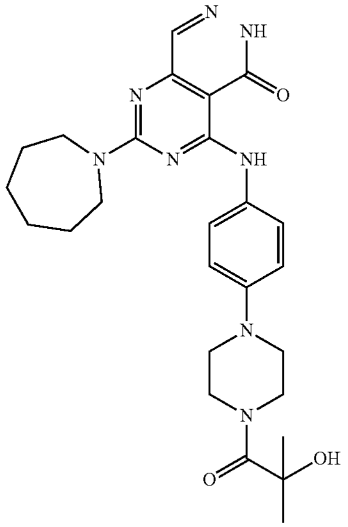 [SMILES: CC(C)(O)C(=O)N1CCN(c2ccc(Nc3nc(N4CCCCCC4)nc(C=N)c3C(N)=O)cc2)CC1] | 12.70 (s, 1H), 11.17 (s, 1H), 7.87 (s, 1H), 7.64 (d, J = 8.8 Hz, 2H), 7.00 (d, J = 9.3 Hz, 2H), 5.46 s, 1H), 3.80 (t, J = 6.0 Hz, 2H), 3.75 (t, J = 5.9 Hz, 2H), 3.29 (m, 4H), 3.12 (m, 4H), 1.77-1.75 n(m, 4H), 1.51 (m, 4H), 1.34 (s, 6H) | 507.3 |
| 215 | 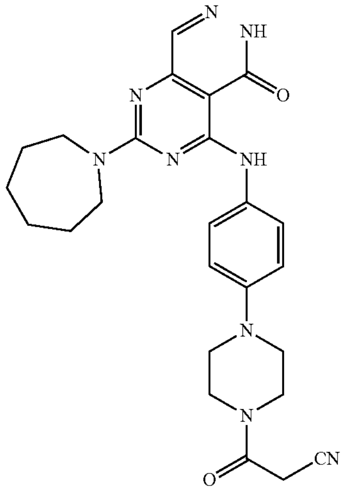 [SMILES: N#CCC(=O)N1CCN(c2ccc(Nc3nc(N4CCCCCC4)nc(C=N)c3C(N)=O)cc2)CC1] | 12.71 (s, 1H), 11.18 (s, 1H), 7.87 (s, 1H), 7.65 (d, J = 9.3 Hz, 2H), 7.00 (d, J = 9.3 Hz, 2H), 4.10 (s, 2H), 3.80 (t, J = 6.1 Hz, 2H), 3.75 (t, J = 5.9 Hz, 2H), 3.61 (t, J = 5.2 Hz, 2H), 3.17 (t, J = 5.2 Hz, 2H), 3.11 (t, J = 5.2 Hz, 2H), 1.77-1.75 (m, 4H), 1.51 (m, 4H) | 488.4 |
| 216 | 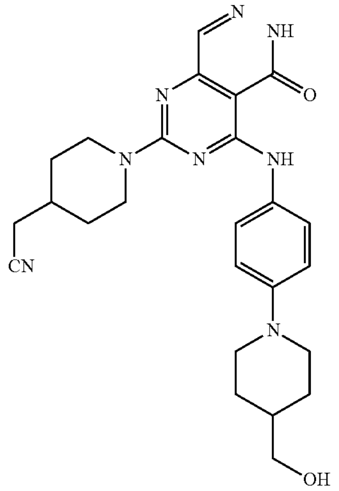 [SMILES: N#CCC1CCN(c2nc(C=N)c(C(N)=O)c(Nc3ccc(N4CCC(CO)CC4)cc3)n2)CC1] | 12.75 (s, 1H), 11.12 (s, 1H), 7.87 (s, 1H), 7.54 (d, J = 9.3 Hz, 2H), 6.97 (d, J = 8.8 Hz, 2H), 4.71 (m, 2H), 4.47 (t, J = 5.4 Hz, 1H), 3.70-3.67 (m, 2H), 3.29 (t, J = 5.9 Hz, 2H), 3.01-2.95 (m, 2H), 2.62-2.52 (m, 4H), 1.97 (m, 1H), 1.84-1.81 (m, 2H), 1.76-1.73 (m, 2H), 1.51-1.28 (m, 1H), 1.25-1.21 (m, 4H) | 475.2 |

TABLE 2-continued
| Ex # | Structure | Physical Data <br> $^1$H-NMR in DMSO-$d_6$ at 400 Hz (δ) | MS m/z |
|---|---|---|---|
| 217 | 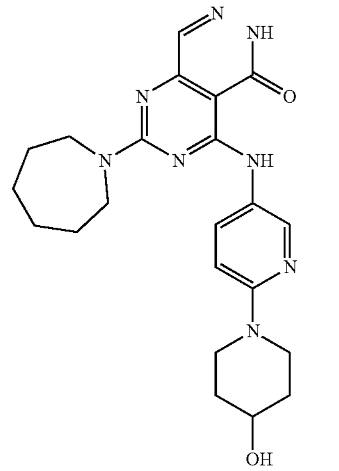 [SMILES: N=Cc1nc(N2CCCCCC2)nc(Nc2ccc(N3CCC(O)CC3)nc2)c1C(N)=O] | 12.70 (s, 1H), 10.97 (s, 1H), 8.43 (d, J = 2.5 Hz, 1H), 7.93 (d, J = 8.8 Hz, 2H), 7.86 (s, 1H), 6.88 (d, J = 9.3 Hz, 1H), 4.68 (d, J = 4.4 Hz, 1H), 4.00-3.94 (m, 2H), 3.79 (t, J = 5.9 Hz, 2H), 3.70 (t, J = 5.9 Hz, 2H), 3.67-3.66 (m, 1H), 3.08-3.02 (m, 2H), 1.79-1.73 (m, 6H), 1.50 (m, 4H), 1.41-1.32 (m, 2H) | 437.3 |
| 218 | 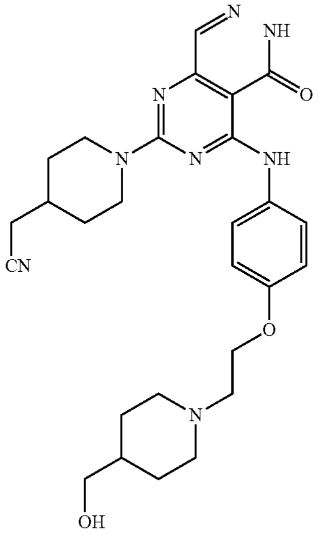 | 12.77 (s, 1H), 11.15 (s, 1H), 7.88 (s, 1H), 7.60 (d, J = 8.8 Hz, 2H), 6.98 (d, J = 9.3 Hz, 2H), 4.86-4.68 (m, 2H), 4.40 (t, J = 5.1 Hz, 1H), 4.07 (d, J = 5.7 Hz, 2H), 3.24 (t, J = 5.9 Hz, 2H), 3.1-2.92 (m, 4H), 2.67 (m, 4H), 2.55-2.53 (m, 1H), 1.99-1.96 (m, 5H), 1.84-1.81 (m, 4H), 1.64-1.61 (m, 4H), 1.34-1.33 (m, 1H), 1.26-1.11 (m, 4H) | 519.3 |
| 219 | 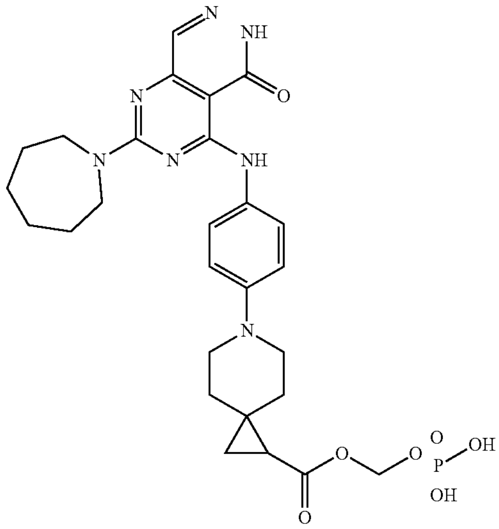 | 12.70 (s, 1H), 11.17 (s, 1H), 7.88 (s, 1H), 7.63 (d, J = 8.8 Hz, 2H), 7.01 (d, J = 8.4 Hz, 2H), 5.53-5.43 (m, 2H), 3.80 (t, J= 6.2 Hz, 2H), 3.75 (t, J = 5.9 Hz, 2H), 3.27-3.06 (m, 3H), 1.77-1.70 (m, 6H), 1.59-1.51 (m, 6H), 1.13-1.09 (m, 2H) | 598.4 |

TABLE 2-continued
| Ex # | Structure | Physical Data $^1$H-NMR in DMSO-$d_6$ at 400 Hz (δ) | MS m/z |
|---|---|---|---|
| 220 | 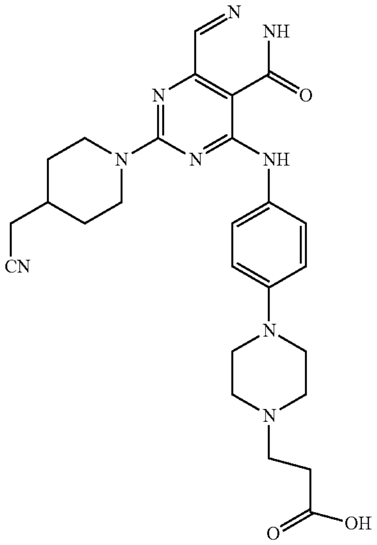 [SMILES: N#CCC1CCN(c2nc(C=N)c(C(N)=O)c(Nc3ccc(N4CCN(CCC(=O)O)CC4)cc3)n2)CC1] | 12.75 (s, 1H), 11.14 (s, 1H), 7.88 (s, 1H), 7.56 (d, J = 8.8 Hz, 2H), 6.98 (d, J = 8.8 Hz, 2H), 4.80-4.60 (m, 2H), 3.13-3.11 (m, 4H), 3.02-2.95 (m, 2H), 2.61-2.52 (m, 6H), 2.42 (t, J = 7.1 Hz, 4H), 1.97 (m, 1H), 1.84-1.81 (m, 2H), 1.23-1.21 (m, 2H) | 516.4 |
| 221 | 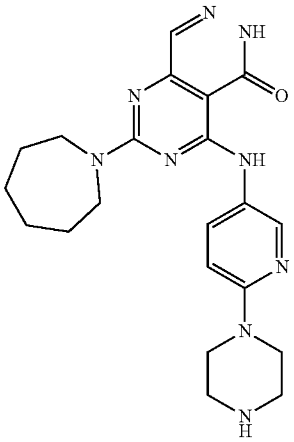 [SMILES: N=Cc1nc(N2CCCCCC2)nc(Nc2ccc(N3CCNCC3)nc2)c1C(N)=O] | 12.75 (s, 1H), 10.98 (s, 1H), 8.45 (d, J = 2.5 Hz, 1H), 7.94 (dd, $J_1$ = 2.4 Hz, $J_2$ = 9.3 Hz, 1H), 7.87 (s, 1H), 6.84 (d, J = 9.3 Hz, 1H), 3.79 (t, J = 5.9 Hz, 2H), 3.70 (t, J = 5.7 Hz, 2H), 3.37-3.35 (m, 4H), 2.78 (m, 4H), 1.73 (m, 4H), 1.50 (m, 4H) | 422.1 |
| 222 | 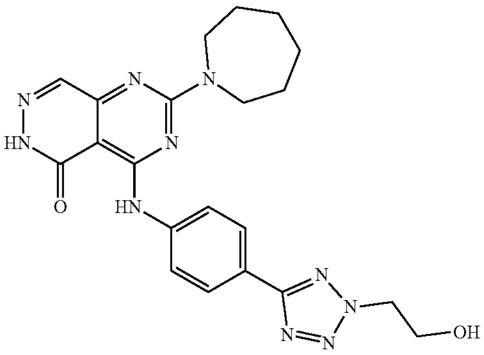 [SMILES: O=c1[nH]ncc2nc(N3CCCCCC3)nc(Nc3ccc(-c4nnn(CCO)n4)cc3)c12] | 12.80 (s, 1H), 1.58 (s, 1H), 8.08 (d, J = 8.8 Hz, 2H), 7.97 (d, J = 8.3 Hz, 2H), 7.91 (s, 1H), 5.09 (t, J = 5.4 Hz, 1H), 4.75 (t, J = 4.9 Hz, 2H), 3.97-3.96 (m, 2H), 3.83 (t, J = 6.4 Hz, 4H), 1.84-1.76 (m, 4H), 1.53 (m, 4H) | 449.3 |

TABLE 2-continued
| Ex # | Structure | Physical Data $^{1}$H-NMR in DMSO-$d_6$ at 400 Hz (δ) | MS m/z |
|---|---|---|---|
| 223 | 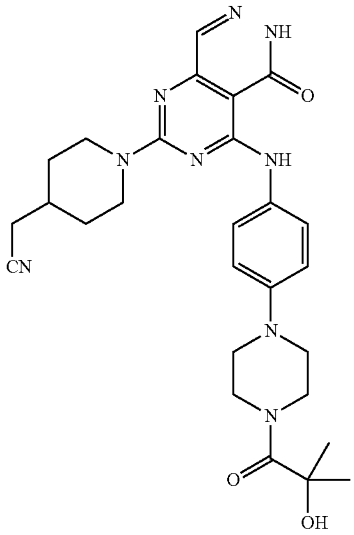 [SMILES: CC(C)(O)C(=O)N1CCN(c2ccc(Nc3nc(N4CCC(CC#N)CC4)nc(C=N)c3C(N)=O)cc2)CC1] | 12.76 (s, 1H), 11.15 (s, 1H), 7.88 (s, 1H), 7.59 (d, J = 8.8 Hz, 2H), 7.01 (d, J = 8.8 Hz, 2H), 5.46 (s, 1H), 4.90-4.60 (m, 2H), 4.10-3.60 (m, 4H), 3.30-3.10 (m, 4H), 3.02-2.96 (m, 2H), 2.55-2.52 (m, 4H), 1.98 (m, 1H), 1.84-1.81 (m, 2H), 1.34 (s, 6H) | 477.2 |
| 224 | 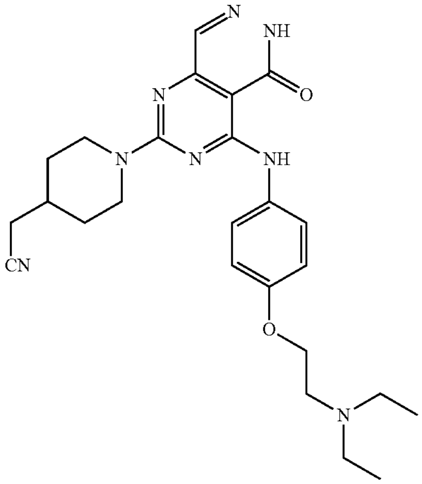 [SMILES: CCN(CC)CCOc1ccc(Nc2nc(N3CCC(CC#N)CC3)nc(C=N)c2C(N)=O)cc1] | 12.78 (s, 1H), 11.17 (s, 1H), 7.89 (s, 1H), 7.64 (d, J = 8.4 Hz, 2H), 7.02 (d, J = 7.8 Hz, 2H), 4.79-4.68 (m, 2H), 4.20-4.00 (m, 4H), 3.02-2.96 (m, 2H), 2.55-2.53 (m, 4H), 1.98-1.91 (m, 1H), 1.84-1.81 (m, 2H), 1.24-1.08 (m, 10H) | |
| 225 | 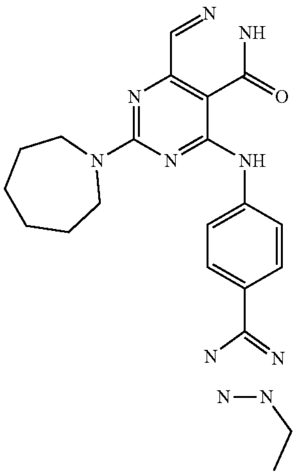 | — | 433.4 |

TABLE 2-continued
| Ex # | Structure | Physical Data $^1$H-NMR in DMSO-$d_6$ at 400 Hz (δ) | MS m/z |
|---|---|---|---|
| 226 | 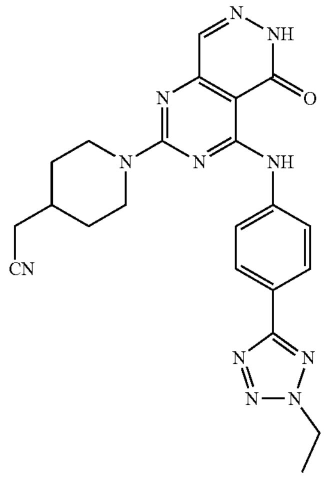 [SMILES: CCn1nnc(-c2ccc(Nc3nc(N4CCC(CC#N)CC4)nc4cn[nH]c(=O)c34)cc2)n1] | 12.70 (s, 1H), 11.58 (s, 1H), 8.11 (d, J = 8.4 Hz, 2H), 7.88 (d, J = 8.8 Hz, 2H), 7.84 (s, 1H), 5.00-4.80 (m, 2H), 4.73 (q, J = 7.3 Hz, 2H), 3.10-2.95 (m, 2H), 2.47 (d, J = 6.4 Hz, 2H), 2.10-1.93 (m, 3H), 1.66 (t, J = 7.4 Hz, 3H), 1.36-1.34 (m, 2H) | 458.3 |
| 227 | 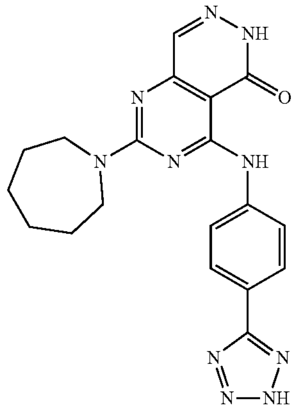 [SMILES: O=c1[nH]ncc2nc(N3CCCCCC3)nc(Nc3ccc(-c4nn[nH]n4)cc3)c12] | 12.82 (s, 1H), 11.61 (s, 1H), 8.07 (d, J = 8.8 Hz, 2H), 8.02 (d, J = 8.8 Hz, 2H), 7.93 (s, 1H), 3.83 (q, J = 6.4 Hz, 4H), 1.84-1.77 (m, 4H), 1.53 (m, 4H) | 403.2 (M − 1) |
| 228 | 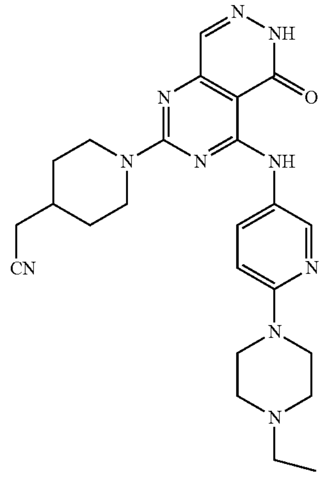 [SMILES: CCN1CCN(c2ccc(Nc3nc(N4CCC(CC#N)CC4)nc4cn[nH]c(=O)c34)cn2)CC1] | 12.76 (s, 1H), 10.97 (s, 1H), 8.42 (d, J = 2.4 Hz, 1H), 7.90-7.87 (m, 2H), 6.90 (d, J = 9.3 Hz, 1H), 4.58-4.49 (m, 2H), 3.46 (m, 4H), 3.00-2.94 (m, 2H), 2.54-2.53 (m, 2H), 2.39 (m, 6H), 1.97-1.95 (m, 1H), 1.83-1.80 (m, 2H), 1.25-1.19 (m, 2H), 1.05 (t, J = 7.1 Hz, 3H) | 476 (M + 2) |

TABLE 2-continued
| Ex # | Structure | Physical Data $^1$H-NMR in DMSO-$d_6$ at 400 Hz (δ) | MS m/z |
|---|---|---|---|
| 229 | 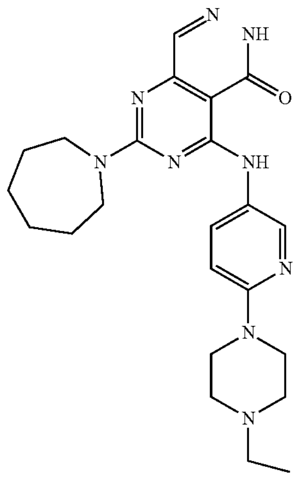 [SMILES: CCN1CCN(c2ccc(Nc3nc(N4CCCCCC4)nc(C=N)c3C(N)=O)cn2)CC1] | 12.71 (s, 1H), 11.00 (s, 1H), 8.46 (d, J = 2.9 Hz, 1H), 7.96 (dd, $J_1$ = 2.8 Hz, $J_2$ = 9.1 Hz, 1H), 7.87 (s, 1H), 6.88 (d, J = 9.3 Hz, 1H), 3.79 (t, J = 6.1 Hz, 2H), 3.70 (t, J = 5.6 Hz, 2H), 3.45 (t, J = 4.9 Hz, 4H), 2.45 (t, J = 4.9 Hz, 4H), 2.36 (q, J = 7.3 Hz, 2H), 1.74 (m, 4H), 1.50 (m, 4H), 1.04 (t, J = 7.1 Hz, 3H) | 450.0 |
| 230 | 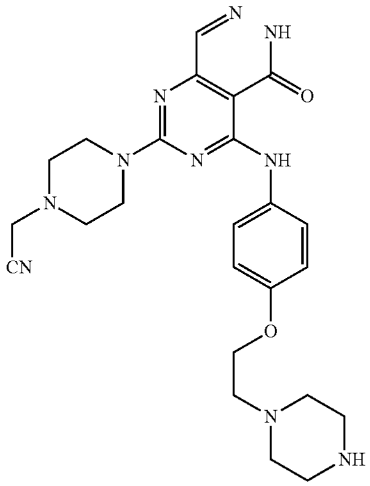 [SMILES: N#CCN1CCN(c2nc(C=N)c(C(N)=O)c(Nc3ccc(OCCN4CCNCC4)cc3)n2)CC1] | 12.80 (bs, 1H), 11.17 (s, 1H), 7.90 (s, 1H), 7.61 (d, J = 8.3 Hz, 1H), 6.99 (d, J = 8.3 Hz, 2H), 4.07 (t, J = 5.6 Hz, 2H), 3.87 (m, 4H), 3.81 (m, 2H), 2.72 (t, J = 4.2 Hz, 4H), 2.66 (t, J = 5.7 Hz, 2H), 2.55 (m, 4H), 2.42 (m, 4H) | 491.1 |
| 231 | 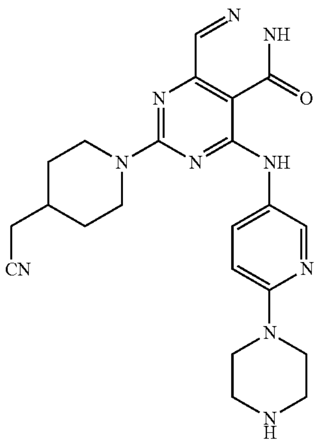 [SMILES: N#CCC1CCN(c2nc(C=N)c(C(N)=O)c(Nc3ccc(N4CCNCC4)nc3)n2)CC1] | 12.80 (bs, 1H), 10.96 (s, 1H), 8.41 (d, J = 2.4 Hz, 1H), 7.87 (s, 1H), 7.86-7.85 (m, 1H), 6.86 (d, J = 9.3 Hz, 1H), 4.48-4.61 (m, 2H), 2.99-2.93 (m, 2H), 2.78 (m, 4H), 2.54-2.53 (m, 6H), 1.96-1.95 (m, 1H), 1.83-1.80 (m, 2H), 1.24-1.19 (m, 2H) | 445.2 (M − 1) |

TABLE 2-continued
| Ex # | Structure | Physical Data: $^1$H-NMR in DMSO-$d_6$ at 400 Hz (δ) | Physical Data: MS m/z |
|---|---|---|---|
| 232 | 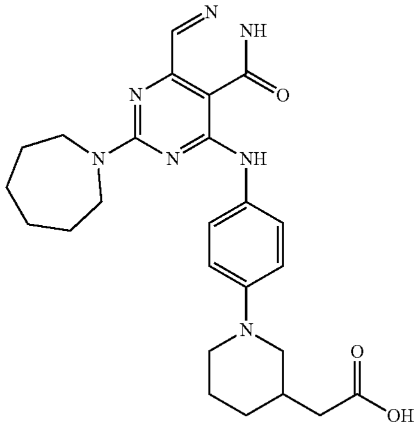 [SMILES: N=Cc1nc(N2CCCCCC2)nc(Nc2ccc(N3CCCC(CC(=O)O)C3)cc2)c1C(N)=O] | 12.70 (s, 1H), 10.96 (s, 1H), 8.41 (d, J = 2.4 Hz, 1H), 7.94 (dd, $J_1$ = 2.4 Hz, $J_2$ = 8.8 Hz, 1H), 7.86 (s, 1H), 6.85 (d, J = 8.8 Hz, 1H), 4.17-4.10 (m, 2H), 3.79 (t, J = 5.9 Hz, 2H), 3.70 (t, J = 5.9 Hz, 2H), 2.83-2.77 (m, 2H), 2.61-2.50 (m, 2H), 2.28-2.11 (m, 2H), 1.90-1.86 (m, 1H), 1.83-1.65 (m, 6H), 1.50-1.42 (m, 4H) | 479.3 |
| 233 | 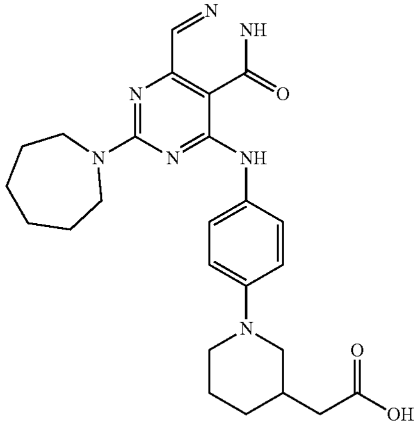 [SMILES: N=Cc1nc(N2CCCCCC2)nc(Nc2ccc(N3CCCC(CC(=O)O)C3)cc2)c1C(N)=O] | 12.71 (s, 1H), 11.16 (s, 1H), 7.85 (s, 1H), 7.59 (d, J = 9.3 Hz, 2H), 6.92 (d, J = 8.8 Hz, 2H), 3.80 (t, J = 5.9 Hz, 2H), 3.75 (t, J = 6.1 Hz, 2H), 3.70-3.55 (m, 3H), 1.90-1.60 (m, 10H), 1.51 (m, 6H) | 478.2 |
| 234 | 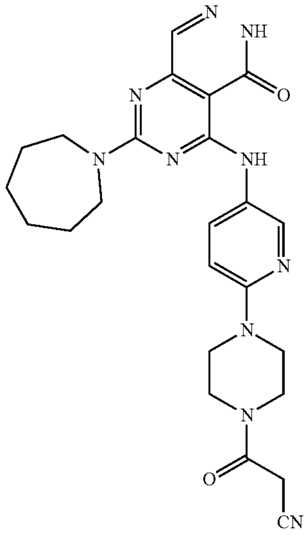 [SMILES: N#CCC(=O)N1CCN(c2ccc(Nc3nc(N4CCCCCC4)nc(C=N)c3C(N)=O)cn2)CC1] | 12.72 (s, 1H), 11.01 (s, 1H), 8.49 (d, J = 2.5 Hz, 1H), 7.99 (dd, $J_1$ = 2.7 Hz, $J_2$ = 9.1 Hz, 1H), 7.87 (s, 1H), 6.94 (d, J = 8.8 Hz, 1H), 4.10 (s, 2H), 3.79 (t, J = 5.9 Hz, 2H), 3.71 (t, J = 6.1 Hz, 2H), 3.59-3.47 (m, 8H), 1.74 (m, 4H), 1.50 (m, 4H) | 489.3 |

TABLE 2-continued
| Ex # | Structure | Physical Data: $^1$H-NMR in DMSO-$d_6$ at 400 Hz (δ) | Physical Data: MS m/z |
|---|---|---|---|
| 235 | 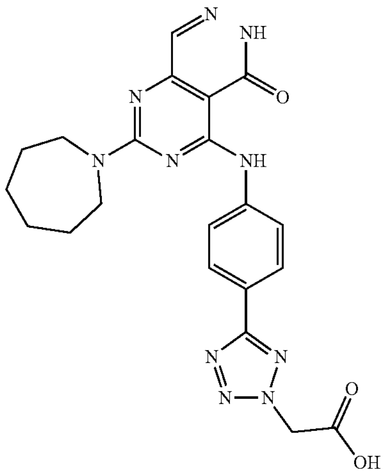 [SMILES: N=Cc1nc(N2CCCCCC2)nc(Nc2ccc(-c3nnn(CC(=O)O)n3)cc2)c1C(N)=O] | 12.80 (s, 1H), 11.55 (s, 1H), 8.06 (d, J = 8.8 Hz, 2H), 7.95 (d, J = 8.8 Hz, 2H), 7.90 (s, 1H), 5.15 (s, 2H), 3.84-3.78 (m, 4H), 1.83-1.76 (m, 4H), 1.52 (m, 4H) | 461.3 (M − 1) |
| 236 | 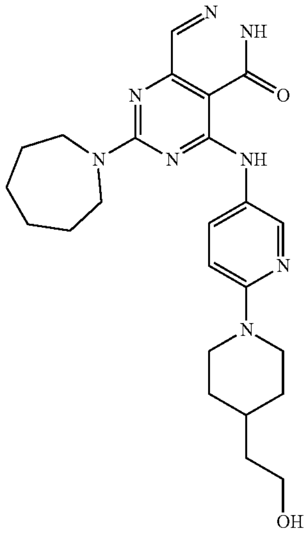 | 12.70 (s, 1H), 10.97 (s, 1H), 8.42 (d, J = 3.0 Hz, 1H), 7.92 (dd, $J_1$ = 2.8 Hz, $J_2$ = 9.1 Hz, 1H), 7.86 (s, 1H), 6.86 (d, J = 9.3 Hz, 1H), 4.36 (t, J = 5.2 Hz, 1H), 4.25-4.21 (m, 2H), 3.79 (t, J = 6.2 Hz, 2H), 3.70 (t, J = 5.9 Hz, 2H), 3.47 (q, J = 6.2 Hz, 2H), 2.77-2.74 (m, 2H), 1.73-1.71 (m, 6H), 1.64-1.59 (m, 1H), 1.50 (m, 4H), 1.38 (q, J = 6.3 Hz, 2H), 1.14-1.10 (m, 2H) | 465.3 |
| 237 | 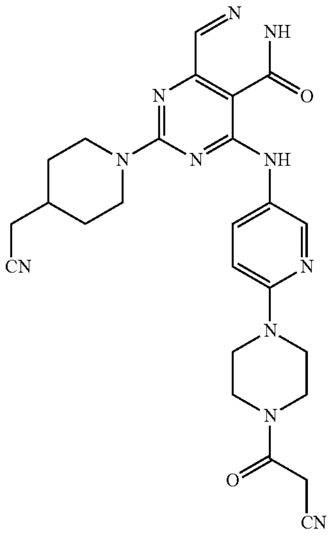 [SMILES: N#CCC(=O)N1CCN(c2ccc(Nc3nc(N4CCC(CC#N)CC4)nc(C=N)c3C(N)=O)cn2)CC1] | 12.77 (s, 1H), 10.98 (s, 1H), 8.45 (d, J = 2.5 Hz, 1H), 7.93 (dd, $J_1$ = 2.7 Hz, $J_2$ = 9.1 Hz, 1H), 7.89 (s, 1H), 6.95 (d, J = 9.3 Hz, 1H), 4.79-4.61 (m, 2H), 4.11 (s, 2H), 3.60-3.54 (m, 4H), 3.51-3.46 (m, 4H), 3.00-2.94 (m, 2H), 2.55-2.53 (m, 2H), 1.97-1.94 (m, 1H), 1.83-1.80 (m, 2H), 1.23-1.17 (m, 2H) | 512.4 (M − 1) |

TABLE 2-continued
| Ex # | Structure | Physical Data | |
|---|---|---|---|
| | | $^1$H-NMR in DMSO-$d_6$ at 400 Hz (δ) | MS m/z |
| 238 | 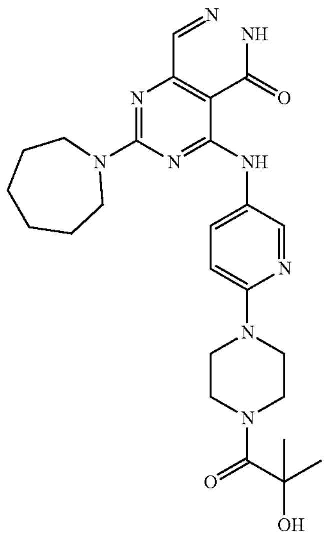 [SMILES: CC(C)(O)C(=O)N1CCN(c2ccc(Nc3nc(N4CCCCCC4)nc(C=N)c3C(N)=O)cn2)CC1] | — | 508.4 |
| 239 | 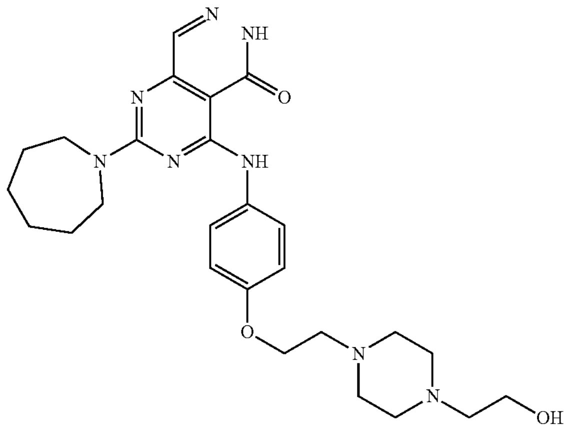 [SMILES: N=Cc1nc(N2CCCCCC2)nc(Nc2ccc(OCCN3CCN(CCO)CC3)cc2)c1C(N)=O] | 12.71 (s, 1H), 11.17 (s, 1H), 7.87 (s, 1H), 7.66 (d, J = 8.8 Hz, 2H), 6.97 (d, J = 8.8 Hz, 2H), 4.40 (bs, 1H), 4.05 (t, J = 5.9 Hz, 2H), 3.80 (t, J = 6.1 Hz, 2H), 3.74 (t, J = 5.9 Hz, 2H), 3.48 (t, J = 6.2 Hz, 2H), 2.67 (t, J = 5.6 Hz, 2H), 2.54 (m, 4H), 2.42-2.33 (m, 6H), 1.76 (m, 4H), 1.51 (m, 4H) | 509.3 |
| 240 | 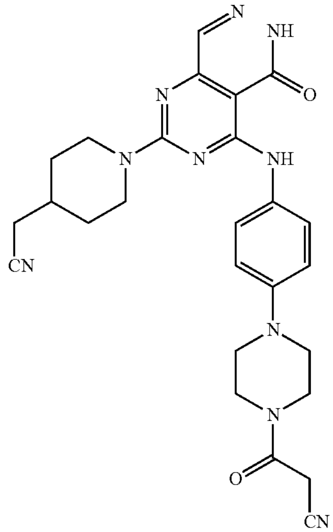 [SMILES: N#CCC(=O)N1CCN(c2ccc(Nc3nc(N4CCC(CC#N)CC4)nc(C=N)c3C(N)=O)cc2)CC1] | 12.76 (s, 1H), 11.16 (s, 1H), 7.88 (s, 1H), 7.59 (d, J = 8.8 Hz, 2H), 7.02 (d, J = 8.8 Hz, 2H), 4.78-4.71 (m, 2H), 4.10 (s, 2H), 3.61 (t, J = 4.9 Hz, 2H), 3.50 (t, J = 4.9 Hz, 2H), 3.18 (t, J = 4.9 Hz, 2H), 3.13 (t, J = 5.2 Hz, 2H), 3.02-2.96 (m, 2H), 2.55-2.52 (m, 2H), 1.98-1.95 (m, 1H), 1.84-1.81 (m, 2H), 1.26-1.23 (m, 2H) | 513.4 |

TABLE 2-continued
| Ex # | Structure | Physical Data $^1$H-NMR in DMSO-$d_6$ at 400 Hz (δ) | MS m/z |
|---|---|---|---|
| 241 | 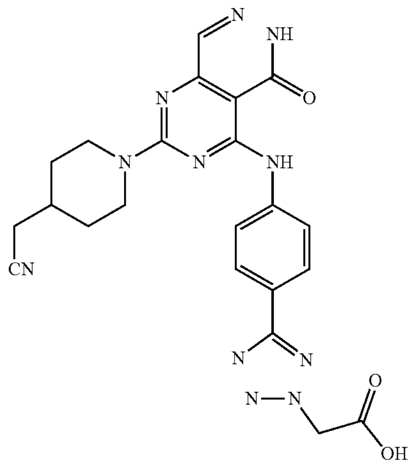 | 12.90 (s, 1H), 11.90 (bs, 1H), 8.09 (d, J = 8.3 Hz, 2H), 7.95 (s, 1H), 7.91 (d, J = 8.8 Hz, 2H), 4.94 (s, 2H), 4.80-4.77 (m, 2H), 3.06-3.00 (m, 2H), 2.56-2.54 (m, 4H), 1.99 (m, 1H), 1.89-1.86 (m, 2H) | 486.4 (M − 1) |
| 242 | 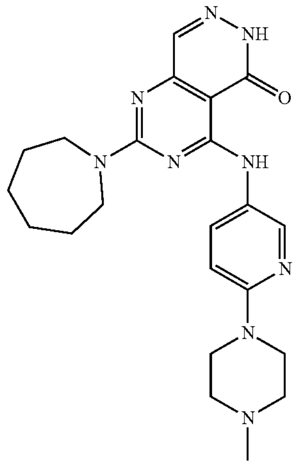 [SMILES: CN1CCN(c2ccc(Nc3nc(N4CCCCCC4)nc4cn[nH]c(=O)c34)cn2)CC1] | 12.71 (s, 1H), 11.99 (s, 1H), 8.47 (d, J = 2.9 Hz, 1H), 7.95 (dd, $J_1$ = 2.7 Hz, $J_2$ = 9.1 Hz, 1H), 7.87 (s, 1H), 6.88 (d, J = 9.3 Hz, 1H), 3.79 (t, J = 6.1 Hz, 2H), 3.70 (t, J = 5.9 Hz, 2H), 3.45 (t, J = 4.7 Hz, 4H), 2.40 (t, J = 4.9 Hz, 4H), 2.22 (s, 3H), 1.74 (m, 4H), 1.50 (m, 4H) | 436.3 |
| 243 | 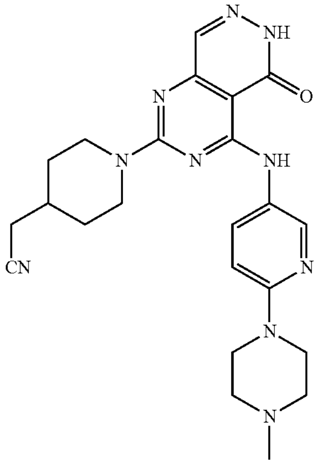 [SMILES: CN1CCN(c2ccc(Nc3nc(N4CCC(CC#N)CC4)nc4cn[nH]c(=O)c34)cn2)CC1] | 12.76 (s, 1H), 10.97 (s, 1H), 8.42 (d, J = 2.5 Hz, 1H), 7.88 (dd, $J_1$ = 2.7 Hz, $J_2$ = 9.1 Hz, 1H), 7.87 (s, 1H), 6.90 (d, J = 8.8 Hz, 1H), 4.79-4.61 (m, 2H), 3.46 (t, J = 4.9 Hz, 4H), 3.00-2.94 (m, 2H), 2.54-2.53 (m, 2H), 2.40 (t, J = 4.9 Hz, 4H), 2.22 (s, 3H), 1.98-1.95 (m, 1H), 1.82-1.80 (m, 2H), 1.23-1.19 (m, 2H) | 461.4 |

TABLE 2-continued
| Ex # | Structure | Physical Data: $^1$H-NMR in DMSO-$d_6$ at 400 Hz (δ) | Physical Data: MS m/z |
|---|---|---|---|
| 244 | 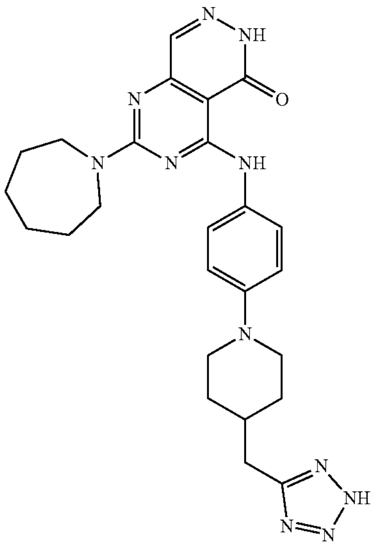 [SMILES: O=c1[nH]ncc2nc(N3CCCCCC3)nc(Nc3ccc(N4CCC(Cc5nn[nH]n5)CC4)cc3)c12] | 12.70 (s, 1H), 11.17 (s, 1H), 7.86 (s, 1H), 7.62 (d, J = 7.3 Hz, 2H), 6.97 (m, 2H), 3.80 (t, J = 6.1 Hz, 2H), 3.75 (t, J = 5.9 Hz, 2H), 3.67-3.64 (m, 2H), 2.89-2.87 (m, 2H), 2.67-2.59 (m, 2H), 1.89 (m, 1H), 1.75-1.68 (m, 6H), 1.51 (m, 4H), 1.37-1.35 (m, 2H) | 502.5 |
| 245 | 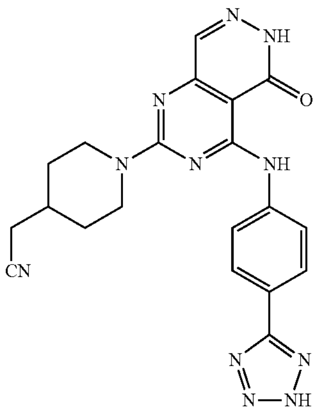 [SMILES: N#CCC1CCN(c2nc(Nc3ccc(-c4nn[nH]n4)cc3)c3c(=O)[nH]ncc3n2)CC1] | 16.70 (s, 1H), 12.87 (s, 1H), 11.60 (s, 1H), 8.09 (d, J = 8.3 Hz, 2H), 7.97 (d, J = 8.4 Hz, 2H), 7.94 (s, 1H), 4.82-4.74 (m, 2H), 3.06 (m, 2H), 2.57-2.53 (m, 2H), 2.01-1.91 (m, 1H), 1.86 (m, 2H), 1.26-1.23 (m, 2H) | 428.3 (M − 1) |
| 246 | 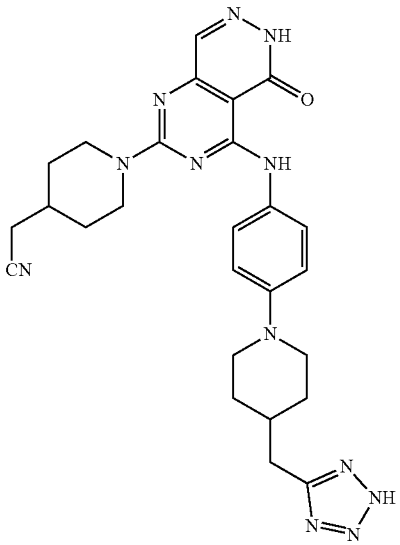 [SMILES: N#CCC1CCN(c2nc(Nc3ccc(N4CCC(Cc5nn[nH]n5)CC4)cc3)c3c(=O)[nH]ncc3n2)CC1] | 16.04 (bs, 1H), 12.75 (s, 1H), 11.13 (s, 1H), 7.87 (s, 1H), 7.55 (d, J = 9.3 Hz, 2H), 6.97 (d, J = 8.8 Hz, 2H), 4.78 (m, 2H), 3.69-3.66 (m, 2H), 3.02-2.95 (m, 2H), 2.88-2.86 (m, 2H), 2.67-2.60 (m, 2H), 2.55-2.30 (m, 2H), 1.97-1.91 (m, 1H), 1.90-1.81 (m, 3H), 1.70-1.67 (m, 2H), 1.39-1.33 (m, 2H), 1.24-1.21 (m, 2H) | 525.5 (M − 1) |

TABLE 2-continued
| Ex # | Structure | Physical Data: $^1$H-NMR in DMSO-$d_6$ at 400 Hz (δ) | Physical Data: MS m/z |
|---|---|---|---|
| 247 | 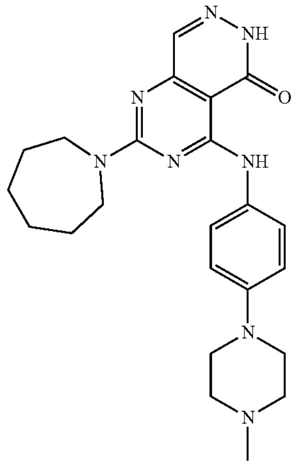 | — | 435.5 |
| 248 | 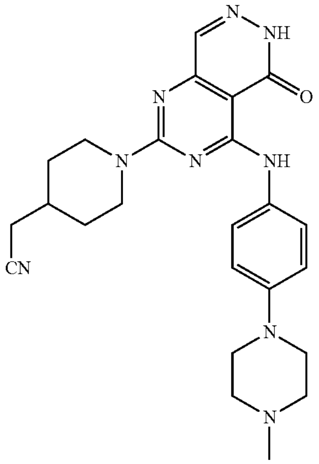 | 12.75 (s, 1H), 11.13 (s, 1H), 7.88 (s, 1H), 7.56 (d, J = 8.8 Hz, 2H), 6.98 (d, J = 9.3 Hz, 2H), 4.78-4.73 (m, 2H), 3.13 (t, J = 4.7 Hz, 4H), 3.02-2.95 (m, 2H), 2.55-2.52 (m, 2H), 2.47 (m, 4H), 2.24 (s, 3H), 1.97-1.95 (m, 1H), 1.84-1.81 (m, 2H), 1.23-1.22 (m, 2H) | 460.5 |
| 249 | 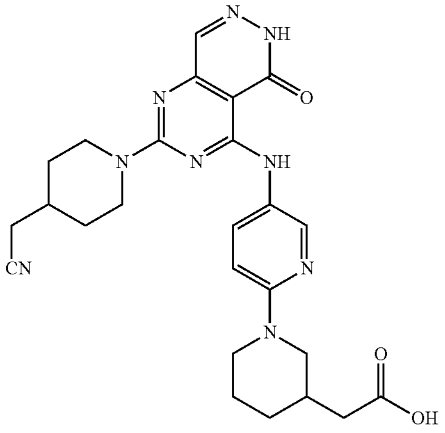 [SMILES: N#CCC1CCN(c2nc(Nc3ccc(N4CCCC(CC(=O)O)C4)nc3)c3c(=O)[nH]ncc3n2)CC1] | 12.76 (s, 1H), 10.94 (s, 1H), 8.38 (d, J = 2.5 Hz, 1H), 7.89-7.86 (m, 2H), 6.87 (d, J = 9.3 Hz, 1H), 4.78-4.61 (m, 2H), 4.19-4.10 (m, 2H), 3.00-2.94 (m, 2H), 2.65-2.55 (m, 2H), 2.54-2.53 (m, 2H), 2.45-2.28 (m, 2H), 1.96-1.80 (m, 6H), 1.23-1.19 (m, 4H) | 504.5 |

TABLE 2-continued
| Ex # | Structure | Physical Data $^1$H-NMR in DMSO-$d_6$ at 400 Hz (δ) | MS m/z |
|---|---|---|---|
| 250 | 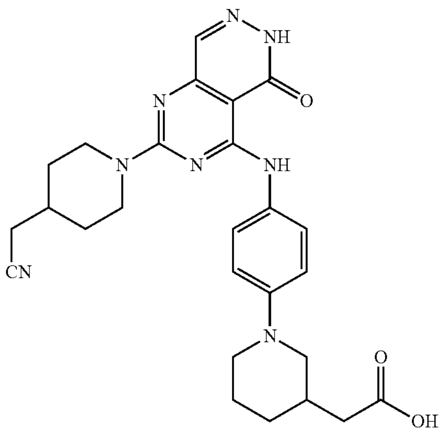 [SMILES: N#CCC1CCN(c2nc(Nc3ccc(N4CCCC(CC(=O)O)C4)cc3)c3c(=O)[nH]ncc3n2)CC1] | 12.74 (bs, 1H), 11.13 (s, 1H), 7.87 (s, 1H), 7.55 (d, J = 8.8 Hz, 2H), 6.95 (d, J = 8.8 Hz, 2H), 4.78 (m, 2H), 3.62-3.55 (m, 2H), 3.01-2.95 (m, 2H), 2.55-2.53 (m, 2H), 2.30-2.09 (m, 2H), 1.98 (m, 2H), 1.84-1.51 (m, 6H), 1.12-1.09 (m, 2H) | 503.4 |
| 251 | 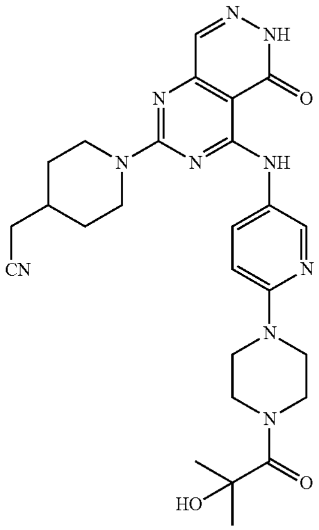 [SMILES: CC(C)(O)C(=O)N1CCN(c2ccc(Nc3nc(N4CCC(CC#N)CC4)nc4cn[nH]c(=O)c34)cn2)CC1] | 12.77 (s, 1H), 10.98 (s, 1H), 8.44 (d, J = 2.4 Hz, 1H), 7.92 (dd, $J_1$ = 2.7 Hz, $J_2$ = 9.1 Hz, 1H), 7.88 (s, 1H), 6.93 (d, J = 9.3 Hz, 1H), 5.47 (s, 1H), 4.54 (m, 2H), 4.06-4.00 (m, 2H), 3.50-3.47 (m, 4H), 3.00-2.94 (m, 2H), 2.55-2.52 (m, 4H), 2.00-1.94 (m, 1H), 1.83-1.80 (m, 2H), 1.34 (s, 6H), 1.25-1.19 (m, 2H) | 531.2 |
| 252 | 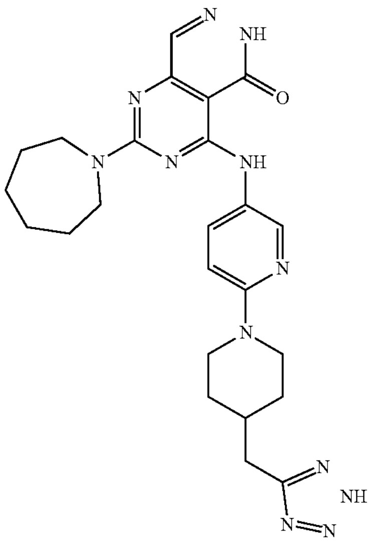 | 16.10 (bs, 1H), 12.71 (s, 1H), 10.98 (s, 1H), 8.43 (d, J = 2.4 Hz, 1H), 7.94 (dd, $J_1$ = 2.7 Hz, $J_2$ = 9.1 Hz, 1H), 7.87 (s, 1H), 6.88 (d, J = 9.3 Hz, 1H), 4.26-4.23 (m, 2H), 3.79 (t, J = 5.9 Hz, 2H), 3.70 (t, J = 5.9 Hz, 2H), 2.85 (d, J = 6.9 Hz, 2H), 2.79-2.73 (m, 2H), 2.00-1.95 (m, 1H), 1.73-1.65 (m, 6H), 1.50 (m, 4H), 1.23-1.21 (m, 2H) | 503.6 |

TABLE 2-continued
| Ex # | Structure | Physical Data $^1$H-NMR in DMSO-$d_6$ at 400 Hz (δ) | MS m/z |
|---|---|---|---|
| 253 | 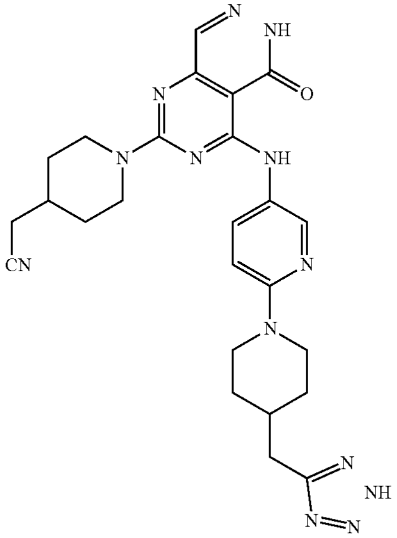 | 16.04 (bs, 1H), 12.76 (s, 1H), 10.95 (s, 1H), 8.39 (d, J = 2.9 Hz, 1H), 7.88 (s, 1H), 7.87 (dd, $J_1$ = 2.7 Hz, $J_2$ = 9.1 Hz, 1H), 6.90 (d, J = 9.3 Hz, 1H), 4.79-4.62 (m, 2H), 4.27-4.24 (m, 2H), 3.00-2.94 (m, 2H), 2.87-2.85 (m, 2H), 2.80-2.74 (m, 2H), 2.54-2.53 (m, 4H), 2.01-1.95 (m, 2H), 1.82-1.80 (m, 2H), 1.82-1.80 (m, 2H), 1.68-1.65 (m, 2H), 1.28-1.19 (m, 4H) | 528.5 |
| 254 | 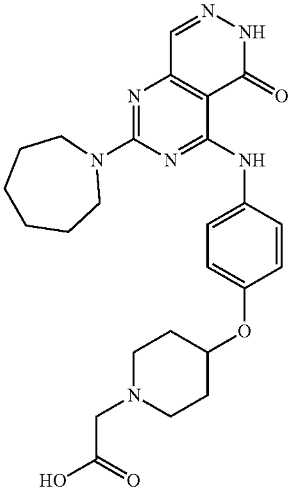 [SMILES: O=C(O)CN1CCC(Oc2ccc(Nc3nc(N4CCCCCC4)nc4cn[nH]c(=O)c34)cc2)CC1] | 12.76 (s, 1H), 11.19 (s, 1H), 7.87 (s, 1H), 7.66 (d, J = 8.8 Hz, 2H), 6.99 (d, J = 9.3 Hz, 2H), 4.42-4.40 (m, 1H), 3.80 (t, J = 5.9 Hz, 2H), 3.74 (t, J = 5.9 Hz, 2H), 3.13 (s, 2H), 2.95-2.92 (m, 2H), 2.67-2.62 (m, 2H), 2.46-2.40 (m, 2H), 1.98 (m, 2H), 1.75-1.70 (m, 6H), 1.51 (m, 4H) | 494.3 |
| 255 | 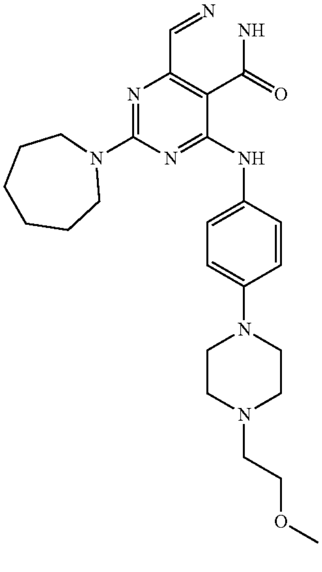 [SMILES: COCCN1CCN(c2ccc(Nc3nc(N4CCCCCC4)nc(C=N)c3C(N)=O)cc2)CC1] | 12.70 (s, 1H), 11.16 (s, 1H), 7.86 (s, 1H), 7.62 (d, J = 8.8 Hz, 2H), 6.95 (d, J = 9.3 Hz, 2H), 3.80 (t, J = 6.0 Hz, 2H), 3.75 (t, J = 5.9 Hz, 2H), 3.47 (t, J = 5.6 Hz, 2H), 3.25 (s, 3H), 3.11 (m, 4H), 2.56 (m, 6H), 1.78-1.74 (m, 4H), 1.51 (m, 4H) | 479.0 |

TABLE 2-continued
| Ex # | Structure | Physical Data $^1$H-NMR in DMSO-$d_6$ at 400 Hz (δ) | MS m/z |
|---|---|---|---|
| 256 | 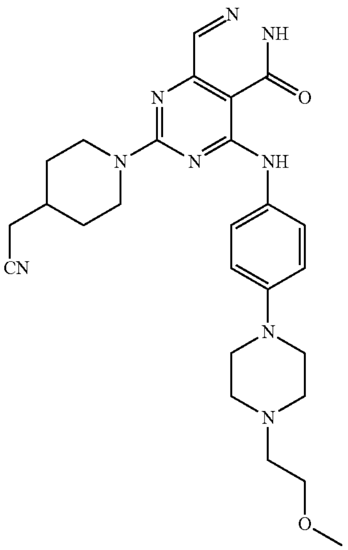 [SMILES: COCCN1CCN(c2ccc(Nc3nc(N4CCC(CC#N)CC4)nc(C=N)c3C(N)=O)cc2)CC1] | 12.76 (s, 1H), 11.14 (s, 1H), 7.88 (s, 1H), 7.56 (d, J = 9.3 Hz, 2H), 6.97 (d, J = 8.8 Hz, 2H), 4.78-4.71 (m, 2H), 3.48 (t, J = 5.7 Hz, 2H), 3.12 (s, 3H), 3.07-2.96 (m, 6H), 2.55-2.53 (m, 8H), 1.98-1.97 (m, 1H), 1.84-1.81 (m, 2H), 1.23-1.20 (m, 2H) | 504.2 |
| 257 | 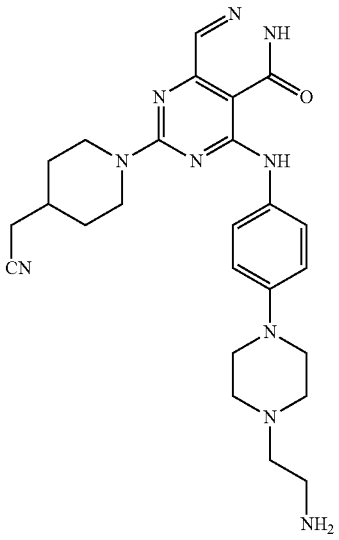 [SMILES: N#CCC1CCN(c2nc(C=N)c(C(N)=O)c(Nc3ccc(N4CCN(CCN)CC4)cc3)n2)CC1] | 11.14 (s, 1H), 7.87 (s, 1H), 7.56 (d, J = 8.8 Hz, 2H), 6.97 (d, J = 8.8 Hz, 2H), 3.98 (m, 2H), 3.12 (m, 4H), 3.07 (m, 2H), 3.07-2.95 (m, 2H), 2.67-2.64 (m, 2H), 2.55-2.53 (m, 4H), 2.37-2.33 (m, 2H), 1.97 (m, 1H), 1.84-1.81 (m, 2H), 1.23-1.20 (m, 2H) | 489.4 |

TABLE 2-continued
| Ex # | Structure | Physical Data $^1$H-NMR in DMSO-$d_6$ at 400 Hz (δ) | MS m/z |
|---|---|---|---|
| 258 | 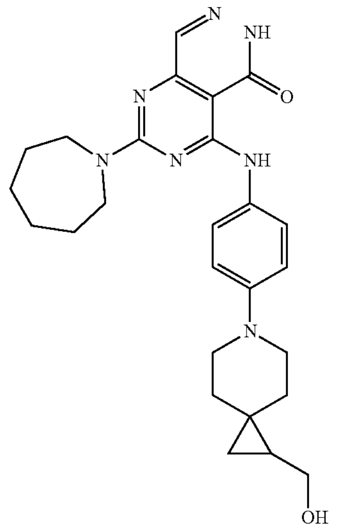 [SMILES: N=Cc1nc(N2CCCCCC2)nc(Nc2ccc(N3CCC4(CC3)CC4CO)cc2)c1C(N)=O] | 12.70 (s, 1H), 11.15 (s, 1H), 7.86 (s, 1H), 7.61 (d, J = 9.3 Hz, 2H), 6.97 (d, J = 8.8 Hz, 2H), 4.41 (t, J = 5.2 Hz, 1H), 3.80 (t, J = 6.2 Hz, 2H), 3.75 (t, J = 5.9 Hz, 2H), 3.56-3.38 (m, 1H), 3.36-3.35 (m, 2H), 3.30-3.23 (m, 1H), 3.13-3.05 (m, 2H), 1.78-1.66 (m, 5H), 1.51 (m, 6H), 1.37-1.27 (m, 1H), 0.89-0.82 (m, 1H), 0.48-0.45 (m, 1H), 0.17-0.15 (m, 1H) | 476.4 |
| 259 | 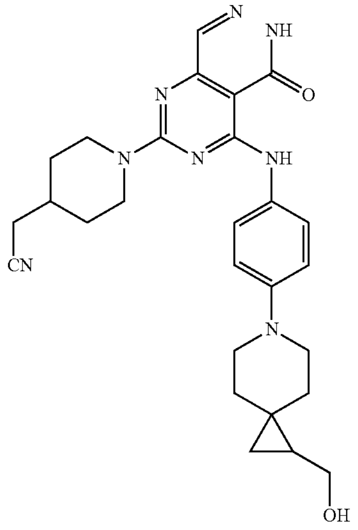 [SMILES: N#CCC1CCN(c2nc(C=N)c(C(N)=O)c(Nc3ccc(N4CCC5(CC4)CC5CO)cc3)n2)CC1] | 12.75 (s, 1H), 11.13 (s, 1H), 7.88 (s, 1H), 7.55 (d, J = 9.3 Hz, 2H), 6.99 (d, J = 9.3 Hz, 2H), 4.76 (m, 2H), 4.41 (t, J = 5.4 Hz, 1H), 3.56-3.51 (m, 1H), 3.37-3.34 (m, 1H), 3.30-3.25 (m, 1H), 3.14-3.06 (m, 2H), 3.02-2.96 (m, 2H), 2.55-2.53 (m, 2H), 1.97-1.96 (m, 1H), 1.84-1.81 (m, 2H), 1.72-1.68 (m, 1H), 1.54-1.47 (m, 2H), 1.36-1.09 (m, 4H), 0.88-0.82 (m, 1H), 0.48-0.45 (m, 1H), 0.18-0.15 (m, 1H) | 501.2 |

TABLE 2-continued
| Ex # | Structure | Physical Data: $^1$H-NMR in DMSO-$d_6$ at 400 Hz (δ) | Physical Data: MS m/z |
|---|---|---|---|
| 260 | 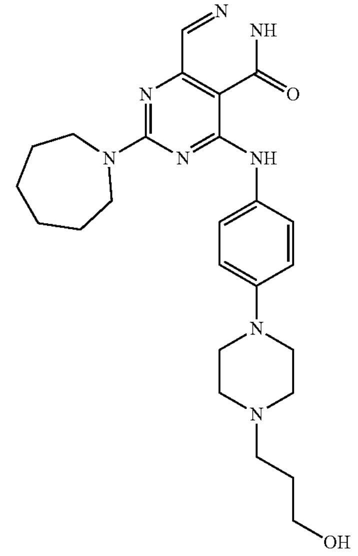 [SMILES: N=Cc1nc(N2CCCCCC2)nc(Nc2ccc(N3CCN(CCCO)CC3)cc2)c1C(N)=O] | 12.70 (s, 1H), 11.16 (s, 1H), 7.86 (s, 1H), 7.62 (d, J = 8.8 Hz, 2H), 6.96 (d, J = 9.3 Hz, 2H), 3.80 (t, J = 6.1 Hz, 2H), 3.75 (t, J = 5.9 Hz, 2H), 3.46 (t, J = 6.1 Hz, 2H), 3.12 (m, 4H), 2.41-2.38 (m, 2H), 1.77-1.74 (m, 4H), 1.63-1.60 (m, 2H), 1.51 (m, 4H) | 479.4 |
| 261 | 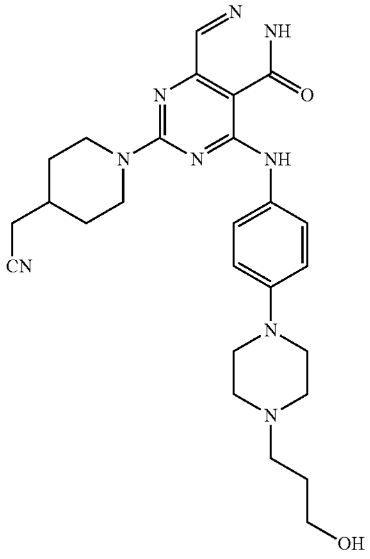 [SMILES: N#CCC1CCN(c2nc(C=N)c(C(N)=O)c(Nc3ccc(N4CCN(CCCO)CC4)cc3)n2)CC1] | 12.76 (s, 1H), 11.14 (s, 1H), 7.88 (s, 1H), 7.56 (d, J = 9.3 Hz, 2H), 6.98 (d, J = 8.8 Hz, 2H), 4.78-4.71 (m, 2H), 3.46 (t, J = 6.4 Hz, 2H), 3.13 (m, 4H), 3.02-2.95 (m, 2H), 2.55-2.53 (m, 6H), 2.42-2.38 (m, 2H), 1.97-1.96 (m, 1H), 1.84-1.81 (m, 2H), 1.65-1.58 (m, 2H), 1.23-1.22 (m, 2H) | 504.4 |

TABLE 2-continued
| Ex # | Structure | Physical Data<br>$^1$H-NMR in DMSO-$d_6$ at 400 Hz (δ) | MS m/z |
| --- | --- | --- | --- |
| 262 | 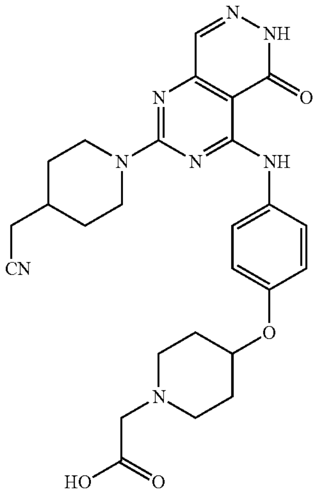 [SMILES: N#CCC1CCN(c2nc(Nc3ccc(OC4CCN(CC(=O)O)CC4)cc3)c3c(=O)[nH]ncc3n2)CC1] | 12.78 (s, 1H), 11.17 (s, 1H), 7.89 (s, 1H), 7.61 (d, J = 8.8 Hz, 2H), 7.02 (d, J = 8.8 Hz, 2H), 4.45-4.44 (m, 2H), 4.43 (m, 1H), 3.22 (s, 2H), 3.02-2.96 (m, 4H), 2.74-2.67 (m, 2H), 2.67 (t, J = 1.8 Hz, 2H), 2.55-2.54 (m, 2H), 2.03-2.00 (m, 3H), 1.84-1.81 (m, 2H), 1.77-1.73 (m, 2H) | 519.4 |
| 263 | 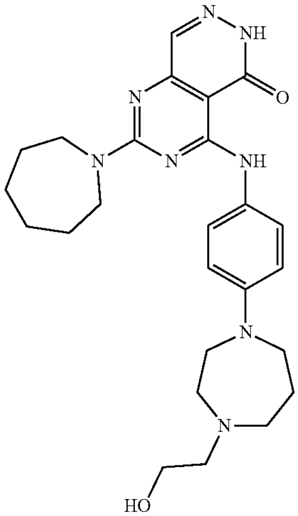 [SMILES: O=c1[nH]ncc2nc(N3CCCCCC3)nc(Nc3ccc(N4CCCN(CCO)CC4)cc3)c12] | 12.67 (s, 1H), 11.08 (s, 1H), 7.84 (s, 1H), 7.55 (d, J = 9.3 Hz, 2H), 6.70 (d, J = 8.8 Hz, 2H), 4.39 (m, 1H), 3.79 (t, J = 6.1 Hz, 25H), 3.74 (t, J = 5.9 Hz, 2H), 3.49-3.42 (m, 6H), 2.79 (m, 2H), 2.62-2.56 (m, 4H), 1.87 (t, J = 5.1 Hz, 2H), 1.77-1.74 (m, 4H), 1.51 (m, 4H) | 479.4 |
| 264 | 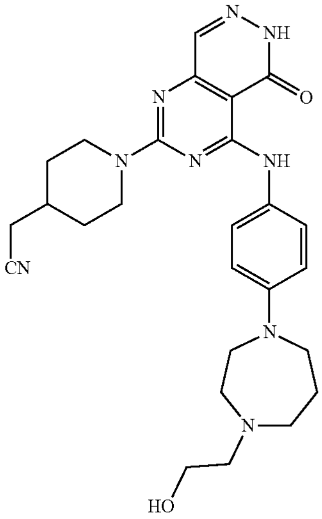 [SMILES: N#CCC1CCN(c2nc(Nc3ccc(N4CCCN(CCO)CC4)cc3)c3c(=O)[nH]ncc3n2)CC1] | 12.73 (s, 1H), 11.06 (s, 1H), 7.86 (s, 1H), 7.50 (d, J = 9.3 Hz, 2H), 6.73 (d, J = 8.8 Hz, 2H), 4.76 (m, 2H), 4.73 (m, 1H), 3.49 (m, 4H), 3.45 (t, J = 6.1 Hz, 2H), 3.00-2.94 (m, 2H), 2.80 (m, 2H), 2.59-2.53 (m, 6H), 1.97-1.94 (m, 1H), 1.88-1.81 (m, 4H), 1.23-1.21 (m, 2H) | 504.4 |

TABLE 2-continued
| Ex # | Structure | Physical Data: $^1$H-NMR in DMSO-$d_6$ at 400 Hz (δ) | MS m/z |
|---|---|---|---|
| 265 | 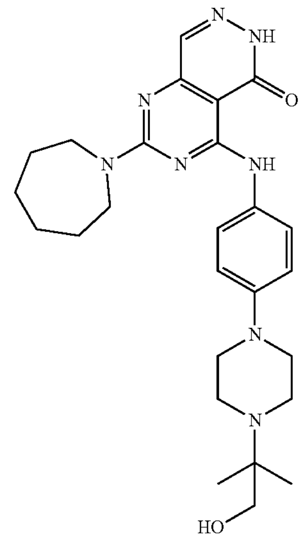 [SMILES: CC(C)(CO)N1CCN(c2ccc(Nc3nc(N4CCCCCC4)nc4cn[nH]c(=O)c34)cc2)CC1] | 12.69 (s, 1H), 11.15 (s, 1H), 7.86 (s, 1H), 7.61 (d, J = 8.8 Hz, 2H), 6.93 (d, J = 8.8 Hz, 2H), 4.28 (m, 1H), 3.80 (t, J = 5.9 Hz, 2H), 3.75 (t, J = 5.9 Hz, 2H), 3.09 (m, 4H), 2.70 (m, 4H), 1.77-1.74 (m, 4H), 1.51 (m, 4H), 1.23 (s, 6H) | 493.5 |
| 266 | 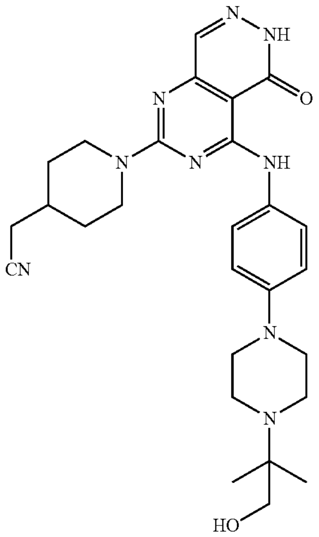 | 12.75 (s, 1H), 11.13 (s, 1H), 7.87 (s, 1H), 7.55 (d, J = 9.3 Hz, 2H), 6.95 (d, J = 8.8 Hz, 2H), 4.72 (m, 2H), 4.27 (m, 1H), 3.09 (m, 4H), 3.02-2.95 (m, 2H), 2.69-2.68 (m, 4H), 2.55-2.53 (m, 2H), 1.99-1.95 (m, 1H), 1.84-1.81 (m, 2H), 1.34-1.17 (m, 4H), 0.98 (s, 6H) | 518.2 |

TABLE 2-continued
| Ex # | Structure | Physical Data $^1$H-NMR in DMSO-$d_6$ at 400 Hz (δ) | MS m/z |
|---|---|---|---|
| 267 | 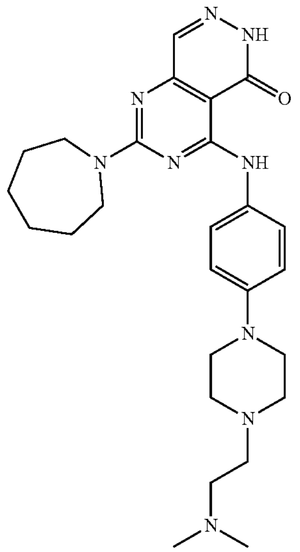 [SMILES: CN(C)CCN1CCN(c2ccc(Nc3nc(N4CCCCCC4)nc4cn[nH]c(=O)c34)cc2)CC1] | — | 492.5 |
| 268 | 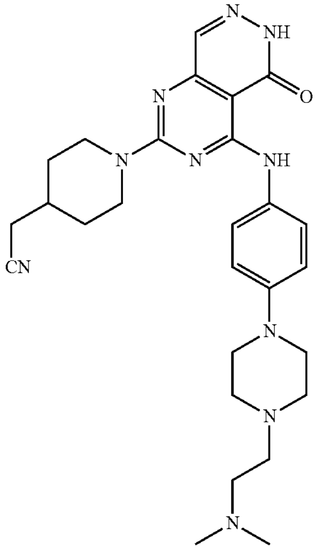 | 12.75 (s, 1H), 11.14 (s, 1H), 7.88 (s, 1H), 7.56 (d, J = 8.8 Hz, 2H), 6.97 (d, J = 8.8 Hz, 2H), 3.12-3.11 (m, 4H), 3.02-2.95 (m, 2H), 2.55-2.53 (m, 6H), 2.23 (s, 6H), 1.99-1.97 (m, 1H), 1.84-1.81 (m, 2H), 1.34-1.23 (m, 6H) | 517.5 |
| 269 | 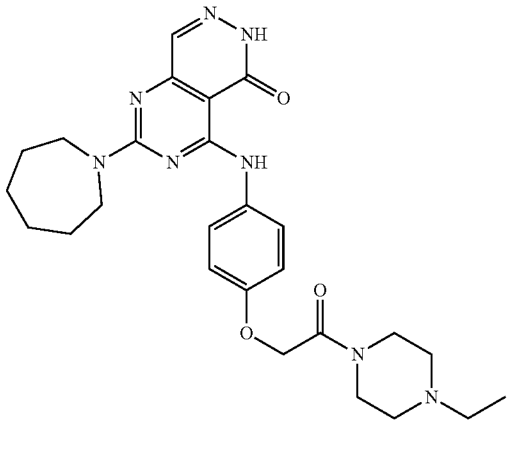 [SMILES: CCN1CCN(C(=O)COc2ccc(Nc3nc(N4CCCCCC4)nc4cn[nH]c(=O)c34)cc2)CC1] | 12.72 (s, 1H), 11.19 (s, 1H), 7.87 (s, 1H), 7.67 (d, J = 8.8 Hz, 2H), 6.95 (d, J = 9.3 Hz, 2H), 4.80 (s, 2H), 3.80 (t, J = 6.1 Hz, 2H), 3.74 (t, J = 5.9 Hz, 2H), 3.46 (m, 6H), 2.33-2.32 (m, 4H), 1.76 (m, 4H), 1.51 (m, 4H), 1.01 (t, J = 7.1 Hz, 3H) | 507.3 |

TABLE 2-continued
| Ex # | Structure | Physical Data $^1$H-NMR in DMSO-$d_6$ at 400 Hz (δ) | MS m/z |
|---|---|---|---|
| 270 | 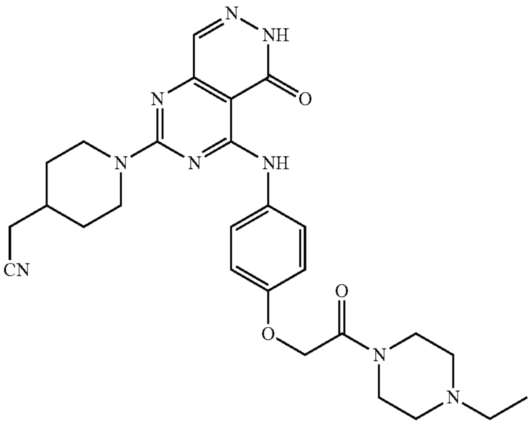 [SMILES: CCN1CCN(C(=O)COc2ccc(Nc3nc(N4CCC(CC#N)CC4)nc4cn[nH]c(=O)c34)cc2)CC1] | — | 532.4 |
| 271 | 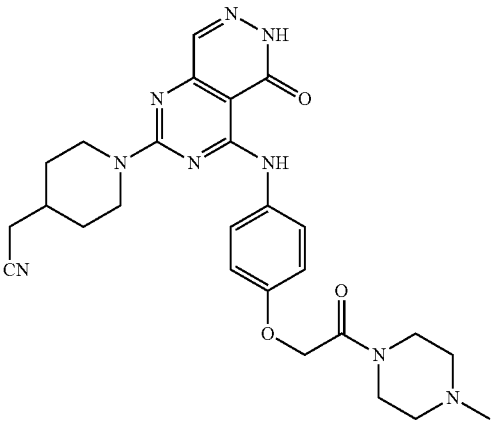 [SMILES: CN1CCN(C(=O)COc2ccc(Nc3nc(N4CCC(CC#N)CC4)nc4cn[nH]c(=O)c34)cc2)CC1] | 12.77 (s, 1H), 11.16 (s, 1H), 7.89 (s, 1H), 7.61 (d, J = 7.8 Hz, 2H), 6.97 (d, J = 8.3 Hz, 2H), 4.81 (s, 2H), 4.69 (m, 2H), 3.51-3.46 (m, 6H), 2.99 (m, 2H), 2.67 (m, 2H), 2.34-2.27 (m, 4H), 2.19 (s, 3H), 1.99-1.91 (m, 1H), 1.84-1.81 (m, 2H) | 518.4 |
| 272 | 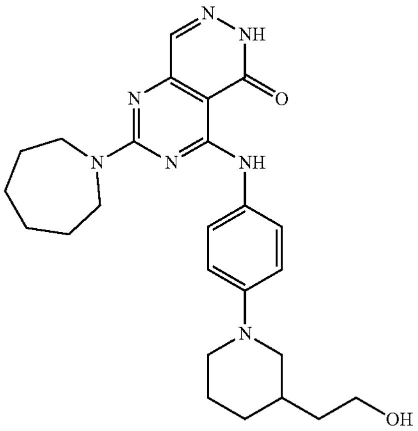 [SMILES: O=c1[nH]ncc2nc(N3CCCCCC3)nc(Nc3ccc(N4CCCC(CCO)C4)cc3)c12] | 12.69 (s, 1H), 11.15 (s, 1H), 7.86 (s, 1H), 7.61 (d, J = 9.2 Hz, 2H), 6.95 (d, J = 8.8 Hz, 2H), 4.41 (t, J = 5.1 Hz, 1H), 3.80 (t, J = 6.1 Hz, 2H), 3.75 (t, J = 5.9 Hz, 2H), 3.59-3.56 (m, 2H), 3.52-3.47 (m, 2H), 1.77-1.69 (m, 8H), 1.51-1.42 (m, 8H) | 464.5 |

TABLE 2-continued
| Ex # | Structure | Physical Data $^1$H-NMR in DMSO-$d_6$ at 400 Hz (δ) | MS m/z |
| --- | --- | --- | --- |
| 273 | 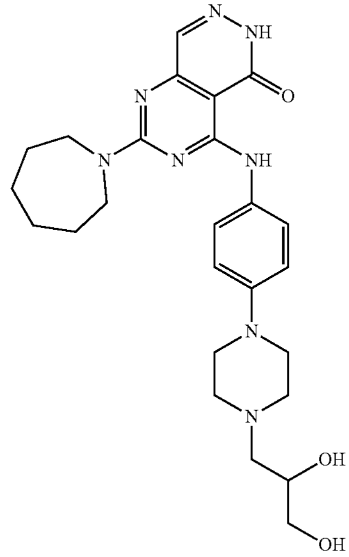 [SMILES: O=c1[nH]ncc2nc(N3CCCCCC3)nc(Nc3ccc(N4CCN(CC(O)CO)CC4)cc3)c12] | 12.70 (s, 1H), 11.16 (s, 1H), 7.86 (s, 1H), 7.62 (d, J = 8.8 Hz, 2H), 6.95 (d, J = 9.3 Hz, 2H), 4.44 (m, 1H), 3.80 (t, J = 6.2 Hz, 2H), 3.75 (t, J = 5.9 Hz, 2H), 3.65 (d, J = 5.4 Hz, 1H), 3.35-3.33 (m, 2H), 3.12 (t, J = 4.4 Hz, 4H), 2.59-2.53 (m, 4H), 2.46-2.42 (m, 2H), 2.33-2.27 (m, 1H), 1.78-1.74 (m, 4H), 1.51 (m, 4H) | 495.2 |
| 274 | 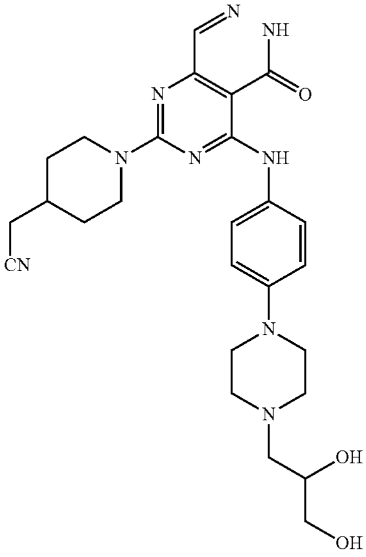 [SMILES: N#CCC1CCN(c2nc(C=N)c(C(N)=O)c(Nc3ccc(N4CCN(CC(O)CO)CC4)cc3)n2)CC1] | 12.75 (s, 1H), 11.14 (s, 1H), 7.88 (s, 1H), 7.56 (d, J = 9.3 Hz, 2H), 6.98 (d, J = 8.8 Hz, 2H), 4.71 (m, 2H), 4.45 (m, 1H), 3.65 (m, 1H), 3.35-3.33 (m, 2H), 3.13 (m, 4H), 3.02-2.96 (m, 2H), 2.60 (m, 4H), 2.52-2.51 (m, 2H), 2.46-2.45 (m, 2H), 2.33-2.01 (m, 1H), 1.99-1.95 (m, 1H), 1.84-1.81 (m, 2H), 1.23-1.21 (m, 2H) | 520.4 |

TABLE 2-continued
| Ex # | Structure | Physical Data $^1$H-NMR in DMSO-$d_6$ at 400 Hz (δ) | MS m/z |
|---|---|---|---|
| 275 | 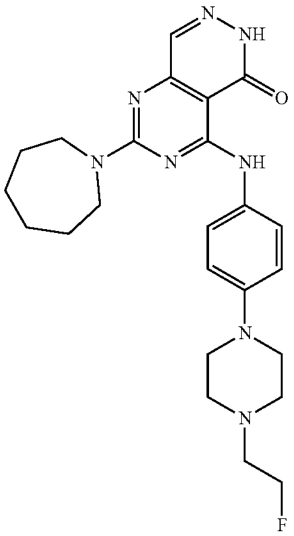 [SMILES: O=c1[nH]ncc2nc(N3CCCCCC3)nc(Nc3ccc(N4CCN(CCF)CC4)cc3)c12] | 12.70 (s, 1H), 11.16 (s, 1H), 7.86 (s, 1H), 7.62 (d, J = 8.8 Hz, 2H), 6.96 (d, J = 8.8 Hz, 2H), 4.64 (t, J = 4.9 Hz, 1H), 4.52 (t, J = 4.9 Hz, 1H), 3.80 (t, J = 6.1 Hz, 2H), 3.75 (t, J = 5.9 Hz, 2H), 3.13 (t, J = 4.9 Hz, 4H), 2.71 (t, J = 4.9 Hz, 1H), 2.64 (t, J = 4.9 Hz, 1H), 2.60 (t, J = 4.7 Hz, 4H), 1.78-1.74 (m, 4H), 1.51 (m, 4H) | 467.3 |
| 276 | 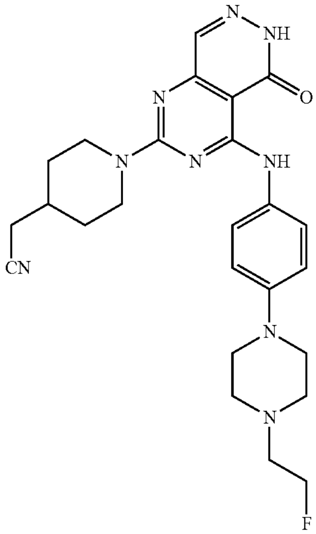 | 12.75 (s, 1H), 11.14 (s, 1H), 7.87 (s, 1H), 7.56 (d, J = 8.8 Hz, 2H), 6.98 (d, J = 8.8 Hz, 2H), 4.77-4.71 (m, 2H), 4.64 (t, J = 4.9 Hz, 1H), 4.52 (t, J = 4.9 Hz, 1H), 3.14 (t, J = 4.9 Hz, 4H), 3.02-2.95 (m, 2H), 2.71 (t, J = 4.4 Hz, 1H), 2.67 (t, J = 2.0 Hz, 1H), 2.64 (t, J = 4.9 Hz, 4H), 2.60-2.53 (m, 2H), 1.98-1.95 (m, 1H), 1.84-1.82 (m, 2H), 1.23-1.21 (m, 2H) | 492.4 |
| 277 | 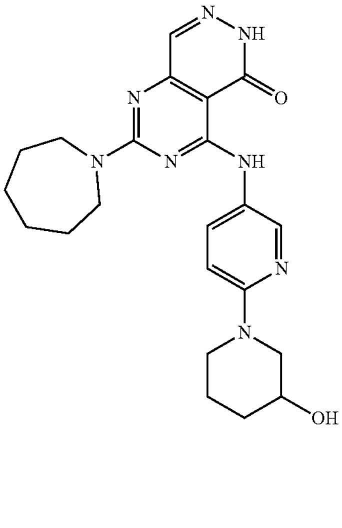 [SMILES: O=c1[nH]ncc2nc(N3CCCCCC3)nc(Nc3ccc(N4CCCC(O)C4)nc3)c12] | 12.70 (s, 1H), 10.96 (s, 1H), 8.42 (d, J = 2.5 Hz, 1H), 7.92 (dd, J1 = 2.4 Hz, J2 = 9.3 Hz, 1H), 7.87 (s, 1H), 6.85 (d, J = 9.3 Hz, 2H), 4.82 (d, J = 4.4 Hz, 1H), 4.16-4.13 (m, 1H), 3.95-3.92 (m, 1H), 3.79 (t, J = 6.1 Hz, 2H), 3.70 (t, J = 4.9 Hz, 2H), 3.51-3.48 (m, 1H), 1.73 (m, 6H), 1.50-1.33 (m, 8H) | 437.4 |

TABLE 2-continued
| Ex # | Structure | Physical Data: $^1$H-NMR in DMSO-$d_6$ at 400 Hz (δ) | Physical Data: MS m/z |
|---|---|---|---|
| 278 | 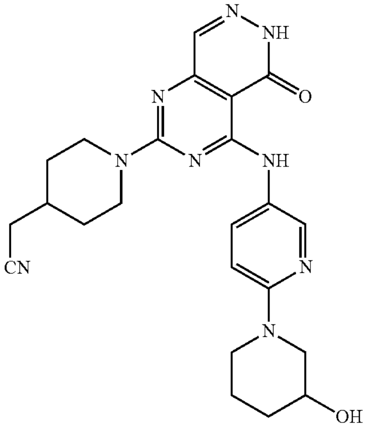 | — | 437.4 |
| 279 | 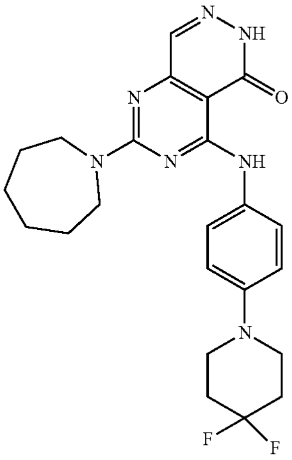 [SMILES: O=c1[nH]ncc2nc(N3CCCCCC3)nc(Nc3ccc(N4CCC(F)(F)CC4)cc3)c12] | 12.70 (s, 1H), 11.18 (s, 1H), 7.86 (s, 1H), 7.64 (d, J = 9.3 Hz, 2H), 7.92 (d, J = 8.9 Hz, 2H), 3.80 (t, J = 6.2 Hz, 2H), 3.75 (t, J = 5.9 Hz, 2H), 3.32-3.30 (m, 4H), 2.10-2.01 (m, 4H), 1.78-1.75 (m, 4H), 1.51 (m, 4H) | 456.2 |
| 280 | 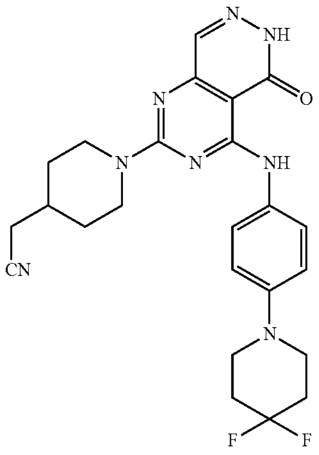 [SMILES: N#CCC1CCN(c2nc(Nc3ccc(N4CCC(F)(F)CC4)cc3)c3c(=O)[nH]ncc3n2)CC1] | 12.76 (s, 1H), 11.16 (s, 1H), 7.88 (s, 1H), 7.59 (d, J = 8.8 Hz, 2H), 7.05 (d, J = 9.3 Hz, 2H), 4.80-4.60 (m, 2H), 3.34-3.31 (m, 4H), 3.02-2.96 (m, 2H), 2.55-2.53 (m, 2H), 2.11-2.01 (m, 4H), 1.99-1.97 (m, 1H), 1.84-1.81 (m, 2H), 1.23-1.21 (m, 2H) | 479.1 |

TABLE 2-continued
| Ex # | Structure | Physical Data $^1H$-NMR in DMSO-$d_6$ at 400 Hz (δ) | MS m/z |
|---|---|---|---|
| 281 | 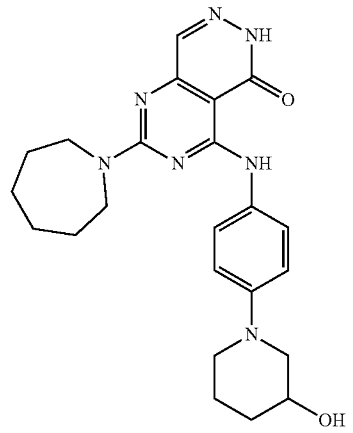 [SMILES: O=c1[nH]ncc2nc(N3CCCCCC3)nc(Nc3ccc(N4CCCC(O)C4)cc3)c12] | — | 436.3 |
| 282 | 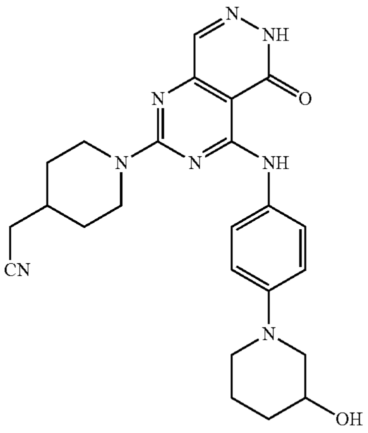 | — | 461.5 |
| 283 | 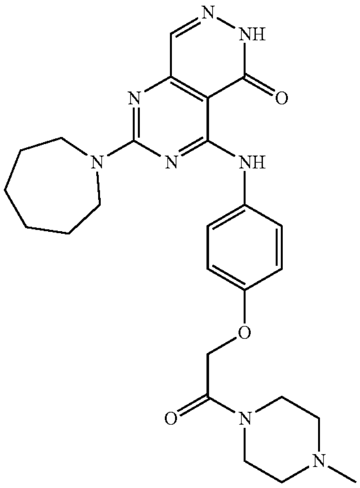 [SMILES: CN1CCN(C(=O)COc2ccc(Nc3nc(N4CCCCCC4)nc4cn[nH]c(=O)c34)cc2)CC1] | 12.72 (s, 1H), 11.19 (s, 1H), 7.87 (s, 1H), 7.67 (d, J = 8.8 Hz, 2H), 6.95 (d, J = 8.8 Hz, 2H), 4.80 (s, 2H), 3.80 (t, J = 5.9 Hz, 2H), 3.74 (t, J = 5.9 Hz, 2H), 3.45 (m, 4H), 2.46-2.26 (m, 4H), 2.18 (s, 3H), 1.76 (m, 4H), 1.51 (m, 4H) | 493.2 |

TABLE 2-continued
| Ex # | Structure | Physical Data $^1$H-NMR in DMSO-$d_6$ at 400 Hz (δ) | MS m/z |
|---|---|---|---|
| 284 | 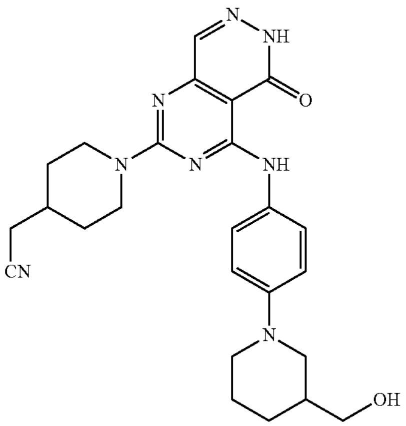 [SMILES: N#CCC1CCN(c2nc(Nc3ccc(N4CCCC(CO)C4)cc3)c3c(=O)[nH]ncc3n2)CC1] | 12.75 (s, 1H), 11.13 (s, 1H), 7.88 (s, 1H), 7.87 (s, 1H), 7.55 (d, J = 9.3 Hz, 2H), 6.96 (d, J = 8.8 Hz, 2H), 4.72 (m, 2H), 4.53 (t, J = 5.2 Hz, 1H), 3.68-3.57 (m, 2H), 3.36-3.34 (m, 2H), 3.01-2.95 (m, 2H), 2.66-2.60 (m, 1H), 2.55-2.53 (m, 2H), 2.43-2.38 (m, 1H), 1.96-1.94 (m, 1H), 1.84-1.82 (m, 2H), 1.73-1.71 (m, 4H), 1.59-1.54 (m, 1H), 1.23-1.21 (m, 2H) | 475.6 |
| 285 | 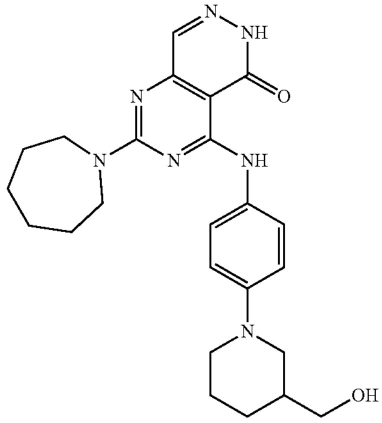 [SMILES: O=c1[nH]ncc2nc(N3CCCCCC3)nc(Nc3ccc(N4CCCC(CO)C4)cc3)c12] | 12.69 (s, 1H), 11.15 (s, 1H), 7.86 (s, 1H), 7.61 (d, J = 8.8 Hz, 2H), 6.94 (d, J = 8.8 Hz, 2H), 4.53 (m, 2H), 3.80 (t, J = 6.2 Hz, 2H), 3.75 (t, J = 5.9 Hz, 2H), 3.69-3.54 (m, 2H), 2.67-2.53 (m, 1H), 2.46-2.33 (m, 1H), 1.78-1.71 (m, 8H), 1.57 (m, 1H), 1.51 (m, 4H), 1.23 (m, 2H) | 450.3 |
| 286 | 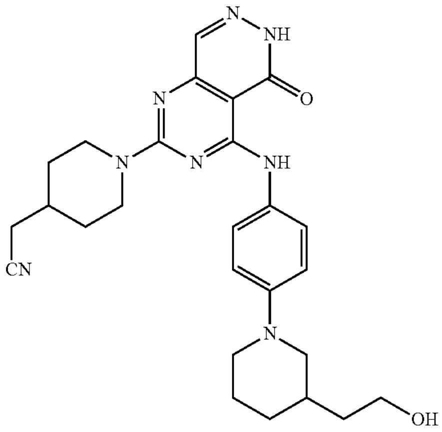 [SMILES: N#CCC1CCN(c2nc(Nc3ccc(N4CCCC(CCO)C4)cc3)c3c(=O)[nH]ncc3n2)CC1] | 12.75 (s, 1H), 11.13 (s, 1H), 7.55 (d, J = 9.3 Hz, 2H), 6.97 (d, J = 8.8 Hz, 2H), 4.80 (m, 2H), 4.41 (t, J = 5.1 Hz, 1H), 3.60-3.53 (m, 4H), 2.99 (m, 2H), 2.55-2.53 (m, 4H), 2.0 (m, 1H), 1.85-1.69 (m, 6H), 1.34-1.22 (m, 4H) . | 489.4 |

TABLE 2-continued
| Ex # | Structure | Physical Data<br>$^1$H-NMR in DMSO-$d_6$ at 400 Hz (δ) | MS m/z |
|---|---|---|---|
| 287 | 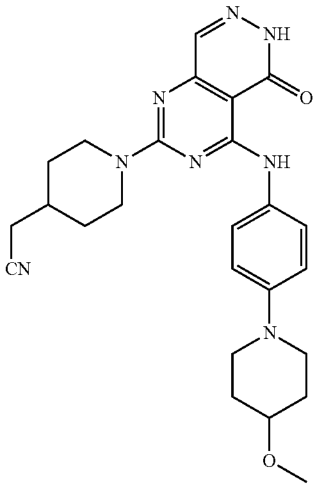 | 12.75 (s, 1H), 11.13 (s, 1H), 7.87 (s, 1H), 7.55 (d, J = 8.8 Hz, 2H), 6.98 (d, J = 9.3 Hz, 2H), 4.90-4.60 (m, 2H), 3.50-3.45 (m, 2H), 3.35-3.33 (m, 1H), 3.27 (s, 3H), 3.01-2.84 (m, 4H), 2.55-2.52 (m, 2H), 1.98-1.81 (m, 5H), 1.56-1.48 (m, 2H), 1.23-1.21 (m, 2H) | 475.2 |
| 288 | 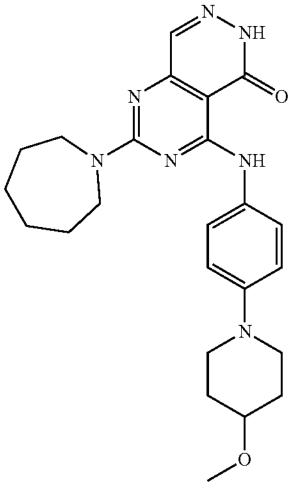 [SMILES: COC1CCN(c2ccc(Nc3nc(N4CCCCCC4)nc4cn[nH]c(=O)c34)cc2)CC1] | 12.70 (s, 1H), 11.16 (s, 1H), 7.86 (s, 1H), 7.61 (d, J = 8.8 Hz, 2H), 6.97 (d, J = 7.3 Hz, 2H), 3.80 (t, J = 6.1 Hz, 2H), 3.75 (t, J = 5.9 Hz, 2H), 3.48-3.44 (m, 3H), 3.27 (s, 3H), 2.87 (m, 2H), 1.95-1.93 (m, 2H), 1.77-1.74 (m, 4H), 1.51 (m, 6H) | 450.4 |
| 289 | 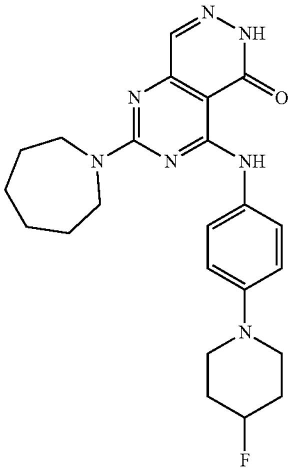 [SMILES: O=c1[nH]ncc2nc(N3CCCCCC3)nc(Nc3ccc(N4CCC(F)CC4)cc3)c12] | 12.70 (s, 1H), 11.16 (s, 1H), 7.86 (s, 1H), 7.62 (d, J = 9.3 Hz, 2H), 6.99 (d, J = 9.3 Hz, 2H), 4.89-4.77 (m, 1H), 3.80 (t, J = 6.2 Hz, 2H), 3.75 (t, J = 5.9 Hz, 2H), 3.36-3.35 (m, 2H), 3.13-3.07 (m, 2H), 2.00-1.92 (m, 2H), 1.82-1.75 (m, 6H), 1.51 (m, 4H) | 438.0 |

TABLE 2-continued
| Ex # | Structure | Physical Data: $^1$H-NMR in DMSO-$d_6$ at 400 Hz (δ) | MS m/z |
|---|---|---|---|
| 290 | 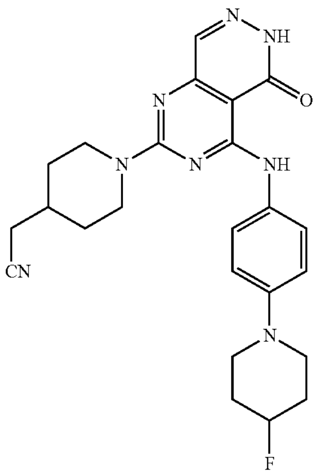 [SMILES: N#CCC1CCN(c2nc(Nc3ccc(N4CCC(F)CC4)cc3)c3c(=O)[nH]ncc3n2)CC1] | 12.75 (s, 1H), 11.14 (s, 1H), 7.88 (s, 1H), 7.56 (d, J = 8.8 Hz, 2H), 7.01 (d, J = 9.3 Hz, 2H), 4.92-4.75 (m, 3H), 3.37-3.34 (m, 2H), 3.15-3.09 (m, 2H), 3.02-2.96 (m, 2H), 2.55-2.52 (m, 4H), 2.03-1.92 (m, 3H), 1.84-1.74 (m, 4H), 1.24-1.21 (m, 2H) | 463.4 |
| 291 | 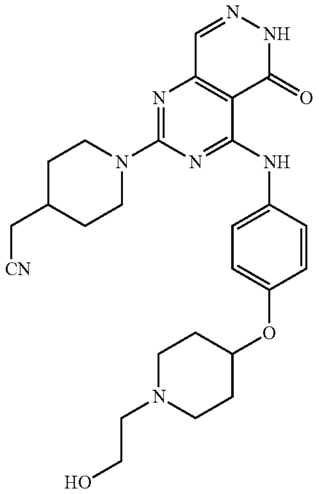 [SMILES: N#CCC1CCN(c2nc(Nc3ccc(OC4CCN(CCO)CC4)cc3)c3c(=O)[nH]ncc3n2)CC1] | 12.78 (s, 1H), 11.19 (s, 1H), 7.90 (s, 1H), 7.64 (d, J = 8.8 Hz, 2H), 7.06 (d, J = 6.9 Hz, 2H), 5.30 (m, 1H), 4.90-4.70 (m, 2H), 4.50 (m, 1H), 3.73 (m, 2H), 3.30-2.96 (m, 6H), 2.56-2.54 (m, 4H), 2.20-2.16 (m, 2H), 1.98-1.81 (m, 5H) | 505.2 |
| 292 | 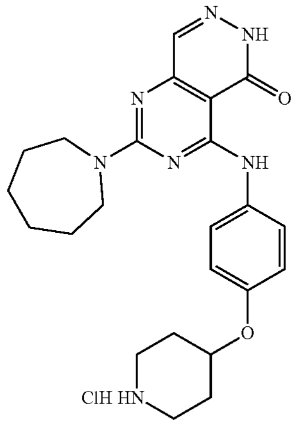 | 12.75 (s, 1H), 11.23 (s, 1H), 8.64 (s, 2H), 7.90 (s, 1H), 7.70 (d, J = 8.8 Hz, 2H), 7.04 (d, J = 9.3 Hz, 2H), 4.64-4.61 (m, 1H), 3.81 (t, J = 6.1 Hz, 2H), 3.75 (t, J = 5.9 Hz, 2H), 3.39-3.37 (m, 2H), 3.24-3.08 (m, 2H), 2.12-2.07 (m, 2H), 1.84-1.76 (m, 6H), 1.51 (m, 4H) | 436.4 |

TABLE 2-continued
| Ex # | Structure | Physical Data: $^1$H-NMR in DMSO-$d_6$ at 400 Hz (δ) | Physical Data: MS m/z |
|---|---|---|---|
| 293 | 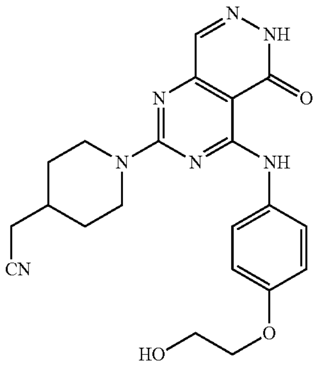 [SMILES: N#CCC1CCN(c2nc(Nc3ccc(OCCO)cc3)c3c(=O)[nH]ncc3n2)CC1] | 12.70 (s, 1H), 11.15 (s, 1H), 7.89 (s, 1H), 7.61 (d, J = 8.8 Hz, 2H), 6.99 (d, J = 9.3 Hz, 2H), 4.86 (t, J = 5.4 Hz, 1H), 4.80-4.69 (m, 2H), 3.99 (t, J = 5.1 Hz, 2H), 3.72 (t, J = 5.1 Hz, 2H), 3.02-2.95 (m, 2H), 2.55-2.53 (m, 2H), 1.97 (m, 1H), 1.84-1.81 (m, 2H), 1.24 (m, 2H) | 420.3 (M − 1) |
| 294 | 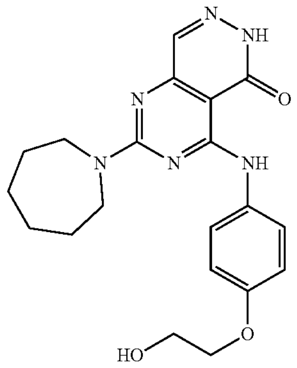 [SMILES: O=c1[nH]ncc2nc(N3CCCCCC3)nc(Nc3ccc(OCCO)cc3)c12] | 12.71 (s, 1H), 11.17 (s, 1H), 7.87 (s, 1H), 7.67 (d, J = 9.3 Hz, 2H), 6.97 (d, J = 9.3 Hz, 2H), 4.85 (t, J = 5.6 Hz, 1H), 3.99 (t, J = 4.9 Hz, 2H), 3.80 (t, J = 6.1 Hz, 2H), 3.76-3.69 (m, 4H), 1.76 (m, 4H), 1.51 (m, 4H) | 397.2 |
| 295 | 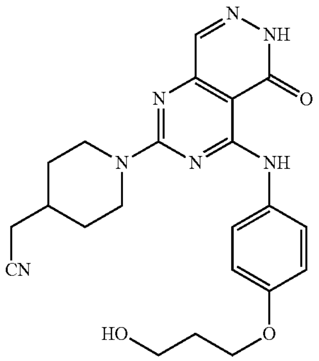 [SMILES: N#CCC1CCN(c2nc(Nc3ccc(OCCCO)cc3)c3c(=O)[nH]ncc3n2)CC1] | 12.76 (s, 1H), 11.20 (s, 1H), 7.89 (s, 1H), 7.61 (d, J = 8.8 Hz, 2H), 6.97 (d, J = 9.3 Hz, 2H), 4.73 (m, 2H), 4.54 (m, 1H), 4.04 (t, J = 6.4 Hz, 2H), 3.56 (t, J = 6.1 Hz, 2H), 3.01-2.95 (m, 2H), 2.55-2.53 (m, 2H), 1.99-1.89 (m, 1H), 1.87-1.81 (m, 4H), 1.23-1.21 (m, 2H) | 436.4 |
| 296 | 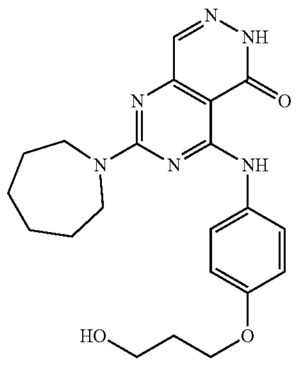 [SMILES: O=c1[nH]ncc2nc(N3CCCCCC3)nc(Nc3ccc(OCCCO)cc3)c12] | 12.71 (s, 1H), 11.17 (s, 1H), 7.87 (s, 1H), 7.66 (d, J = 8.8 Hz, 2H), 6.95 (d, J = 9.3 Hz, 2H), 4.54 (t, J = 5.4 Hz, 1H), 4.03 (t, J = 6.4 Hz, 2H), 3.80 (t, J = 5.9 Hz, 2H), 3.74 (t, J = 5.9 Hz, 2H), 3.58-3.54 (m, 2H), 1.86 (t, J = 6.4 Hz, 2H), 1.76 (m, 4H), 1.51 (m, 4H) | 411.3 |

TABLE 2-continued
| Ex # | Structure | Physical Data $^1$H-NMR in DMSO-$d_6$ at 400 Hz (δ) | MS m/z |
|---|---|---|---|
| 297 | 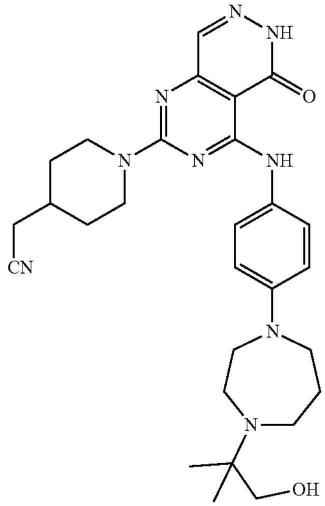 [SMILES: CC(C)(CO)N1CCCN(c2ccc(Nc3nc(N4CCC(CC#N)CC4)nc4cn[nH]c(=O)c34)cc2)CC1] | 12.72 (s, 1H), 11.05 (s, 1H), 7.86 (s, 3H), 7.49 (d, J = 8.8 Hz, 2H), 6.73 (d, J = 8.8 Hz, 2H), 4.75 (m, 2H), 3.51 (t, J = 5.4 Hz, 4H), 3.29 (m, 2H), 3.00-2.67 (m, 5H), 2.55-2.53 (m, 2H), 1.97-1.94 (m, 1H), 1.83-1.81 (m, 4H), 1.23-1.21 (m, 4H), 1.00 (s, 6H) | 532.3 |
| 298 | 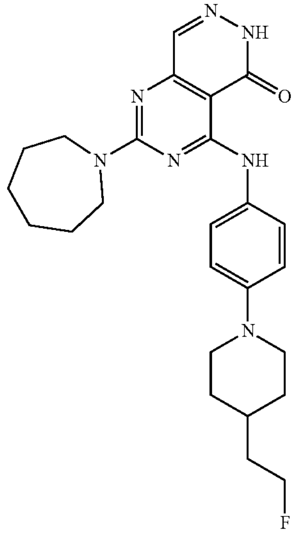 | 12.69 (s, 1H), 11.15 (s, 1H), 7.86 (s, 1H), 7.61 (d, J = 9.3 Hz, 2H), 6.95 (d, J = 8.8 Hz, 2H), 4.60 (t, J = 5.9 Hz, 1H), 4.48 (t, J = 5.9 Hz, 1H), 3.80 (t, J = 6.1 Hz, 2H), 3.76 (t, J = 5.9 Hz, 2H), 3.67-3.64 (m, 2H), 2.66-2.59 (m, 2H), 1.78-1.76 (m, 6H), 1.64-1.58 (m, 3H), 1.51 (m, 4H), 1.31-1.23 (m, 2H) | 466.4 |
| 299 | 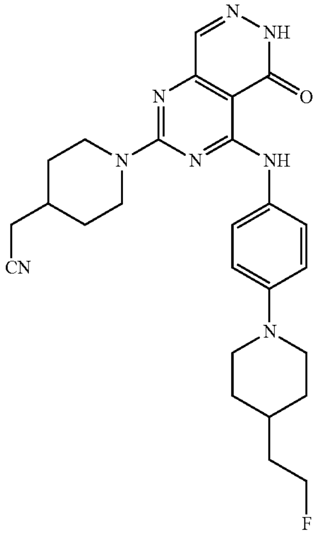 [SMILES: N#CCC1CCN(c2nc(Nc3ccc(N4CCC(CCF)CC4)cc3)c3c(=O)[nH]ncc3n2)CC1] | 12.75 (s, 1H), 11.13 (s, 1H), 7.87 (s, 1H), 7.55 (d, J = 8.8 Hz, 2H), 6.97 (d, J = 9.3 Hz, 2H), 4.77-4.71 (m, 2H), 4.60 (t, J = 6.1 Hz, 1H), 4.48 (t, J = 5.9 Hz, 1H), 3.68-3.65 (m, 2H), 3.01-2.95 (m, 2H), 2.67-2.60 (m, 2H), 2.55-2.53 (m, 2H), 1.98-1.95 (m, 1H), 1.84-1.76 (m, 4H), 1.67 (q, J = 6.4 Hz, 1H), 1.62-1.52 (m, 2H), 1.34-1.21 (m, 4H) | |

TABLE 2-continued
| Ex # | Structure | Physical Data: $^1$H-NMR in DMSO-$d_6$ at 400 Hz (δ) | Physical Data: MS m/z |
|---|---|---|---|
| 300 | 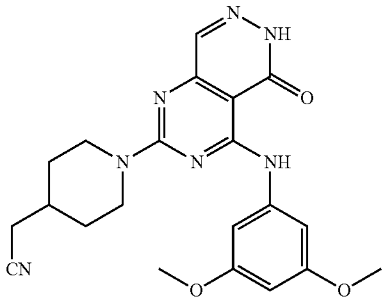 [SMILES: COc1cc(Nc2nc(N3CCC(CC#N)CC3)nc3cn[nH]c(=O)c23)cc(OC)c1] | 12.81 (s, 1H), 11.37 (s, 1H), 7.90 (s, 1H), 6.96 (d, J = 2.4 Hz, 1H), 6.27 (t, J = 2.2 Hz, 1H), 3.76 (s, 6H), 3.03 (m, 2H), 2.55-2.53 (m, 2H), 1.99-1.96 (m, 1H), 1.84-1.81 (m, 2H), 1.25-1.23 (m, 2H) | 422.3 |
| 301 | 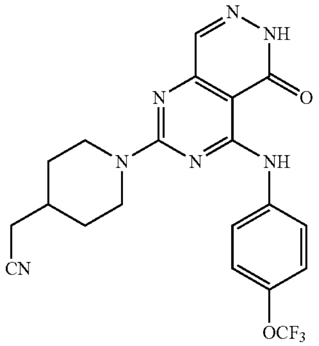 [SMILES: N#CCC1CCN(c2nc(Nc3ccc(OC(F)(F)F)cc3)c3c(=O)[nH]ncc3n2)CC1] | 12.83 (s, 1H), 11.44 (s, 1H), 7.92 (s, 1H), 7.86-7.82 (m, 2H), 7.42 (d, J = 8.3 Hz, 2H), 4.80-4.67 (m, 2H), 3.02 (m, 2H), 2.56-2.53 (m, 2H), 2.00-1.96 (m, 1H), 1.86-1.84 (m, 2H), 1.25-1.23 (m, 2H) | 446.3 |
| 302 | 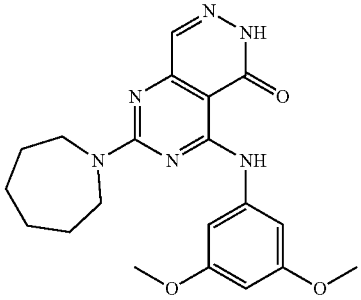 [SMILES: COc1cc(Nc2nc(N3CCCCCC3)nc3cn[nH]c(=O)c23)cc(OC)c1] | 12.76 (s, 1H), 11.43 (s, 1H), 7.89 (s, 1H), 6.99 (d, J = 1.9 Hz, 2H), 6.26 (t, J = 2.2 Hz, 1H), 3.80 (q, J = 5.4 Hz, 4H), 3.76 (m, 6H), 1.76 (s, 6H), 1.76 (m, 4H), 1.51 (m, 4H) | 379.3 |
| 303 | 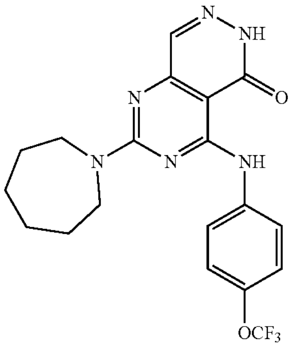 [SMILES: O=c1[nH]ncc2nc(N3CCCCCC3)nc(Nc3ccc(OC(F)(F)F)cc3)c12] | 12.78 (s, 1H), 11.45 (s, 1H), 7.91 (s, 1H), 7.89 (d, J = 9.3 Hz, 2H), 7.40 (d, J = 8.3 Hz, 2H), 3.82 (q, J = 6.1 Hz, 2H), 3.76 (t, J = 5.9 Hz, 2H), 1.77 (t, J = 5.6 Hz, 4H), 1.51 (m, 4H) | 421.3 |

TABLE 2-continued
| Ex # | Structure | Physical Data $^1H$-NMR in DMSO-$d_6$ at 400 Hz (δ) | MS m/z |
|---|---|---|---|
| 304 | 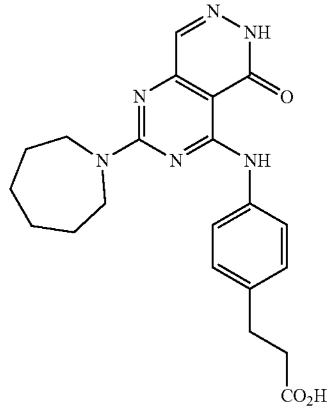 [SMILES: O=C(O)CCc1ccc(Nc2nc(N3CCCCCC3)nc3cn[nH]c(=O)c23)cc1] | 12.73 (s, 1H), 11.31 (s, 1H), 7.88 (s, 1H), 7.68 (d, J = 8.4 Hz, 2H), 7.24 (d, J = 8.3 Hz, 2H), 3.81 (t, J = 6.1 Hz, 2H), 3.76 (t, J = 5.9 Hz, 2H), 2.81 (t, J = 7.6 Hz, 2H), 2.55-2.53 (m, 2H), 1.79-1.75 (m, 4H), 1.51 (m, 4H) | 409.5 |
| 305 | 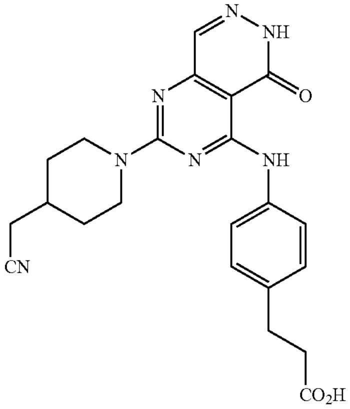 [SMILES: N#CCC1CCN(c2nc(Nc3ccc(CCC(=O)O)cc3)c3c(=O)[nH]ncc3n2)CC1] | 12.79 (s, 1H), 11.29 (s, 1H), 7.90 (s, 1H), 7.63 (d, J = 8.8 Hz, 2H), 7.27 (d, J = 8.3 Hz, 2H), 4.90-4.60 (m 2H), 3.02 (m, 2H), 2.82 (t, J = 7.3 Hz, 2H), 2.56-2.53 (m, 4H), 1.98-1.97 (m, 1H), 1.85-1.82 (m, 2H), 1.23 (m, 2H) | 434.0 |
| 306 | 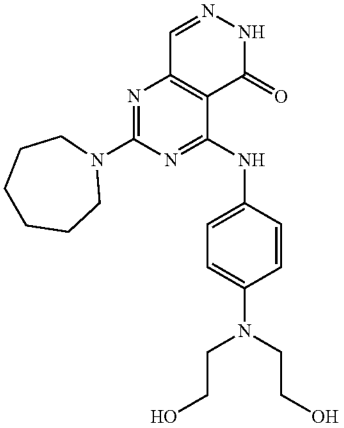 [SMILES: O=c1[nH]ncc2nc(N3CCCCCC3)nc(Nc3ccc(N(CCO)CCO)cc3)c12] | 12.67 (s, 1H), 11.05 (s, 1H), 7.84 (s, 1H), 7.54 (d, J = 8.8 Hz, 2H), 6.70 (d, J = 8.8 Hz, 2H), 4.73 (t, J = 5.4 Hz, 2H), 3.79 (t, J = 5.9 Hz, 2H), 3.74 (t, J = 5.9 Hz, 2H), 3.56-3.52 (m, 4H), 3.42-3.39 (m, 4H), 1.75 (t, J = 4.4 Hz, 4H), 1.51 (m, 4H) | 440.4 |

TABLE 2-continued
| Ex # | Structure | Physical Data $^1$H-NMR in DMSO-$d_6$ at 400 Hz (δ) | MS m/z |
|---|---|---|---|
| 307 | 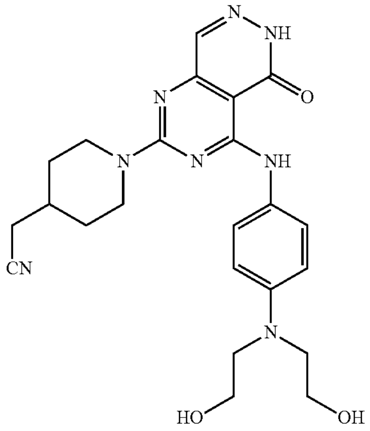 [SMILES: N#CCC1CCN(c2nc(Nc3ccc(N(CCO)CCO)cc3)c3c(=O)[nH]ncc3n2)CC1] | 12.72 (s, 1H), 11.03 (s, 1H), 7.86 (s, 1H), 7.48 (d, J = 8.8 Hz, 2H), 6.72 (d, J = 9.3 Hz, 2H), 4.75-4.42 (m, 4H), 3.57-3.52 (m, 4H), 3.43-3.40 (m, 4H), 3.00-2.97 (m, 2H), 2.55-2.52 (m, 2H), 2.00-1.90 (m, 1H), 1.84-1.81 (m, 2H), 1.23-1.22 (m, 2H) | 465.3 |
| 308 | 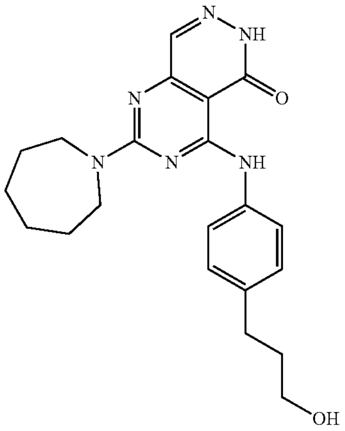 [SMILES: O=c1[nH]ncc2nc(N3CCCCCC3)nc(Nc3ccc(CCCO)cc3)c12] | 12.73 (s, 1H), 11.30 (s, 1H), 7.87 (s, 1H), 7.67 (d, J = 8.4 Hz, 2H), 7.20 (d, J = 8.8 Hz, 2H), 4.45 (t, J = 5.2 Hz, 1H), 3.80 (t, J = 6.2 Hz, 2H), 3.75 (t, J = 5.9 Hz, 2H), 3.42 (q, J = 7.9 Hz, 2H), 1.78-1.70 (m, 6H), 1.51 (m, 4H) | 395.3 |
| 309 | 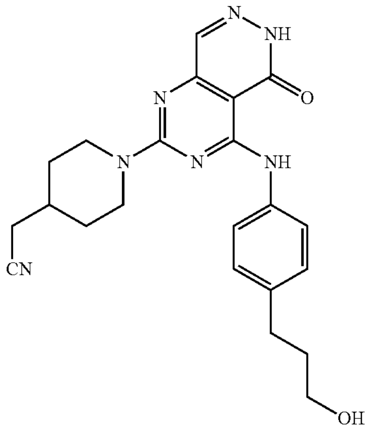 [SMILES: N#CCC1CCN(c2nc(Nc3ccc(CCCO)cc3)c3c(=O)[nH]ncc3n2)CC1] | 12.76 (s, 1H), 11.28 (s, 1H), 7.90 (s, 1H), 7.62 (d, J = 8.3 Hz, 2H), 7.24 (d, J = 8.4 Hz, 2H), 4.80-4.60 (m, 2H), 4.46 (t, J = 5.6 Hz, 1H), 3.42 (q, J = 6.4 Hz, 2H), 3.04-3.01 (m, 2H), 2.60 (t, J = 7.6 Hz, 2H), 2.55-2.52 (m, 2H), 1.99-1.96 (m, 1H), 1.85-1.82 (m, 2H), 1.76-1.69 (m, 2H), 1.23-1.22 (m, 2H) | 420.3 |

TABLE 2-continued
| Ex # | Structure | Physical Data $^1$H-NMR in DMSO-$d_6$ at 400 Hz (δ) | MS m/z |
|---|---|---|---|
| 310 | 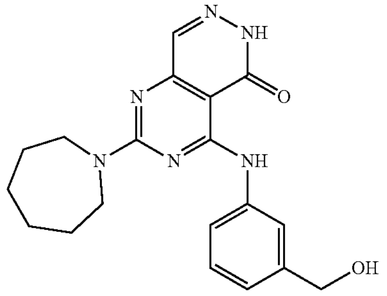 [SMILES: O=c1[nH]ncc2nc(N3CCCCCC3)nc(Nc3cccc(CO)c3)c12] | 12.76 (s, 1H), 11.39 (s, 1H), 7.89 (s, 1H), 7.86 (s, 1H), 7.59-7.57 (m, 1H), 7.33 (t, J = 7.8 Hz, 1H), 7.05 (d, J = 7.8 Hz, 1H), 5.21 (t, J = 5.6 Hz, 1H), 4.52 (d, J = 5.9 Hz, 2H), 3.83-3.78 (m, 4H), 1.80-1.76 (m, 4H), 1.52 (m, 4H) | 367.3 |
| 311 | 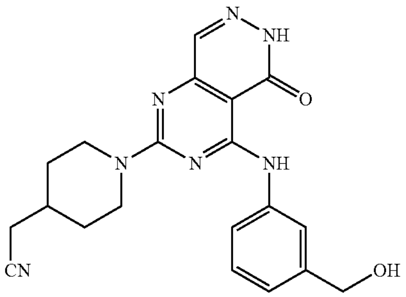 [SMILES: N#CCC1CCN(c2nc(Nc3cccc(CO)c3)c3c(=O)[nH]ncc3n2)CC1] | 12.81 (s, 1H), 11.35 (s, 1H), 7.91 (s, 1H), 7.86 (s, 1H), 7.51 (d, J = 9.3 Hz, 1H), 7.34 (t, J = 7.9 Hz, 1H), 7.05 (d, J = 7.3 Hz, 1H), 5.24 (t, J = 5.9 Hz, 1H), 4.79 (m, 2H), 4.53 (d, J = 5.9 Hz, 2H), 3.04-2.98 (m, 2H), 2.56-2.52 (m, 2H), 1.99-1.98 (m, 1H), 1.86-1.82 (m, 2H), 1.23 (m, 2H) | 392.3 |
| 312 | 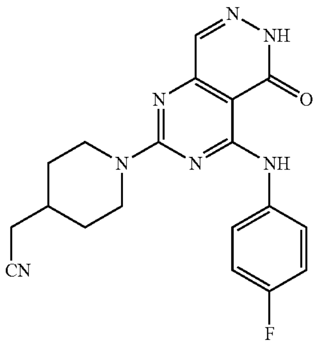 [SMILES: N#CCC1CCN(c2nc(Nc3ccc(F)cc3)c3c(=O)[nH]ncc3n2)CC1] | 12.79 (s, 1H), 11.30 (s, 1H), 7.89 (s, 1H), 7.64 (d, J = 8.3 Hz, 2H), 7.26 (d, J = 8.3 Hz, 2H), 4.79-4.70 (m, 2H), 4.52 (t, J = 5.8 Hz, 1H), 4.40 (t, J = 5.9 Hz, 1H), 3.00 (m, 2H), 2.67 (t, J = 7.6 Hz, 2H), 2.55-2.54 (m, 2H), 2.09-1.89 (m, 3H), 1.85-1.82 (m, 2H), 1.24 (m, 2H) | 420.3 |
| 313 | 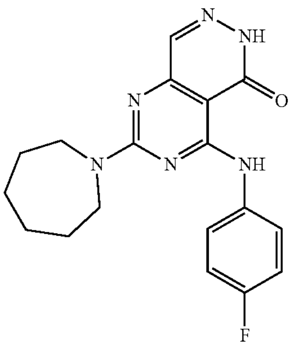 [SMILES: O=c1[nH]ncc2nc(N3CCCCCC3)nc(Nc3ccc(F)cc3)c12] | 12.74 (s, 1H), 11.29 (s, 1H), 7.88 (s, 1H), 7.79-7.76 (m, 2H), 7.25-7.20 (m, 2H), 3.80 (t, J = 6.1 Hz, 2H), 3.73 (t, J = 5.9 Hz, 2H), 1.76-1.75 (m, 4H), 1.50 (m, 4H) | 355.4 |

TABLE 2-continued
| Ex # | Structure | Physical Data<br>$^1$H-NMR in DMSO-$d_6$ at 400 Hz (δ) | MS m/z |
|---|---|---|---|
| 314 | 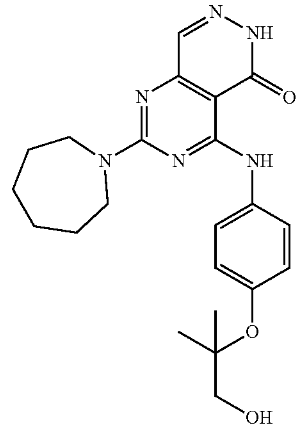 [SMILES: CC(C)(CO)Oc1ccc(Nc2nc(N3CCCCCC3)nc3cn[nH]c(=O)c23)cc1] | 12.72 (s, 1H), 11.25 (s, 1H), 7.87 (s, 1H), 7.66 (d, J = 8.3 Hz, 2H), 7.03 (d, J = 8.8 Hz, 2H), 4.87 (t, J = 5.9 Hz, 1H), 3.80 (t, J = 6.1 Hz, 2H), 3.74 (t, J = 6.1 Hz, 2H), 3.38 (d, J = 5.9 Hz, 2H), 1.75 (m, 4H), 1.51 (m, 4H), 1.19 (m, 6H) | 425.3 |
| 315 | 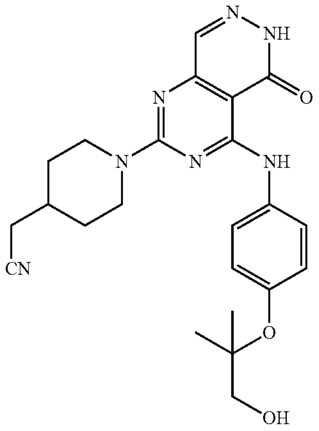 [SMILES: CC(C)(CO)Oc1ccc(Nc2nc(N3CCC(CC#N)CC3)nc3cn[nH]c(=O)c23)cc1] | 12.78 (s, 1H), 11.24 (s, 1H), 7.89 (s, 1H), 7.62-7.60 (m, 2H), 7.05 (dd, $J_1$ = 2.0, $J_2$ = 6.9 Hz, 2H), 4.88 (t, J = 5.6 Hz, 1H), 4.80-4.60 (m, 2H), 3.38 (d, J = 5.9 Hz, 2H), 2.99 (m, 2H), 2.55-2.53 (m, 2H), 1.99 (m, 1H), 1.85-1.82 (m, 2H), 1.24-1.23 (m, 2H), 1.19 (s, 6H) | 449.1 |
| 316 | 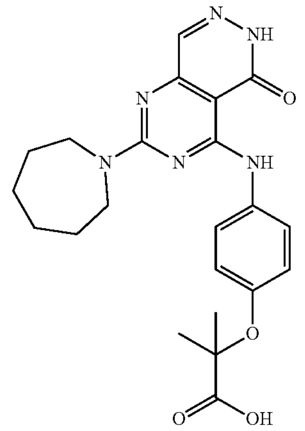 [SMILES: CC(C)(Oc1ccc(Nc2nc(N3CCCCCC3)nc3cn[nH]c(=O)c23)cc1)C(=O)O] | 13.00 (s, 1H), 12.72 (s, 1H), 11.20 (s, 1H), 7.87 (s, 1H), 7.65 (d, J = 8.8 Hz, 2H), 6.87 (d, J = 8.8 Hz, 2H), 3.80 (t, J = 5.9 Hz, 2H), 3.73 (t, J = 5.9 Hz, 2H), 1.75-1.74 (m, 4H), 1.50 (m, 10H) | 437.2 |

TABLE 2-continued
| Ex # | Structure | Physical Data $^1$H-NMR in DMSO-$d_6$ at 400 Hz (δ) | MS m/z |
|---|---|---|---|
| 317 | 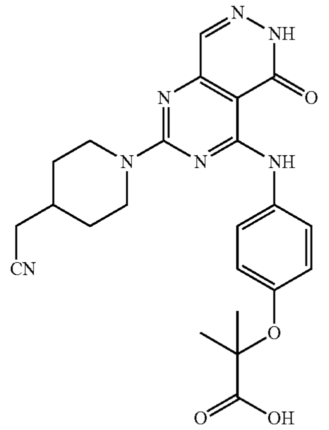 [SMILES: CC(C)(Oc1ccc(Nc2nc(N3CCC(CC#N)CC3)nc3cn[nH]c(=O)c23)cc1)C(=O)O] | 12.76 (s, 1H), 11.18 (s, 1H), 7.87 (s, 1H), 7.58 (d, J = 8.8 Hz, 2H), 6.89 (d, J = 8.8 Hz, 2H), 4.78-4.66 (m, 2H), 3.01-2.95 (m, 2H), 2.55-2.53 (m, 2H), 2.00-1.93 (m, 1H), 1.84-1.81 (m, 2H), 1.51 (s, 6H), 1.26-1.18 (m, 2H) | 462.2 (M − 1) |
| 318 | 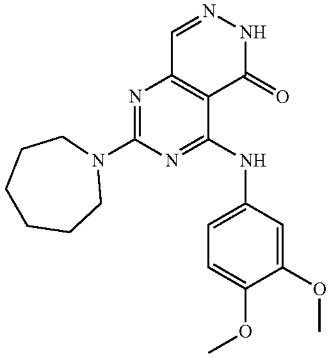 [SMILES: COc1ccc(Nc2nc(N3CCCCCC3)nc3cn[nH]c(=O)c23)cc1OC] | 12.72 (s, 1H), 12.28 (s, 1H), 7.87 (s, 1H), 7.54 (d, J = 2.5 Hz, 1H), 7.16 (dd, $J_1$ = 2.4 Hz, $J_2$ = 8.8 Hz, 1H), 6.96 (d, J = 8.8 Hz, 1H), 3.82-3.80 (m, 4H), 3.79 (s, 3H), 3.75 (s, 3H), 1.75 (m, 4H), 1.51 (m, 4H) | 397.2 |
| 319 | 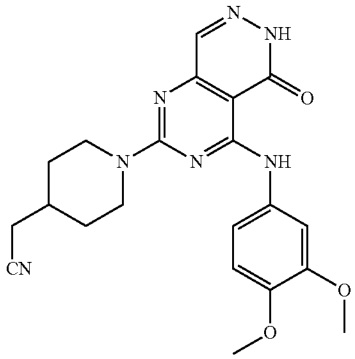 [SMILES: COc1ccc(Nc2nc(N3CCC(CC#N)CC3)nc3cn[nH]c(=O)c23)cc1OC] | 12.78 (s, 1H), 11.22 (s, 1H), 7.89 (s, 1H), 7.56 (d, J = 4.4 Hz, 1H), 7.08 (dd, $J_1$ = 2.3 Hz, $J_2$ = 8.6 Hz, 1H), 6.98 (d, J = 8.3 Hz, 1H), 4.78 (m, 2H), 3.79 (s, 3H), 3.76 (s, 3H), 3.00 (m, 2H), 2.55-2.52 (m, 2H), 1.98-1.96 (m, 1H), 1.83-1.80 (m, 2H), 1.23 (m, 2H) | 420.0 (M − 1) |
| 320 | 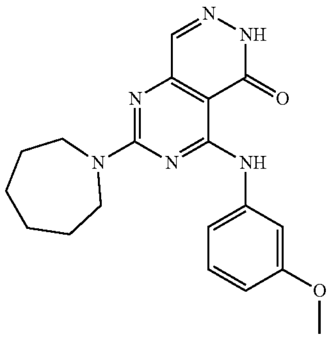 [SMILES: COc1cccc(Nc2nc(N3CCCCCC3)nc3cn[nH]c(=O)c23)c1] | 12.76 (s, 1H), 11.44 (s, 1H), 7.90 (s, 1H), 7.62 (t, J = 2.2 Hz, 1H), 7.28 (t, J = 8.3 Hz, 1H), 7.15 (dd, $J_1$ = 1.2 Hz, $J_2$ = 8.1 Hz, 1H), 6.69 (dd, $J_1$ = 2.0 Hz, $J_2$ = 8.3 Hz, 1H), 3.82 (t, J = 6.1 Hz, 4H), 3.78 (s, 3H), 1.77-1.76 (m, 4H), 1.52 (m, 4H) | 367.2 |

TABLE 2-continued
| Ex # | Structure | Physical Data $^1$H-NMR in DMSO-$d_6$ at 400 Hz (δ) | MS m/z |
|---|---|---|---|
| 321 | 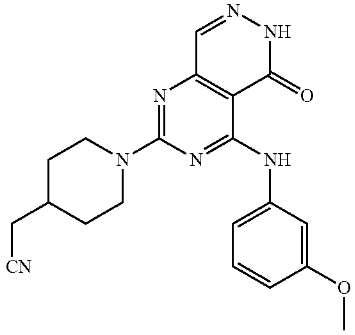 [SMILES: COc1cccc(Nc2nc(N3CCC(CC#N)CC3)nc3cn[nH]c(=O)c23)c1] | 12.81 (s, 1H), 11.39 (s, 1H), 7.91 (s, 1H), 7.58 (t, J = 2.0 Hz, 1H), 7.36 (t, J = 8.1 Hz, 1H), 7.10 (d, J = 9.3 Hz, 1H), 6.71 (dd, $J_1$ = 2.2 Hz, $J_2$ = 8.1 Hz, 1H), 4.79 (m, 2H), 3.79 (s, 3H), 3.03 (m, 2H), 2.56-2.59 (m, 2H), 2.09-1.98 (m, 1H), 1.84-1.82 (m, 2H), 1.23 (m, 2H) | 390.3 (M − 1) |
| 322 | 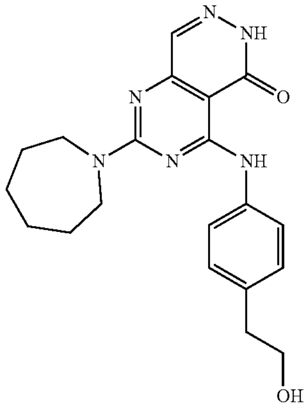 [SMILES: O=c1[nH]ncc2nc(N3CCCCCC3)nc(Nc3ccc(CCO)cc3)c12] | 12.73 (s, 1H), 11.31 (s, 1H), 7.88 (s, 1H), 7.68 (d, J = 8.3 Hz, 2H), 7.23 (d, J = 8.3 Hz, 2H), 4.63 (t, J = 5.7 Hz, 1H), 3.81 (t, J = 6.1 Hz, 2H), 3.77 (t, J = 5.9 Hz, 2H), 3.60 (q, J = 7.3 Hz, 2H), 2.71 (t, J = 6.9 Hz, 2H), 1.78-1.75 (m, 4H), 1.51 (m, 4H) | 379.3 (M − 1) |
| 323 | 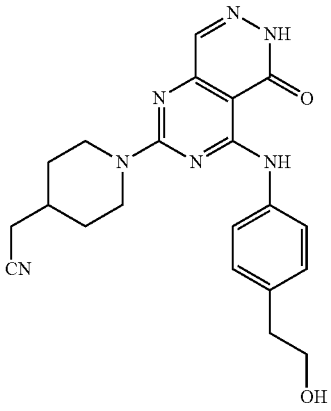 [SMILES: N#CCC1CCN(c2nc(Nc3ccc(CCO)cc3)c3c(=O)[nH]ncc3n2)CC1] | 12.79 (s, 1H), 11.29 (s, 1H), 7.90 (s, 1H), 7.62 (d, J = 8.3 Hz, 2H), 7.25 (d, J = 8.3 Hz, 2H), 4.71 (m, 2H), 4.63 (t, J = 5.1 Hz, 1H), 3.61 (q, J = 7.1 Hz, 2H), 3.01 (m, 2H), 2.72 (t, J = 7.1 Hz, 2H), 2.72 (t, J = 7.1 Hz, 2H), 2.55-2.54 (m, 2H), 1.98 (m, 1H), 1.85-1.82 (m, 2H), 1.23 (m, 2H) | 404.2 (M − 1) |

TABLE 2-continued
| Ex # | Structure | Physical Data $^1$H-NMR in DMSO-$d_6$ at 400 Hz (δ) | Physical Data MS m/z |
|---|---|---|---|
| 324 | 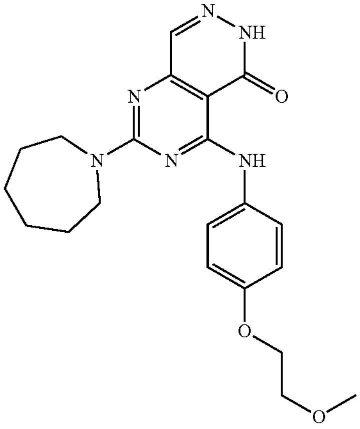 [SMILES: COCCOc1ccc(Nc2nc(N3CCCCCC3)nc3cn[nH]c(=O)c23)cc1] | 12.71 (s, 1H), 11.17 (s, 1H), 7.87 (s, 1H), 7.66 (dd, $J_1$ = 2.0 Hz, $J_2$ = 6.9 Hz, 2H), 6.96 (dd, $J_1$ = 2.2 Hz, $J_2$ = 7.1 Hz, 2H), 4.10-4.08 (m, 2H), 3.80 (t, J = 6.1 Hz, 2H), 3.73 (t, J = 5.9 Hz, 2H), 3.67-3.64 (m, 2H), 3.31 (s, 3H), 1.75 (m, 4H), 1.50 (m, 4H) | 411.3 |
| 325 | 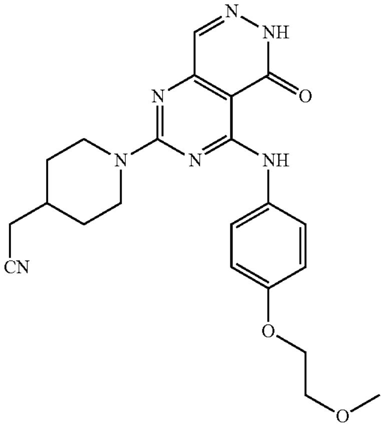 [SMILES: COCCOc1ccc(Nc2nc(N3CCC(CC#N)CC3)nc3cn[nH]c(=O)c23)cc1] | 12.77 (s, 1H), 11.15 (s, 1H), 7.89 (s, 1H), 7.61 (d, J = 8.8 Hz, 2H), 6.99 (d, J = 9.2 Hz, 2H), 4.90-4.60 (m, 2H), 4.10 (t, J = 4.7 Hz, 2H), 3.66 (t, J = 4.7 Hz, 2H), 3.02-2.95 (m, 2H), 2.55-2.53 (m, 2H), 2.09-1.97 (m, 1H), 1.84-1.81 (m, 2H), 1.24-1.10 (m, 2H) | 436.5 |
| 326 | 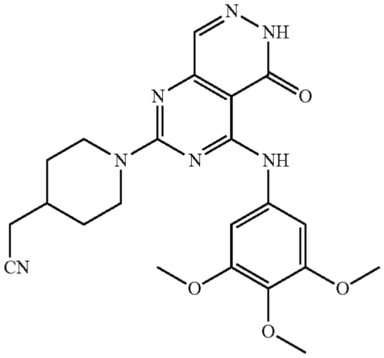 [SMILES: COc1cc(Nc2nc(N3CCC(CC#N)CC3)nc3cn[nH]c(=O)c23)cc(OC)c1OC] | 12.81 (s, 1H), 11.31 (s, 1H), 7.91 (s, 1H), 7.10 (s, 2H), 4.80 (m, 2H), 3.81 (s, 6H), 3.65 (s, 3H), 3.02 (m, 2H), 2.55-2.53 (m, 2H), 1.99 (m, 1H), 1.83-1.80 (m, 2H), 1.24 (m, 2H) | 452.3 |
| 327 | 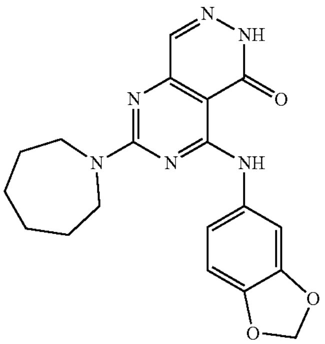 [SMILES: O=c1[nH]ncc2nc(N3CCCCCC3)nc(Nc3ccc4c(c3)OCO4)c12] | 12.70 (s, 1H), 11.41 (s, 1H), 7.88 (s, 1H), 7.63 (s, 1H), 7.02 (dd, $J_1$ = 1.9 Hz, $J_2$ = 8.3 Hz, 1H), 6.92 (d, J = 8.3 Hz, 1H), 6.03 (s, 2H), 3.80 (t, J = 5.9 Hz, 2H), 3.73 (t, J = 5.7 Hz, 2H), 1.75 (m, 4H), 1.51 (m, 4H) | 381.3 |

TABLE 2-continued
| Ex # | Structure | Physical Data $^1H$-NMR in DMSO-$d_6$ at 400 Hz (δ) | MS m/z |
|---|---|---|---|
| 328 | 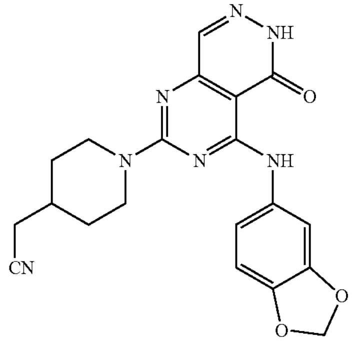 | 11.20 (s, 1H), 7.89 (s, 1H), 7.47 (d, J = 1.9 Hz, 1H), 7.05 (dd, $J_1$ = 2.0 Hz, $J_2$ = 8.3 Hz, 1H), 6.90 (d, J = 8.3 Hz, 1H), 6.01 (s, 2H), 4.80 (m, 2H), 3.04-2.97 (m, 2H), 2.04-2.01 (m, 1H), 1.89-1.85 (m, 2H), 1.29-1.25 (m, 2H) | 406.2 |
| 329 | 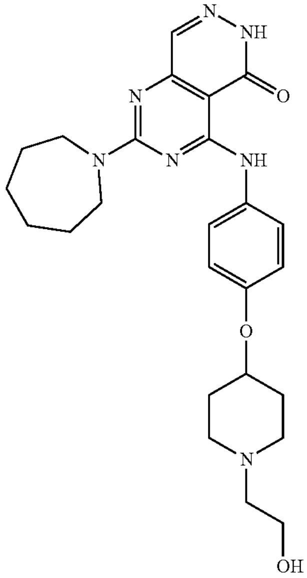 [SMILES: O=c1[nH]ncc2nc(N3CCCCCC3)nc(Nc3ccc(OC4CCN(CCO)CC4)cc3)c12] | — | 480.4 |
| 330 | 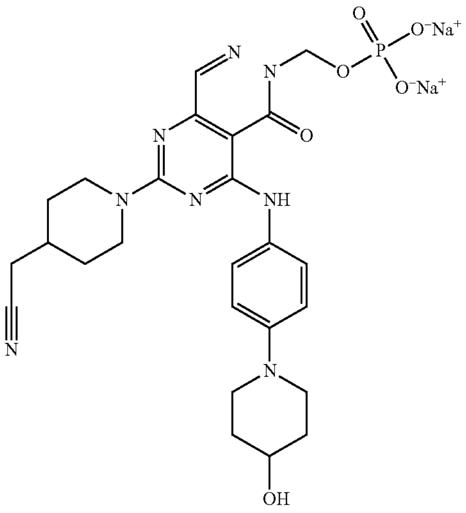 | 7.83 (s, 1H), 7.46 (d, J = 8.8 Hz, 2H), 7.01 (d, J = 9.3 Hz, 2H), 5.62 (bs, 2H), 4.50 (m, 2H), 3.90-3.86 (m, 1H), 3.49-3.46 (m, 2H), 2.88-2.83 (m, 4H), 2.53 (d, J = 6.4 Hz, 2H), 2.07-2.05 (m, 3H), 1.89-1.86 (m, 2H), 1.74-1.68 (m, 2H), 1.22-1.20 (m, 2H) | 569.0 (M − 1) |

TABLE 2-continued
| Ex # | Structure | Physical Data $^{1}$H-NMR in DMSO-$d_6$ at 400 Hz (δ) | MS m/z |
|---|---|---|---|
| 331 | 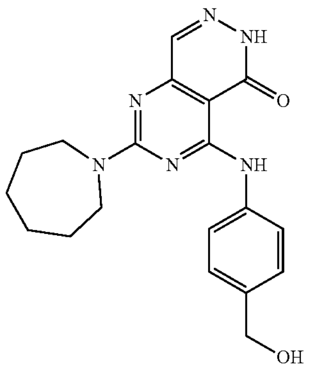 [SMILES: O=c1[nH]ncc2nc(N3CCCCCC3)nc(Nc3ccc(CO)cc3)c12] | 12.74 (s, 1H), 11.33 (s, 1H), 7.89 (s, 1H), 7.72 (d, J = 8.3 Hz, 2H), 7.32 (d, J = 8.3 Hz, 2H), 5.15 (t, J = 5.8 Hz, 1H), 4.48 (d, J = 5.9 Hz, 2H), 3.81 (t, J = 6.1 Hz, 2H), 3.77 (t, J = 5.9 Hz, 2H), 1.79-1.75 (m, 4H), 1.51 (m, 4H) | 365.0 (M − 1) |
| 332 | 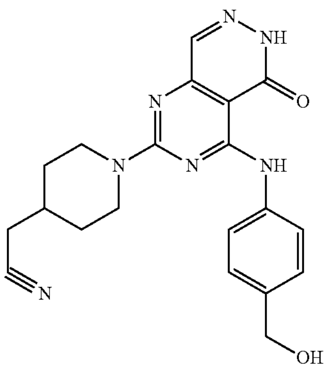 [SMILES: N#CCC1CCN(c2nc(Nc3ccc(CO)cc3)c3c(=O)[nH]ncc3n2)CC1] | 12.80 (s, 1H), 11.30 (s, 1H), 7.90 (s, 1H), 7.66 (d, J = 8.3 Hz, 2H), 7.35 (d, J = 8.3 Hz, 2H), 5.16 (t, J = 5.6 Hz, 1H), 4.79-4.71 (m, 2H), 4.49 (d, J = 5.9 Hz, 2H), 3.01-2.98 (m, 2H), 2.55-2.54 (m, 2H), 2.01-1.95 (m, 1H), 1.85-1.82 (m, 2H), 1.23 (m, 2H) | 390.3 (M − 1) |
| 333 | 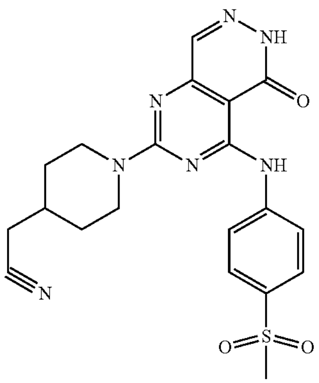 [SMILES: CS(=O)(=O)c1ccc(Nc2nc(N3CCC(CC#N)CC3)nc3cn[nH]c(=O)c23)cc1] | 12.88 (s, 1H), 11.71 (s, 1H), 8.00-7.94 (m, 5H), 4.81-4.70 (m, 2H), 3.21 (s, 3H), 3.04 (m, 2H), 2.57-2.55 (m, 2H), 2.01-2.00 (m, 1H), 1.87 (m, 2H), 1.25-1.23 (m, 2H) | 440.3 |
| 334 | 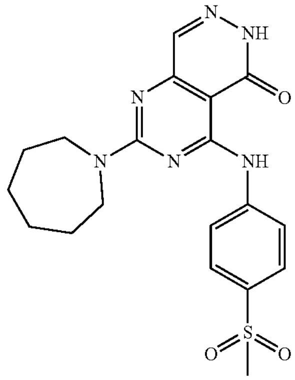 [SMILES: CS(=O)(=O)c1ccc(Nc2nc(N3CCCCCC3)nc3cn[nH]c(=O)c23)cc1] | 12.83 (s, 1H), 11.72 (s, 1H), 8.03 (d, J = 8.8 Hz, 2H), 7.92 (d, J = 5.4 Hz, 2H), 7.92 (s, 1H), 3.84-3.78 (m, 4H), 3.21 (s, 3H), 1.83-1.76 (m, 4H), 1.52 (m, 4H) | 415.4 |

TABLE 2-continued
| Ex # | Structure | Physical Data $^1$H-NMR in DMSO-$d_6$ at 400 Hz (δ) | MS m/z |
|---|---|---|---|
| 335 | 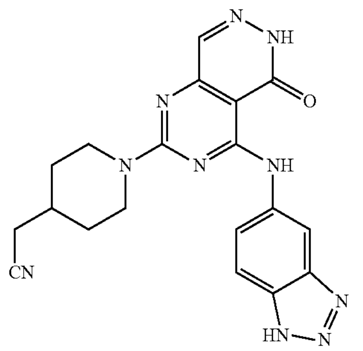 [SMILES: N#CCC1CCN(c2nc(Nc3ccc4[nH]nnc4c3)c3c(=O)[nH]ncc3n2)CC1] | 15.68 (s, 1H), 12.86 (s, 1H), 11.63 (s, 1H), 8.53 (s, 1H), 7.99-7.94 (m, 2H), 7.38 (bs, 1H), 4.80 (m, 2H), 3.07 (m, 2H), 2.58-2.56 (m, 2H), 2.02-1.99 (m, 1H), 1.88 (m, 2H), 1.27-1.23 (m, 2H) | 401.4 (M − 1) |
| 336 | 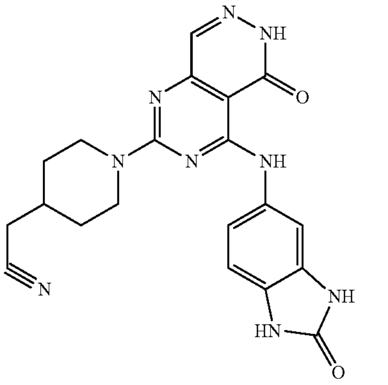 [SMILES: N#CCC1CCN(c2nc(Nc3ccc4[nH]c(=O)[nH]c4c3)c3c(=O)[nH]ncc3n2)CC1] | 12.77 (s, 1H), 11.29 (s, 1H), 10.80 (s, 1H), 11.60 (s, 1H), 7.91 (s, 1H), 7.89 (s, 1H), 7.67 (d, J = 1.0 Hz, 1H), 7.02-7.00 (m, 1H), 7.00-6.91 (m, 1H), 4.78-4.71 (m, 2H), 3.03-2.97 (m, 2H), 2.56-2.54 (m, 2H), 1.99-1.93 (m, 1H), 1.86 (m, 2H), 1.24-1.23 (m, 2H) | 416.2 (M − 1) |
| 337 | 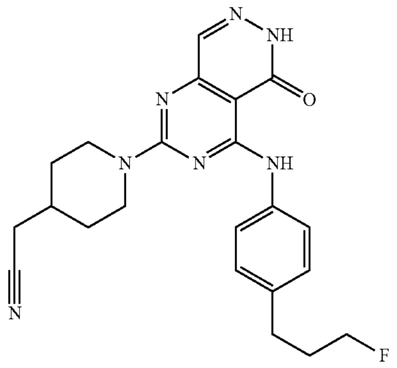 [SMILES: N#CCC1CCN(c2nc(Nc3ccc(CCCF)cc3)c3c(=O)[nH]ncc3n2)CC1] | 12.79 (s, 1H), 11.30 (s, 1H), 7.89 (s, 1H), 7.64 (d, J = 8.3 Hz, 2H), 7.26 (d, J = 8.3 Hz, 2H), 4.79-4.70 (m, 2H), 4.52 (t, J = 5.9 Hz, 1H), 4.40 (t, J = 5.9 Hz, 1H), 3.00 (m, 2H), 2.67 (t, J = 7.6 Hz, 2H), 2.55-2.54 (m, 2H), 2.01-1.91 (m, 3H), 1.85-1.82 (m, 2H), 1.24 (m, 2H) | 420.3 (M − 1) |
| 338 | 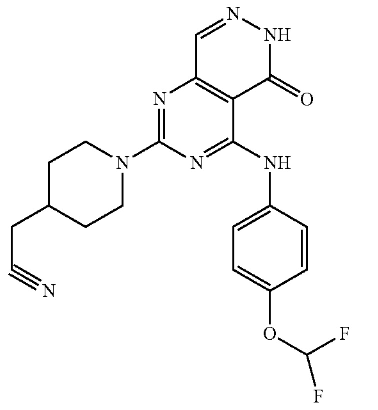 [SMILES: N#CCC1CCN(c2nc(Nc3ccc(OC(F)F)cc3)c3c(=O)[nH]ncc3n2)CC1] | 12.81 (s, 1H), 11.33 (s, 1H), 7.91 (s, 1H), 7.77 (dd, $J_1$ = 2.0 Hz, $J_2$ = 6.8 Hz, 2H), 7.25-7.21 (m, 2H), 4.80-4.67 (m, 2H), 3.04-2.98 (m, 2H), 2.56-2.53 (m, 2H), 2.01-1.96 (m, 1H), 1.86-1.83 (m, 2H), 1.24-1.21 (m, 2H) | 426.0 (M − 1) |

TABLE 2-continued

| Ex # | Structure | Physical Data $^1$H-NMR in DMSO-$d_6$ at 400 Hz (δ) | MS m/z |
|---|---|---|---|
| 339 | 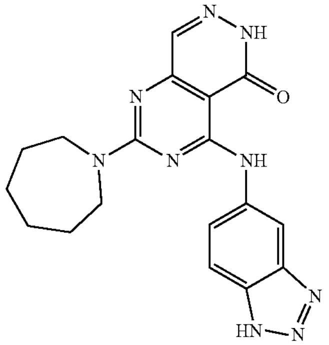 [SMILES: O=c1[nH]ncc2nc(N3CCCCCC3)nc(Nc3ccc4[nH]nnc4c3)c12] | 15.67 (s, 1H), 12.81 (s, 1H), 11.68 (s, 1H), 8.63 (s, 1H), 8.00 (m, 1H), 7.92 (s, 1H), 7.33 (m, 1H), 3.84 (t, J = 5.9 Hz, 4H), 1.86-1.78 (m, 4H), 1.54 (m, 4H) | 378.2 |

The following compounds are anticipated to result in MS having $M^+$ values noted in the following Table B.

TABLE B

| Structure | IUPAC Name | $M^+$ |
|---|---|---|
| 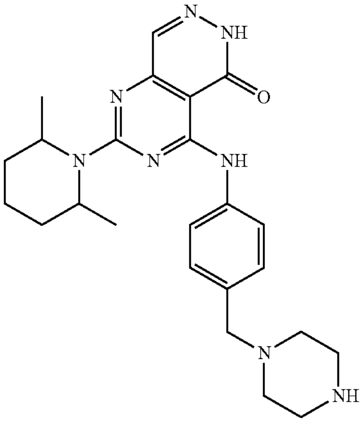 [SMILES: CC1CCCC(C)N1c1nc(Nc2ccc(CN3CCNCC3)cc2)c2c(=O)[nH]ncc2n1] | 2-(2,6-dimethylpiperidin-1-yl)-4-((4-(piperazin-1-ylmethyl)phenyl)amino)pyrimido[4,5-d]pyridazin-5(6H)-one | 448.3 |
| 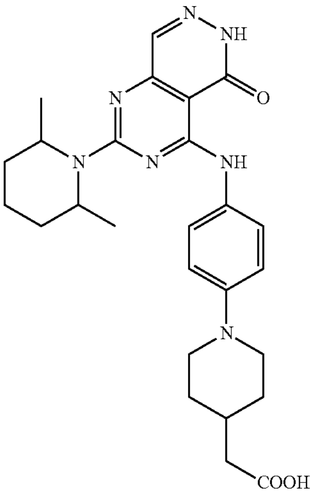 [SMILES: CC1CCCC(C)N1c1nc(Nc2ccc(N3CCC(CC(=O)O)CC3)cc2)c2c(=O)[nH]ncc2n1] | 2-(1-(4-((2-(2,6-dimethylpiperidin-1-yl)-5-oxo-5,6-dihydropyrimido[4,5-d]pyridazin-4-yl)amino)phenyl)piperidin-4-yl)acetic acid | 491.3 |

TABLE B-continued
| Structure | IUPAC Name | M+ |
|---|---|---|
| 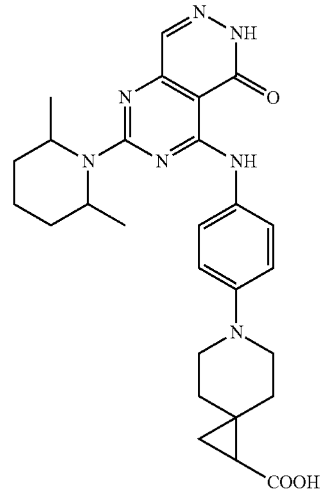 [SMILES: CC1CCCC(C)N1c1nc(Nc2ccc(N3CCC4(CC3)CC4C(=O)O)cc2)c2c(=O)[nH]ncc2n1] | 6-(4-((2-(2,6-dimethylpiperidin-1-yl)-5-oxo-5,6-dihydropyrimido[4,5-d]pyridazin-4-yl)amino)phenyl)-6-azaspiro[2.5]octane-1-carboxylic acid | 503.3 |
| 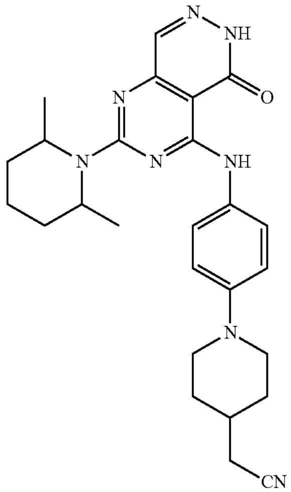 [SMILES: CC1CCCC(C)N1c1nc(Nc2ccc(N3CCC(CC#N)CC3)cc2)c2c(=O)[nH]ncc2n1] | 2-(1-(4-((2-(2,6-dimethylpiperidin-1-yl)-5-oxo-5,6-dihydropyrimido[4,5-d]pyridazin-4-yl)amino)phenyl)piperidin-4-yl)acetonitrile | 472.3 |
| 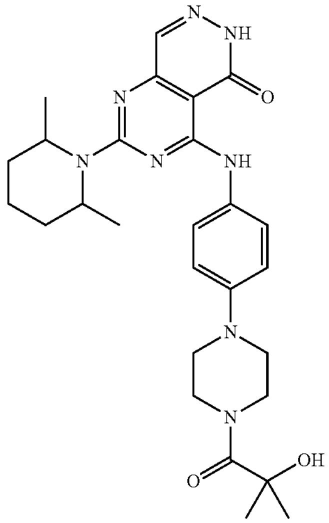 [SMILES: CC1CCCC(C)N1c1nc(Nc2ccc(N3CCN(C(=O)C(C)(C)O)CC3)cc2)c2c(=O)[nH]ncc2n1] | 2-(2,6-dimethylpiperidin-1-yl)-4-((4-(4-(2-hydroxy-2-methylpropanoyl)piperazin-1-yl)phenyl)amino)pyrimido[4,5-d]pyridazin-5(6H)-one | 519.3 |

TABLE B-continued
| Structure | IUPAC Name | M+ |
|---|---|---|
| 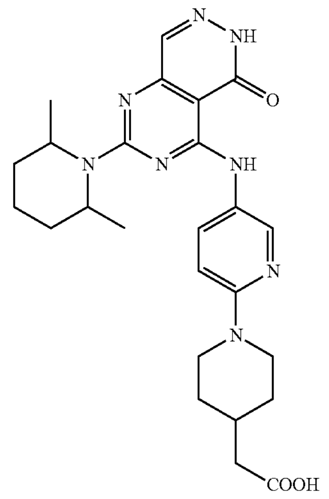 [SMILES: CC1CCCC(C)N1c1nc(Nc2ccc(N3CCC(CC(=O)O)CC3)nc2)c2c(=O)[nH]ncc2n1] | 2-(1-(5-((2-(2,6-dimethylpiperidin-1-yl)-5-oxo-5,6-dihydropyrimido[4,5-d]pyridazin-4-yl)amino)pyridin-2-yl)piperidin-4-yl)acetic acid | 492.3 |
| 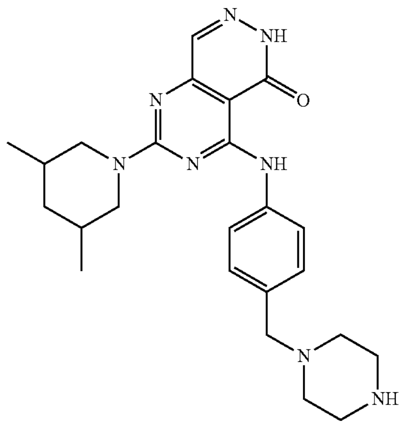 | 2-(3,5-dimethylpiperidin-1-yl)-4-((4-(piperazin-1-ylmethyl)phenyl)amino)pyrimido[4,5-d]pyridazin-5(6H)-one | 448.3 |
| 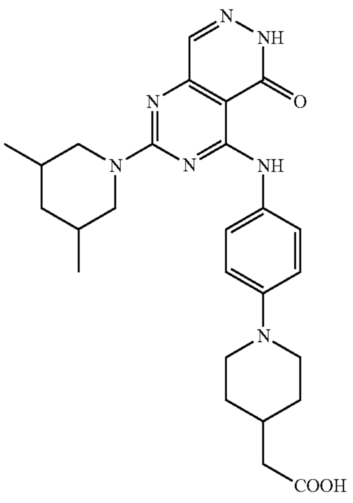 | 2-(1-(4-((2-(3,5-dimethylpiperidin-1-yl)-5-oxo-5,6-dihydropyrimido[4,5-d]pyridazin-4-yl)amino)phenyl)piperidin-4-yl)acetic acid | 491.3 |

TABLE B-continued
| Structure | IUPAC Name | M+ |
|---|---|---|
| 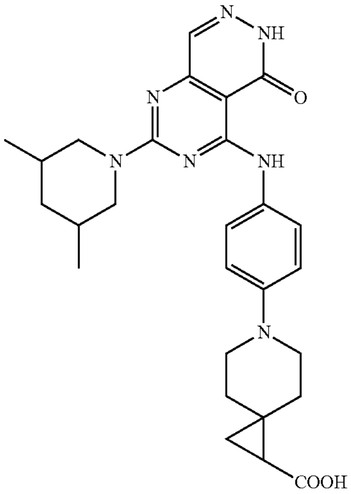 | 6-(4-((2-(3,5-dimethylpiperidin-1-yl)-5-oxo-5,6-dihydropyrimido[4,5-d]pyridazin-4-yl)amino)phenyl)-6-azaspiro[2.5]octane-1-carboxylic acid | 503.3 |
| 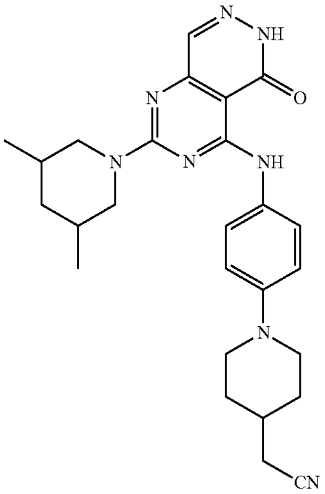 [SMILES: CC1CC(C)CN(c2nc(Nc3ccc(N4CCC(CC#N)CC4)cc3)c3c(=O)[nH]ncc3n2)C1] | 2-(1-(4-((2-(3,5-dimethylpiperidin-1-yl)-5-oxo-5,6-dihydropyrimido[4,5-d]pyridazin-4-yl)amino)phenyl)piperidin-4-yl)acetonitrile | 472.3 |
| 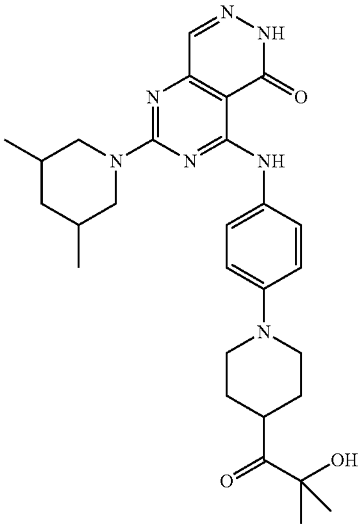 [SMILES: CC1CC(C)CN(c2nc(Nc3ccc(N4CCC(C(=O)C(C)(C)O)CC4)cc3)c3c(=O)[nH]ncc3n2)C1] | 2-(3,5-dimethylpiperidin-1-yl)-4-((4-(4-(2-hydroxy-2-methylpropanoyl)piperidin-1-yl)phenyl)amino)pyrimido[4,5-d]pyridazin-5(6H)-one | 519.3 |

TABLE B-continued
| Structure | IUPAC Name | M+ |
|---|---|---|
| 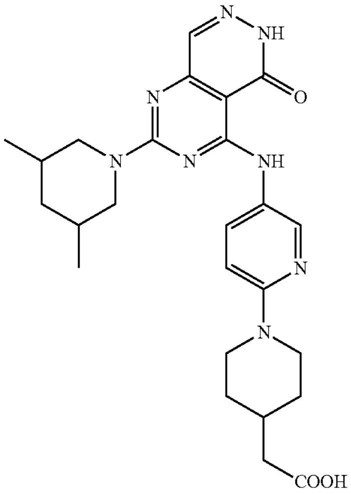 | 2-(1-(5-((2-(3,5-dimethylpiperidin-1-yl)-5-oxo-5,6-dihydropyrimido[4,5-d]pyridazin-4-yl)amino)pyridin-2-yl)piperidin-4-yl)acetic acid | 492.3 |
| 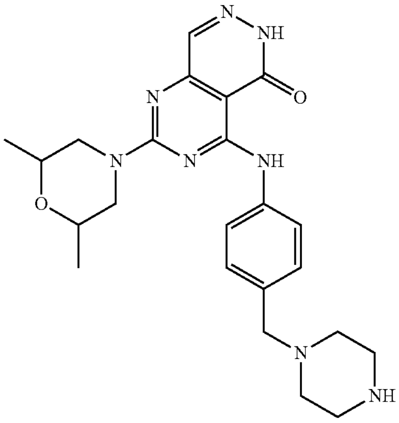 | 2-(2,6-dimethylmorpholino)-4-((4-(piperazin-1-ylmethyl)phenyl)amino)pyrimido[4,5-d]pyridazin-5(6H)-one | 450.1 |
| 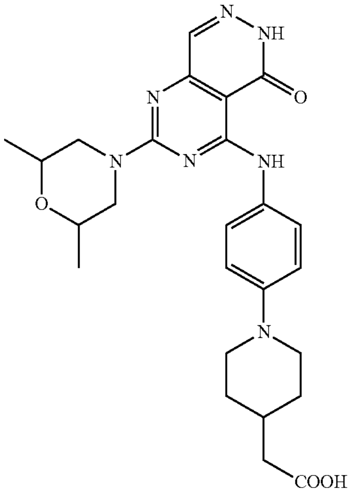 | 2-(1-(4-((2-(2,6-dimethylmorpholino)-5-oxo-5,6-dihydropyrimido[4,5-d]pyridazin-4-yl)amino)phenyl)piperidin-4-yl)acetic acid | 493.2 |

TABLE B-continued
| Structure | IUPAC Name | M+ |
| --- | --- | --- |
| 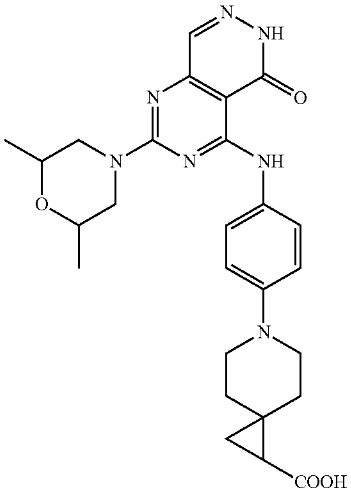 | 6-(4-((2-(2,6-dimethylmorpholino)-5-oxo-5,6-dihydropyrimido[4,5-d]pyridazin-4-yl)amino)phenyl)-6-azaspiro[2.5]octane-1-carboxylic acid | 505.2 |
| 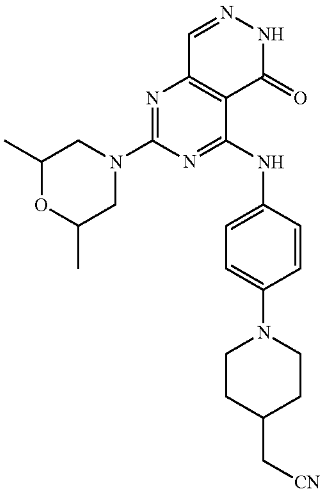 | 2-(1-(4-((2-(2,6-dimethylmorpholino)-5-oxo-5,6-dihydropyrimido[4,5-d]pyridazin-4-yl)amino)phenyl)piperidin-4-yl)acetonitrile | 474.3 |
| 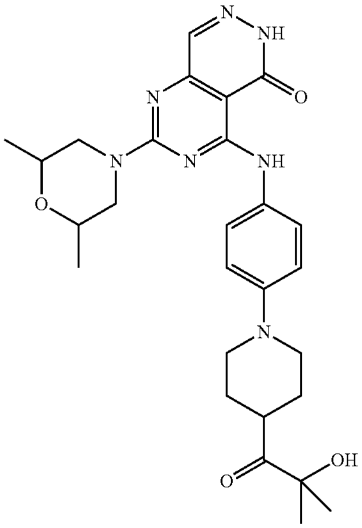 [SMILES: CC1CN(c2nc(Nc3ccc(N4CCC(C(=O)C(C)(C)O)CC4)cc3)c3c(=O)[nH]ncc3n2)CC(C)O1] | 2-(2,6-dimethylmorpholino)-4-((4-(4-(2-hydroxy-2-methylpropanoyl)piperidin-1-yl)phenyl)amino)pyrimido[4,5-d]pyridazin-5(6H)-one | 502.3 |

TABLE B-continued
| Structure | IUPAC Name | M+ |
|---|---|---|
| 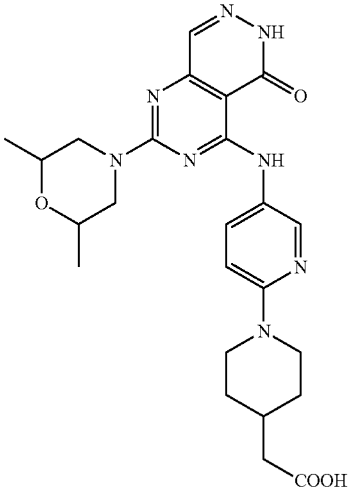 | 2-(1-(5-((2-(2,6-dimethylmorpholino)-5-oxo-5,6-dihydropyrimido[4,5-d]pyridazin-4-yl)amino)pyridin-2-yl)piperidin-4-yl)acetic acid | 494.2 |
| 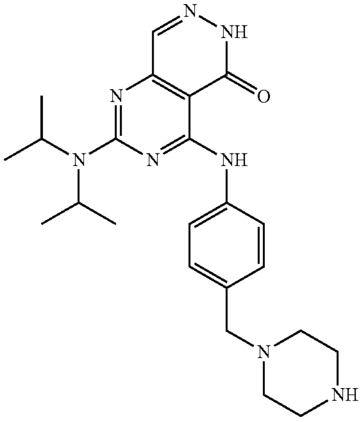 [SMILES: CC(C)N(c1nc(Nc2ccc(CN3CCNCC3)cc2)c2c(=O)[nH]ncc2n1)C(C)C] | 2-(diisopropylamino)-4-((4-(piperazin-1-ylmethyl)phenyl)amino)pyrimido[4,5-d]pyridazin-5(6H)-one | 436.3 |
| 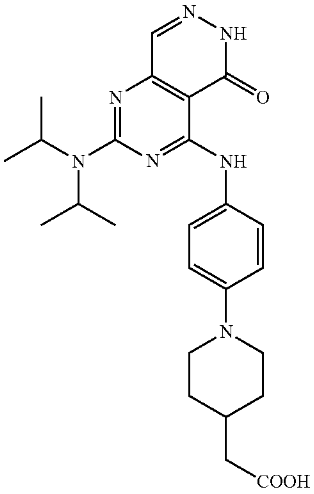 [SMILES: CC(C)N(c1nc(Nc2ccc(N3CCC(CC(=O)O)CC3)cc2)c2c(=O)[nH]ncc2n1)C(C)C] | 2-(1-(4-((2-(diisopropylamino)-5-oxo-5,6-dihydropyrimido[4,5-d]pyridazin-4-yl)amino)phenyl)piperidin-4-yl)acetic acid | 479.3 |

TABLE B-continued
| Structure | IUPAC Name | M+ |
| --- | --- | --- |
| 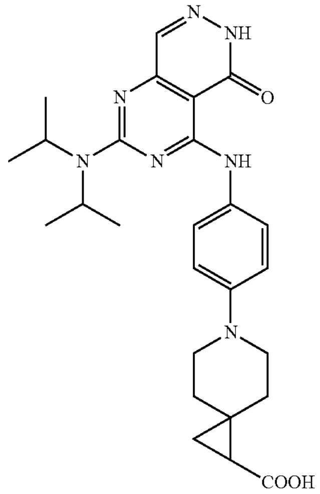 [SMILES: CC(C)N(c1nc(Nc2ccc(N3CCC4(CC3)CC4C(=O)O)cc2)c2c(=O)[nH]ncc2n1)C(C)C] | 6-(4-((2-(diisopropylamino)-5-oxo-5,6-dihydropyrimido[4,5-d]pyridazin-4-yl)amino)phenyl)-6-azaspiro[2.5]octane-1-carboxylic acid | 491.3 |
| 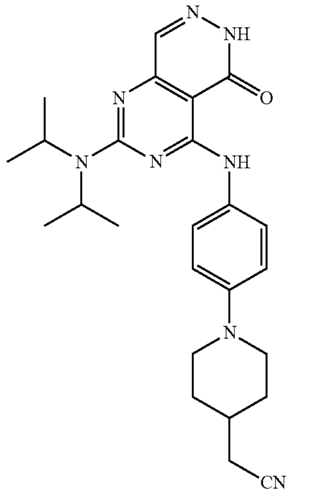 [SMILES: CC(C)N(c1nc(Nc2ccc(N3CCC(CC#N)CC3)cc2)c2c(=O)[nH]ncc2n1)C(C)C] | 2-(1-(4-((2-(diisopropylamino)-5-oxo-5,6-dihydropyrimido[4,5-d]pyridazin-4-yl)amino)phenyl)piperidin-4-yl)acetonitrile | 460.3 |
| 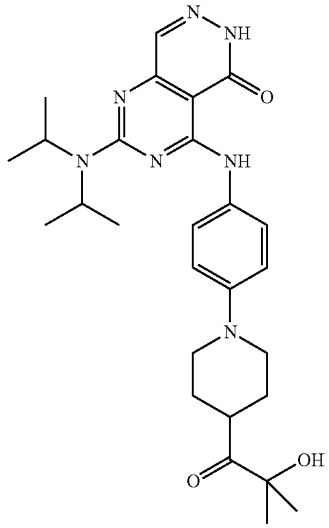 [SMILES: CC(C)N(c1nc(Nc2ccc(N3CCC(C(=O)C(C)(C)O)CC3)cc2)c2c(=O)[nH]ncc2n1)C(C)C] | 2-(diisopropylamino)-4-((4-(4-(2-hydroxy-2-methylpropanoyl)piperidin-1-yl)phenyl)amino)pyrimido[4,5-d]pyridazin-5(6H)-one | 507.3 |

TABLE B-continued
| Structure | IUPAC Name | M+ |
|---|---|---|
| 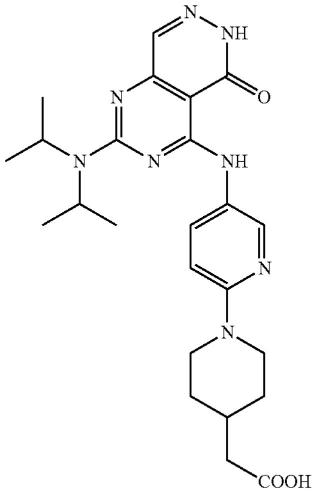 [SMILES: CC(C)N(c1nc(Nc2ccc(N3CCC(CC(=O)O)CC3)nc2)c2c(=O)[nH]ncc2n1)C(C)C] | 2-(1-(5-((2-(diisopropylamino)-5-oxo-5,6-dihydropyrimido[4,5-d]pyridazin-4-yl)amino)pyridin-2-yl)piperidin-4-yl)acetic acid | 480.3 |
| 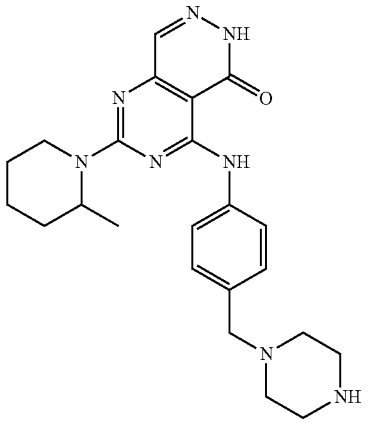 [SMILES: CC1CCCCN1c1nc(Nc2ccc(CN3CCNCC3)cc2)c2c(=O)[nH]ncc2n1] | 2-(2-methylpiperidin-1-yl)-4-((4-(piperazin-1-ylmethyl)phenyl)amino)pyrimido[4,5-d]pyridazin-5(6H)-one | 434.3 |
| 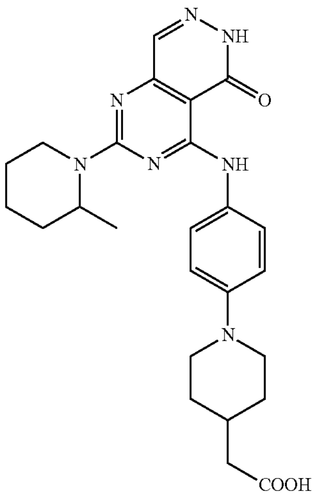 [SMILES: CC1CCCCN1c1nc(Nc2ccc(N3CCC(CC(=O)O)CC3)cc2)c2c(=O)[nH]ncc2n1] | 2-(1-(4-((2-(2-methylpiperidin-1-yl)-5-oxo-5,6-dihydropyrimido[4,5-d]pyridazin-4-yl)amino)phenyl)piperidin-4-yl)acetic acid | 477.3 |

TABLE B-continued
| Structure | IUPAC Name | M+ |
|---|---|---|
| 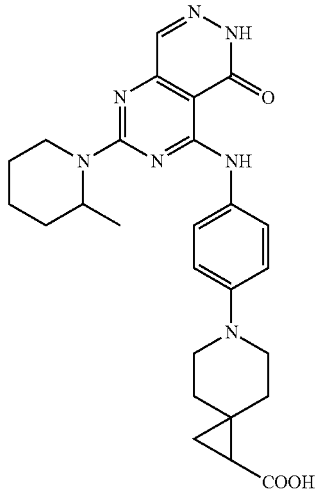 [SMILES: CC1CCCCN1c1nc(Nc2ccc(N3CCC4(CC3)CC4C(=O)O)cc2)c2c(=O)[nH]ncc2n1] | 6-(4-((2-(2-methylpiperidin-1-yl)-5-oxo-5,6-dihydropyrimido[4,5-d]pyridazin-4-yl)amino)phenyl)-6-azaspiro[2.5]octane-1-carboxylic acid | 489.3 |
| 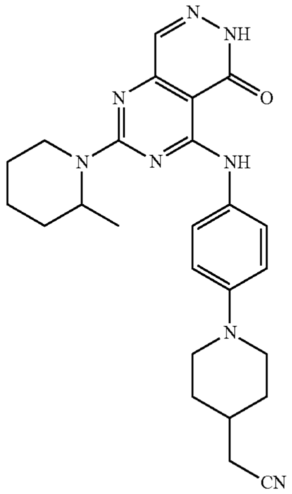 [SMILES: CC1CCCCN1c1nc(Nc2ccc(N3CCC(CC#N)CC3)cc2)c2c(=O)[nH]ncc2n1] | 2-(1-(4-((2-(2-methylpiperidin-1-yl)-5-oxo-5,6-dihydropyrimido[4,5-d]pyridazin-4-yl)amino)phenyl)piperidin-4-yl)acetonitrile | 458.3 |
| 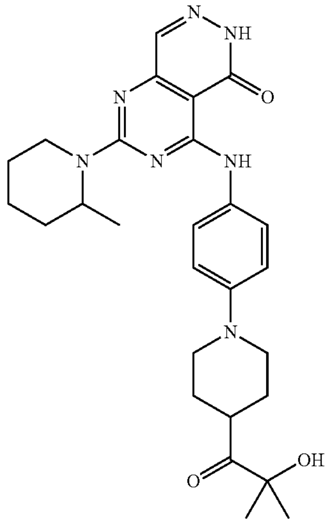 [SMILES: CC1CCCCN1c1nc(Nc2ccc(N3CCC(C(=O)C(C)(C)O)CC3)cc2)c2c(=O)[nH]ncc2n1] | 4-((4-(4-(2-hydroxy-2-methylpropanyl)piperdin-1-yl)phenyl)amino)-2-(2-methylpiperidin-1-yl)pyrimido[4,5-d]pyridazin-5(6H)-one | 505.3 |

TABLE B-continued
| Structure | IUPAC Name | M+ |
|---|---|---|
| 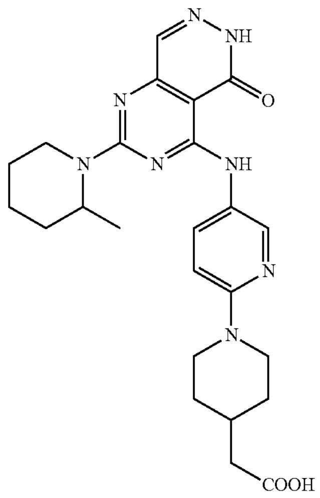 [SMILES: CC1CCCCN1c1nc(Nc2ccc(N3CCC(CC(=O)O)CC3)nc2)c2c(=O)[nH]ncc2n1] | 2-(1-(5-((2-(2-methylpiperidin-1-yl)-5-oxo-5,6-dihydropyrimido[4,5-d]pyridazin-4-yl)amino)pyridin-2-yl)piperidin-4-yl)acetic acid | 478.2 |
| 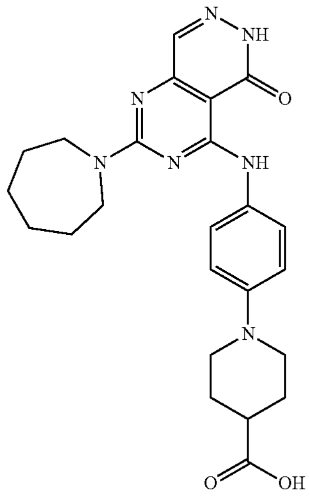 | 1-(4-((2-(azepan-1-yl)-5-oxo-5,6-dihydropyrimido[4,5-d]pyridazin-4-yl)amino)phenyl)piperidine-4-carboxylic acid | 463.2 |
| 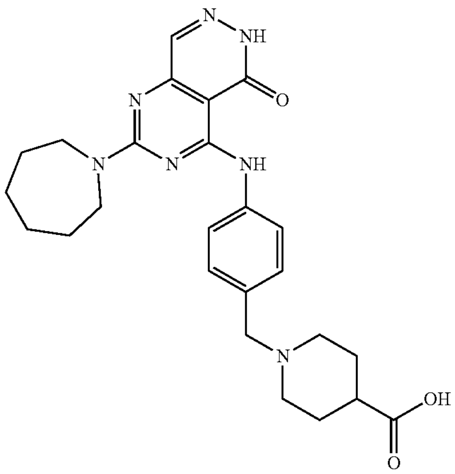 | 1-(4-((2-(azepan-1-yl)-5-oxo-5,6-dihydropyrimido[4,5-d]pyridazin-4-yl)amino)benzyl)piperidine-4-carboxylic acid | 477.3 |

TABLE B-continued
| Structure | IUPAC Name | M⁺ |
|---|---|---|
| 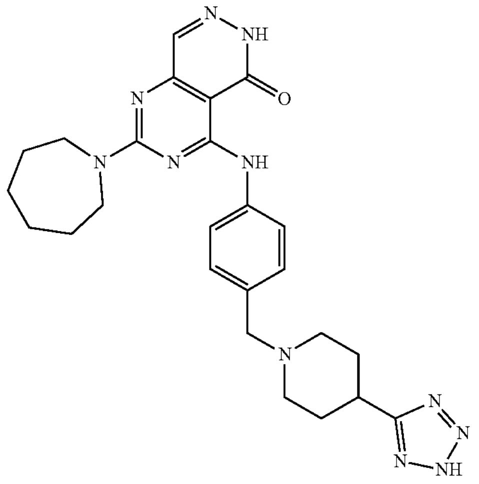 [SMILES: O=c1[nH]ncc2nc(N3CCCCCC3)nc(Nc3ccc(CN4CCC(c5nn[nH]n5)CC4)cc3)c12] | 4-((4-((4-(2H-tetrazol-5-yl)piperidin-1-yl)methyl)phenyl)amino)-2-(azepan-1-yl)pyrimido[4,5-d]pyridazin-5(6H)-one | 501.3 |
| 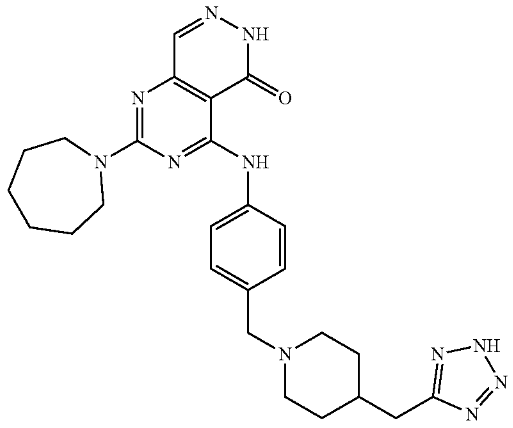 | 4-((4-((4-((2H-tetrazol-5-yl)methyl)piperidin-1-yl)methyl)phenyl)amino)-2-(azepan-1-yl)pyrimido[4,5-d]pyridazin-5(6H)-one | 515.3 |
| 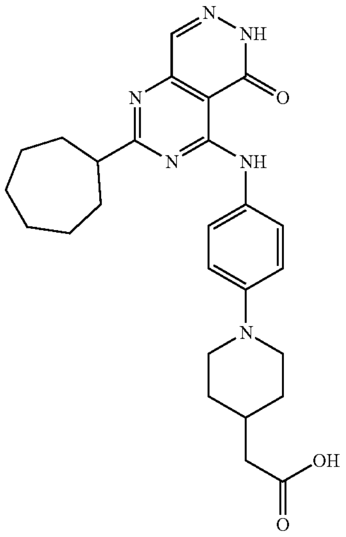 | 2-(1-(4-((2-cycloheptyl-5-oxo-5,6-dihydropyrimido[4,5-d]pyridazin-4-yl)amino)phenyl)piperidin-4-yl)acetic acid | 476.3 |

TABLE B-continued
| Structure | IUPAC Name | M+ |
|---|---|---|
| 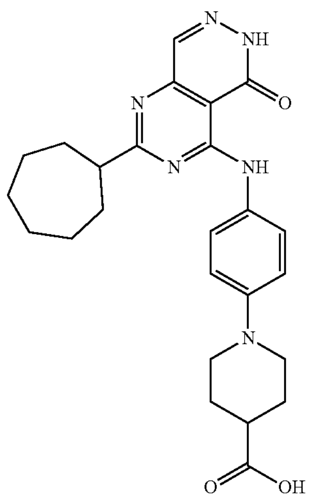 | 1-(4-((2-cycloheptyl-5-oxo-5,6-dihydropyrimido[4,5-d]pyridazin-4-yl)amino)phenyl)piperidine-4-carboxylic acid | 462.2 |
| 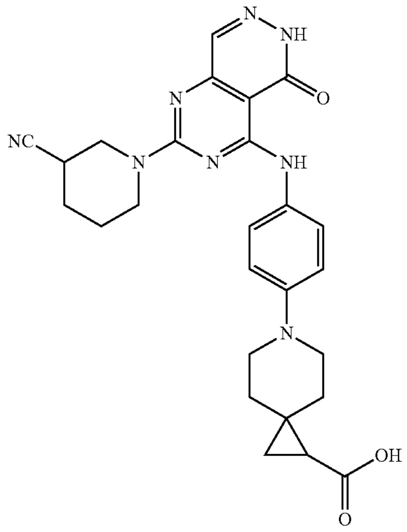 [SMILES: N#CC1CCCN(c2nc(Nc3ccc(N4CCC5(CC4)CC5C(=O)O)cc3)c3c(=O)[nH]ncc3n2)C1] | 6-(4-((2-(3-cyanopiperidin-1-yl)-5-oxo-5,6-dihydropyrimido[4,5-d]pyridazin-4-yl)amino)phenyl)-6-azaspiro[2.5]octane-1-carboxylic acid | 500.2 |
| 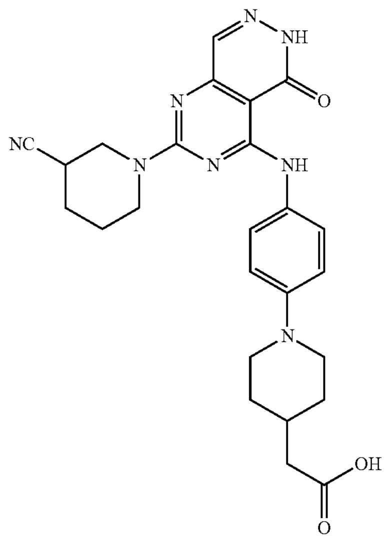 [SMILES: N#CC1CCCN(c2nc(Nc3ccc(N4CCC(CC(=O)O)CC4)cc3)c3c(=O)[nH]ncc3n2)C1] | 2-(1-(4-((2-(3-cyanopiperidin-1-yl)-5-oxo-5,6-dihydropyrimido[4,5-d]pyridazin-4-yl)amino)phenyl)piperidin-4-yl)acetic acid | 488.2 |

TABLE B-continued
| Structure | IUPAC Name | M+ |
| --- | --- | --- |
| 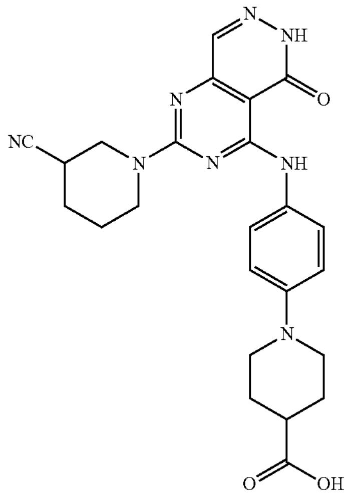 [SMILES: N#CC1CCCN(c2nc(Nc3ccc(N4CCC(C(=O)O)CC4)cc3)c3c(=O)[nH]ncc3n2)C1] | 1-(4-((2-(3-cyanopiperidin-1-yl)-5-oxo-5,6-dihydropyrimido[4,5-d]pyridazin-4-yl)amino)phenyl)piperidine-4-carboxylic acid | 474.2 |
| 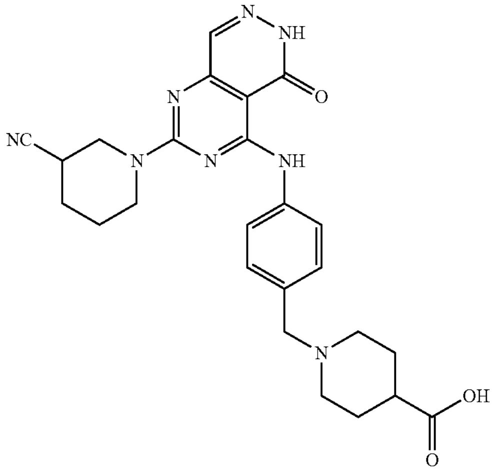 [SMILES: N#CC1CCCN(c2nc(Nc3ccc(CN4CCC(C(=O)O)CC4)cc3)c3c(=O)[nH]ncc3n2)C1] | 1-(4-((2-(3-cyanopiperidin-1-yl)-5-oxo-5,6-dihydropyrimido[4,5-d]pyridazin-4-yl)amino)benzyl)piperidine-4-carboxylic acid | 488.2 |
| 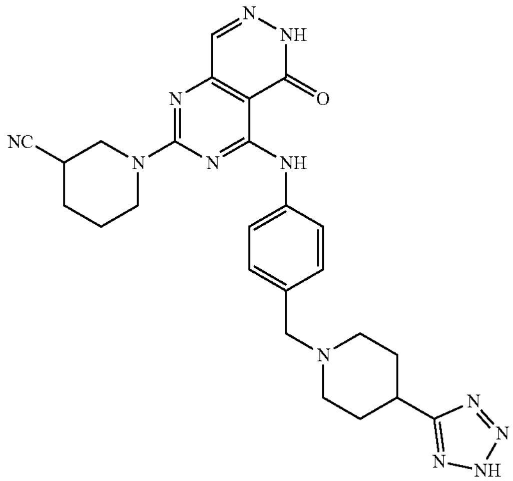 [SMILES: N#CC1CCCN(c2nc(Nc3ccc(CN4CCC(c5nn[nH]n5)CC4)cc3)c3c(=O)[nH]ncc3n2)C1] | 1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-3-carbonitrile | 512.3 |

TABLE B-continued
| Structure | IUPAC Name | M+ |
|---|---|---|
| 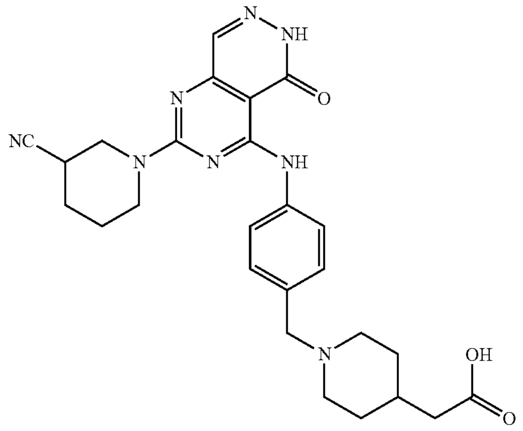 [SMILES: N#CC1CCCN(c2nc(Nc3ccc(CN4CCC(CC(=O)O)CC4)cc3)c3c(=O)[nH]ncc3n2)C1] | 2-(1-(4-((2-(3-cyanopiperidin-1-yl)-5-oxo-5,6-dihydropyrimido[4,5-d]pyridazin-4-yl)amino)benzyl)piperidin-4-yl)acetic acid | 502.2 |
| 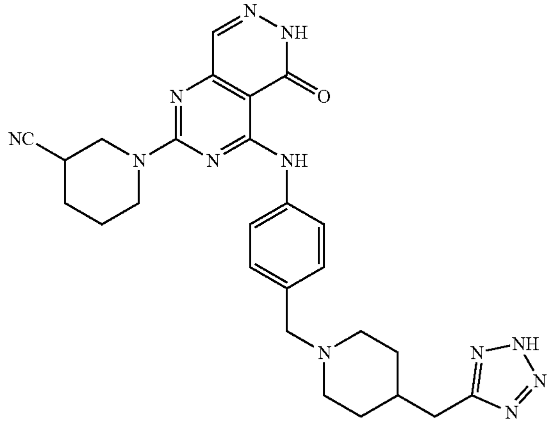 [SMILES: N#CC1CCCN(c2nc(Nc3ccc(CN4CCC(Cc5nn[nH]n5)CC4)cc3)c3c(=O)[nH]ncc3n2)C1] | 1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-3-carbonitrile | 526.3 |
| 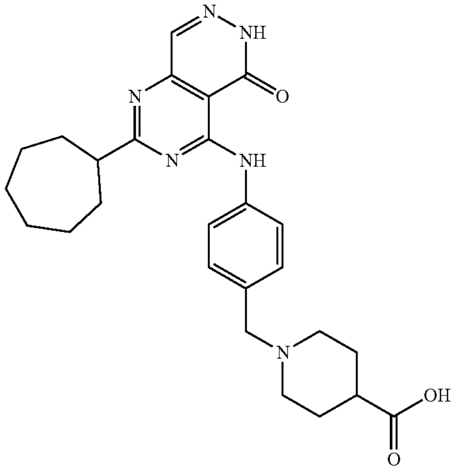 | 1-(4-((2-cycloheptyl-5-oxo-5,6-dihydropyrimido[4,5-d]pyridazin-4-yl)amino)benzyl)piperidine-4-carboxylic acid | 476.3 |

TABLE B-continued
| Structure | IUPAC Name | M+ |
|---|---|---|
| 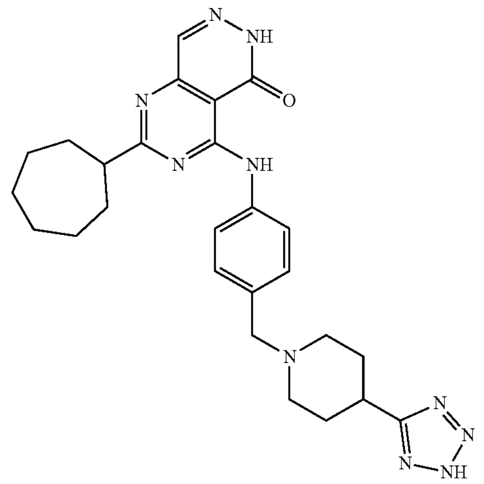 | 4-((4-((4-(2H-tetrazol-5-yl)piperidin-1-yl)methyl)phenyl)amino)-2-cycloheptylpyrimido[4,5-d]pyridazin-5(6H)-one | 500.3 |
| 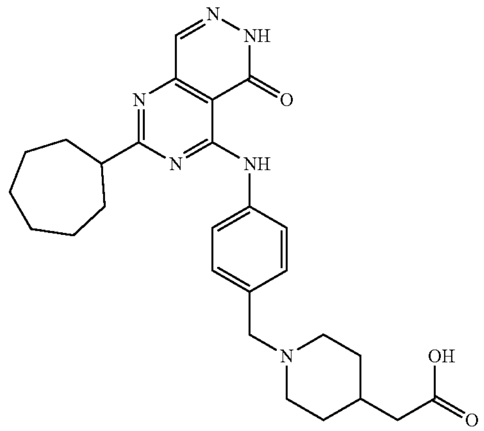 | 2-(1-(4-((2-cycloheptyl-5-oxo-5,6-dihydropyrimido[4,5-d]pyridazin-4-yl)amino)benzyl)piperidin-4-yl)acetic acid | 490.3 |
| 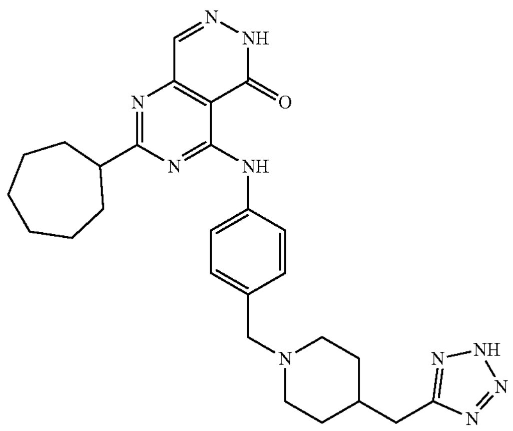 | 4-((4-((4-((2H-tetrazol-5-yl)methyl)piperidin-1-yl)methyl)phenyl)amino)-2-cycloheptylpyrimido[4,5-d]pyridazin-5(6H)-one | 514.3 |

TABLE B-continued

| Structure | IUPAC Name | M+ |
|---|---|---|
| 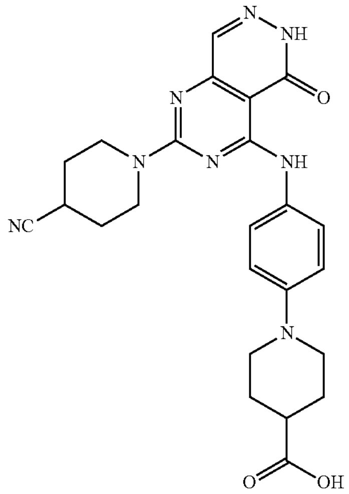 [SMILES: N#CC1CCN(c2nc(Nc3ccc(N4CCC(C(=O)O)CC4)cc3)c3c(=O)[nH]ncc3n2)CC1] | 1-(4-((2-(4-cyanopiperidin-1-yl)-5-oxo-5,6-dihydropyrimido[4,5-d]pyridazin-4-yl)amino)phenyl)piperidine-4-carboxylic acid | 474.2 |
| 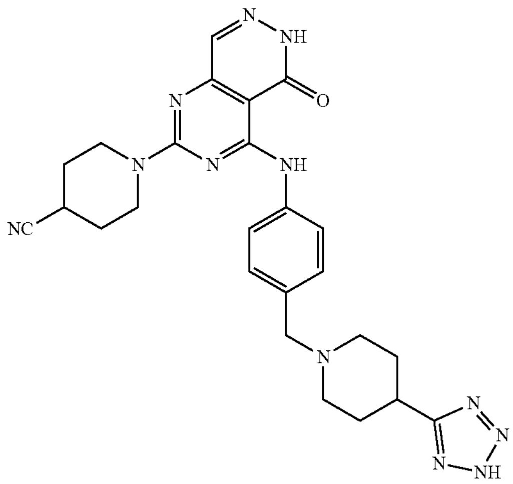 [SMILES: N#CC1CCN(c2nc(Nc3ccc(CN4CCC(c5nn[nH]n5)CC4)cc3)c3c(=O)[nH]ncc3n2)CC1] | 1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-4-carbonitrile | 512.3 |
| 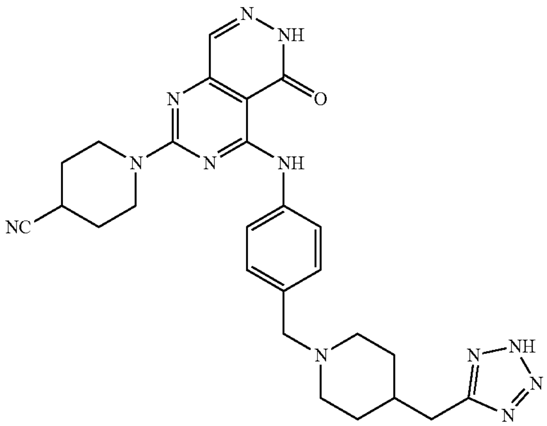 [SMILES: N#CC1CCN(c2nc(Nc3ccc(CN4CCC(Cc5nn[nH]n5)CC4)cc3)c3c(=O)[nH]ncc3n2)CC1] | 1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-4-carbonitrile | 526.3 |

TABLE B-continued

| Structure | IUPAC Name | M+ |
| --- | --- | --- |
| 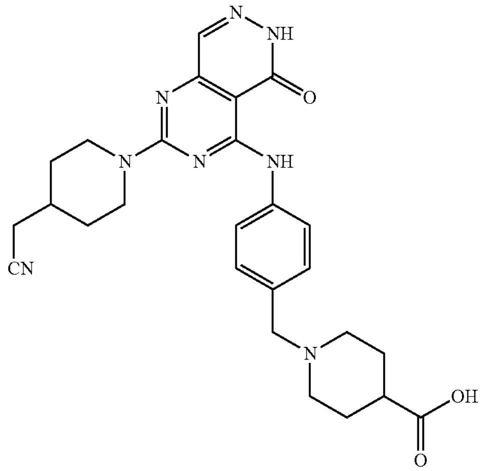 [SMILES: N#CCC1CCN(c2nc(Nc3ccc(CN4CCC(C(=O)O)CC4)cc3)c3c(=O)[nH]ncc3n2)CC1] | 1-(4-((2-(4-(cyanomethyl)piperidin-1-yl)-5-oxo-5,6-dihydropyrimido[4,5-d]pyridazin-4-yl)amino)benzyl)piperidine-4-carboxylic acid | 502.2 |
| 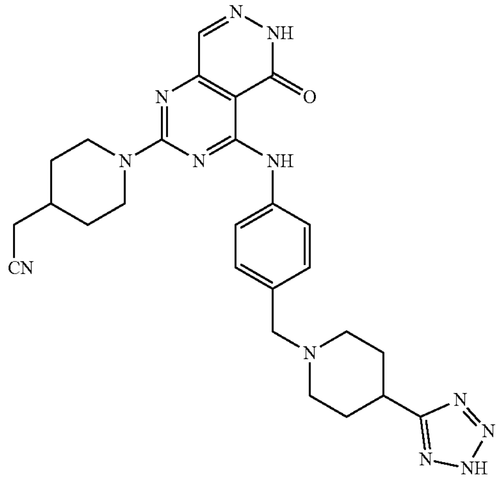 [SMILES: N#CCC1CCN(c2nc(Nc3ccc(CN4CCC(c5nn[nH]n5)CC4)cc3)c3c(=O)[nH]ncc3n2)CC1] | 2-(1-(4-((4-((4-(2H-tetrazol-5-yl)piperidin-1-yl)methyl)phenyl)amino)-5-oxo-5,6-dihydropyrimido[4,5-d]pyridazin-2-yl)piperidin-4-yl)acetonitrile | 526.3 |
| 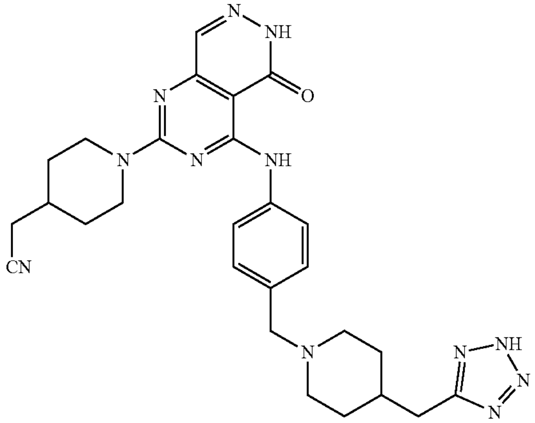 | 2-(1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidin-4-yl)acetonitrile | 540.3 |

TABLE B-continued

| Structure | IUPAC Name | M+ |
|---|---|---|
| 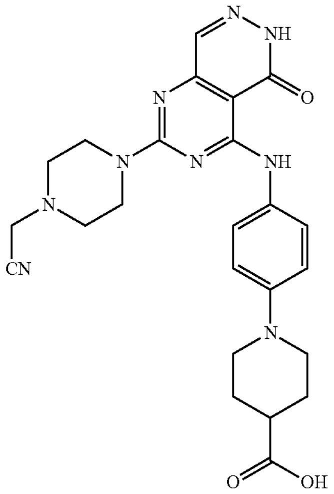 [SMILES: N#CCN1CCN(c2nc(Nc3ccc(N4CCC(C(=O)O)CC4)cc3)c3c(=O)[nH]ncc3n2)CC1] | 1-(4-((2-(4-(cyanomethyl)piperazin-1-yl)-5-oxo-5,6-dihydropyrimido[4,5-d]pyridazin-4-yl)amino)phenyl)piperidine-4-carboxylic acid | 489.2 |
| 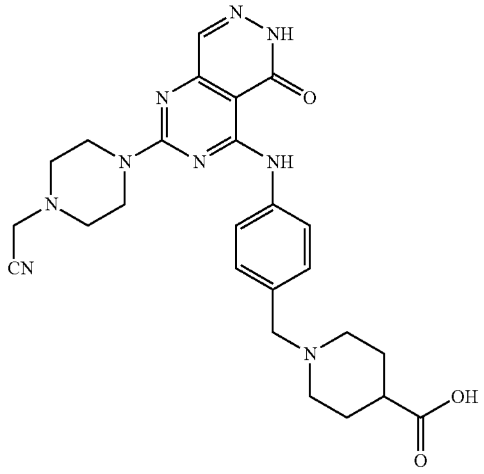 [SMILES: N#CCN1CCN(c2nc(Nc3ccc(CN4CCC(C(=O)O)CC4)cc3)c3c(=O)[nH]ncc3n2)CC1] | 1-(4-((2-(4-(cyanomethyl)piperazin-1-yl)-5-oxo-5,6-dihydropyrimido[4,5-d]pyridazin-4-yl)amino)benzyl)piperidine-4-carboxylic acid | 503.2 |
| 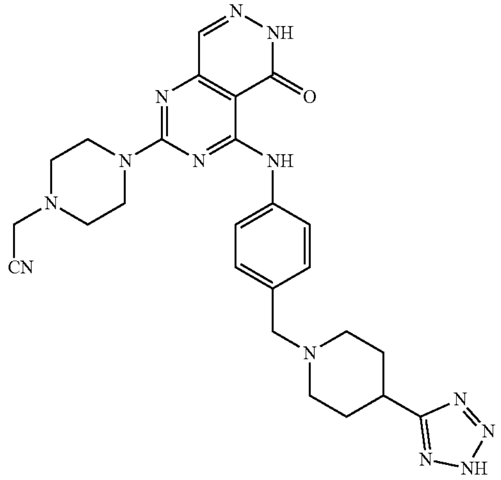 [SMILES: N#CCN1CCN(c2nc(Nc3ccc(CN4CCC(c5nn[nH]n5)CC4)cc3)c3c(=O)[nH]ncc3n2)CC1] | 2-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)acetonitrile | 527.3 |

TABLE B-continued
| Structure | IUPAC Name | M+ |
| --- | --- | --- |
| 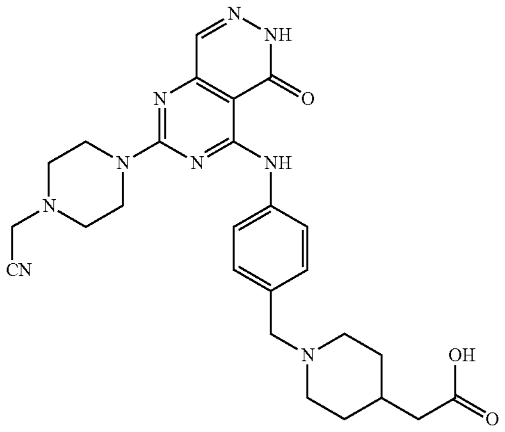 [SMILES: N#CCN1CCN(c2nc(Nc3ccc(CN4CCC(CC(=O)O)CC4)cc3)c3c(=O)[nH]ncc3n2)CC1] | 2-(1-(4-((2-(4-(cyanomethyl)piperazin-1-yl)-5-oxo-5,6-dihydropyrimido[4,5-d]pyridazin-4-yl)amino)benzyl)piperidin-4-yl)acetic acid | 517.3 |
| 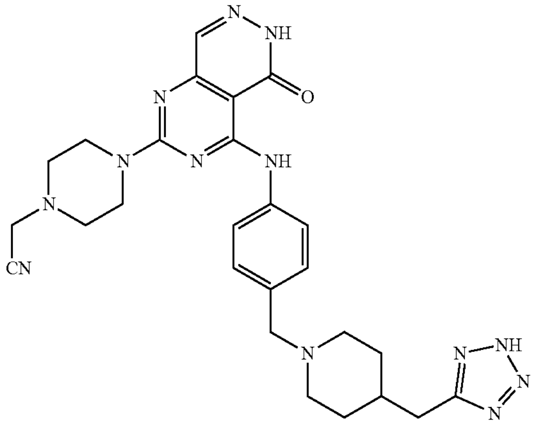 | 2-(4-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperazin-1-yl)acetonitrile | 541.3 |
| 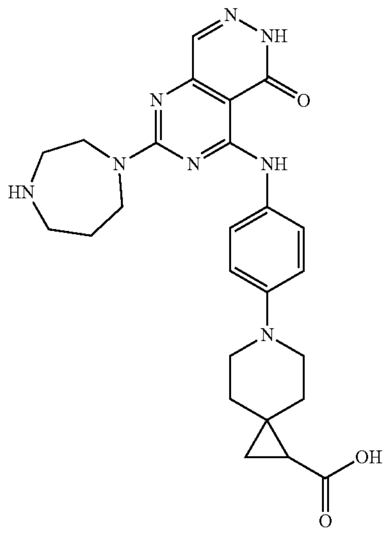 [SMILES: O=C(O)C1CC12CCN(c1ccc(Nc3nc(N4CCCNCC4)nc4cn[nH]c(=O)c34)cc1)CC2] | 6-(4-((2-(1,4-diazepan-1-yl)-5-oxo-5,6-dihydropyrimido[4,5-d]pyridazin-4-yl)amino)phenyl)-6-azaspiro[2.5]octane-1-carboxylic acid | 490.2 |

TABLE B-continued
| Structure | IUPAC Name | M+ |
|---|---|---|
| 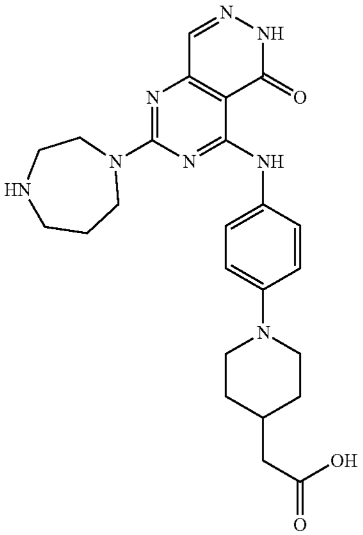 [SMILES: O=C(O)CC1CCN(c2ccc(Nc3nc(N4CCCNCC4)nc4cn[nH]c(=O)c34)cc2)CC1] | 2-(1-(4-((2-(1,4-diazepan-1-yl)-5-oxo-5,6-dihydropyrimido[4,5-d]pyridazin-4-yl)amino)phenyl)piperidin-4-yl)acetic acid | 478.2 |
| 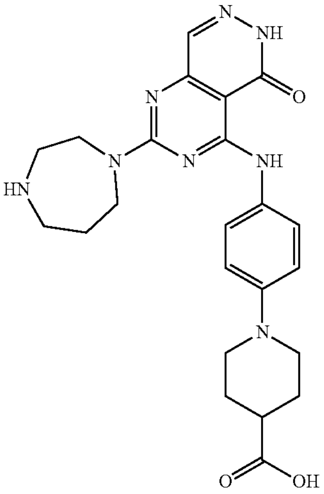 [SMILES: O=C(O)C1CCN(c2ccc(Nc3nc(N4CCCNCC4)nc4cn[nH]c(=O)c34)cc2)CC1] | 1-(4-((2-(1,4-diazepan-1-yl)-5-oxo-5,6-dihydropyrimido[4,5-d]pyridazin-4-yl)amino)phenyl)piperidine-4-carboxylic acid | 464.2 |
| 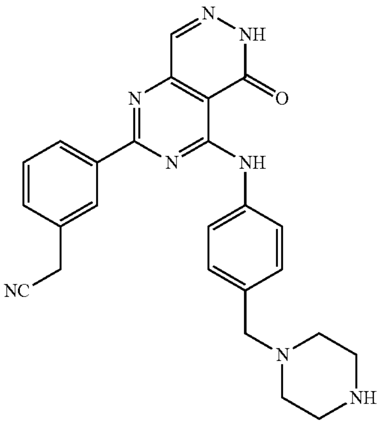 [SMILES: N#CCc1cccc(-c2nc(Nc3ccc(CN4CCNCC4)cc3)c3c(=O)[nH]ncc3n2)c1] | 1-(4-((2-(1,4-diazepan-1-yl)-5-oxo-5,6-dihydropyrimido[4,5-d]pyridazin-4-yl)amino)benzyl)piperidine-4-carboxylic acid | 452.2 |

TABLE B-continued
| Structure | IUPAC Name | M+ |
| --- | --- | --- |
| 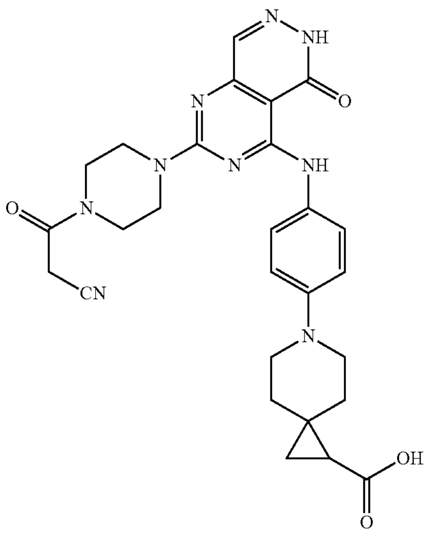 [SMILES: N#CCC(=O)N1CCN(c2nc(Nc3ccc(N4CCC5(CC4)CC5C(=O)O)cc3)c3c(=O)[nH]ncc3n2)CC1] | 6-(4-((2-(4-(2-cyanoacetyl)piperazin-1-yl)-5-oxo-5,6-dihydropyrimido[4,5-d]pyridazin-4-yl)amino)phenyl)-6-azaspiro[2.5]octane-1-carboxylic acid | 543.2 |
| 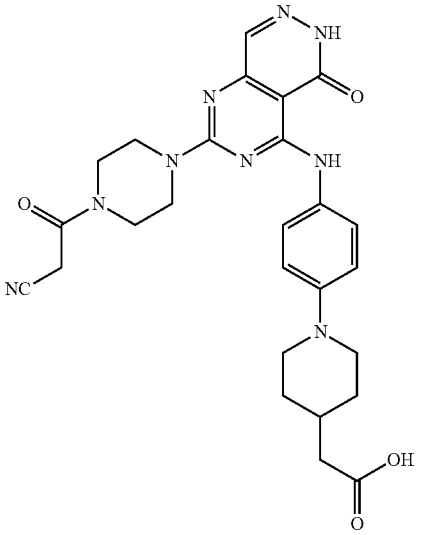 | 2-(1-(4-((2-(4-(2-cyanoacetyl)piperazin-1-yl)-5-oxo-5,6-dihydropyrimido[4,5-d]pyridazin-4-yl)amino)phenyl)piperidin-4-yl)acetic acid | 531.2 |
| 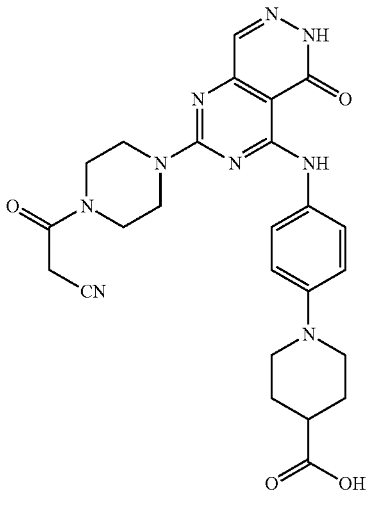 [SMILES: N#CCC(=O)N1CCN(c2nc(Nc3ccc(N4CCC(C(=O)O)CC4)cc3)c3c(=O)[nH]ncc3n2)CC1] | 1-(4-((2-(4-(2-cyanoacetyl)piperazin-1-yl)-5-oxo-5,6-dihydropyrimido[4,5-d]pyridazin-4-yl)amino)phenyl)piperidine-4-carboxylic acid | 517.2 |

TABLE B-continued

| Structure | IUPAC Name | M+ |
| --- | --- | --- |
| 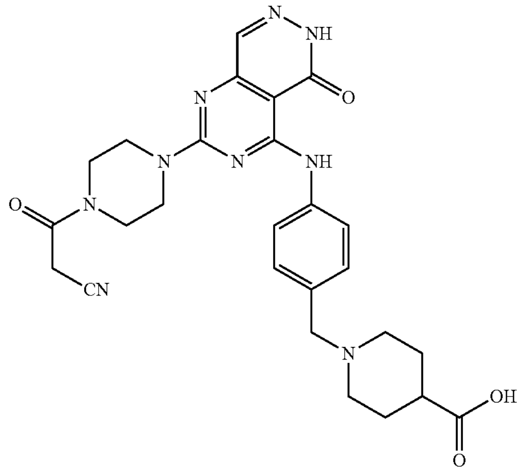 [SMILES: N#CCC(=O)N1CCN(c2nc(Nc3ccc(CN4CCC(C(=O)O)CC4)cc3)c3c(=O)[nH]ncc3n2)CC1] | 1-(4-((2-(4-(2-cyanoacetyl)piperazin-1-yl)-5-oxo-5,6-dihydropyrimido[4,5-d]pyridazin-4-yl)amino)benzyl)piperidine-4-carboxylic acid | 531.2 |
| 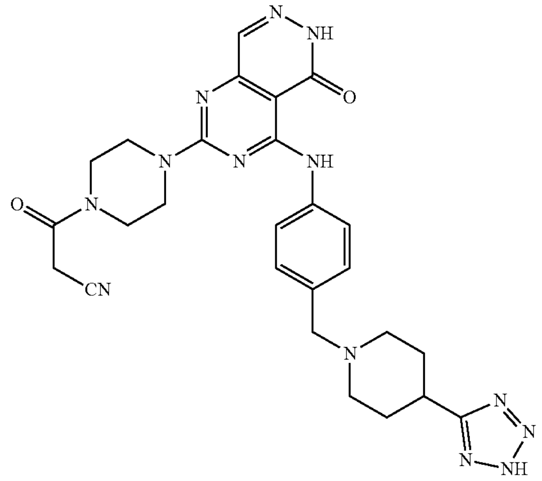 [SMILES: N#CCC(=O)N1CCN(c2nc(Nc3ccc(CN4CCC(c5nn[nH]n5)CC4)cc3)c3c(=O)[nH]ncc3n2)CC1] | 3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)-3-oxopropanenitrile | 555.3 |
| 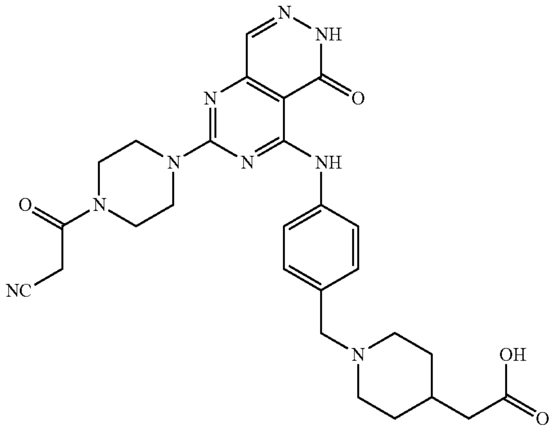 | 2-(1-(4-((2-(4-(2-cyanoacetyl)piperazin-1-yl)-5-oxo-5,6-dihydropyrimido[4,5-d]pyridazin-4-yl)amino)benzyl)piperidin-4-yl)acetic acid | 545.3 |

TABLE B-continued

| Structure | IUPAC Name | M+ |
|---|---|---|
| 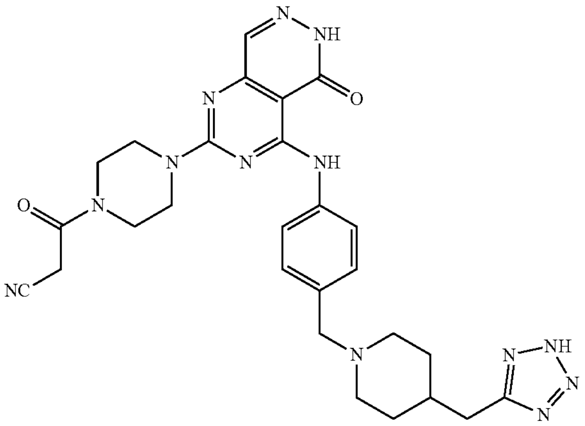 [SMILES: N#CCC(=O)N1CCN(c2nc(Nc3ccc(CN4CCC(Cc5nn[nH]n5)CC4)cc3)c3c(=O)[nH]ncc3n2)CC1] | 4-((4-((4-((2H-tetrazol-5-yl)methyl)piperidin-1-yl)methyl)phenyl)amino)-2-(4-(2-isocyanoacetyl)piperazin-1-yl)pyrimido[4,5-d]pyridazin-5(6H)-one | 569.3 |
| 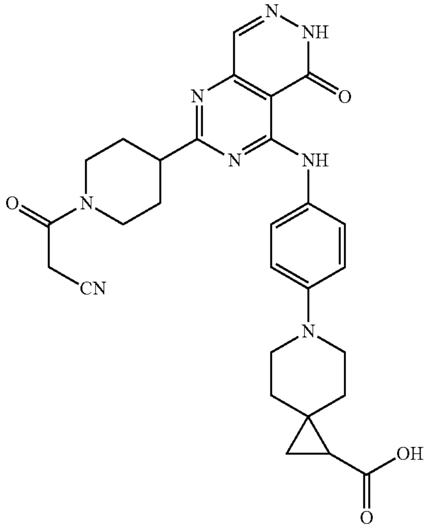 [SMILES: N#CCC(=O)N1CCC(c2nc(Nc3ccc(N4CCC5(CC4)CC5C(=O)O)cc3)c3c(=O)[nH]ncc3n2)CC1] | 6-(4-((2-(1-(2-cyanoacetyl)piperidin-4-yl)-5-oxo-5,6-dihydropyrimido[4,5-d]pyridazin-4-yl)amino)phenyl)-6-azaspiro[2.5]octane-1-carboxylic acid | 542.2 |
| 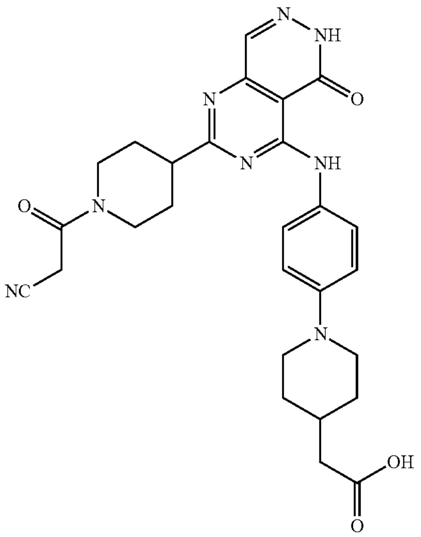 | 2-(1-(4-((2-(1-(2-cyanoacetyl)piperidin-4-yl)-5-oxo-5,6-dihydropyrimido[4,5-d]pyridazin-4-yl)amino)phenyl)piperidin-4-yl)acetic acid | 530.2 |

TABLE B-continued

| Structure | IUPAC Name | M+ |
| --- | --- | --- |
| 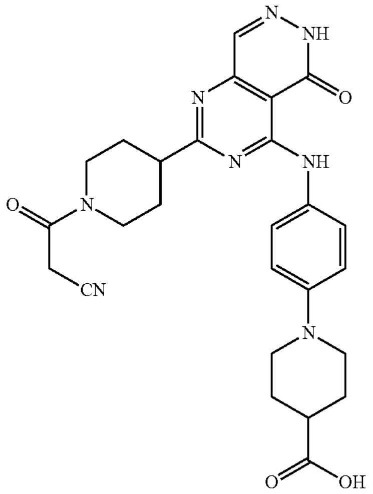 [SMILES: N#CCC(=O)N1CCC(c2nc(Nc3ccc(N4CCC(C(=O)O)CC4)cc3)c3c(=O)[nH]ncc3n2)CC1] | 1-(4-((2-(1-(2-cyanoacetyl)piperidin-4-yl)-5-oxo-5,6-dihydropyrimido[4,5-d]pyridazin-4-yl)amino)phenyl)piperidine-4-carboxylic acid | 516.2 |
| 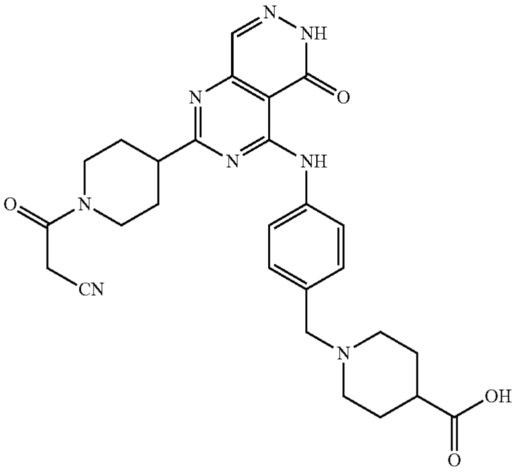 [SMILES: N#CCC(=O)N1CCC(c2nc(Nc3ccc(CN4CCC(C(=O)O)CC4)cc3)c3c(=O)[nH]ncc3n2)CC1] | 1-(4-((2-(1-(2-cyanoacetyl)piperidin-4-yl)-5-oxo-5,6-dihydropyrimido[4,5-d]pyridazin-4-yl)amino)benzyl)piperidine-4-carboxylic acid | 530.2 |
| 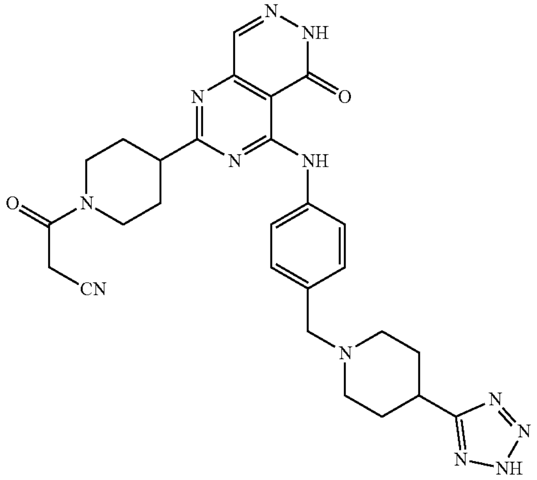 [SMILES: N#CCC(=O)N1CCC(c2nc(Nc3ccc(CN4CCC(c5nn[nH]n5)CC4)cc3)c3c(=O)[nH]ncc3n2)CC1] | 3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperidin-1-yl)-3-oxopropanenitrile | 554.3 |

TABLE B-continued

| Structure | IUPAC Name | M+ |
|---|---|---|
| 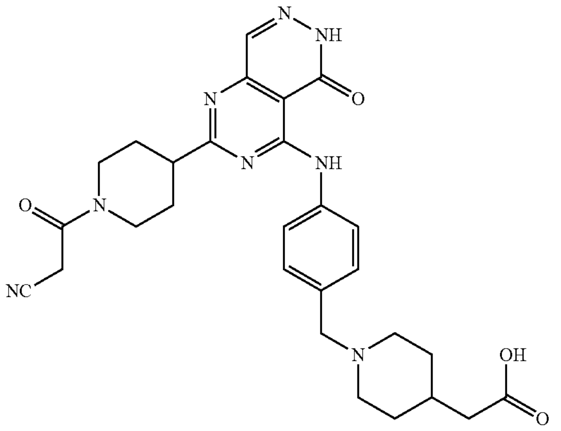 | 2-(1-(4-((2-(1-(2-cyanoacetyl)piperidin-4-yl)-5-oxo-5,6-dihydropyrimido[4,5-d]pyridazin-4-yl)amino)benzyl)piperidin-4-yl)acetic acid | 544.3 |
| 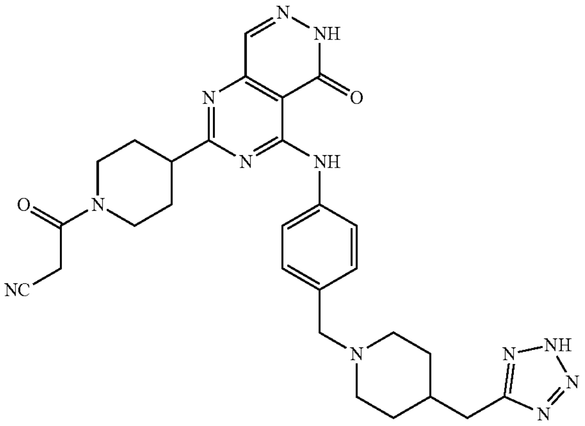 | 4-((4-((4-((2H-tetrazol-5-yl)methyl)piperidin-1-yl)methyl)phenyl)amino)-2-(1-(2-isocyanoacetyl)piperidin-4-yl)pyrimido[4,5-d]pyridazin-5(6H)-one | 568.3 |

Example 340: Inhibition of Enzymatic Syk Kinase Activity

The objective of this assay was to examine by radiometric method the ability of compounds to inhibit Syk kinase enzyme.

A. Background

Spleen tyrosine kinase (Syk) is a cytosolic protein tyrosine kinase that plays a crucial role in inflammatory and allergic responses. Syk triggers IgE and IgG receptor mediated signaling in mast cells, basophils, and macrophages leading to degranulation and cytokine release. Abnormal function of Syk has also been implicated in several instances of hematopoietic malignancies.

Syk is capable of phosphorylating substrates such as VAV, LAT, SLP-76, which in turn activate MAPK, PLCγ signaling pathways. Crystallization studies of the Syk catalytic domain (360-635) showed more activity compared to the full length Syk enzyme. This in vitro assay tests the ability of syk to phosphorylate a substrate peptide in the presence of ATP. By using a radio-labeled form of ATP, it is possible to measure the amount of phosphorylation of the substrate. The enzyme transfers a radio-labeled phosphate group from γ32 P labeled ATP to pG4T. Briefly the enzyme was incubated with substrate, radio-labeled & cold ATP and substrate in buffer with or without compounds. At the end of the reaction, the reaction mixture was transferred on to a Multiscreen filter plate and unreacted $\gamma^{32}$P ATP was washed off. The filter plate was dried and the radioactivity was measured on a scintillation counter to estimate the incorporated radioactivity on the substrate. The percent inhibition of activity of the enzyme was calculated by comparing counts in the presence and absence of compounds.

B. Reagents and Instruments

TABLE 3

| Reagent | Supplier |
|---|---|
| Poly (Glu, Tyr) sodium salt (4:1) | Sigma, Cat #P0275 |
| Syk (356-635 amino acids)-catalytic domain of the full length Syk enzyme* | n/a |
| Whatman ® P81 Chromatography paper | Whatman Cat #3698-915 |
| Microtest ™ V-Bottom plates | Tarsons, Cat #941396 |
| ATP | Sigma, Cat #A7699) |
| [γ-$^{32}$P] ATP | Jonaki Lab, Hyderabad, Cat #PLC101 |
| Microscint-O ™ reagent | Perkin-Elmer, Cat #6013611 |
| DMSO | Sigma, Cat #D2650 |
| Top Count ® NXL instrument | Perkin Elmer |
| Optiplate ® 96 well microplate | Perkin-Elmer; Cat #6005299 |
| TopSeal-A ® 96 well microplate | Perkin Elmer; Cat #6005185 |

Figure 2A:
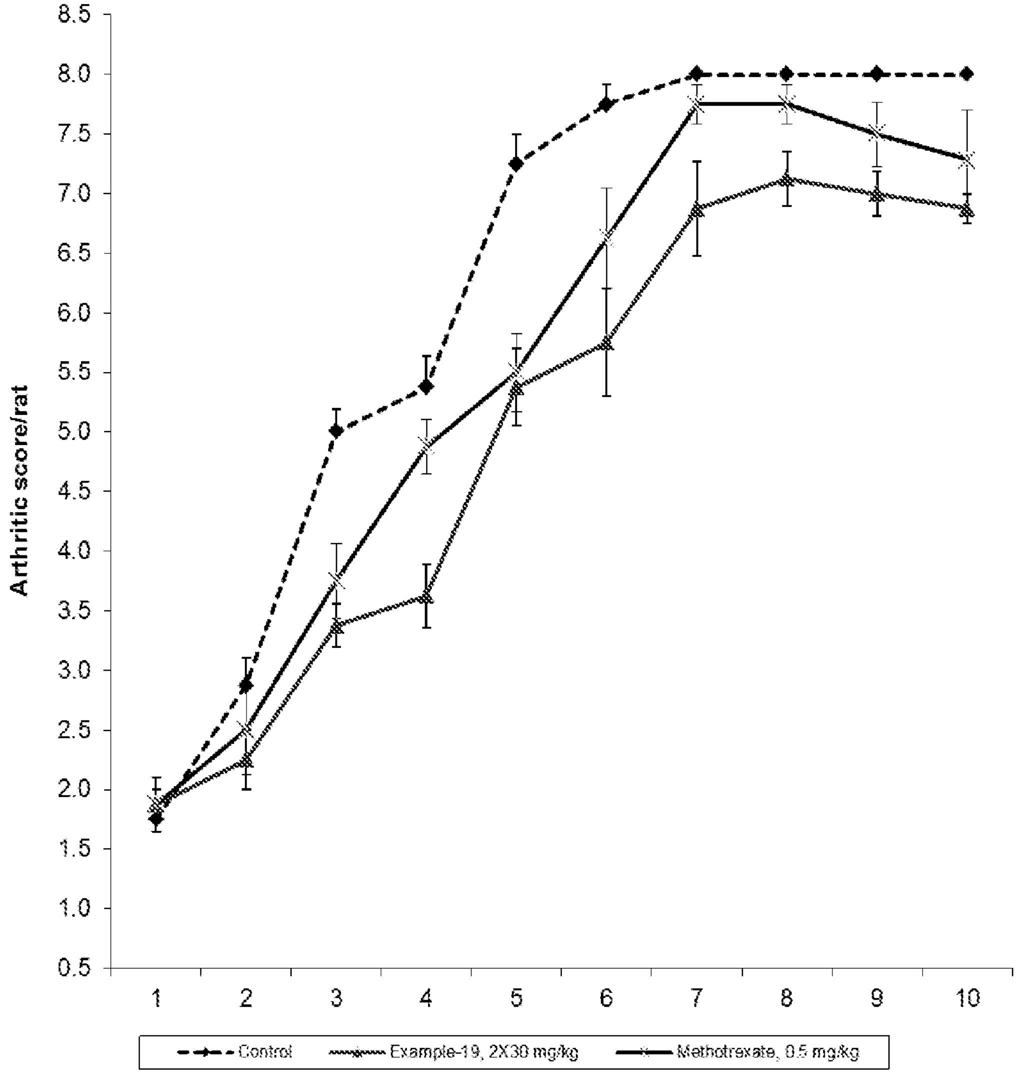

*See, FIG. 2A of Law, "Molecular Cloning of Human Syk", J. Biol. Chem., 269(16): 12310-12319 (1994) which provides the full-length amino acid sequence for human Syk. the fragment utilized included a C'-terminal tag of 4 amino acids and a stretch of 15 amino acids N-terminal to the kinase domain, starting at amino acid 356.

See, also, Yagi, "Cloning of the cDNA for the Deleted SYK Kinase Homologous to ZAP-70 from Human Basophilic Leukemia Cell Line (KU812)", Biochem. Biophys. Res. Commun., 200(1):28-34 (1994). Both of these publications are incorporated by reference herein.

TABLE 4

| Tris Buffer composition | |
|---|---|
| Reagent | Supplier |
| 50 mM tris-hydrochloride (Tris) | Sigma, Cat #T5941 |
| 10 mM magnesium chloride ($MgCl_2$) | Sigma, Cat #M9272 |
| 2.5 mM Di thiotretol (DTT) | Sigma, Cat #D-0632 |
| 500 μM sodium orthovanadate | Sigma, Cat. #S6508 |
| 500 μM ethylene glycol tetra acetic acid (EGTA) | Sigma, Cat #E3889 |
| 0.001% Triton ® X-100 reagent (surfactant with molecule formula of $C_{14}H_{22}O(C_2H_4O)n$ (n = 9-10) | Loba Chemie, CAS #9002-93-1 |

C. Protocol 2.5 μL of 10% DMSO or compound in 10% DMSO was added to the wells in a 96 well V-bottom plate. Optimized concentration of in-house Syk enzyme (different batches of Syk (356-635) kinase domain) were used at optimized concentrations) ranging from 0.035 ng to 7.5 ng/reaction diluted in assay buffer was added to a total volume of 12.5 μL). Compound and protein were incubated for 30 minutes at room temperature on a plate shaker. Ten μL of a substrate mix containing 100 μM ATP (0.25 μL), γ-$P^{32}$-ATP (0.1 μL; 10 μCi/μL), pG4T (0.25 μL; 10 mg/mL) and 1× assay buffer (9.4 μL) was added to all the wells. Samples were incubated at 30° C. for 10 minutes after mixing. The reaction was stopped by the addition of 8N HCl (13 μL) containing 100 mM ATP. Thirty μL of sample was transferred to the center of a 2×2 $cm^2$ Whatman® P81 chromatography paper. After allowing the sample to dry for one minute, the assay squares were washed 3 times for 5 minutes each in ortho-phosphoric acid (0.5%) and once in acetone. Assay squares were dried for 15 minutes in a 30° C. oven and transferred to 96 well optiplate. Microscint-O® reagent (100 μL, Perkin Elmer) was added to each well, the plate was sealed with Topseal®-A microplates and incubated for 10 minutes at room temperature at very low speed on rocker and the plate was read in the Topcount® NXL instrument.

The following calculations were made:

$$\text{Fold induction} = \text{radioactivity counts (uncorrected values) in positive control/substrate control.}$$

Percent inhibition was calculated with the corrected values:

$$\%\ \text{inhibition} = 100 - \frac{\{CPM\ \text{for reaction containing compound} * 100\}}{(CPM\ \text{for positive control})}$$

The % inhibitions of the compound vs. concentrations of NCE were plotted using Graphpad® Prism software to calculate the $IC_{50}$ of the active NCE.

See, Rossi, J. Allergy Clin. Immunol. (2006), 118(3):749-755 and Eva Papp, "Steady State Kinetics of Spleen Tyrosine Kinase Investigated by a Real Time Fluorescence Assay", Biochemistry (2007) 46:15103-15114, which are hereby incorporated by reference.

Example 341: Inhibition of Enzymatic JAK2 Kinase Activity

The objective of this assay was to screen compounds in a Time-resolved fluorescence resonance energy transfer (TR-FRET) Enzymatic assay method for their potential to inhibit JAK2 (Janus kinase) activity. Compounds which inhibit Syk and JAK2 in these studies may be potentially used in treating inflammation.

A. Background

JAK 2 (Janus kinase 2) is a family of intracellular non-receptor tyrosine kinases that transduce cytokine-mediated signals via the JAK-STAT pathway. These kinases have apparent molecular weight of about 130 Kda. They were initially named "just another kinase" 1 & 2 (since they were just two of a large number of discoveries in a PCR-based screen of kinases), but were ultimately published as "Janus kinase". JAKs possess two near-identical phosphate-transferring domains. One domain exhibits the kinase activity while the other negatively regulates the kinase activity of the first. They are crucial signal transducers for a variety of cytokines, growth factors and interferons.

TR-FRET assays are homogeneous proximity assays where Eu-labeled antiphosphotyrosine antibody binds to the phosphorylated substrates labeled with Ulight fluorescence acceptor. Eu can transfer energy to Ulight accepter in the complex and the interaction of two dye-labeled binding partners is detected by the energy transfer between a donor and an acceptor dye, and the subsequent light emission by the acceptor dye. The intensity of the light emission is proportional to the level of Ulight peptide phosphorylation. See, Rodig, "Disruption of the Jak1 gene demonstrates obligatory and nonredundant roles of the JAKs in cytokine-induced biologic responses", Cell, 93(3):373-83 (1998) and Yamaoka, "The Janus kinases (Jaks)", Genome Biology, 5:253 (2004), which are incorporated herein by reference.

B. Reagents and Equipment

TABLE 5

| Reagent | Supplier |
|---|---|
| Ultra light poly GT (4:1) substrate | Perkin Elmer; Cat #TRF-0100-D |
| JAK2 | Upstate; Cat #14-640 |
| Lance ® Eu-W1024 Anti-phosphotyrosine (P-Tyr-100) reagent | Perkin Elmer; Cat #AD0203 |
| dimethyl sulfoxide (DMSO) | SpectroChem; Cat #0704209 |
| ATP | Sigma; Cat #A7699 |
| Wallac ® 1420 multilabel counter victor 3 instrument | Perkin Elmer, Finland |
| Lumitrac ® 200 384-well plates, medium binding, flat bottom, white color | Greiner-Bio; Cat #781075 |

TABLE 6

| Tris Buffer composition | |
|---|---|
| Reagent | Supplier |
| 50 mM Tris | Sigma, Cat #T5941 |
| 20 mM $MgCl_2$ | Sigma, Cat #M9272 |
| 2 mM DTT | Sigma, Cat #D-0632 |
| 0.01% Tween ®20 reagent (Polyoxyethylene (20) sorbitan monolaurate surfactant) | Sigma; Cat #1379 |

C. Protocol

Two μL of 10% DMSO in blank, substrate control and positive control wells and 2 μL of test compound in test wells was added. Thirteen μL of assay buffer in blank and substrate control wells and 13 μL of Enzyme buffer mix in positive and test wells was added. The reaction mixture was incubated for 30 minutes at RT on a plate shaker. Ultra Light-pGT substrate (5 μL) [poly Glu-Tyr (4:1) labeled with U Light™ dye, a tyrosine kinase substrate] and ATP mix was added to all wells. The reaction plate was incubated for 60 minutes at RT on a plate shaker. The reaction was stopped by adding 40 mM EDTA (10 μL) in buffer. Ten μL of antibody was added to all the wells. The plate was read in a Wallac® 1420 Multilabel Counter Victor 3 instrument (Ex: 340 nm Em: 615 & 665 nm) The following calculations were made:

F@ 665 Value-Buffer blank

F@ 615 Value-Buffer blank

Ratio: (F@665 Buffer blank/F@615 Buffer blank)*10000

Ratio of F@665/F@615- Substrate Blank

% Activity=(Test Sample/Positive control)*100

% Inhibition=(100-% Activity)

TABLE 7

| | | $IC_{50}$ ≥100 nM = A; ≤100 nM = B; ≤50 nM = C; ≤10 nM = D | |
|---|---|---|---|
| Ex. # | Structure | Syk | JAK2 |
| 1 | 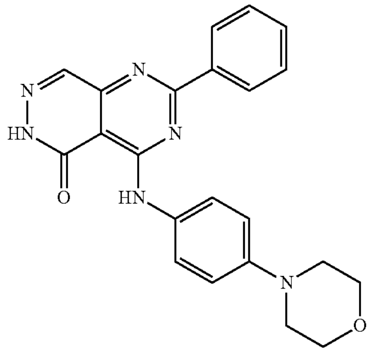 [SMILES: O=c1[nH]ncc2nc(-c3ccccc3)nc(Nc3ccc(N4CCOCC4)cc3)c12] | C | C |
| 2 | 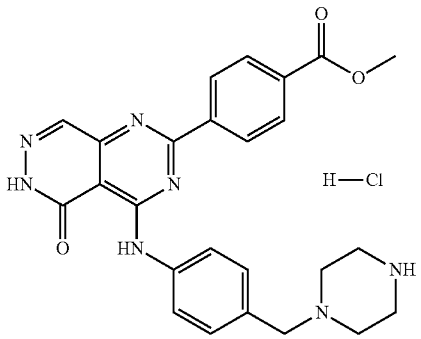 [SMILES: COC(=O)c1ccc(-c2nc(Nc3ccc(CN4CCNCC4)cc3)c3c(=O)[nH]ncc3n2)cc1 ; Cl] | B | A |
| 3 | 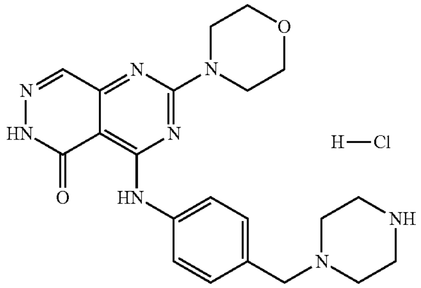 | A | B |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 4 | 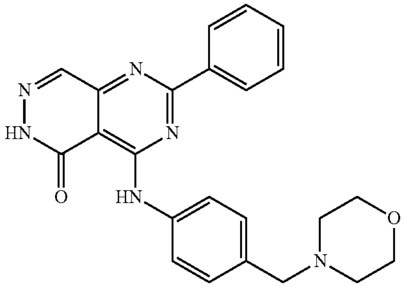 [SMILES: O=c1[nH]ncc2nc(-c3ccccc3)nc(Nc3ccc(CN4CCOCC4)cc3)c12] | B | C |
| 5 | 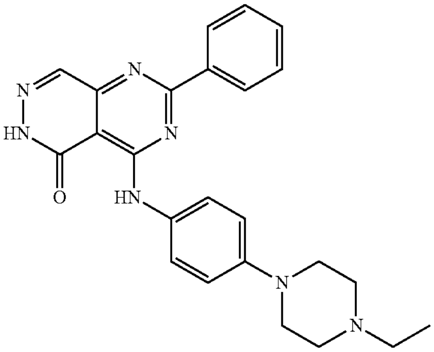 [SMILES: CCN1CCN(c2ccc(Nc3nc(-c4ccccc4)nc4cn[nH]c(=O)c34)cc2)CC1] | D | C |
| 6 | 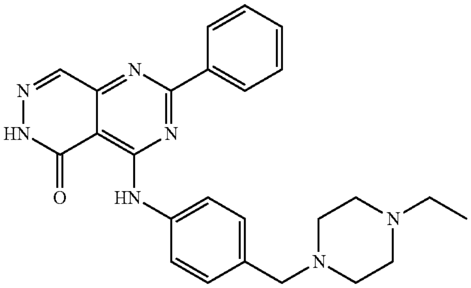 [SMILES: CCN1CCN(Cc2ccc(Nc3nc(-c4ccccc4)nc4cn[nH]c(=O)c34)cc2)CC1] | C | C |
| 7 | 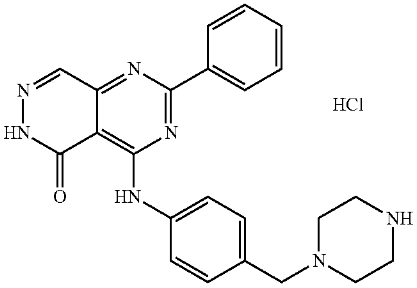 [SMILES: O=c1[nH]ncc2nc(-c3ccccc3)nc(Nc3ccc(CN4CCNCC4)cc3)c12 ; Cl] HCl | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 8 | 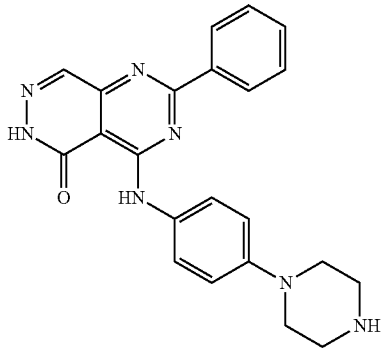 [SMILES: O=c1[nH]ncc2nc(-c3ccccc3)nc(Nc3ccc(N4CCNCC4)cc3)c12] | D | D |
| 9 | 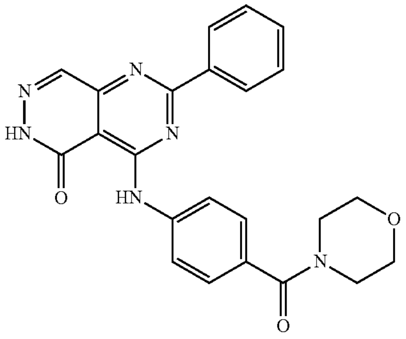 [SMILES: O=C(c1ccc(Nc2nc(-c3ccccc3)nc3cn[nH]c(=O)c23)cc1)N1CCOCC1] | A | — |
| 10 | 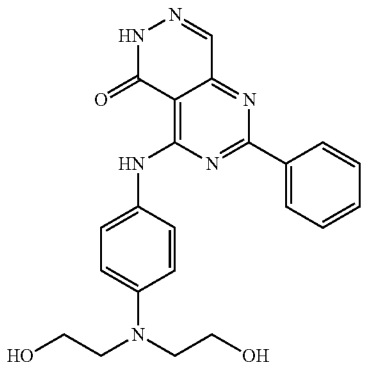 [SMILES: O=c1[nH]ncc2nc(-c3ccccc3)nc(Nc3ccc(N(CCO)CCO)cc3)c12] | C | B |
| 11 | 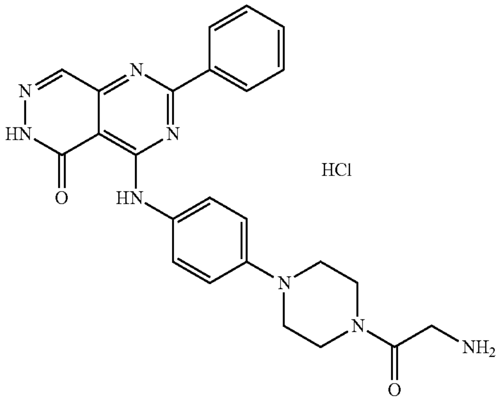 [SMILES: NCC(=O)N1CCN(c2ccc(Nc3nc(-c4ccccc4)nc4cn[nH]c(=O)c34)cc2)CC1 ; Cl] HCl | C | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 12 | 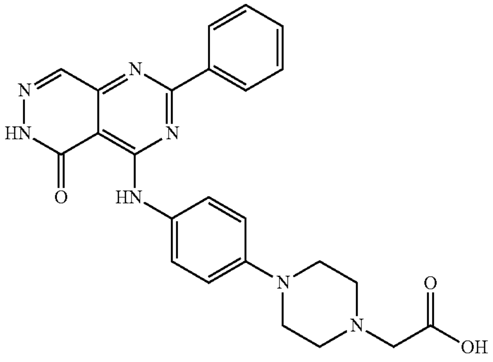 | C | D |
| 13 | 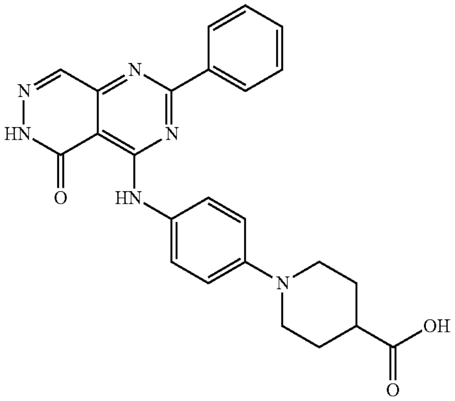 [SMILES: O=C(O)C1CCN(c2ccc(Nc3nc(-c4ccccc4)nc4cn[nH]c(=O)c34)cc2)CC1] | C | D |
| 14 | 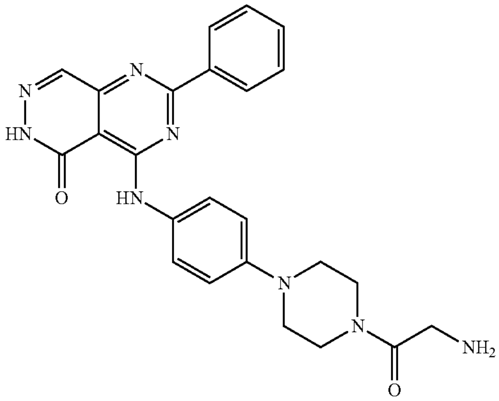 [SMILES: NCC(=O)N1CCN(c2ccc(Nc3nc(-c4ccccc4)nc4cn[nH]c(=O)c34)cc2)CC1] | D | — |
| 15 | 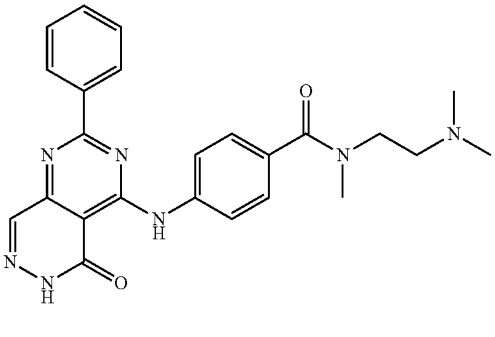 [SMILES: CN(C)CCN(C)C(=O)c1ccc(Nc2nc(-c3ccccc3)nc3cn[nH]c(=O)c23)cc1] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 16 | 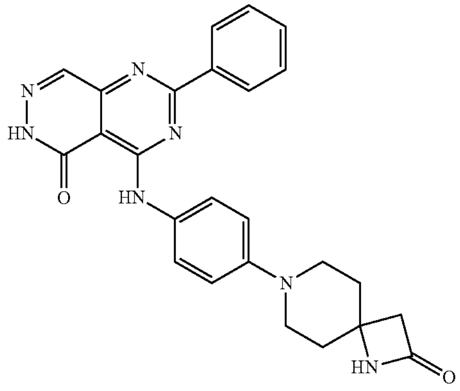 [SMILES: O=C1CC2(CCN(c3ccc(Nc4nc(-c5ccccc5)nc5cn[nH]c(=O)c45)cc3)CC2)N1] | A | — |
| 17 | 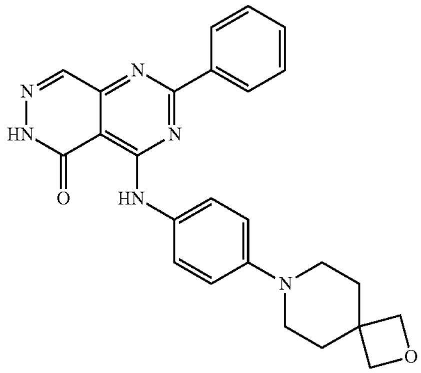 [SMILES: O=c1[nH]ncc2nc(-c3ccccc3)nc(Nc3ccc(N4CCC5(CC4)COC5)cc3)c12] | A | — |
| 18 | 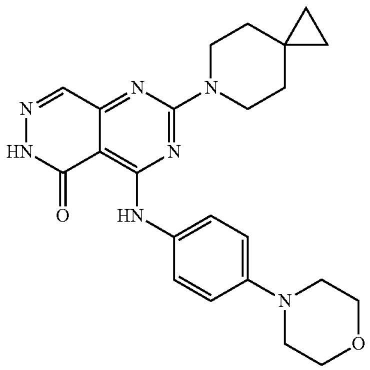 [SMILES: O=c1[nH]ncc2nc(N3CCC4(CC3)CC4)nc(Nc3ccc(N4CCOCC4)cc3)c12] | A | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 19 | 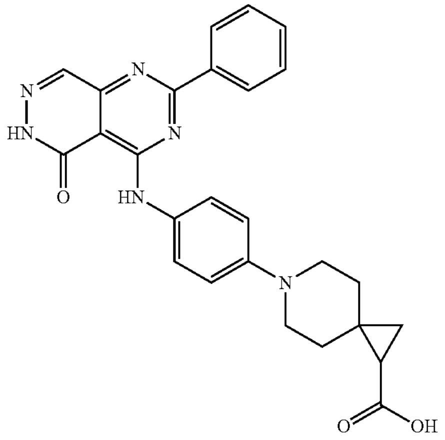 [SMILES: O=C(O)C1CC12CCN(c1ccc(Nc3nc(-c4ccccc4)nc4cn[nH]c(=O)c34)cc1)CC2] | C | D |
| 20 | 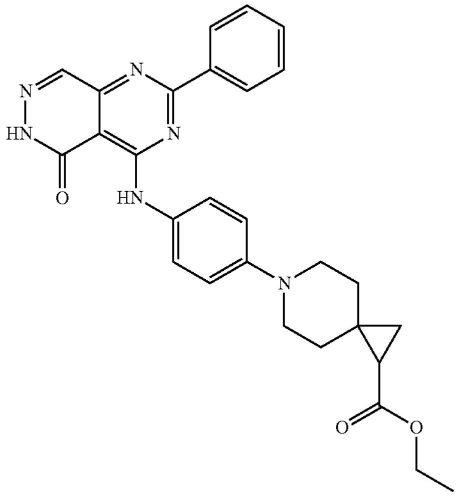 [SMILES: CCOC(=O)C1CC12CCN(c1ccc(Nc3nc(-c4ccccc4)nc4cn[nH]c(=O)c34)cc1)CC2] | A | — |
| 21 | 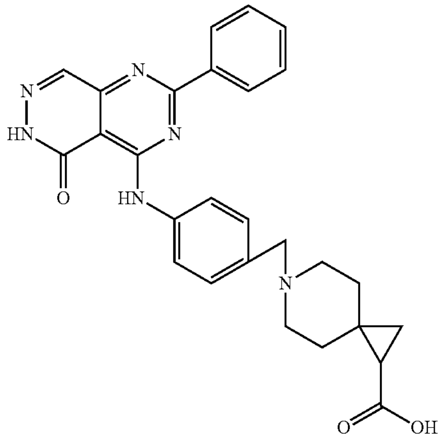 [SMILES: O=C(O)C1CC12CCN(Cc1ccc(Nc3nc(-c4ccccc4)nc4cn[nH]c(=O)c34)cc1)CC2] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 22 | 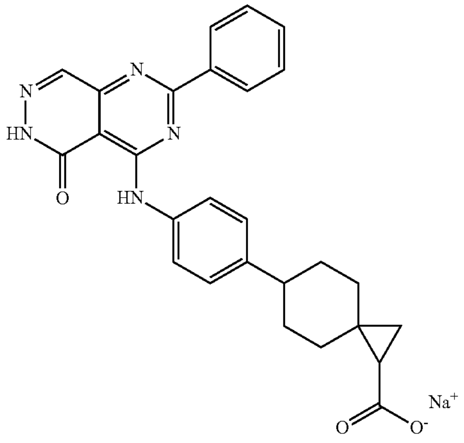 [SMILES: O=C([O-])C1CC12CCC(c1ccc(Nc3nc(-c4ccccc4)nc4cn[nH]c(=O)c34)cc1)CC2 ; [Na+]] | B | C |
| 23 | 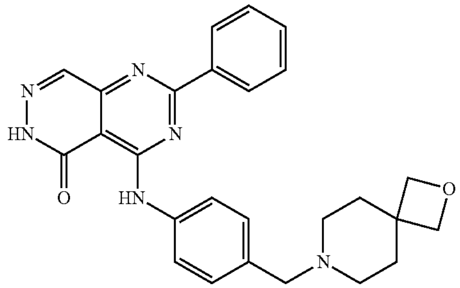 [SMILES: O=c1[nH]ncc2nc(-c3ccccc3)nc(Nc3ccc(CN4CCC5(CC4)COC5)cc3)c12] | C | B |
| 24 | 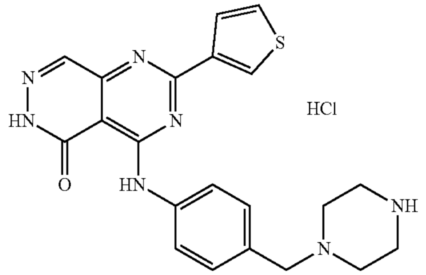 [SMILES: O=c1[nH]ncc2nc(-c3ccsc3)nc(Nc3ccc(CN4CCNCC4)cc3)c12 ; Cl] HCl | D | B |
| 25 | 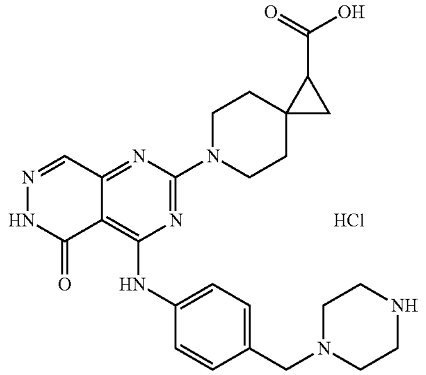 [SMILES: O=C(O)C1CC12CCN(c1nc(Nc3ccc(CN4CCNCC4)cc3)c3c(=O)[nH]ncc3n1)CC2 ; Cl] HCl | C | B |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 26 | 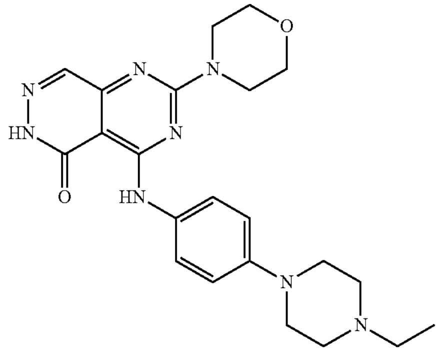 [SMILES: CCN1CCN(c2ccc(Nc3nc(N4CCOCC4)nc4cn[nH]c(=O)c34)cc2)CC1] | D | B |
| 27 | 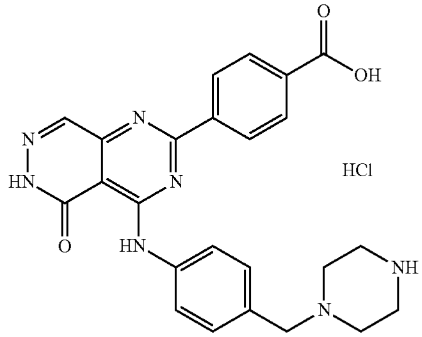 [SMILES: O=C(O)c1ccc(-c2nc(Nc3ccc(CN4CCNCC4)cc3)c3c(=O)[nH]ncc3n2)cc1 ; Cl] HCl | A | A |
| 28 | 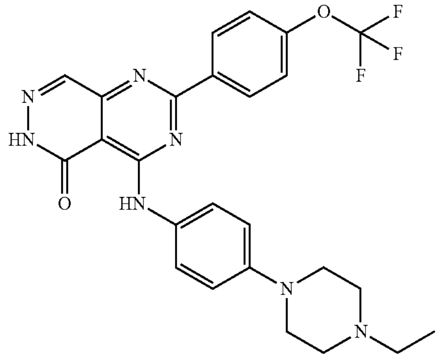 [SMILES: CCN1CCN(c2ccc(Nc3nc(-c4ccc(OC(F)(F)F)cc4)nc4cn[nH]c(=O)c34)cc2)CC1] | A | A |
| 29 | 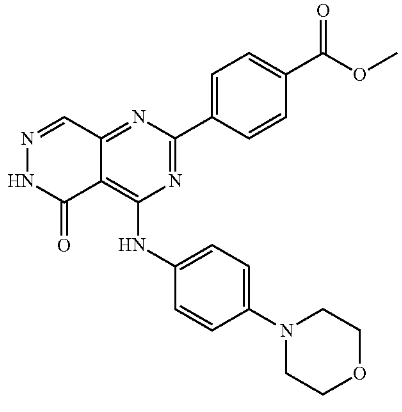 [SMILES: COC(=O)c1ccc(-c2nc(Nc3ccc(N4CCOCC4)cc3)c3c(=O)[nH]ncc3n2)cc1] | A | — |

TABLE 7-continued
| | | IC50 ≥100 nM = A; ≤100 nM = B; ≤50 nM = C; ≤10 nM = D | |
|---|---|---|---|
| Ex. # | Structure | Syk | JAK2 |
| 30 | 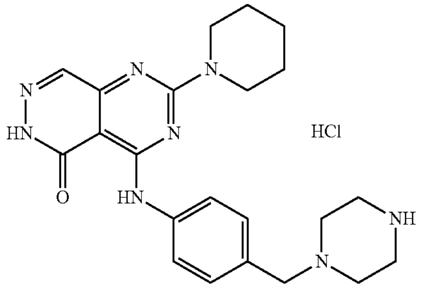 [SMILES: O=c1[nH]ncc2nc(N3CCCCC3)nc(Nc3ccc(CN4CCNCC4)cc3)c12 ; Cl] HCl | C | C |
| 31 | 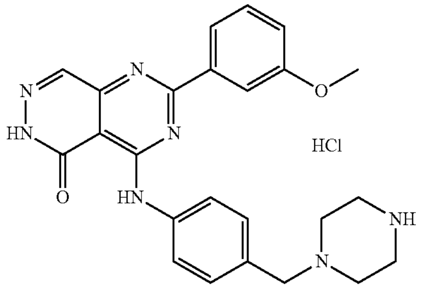 [SMILES: COc1cccc(-c2nc(Nc3ccc(CN4CCNCC4)cc3)c3c(=O)[nH]ncc3n2)c1 ; Cl] HCl | C | A |
| 32 | 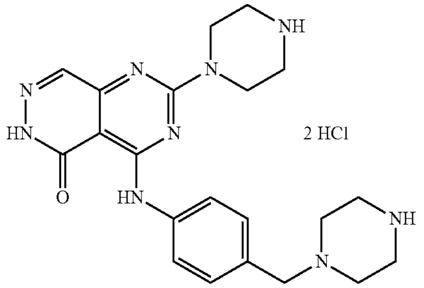 [SMILES: O=c1[nH]ncc2nc(N3CCNCC3)nc(Nc3ccc(CN4CCNCC4)cc3)c12] 2 HCl | B | A |
| 33 | 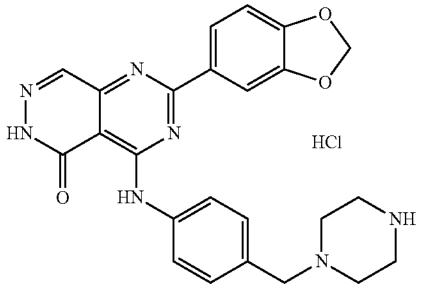 [SMILES: O=c1[nH]ncc2nc(-c3ccc4c(c3)OCO4)nc(Nc3ccc(CN4CCNCC4)cc3)c12 ; Cl] HCl | C | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 34 | 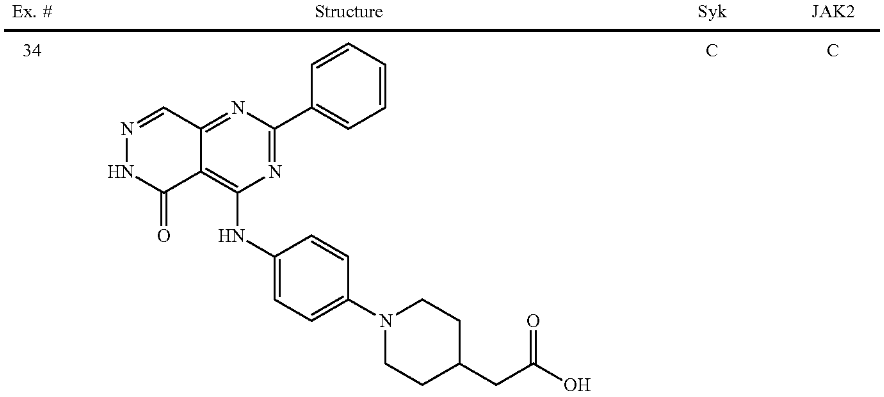 | C | C |
| 35 | 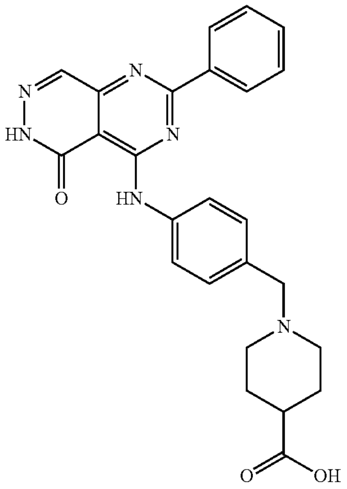 [SMILES: O=C(O)C1CCN(Cc2ccc(Nc3nc(-c4ccccc4)nc4cn[nH]c(=O)c34)cc2)CC1] | C | C |
| 36 | 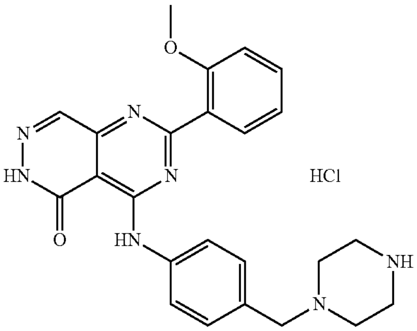 [SMILES: COc1ccccc1-c1nc(Nc2ccc(CN3CCNCC3)cc2)c2c(=O)[nH]ncc2n1 ; Cl] HCl | A | B |
| 37 | 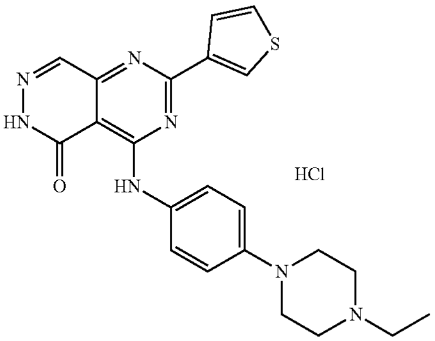 [SMILES: CCN1CCN(c2ccc(Nc3nc(-c4ccsc4)nc4cn[nH]c(=O)c34)cc2)CC1 ; Cl] HCl | D | B |

TABLE 7-continued
| | | $IC_{50}$ ≥100 nM = A; ≤100 nM = B; ≤50 nM = C; ≤10 nM = D | |
|---|---|---|---|
| Ex. # | Structure | Syk | JAK2 |
| 38 | 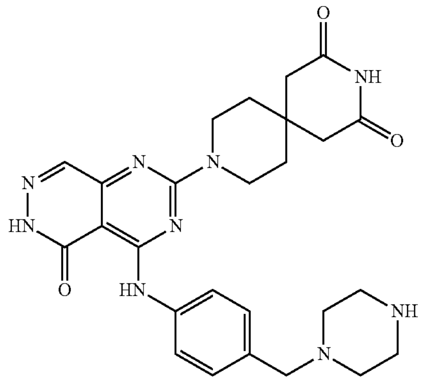 [SMILES: O=C1CC2(CCN(c3nc(Nc4ccc(CN5CCNCC5)cc4)c4c(=O)[nH]ncc4n3)CC2)CC(=O)N1] | A | — |
| 39 | 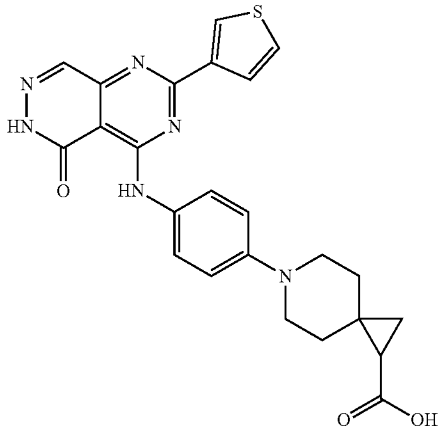 [SMILES: O=C(O)C1CC12CCN(c1ccc(Nc3nc(-c4ccsc4)nc4cn[nH]c(=O)c34)cc1)CC2] | C | C |
| 40 | 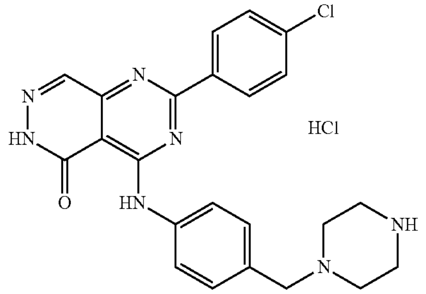 [SMILES: O=c1[nH]ncc2nc(-c3ccc(Cl)cc3)nc(Nc3ccc(CN4CCNCC4)cc3)c12 ; Cl] HCl | C | A |
| 41 | 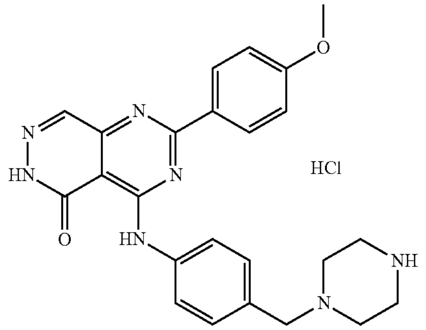 [SMILES: COc1ccc(-c2nc(Nc3ccc(CN4CCNCC4)cc3)c3c(=O)[nH]ncc3n2)cc1 ; Cl] HCl | B | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 42 | 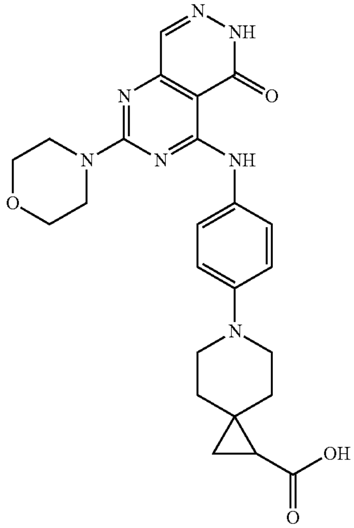 [SMILES: O=C(O)C1CC12CCN(c1ccc(Nc3nc(N4CCOCC4)nc4cn[nH]c(=O)c34)cc1)CC2] | B | C |
| 43 | 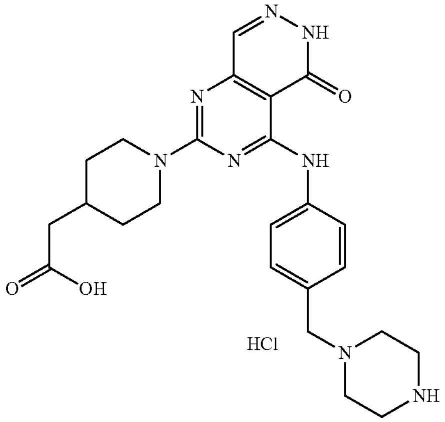 [SMILES: O=C(O)CC1CCN(c2nc(Nc3ccc(CN4CCNCC4)cc3)c3c(=O)[nH]ncc3n2)CC1 ; Cl] | C | B |
| 44 | 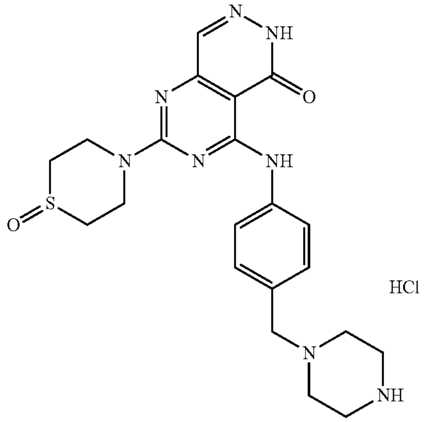 [SMILES: O=c1[nH]ncc2nc(N3CCS(=O)CC3)nc(Nc3ccc(CN4CCNCC4)cc3)c12 ; Cl] | A | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 45 | 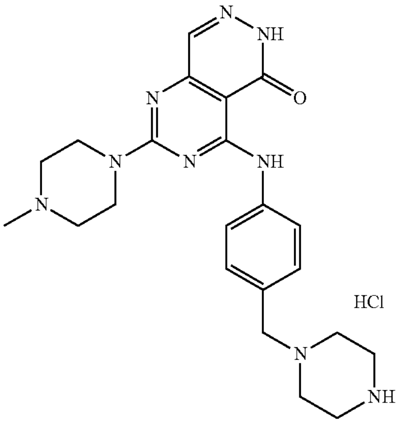 [SMILES: CN1CCN(c2nc(Nc3ccc(CN4CCNCC4)cc3)c3c(=O)[nH]ncc3n2)CC1 ; Cl] HCl | A | A |
| 46 | 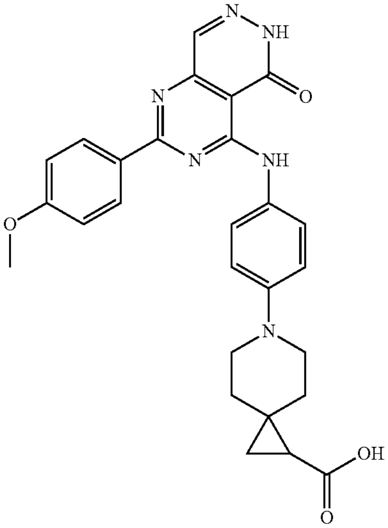 | B | B |
| 47 | 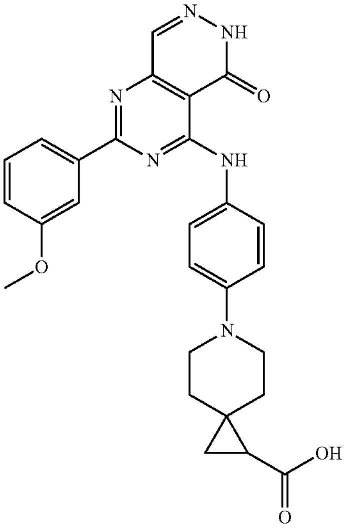 [SMILES: COc1cccc(-c2nc(Nc3ccc(N4CCC5(CC4)CC5C(=O)O)cc3)c3c(=O)[nH]ncc3n2)c1] | B | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 48 | 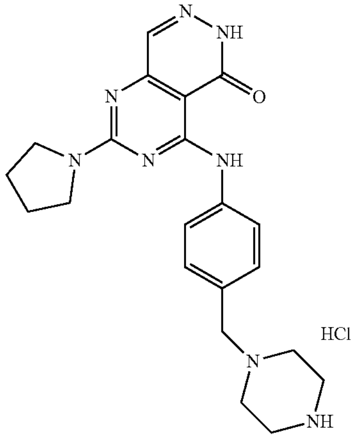 [SMILES: O=c1[nH]ncc2nc(N3CCCC3)nc(Nc3ccc(CN4CCNCC4)cc3)c12 ; Cl] | B | B |
| 49 | 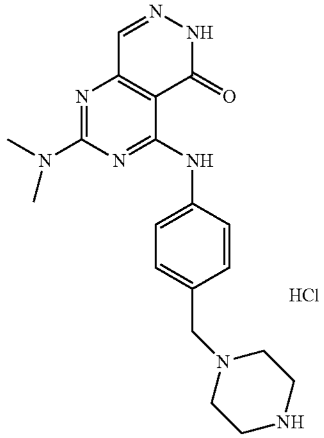 [SMILES: CN(C)c1nc(Nc2ccc(CN3CCNCC3)cc2)c2c(=O)[nH]ncc2n1 ; Cl] | B | B |
| 50 | 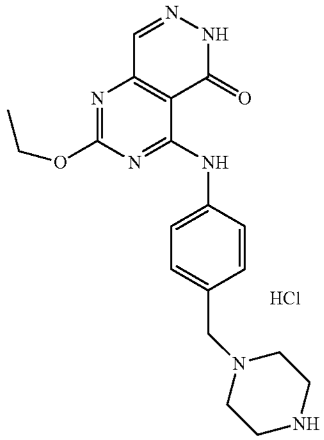 [SMILES: CCOc1nc(Nc2ccc(CN3CCNCC3)cc2)c2c(=O)[nH]ncc2n1 ; Cl] | D | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 51 | 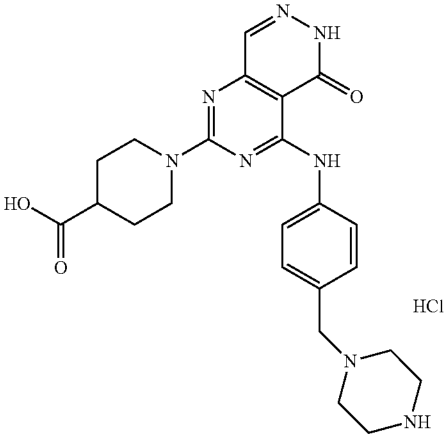 [SMILES: O=C(O)C1CCN(c2nc(Nc3ccc(CN4CCNCC4)cc3)c3c(=O)[nH]ncc3n2)CC1 ; Cl] HCl | A | A |
| 52 | 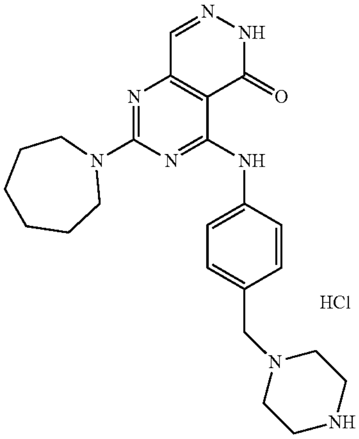 [SMILES: O=c1[nH]ncc2nc(N3CCCCCC3)nc(Nc3ccc(CN4CCNCC4)cc3)c12 ; Cl] HCl | D | D |
| 53 | 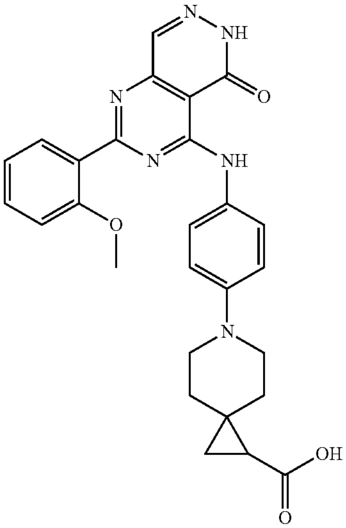 [SMILES: COc1ccccc1-c1nc(Nc2ccc(N3CCC4(CC3)CC4C(=O)O)cc2)c2c(=O)[nH]ncc2n1] | A | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 54 | 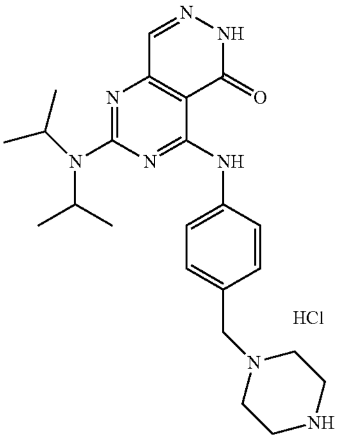 [SMILES: CC(C)N(c1nc(Nc2ccc(CN3CCNCC3)cc2)c2c(=O)[nH]ncc2n1)C(C)C ; Cl] | D | D |
| 55 | 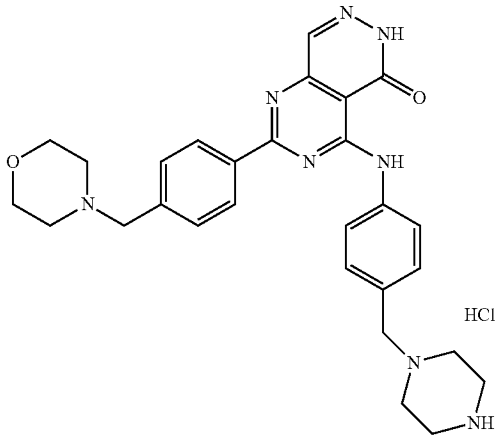 [SMILES: O=c1[nH]ncc2nc(-c3ccc(CN4CCOCC4)cc3)nc(Nc3ccc(CN4CCNCC4)cc3)c12 ; Cl] | A | A |
| 56 | 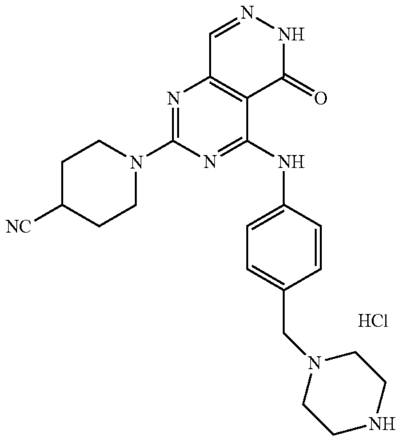 [SMILES: N#CC1CCN(c2nc(Nc3ccc(CN4CCNCC4)cc3)c3c(=O)[nH]ncc3n2)CC1 ; Cl] | A | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 57 | 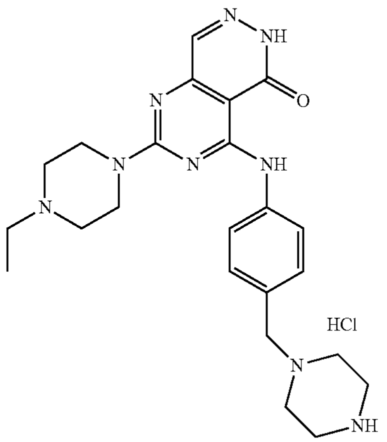 [SMILES: CCN1CCN(c2nc(Nc3ccc(CN4CCNCC4)cc3)c3c(=O)[nH]ncc3n2)CC1 ; Cl] | — | — |
| 58 | 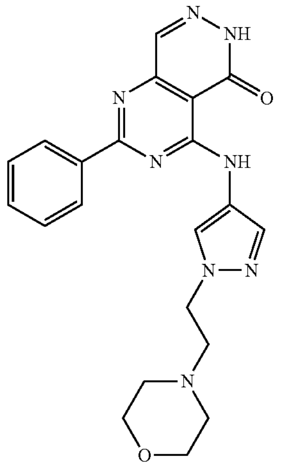 [SMILES: O=c1[nH]ncc2nc(-c3ccccc3)nc(Nc3cnn(CCN4CCOCC4)c3)c12] | A | C |
| 59 | 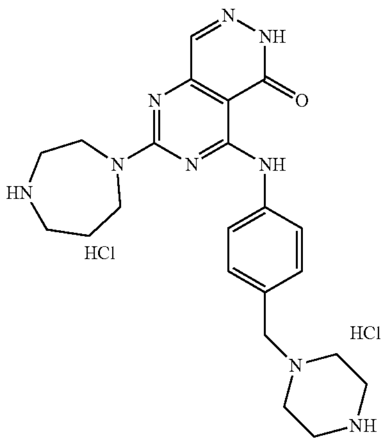 [SMILES: O=c1[nH]ncc2nc(N3CCCNCC3)nc(Nc3ccc(CN4CCNCC4)cc3)c12 ; Cl ; Cl] | C | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 60 | 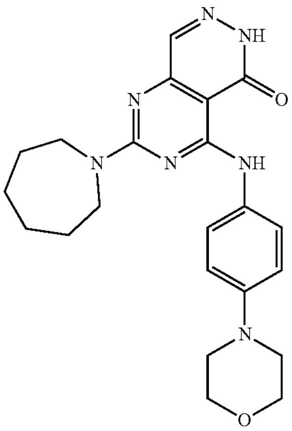 [SMILES: O=c1[nH]ncc2nc(N3CCCCCC3)nc(Nc3ccc(N4CCOCC4)cc3)c12] | D | D |
| 61 | 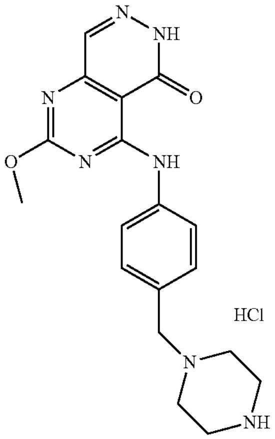 [SMILES: COc1nc(Nc2ccc(CN3CCNCC3)cc2)c2c(=O)[nH]ncc2n1 ; Cl] HCl | A | — |
| 62 | 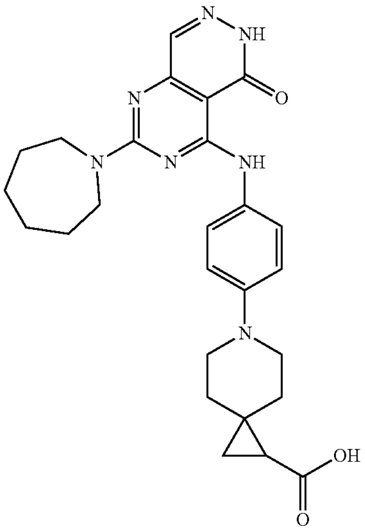 [SMILES: O=C(O)C1CC12CCN(c1ccc(Nc3nc(N4CCCCCC4)nc4cn[nH]c(=O)c34)cc1)CC2] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 63 | 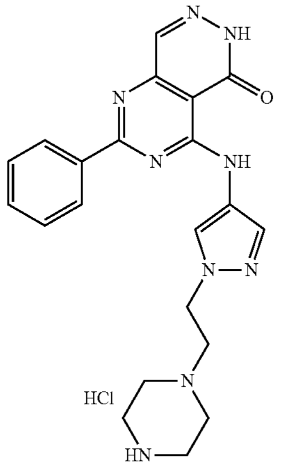 [SMILES: O=c1[nH]ncc2nc(-c3ccccc3)nc(Nc3cnn(CCN4CCNCC4)c3)c12 ; Cl] | A | — |
| 64 | 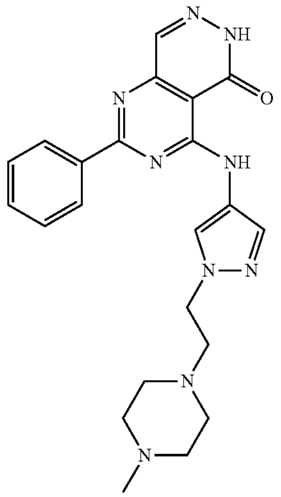 [SMILES: CN1CCN(CCn2cc(Nc3nc(-c4ccccc4)nc4cn[nH]c(=O)c34)cn2)CC1] | A | — |
| 65 | 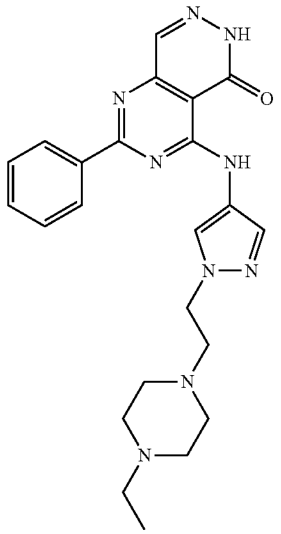 [SMILES: CCN1CCN(CCn2cc(Nc3nc(-c4ccccc4)nc4cn[nH]c(=O)c34)cn2)CC1] | A | — |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 66 | 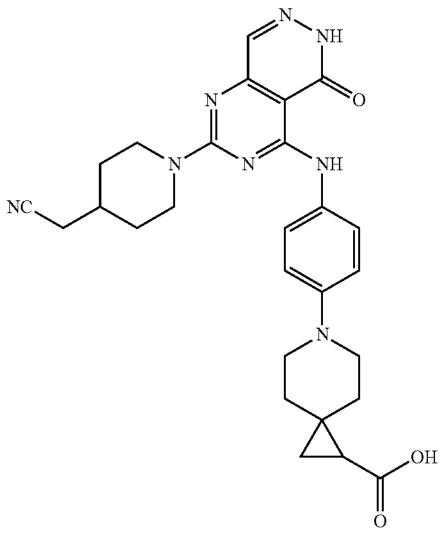 [SMILES: N#CCC1CCN(c2nc(Nc3ccc(N4CCC5(CC4)CC5C(=O)O)cc3)c3c(=O)[nH]ncc3n2)CC1] | C | |
| 67 | 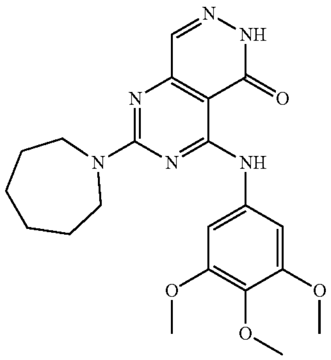 [SMILES: COc1cc(Nc2nc(N3CCCCCC3)nc3cn[nH]c(=O)c23)cc(OC)c1OC] | A | |
| 68 | 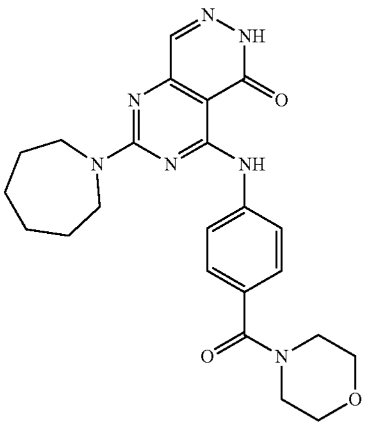 [SMILES: O=C(c1ccc(Nc2nc(N3CCCCCC3)nc3cn[nH]c(=O)c23)cc1)N1CCOCC1] | B | |

TABLE 7-continued
| Ex. # | Structure | IC50 ≥100 nM = A; ≤100 nM = B; ≤50 nM = C; ≤10 nM = D Syk | JAK2 |
|---|---|---|---|
| 69 | 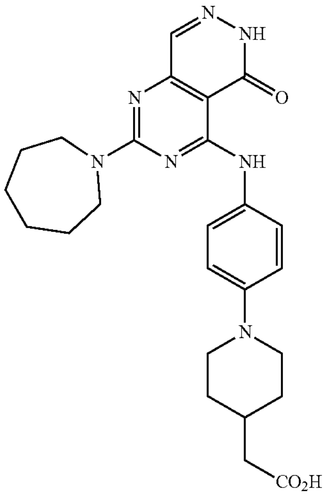 [SMILES: O=C(O)CC1CCN(c2ccc(Nc3nc(N4CCCCCC4)nc4cn[nH]c(=O)c34)cc2)CC1] | D | |
| 70 | 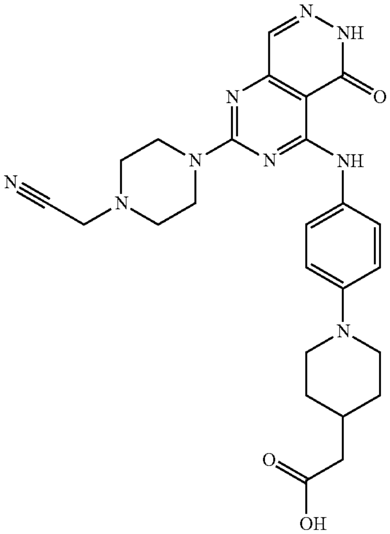 [SMILES: N#CCN1CCN(c2nc(Nc3ccc(N4CCC(CC(=O)O)CC4)cc3)c3c(=O)[nH]ncc3n2)CC1] | B | A |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 71 | 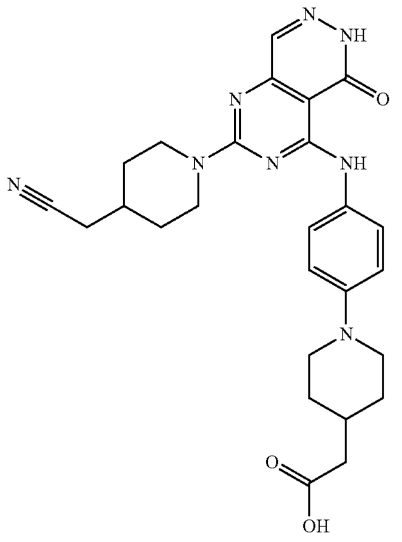 [SMILES: N#CCC1CCN(c2nc(Nc3ccc(N4CCC(CC(=O)O)CC4)cc3)c3c(=O)[nH]ncc3n2)CC1] | A | A |
| 72 | 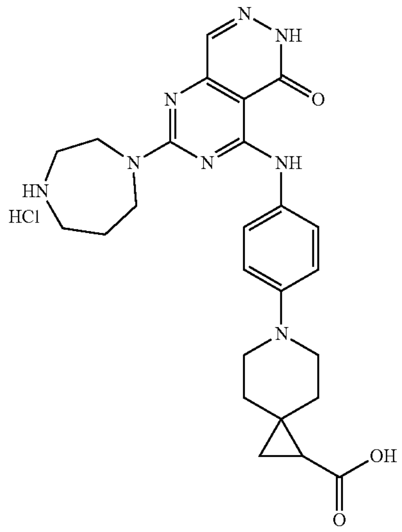 [SMILES: Cl ; O=C(O)C1CC12CCN(c1ccc(Nc3nc(N4CCCNCC4)nc4cn[nH]c(=O)c34)cc1)CC2] | C | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 73 | 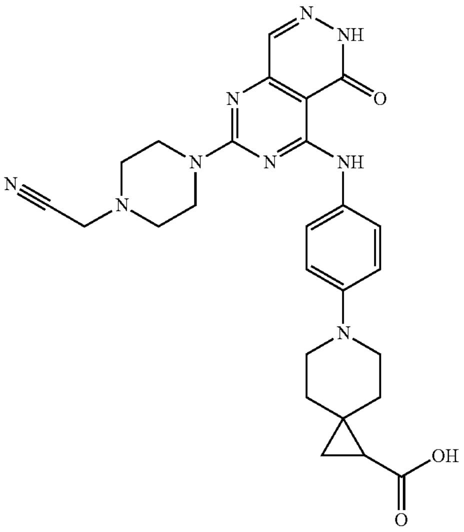 [SMILES: N#CCN1CCN(c2nc(Nc3ccc(N4CCC5(CC4)CC5C(=O)O)cc3)c3c(=O)[nH]ncc3n2)CC1] | B | — |
| 74 | 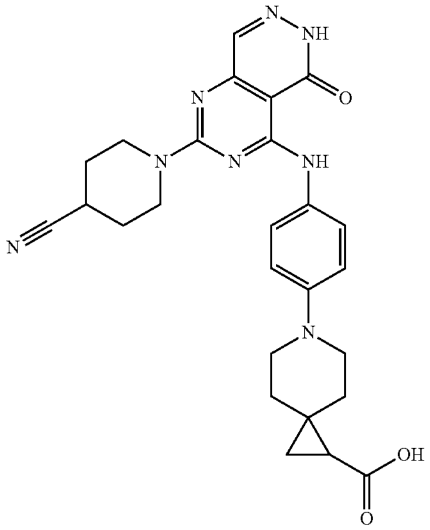 [SMILES: N#CC1CCN(c2nc(Nc3ccc(N4CCC5(CC4)CC5C(=O)O)cc3)c3c(=O)[nH]ncc3n2)CC1] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 75 | 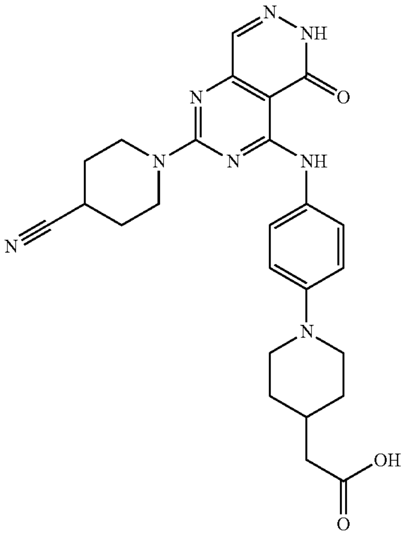 [SMILES: N#CC1CCN(c2nc(Nc3ccc(N4CCC(CC(=O)O)CC4)cc3)c3c(=O)[nH]ncc3n2)CC1] | B | — |
| 76 | 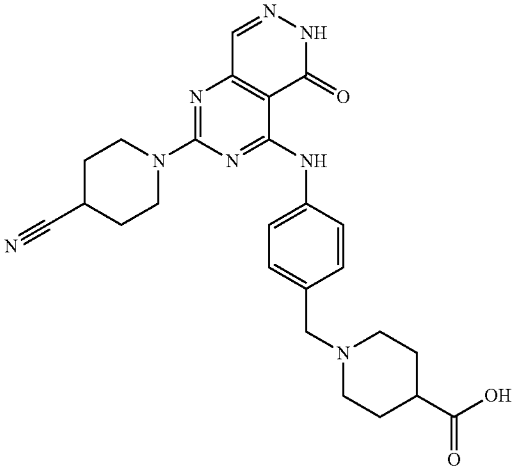 [SMILES: N#CC1CCN(c2nc(Nc3ccc(CN4CCC(C(=O)O)CC4)cc3)c3c(=O)[nH]ncc3n2)CC1] | A | — |
| 77 | 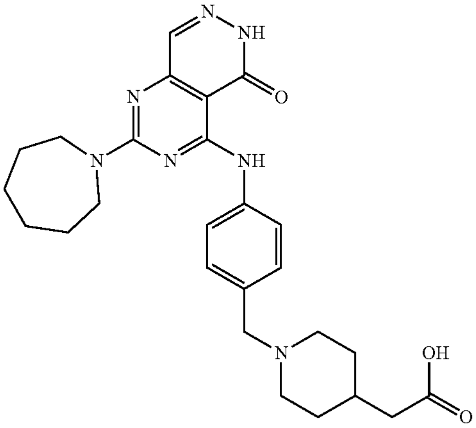 [SMILES: O=C(O)CC1CCN(Cc2ccc(Nc3nc(N4CCCCCC4)nc4cn[nH]c(=O)c34)cc2)CC1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 78 | 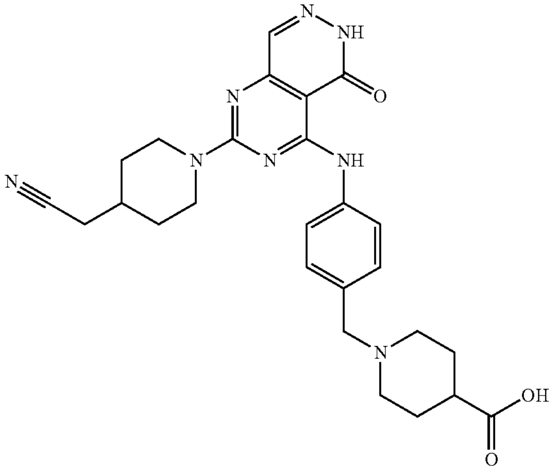 [SMILES: N#CCC1CCN(c2nc(Nc3ccc(CN4CCC(C(=O)O)CC4)cc3)c3c(=O)[nH]ncc3n2)CC1] | B | — |
| 79 | 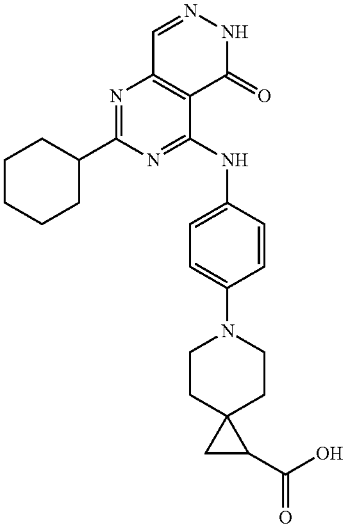 [SMILES: O=C(O)C1CC12CCN(c1ccc(Nc3nc(C4CCCCC4)nc4cn[nH]c(=O)c34)cc1)CC2] | C | D |
| 80 | 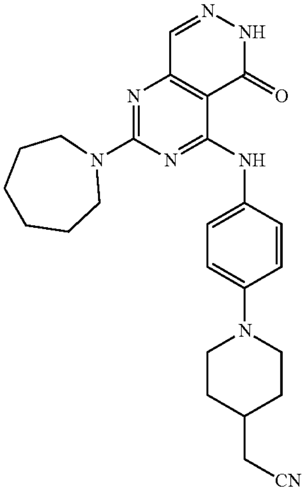 [SMILES: N#CCC1CCN(c2ccc(Nc3nc(N4CCCCCC4)nc4cn[nH]c(=O)c34)cc2)CC1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 81 | 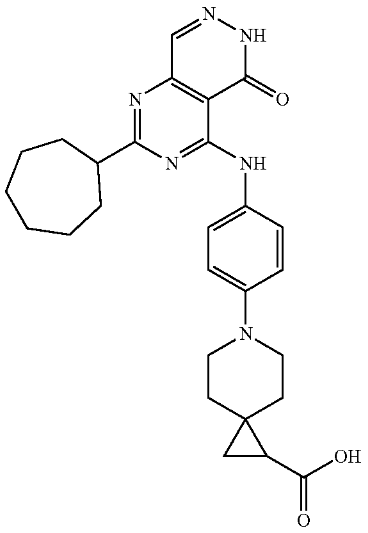 | C | D |
| 82 | 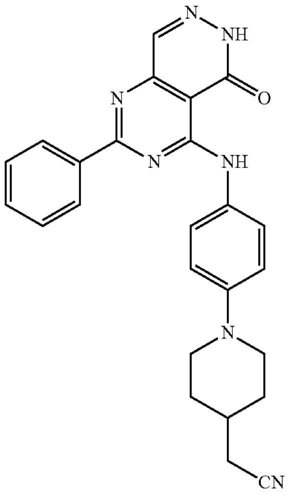 [SMILES: N#CCC1CCN(c2ccc(Nc3nc(-c4ccccc4)nc4cn[nH]c(=O)c34)cc2)CC1] | A | — |
| 83 | 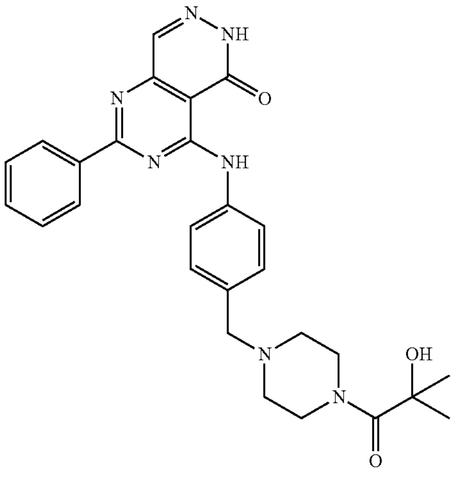 [SMILES: CC(C)(O)C(=O)N1CCN(Cc2ccc(Nc3nc(-c4ccccc4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 84 | 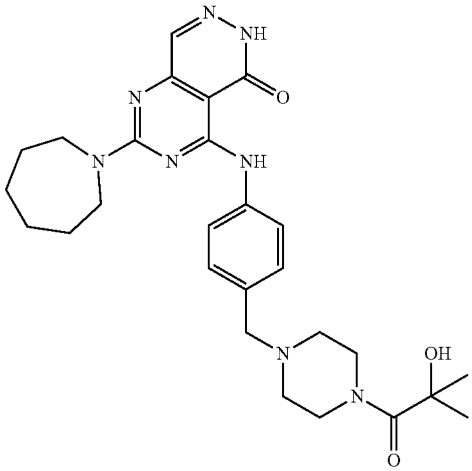 [SMILES: CC(C)(O)C(=O)N1CCN(Cc2ccc(Nc3nc(N4CCCCCC4)nc4cn[nH]c(=O)c34)cc2)CC1] | C | D |
| 85 | 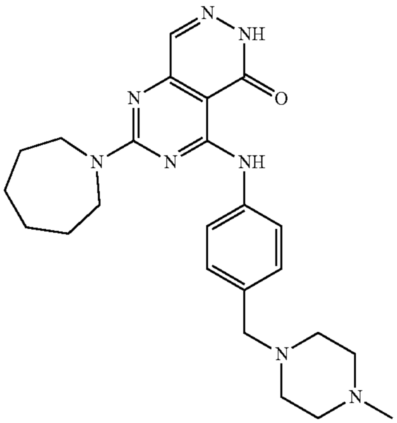 [SMILES: CN1CCN(Cc2ccc(Nc3nc(N4CCCCCC4)nc4cn[nH]c(=O)c34)cc2)CC1] | C | D |
| 86 | 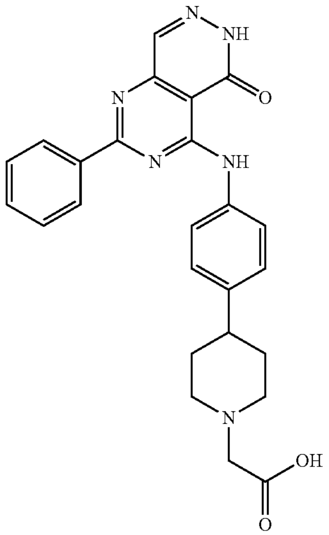 [SMILES: O=C(O)CN1CCC(c2ccc(Nc3nc(-c4ccccc4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 87 | 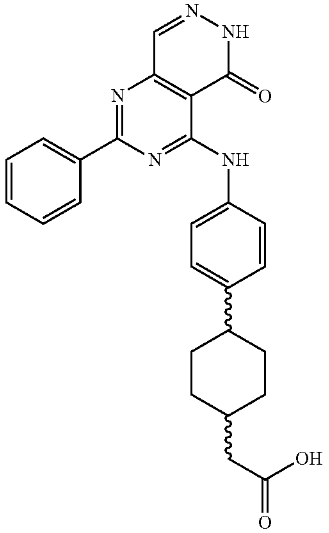 [SMILES: O=C(O)CC1CCC(c2ccc(Nc3nc(-c4ccccc4)nc4cn[nH]c(=O)c34)cc2)CC1] | C | B |
| 88 | 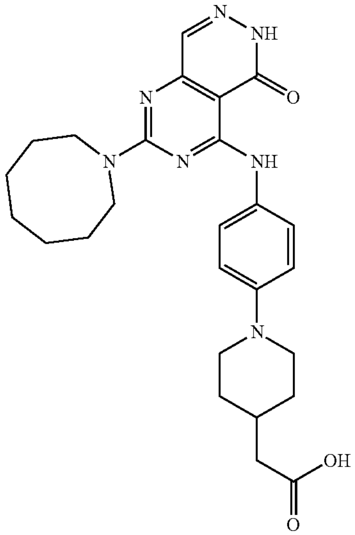 [SMILES: O=C(O)CC1CCN(c2ccc(Nc3nc(N4CCCCCCC4)nc4cn[nH]c(=O)c34)cc2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 89 | 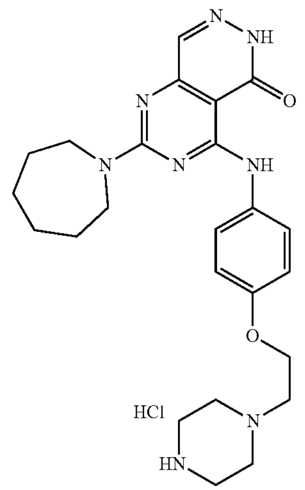 [SMILES: O=c1[nH]ncc2nc(N3CCCCCC3)nc(Nc3ccc(OCCN4CCNCC4)cc3)c12 ; Cl] | C | C |
| 90 | 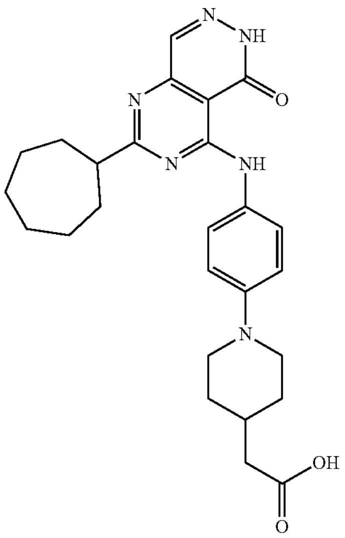 | B | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 91 | 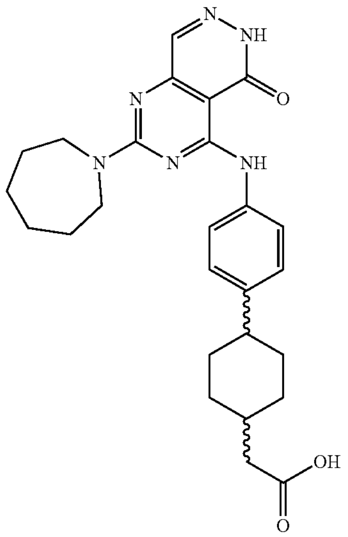 [SMILES: O=C(O)CC1CCC(c2ccc(Nc3nc(N4CCCCCC4)nc4cn[nH]c(=O)c34)cc2)CC1] | D | C |
| 92 | 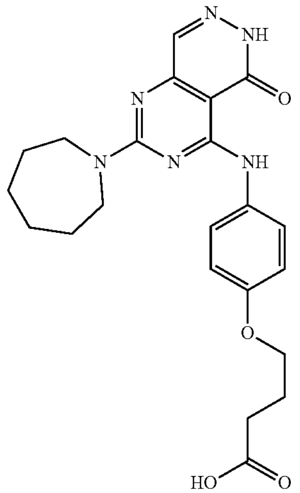 [SMILES: O=C(O)CCCOc1ccc(Nc2nc(N3CCCCCC3)nc3cn[nH]c(=O)c23)cc1] | D | C |
| 93 | 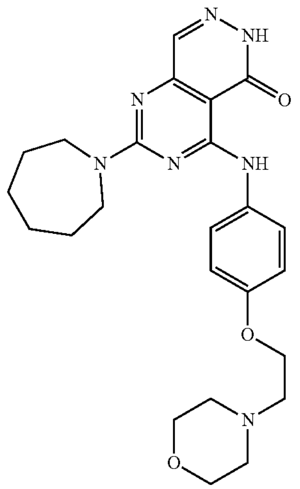 [SMILES: O=c1[nH]ncc2nc(N3CCCCCC3)nc(Nc3ccc(OCCN4CCOCC4)cc3)c12] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 94 | 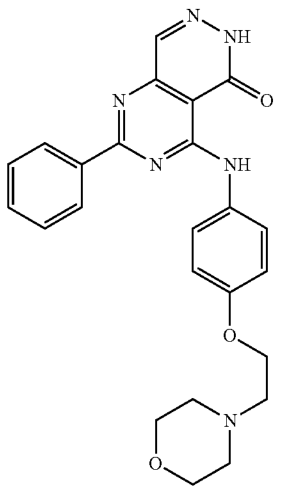 [SMILES: O=c1[nH]ncc2nc(-c3ccccc3)nc(Nc3ccc(OCCN4CCOCC4)cc3)c12] | B | — |
| 95 | 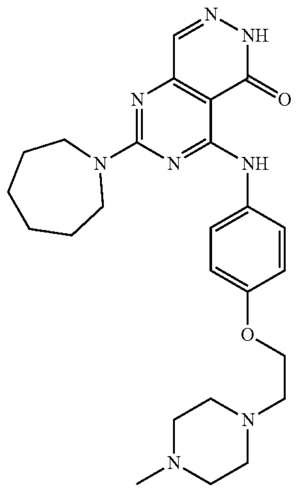 [SMILES: CN1CCN(CCOc2ccc(Nc3nc(N4CCCCCC4)nc4cn[nH]c(=O)c34)cc2)CC1] | C | C |
| 96 | 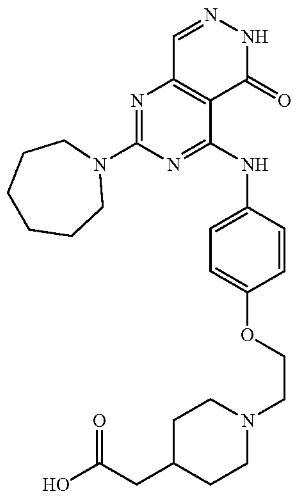 [SMILES: O=C(O)CC1CCN(CCOc2ccc(Nc3nc(N4CCCCCC4)nc4cn[nH]c(=O)c34)cc2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 97 | 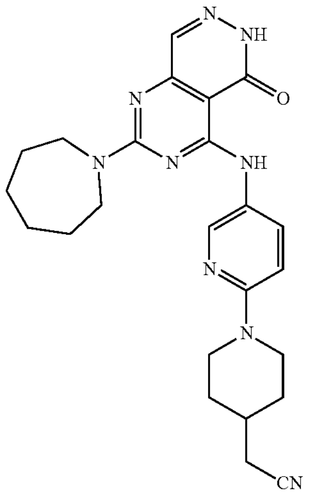 [SMILES: N#CCC1CCN(c2ccc(Nc3nc(N4CCCCCC4)nc4cn[nH]c(=O)c34)cn2)CC1] | A | — |
| 98 | 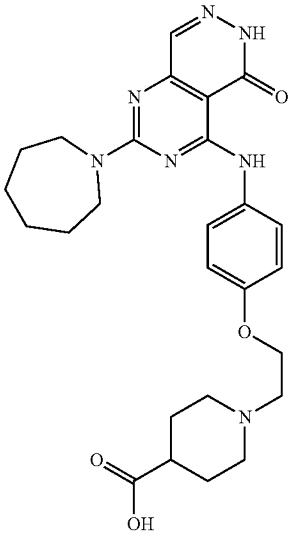 [SMILES: O=C(O)C1CCN(CCOc2ccc(Nc3nc(N4CCCCCC4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 99 | 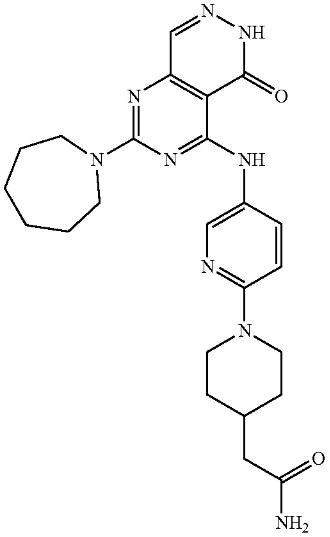 | D | C |
| 100 | 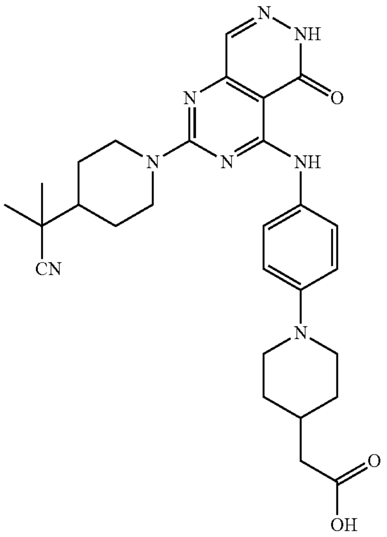 [SMILES: CC(C)(C#N)C1CCN(c2nc(Nc3ccc(N4CCC(CC(=O)O)CC4)cc3)c3c(=O)[nH]ncc3n2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 101 | 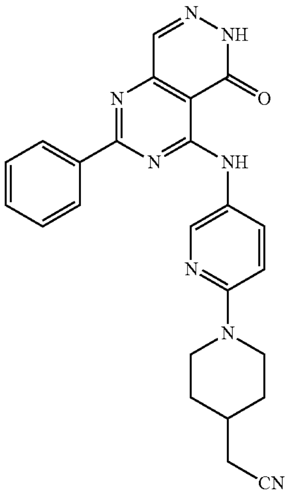 [SMILES: N#CCC1CCN(c2ccc(Nc3nc(-c4ccccc4)nc4cn[nH]c(=O)c34)cn2)CC1] | A | A |
| 102 | 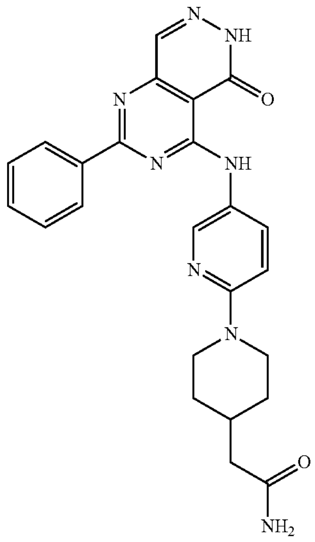 [SMILES: NC(=O)CC1CCN(c2ccc(Nc3nc(-c4ccccc4)nc4cn[nH]c(=O)c34)cn2)CC1] | C | A |
| 103 | 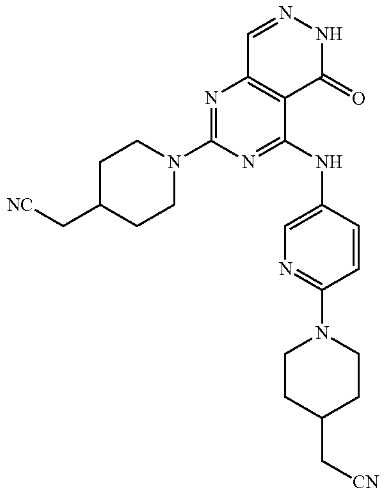 [SMILES: N#CCC1CCN(c2ccc(Nc3nc(N4CCC(CC#N)CC4)nc4cn[nH]c(=O)c34)cn2)CC1] | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 104 | 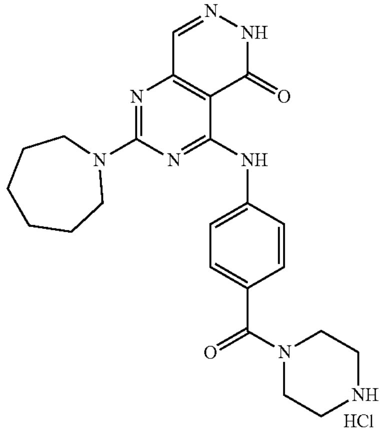 [SMILES: O=C(c1ccc(Nc2nc(N3CCCCCC3)nc3cn[nH]c(=O)c23)cc1)N1CCNCC1 ; Cl] | C | D |
| 105 | 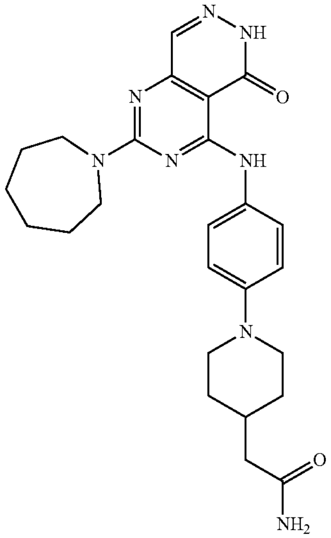 | D | D |
| 106 | 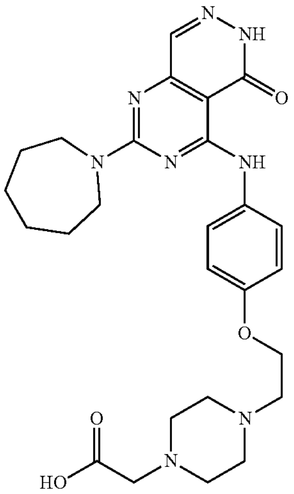 [SMILES: O=C(O)CN1CCN(CCOc2ccc(Nc3nc(N4CCCCCC4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 107 | 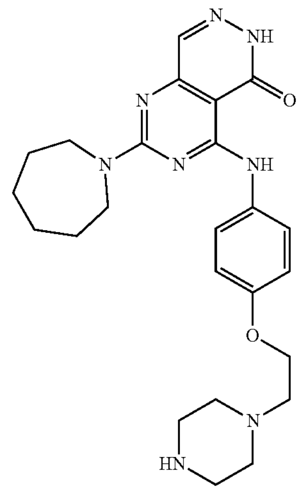 [SMILES: O=c1[nH]ncc2nc(N3CCCCCC3)nc(Nc3ccc(OCCN4CCNCC4)cc3)c12] | D | C |
| 108 | 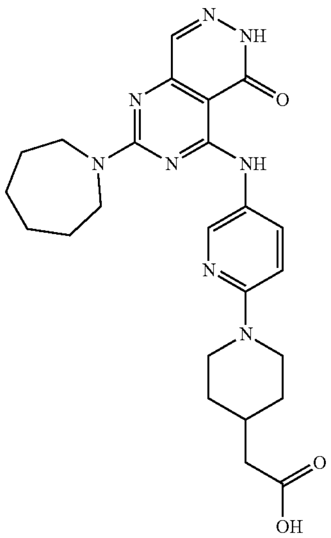 [SMILES: O=C(O)CC1CCN(c2ccc(Nc3nc(N4CCCCCC4)nc4cn[nH]c(=O)c34)cn2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 109 | 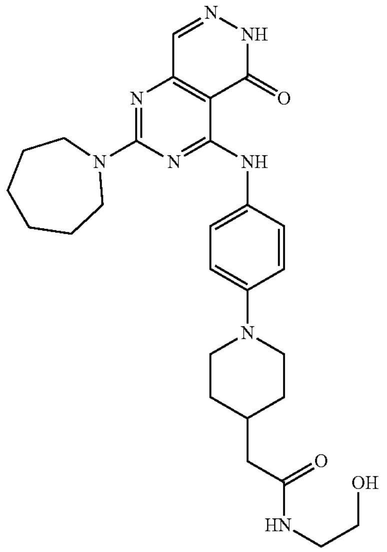 [SMILES: O=C(CC1CCN(c2ccc(Nc3nc(N4CCCCCC4)nc4cn[nH]c(=O)c34)cc2)CC1)NCCO] | D | D |
| 110 | 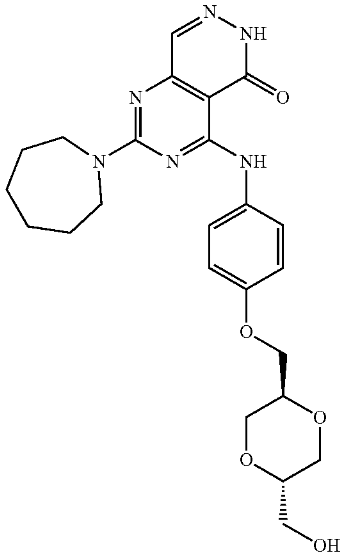 [SMILES: O=c1[nH]ncc2nc(N3CCCCCC3)nc(Nc3ccc(OC[C@@H]4CO[C@@H](CO)CO4)cc3)c12] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 111 | 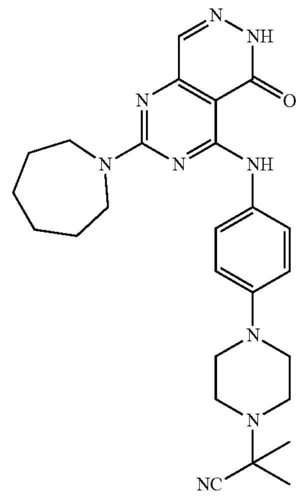 [SMILES: CC(C)(C#N)N1CCN(c2ccc(Nc3nc(N4CCCCCC4)nc4cn[nH]c(=O)c34)cc2)CC1] | C | A |
| 112 | 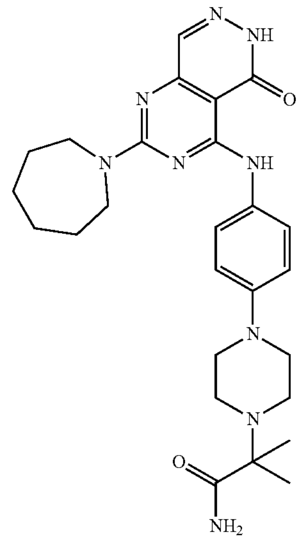 [SMILES: CC(C)(C(N)=O)N1CCN(c2ccc(Nc3nc(N4CCCCCC4)nc4cn[nH]c(=O)c34)cc2)CC1] | C | D |
| 113 | 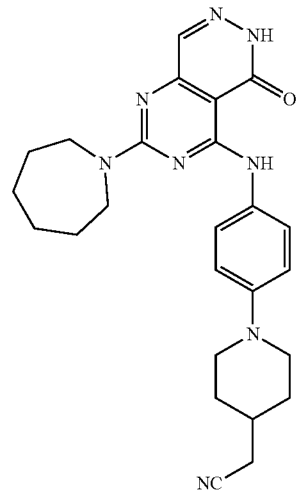 [SMILES: N#CCC1CCN(c2ccc(Nc3nc(N4CCCCCC4)nc4cn[nH]c(=O)c34)cc2)CC1] | A | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 114 | 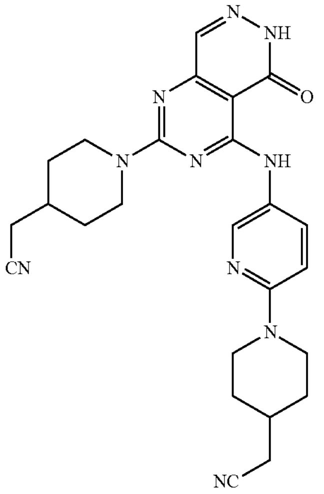 [SMILES: N#CCC1CCN(c2ccc(Nc3nc(N4CCC(CC#N)CC4)nc4cn[nH]c(=O)c34)cn2)CC1] | D | C |
| 115 | 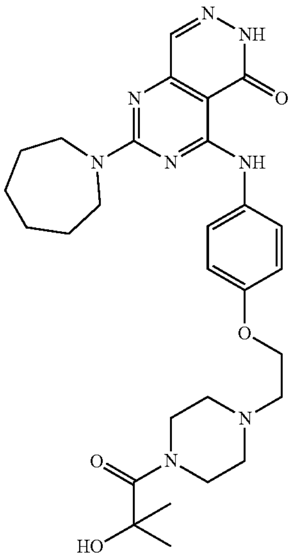 [SMILES: CC(C)(O)C(=O)N1CCN(CCOc2ccc(Nc3nc(N4CCCCCC4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 116 | 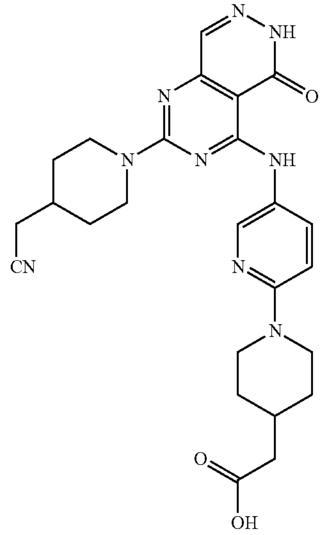 [SMILES: N#CCC1CCN(c2nc(Nc3ccc(N4CCC(CC(=O)O)CC4)nc3)c3c(=O)[nH]ncc3n2)CC1] | C | C |
| 117 | 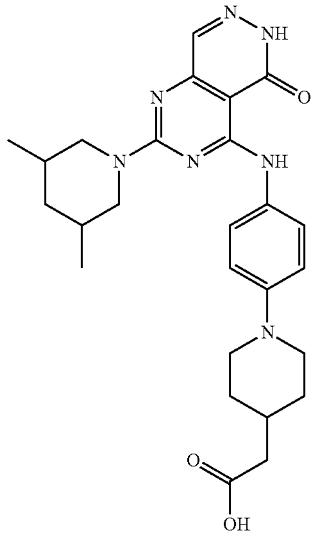 [SMILES: CC1CC(C)CN(c2nc(Nc3ccc(N4CCC(CC(=O)O)CC4)cc3)c3c(=O)[nH]ncc3n2)C1] | C | D |

TABLE 7-continued
| Ex. # | Structure | IC50 ≥100 nM = A; ≤100 nM = B; ≤50 nM = C; ≤10 nM = D Syk | JAK2 |
| --- | --- | --- | --- |
| 118 | 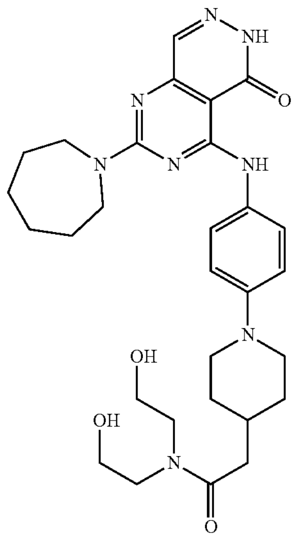 [SMILES: O=C(CC1CCN(c2ccc(Nc3nc(N4CCCCCC4)nc4cn[nH]c(=O)c34)cc2)CC1)N(CCO)CCO] | C | D |
| 119 | 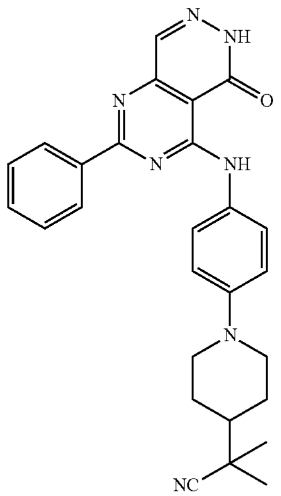 [SMILES: CC(C)(C#N)C1CCN(c2ccc(Nc3nc(-c4ccccc4)nc4cn[nH]c(=O)c34)cc2)CC1] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 120 | 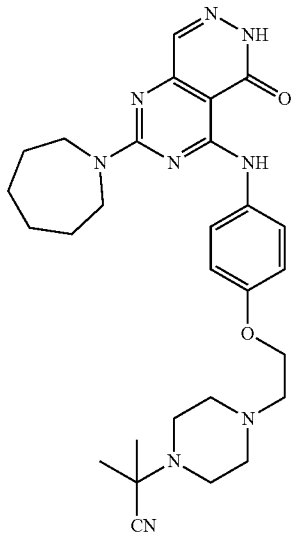 [SMILES: CC(C)(C#N)N1CCN(CCOc2ccc(Nc3nc(N4CCCCCC4)nc4cn[nH]c(=O)c34)cc2)CC1] | C | C |
| 121 | 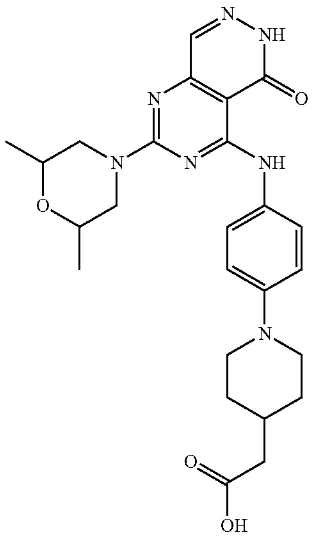 [SMILES: CC1CN(c2nc(Nc3ccc(N4CCC(CC(=O)O)CC4)cc3)c3c(=O)[nH]ncc3n2)CC(C)O1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 122 | 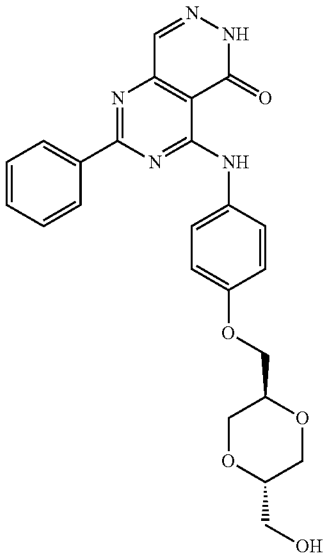 [SMILES: O=c1[nH]ncc2nc(-c3ccccc3)nc(Nc3ccc(OC[C@@H]4CO[C@@H](CO)CO4)cc3)c12] | A | — |
| 123 | 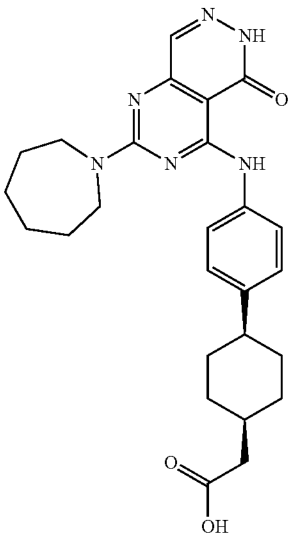 [SMILES: O=C(O)C[C@H]1CC[C@@H](c2ccc(Nc3nc(N4CCCCCC4)nc4cn[nH]c(=O)c34)cc2)CC1] | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 124 | 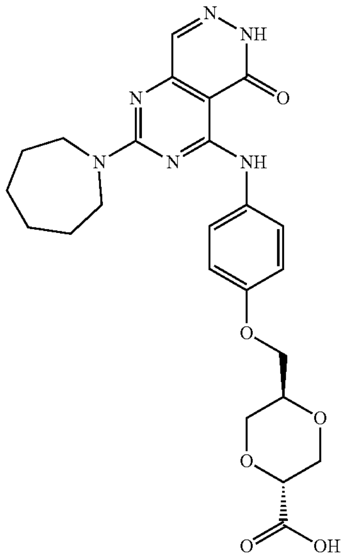 [SMILES: O=C(O)[C@H]1CO[C@H](COc2ccc(Nc3nc(N4CCCCCC4)nc4cn[nH]c(=O)c34)cc2)CO1] | D | D |
| 125 | 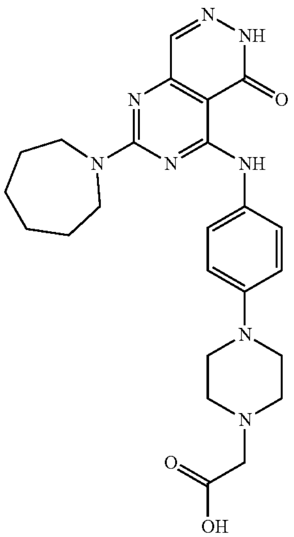 [SMILES: O=C(O)CN1CCN(c2ccc(Nc3nc(N4CCCCCC4)nc4cn[nH]c(=O)c34)cc2)CC1] | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 126 | 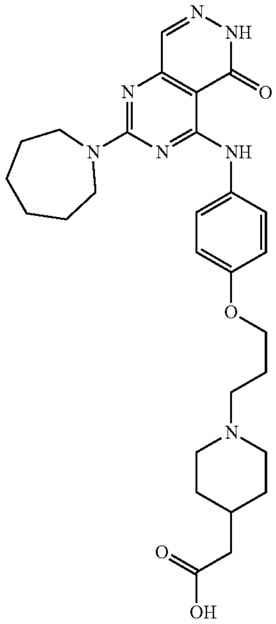 [SMILES: O=C(O)CC1CCN(CCCOc2ccc(Nc3nc(N4CCCCCC4)nc4cn[nH]c(=O)c34)cc2)CC1] | B | C |
| 127 | 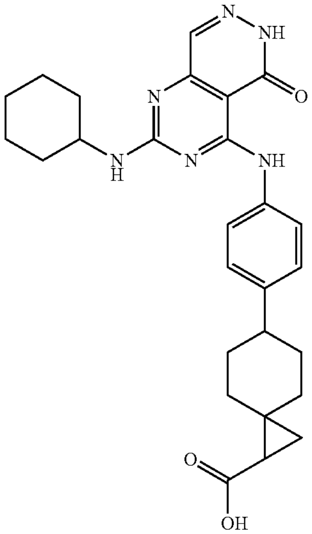 [SMILES: O=C(O)C1CC12CCC(c1ccc(Nc3nc(NC4CCCCC4)nc4cn[nH]c(=O)c34)cc1)CC2] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 128 | 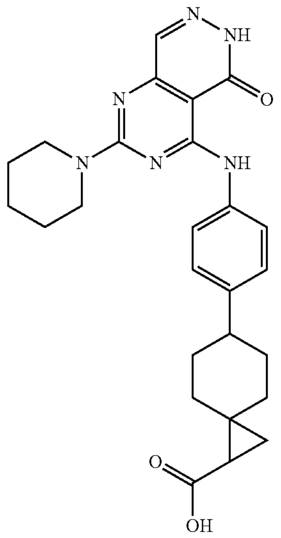 [SMILES: O=C(O)C1CC12CCC(c1ccc(Nc3nc(N4CCCCC4)nc4cn[nH]c(=O)c34)cc1)CC2] | C | C |
| 129 | 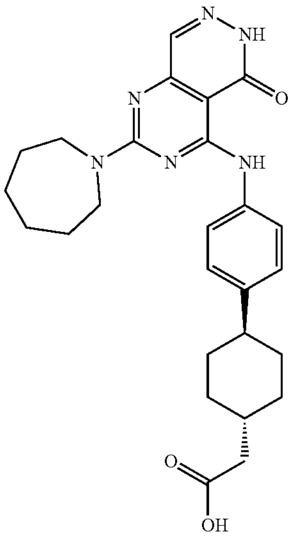 [SMILES: O=C(O)C[C@H]1CC[C@H](c2ccc(Nc3nc(N4CCCCCC4)nc4cn[nH]c(=O)c34)cc2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 130 | 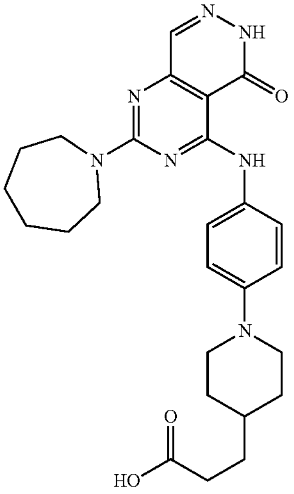 [SMILES: O=C(O)CCC1CCN(c2ccc(Nc3nc(N4CCCCCC4)nc4cn[nH]c(=O)c34)cc2)CC1] | D | D |
| 131 | 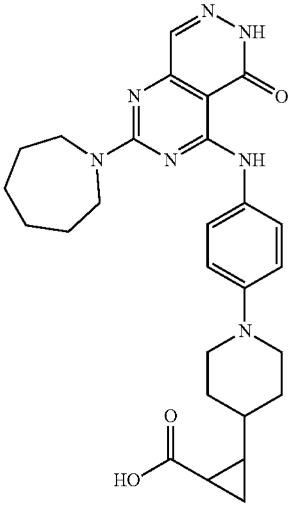 [SMILES: O=C(O)C1CC1C1CCN(c2ccc(Nc3nc(N4CCCCCC4)nc4cn[nH]c(=O)c34)cc2)CC1] | D | D |
| 132 | 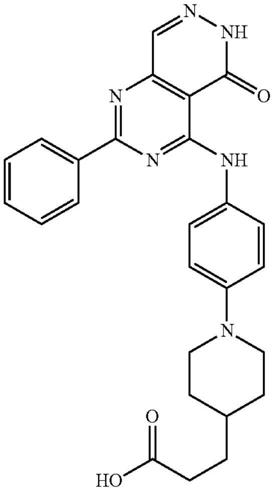 [SMILES: O=C(O)CCC1CCN(c2ccc(Nc3nc(-c4ccccc4)nc4cn[nH]c(=O)c34)cc2)CC1] | C | D |

TABLE 7-continued
| Ex. # | Structure | $IC_{50}$ ≥100 nM = A; ≤100 nM = B; ≤50 nM = C; ≤10 nM = D Syk | JAK2 |
|---|---|---|---|
| 133 | 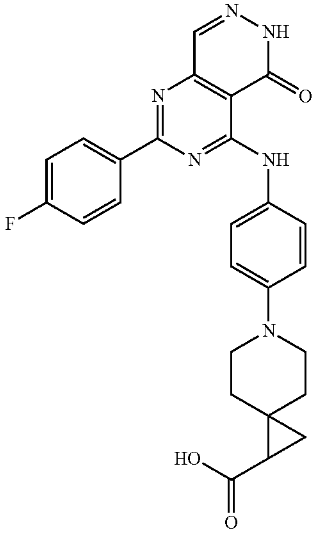 [SMILES: O=C(O)C1CC12CCN(c1ccc(Nc3nc(-c4ccc(F)cc4)nc4cn[nH]c(=O)c34)cc1)CC2] | B | C |
| 134 | 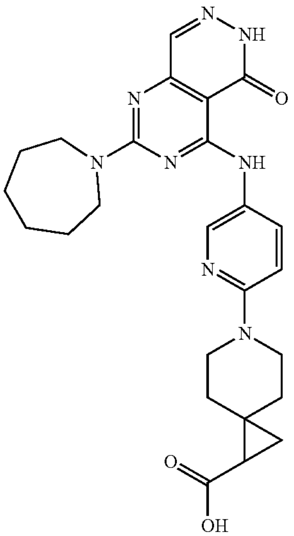 [SMILES: O=C(O)C1CC12CCN(c1ccc(Nc3nc(N4CCCCCC4)nc4cn[nH]c(=O)c34)cn1)CC2] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 135 | 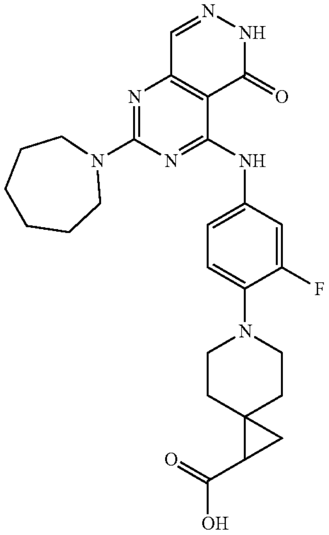 [SMILES: O=C(O)C1CC12CCN(c1ccc(Nc3nc(N4CCCCCC4)nc4cn[nH]c(=O)c34)cc1F)CC2] | D | D |
| 136 | 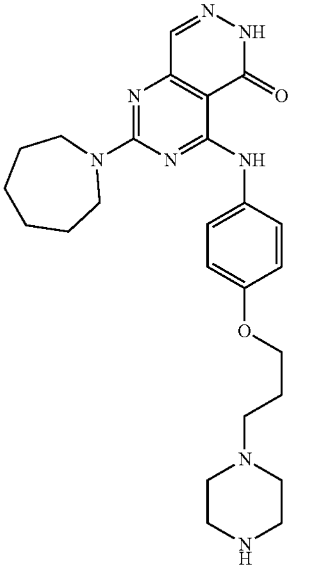 [SMILES: O=c1[nH]ncc2nc(N3CCCCCC3)nc(Nc3ccc(OCCCN4CCNCC4)cc3)c12] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 137 | 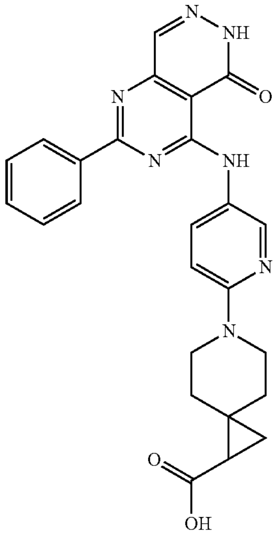 [SMILES: O=C(O)C1CC12CCN(c1ccc(Nc3nc(-c4ccccc4)nc4cn[nH]c(=O)c34)cn1)CC2] | A | — |
| 138 | 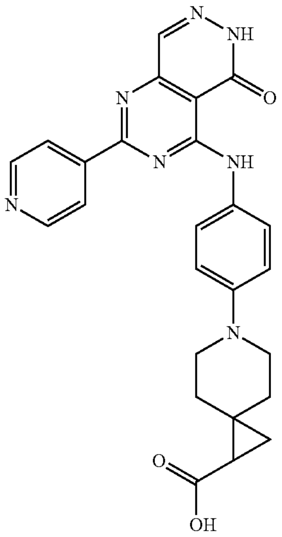 [SMILES: O=C(O)C1CC12CCN(c1ccc(Nc3nc(-c4ccncc4)nc4cn[nH]c(=O)c34)cc1)CC2] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 139 | 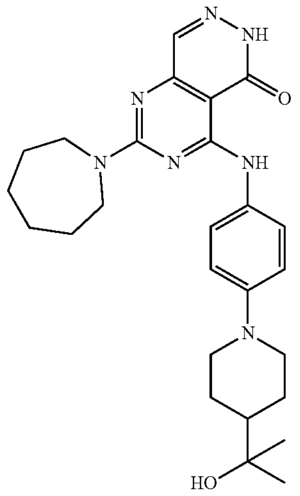 | C | D |
| 140 | 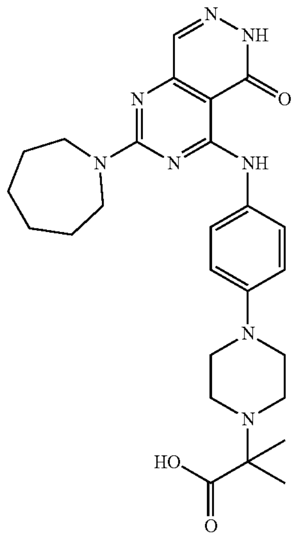 [SMILES: CC(C)(C(=O)O)N1CCN(c2ccc(Nc3nc(N4CCCCCC4)nc4cn[nH]c(=O)c34)cc2)CC1] | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 141 | 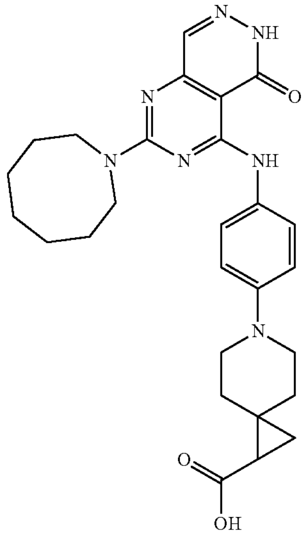 [SMILES: O=C(O)C1CC12CCN(c1ccc(Nc3nc(N4CCCCCCC4)nc4cn[nH]c(=O)c34)cc1)CC2] | C | D |
| 142 | 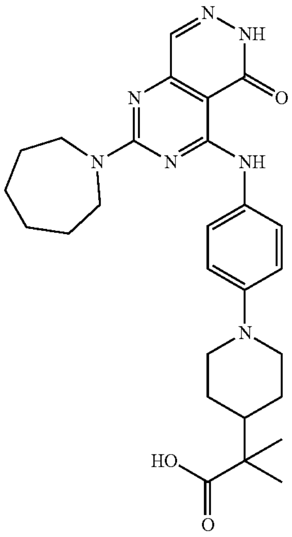 [SMILES: CC(C)(C(=O)O)C1CCN(c2ccc(Nc3nc(N4CCCCCC4)nc4cn[nH]c(=O)c34)cc2)CC1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 143 | 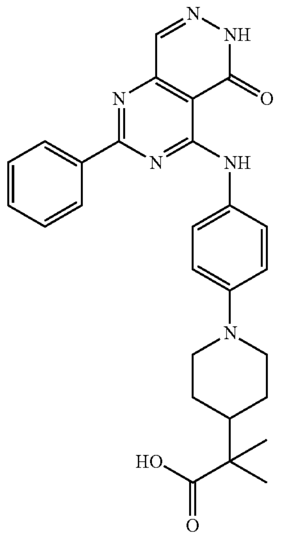 [SMILES: CC(C)(C(=O)O)C1CCN(c2ccc(Nc3nc(-c4ccccc4)nc4cn[nH]c(=O)c34)cc2)CC1] | C | A |
| 144 | 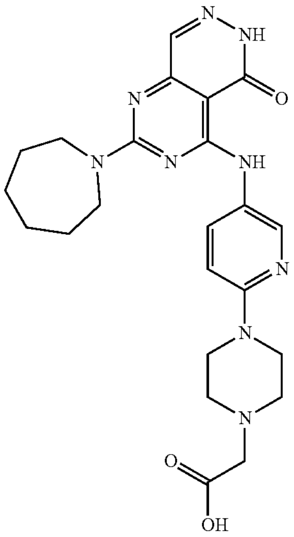 [SMILES: O=C(O)CN1CCN(c2ccc(Nc3nc(N4CCCCCC4)nc4cn[nH]c(=O)c34)cn2)CC1] | B | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 145 | 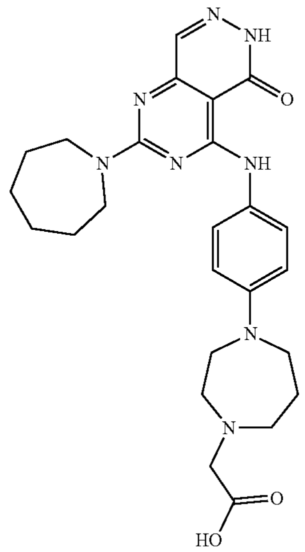 [SMILES: O=C(O)CN1CCCN(c2ccc(Nc3nc(N4CCCCCC4)nc4cn[nH]c(=O)c34)cc2)CC1] | D | D |
| 146 | 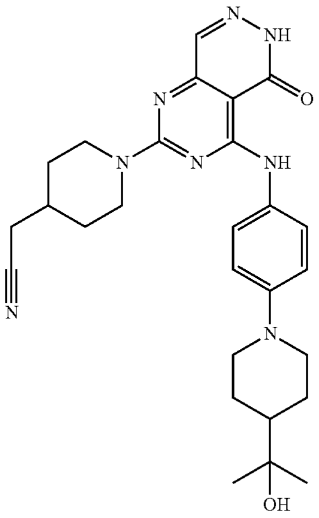 [SMILES: CC(C)(O)C1CCN(c2ccc(Nc3nc(N4CCC(CC#N)CC4)nc4cn[nH]c(=O)c34)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 147 | 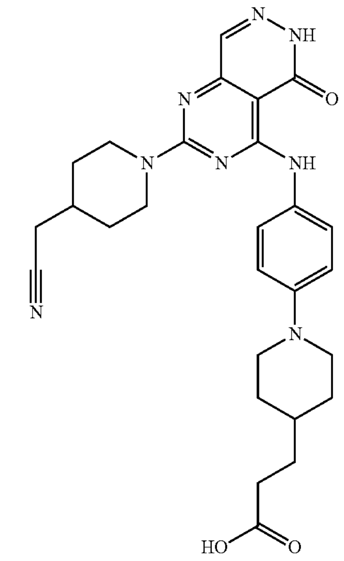 [SMILES: N#CCC1CCN(c2nc(Nc3ccc(N4CCC(CCC(=O)O)CC4)cc3)c3c(=O)[nH]ncc3n2)CC1] | D | C |
| 148 | 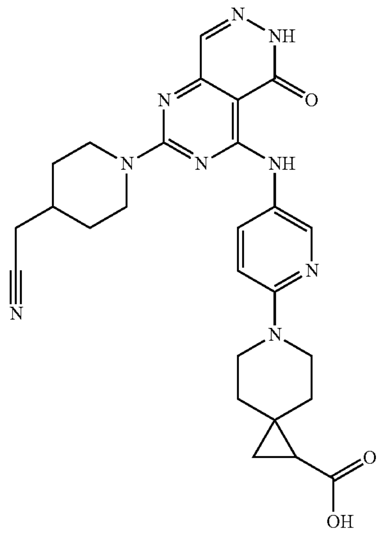 [SMILES: N#CCC1CCN(c2nc(Nc3ccc(N4CCC5(CC4)CC5C(=O)O)nc3)c3c(=O)[nH]ncc3n2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 149 | 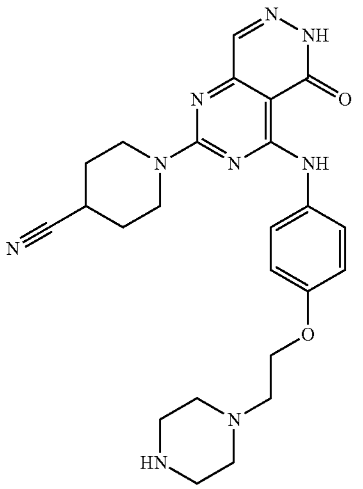 [SMILES: N#CC1CCN(c2nc(Nc3ccc(OCCN4CCNCC4)cc3)c3c(=O)[nH]ncc3n2)CC1] | A | — |
| 150 | 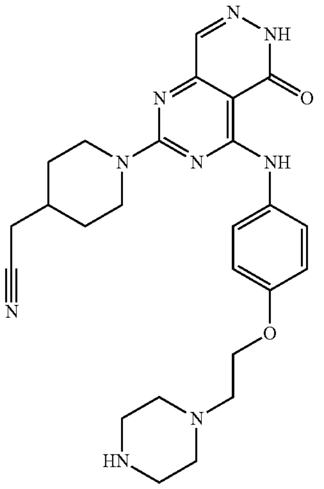 [SMILES: N#CCC1CCN(c2nc(Nc3ccc(OCCN4CCNCC4)cc3)c3c(=O)[nH]ncc3n2)CC1] | C | A |
| 151 | 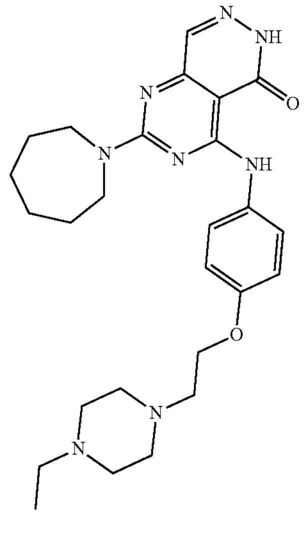 [SMILES: CCN1CCN(CCOc2ccc(Nc3nc(N4CCCCCC4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 152 | 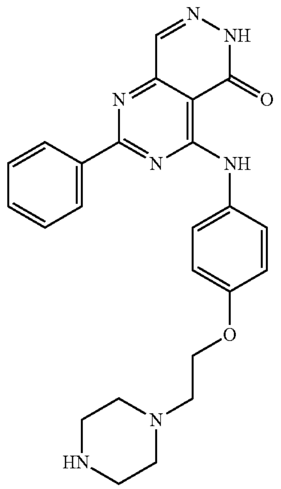 [SMILES: O=c1[nH]ncc2nc(-c3ccccc3)nc(Nc3ccc(OCCN4CCNCC4)cc3)c12] | C | A |
| 153 | 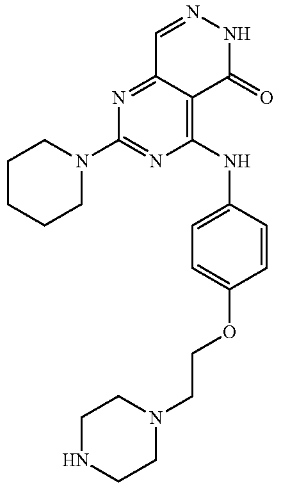 [SMILES: O=c1[nH]ncc2nc(N3CCCCC3)nc(Nc3ccc(OCCN4CCNCC4)cc3)c12] | C | B |
| 154 | 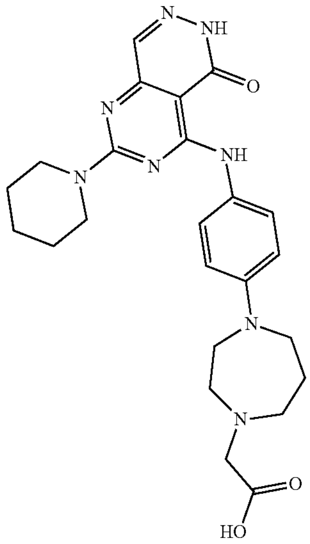 [SMILES: O=C(O)CN1CCCN(c2ccc(Nc3nc(N4CCCCC4)nc4cn[nH]c(=O)c34)cc2)CC1] | C | C |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 155 | 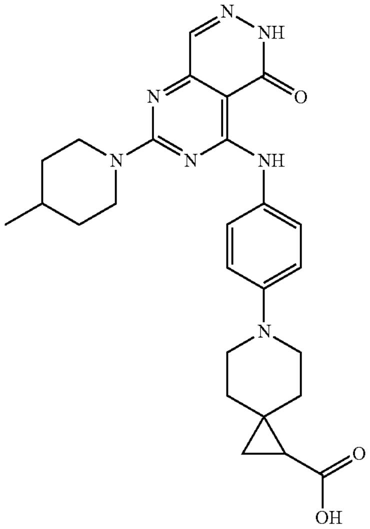 [SMILES: CC1CCN(c2nc(Nc3ccc(N4CCC5(CC4)CC5C(=O)O)cc3)c3c(=O)[nH]ncc3n2)CC1] | C | C |
| 156 | 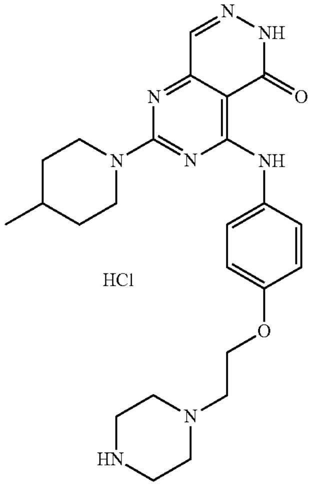 [SMILES: CC1CCN(c2nc(Nc3ccc(OCCN4CCNCC4)cc3)c3c(=O)[nH]ncc3n2)CC1 ; Cl] | C | B |

TABLE 7-continued
| Ex. # | Structure | IC50 ≥100 nM = A; ≤100 nM = B; ≤50 nM = C; ≤10 nM = D Syk | JAK2 |
|---|---|---|---|
| 157 | 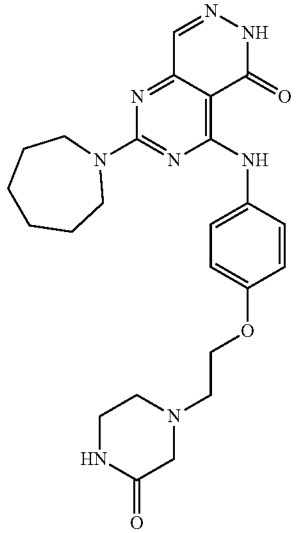 [SMILES: O=C1CN(CCOc2ccc(Nc3nc(N4CCCCCC4)nc4cn[nH]c(=O)c34)cc2)CCN1] | C | C |
| 158 | 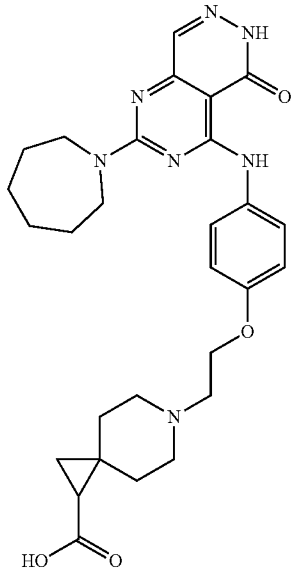 [SMILES: O=C(O)C1CC12CCN(CCOc1ccc(Nc3nc(N4CCCCCC4)nc4cn[nH]c(=O)c34)cc1)CC2] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 159 | 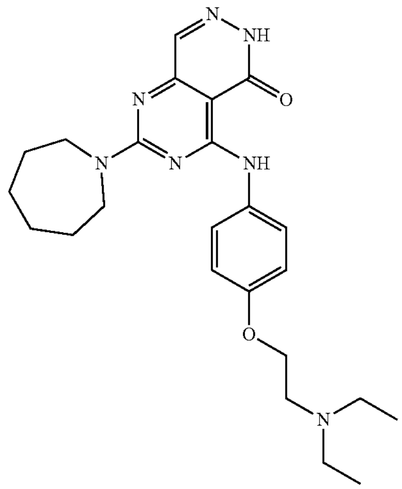 [SMILES: CCN(CC)CCOc1ccc(Nc2nc(N3CCCCCC3)nc3cn[nH]c(=O)c23)cc1] | C | D |
| 160 | 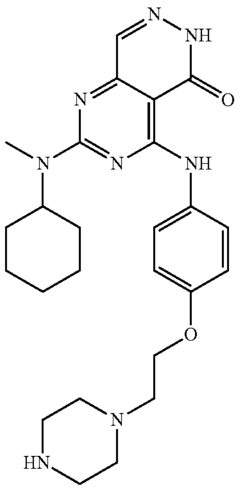 [SMILES: CN(c1nc(Nc2ccc(OCCN3CCNCC3)cc2)c2c(=O)[nH]ncc2n1)C1CCCCC1] | C | C |
| 161 | 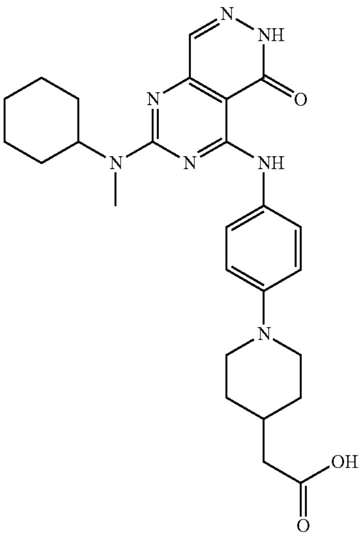 [SMILES: CN(c1nc(Nc2ccc(N3CCC(CC(=O)O)CC3)cc2)c2c(=O)[nH]ncc2n1)C1CCCCC1] | C | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 162 | 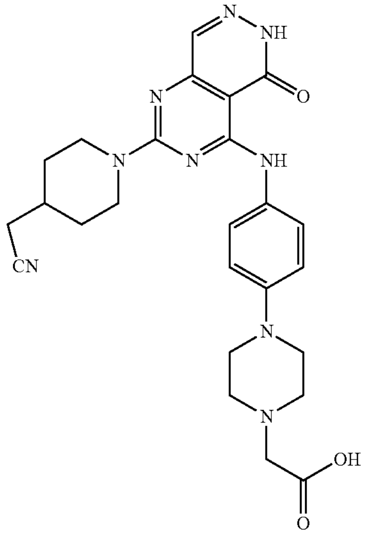 [SMILES: N#CCC1CCN(c2nc(Nc3ccc(N4CCN(CC(=O)O)CC4)cc3)c3c(=O)[nH]ncc3n2)CC1] | D | D |
| 163 | 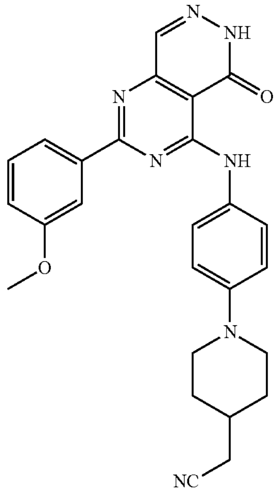 [SMILES: COc1cccc(-c2nc(Nc3ccc(N4CCC(CC#N)CC4)cc3)c3c(=O)[nH]ncc3n2)c1] | A | — |
| 164 | 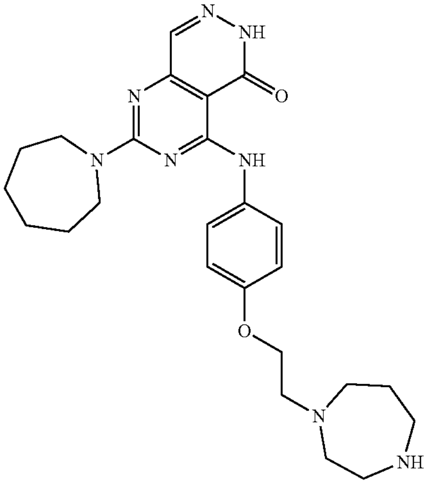 [SMILES: O=c1[nH]ncc2nc(N3CCCCCC3)nc(Nc3ccc(OCCN4CCCNCC4)cc3)c12] | C | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 165 | 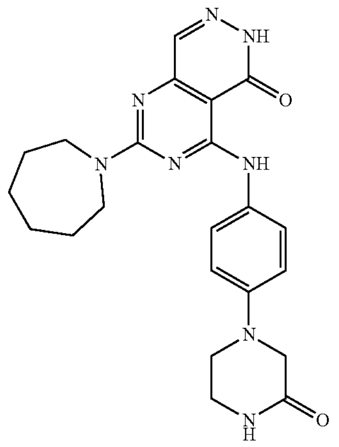 [SMILES: O=C1CN(c2ccc(Nc3nc(N4CCCCCC4)nc4cn[nH]c(=O)c34)cc2)CCN1] | B | D |
| 166 | 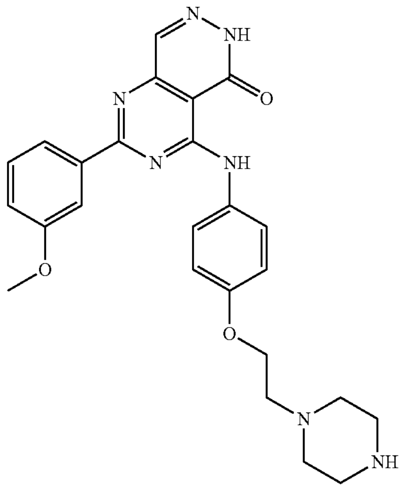 [SMILES: COc1cccc(-c2nc(Nc3ccc(OCCN4CCNCC4)cc3)c3c(=O)[nH]ncc3n2)c1] | C | C |
| 167 | 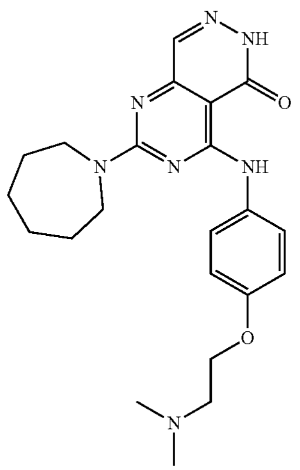 [SMILES: CN(C)CCOc1ccc(Nc2nc(N3CCCCCC3)nc3cn[nH]c(=O)c23)cc1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 168 | 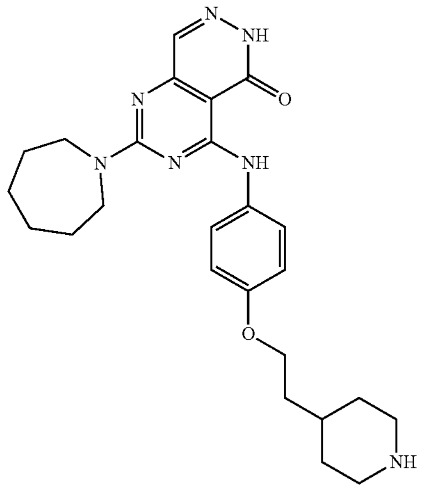 [SMILES: O=c1[nH]ncc2nc(N3CCCCCC3)nc(Nc3ccc(OCCC4CCNCC4)cc3)c12] | C | C |
| 169 | 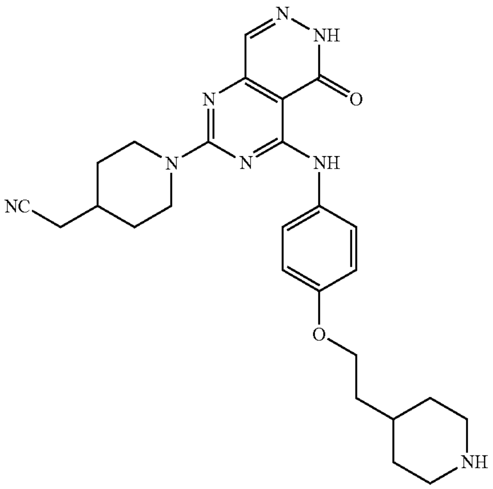 [SMILES: N#CCC1CCN(c2nc(Nc3ccc(OCCC4CCNCC4)cc3)c3c(=O)[nH]ncc3n2)CC1] | C | C |
| 170 | 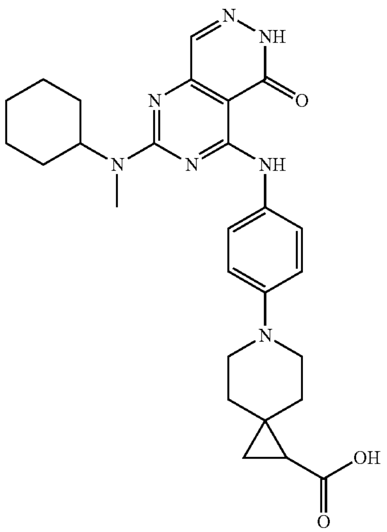 [SMILES: CN(c1nc(Nc2ccc(N3CCC4(CC3)CC4C(=O)O)cc2)c2c(=O)[nH]ncc2n1)C1CCCCC1] | C | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 171 | 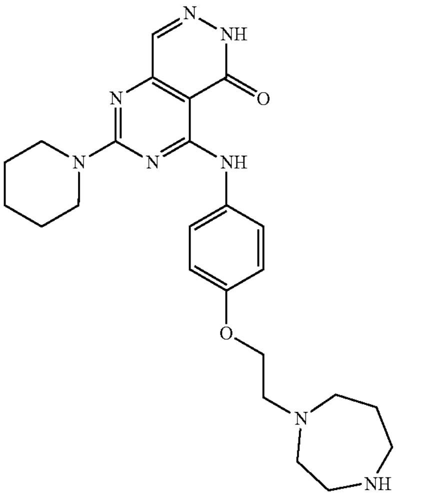 [SMILES: O=c1[nH]ncc2nc(N3CCCCC3)nc(Nc3ccc(OCCN4CCCNCC4)cc3)c12] | C | C |
| 172 | 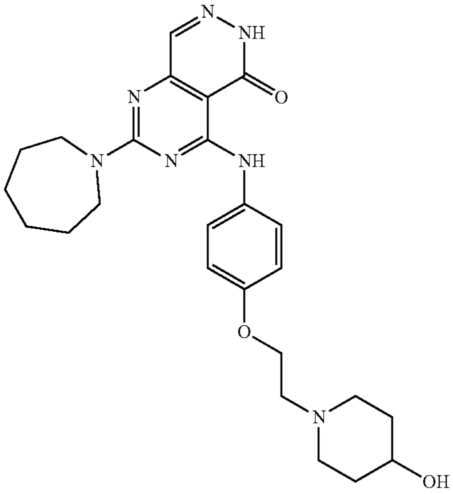 [SMILES: O=c1[nH]ncc2nc(N3CCCCCC3)nc(Nc3ccc(OCCN4CCC(O)CC4)cc3)c12] | C | D |
| 173 | 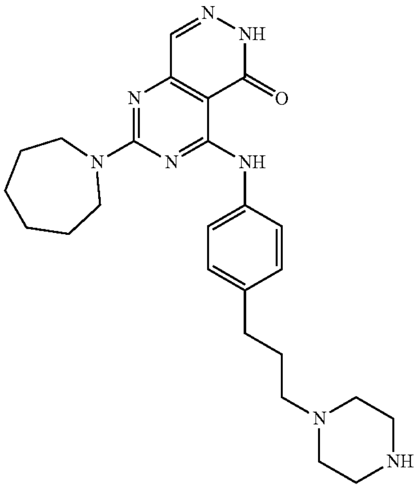 [SMILES: O=c1[nH]ncc2nc(N3CCCCCC3)nc(Nc3ccc(CCCN4CCNCC4)cc3)c12] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 174 | 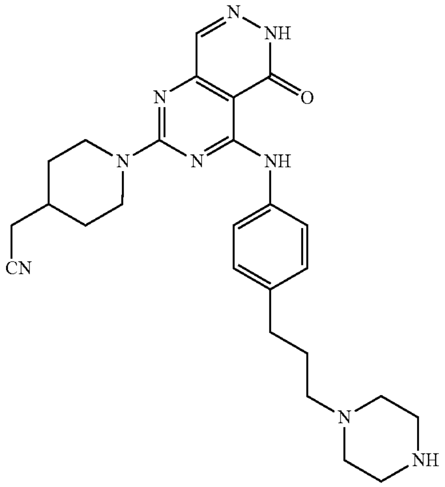 [SMILES: N#CCC1CCN(c2nc(Nc3ccc(CCCN4CCNCC4)cc3)c3c(=O)[nH]ncc3n2)CC1] | C | C |
| 175 | 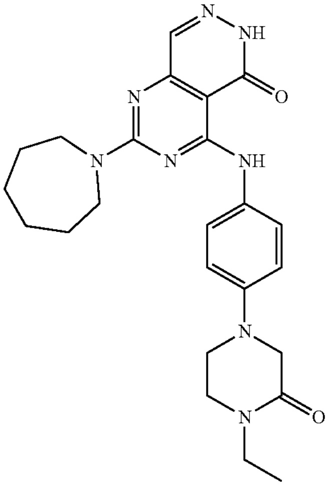 [SMILES: CCN1CCN(c2ccc(Nc3nc(N4CCCCCC4)nc4cn[nH]c(=O)c34)cc2)CC1=O] | D | D |
| 176 | 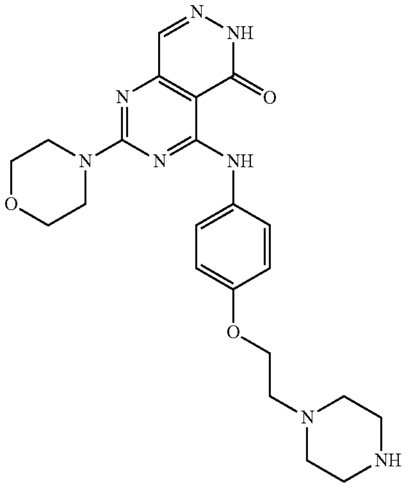 [SMILES: O=c1[nH]ncc2nc(N3CCOCC3)nc(Nc3ccc(OCCN4CCNCC4)cc3)c12] | A | — |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 177 | 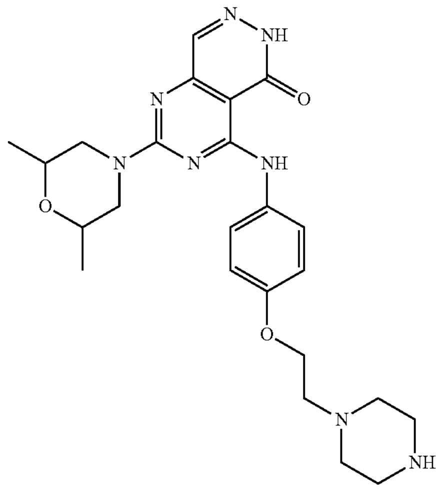 [SMILES: CC1CN(c2nc(Nc3ccc(OCCN4CCNCC4)cc3)c3c(=O)[nH]ncc3n2)CC(C)O1] | A | — |
| 178 | 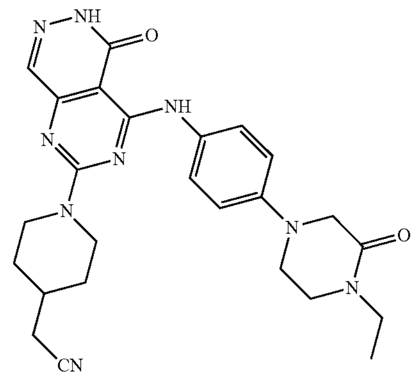 [SMILES: CCN1CCN(c2ccc(Nc3nc(N4CCC(CC#N)CC4)nc4cn[nH]c(=O)c34)cc2)CC1=O] | D | D |
| 179 | 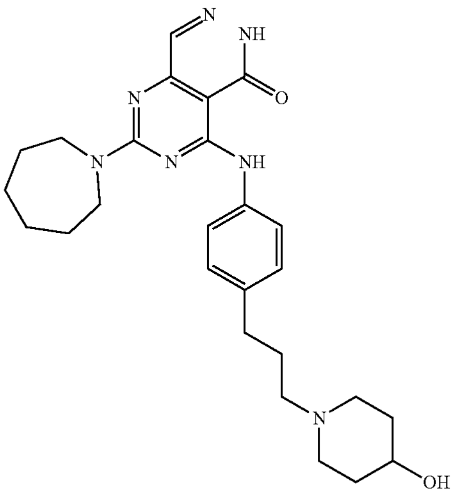 [SMILES: N=Cc1nc(N2CCCCCC2)nc(Nc2ccc(CCCN3CCC(O)CC3)cc2)c1C(N)=O] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 180 | 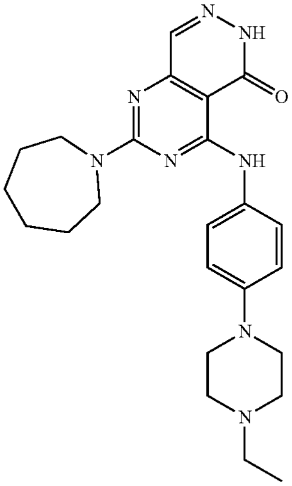 [SMILES: CCN1CCN(c2ccc(Nc3nc(N4CCCCCC4)nc4cn[nH]c(=O)c34)cc2)CC1] | D | D |
| 181 | 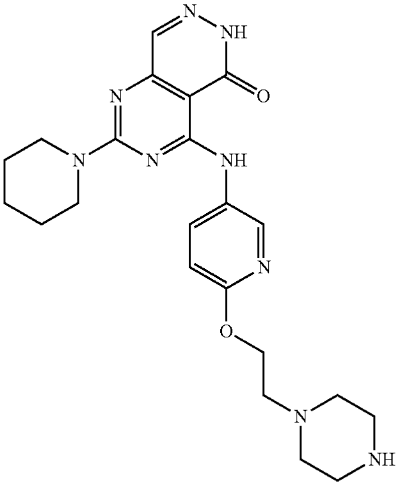 [SMILES: O=c1[nH]ncc2nc(N3CCCCC3)nc(Nc3ccc(OCCN4CCNCC4)nc3)c12] | A | A |
| 182 | 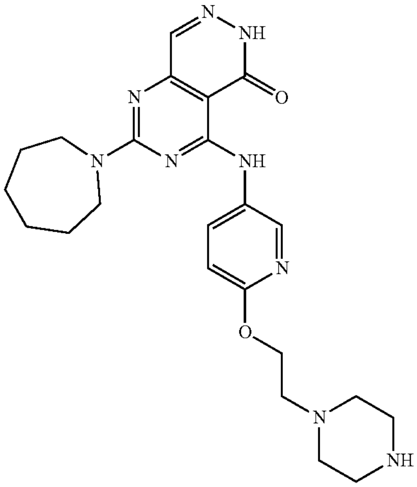 [SMILES: O=c1[nH]ncc2nc(N3CCCCCC3)nc(Nc3ccc(OCCN4CCNCC4)nc3)c12] | B | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 183 | 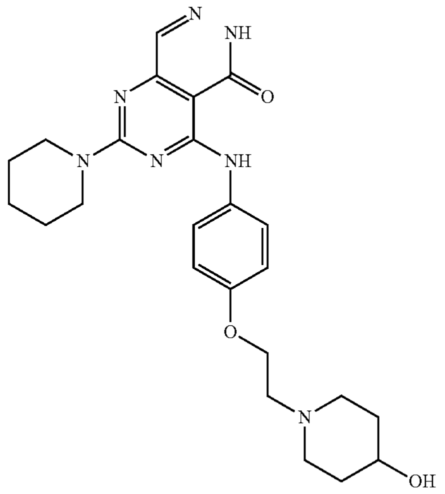 [SMILES: N=Cc1nc(N2CCCCC2)nc(Nc2ccc(OCCN3CCC(O)CC3)cc2)c1C(N)=O] | D | C |
| 184 | 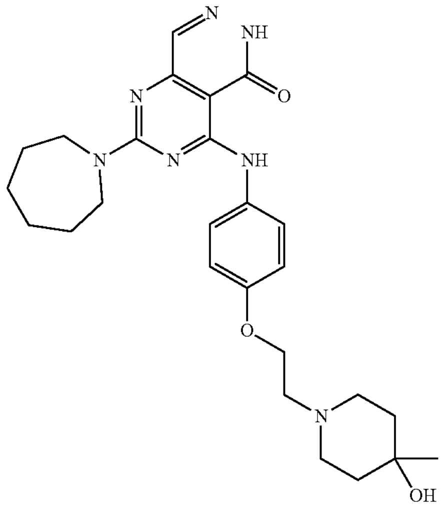 [SMILES: CC1(O)CCN(CCOc2ccc(Nc3nc(N4CCCCCC4)nc(C=N)c3C(N)=O)cc2)CC1] | D | D |
| 185 | 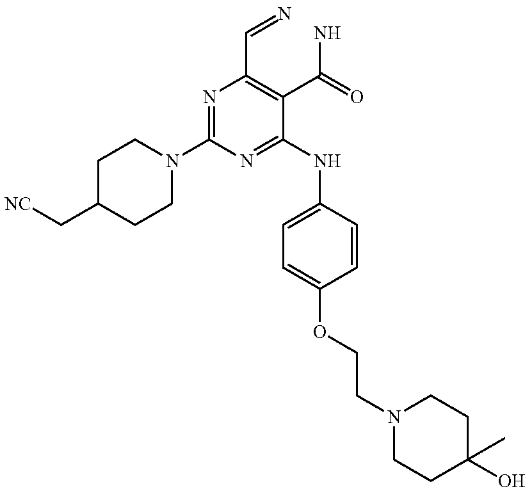 [SMILES: CC1(O)CCN(CCOc2ccc(Nc3nc(N4CCC(CC#N)CC4)nc(C=N)c3C(N)=O)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 186 | 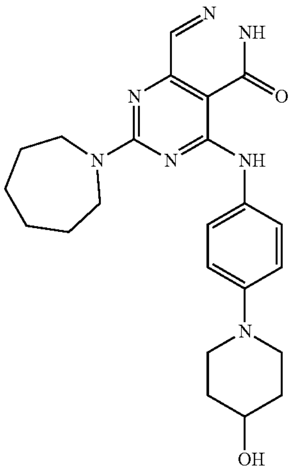 | D | B |
| 187 | 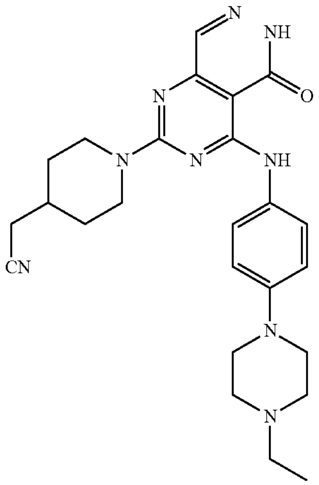 [SMILES: CCN1CCN(c2ccc(Nc3nc(N4CCC(CC#N)CC4)nc(C=N)c3C(N)=O)cc2)CC1] | D | C |
| 188 | 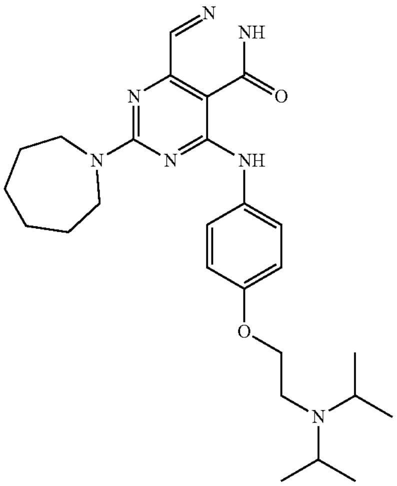 [SMILES: CC(C)N(CCOc1ccc(Nc2nc(N3CCCCCC3)nc(C=N)c2C(N)=O)cc1)C(C)C] | C | C |

TABLE 7-continued
| Ex. # | Structure | IC $_{50}$ ≥100 nM = A; ≤100 nM = B; ≤50 nM = C; ≤10 nM = D Syk | JAK2 |
|---|---|---|---|
| 189 | 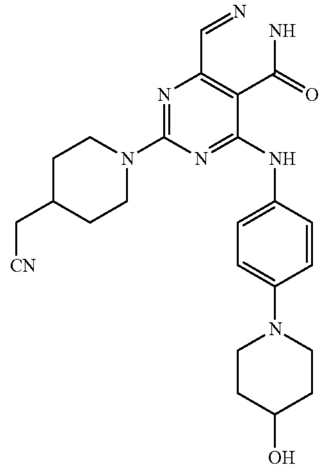 [SMILES: N#CCC1CCN(c2nc(C=N)c(C(N)=O)c(Nc3ccc(N4CCC(O)CC4)cc3)n2)CC1] | D | C |
| 190 | 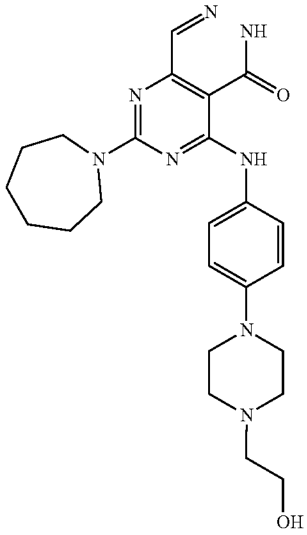 [SMILES: N=Cc1nc(N2CCCCCC2)nc(Nc2ccc(N3CCN(CCO)CC3)cc2)c1C(N)=O] | D | D |
| 191 | 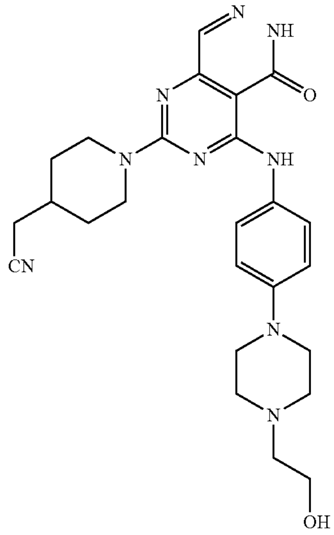 | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 192 | 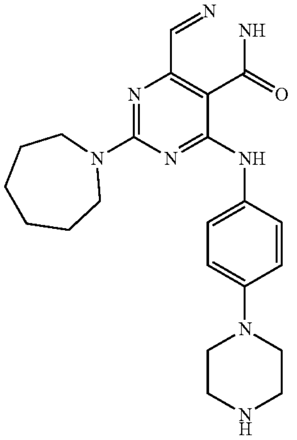 | D | D |
| 193 | 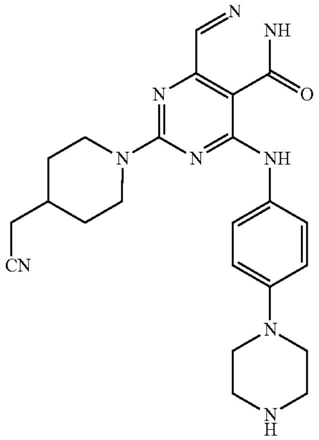 | D | D |
| 194 | 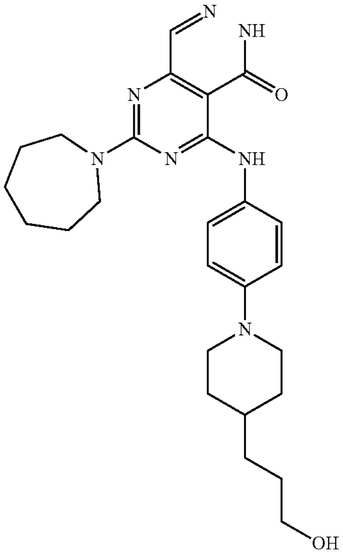 | A | — |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 195 | 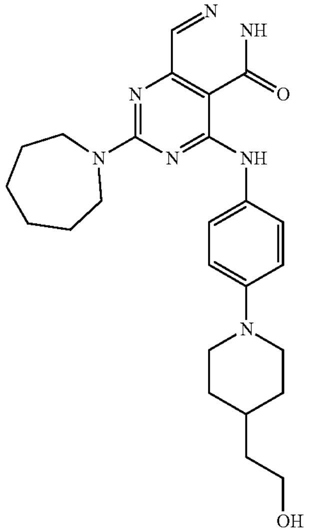 [SMILES: N=Cc1nc(N2CCCCCC2)nc(Nc2ccc(N3CCC(CCO)CC3)cc2)c1C(N)=O] | D | D |
| 196 | 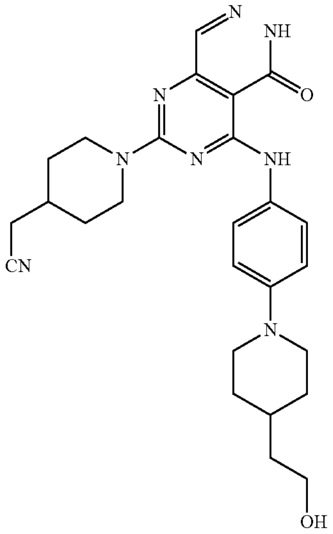 | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 197 | 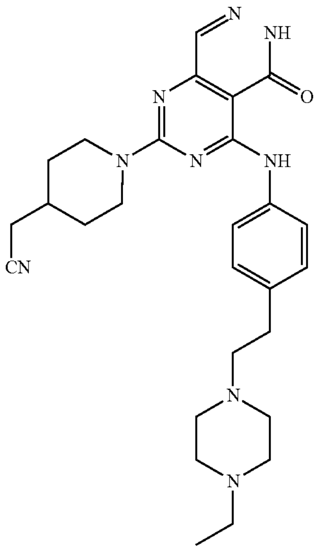 [SMILES: CCN1CCN(CCc2ccc(Nc3nc(N4CCC(CC#N)CC4)nc(C=N)c3C(N)=O)cc2)CC1] | D | D |
| 198 | 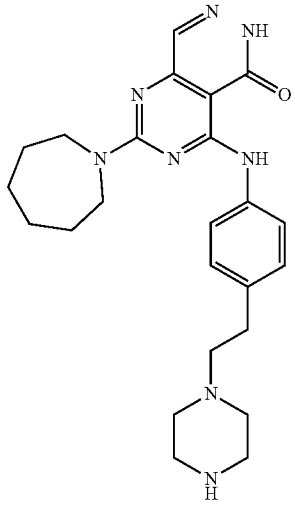 [SMILES: N=Cc1nc(N2CCCCCC2)nc(Nc2ccc(CCN3CCNCC3)cc2)c1C(N)=O] | D | D |
| 199 | 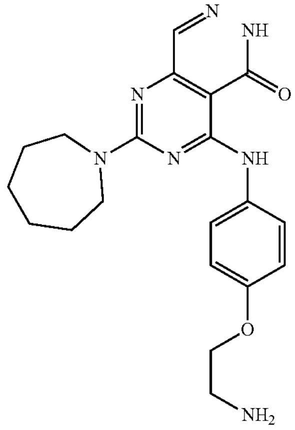 [SMILES: N=Cc1nc(N2CCCCCC2)nc(Nc2ccc(OCCN)cc2)c1C(N)=O] | D | D |

TABLE 7-continued
| Ex. # | Structure | Syk | JAK2 |
|---|---|---|---|
| | | IC$_{50}$ ≥100 nM = A; ≤100 nM = B; ≤50 nM = C; ≤10 nM = D | |
| 200 | 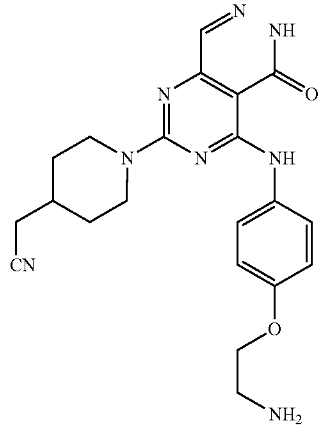 [SMILES: N#CCC1CCN(c2nc(C=N)c(C(N)=O)c(Nc3ccc(OCCN)cc3)n2)CC1] | D | C |
| 201 | 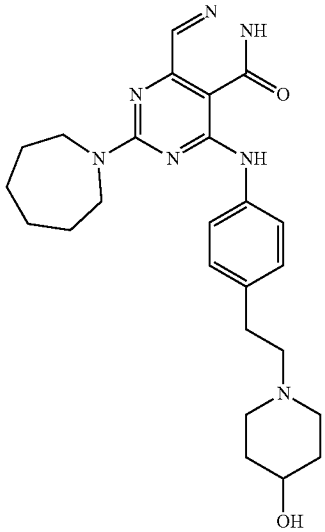 [SMILES: N=Cc1nc(N2CCCCCC2)nc(Nc2ccc(CCN3CCC(O)CC3)cc2)c1C(N)=O] | D | D |
| 202 | 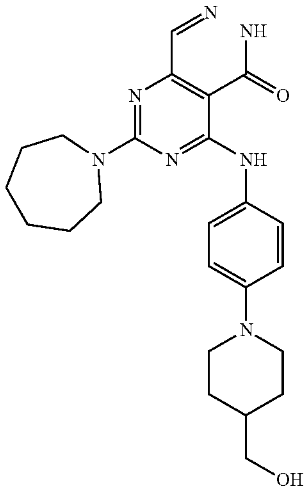 [SMILES: N=Cc1nc(N2CCCCCC2)nc(Nc2ccc(N3CCC(CO)CC3)cc2)c1C(N)=O] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 203 | 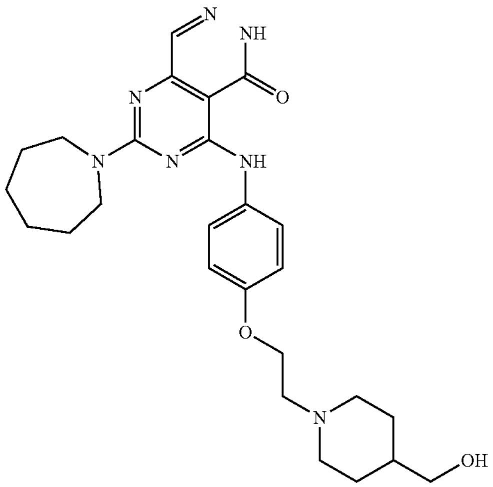 [SMILES: N=Cc1nc(N2CCCCCC2)nc(Nc2ccc(OCCN3CCC(CO)CC3)cc2)c1C(N)=O] | C | D |
| 204 | 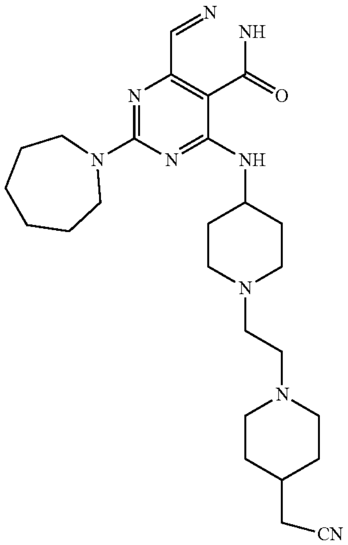 [SMILES: N#CCC1CCN(CCN2CCC(Nc3nc(N4CCCCCC4)nc(C=N)c3C(N)=O)CC2)CC1] | A | — |

TABLE 7-continued
| Ex. # | Structure | Syk | JAK2 |
|---|---|---|---|
| | | IC50 ≥100 nM = A; ≤100 nM = B; ≤50 nM = C; ≤10 nM = D | |
| 205 | 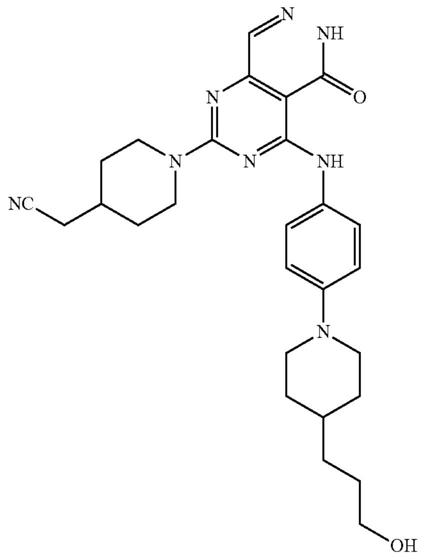 [SMILES: N#CCC1CCN(c2nc(C=N)c(C(N)=O)c(Nc3ccc(N4CCC(CCCO)CC4)cc3)n2)CC1] | C | C |
| 206 | 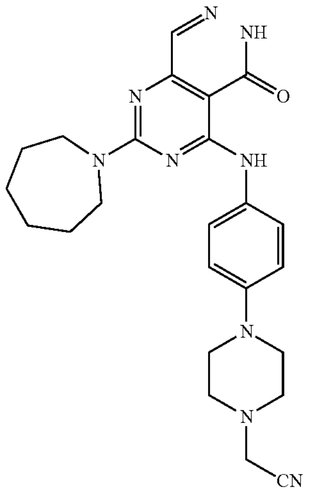 [SMILES: N#CCN1CCN(c2ccc(Nc3nc(N4CCCCCC4)nc(C=N)c3C(N)=O)cc2)CC1] | C | D |
| 207 | 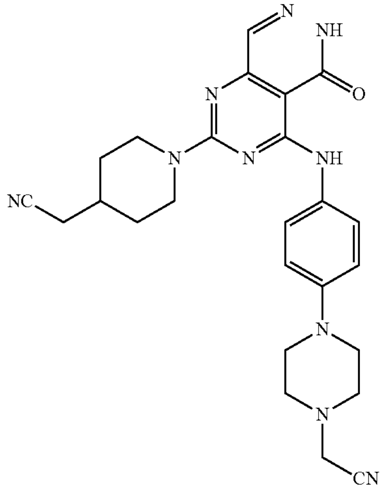 [SMILES: N#CCC1CCN(c2nc(C=N)c(C(N)=O)c(Nc3ccc(N4CCN(CC#N)CC4)cc3)n2)CC1] | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 208 | 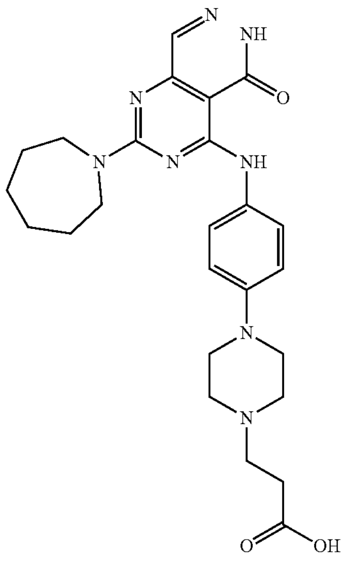 [SMILES: N=Cc1nc(N2CCCCCC2)nc(Nc2ccc(N3CCN(CCC(=O)O)CC3)cc2)c1C(N)=O] | D | D |
| 209 | 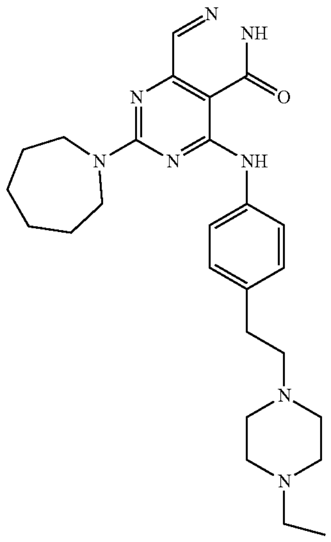 [SMILES: CCN1CCN(CCc2ccc(Nc3nc(N4CCCCCC4)nc(C=N)c3C(N)=O)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 210 | 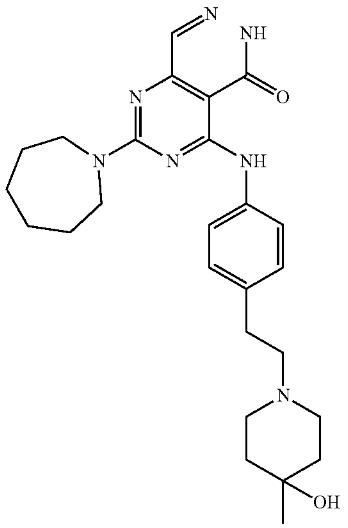 [SMILES: CC1(O)CCN(CCc2ccc(Nc3nc(N4CCCCCC4)nc(C=N)c3C(N)=O)cc2)CC1] | C | D |
| 211 | 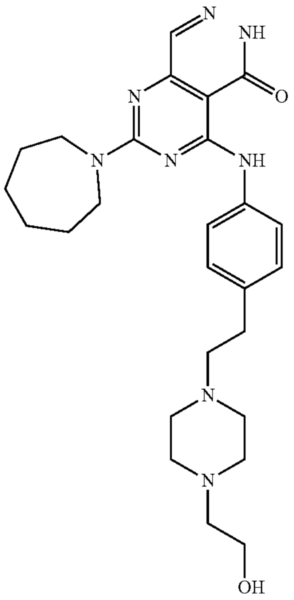 [SMILES: N=Cc1nc(N2CCCCCC2)nc(Nc2ccc(CCN3CCN(CCO)CC3)cc2)c1C(N)=O] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 212 | 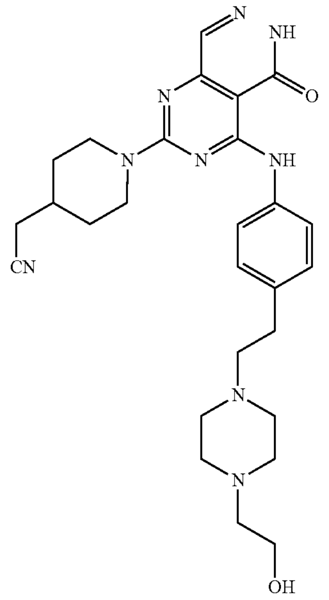 [SMILES: N#CCC1CCN(c2nc(C=N)c(C(N)=O)c(Nc3ccc(CCN4CCN(CCO)CC4)cc3)n2)CC1] | C | C |
| 213 | 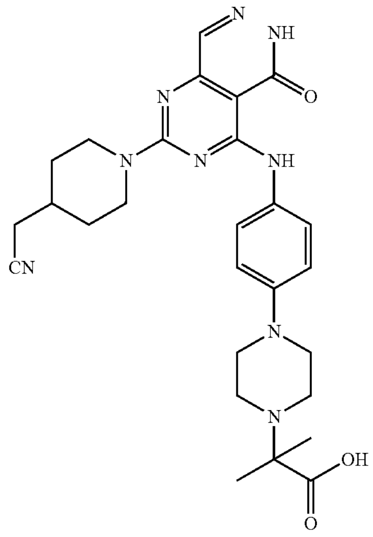 [SMILES: CC(C)(C(=O)O)N1CCN(c2ccc(Nc3nc(N4CCC(CC#N)CC4)nc(C=N)c3C(N)=O)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 214 | 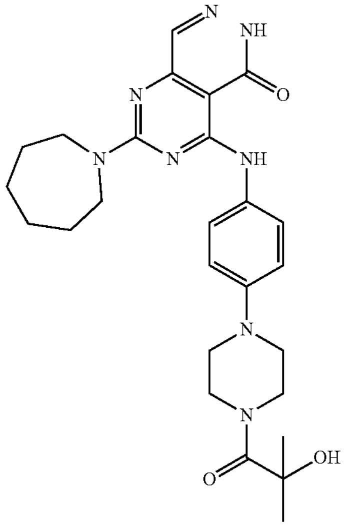 [SMILES: CC(C)(O)C(=O)N1CCN(c2ccc(Nc3nc(N4CCCCCC4)nc(C=N)c3C(N)=O)cc2)CC1] | D | D |
| 215 | 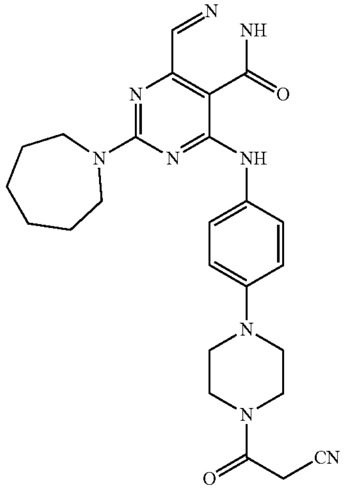 [SMILES: N#CCC(=O)N1CCN(c2ccc(Nc3nc(N4CCCCCC4)nc(C=N)c3C(N)=O)cc2)CC1] | D | D |
| 216 | 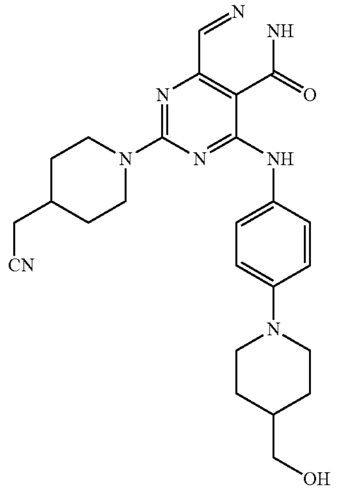 [SMILES: N#CCC1CCN(c2nc(C=N)c(C(N)=O)c(Nc3ccc(N4CCC(CO)CC4)cc3)n2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 217 | 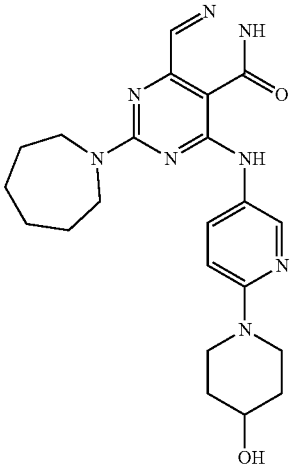 [SMILES: N=Cc1nc(N2CCCCCC2)nc(Nc2ccc(N3CCC(O)CC3)nc2)c1C(N)=O] | C | C |
| 218 | 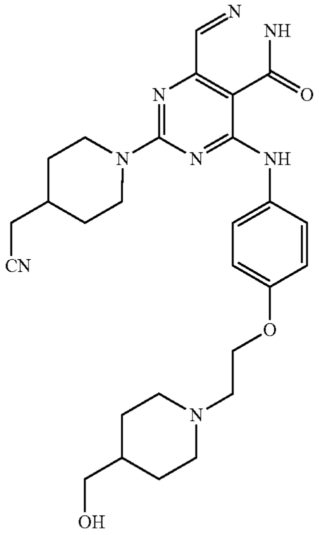 [SMILES: N#CCC1CCN(c2nc(C=N)c(C(N)=O)c(Nc3ccc(OCCN4CCC(CO)CC4)cc3)n2)CC1] | C | C |
| 219 | 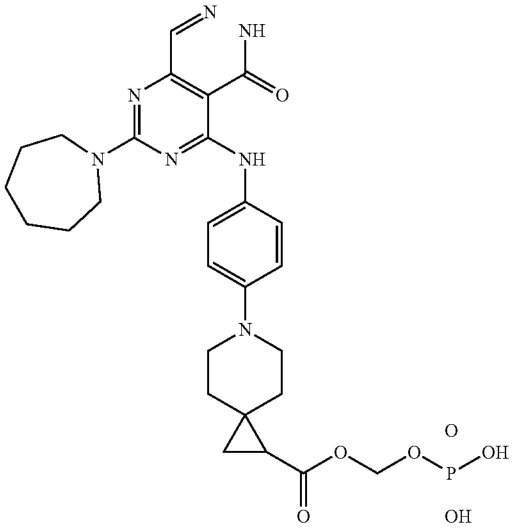 | D | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 220 | 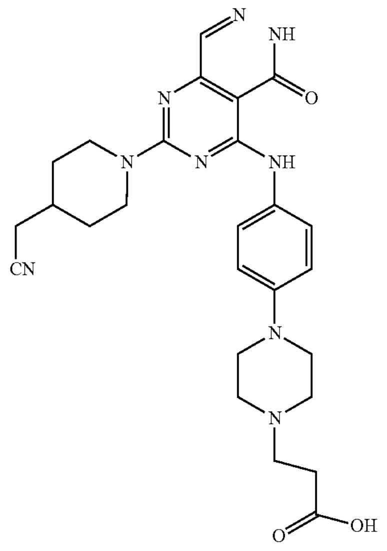 [SMILES: N#CCC1CCN(c2nc(C=N)c(C(N)=O)c(Nc3ccc(N4CCN(CCC(=O)O)CC4)cc3)n2)CC1] | D | D |
| 221 | 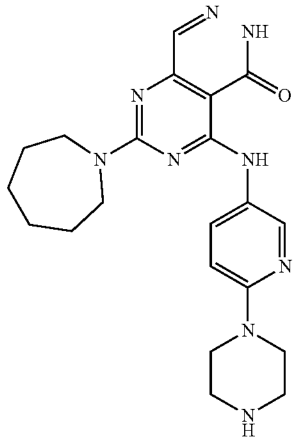 [SMILES: N=Cc1nc(N2CCCCCC2)nc(Nc2ccc(N3CCNCC3)nc2)c1C(N)=O] | C | D |
| 222 | 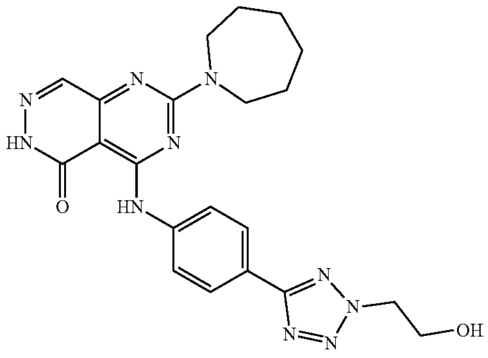 [SMILES: O=c1[nH]ncc2nc(N3CCCCCC3)nc(Nc3ccc(-c4nnn(CCO)n4)cc3)c12] | B | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 223 | 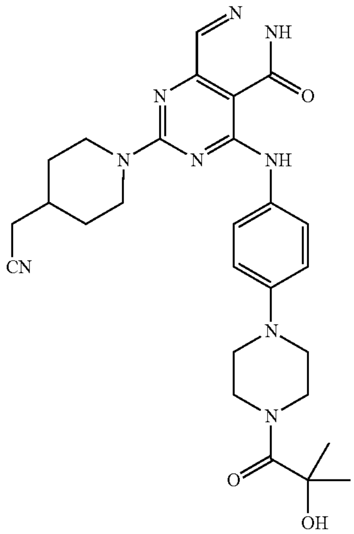 [SMILES: CC(C)(O)C(=O)N1CCN(c2ccc(Nc3nc(N4CCC(CC#N)CC4)nc(C=N)c3C(N)=O)cc2)CC1] | D | D |
| 224 | 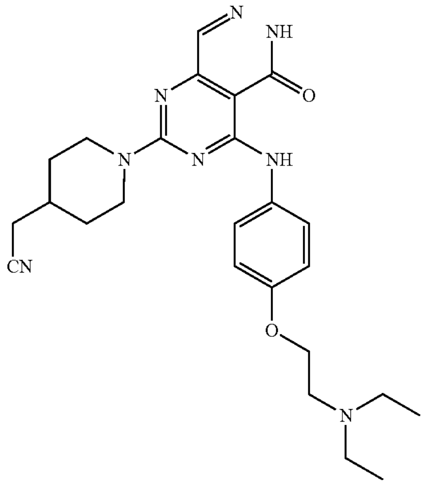 [SMILES: CCN(CC)CCOc1ccc(Nc2nc(N3CCC(CC#N)CC3)nc(C=N)c2C(N)=O)cc1] | C | C |
| 225 | 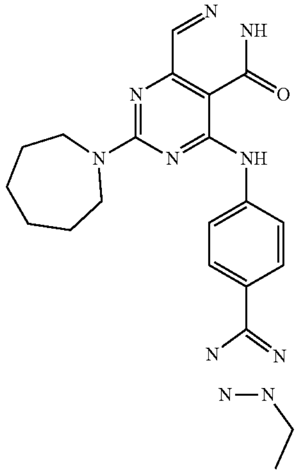 | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 226 | 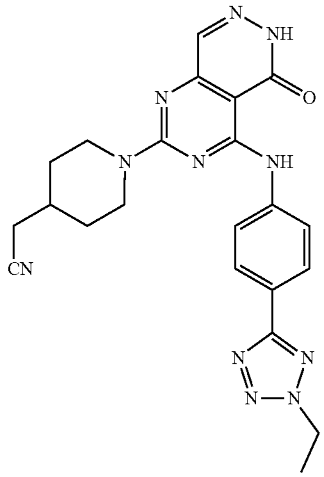 [SMILES: CCn1nnc(-c2ccc(Nc3nc(N4CCC(CC#N)CC4)nc4cn[nH]c(=O)c34)cc2)n1] | A | — |
| 227 | 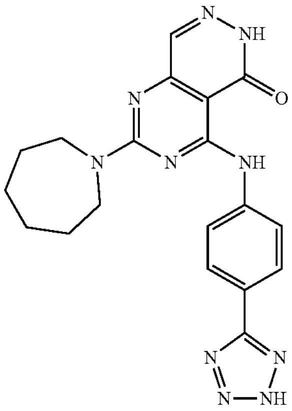 [SMILES: O=c1[nH]ncc2nc(N3CCCCCC3)nc(Nc3ccc(-c4nn[nH]n4)cc3)c12] | C | D |
| 228 | 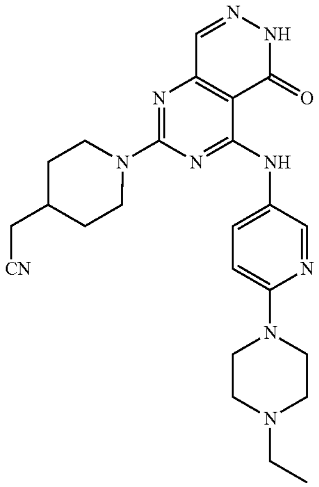 [SMILES: CCN1CCN(c2ccc(Nc3nc(N4CCC(CC#N)CC4)nc4cn[nH]c(=O)c34)cn2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 229 | 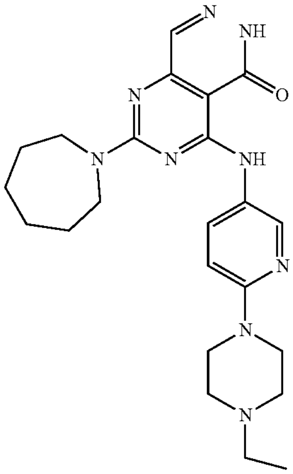 [SMILES: CCN1CCN(c2ccc(Nc3nc(N4CCCCCC4)nc(C=N)c3C(N)=O)cn2)CC1] | C | D |
| 230 | 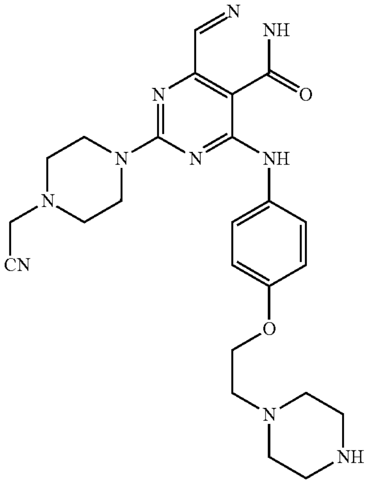 [SMILES: N#CCN1CCN(c2nc(C=N)c(C(N)=O)c(Nc3ccc(OCCN4CCNCC4)cc3)n2)CC1] | A | — |
| 231 | 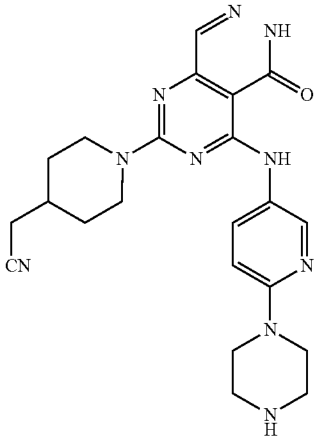 [SMILES: N#CCC1CCN(c2nc(C=N)c(C(N)=O)c(Nc3ccc(N4CCNCC4)nc3)n2)CC1] | C | B |

TABLE 7-continued
| | | IC50 ≥100 nM = A; ≤100 nM = B; ≤50 nM = C; ≤10 nM = D | |
|---|---|---|---|
| Ex. # | Structure | Syk | JAK2 |
| 232 | 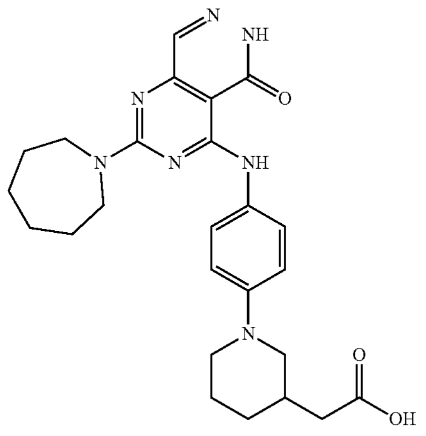 [SMILES: N=Cc1nc(N2CCCCCC2)nc(Nc2ccc(N3CCCC(CC(=O)O)C3)cc2)c1C(N)=O] | C | D |
| 233 | 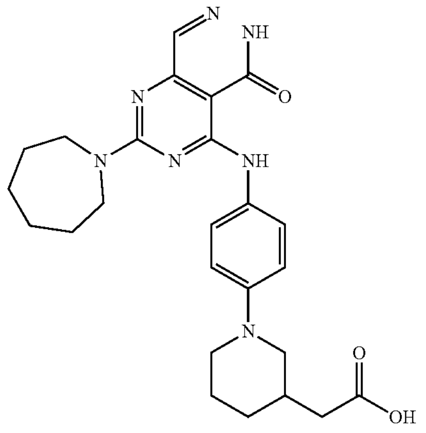 [SMILES: N=Cc1nc(N2CCCCCC2)nc(Nc2ccc(N3CCCC(CC(=O)O)C3)cc2)c1C(N)=O] | D | D |
| 234 | 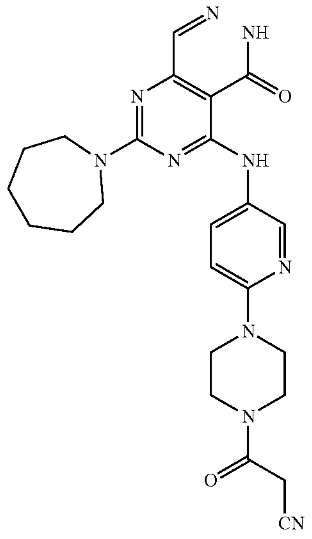 [SMILES: N#CCC(=O)N1CCN(c2ccc(Nc3nc(N4CCCCCC4)nc(C=N)c3C(N)=O)cn2)CC1] | C | D |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 235 | 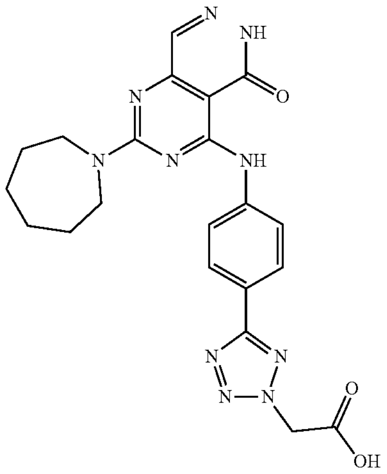 [SMILES: N=Cc1nc(N2CCCCCC2)nc(Nc2ccc(-c3nnn(CC(=O)O)n3)cc2)c1C(N)=O] | C | C |
| 236 | 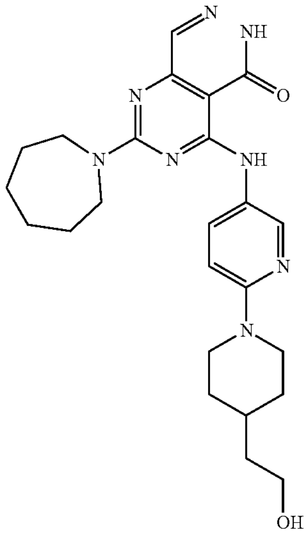 [SMILES: N=Cc1nc(N2CCCCCC2)nc(Nc2ccc(N3CCC(CCO)CC3)nc2)c1C(N)=O] | B | C |
| 237 | 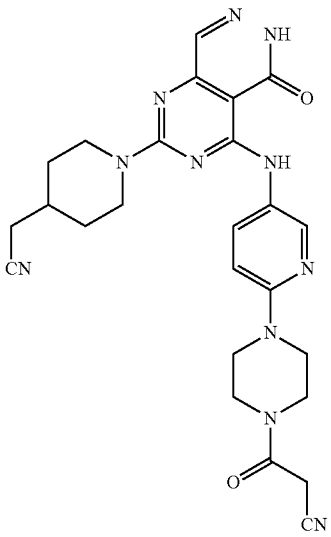 | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 238 | 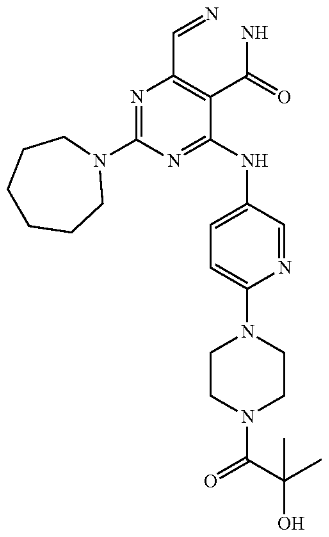 [SMILES: CC(C)(O)C(=O)N1CCN(c2ccc(Nc3nc(N4CCCCCC4)nc(C=N)c3C(N)=O)cn2)CC1] | C | D |
| 239 | 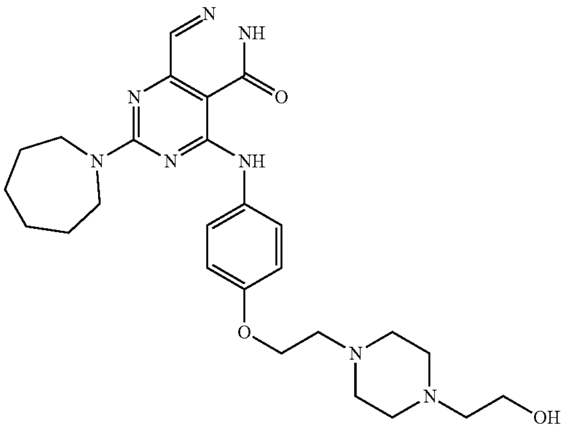 [SMILES: N=Cc1nc(N2CCCCCC2)nc(Nc2ccc(OCCN3CCN(CCO)CC3)cc2)c1C(N)=O] | B | C |
| 240 | 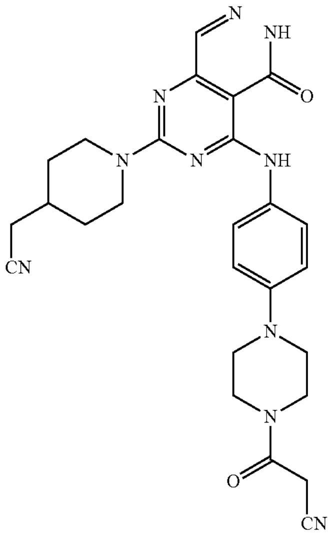 | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 241 | 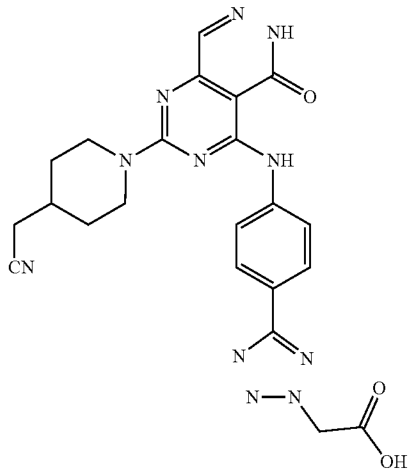 | A | — |
| 242 | 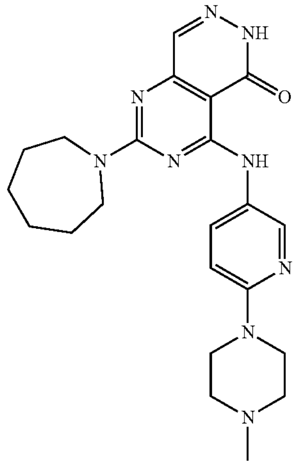 [SMILES: CN1CCN(c2ccc(Nc3nc(N4CCCCCC4)nc4cn[nH]c(=O)c34)cn2)CC1] | C | C |
| 243 | 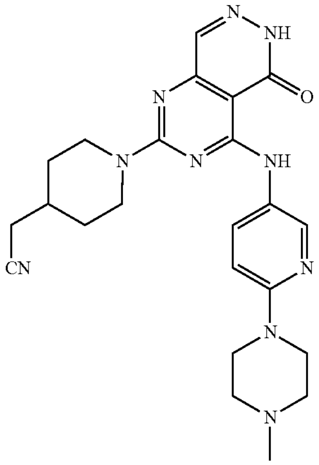 [SMILES: CN1CCN(c2ccc(Nc3nc(N4CCC(CC#N)CC4)nc4cn[nH]c(=O)c34)cn2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 244 | 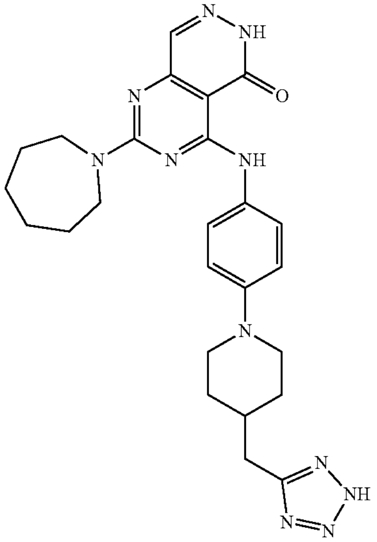 [SMILES: O=c1[nH]ncc2nc(N3CCCCCC3)nc(Nc3ccc(N4CCC(Cc5nn[nH]n5)CC4)cc3)c12] | D | D |
| 245 | 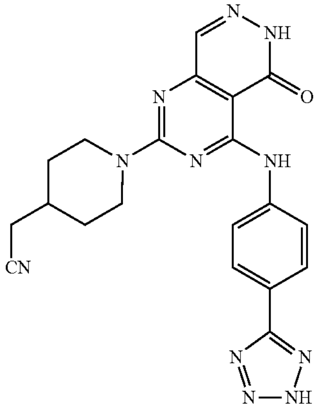 [SMILES: N#CCC1CCN(c2nc(Nc3ccc(-c4nn[nH]n4)cc3)c3c(=O)[nH]ncc3n2)CC1] | C | C |
| 246 | 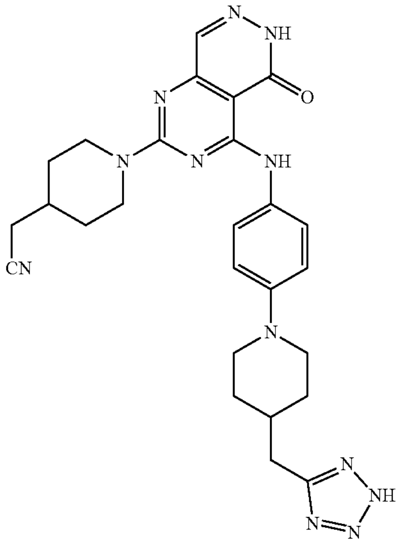 [SMILES: N#CCC1CCN(c2nc(Nc3ccc(N4CCC(Cc5nn[nH]n5)CC4)cc3)c3c(=O)[nH]ncc3n2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 247 | 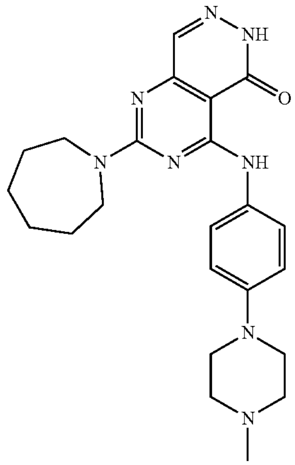 | D | D |
| 248 | 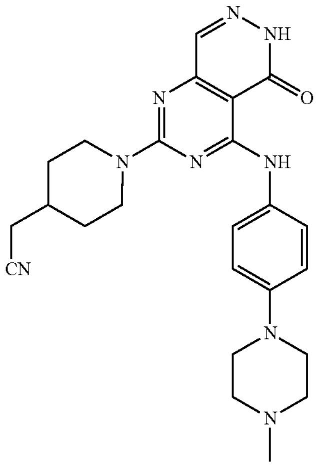 | D | D |
| 249 | 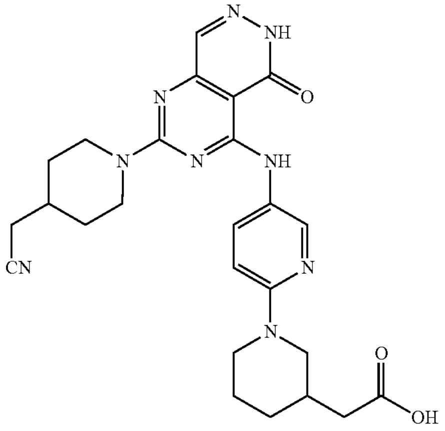 | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 250 | 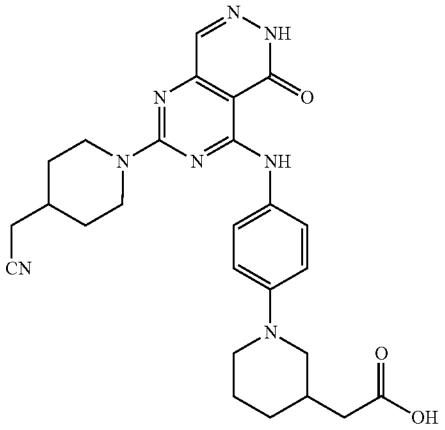 | C | D |
| 251 | 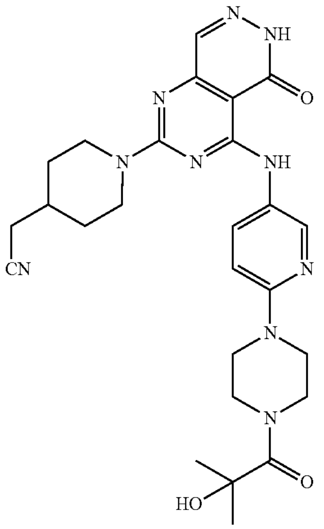 [SMILES: CC(C)(O)C(=O)N1CCN(c2ccc(Nc3nc(N4CCC(CC#N)CC4)nc4cn[nH]c(=O)c34)cn2)CC1] | C | C |
| 252 | 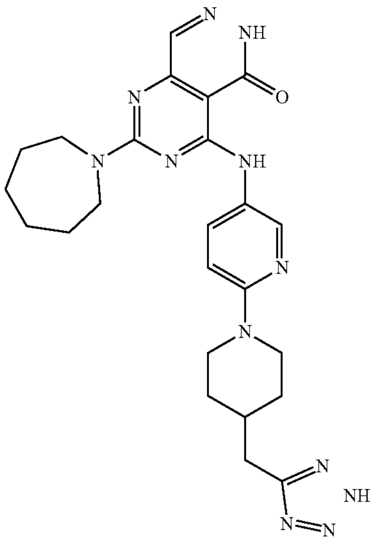 | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 253 | 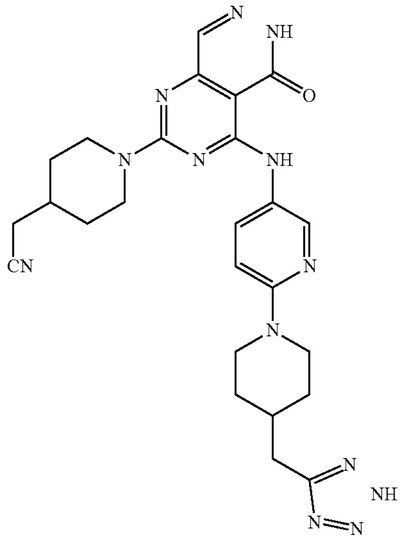 | C | D |
| 254 | 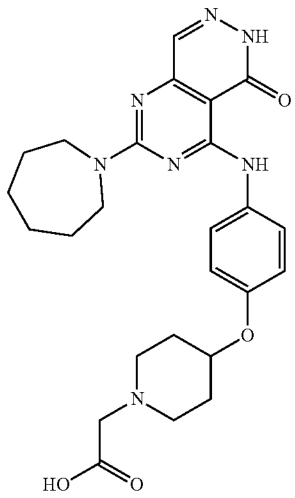 [SMILES: O=C(O)CN1CCC(Oc2ccc(Nc3nc(N4CCCCCC4)nc4cn[nH]c(=O)c34)cc2)CC1] | D | C |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 255 | 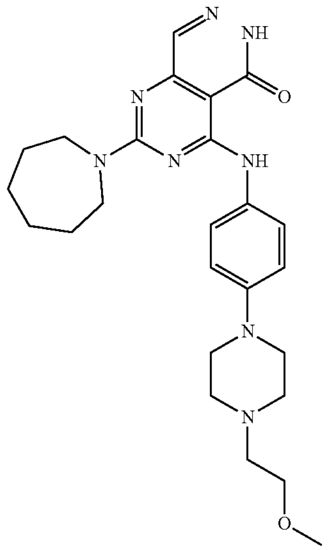 [SMILES: COCCN1CCN(c2ccc(Nc3nc(N4CCCCCC4)nc(C=N)c3C(N)=O)cc2)CC1] | C | D |
| 256 | 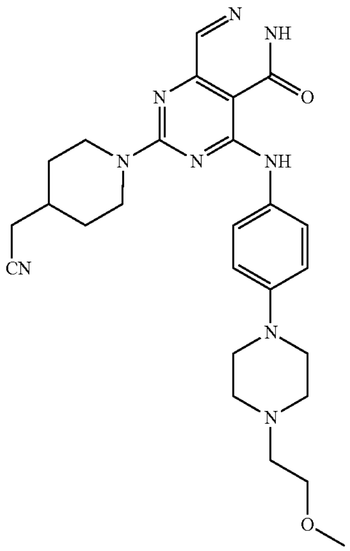 [SMILES: COCCN1CCN(c2ccc(Nc3nc(N4CCC(CC#N)CC4)nc(C=N)c3C(N)=O)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 257 | 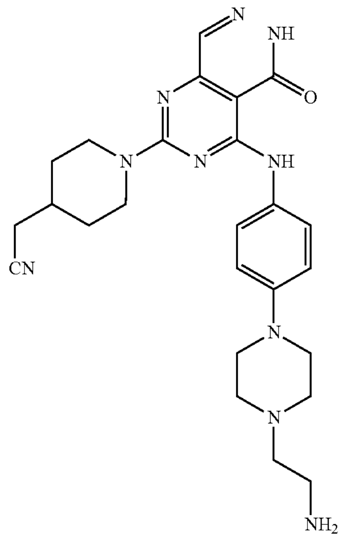 [SMILES: N#CCC1CCN(c2nc(C=N)c(C(N)=O)c(Nc3ccc(N4CCN(CCN)CC4)cc3)n2)CC1] | D | C |
| 258 | 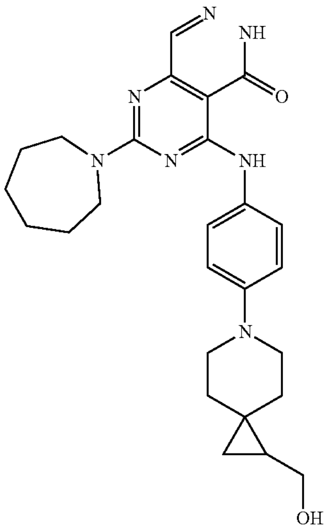 [SMILES: N=Cc1nc(N2CCCCCC2)nc(Nc2ccc(N3CCC4(CC3)CC4CO)cc2)c1C(N)=O] | B | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 259 | 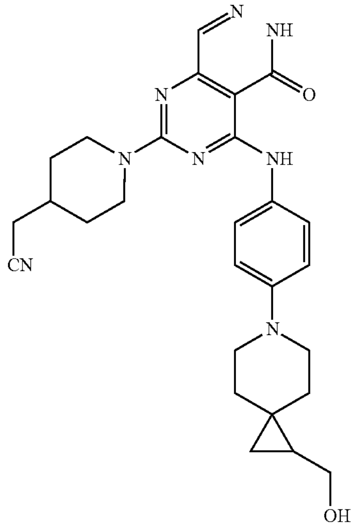 [SMILES: N#CCC1CCN(c2nc(C=N)c(C(N)=O)c(Nc3ccc(N4CCC5(CC4)CC5CO)cc3)n2)CC1] | C | C |
| 260 | 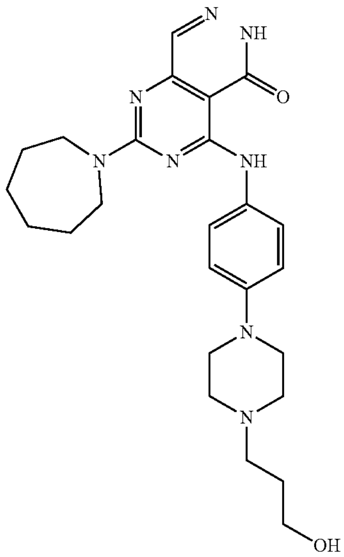 | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 261 | 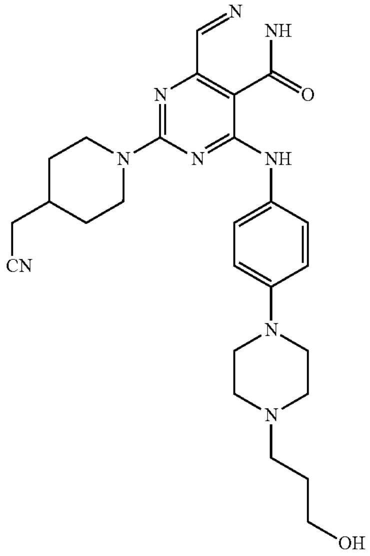 [SMILES: N#CCC1CCN(c2nc(C=N)c(C(N)=O)c(Nc3ccc(N4CCN(CCCO)CC4)cc3)n2)CC1] | D | C |
| 262 | 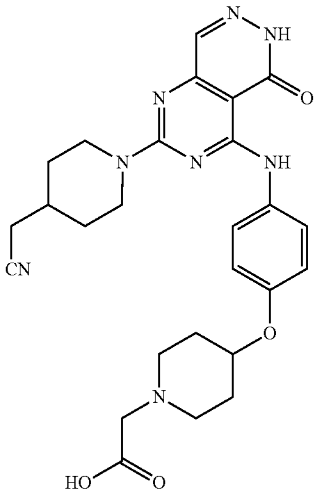 [SMILES: N#CCC1CCN(c2nc(Nc3ccc(OC4CCN(CC(=O)O)CC4)cc3)c3c(=O)[nH]ncc3n2)CC1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 263 | 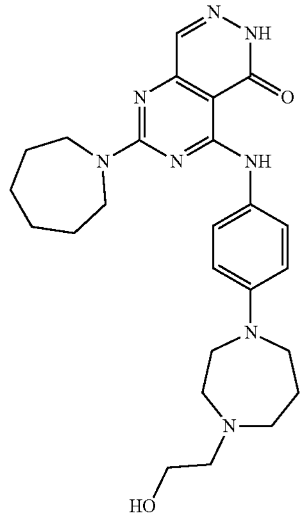 [SMILES: O=c1[nH]ncc2nc(N3CCCCCC3)nc(Nc3ccc(N4CCCN(CCO)CC4)cc3)c12] | D | D |
| 264 | 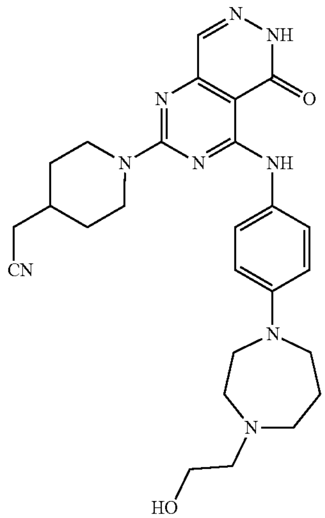 [SMILES: N#CCC1CCN(c2nc(Nc3ccc(N4CCCN(CCO)CC4)cc3)c3c(=O)[nH]ncc3n2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 265 | 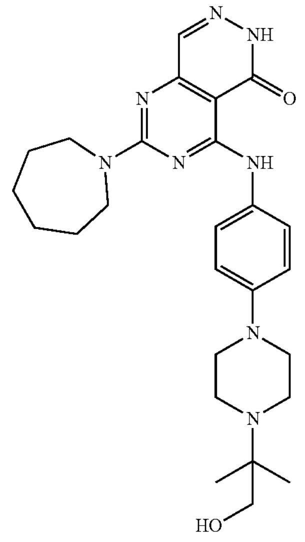 [SMILES: CC(C)(CO)N1CCN(c2ccc(Nc3nc(N4CCCCCC4)nc4cn[nH]c(=O)c34)cc2)CC1] | D | D |
| 266 | 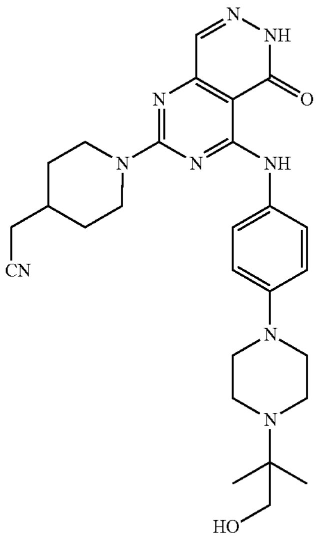 [SMILES: CC(C)(CO)N1CCN(c2ccc(Nc3nc(N4CCC(CC#N)CC4)nc4cn[nH]c(=O)c34)cc2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 267 | 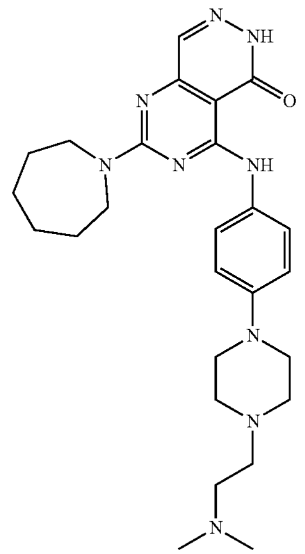 [SMILES: CN(C)CCN1CCN(c2ccc(Nc3nc(N4CCCCCC4)nc4cn[nH]c(=O)c34)cc2)CC1] | D | D |
| 268 | 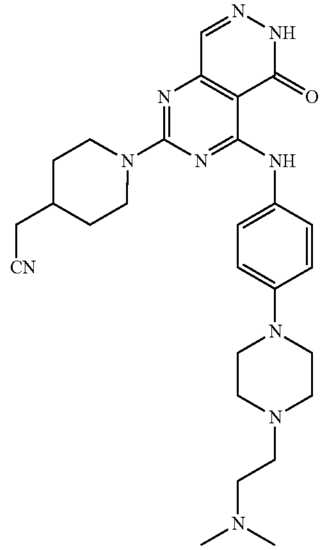 [SMILES: CN(C)CCN1CCN(c2ccc(Nc3nc(N4CCC(CC#N)CC4)nc4cn[nH]c(=O)c34)cc2)CC1] | D | C |
| 269 | 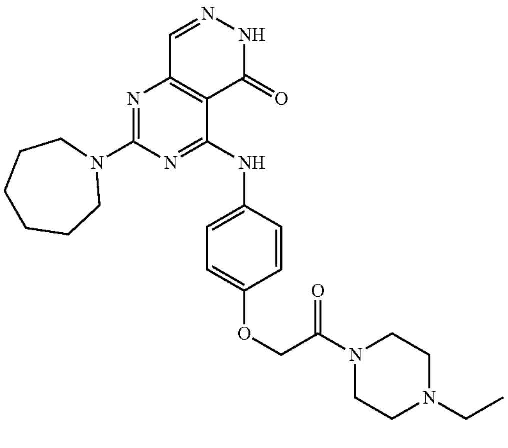 [SMILES: CCN1CCN(C(=O)COc2ccc(Nc3nc(N4CCCCCC4)nc4cn[nH]c(=O)c34)cc2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 270 | 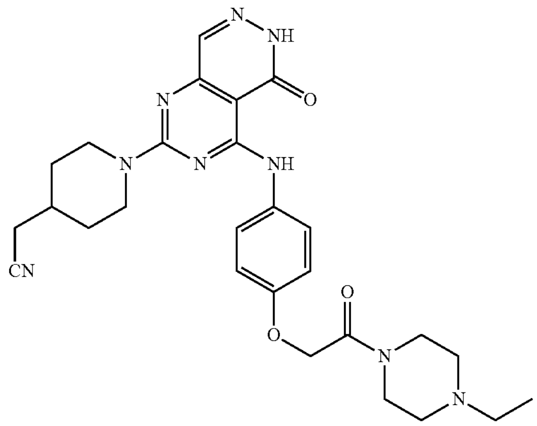 [SMILES: CCN1CCN(C(=O)COc2ccc(Nc3nc(N4CCC(CC#N)CC4)nc4cn[nH]c(=O)c34)cc2)CC1] | C | C |
| 271 | 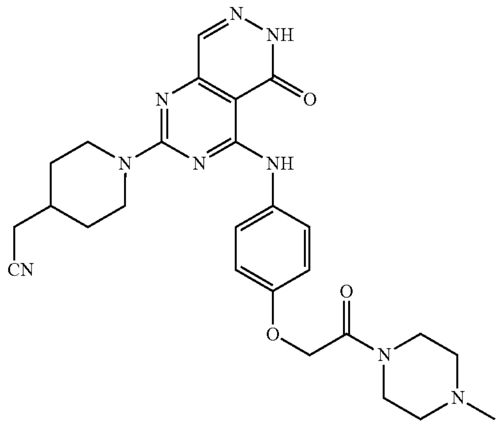 [SMILES: CN1CCN(C(=O)COc2ccc(Nc3nc(N4CCC(CC#N)CC4)nc4cn[nH]c(=O)c34)cc2)CC1] | D | C |
| 272 | 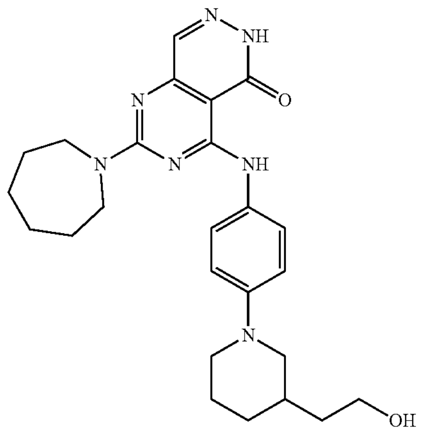 [SMILES: O=c1[nH]ncc2nc(N3CCCCCC3)nc(Nc3ccc(N4CCCC(CCO)C4)cc3)c12] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 273 | 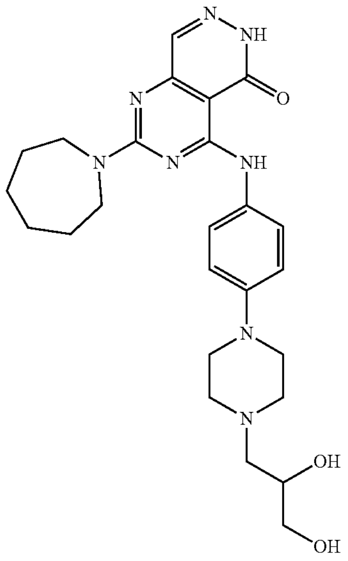 [SMILES: O=c1[nH]ncc2nc(N3CCCCCC3)nc(Nc3ccc(N4CCN(CC(O)CO)CC4)cc3)c12] | D | D |
| 274 | 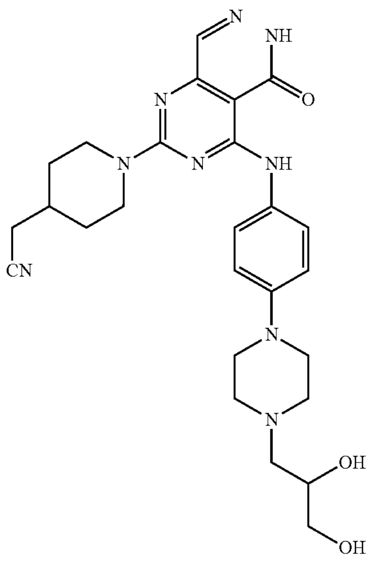 [SMILES: N#CCC1CCN(c2nc(C=N)c(C(N)=O)c(Nc3ccc(N4CCN(CC(O)CO)CC4)cc3)n2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 275 | 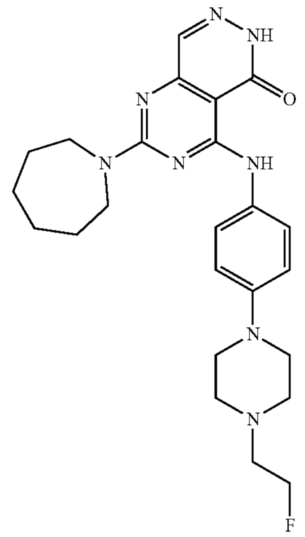 [SMILES: O=c1[nH]ncc2nc(N3CCCCCC3)nc(Nc3ccc(N4CCN(CCF)CC4)cc3)c12] | D | D |
| 276 | 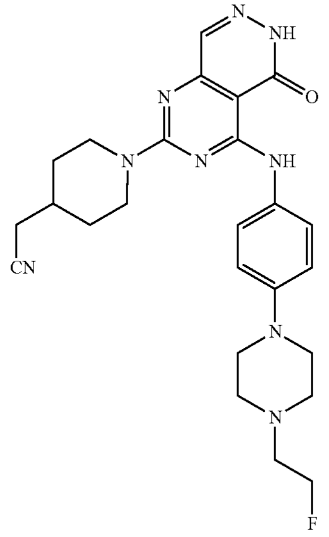 [SMILES: N#CCC1CCN(c2nc(Nc3ccc(N4CCN(CCF)CC4)cc3)c3c(=O)[nH]ncc3n2)CC1] | D | C |
| 277 | 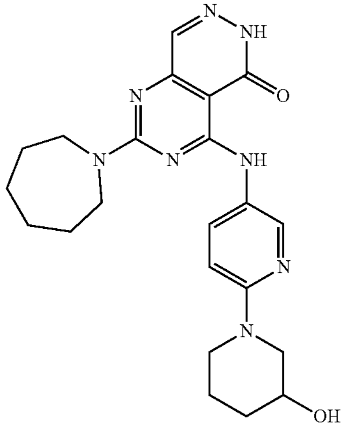 | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 278 | 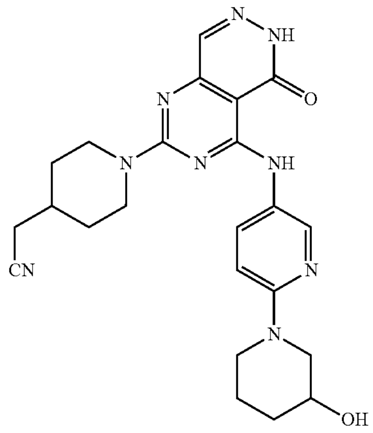 [SMILES: N#CCC1CCN(c2nc(Nc3ccc(N4CCCC(O)C4)nc3)c3c(=O)[nH]ncc3n2)CC1] | C | C |
| 279 | 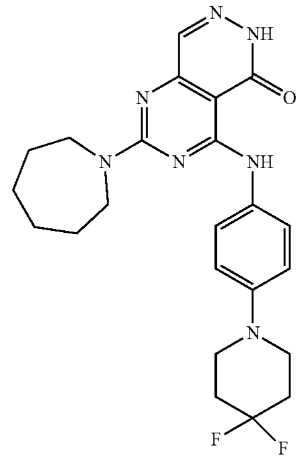 [SMILES: O=c1[nH]ncc2nc(N3CCCCCC3)nc(Nc3ccc(N4CCC(F)(F)CC4)cc3)c12] | A | — |
| 280 | 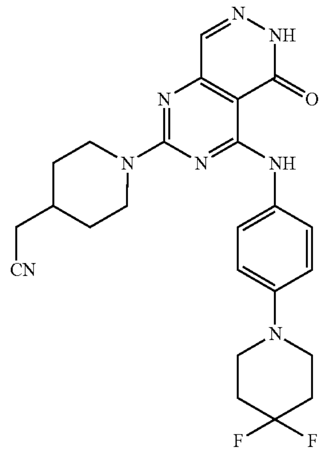 [SMILES: N#CCC1CCN(c2nc(Nc3ccc(N4CCC(F)(F)CC4)cc3)c3c(=O)[nH]ncc3n2)CC1] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 281 | 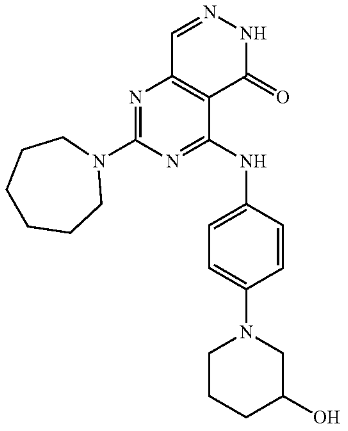 | C | D |
| 282 | 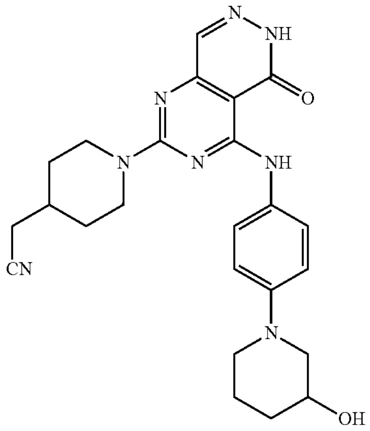 [SMILES: N#CCC1CCN(c2nc(Nc3ccc(N4CCCC(O)C4)cc3)c3c(=O)[nH]ncc3n2)CC1] | C | D |
| 283 | 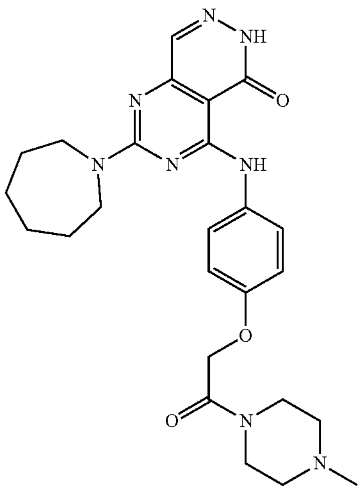 [SMILES: CN1CCN(C(=O)COc2ccc(Nc3nc(N4CCCCCC4)nc4cn[nH]c(=O)c34)cc2)CC1] | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 284 | 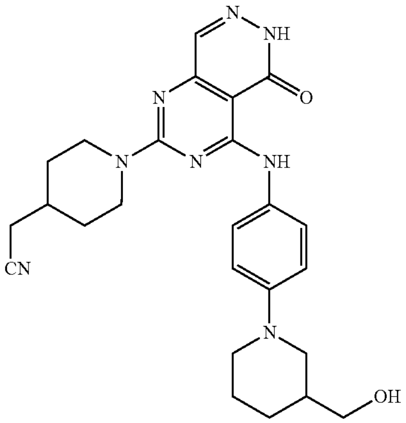 [SMILES: N#CCC1CCN(c2nc(Nc3ccc(N4CCCC(CO)C4)cc3)c3c(=O)[nH]ncc3n2)CC1] | D | D |
| 285 | 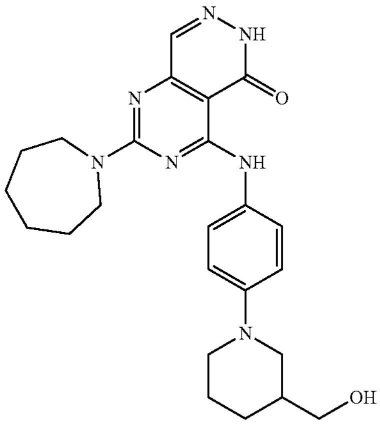 [SMILES: O=c1[nH]ncc2nc(N3CCCCCC3)nc(Nc3ccc(N4CCCC(CO)C4)cc3)c12] | C | C |
| 286 | 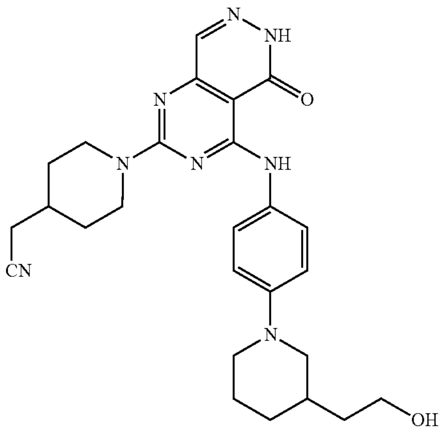 [SMILES: N#CCC1CCN(c2nc(Nc3ccc(N4CCCC(CCO)C4)cc3)c3c(=O)[nH]ncc3n2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 287 | 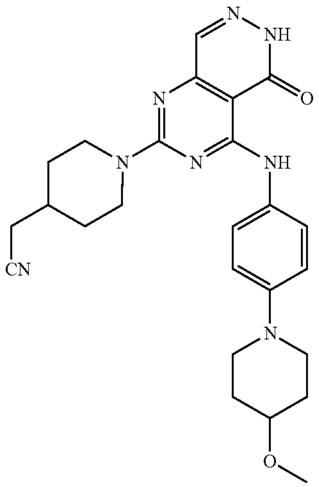 [SMILES: COC1CCN(c2ccc(Nc3nc(N4CCC(CC#N)CC4)nc4cn[nH]c(=O)c34)cc2)CC1] | C | C |
| 288 | 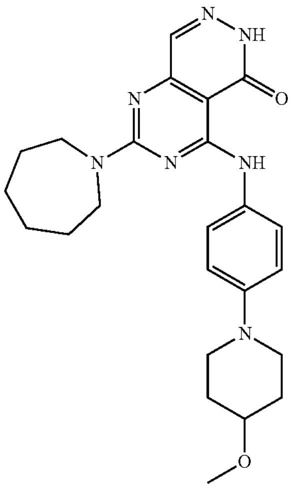 [SMILES: COC1CCN(c2ccc(Nc3nc(N4CCCCCC4)nc4cn[nH]c(=O)c34)cc2)CC1] | C | C |
| 289 | 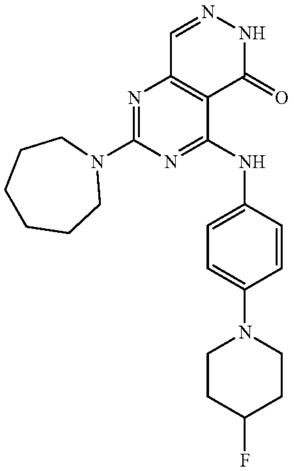 [SMILES: O=c1[nH]ncc2nc(N3CCCCCC3)nc(Nc3ccc(N4CCC(F)CC4)cc3)c12] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 290 | 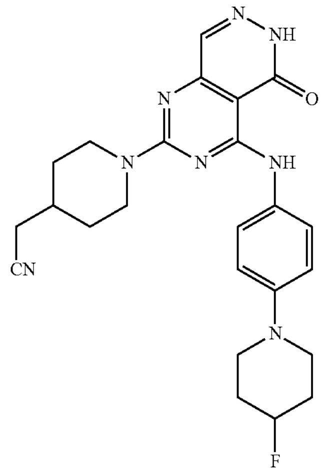 [SMILES: N#CCC1CCN(c2nc(Nc3ccc(N4CCC(F)CC4)cc3)c3c(=O)[nH]ncc3n2)CC1] | C | C |
| 291 | 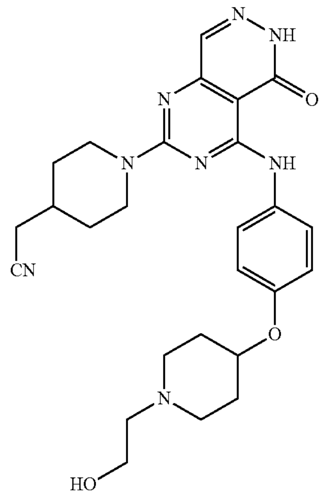 [SMILES: N#CCC1CCN(c2nc(Nc3ccc(OC4CCN(CCO)CC4)cc3)c3c(=O)[nH]ncc3n2)CC1] | C | C |
| 292 | 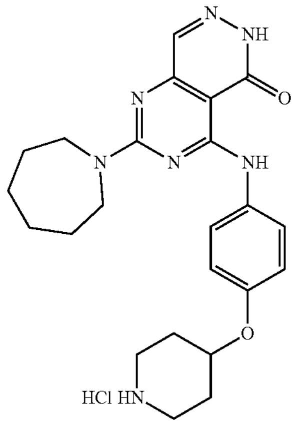 | D | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 293 | 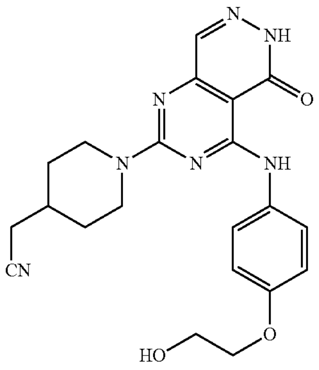 [SMILES: N#CCC1CCN(c2nc(Nc3ccc(OCCO)cc3)c3c(=O)[nH]ncc3n2)CC1] | B | C |
| 294 | 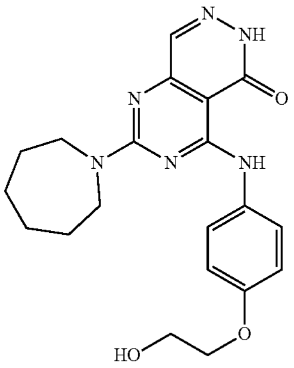 [SMILES: O=c1[nH]ncc2nc(N3CCCCCC3)nc(Nc3ccc(OCCO)cc3)c12] | C | C |
| 295 | 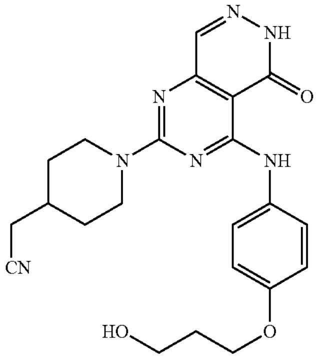 [SMILES: N#CCC1CCN(c2nc(Nc3ccc(OCCCO)cc3)c3c(=O)[nH]ncc3n2)CC1] | C | C |
| 296 | 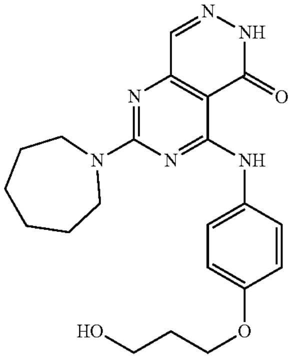 [SMILES: O=c1[nH]ncc2nc(N3CCCCCC3)nc(Nc3ccc(OCCCO)cc3)c12] | B | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 297 | 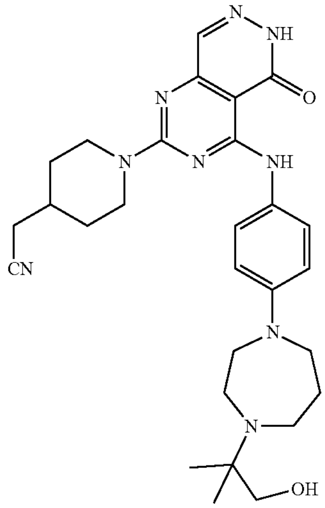 [SMILES: CC(C)(CO)N1CCCN(c2ccc(Nc3nc(N4CCC(CC#N)CC4)nc4cn[nH]c(=O)c34)cc2)CC1] | D | C |
| 298 | 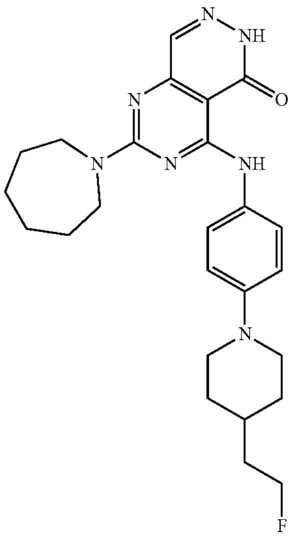 [SMILES: O=c1[nH]ncc2nc(N3CCCCCC3)nc(Nc3ccc(N4CCC(CCF)CC4)cc3)c12] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 299 | 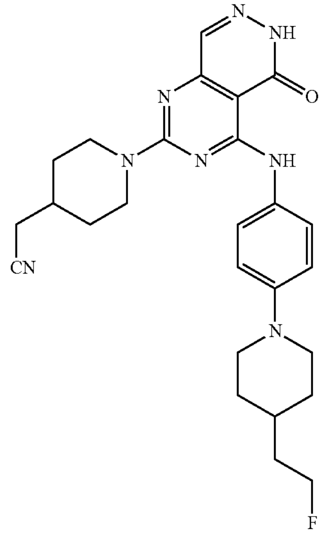 | C | C |
| 300 | 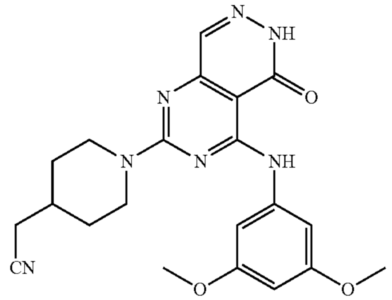 [SMILES: COc1cc(Nc2nc(N3CCC(CC#N)CC3)nc3cn[nH]c(=O)c23)cc(OC)c1] | A | — |
| 301 | 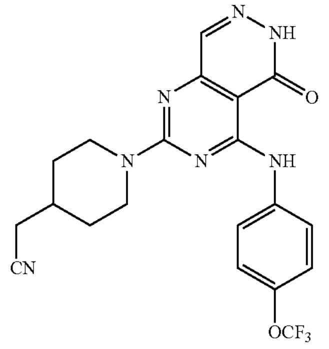 [SMILES: N#CCC1CCN(c2nc(Nc3ccc(OC(F)(F)F)cc3)c3c(=O)[nH]ncc3n2)CC1] | A | — |
| 302 | 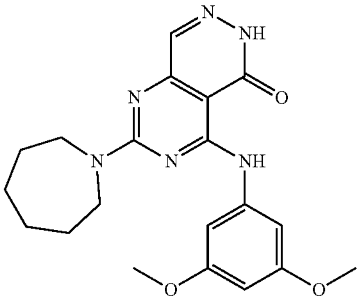 [SMILES: COc1cc(Nc2nc(N3CCCCCC3)nc3cn[nH]c(=O)c23)cc(OC)c1] | A | — |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 303 | 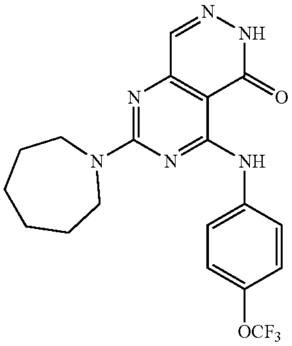 [SMILES: O=c1[nH]ncc2nc(N3CCCCCC3)nc(Nc3ccc(OC(F)(F)F)cc3)c12] | A | — |
| 304 | 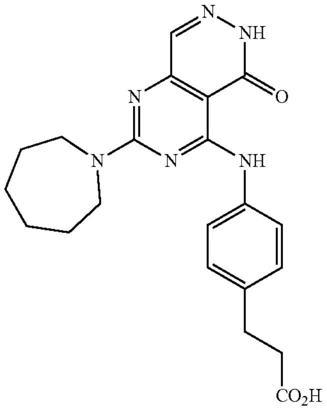 [SMILES: O=C(O)CCc1ccc(Nc2nc(N3CCCCCC3)nc3cn[nH]c(=O)c23)cc1] | D | D |
| 305 | 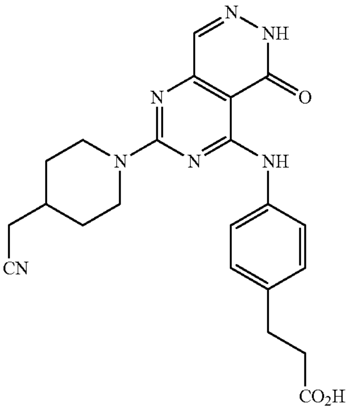 [SMILES: N#CCC1CCN(c2nc(Nc3ccc(CCC(=O)O)cc3)c3c(=O)[nH]ncc3n2)CC1] | D | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 306 | 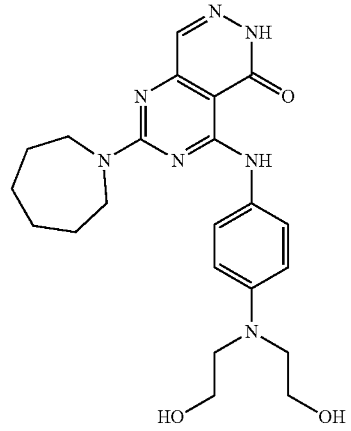 [SMILES: O=c1[nH]ncc2nc(N3CCCCCC3)nc(Nc3ccc(N(CCO)CCO)cc3)c12] | D | D |
| 307 | 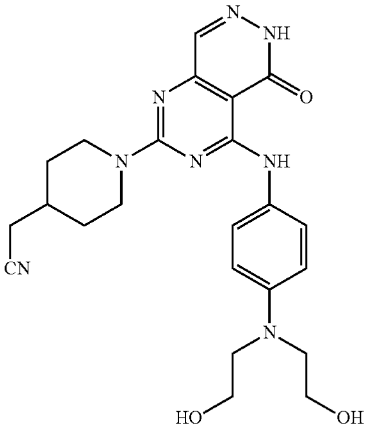 [SMILES: N#CCC1CCN(c2nc(Nc3ccc(N(CCO)CCO)cc3)c3c(=O)[nH]ncc3n2)CC1] | D | D |
| 308 | 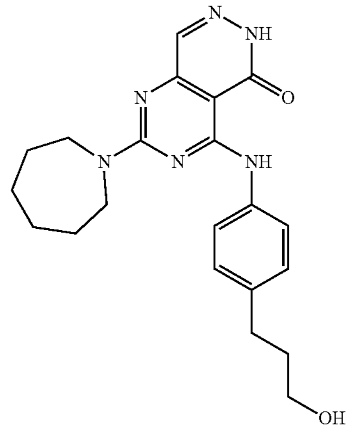 [SMILES: O=c1[nH]ncc2nc(N3CCCCCC3)nc(Nc3ccc(CCCO)cc3)c12] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 309 | 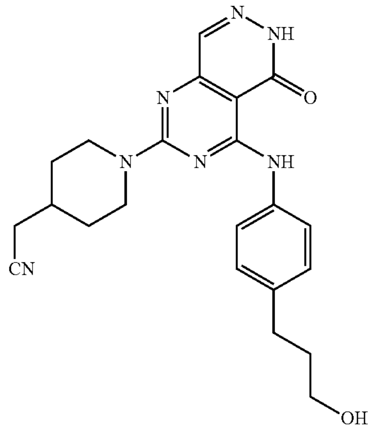 [SMILES: N#CCC1CCN(c2nc(Nc3ccc(CCCO)cc3)c3c(=O)[nH]ncc3n2)CC1] | C | C |
| 310 | 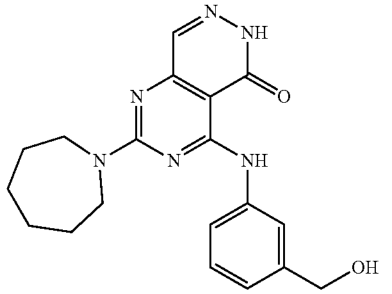 [SMILES: O=c1[nH]ncc2nc(N3CCCCCC3)nc(Nc3cccc(CO)c3)c12] | A | — |
| 311 | 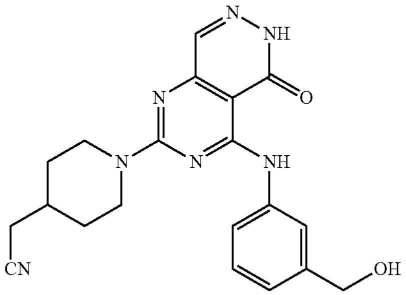 [SMILES: N#CCC1CCN(c2nc(Nc3cccc(CO)c3)c3c(=O)[nH]ncc3n2)CC1] | A | — |
| 312 | 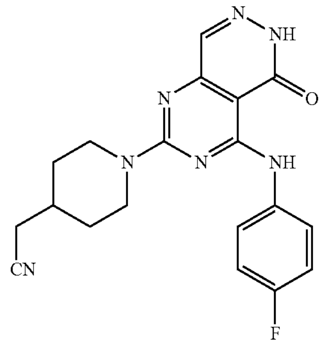 [SMILES: N#CCC1CCN(c2nc(Nc3ccc(F)cc3)c3c(=O)[nH]ncc3n2)CC1] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 313 | 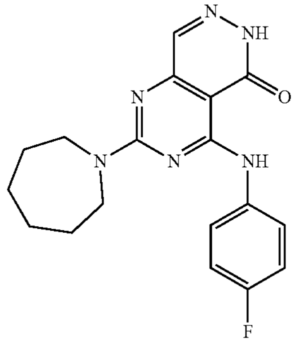 [SMILES: O=c1[nH]ncc2nc(N3CCCCCC3)nc(Nc3ccc(F)cc3)c12] | A | — |
| 314 | 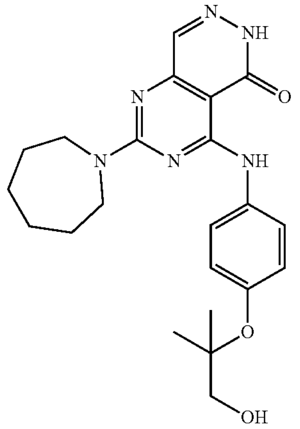 [SMILES: CC(C)(CO)Oc1ccc(Nc2nc(N3CCCCCC3)nc3cn[nH]c(=O)c23)cc1] | C | D |
| 315 | 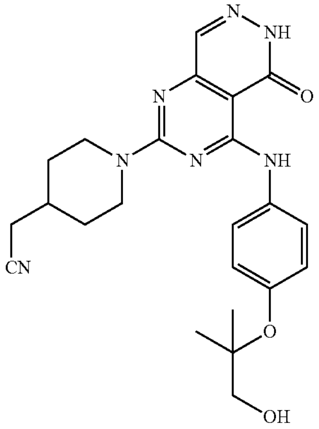 [SMILES: CC(C)(CO)Oc1ccc(Nc2nc(N3CCC(CC#N)CC3)nc3cn[nH]c(=O)c23)cc1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 316 | 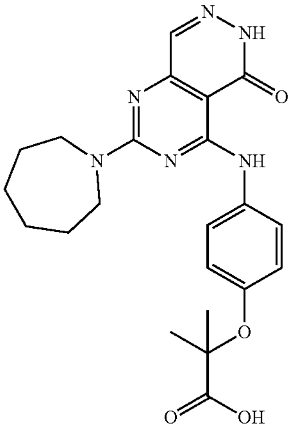 [SMILES: CC(C)(Oc1ccc(Nc2nc(N3CCCCCC3)nc3cn[nH]c(=O)c23)cc1)C(=O)O] | C | D |
| 317 | 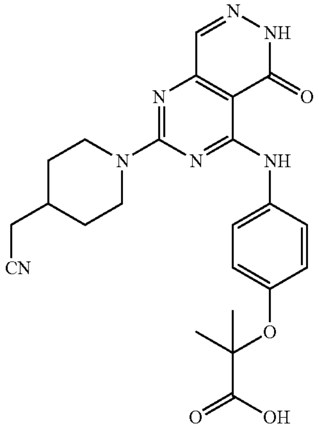 [SMILES: CC(C)(Oc1ccc(Nc2nc(N3CCC(CC#N)CC3)nc3cn[nH]c(=O)c23)cc1)C(=O)O] | A | — |
| 318 | 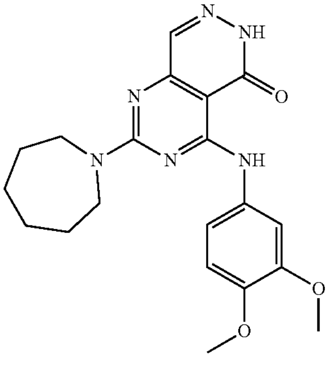 [SMILES: COc1ccc(Nc2nc(N3CCCCCC3)nc3cn[nH]c(=O)c23)cc1OC] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 319 | 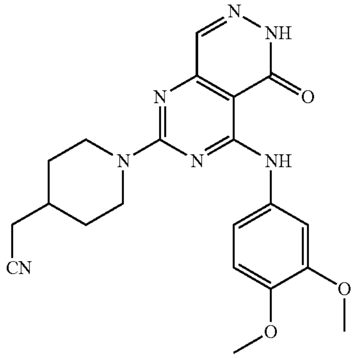 [SMILES: COc1ccc(Nc2nc(N3CCC(CC#N)CC3)nc3cn[nH]c(=O)c23)cc1OC] | A | — |
| 320 | 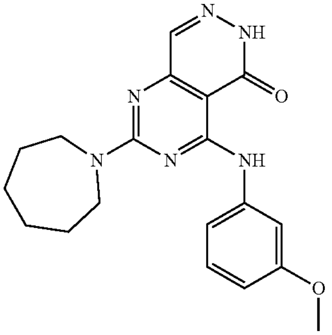 [SMILES: COc1cccc(Nc2nc(N3CCCCCC3)nc3cn[nH]c(=O)c23)c1] | A | — |
| 321 | 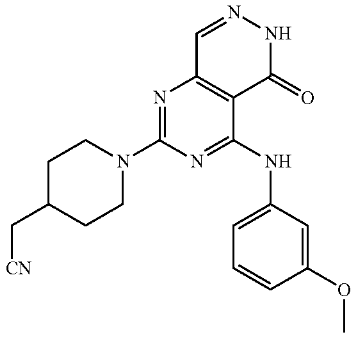 [SMILES: COc1cccc(Nc2nc(N3CCC(CC#N)CC3)nc3cn[nH]c(=O)c23)c1] | A | — |
| 322 | 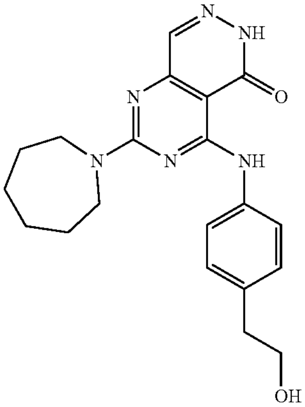 [SMILES: O=c1[nH]ncc2nc(N3CCCCCC3)nc(Nc3ccc(CCO)cc3)c12] | C | D |

TABLE 7-continued
| Ex. # | Structure | IC50 ≥100 nM = A; ≤100 nM = B; ≤50 nM = C; ≤10 nM = D Syk | JAK2 |
|---|---|---|---|
| 323 | 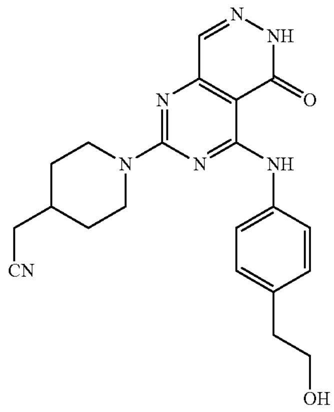 [SMILES: N#CCC1CCN(c2nc(Nc3ccc(CCO)cc3)c3c(=O)[nH]ncc3n2)CC1] | C | C |
| 324 | 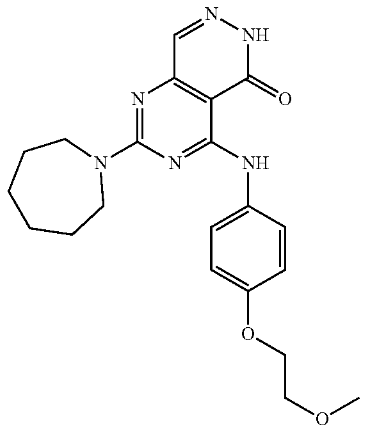 [SMILES: COCCOc1ccc(Nc2nc(N3CCCCCC3)nc3cn[nH]c(=O)c23)cc1] | C | C |
| 325 | 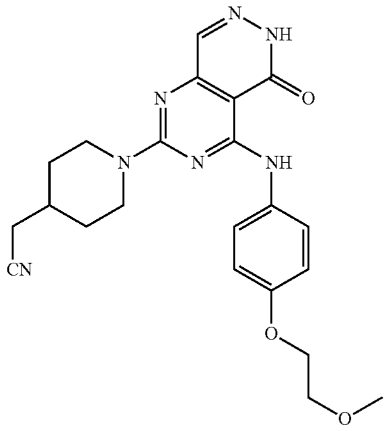 [SMILES: COCCOc1ccc(Nc2nc(N3CCC(CC#N)CC3)nc3cn[nH]c(=O)c23)cc1] | C | C |

TABLE 7-continued
| Ex. # | Structure | IC$_{50}$ ≥100 nM = A; ≤100 nM = B; ≤50 nM = C; ≤10 nM = D Syk | JAK2 |
|---|---|---|---|
| 326 | 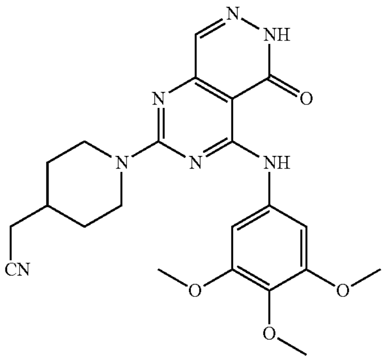 [SMILES: COc1cc(Nc2nc(N3CCC(CC#N)CC3)nc3cn[nH]c(=O)c23)cc(OC)c1OC] | A | — |
| 327 | 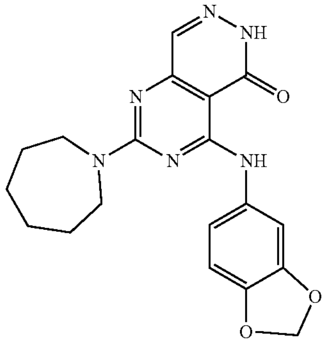 [SMILES: O=c1[nH]ncc2nc(N3CCCCCC3)nc(Nc3ccc4c(c3)OCO4)c12] | A | — |
| 328 | 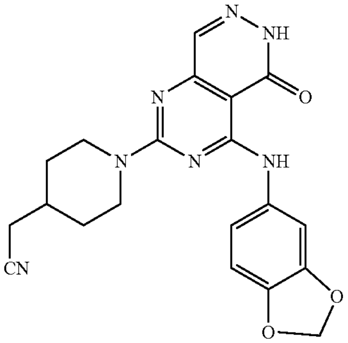 [SMILES: N#CCC1CCN(c2nc(Nc3ccc4c(c3)OCO4)c3c(=O)[nH]ncc3n2)CC1] | A | — |

TABLE 7-continued
| Ex. # | Structure | IC50 ≥100 nM = A; ≤100 nM = B; ≤50 nM = C; ≤10 nM = D Syk | JAK2 |
|---|---|---|---|
| 329 | 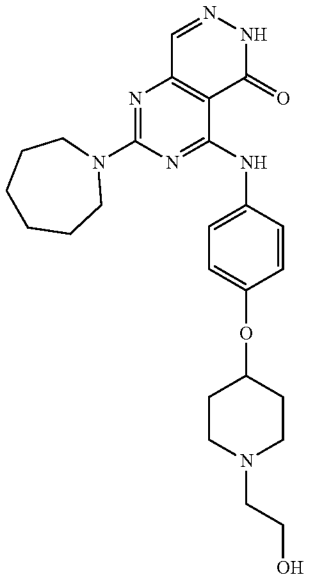 [SMILES: O=c1[nH]ncc2nc(N3CCCCCC3)nc(Nc3ccc(OC4CCN(CCO)CC4)cc3)c12] | D | D |
| 330 | 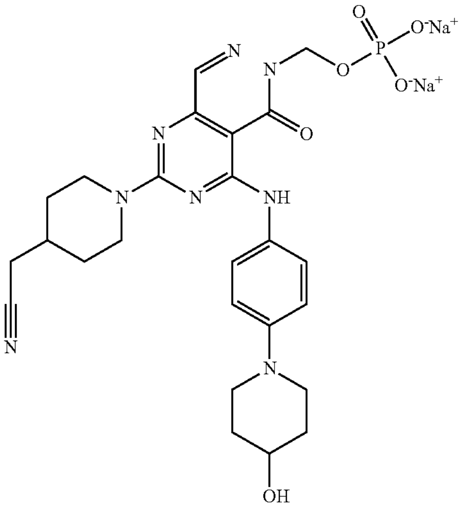 | A | — |
| 331 | 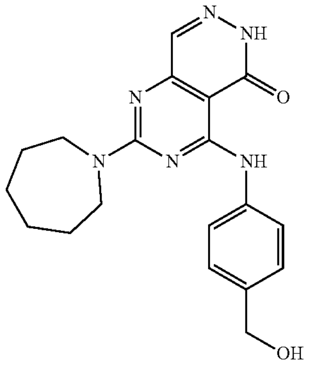 [SMILES: O=c1[nH]ncc2nc(N3CCCCCC3)nc(Nc3ccc(CO)cc3)c12] | C | A |

TABLE 7-continued
| Ex. # | Structure | IC50 ≥100 nM = A; ≤100 nM = B; ≤50 nM = C; ≤10 nM = D Syk | JAK2 |
|---|---|---|---|
| 332 | 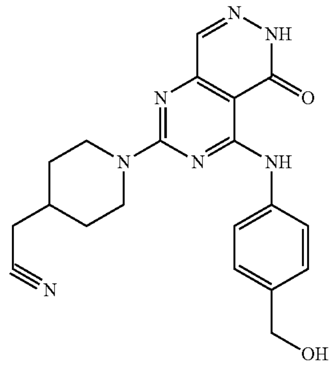 [SMILES: N#CCC1CCN(c2nc(Nc3ccc(CO)cc3)c3c(=O)[nH]ncc3n2)CC1] | B | — |
| 333 | 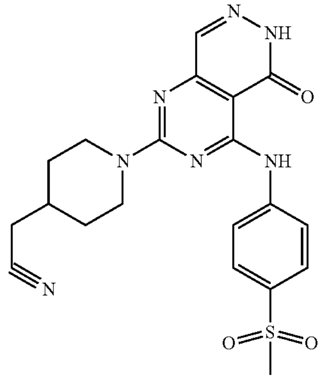 [SMILES: CS(=O)(=O)c1ccc(Nc2nc(N3CCC(CC#N)CC3)nc3cn[nH]c(=O)c23)cc1] | A | — |
| 334 | 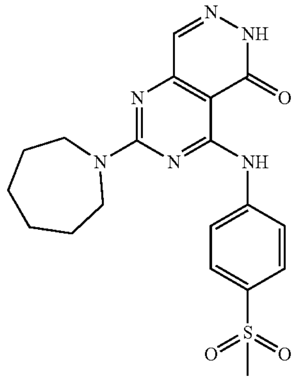 [SMILES: CS(=O)(=O)c1ccc(Nc2nc(N3CCCCCC3)nc3cn[nH]c(=O)c23)cc1] | C | D |
| 335 | 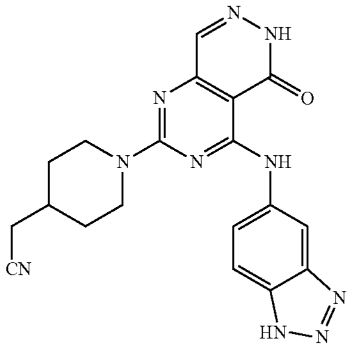 [SMILES: N#CCC1CCN(c2nc(Nc3ccc4[nH]nnc4c3)c3c(=O)[nH]ncc3n2)CC1] | C | C |

TABLE 7-continued
| Ex. # | Structure | IC50 ≥100 nM = A; ≤100 nM = B; ≤50 nM = C; ≤10 nM = D Syk | JAK2 |
|---|---|---|---|
| 336 | 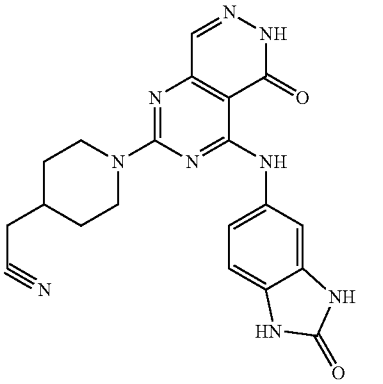 [SMILES: N#CCC1CCN(c2nc(Nc3ccc4[nH]c(=O)[nH]c4c3)c3c(=O)[nH]ncc3n2)CC1] | C | C |
| 337 | 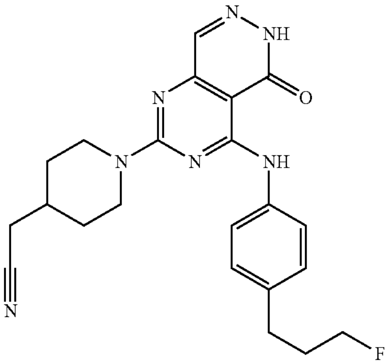 [SMILES: N#CCC1CCN(c2nc(Nc3ccc(CCCF)cc3)c3c(=O)[nH]ncc3n2)CC1] | C | C |
| 338 | 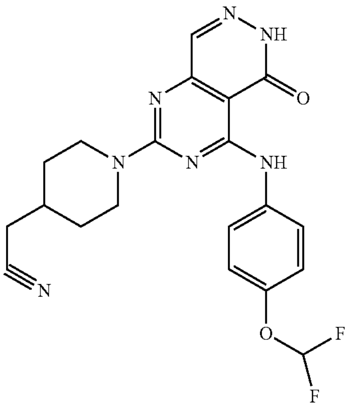 [SMILES: N#CCC1CCN(c2nc(Nc3ccc(OC(F)F)cc3)c3c(=O)[nH]ncc3n2)CC1] | B | A |
| 339 | 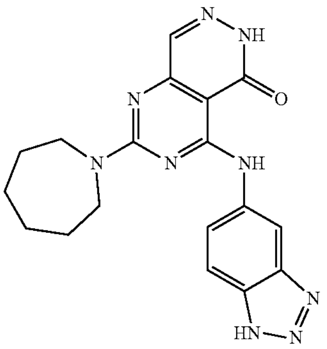 [SMILES: O=c1[nH]ncc2nc(N3CCCCCC3)nc(Nc3ccc4[nH]nnc4c3)c12] | D | C |

Example 342: Degranulation Assay

The objective of this assay was to examine by Fluorescence method the effect of compounds on β-hexosaminidase release during immune complex mediated degranulation in $RBL2H_3$ cells.

A. Introduction

Auto-antibodies and their immune complexes (ICs) reacting with self antigens through immunoglobulin receptors have been implicated widely in inflammation and chronic inflammatory disease such as rheumatoid arthritis. Activation of the high affinity receptor for immunoglobulin E (IgE), FcεRI, which is expressed on the surface of mast cells and basophils, plays a central role in the initiation of these allergic responses. Following aggregation of the receptor by ICs, the mast cell release a variety of potent biologically active molecules, including cytokines, lipid-derived mediators, amines, protease, and proteoglycans. Anti-DNP (anti-dinitrophenyl) IgE treated $RBL2H_3$ cells on stimulation with DNP-BSA leads to FcεR1 cross linking which mediates release of various pro-inflammatory molecules including β-hexosaminidase.

Compounds were tested for their ability to inhibit the ability of this immune complex to mediate β-hexosaminidase release, in an enzyme assay with p-nitrophenyl-β-D-glucosaminide as substrate. The fluorescence of the product 4-methylumbellifernone was monitored (Excitation 355 nm; Emission 460 nm).

B. Reagents and Instruments

TABLE 8

| Reagent | Supplier |
|---|---|
| Rat Basophilic Leukemia cell line (RBL2H3 cell line) | ATCC, Cat # CRL-2256 |
| Minimum Essential Medium (MEM) | GIBCO, Cat # 12571 |
| Fetal Bovine Serum (FBS) | Hyclone, Cat # SH30071.03 |
| Pencilin (10000 unit/mL)-Streptomycin (10,000 μg/mL) (Penstrep ® reagent) | GIBCO, Cat #15140-122 |
| MEM Sodium Pyruvate solution, 100 mM | GIBCO, Cat # 11360 |
| Nonessential amino acid (NEAA) | GIBCO, Cat # 11140 |
| 0.1% Trypsin and 0.1% EDTA (0.1% TE) | SAFC Biosciences, Cat # 59417C |
| 96-well flat bottom plate | Falcon, Cat # 3072 |
| 100% Dimethyl Sulfoxide (DMSO; Vehicle) | SIGMA-D-5879 |
| SPE-7 | Anti-Dinitrophenyl (DNP) Monoclonal Rat IgE, Clone SPE-7 (Sigma, Cat #D8406) |
| 2,4-Dinitrophenylated Albumin from bovine serum (DNP-BSA) | Invitrogen, Cat #A23018 |
| 4-Methylumbelliferyl N-acetyl-β-D-glucosaminide dihydrate (β-NAG) | Sigma, Cat #2133 |
| 0.1M Sodium Carbonate/Sodium Bicarbonate, pH 10.08 (Stop Solution) | $Na_2CO_3$: Sigma, Cat # S5761 $NaHCO_3$: Sd fine-Chemicals Ltd, Cat # 40121 |
| Phosphate Buffer Saline (PBS) | Himedia, Cat # TS1006 |
| 96 well View Plate | PerkinElmer, Part #6005182 |
| 24 well plate | Falcon, Cat # 3047 |
| Victor ™ X5 Multi label plate Fluorescence Reader | Perkin-Elmer, Product #2030-0050 |

TABLE 9

| Pipes Buffer composition | |
|---|---|
| Reagent | Supplier |
| 25 mM piperazine-1,4-bis (2-ethanesulfonic acid) (Pipes) | Sigma Cat # P1851 |
| 125 mM sodium chloride (NaCl) | Qualigens Cat # 15918 |
| 2.7 mM potassium chloride (KCl) | Sigma Cat # P9541 |
| 5.6 mM anhydrous D-glucose | Qualigens Cat # 24415 |
| 1 mM calcium chloride ($CaCl_2$) | Qualigens Cat # 22205 |
| 0.1% bovine serum albumin (BSA) | Sigma Cat # A7030 |

C. Protocols (i) Protocol A: 24 well format $RBL2H_3$ cells were maintained in MEM complete media containing 10% FBS at 70%-80% confluence in a mammalian cell culture $CO_2$ incubator with 5% $CO_2$ at 37° C. $2\times10^5$ cells/well were plated in 1 mL of complete media and incubated for 5 hours for cell attachment. Complete media was replaced with 1 mL of serum free MEM media containing 1.2 μg/mL of anti-DNP rat IgE as sensitizing agent and further incubated overnight with 5% $CO_2$ at 37° C. The following day, cells were washed with serum free media and further treated with various concentrations of test compounds (in 0.1% DMSO) for 45 minutes at 37° C. and 5% $CO_2$. Cells were further stimulated with 5 μg/mL of DNP-BSA for 60 minutes. Plates were centrifuged for 5 minutes at 1000 rpm and 25 μL of culture supernatant was transferred from each assay well into a 96 well black coated plate. 25 μL β-NAG substrate was added to this mixture and incubated at room temperature for 30 minutes. The reaction was terminated with 100 μL of stop solution and fluorescence was monitored. (Excitation 355 nm; Emission 460 nm) See, Sanderson, (2010), Cellular Immunology, 262(1): 28-34 and Silverman, (2006) MCB, 26(5):1826-1838, which are incorporated herein by reference.

The % release of β-Hexosaminidase for the test compound was calculated using the following formula:

$$\%\ \beta\text{-Hexosaminidase release} = \left(\frac{\text{test compound} - DMSO\ \text{control}}{IgE\ \text{control} - DMSO\ \text{Control}}\right)\times 100$$

(ii) Protocol B: 96 well format $RBL2H_3$ cells were maintained in MEM complete media containing 10% FBS at 70-80% confluence in a mammalian cell culture $CO_2$ incubator with 5% $CO_2$ at 37° C. $5\times10^4$ cells/well were plated in 200 μL of complete media containing 0.3 μg/mL of anti-DNP rat IgE as sensitizing agent for 24 hours at 37° C. & 5% $CO_2$. The following day, cells were washed twice with PIPES buffer for 10 minutes at 37° C. and replenished with serum free MEM media. Cells were treated with various concentrations of test compounds (in 0.5% DMSO) for 15 minutes at 37° C. and 5% $CO_2$. The cells were further stimulated with 0.1 μg/mL of DNP-BSA for 45 minutes. The plates were spun for 5 minutes at 2000 rpm and 25 μL of culture supernatant was then transferred from each assay well into a 96 well black coated plate. Fifth μL β-NAG substrate was added and incubated at RT for 30 minutes. After incubation with substrate, 150 μL of stop solution was added and fluorescence was monitored. (Excitation 355 nm; Emission 460 nm). See, Yamamoto, JPET, 306(3):1174-1181 (2003) and Taylor, MCB, 15(8): 4149-4157 (1995), which are herein incorporated by reference.

Release of β-hexosaminidase during the degranulation process by immune complex mediated FcεRI stimulation is through the SYK pathway. The % inhibition of β-hexosaminidase release by Syk inhibitor gives information with regard to its Syk inhibition potency. Thus compounds having lower $EC_{50}$ values are more potent in inhibiting immune complex mediated Syk signaling during degranulation process.

TABLE 10

| Ex. # | Degranulation % inhibition at 1 μM | Degranulation $EC_{50}$ (nM) | Assay Protocol |
|---|---|---|---|
| 1 | 85 | — | A |
| 5 | 100 | 39 | A |
| 6 | 50 | — | A |
| 7 | 92 | 86 | A |
| 8 | 98 | — | A |
| 10 | 100 | — | A |
| 11 | 100 | — | A |
| 13 | 100 | 47 | A |
| 19 | 100 | 19 | A |
| 24 | 83 | — | B |
| 25 | 79 | — | A |
| 26 | 67 | — | B |
| 30 | 99 | — | B |
| 33 | 58 | — | B |
| 34 | 80 | 378 | B |
| 35 | 19 | — | B |
| 39 | 100 | — | B |
| 43 | 13 | — | B |
| 47 | 100 | 132 | B |
| 48 | 100 | — | B |
| 50 | 49 | — | B |
| 52 | 100 | 1 | B |
| 54 | 100 | 13 | B |
| 60 | 100 | 18 | B |
| 62 | 100 | 49 | B |
| 66 | 75 | 352 | B |
| 68 | 100 | 1.2 | B |
| 69 | 100 | 31 | B |
| 71 | 65 | 1017 | B |
| 88 | 100 | 76 | B |
| 89 | 100 | — | B |
| 91 | 100 | 154 | B |
| 92 | 100 | 111 | B |
| 93 | 49 | — | B |
| 95 | 35 | — | B |
| 96 | 85 | 280 | B |
| 98 | 62 | 593 | B |
| 99 | 94 | 44 | B |
| 103 | 87 | 32 | B |
| 104 | 100 | 110 | B |
| 107 | 91 | 94 | B |
| 108 | 98 | 68 | B |
| 116 | 65 | 273 | B |
| 117 | 89 | 95 | B |
| 118 | 87 | 153 | B |
| 121 | 98 | 156 | B |
| 123 | 90 | 116 | B |
| 125 | 38 | 238 | B |
| 131 | 98 | 35 | B |
| 132 | 99 | 24 | B |
| 133 | 98 | 25 | B |
| 145 | 52 | 98 | B |
| 146 | 66 | 26 | B |
| 147 | 49 | 152 | B |
| 151 | — | 24 | B |
| 153 | 47 | 324 | B |
| 154 | 23 | 2320 | B |
| 155 | — | 27 | B |
| 157 | 70 | 42 | B |
| 158 | 53 | 162 | B |
| 159 | 68 | 56 | B |
| 161 | 74 | 39 | B |
| 162 | 27 | 281 | B |
| 164 | — | 55 | B |
| 169 | 17 | 230 | B |
| 170 | 39 | 107 | B |

TABLE 10-continued

| Ex. # | Degranulation % inhibition at 1 μM | Degranulation $EC_{50}$ (nM) | Assay Protocol |
|---|---|---|---|
| 172 | 50 | 101 | B |
| 173 | 66 | 29 | B |
| 174 | 99 | 15 | B |
| 175 | 98 | 6 | B |
| 178 | 73 | 39 | B |
| 179 | 45 | 9 | B |
| 180 | 70 | 3 | B |
| 183 | 41 | 83 | B |
| 184 | 65 | 33 | B |
| 185 | 83 | 29 | B |
| 186 | 93 | 10 | B |
| 187 | 100 | 12 | B |
| 189 | 98 | 14 | B |
| 190 | 83 | 21 | B |
| 191 | 92 | 21 | B |
| 192 | 82 | 27 | B |
| 193 | 93 | 17 | B |
| 200 | 71 | 66 | B |
| 201 | 88 | 31 | B |
| 208 | 21 | 14 | B |
| 209 | 81 | 29 | B |
| 210 | 79 | 22 | B |
| 211 | 53 | 49 | B |
| 212 | 71 | 28 | B |
| 213 | 78 | 33 | B |
| 214 | 78 | 19 | B |
| 215 | 96 | 12 | B |
| 216 | 92 | 21 | B |
| 218 | 33 | 123 | B |
| 219 | 45 | 96 | B |
| 231 | 0 | 367 | B |
| 232 | 0 | 619 | B |
| 233 | 20 | 174 | B |
| 244 | 23 | 306 | B |
| 248 | 99 | 19 | B |
| 254 | 24 | 1200 | B |
| 256 | 73 | 33 | B |
| 261 | 87 | 39 | B |
| 264 | 75 | 54 | B |
| 265 | 79 | 30 | B |
| 266 | 99 | 10 | B |
| 267 | 90 | 21 | B |
| 268 | 93 | 20 | B |
| 273 | 91 | 21 | B |
| 274 | 59 | 81 | B |
| 275 | 73 | 15 | B |
| 276 | 91 | 24 | B |
| 277 | 74 | 42 | B |
| 283 | 71 | 39 | B |
| 284 | 92 | 21 | B |
| 287 | 97 | 20 | B |
| 290 | 100 | 20 | B |
| 292 | 65 | 83 | B |
| 297 | 99 | 18 | B |
| 304 | 70 | 55 | B |
| 305 | 17 | 834 | B |
| 306 | 100 | 15 | B |
| 307 | 14 | 312 | B |
| 329 | 69 | 62 | B |
| 339 | 83 | 31 | B |

Example 343: In Vivo Assay—Chronic Study

A. Introduction

Collagen Induced Arthritis (CIA) is a well characterized model of human rheumatoid arthritis (RA) that can be induced in susceptible animals following immunization with type II collagen (cII) in Freund's adjuvant. CIA exhibits several features of human RA such as severe swelling/inflammation of joints, synovial hyperplasia, cartilage destruction and bone erosion. Pathophysiology of CIA consists of T cell component, as evidenced by increased infiltration of T-cells in joint synovium and also, by attenuation of CIA in T-cell deficient mice. CIA development involves B cell component too, as is evidenced by circulating cII antibody in disease animals and also, failure to develop the disease in xid mice/B cell deficient mice/CXCR5 null mice. Recently, a significant role of macrophages has also been suggested in the pathogenesis of CIA as well as human RA. See, Pine, "Inflammation and bone erosion are suppressed in models of rheumatoid arthritis following treatment with a novel Syk inhibitor", Clin. Immunol., 2007, 124(3):244-57; Xiong cha, "Suppression of the onset and progression of collagen-induced arthritis in rats by QFGJS, a preparation from an anti-arthritic Chinese herbal formula", J. Ethnopharmacology (2007) 110:39-48; and Stolina, "The evolving systemic and local biomarker milieu at different stages of disease progression in rat collagen induced arthritis", Biomarkers (2008) 13(7-8):692-712, which are herein incorporated by reference.

B. Method (i) Induction of CIA:

Female Lewis rats (8 per group, 6-8 weeks old) were immunized on day 1 with type II collagen (Immunization grade Bovine type II; Chondrex; Cat #20021) emulsified with Complete Freund's Adjuvant (Sigma; Cat # F5881) at a final concentration of 1.2 mg/mL). For the initial immunization, the animals were injected at the base of the tail with 300 μg of the cII (0.25 mL/rat). A booster injection of the same type II collagen emulsified with Incomplete Freund's Adjuvant (Sigma, Cat #F5506) (0.25 mL/rat) was given to the animals on day 8 at the base of the tail (100 μg). The final cII concentration in the booster was 0.4 μg/mL.

(ii) Dosage regimen

Animals with an arthritic score of ≥1 were grouped and dosing with test compound (30 mg/kg bid) or methotrexate (0.5 mg/kg) started between about day 12 to day 14, with daily dosing of their respective compounds continuing for 10 days.

(iii) Measurements:

Edema: Paw volumes are measured by Plethysmometry for the animals before induction of CIA (Basal readings) and on Day 1, 3, 6 and 9 of dosing period. Both hind paw volumes were measured and edema was calculated by subtracting from the basal mean.

Arthritic score: Animals were scored for the symptoms of arthritis every day starting from Day of onset of disease till the end of the study. Both the hind paws were scored and the total scores were averaged and compared with control. The scoring pattern was as follows:

TABLE 11

| Severity score | Gross pathology |
|---|---|
| 0 | No evidence of erythema or swelling |
| 1 | Erythema and mild swelling confined to mid foot or ankle joint |
| 2 | Erythema and moderate swelling extending from ankle to mid foot |
| 3 | Erythema and moderate swelling extending from ankle to metatarsal joints |
| 4 | Erythema and severe swelling ankle, foot and digits |

C. Results (i) Calculations

The percent inhibition of Edema was calculated with respect to control by the formula:

$$\%\ \text{inhibition of Edema} = \left(1 - \left\{\frac{\dfrac{\text{Mean Edema in treated animals on day } `n\text{'}}{(\text{Mean Edema in treated animals on day } `0\text{'})}}{\dfrac{(\text{Mean Edema in control animals on day } `n\text{'})}{(\text{Mean Edema in control animals on day } `0\text{'})}}\right\}\right) \times 100$$

The percent inhibition of Arthritic score was calculated with respect to control by the formula:

$$\%\ \text{inhibition of Score} = \left(1 - \left\{\frac{\dfrac{\text{Mean score in treated animals on day } `n\text{'}}{(\text{Mean score in treated animals on day } `0\text{'})}}{\dfrac{(\text{Mean score in control animals on day } `n\text{'})}{(\text{Mean score in control animals on day } `0\text{'})}}\right\}\right) \times 100$$

(ii) Statistical Analysis

Means of different groups were compared with control using one way ANOVA followed by Dunnett's test. Significance is represented as follows.

Figure 1B:
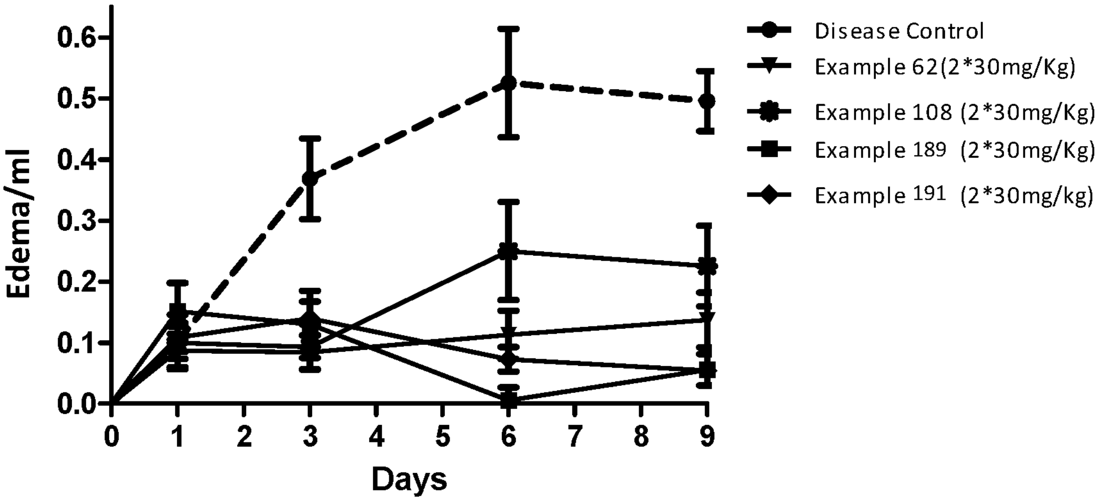
Figure 2B:
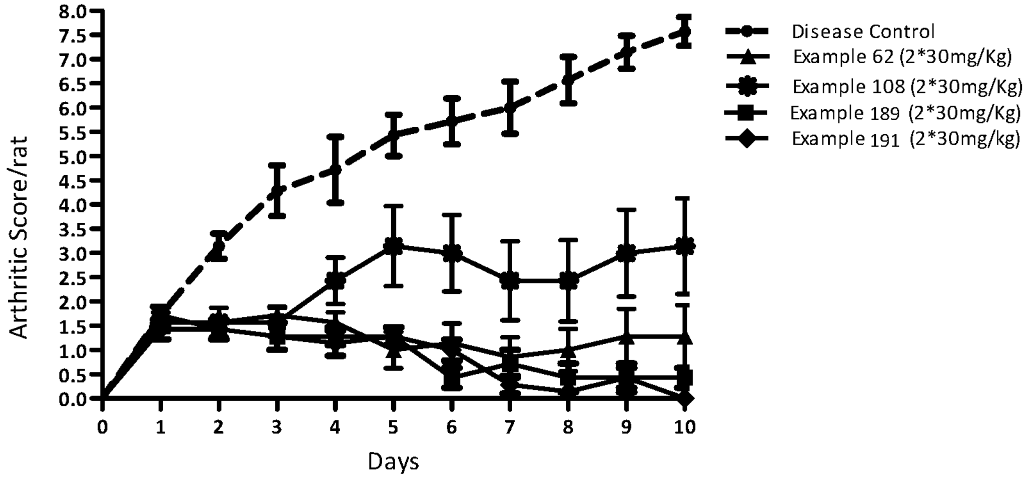

This example illustrates that the compounds may be utilized for treating inflammation. See FIGS. 1-2.

TABLE 12

| Group | Percent inhibition of Edema (Day 9 of dosing) | Percent inhibition of Arthritic score (Day 10 of dosing) |
|---|---|---|
| Control | 0 | 0 |
| Example 19 (2 × 30 mg/Kg) | 5** | 20* |
| Methotrexate (0.5 mg/Kg) | 6 | 15 |
| Example 62 (2 × 30 mg/Kg) | 69*** | 81*** |
| Example 108 (2 × 30 mg/Kg) | 42*** | 53*** |
| Example 189 (2 × 30 mg/Kg) | 90*** | 94*** |
| Example 191 (2 × 30 mg/Kg) | 90*** | 100*** |

*p < 0.05,
**p < 0.01,
***p < 0.001

Example 344: In Vivo Assay—Acute Study

A. Introduction

Arthus reaction is a type of local type III hypersensitivity reaction. Type III hypersensitivity reactions are immune complex-mediated, and involve the deposition of antigen/antibody complexes mainly in the vascular walls, serosa (pleura, pericardium, synovium), and glomeruli. This involves formation of antigen/antibody complexes after the intradermal injection of an antibody. If the animal was previously injected with antigen and dye (has circulating antigen), an Arthus reaction occurs. This manifests as local vasculitis due to deposition of immune complexes in dermal blood vessels. Activation of complement and recruitment of PMNs ensue, resulting in an inflammatory response and extravasation of dye to the skin. Compounds which can inhibit this complex process can have therapeutic implications in wide range of inflammatory and auto-immune disorders. See, Pine, "Inflammation and bone erosion are suppressed in models of rheumatoid arthritis following treatment with a novel Syk inhibitor"; Clin. Immunol. (2007) 124 (3): 244-57; and Sylvia, "R-406, an Orally Available Spleen Tyrosine Kinase Inhibitor Blocks Fc Receptor Signaling and Reduces Immune Complex-Mediated Inflammation", JPET 319:998-1008, 2006, which are herein incorporated by reference.

B. Immunization and Challenge

Female c57BL/6 mice were given an antigen injection in which the antigen was 0.1% Ovalbumin (OVA) in PBS containing 1% Evans blue (EB) at the concentration of 10 mL/kg intravenously under Isoflurane anesthesia [2.5 mg/mouse with a body weight of 25 g]. Ten minutes after antigen injection; the animals were injected with the rabbit anti-OVA IgG (50 μg in 25 L/site) (Polysciences; Cat #23744) intradermally on the shaved back at two top locations. Animals were also injected with phosphate buffered saline (PBS, 25 μL) intradermally on the back at two bottom and opposite locations to serve as negative control. The mice were euthanized by cervical dislocation 4 hours after antigen (Ovalbumin) challenge. Skin tissue was assessed for edema by tracing the edema area on to a transparent plastic sheet. Punch biopsies of the injection sites were collected.

C. Measurements (i) Area of Extravasation

Edema area was measured manually by scale. Two diameters were taken and averaged for each animal.

(ii) Extent of Dye Extravasation

Punch biopsies of the injection sites (using 10 mm skin biopsy punches) were incubated in 2 mL of sodium sulfate: acetone mixture (0.6+1.4 mL) at room temperature for 16-18 hours. The supernatants were removed from digested tissues by centrifuging at 4000 rpm for 10 minutes, filtered and were read spectrophotometrically at 610 nm.

D. Data Analysis

The percent inhibition of dye leakage was calculated with respect to control by the formula:

$$\text{Percent inhibition of OD} = \left\{1 - \left(\frac{\text{Mean OD in treated animals}}{\text{Mean OD in control animals}}\right)\right\} \times 100$$

The percent inhibition of edema area was calculated with respect to control by the formula:

$$\text{Percent inhibition of edema area} = \left\{1 - \left(\frac{\text{Mean edema area in treated animals}}{\text{Mean edema area in control animals}}\right)\right\} \times 100$$

E. Statistical Analysis:

Means of different groups were compared with control using One way ANOVA followed by Dunnett's test. Significance was represented as follows.

This example illustrates that the compounds described herein may be utilized in treating inflammation.

TABLE 13

Efficacy of NCEs in Arthus reaction model in mice

| Example | Dose (mg/Kg) | Edema area % Inhibition | OD % Inhibition |
|---|---|---|---|
| 7 | 30 | 74*** | 65*** |
| | 10 | 53*** | 36 |
| | 10 | 30 | NE |

TABLE 13-continued

Efficacy of NCEs in Arthus reaction model in mice

| Example | Dose (mg/Kg) | Edema area % Inhibition | OD % Inhibition |
|---|---|---|---|
| 13 | 10 | 53*** | 27 |
| | 30 | 40** | 30 |
| 19 | 3 | 48*** | 53*** |
| | 30 | 60*** | 60*** |
| 7 | 3 | 41*** | 40*** |
| | 10 | 45*** | 41*** |
| | 30 | 68*** | 67*** |

*$p < 0.05$,
**$p < 0.01$,
***$p < 0.001$

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A pharmaceutical composition comprising a compound of Formula (I):

(I)

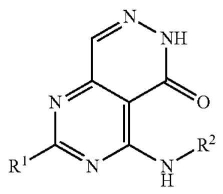

wherein:

$R^1$ is $NR^4R^5$, optionally substituted $C_1$ to $C_6$ alkoxy, optionally substituted $C_6$ to $C_{14}$ aryl, optionally substituted heteroaryl, optionally substituted 3-10 membered monocyclic or bicyclic cycloalkyl, or optionally substituted 3-10 membered monocyclic or bicyclic heterocyclyl, wherein:

(i) 3-4 membered cycloalkyl and heterocyclyl are saturated;

(ii) hydrogen atoms on the same carbon atom of said cycloalkyl or heterocyclyl are optionally replaced with an optionally substituted 3-6 membered cycloalkyl or heterocyclyl to form a spirocycloalkyl or spiroheterocyclyl; and (iii) hydrogen atoms on the same atom of said cycloalkyl or heterocyclyl are optionally replaced with 0 to form an oxo substituent;

$R^2$ is optionally substituted phenyl, —O—($C_1$ to $C_6$ alkyl)-optionally substituted phenyl, or optionally substituted 5-6 membered heteroaryl, with the proviso that when $R^2$ is 4-pyridyl, the 4-pyridyl lacks a carbonyl substituent at the 2nd position;

$R^4$ and $R^5$ are:

(a) independently selected from the group consisting of H, $C_1$ to $C_6$ alkyl, $C_1$ to $C_6$ hydroxyalkyl, $C_3$ to $C_8$ cycloalkyl, and —($C_1$ to $C_6$ alkyl)N($C_1$ to $C_6$ alkyl)($C_1$ to $C_6$ alkyl);

(b) joined to form an optionally substituted 3-8 membered heterocyclyl, wherein;

(bi) hydrogen atoms on the same carbon atom of said heterocyclyl are optionally replaced with an optionally substituted 3-6 membered cycloalkyl or heterocyclyl to form a spirocycloalkyl or spiroheterocyclyl; and (bii) hydrogen atoms on the same atom of said heterocyclyl (b), cycloalkyl (bi), or heterocyclyl (bi), are optionally replaced with 0 to form an oxo substituent;

or a pharmaceutically acceptable salt or ester thereof, a pharmaceutically acceptable carrier, and one or more excipients.

2. The pharmaceutical composition according to claim 1, wherein $R^2$ is phenyl substituted with $C(O)NR^4R^5$.

3. The pharmaceutical composition according to claim 1, where $R^2$ is phenyl substituted with $NR^4R^5$.

4. The pharmaceutical composition according to claim 1, where $R^2$ is phenyl substituted with ($C_1$ to $C_6$ alkyl)$NR^4R^5$.

5. The pharmaceutical composition according to claim 1, wherein $R^4$ and $R^5$ are joined to form an optionally substituted piperidine or diazepane.

6. The pharmaceutical composition according to claim 1, wherein $R^4$ and $R^5$ are ($C_1$ to $C_6$ hydroxyalkyl).

7. The pharmaceutical composition according to claim 1, wherein $R^4$ and $R^5$ are joined to form an optionally substituted 6-membered ring.

8. The pharmaceutical composition according to claim 1, wherein $R^2$ is a heteroaryl substituted with ($C_1$ to $C_6$ alkyl) $NR^4R^5$.

9. The pharmaceutical composition according to claim 1, wherein $R^2$ is a heteroaryl substituted with $NR^4R^5$.

10. The pharmaceutical composition according to claim 1, wherein $R^2$ is phenyl substituted with one or more $C_1$ to $C_6$ alkoxy, ($C_1$ to $C_6$ alkyl)halogen, $C_1$ to $C_6$ trifluoroalkoxy, ($C_1$ to $C_6$ alkyl)C(O(OH, halogen, optionally substituted $C_3$ to $C_8$ cycloalkyl, optionally substituted heterocyclyl, optionally substituted heteroaryl, —O—($C_1$ to $C_6$ alkyl)C(O)OH, —O—($C_1$ to $C_6$ alkyl)-$NR^4R^5$, —O-(optionally substituted heterocycle), —O($C_1$ to $C_6$ alkyl)-N($C_1$ to $C_6$ alkyl)($C_1$ to $C_6$ alkyl), —O—($C_1$ to $C_6$ alkyl)$NH_2$, $C_1$ to $C_6$ hydroxyalkyl, —O—($C_1$ to $C_6$ hydroxyalkyl), O—($C_1$ to $C_6$ alkyl)-C(O)OH, —$C_1$ to $C_6$ alkoxy-$C_1$ to $C_6$ alkoxy, O-(heterocycle)-($C_1$ to $C_6$ hydroxyalkyl), $SO_2$—($C_1$ to $C_6$ alkyl), or —($C_1$ to $C_6$ alkyl)-($C_1$ to $C_6$ alkoxy)-halogen.

11. The pharmaceutical composition according to claim 1, wherein $R^2$ is —O—($C_1$ to $C_6$ alkyl)$NR^4R^5$.

12. The pharmaceutical composition according to claim 1, wherein $R^2$ is aryl substituted with —O—($C_1$ to $C_6$ alkyl)-heterocycle.

13. The pharmaceutical composition according to claim 1, wherein $R^1$ is N($C_1$ to $C_6$ alkyl)($C_1$ to $C_6$ alkyl) or $C_1$ to $C_6$ alkoxy.

14. The pharmaceutical composition according to claim 1, wherein $R^1$ is optionally substituted phenyl.

15. The pharmaceutical composition according to claim 1, wherein $R^1$ is optionally substituted 5-9 membered saturated heterocyclyl.

16. The pharmaceutical composition according to claim 1, wherein $R^1$ is a heterocyclyl of the structure:

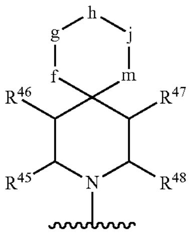

wherein:

f, g, h, j, and m are, independently, absent, ($CH_2$), CH($R^3$), Z, or C═O;

$R^3$ is H, C(O)OH, or C(O)O(C) to $C_6$ alkyl);

$R^{45}$, $R^{46}$, $R^{47}$, and $R^{48}$ are, independently, H or $C_1$ to $C_6$ alkyl; and Z is O, S, SO, $SO_2$, or NH.

17. The pharmaceutical composition according to claim 1, wherein $R^1$ is a heteroaryl.

18. The pharmaceutical composition according to claim 1, wherein $R^1$ is a monocyclic $C_3$ to $C_8$ cycloalkyl.

19. The pharmaceutical composition according to claim 1, wherein $R^1$ is piperidine substituted with C(O)($C_1$ to $C_6$ alkyl)CN.

20. The pharmaceutical composition according claim 1, wherein the compound is a salt of an acid.

21. The pharmaceutical composition according to claim 20, wherein said acid is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic.

22. The pharmaceutical composition according to claim 1, wherein the compound is:

4-(4-morpholinophenylamino)-2-phenylpyrimido[4,5-d]pyridazin-5(6H)-one;

methyl 4-(5-oxo-4-(4-(piperazin-1-ylmethyl)phenylamino)-5,6-dihydropyrimido[4,5-d]pyridazin-2-yl)benzoate hydrochloride;

2-morpholino-4-(4-(piperazin-1-ylmethyl)phenylamino)pyrimido[4,5-d]pyridazin-5(6H)-one hydrochloride;

4-(4-(morpholinomethyl)phenylamino)-2-phenylpyrimido[4,5-d]pyridazin-5(6H)-one;

4-(4-(4-ethylpiperazin-1-yl)phenylamino)-2-phenylpyrimido[4,5-d]pyridazin-5(6H)-one;

4-(4-((4-ethylpiperazin-1-yl)methyl)phenylamino)-2-phenylpyrimido[4,5-d]pyridazin-5(6H)-one;

2-phenyl-4-(4-(piperazin-1-ylmethyl)phenylamino)pyrimido[4,5-d]pyridazin-5(6H)-one hydrochloride;

2-phenyl-4-(4-(piperazin-1-yl)phenylamino)pyrimido[4,5-d]pyridazin-5(6H)-one;

4-(4-(morpholine-4-carbonyl)phenylamino)-2-phenylpyrimido[4,5-d]pyridazin-5(6H)-one;

4-(4-(bis(2-hydroxyethyl)amino)phenylamino)-2-phenylpyrimido[4,5-d]pyridazin-5(6H)-one;

4-(4-(4-(2-aminoacetyl)piperazin-1-yl)phenylamino)-2-phenylpyrimido[4,5-d]pyridazin-5(6H)-one hydrochloride;

2-(4-(4-(5-oxo-2-phenyl-5,6-dihydropyrimido[4,5-d]pyridazin-4-ylamino)phenyl)piperazin-1-yl)acetic acid;

1-(4-(5-oxo-2-phenyl-5,6-dihydropyrimido[4,5-d]pyridazin-4-ylamino)phenyl)piperidine-4-carboxylic acid;

4-(4-(4-(2-aminoacetyl)piperazin-1-yl)phenylamino)-2-phenylpyrimido[4,5-d]pyridazin-5(6H)-one;

N-(2-(dimethylamino)ethyl)-N-methyl-4-(5-oxo-2-phenyl-5,6-dihydropyrimido[4,5-d]pyridazin-4-ylamino)benzamide;

4-(4-(2-oxo-1,7-diazaspiro[3.5]nonan-7-yl)phenylamino)-2-phenylpyrimido[4,5-d]pyridazin-5(6H)-one;

4-(4-(2-oxa-7-azaspiro[3.5]nonan-7-yl)phenylamino)-2-phenylpyrimido[4,5-d]pyridazin-5(6H)-one;

4-(4-morpholinophenylamino)-2-(6-azaspiro[2.5]octan-6-yl)pyrimido[4,5-d]pyridazin-5(6H)-one;

6-(4-(5-oxo-2-phenyl-5,6-dihydropyrimido[4,5-d]pyridazin-4-ylamino)phenyl)-6-azaspiro[2.5]octane-1-carboxylic acid;

ethyl 6-(4-(5-oxo-2-phenyl-5,6-dihydropyrimido[4,5-d]pyridazin-4-ylamino)phenyl)-6-azaspiro[2.5]octane-1-carboxylate;

6-(4-(5-oxo-2-phenyl-5,6-dihydropyrimido[4,5-d]pyridazin-4-ylamino)benzyl)-6-azaspiro[2.5]octane-1-carboxylic acid;

sodium 6-(4-(5-oxo-2-phenyl-5,6-dihydropyrimido[4,5-d]pyridazin-4-ylamino)phenyl)-6-azaspiro[2.5]octane-1-carboxylate;

4-(4-(2-oxa-7-azaspiro[3.5]nonan-7-ylmethyl)phenylamino)-2-phenylpyrimido[4,5-d]pyridazin-5(6H)-one;

4-(4-(piperazin-1-ylmethyl)phenylamino)-2-(thiophen-3-yl)pyrimido[4,5-d]pyridazin-5(6H)-one hydrochloride;

6-(5-oxo-4-(4-(piperazin-1-ylmethyl)phenylamino)-5,6-dihydropyrimido[4,5-d]pyridazin-2-yl)-6-azaspiro[2.5]octane-1-carboxylic acid hydrochloride;

4-(4-(4-ethylpiperazin-1-yl)phenylamino)-2-morpholinopyrimido[4,5-d]pyridazin-5(6H)-one;

4-(5-oxo-4-(4-(piperazin-1-ylmethyl)phenylamino)-5,6-dihydropyrimido[4,5-d]pyridazin-2-yl)benzoic acid hydrochloride;

4-(4-(4-ethylpiperazin-1-yl)phenylamino)-2-(4-(trifluoromethoxy)phenyl)pyrimido[4,5-d]pyridazin-5(6H)-one;

methyl 4-(4-(4-morpholinophenylamino)-5-oxo-5,6-dihydropyrimido[4,5-d]pyridazin-2-yl)benzoate;

4-(4-(piperazin-1-ylmethyl)phenylamino)-2-(piperidin-1-yl)pyrimido[4,5-d]pyridazin-5(6H)-one hydrochloride;

2-(3-methoxyphenyl)-4-(4-(piperazin-1-ylmethyl)phenylamino)pyrimido[4,5-d]pyridazin-5(6H)-one hydrochloride;

2-(piperazin-1-yl)-4-(4-(piperazin-1-ylmethyl)phenylamino)pyrimido[4,5-d]pyridazin-5(6H)-one dihydrochloride;

2-(benzo[d][1,3]dioxol-5-yl)-4-(4-(piperazin-1-ylmethyl)phenylamino)pyrimido[4,5-d]pyridazin-5(6H)-one hydrochloride;

2-(1-(4-(5-oxo-2-phenyl-5,6-dihydropyrimido[4,5-d]pyridazin-4-ylamino)phenyl)piperidin-4-yl)acetic acid;

1-(4-(5-oxo-2-phenyl-5,6-dihydropyrimido[4,5-d]pyridazin-4-ylamino)benzyl)piperidine-4-carboxylic acid;

2-(2-methoxyphenyl)-4-(4-(piperazin-1-ylmethyl)phenylamino)pyrimido[4,5-d]pyridazin-5(6H)-one hydrochloride;

4-(4-(4-ethylpiperazin-1-yl)phenylamino)-2-(thiophen-3-yl)pyrimido[4,5-d]pyridazin-5(6H)-one hydrochloride;

9-(5-oxo-4-(4-(piperazin-1-ylmethyl)phenylamino)-5,6-dihydropyrimido[4,5-d]pyridazin-2-yl)-3,9-diazaspiro[5.5]undecane-2,4-dione hydrochloride;

6-(4-(5-oxo-2-(thiophen-3-yl)-5,6-dihydropyrimido[4,5-d]pyridazin-4-ylamino)phenyl)-6-azaspiro[2.5]octane-1-carboxylic acid;

2-(4-chlorophenyl)-4-(4-(piperazin-1-ylmethyl)phenylamino)pyrimido[4,5-d]pyridazin-5(6H)-one hydrochloride;

2-(4-methoxyphenyl)-4-(4-(piperazin-1-ylmethyl)phenylamino)pyrimido[4,5-d]pyridazin-5(6H)-one hydrochloride;

6-(4-((2-morpholino-5-oxo-5,6-dihydropyrimido[4,5-d]pyridazin-4-yl)amino)phenyl)-6-azaspiro[2.5]octane-1-carboxylic acid;

2-(1-(5-oxo-4-((4-(piperazin-1-ylmethyl)phenyl)amino)-5,6-dihydropyrimido[4,5-d]pyridazin-2-yl)piperidin-4-yl)acetic acid hydrochloride;

2-(1-oxidothiomorpholino)-4-((4-(piperazin-1-ylmethyl)phenyl)amino)pyrimido[4,5-d]pyridazin-5(6H)-one hydrochloride;

2-(4-methylpiperazin-1-yl)-4-((4-(piperazin-1-ylmethyl)phenyl)amino)pyrimido[4,5-d]pyridazin-5(6H)-one hydrochloride;

6-(4-((2-(4-methoxyphenyl)-5-oxo-5,6-dihydropyrimido[4,5-d]pyridazin-4-yl)amino)phenyl)-6-azaspiro[2.5]octane-1-carboxylic acid;

6-(4-((2-(3-methoxyphenyl)-5-oxo-5,6-dihydropyrimido[4,5-d]pyridazin-4-yl)amino)phenyl)-6-azaspiro[2.5]octane-1-carboxylic acid;

4-((4-(piperazin-1-ylmethyl)phenyl)amino)-2-(pyrrolidin-1-yl)pyrimido[4,5-d]pyridazin-5(6H)-one hydrochloride;

2-(dimethylamino)-4-((4-(piperazin-1-ylmethyl)phenyl)amino)pyrimido[4,5-d]pyridazin-5(6H)-one hydrochloride;

2-ethoxy-4-((4-(piperazin-1-ylmethyl)phenyl)amino)pyrimido[4,5-d]pyridazin-5(6H)-one hydrochloride;

1-(5-oxo-4-((4-(piperazin-1-ylmethyl)phenyl)amino)-5,6-dihydropyrimido[4,5-d]pyridazin-2-yl)piperidine-4-carboxylic acid hydrochloride;

2-(azepan-1-yl)-4-((4-(piperazin-1-ylmethyl)phenyl)amino)pyrimido[4,5-d]pyridazin-5(6H)-one hydrochloride;

6-(4-((2-(2-methoxyphenyl)-5-oxo-5,6-dihydropyrimido[4,5-d]pyridazin-4-yl)amino)phenyl)-6-azaspiro[2.5]octane-1-carboxylic acid;

2-(diisopropylamino)-4-((4-(piperazin-1-ylmethyl)phenyl)amino)pyrimido[4,5-d]pyridazin-5(6H)-one hydrochloride;

2-(4-(morpholinomethyl)phenyl)-4-((4-(piperazin-1-ylmethyl)phenyl)amino)pyrimido[4,5-d]pyridazin-5(6H)-one hydrochloride;

1-(5-oxo-4-((4-(piperazin-1-ylmethyl)phenyl)amino)-5,6-dihydropyrimido[4,5-d]pyridazin-2-yl)piperidine-4-carbonitrile hydrochloride;

2-(4-ethylpiperazin-1-yl)-4-((4-(piperazin-1-ylmethyl)phenyl)amino)pyrimido[4,5-d]pyridazin-5(6H)-one hydrochloride;

4-((1-(2-morpholinoethyl)-1H-pyrazol-4-yl)amino)-2-phenylpyrimido[4,5-d]pyridazin-5(6H)-one;

2-(1,4-diazepan-1-yl)-4-((4-(piperazin-1-ylmethyl)phenyl)amino)pyrimido[4,5-d]pyridazin-5(6H)-one dihydrochloride;

2-(azepan-1-yl)-4-((4-morpholinophenyl)amino)pyrimido[4,5-d]pyridazin-5(6H)-one;

2-methoxy-4-((4-(piperazin-1-ylmethyl)phenyl)amino)pyrimido[4,5-d]pyridazin-5(6H)-one hydrochloride;

6-(4-((2-(azepan-1-yl)-5-oxo-5,6-dihydropyrimido[4,5-d]pyridazin-4-yl)amino)phenyl)-6-azaspiro[2.5]octane-1-carboxylic acid;

2-phenyl-4-((1-(2-(piperazin-1-yl)ethyl)-1H-pyrazol-4-yl)amino)pyrimido[4,5-d]pyridazin-5(6H)-one hydrochloride;

4-((1-(2-(4-methylpiperazin-1-yl)ethyl)-1H-pyrazol-4-yl)amino)-2-phenylpyrimido[4,5-d]pyridazin-5(6H)-one;

4-((1-(2-(4-ethylpiperazin-1-yl)ethyl)-1H-pyrazol-4-yl)amino)-2-phenylpyrimido[4,5-d]pyridazin-5(6H)-one;

6-(4-((2-(4-(cyanomethyl)piperidin-1-yl)-5-oxo-5,6-dihydropyrimido[4,5-d]pyridazin-4-yl)amino)phenyl)-6-azaspiro[2.5]octane-1-carboxylic acid;

2-(azepan-1-yl)-4-((3,4,5-trimethoxyphenyl)amino)pyrimido[4,5-d]pyridazin-5(6H)-one;

2-(azepan-1-yl)-4-((4-(morpholine-4-carbonyl)phenyl)amino)pyrimido[4,5-d]pyridazin-5(6H)-one;

2-(1-(4-((2-(azepan-1-yl)-5-oxo-5,6-dihydropyrimido[4,5-d]pyridazin-4-yl)amino)phenyl)piperidin-4-yl)acetic acid;

2-(1-(4-((2-(4-(cyanomethyl)piperazin-1-yl)-5-oxo-5,6-dihydropyrimido[4,5-d]pyridazin-4-yl)amino)phenyl)piperidin-4-yl)acetic acid;

2-(1-(4-((2-(4-(cyanomethyl)piperidin-1-yl)-5-oxo-5,6-dihydropyrimido[4,5-d]pyridazin-4-yl)amino)phenyl)piperidin-4-yl)acetic acid;

6-(4-((2-(1,4-diazepan-1-yl)-5-oxo-5,6-dihydropyrimido[4,5-d]pyridazin-4-yl)amino)phenyl)-6-azaspiro[2.5]octane-1-carboxylic acid hydrochloride;

6-(4-((2-(4-(cyanomethyl)piperazin-1-yl)-5-oxo-5,6-dihydropyrimido[4,5-d]pyridazin-4-yl)amino)phenyl)-6-azaspiro[2.5]octane-1-carboxylic acid;

6-(4-((2-(4-cyanopiperidin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(4-cyanopiperidin-1-yl)-5-oxo-5,6-dihydropyrimido[4,5-d]pyridazin-4-yl)amino)phenyl)piperidin-4-yl)acetic acid;

1-(4-((2-(4-cyanopiperidin-1-yl)-5-oxo-5,6-dihydropyrimido[4,5-d]pyridazin-4-yl)amino)benzyl)piperidine-4-carboxylic acid;

2-(1-(4-((2-(azepan-1-yl)-5-oxo-5,6-dihydropyrimido[4,5-d]pyridazin-4-yl)amino)benzyl)piperidin-4-yl)acetic acid;

1-(4-((2-(4-(cyanomethyl)piperidin-1-yl)-5-oxo-5,6-dihydropyrimido[4,5-d]pyridazin-4-yl)amino)benzyl)piperidine-4-carboxylic acid;

6-(4-((2-cyclohexyl-5-oxo-5,6-dihydropyrimido[4,5-d]pyridazin-4-yl)amino)phenyl)-6-azaspiro[2.5]octane-1-carboxylic acid;

2-(1-(4-((2-(azepan-1-yl)-5-oxo-5,6-dihydropyrimido[4,5-d]pyridazin-4-yl)amino)phenyl)piperidin-4-yl)acetonitrile;

6-(4-((2-cycloheptyl-5-oxo-5,6-dihydropyrimido[4,5-d]pyridazin-4-yl)amino)phenyl)-6-azaspiro[2.5]octane-1-carboxylic acid;

2-(1-(4-((5-oxo-2-phenyl-5,6-dihydropyrimido[4,5-d]pyridazin-4-yl)amino)phenyl)piperidin-4-yl)acetonitrile;

4-((4-((4-(2-hydroxy-2-methylpropanoyl)piperazin-1-yl)methyl)phenyl)amino)-2-phenylpyrimido[4,5-d]pyridazin-5(6H)-one;

2-(azepan-1-yl)-4-((4-((4-(2-hydroxy-2-methylpropanoyl)piperazin-1-yl)methyl)phenyl)amino)pyrimido[4,5-d]pyridazin-5(6H)-one;

2-(azepan-1-yl)-4-((4-((4-methylpiperazin-1-yl)methyl)phenyl)amino)pyrimido[4,5-d]pyridazin-5(6H)-one;

2-(4-(4-((5-oxo-2-phenyl-5,6-dihydropyrimido[4,5-d]pyridazin-4-yl)amino)phenyl)piperidin-1-yl)acetic acid;

2-(4-(4-((5-oxo-2-phenyl-5,6-dihydropyrimido[4,5-d]pyridazin-4-yl)amino)phenyl)cyclohexyl)acetic acid;

2-(1-(4-((2-(azocan-1-yl)-5-oxo-5,6-dihydropyrimido[4,5-d]pyridazin-4-yl)amino)phenyl)piperidin-4-yl)acetic acid;

2-(azepan-1-yl)-4-((4-(2-(piperazin-1-yl)ethoxy)phenyl)amino)pyrimido[4,5-d]pyridazin-5(6H)-one hydrochloride;

2-(1-(4-((2-cycloheptyl-5-oxo-5,6-dihydropyrimido[4,5-d]pyridazin-4-yl)amino)phenyl)piperidin-4-yl)acetic acid;

2-(4-(4-((2-(azepan-1-yl)-5-oxo-5,6-dihydropyrimido[4,5-d]pyridazin-4-yl)amino)phenyl)cyclohexyl)acetic acid;

4-(4-((2-(azepan-1-yl)-5-oxo-5,6-dihydropyrimido[4,5-d]pyridazin-4-yl)amino)phenoxy)butanoic acid;

2-(azepan-1-yl)-4-((4-(2-morpholinoethoxy)phenyl)amino)pyrimido[4,5-d]pyridazin-5(6H)-one;

4-((4-(2-morpholinoethoxy)phenyl)amino)-2-phenylpyrimido[4,5-d]pyridazin-5(6H)-one;

2-(azepan-1-yl)-4-((4-(2-(4-methylpiperazin-1-yl)ethoxy)phenyl)amino)pyrimido[4,5-d]pyridazin-5(6H)-one;

2-(1-(2-(4-((2-(azepan-1-yl)-5-oxo-5,6-dihydropyrimido[4,5-d]pyridazin-4-yl)amino)phenoxy)ethyl)piperidin-4-yl)acetic acid;

2-(1-(5-((2-(azepan-1-yl)-5-oxo-5,6-dihydropyrimido[4,5-d]pyridazin-4-yl)amino)pyridin-2-yl)piperidin-4-yl)acetonitrile;

1-(2-(4-((2-(azepan-1-yl)-5-oxo-5,6-dihydropyrimido[4,5-d]pyridazin-4-yl)amino)phenoxy)ethyl)piperidine-4-carboxylic acid;

2-(1-(5-((2-(azepan-1-yl)-5-oxo-5,6-dihydropyrimido[4,5-d]pyridazin-4-yl)amino)pyridin-2-yl)piperidin-4-yl)acetamide;

2-(1-(4-((2-(4-(2-cyanopropan-2-yl)piperidin-1-yl)-5-oxo-5,6-dihydropyrimido[4,5-d]pyridazin-4-yl)amino)phenyl)piperidin-4-yl)acetic acid;

2-(1-(5-((5-oxo-2-phenyl-5,6-dihydropyrimido[4,5-d]pyridazin-4-yl)amino)pyridin-2-yl)piperidin-4-yl)acetonitrile;

2-(1-(5-((5-oxo-2-phenyl-5,6-dihydropyrimido[4,5-d]pyridazin-4-yl)amino)pyridin-2-yl)piperidin-4-yl)acetamide;

2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetonitrile;

2-(azepan-1-yl)-4-((4-(piperazine-1-carbonyl)phenyl)amino)pyrimido[4,5-d]pyridazin-5(6H)-one hydrochloride;

2-(1-(4-((2-(azepan-1-yl)-5-oxo-5,6-dihydropyrimido[4,5-d]pyridazin-4-yl)amino)phenyl)piperidin-4-yl)acetamide;

2-(4-(2-(4-((2-(azepan-1-yl)-5-oxo-5,6-dihydropyrimido[4,5-d]pyridazin-4-yl)amino)phenoxy)ethyl)piperazin-1-yl)acetic acid;

2-(azepan-1-yl)-4-((4-(2-(piperazin-1-yl)ethoxy)phenyl)amino)pyrimido[4,5-d]pyridazin-5(6H)-one;

2-(1-(5-((2-(azepan-1-yl)-5-oxo-5,6-dihydropyrimido[4,5-d]pyridazin-4-yl)amino)pyridin-2-yl)piperidin-4-yl)acetic acid;

2-(1-(4-((2-(azepan-1-yl)-5-oxo-5,6-dihydropyrimido[4,5-d]pyridazin-4-yl)amino)phenyl)piperidin-4-yl)-N-(2-hydroxyethyl)acetamide;

2-(azepan-1-yl)-4-((4-(((2S,5S)-5-(hydroxymethyl)-1,4-dioxan-2-yl)methoxy)phenyl)amino)pyrimido[4,5-d]pyridazin-5(6H)-one;

2-(4-(4-((2-(azepan-1-yl)-5-oxo-5,6-dihydropyrimido[4,5-d]pyridazin-4-yl)amino)phenyl)piperazin-1-yl)-2-methylpropanenitrile;

2-(4-(4-((2-(azepan-1-yl)-5-oxo-5,6-dihydropyrimido[4,5-d]pyridazin-4-yl)amino)phenyl)piperazin-1-yl)-2-methylpropanamide;

2-(1-(4-((2-(azepan-1-yl)-5-oxo-5,6-dihydropyrimido[4,5-d]pyridazin-4-yl)amino)phenyl)piperidin-4-yl)acetonitrile;

2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetonitrile;

2-(azepan-1-yl)-4-((4-(2-(4-(2-hydroxy-2-methylpropanoyl)piperazin-1-yl)ethoxy)phenyl)amino)pyrimido[4,5-d]pyridazin-5(6H)-one;

2-(1-(5-((2-(4-(cyanomethyl)piperidin-1-yl)-5-oxo-5,6-dihydropyrimido[4,5-d]pyridazin-4-yl)amino)pyridin-2-yl)piperidin-4-yl)acetic acid;

2-(1-(4-((2-(3,5-dimethylpiperidin-1-yl)-5-oxo-5,6-dihydropyrimido[4,5-d]pyridazin-4-yl)amino)phenyl)piperidin-4-yl)acetic acid;

2-(1-(4-((2-(azepan-1-yl)-5-oxo-5,6-dihydropyrimido[4,5-d]pyridazin-4-yl)amino)phenyl)piperidin-4-yl)-N,N-bis(2-hydroxyethyl)acetamide;

2-methyl-2-(1-(4-((5-oxo-2-phenyl-5,6-dihydropyrimido[4,5-d]pyridazin-4-yl)amino)phenyl)piperidin-4-yl)propanenitrile;

2-(4-(2-(4-((2-(azepan-1-yl)-5-oxo-5,6-dihydropyrimido[4,5-d]pyridazin-4-yl)amino)phenoxy)ethyl)piperazin-1-yl)-2-methylpropanenitrile;

2-(1-(4-((2-(2,6-dimethylmorpholino)-5-oxo-5,6-dihydropyrimido[4,5-d]pyridazin-4-yl)amino)phenyl)piperidin-4-yl)acetic acid;

4-((4-(((2S,5S)-5-(hydroxymethyl)-1,4-dioxan-2-yl)methoxy)phenyl)amino)-2-phenylpyrimido[4,5-d]pyridazin-5(6H)-one;

2-((1S,4S)-4-(4-((2-(azepan-1-yl)-5-oxo-5,6-dihydropyrimido[4,5-d]pyridazin-4-yl)amino)phenyl)cyclohexyl)acetic acid;

(2R,5S)-5-((4-((2-(azepan-1-yl)-5-oxo-5,6-dihydropyrimido[4,5-d]pyridazin-4-yl)amino)phenoxy)methyl)-1,4-dioxane-2-carboxylic acid;

2-(4-(4-((2-(azepan-1-yl)-5-oxo-5,6-dihydropyrimido[4,5-d]pyridazin-4-yl)amino)phenyl)piperazin-1-yl)acetic acid;

2-(1-(3-(4-((2-(azepan-1-yl)-5-oxo-5,6-dihydropyrimido[4,5-d]pyridazin-4-yl)amino)phenoxy)propyl)piperidin-4-yl)acetic acid;

6-(4-((2-(cyclohexylamino)-5-oxo-5,6-dihydropyrimido[4,5-d]pyridazin-4-yl)amino)phenyl)spiro[2.5]octane-1-carboxylic acid;

6-(4-((5-oxo-2-(piperidin-1-yl)-5,6-dihydropyrimido[4,5-d]pyridazin-4-yl)amino)phenyl)spiro[2.5]octane-1-carboxylic acid;

2-((1R,4R)-4-(4-((2-(azepan-1-yl)-5-oxo-5,6-dihydropyrimido[4,5-d]pyridazin-4-yl)amino)phenyl)cyclohexyl)acetic acid;

3-(1-(4-((2-(azepan-1-yl)-5-oxo-5,6-dihydropyrimido[4,5-d]pyridazin-4-yl)amino)phenyl)piperidin-4-yl)propanoic acid;

2-(1-(4-((2-(azepan-1-yl)-5-oxo-5,6-dihydropyrimido[4,5-d]pyridazin-4-yl)amino)phenyl)piperidin-4-yl)cyclopropanecarboxylic acid;

3-(1-(4-((5-oxo-2-phenyl-5,6-dihydropyrimido[4,5-d]pyridazin-4-yl)amino)phenyl)piperidin-4-yl)propanoic acid;

6-(4-((2-(4-fluorophenyl)-5-oxo-5,6-dihydropyrimido[4,5-d]pyridazin-4-yl)amino)phenyl)-6-azaspiro[2.5]octane-1-carboxylic acid;

6-(5-((2-(azepan-1-yl)-5-oxo-5,6-dihydropyrimido[4,5-d]pyridazin-4-yl)amino)pyridin-2-yl)-6-azaspiro[2.5]octane-1-carboxylic acid;

6-(4-((2-(azepan-1-yl)-5-oxo-5,6-dihydropyrimido[4,5-d]pyridazin-4-yl)amino)-2-fluorophenyl)-6-azaspiro[2.5]octane-1-carboxylic acid;

2-(azepan-1-yl)-4-((4-(3-(piperazin-1-yl)propoxy)phenyl)amino)pyrimido[4,5-d]pyridazin-5(6H)-one;

6-(5-((5-oxo-2-phenyl-5,6-dihydropyrimido[4,5-d]pyridazin-4-yl)amino)pyridin-2-yl)-6-azaspiro[2.5]octane-1-carboxylic acid;

6-(4-((5-oxo-2-(pyridin-4-yl)-5,6-dihydropyrimido[4,5-d]pyridazin-4-yl)amino)phenyl)-6-azaspiro[2.5]octane-1-carboxylic acid;

2-(azepan-1-yl)-4-((4-(4-(2-hydroxypropan-2-yl)piperidin-1-yl)phenyl)amino)pyrimido[4,5-d]pyridazin-5(6H)-one;

2-(4-(4-((2-(azepan-1-yl)-5-oxo-5,6-dihydropyrimido[4,5-d]pyridazin-4-yl)amino)phenyl)piperazin-1-yl)-2-methylpropanoic acid;

6-(4-((2-(azocan-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(azepan-1-yl)-5-oxo-5,6-dihydropyrimido[4,5-d]pyridazin-4-yl)amino)phenyl)piperidin-4-yl)-2-methylpropanoic acid;

2-methyl-2-(1-(4-((5-oxo-2-phenyl-5,6-dihydropyrimido[4,5-d]pyridazin-4-yl)amino)phenyl)piperidin-4-yl)propanoic acid;

2-(2,6-dimethylpiperidin-1-yl)-4-((4-(piperazin-1-ylmethyl)phenyl)amino)pyrimido[4,5-d]pyridazin-5(6H)-one;

2-(1-(4-((2-(2,6-dimethylpiperidin-1-yl)-5-oxo-5,6-dihydropyrimido[4,5-d]pyridazin-4-yl)amino)phenyl)piperidin-4-yl)acetic acid;

6-(4-((2-(2,6-dimethylpiperidin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(2,6-dimethylpiperidin-1-yl)-5-oxo-5,6-dihydropyrimido[4,5-d]pyridazin-4-yl)amino)phenyl)piperidin-4-yl)acetonitrile;

2-(2,6-dimethylpiperidin-1-yl)-4-((4-(4-(2-hydroxy-2-methylpropanoyl)piperazin-1-yl)phenyl)amino)pyrimido[4,5-d]pyridazin-5(6H)-one;

2-(1-(5-((2-(2,6-dimethylpiperidin-1-yl)-5-oxo-5,6-dihydropyrimido[4,5-d]pyridazin-4-yl)amino)pyridin-2-yl)piperidin-4-yl)acetic acid;

2-(3,5-dimethylpiperidin-1-yl)-4-((4-(piperazin-1-ylmethyl)phenyl)amino)pyrimido[4,5-d]pyridazin-5(6H)-one;

2-(1-(4-((2-(3,5-dimethylpiperidin-1-yl)-5-oxo-5,6-dihydropyrimido[4,5-d]pyridazin-4-yl)amino)phenyl)piperidin-4-yl)acetic acid;

6-(4-((2-(3,5-dimethylpiperidin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(3,5-dimethylpiperidin-1-yl)-5-oxo-5,6-dihydropyrimido[4,5-d]pyridazin-4-yl)amino)phenyl)piperidin-4-yl)acetonitrile;

2-(3,5-dimethylpiperidin-1-yl)-4-((4-(4-(2-hydroxy-2-methylpropanoyl)piperidin-1-yl)phenyl)amino)pyrimido[4,5-d]pyridazin-5(6H)-one;

2-(1-(5-((2-(3,5-dimethylpiperidin-1-yl)-5-oxo-5,6-dihydropyrimido[4,5-d]pyridazin-4-yl)amino)pyridin-2-yl)piperidin-4-yl)acetic acid;

2-(2,6-dimethylmorpholino)-4-((4-(piperazin-1-ylmethyl)phenyl)amino)pyrimido[4,5-d]pyridazin-5(6H)-one;

2-(1-(4-((2-(2,6-dimethylmorpholino)-5-oxo-5,6-dihydropyrimido[4,5-d]pyridazin-4-yl)amino)phenyl)piperidin-4-yl)acetic acid;

6-(4-((2-(2,6-dimethylmorpholino)-5-oxo-5,6-dihydropyrimido[4,5-d]pyridazin-4-yl)amino)phenyl)-6-azaspiro[2.5]octane-1-carboxylic acid;

2-(1-(4-((2-(2,6-dimethylmorpholino)-5-oxo-5,6-dihydropyrimido[4,5-d]pyridazin-4-yl)amino)phenyl)piperidin-4-yl)acetonitrile;

2-(2,6-dimethylmorpholino)-4-((4-(4-(2-hydroxy-2-methylpropanoyl)piperidin-1-yl)phenyl)amino)pyrimido[4,5-d]pyridazin-5(6H)-one;

2-(1-(5-((2-(2,6-dimethylmorpholino)-5-oxo-5,6-dihydropyrimido[4,5-d]pyridazin-4-yl)amino)pyridin-2-yl)piperidin-4-yl)acetic acid;

2-(diisopropylamino)-4-((4-(piperazin-1-ylmethyl)phenyl)amino)pyrimido[4,5-d]pyridazin-5(6H)-one;

2-(1-(4-((2-(diisopropylamino)-5-oxo-5,6-dihydropyrimido[4,5-d]pyridazin-4-yl)amino)phenyl)piperidin-4-yl)acetic acid;

6-(4-((2-(diisopropylamino)-5-oxo-5,6-dihydropyrimido[4,5-d]pyridazin-4-yl)amino)phenyl)-6-azaspiro[2.5]octane-1-carboxylic acid;

2-(1-(4-((2-(diisopropylamino)-5-oxo-5,6-dihydropyrimido[4,5-d]pyridazin-4-yl)amino)phenyl)piperidin-4-yl)acetonitrile;

2-(diisopropylamino)-4-((4-(4-(2-hydroxy-2-methylpropanoyl)piperidin-1-yl)phenyl)amino)pyrimido[4,5-d]pyridazin-5(6H)-one;

2-(1-(5-((2-(diisopropylamino)-5-oxo-5,6-dihydropyrimido[4,5-d]pyridazin-4-yl)amino)pyridin-2-yl)piperidin-4-yl)acetic acid;

2-(2-methylpiperidin-1-yl)-4-((4-(piperazin-1-ylmethyl)phenyl)amino)pyrimido[4,5-d]pyridazin-5(6H)-one;

2-(1-(4-((2-(2-methylpiperidin-1-yl)-5-oxo-5,6-dihydropyrimido[4,5-d]pyridazin-4-yl)amino)phenyl)piperidin-4-yl)acetic acid;

6-(4-((2-(2-methylpiperidin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(2-methylpiperidin-1-yl)-5-oxo-5,6-dihydropyrimido[4,5-d]pyridazin-4-yl)amino)phenyl)piperidin-4-yl)acetonitrile;

4-((4-(4-(2-hydroxy-2-methylpropanoyl)piperidin-1-yl)phenyl)amino)-2-(2-methylpiperidin-1-yl)pyrimido[4,5-d]pyridazin-5(6H)-one;

2-(1-(5-((2-(2-methylpiperidin-1-yl)-5-oxo-5,6-dihydropyrimido[4,5-d]pyridazin-4-yl)amino)pyridin-2-yl)piperidin-4-yl)acetic acid;

1-(4-((2-(azepan-1-yl)-5-oxo-5,6-dihydropyrimido[4,5-d]pyridazin-4-yl)amino)phenyl)piperidine-4-carboxylic acid;

1-(4-((2-(azepan-1-yl)-5-oxo-5,6-dihydropyrimido[4,5-d]pyridazin-4-yl)amino)benzyl)piperidine-4-carboxylic acid;

4-((4-((4-(2H-tetrazol-5-yl)piperidin-1-yl)methyl)phenyl)amino)-2-(azepan-1-yl)pyrimido[4,5-d]pyridazin-5(6H)-one;

4-((4-((4-((2H-tetrazol-5-yl)methyl)piperidin-1-yl)methyl)phenyl)amino)-2-(azepan-1-yl)pyrimido[4,5-d]pyridazin-5(6H)-one;

2-(1-(4-((2-cycloheptyl-5-oxo-5,6-dihydropyrimido[4,5-d]pyridazin-4-yl)amino)phenyl)piperidin-4-yl)acetic acid;

1-(4-((2-cycloheptyl-5-oxo-5,6-dihydropyrimido[4,5-d]pyridazin-4-yl)amino)phenyl)piperidine-4-carboxylic acid;

6-(4-((2-(3-cyanopiperidin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(3-cyanopiperidin-1-yl)-5-oxo-5,6-dihydropyrimido[4,5-d]pyridazin-4-yl)amino)phenyl)piperidin-4-yl)acetic acid;

1-(4-((2-(3-cyanopiperidin-1-yl)-5-oxo-5,6-dihydropyrimido[4,5-d]pyridazin-4-yl)amino)phenyl)piperidine-4-carboxylic acid;

1-(4-((2-(3-cyanopiperidin-1-yl)-5-oxo-5,6-dihydropyrimido[4,5-d]pyridazin-4-yl)amino)benzyl)piperidine-4-carboxylic acid;

1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-3-carbonitrile;

2-(1-(4-((2-(3-cyanopiperidin-1-yl)-5-oxo-5,6-dihydropyrimido[4,5-d]pyridazin-4-yl)amino)benzyl)piperidin-4-yl)acetic acid;

1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-3-carbonitrile;

1-(4-((2-cycloheptyl-5-oxo-5,6-dihydropyrimido[4,5-d]pyridazin-4-yl)amino)benzyl)piperidine-4-carboxylic acid;

4-((4-((4-(2H-tetrazol-5-yl)piperidin-1-yl)methyl)phenyl)amino)-2-cycloheptylpyrimido[4,5-d]pyridazin-5(6H)-one;

2-(1-(4-((2-cycloheptyl-5-oxo-5,6-dihydropyrimido[4,5-d]pyridazin-4-yl)amino)benzyl)piperidin-4-yl)acetic acid;

4-((4-((4-((2H-tetrazol-5-yl)methyl)piperidin-1-yl)methyl)phenyl)amino)-2-cycloheptylpyrimido[4,5-d]pyridazin-5(6H)-one;

1-(4-((2-(4-cyanopiperidin-1-yl)-5-oxo-5,6-dihydropyrimido[4,5-d]pyridazin-4-yl)amino)phenyl)piperidine-4-carboxylic acid;

1-(4-((4-((4-(2H-tetrazol-5-yl)piperidin-1-yl)methyl)phenyl)amino)-5-oxo-5,6-dihydropyrimido[4,5-d]pyridazin-2-yl)piperidine-4-carbonitrile;

1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidine-4-carbonitrile;

1-(4-((2-(4-(cyanomethyl)piperidin-1-yl)-5-oxo-5,6-dihydropyrimido[4,5-d]pyridazin-4-yl)amino)benzyl)piperidine-4-carboxylic acid;

2-(1-(4-((4-((4-(2H-tetrazol-5-yl)piperidin-1-yl)methyl)phenyl)amino)-5-oxo-5,6-dihydropyrimido[4,5-d]pyridazin-2-yl)piperidin-4-yl)acetonitrile;

2-(1-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperidin-4-yl)acetonitrile;

1-(4-((2-(4-(cyanomethyl)piperazin-1-yl)-5-oxo-5,6-dihydropyrimido[4,5-d]pyridazin-4-yl)amino)phenyl)piperidine-4-carboxylic acid;

1-(4-((2-(4-(cyanomethyl)piperazin-1-yl)-5-oxo-5,6-dihydropyrimido[4,5-d]pyridazin-4-yl)amino)benzyl)piperidine-4-carboxylic acid;

2-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)acetonitrile;

2-(1-(4-((2-(4-(cyanomethyl)piperazin-1-yl)-5-oxo-5,6-dihydropyrimido[4,5-d]pyridazin-4-yl)amino)benzyl)piperidin-4-yl)acetic acid;

2-(4-(4-((4-((4-((2H-tetrazol-5-yl)methyl)piperidin-1-yl)methyl)phenyl)amino)-5-oxo-5,6-dihydropyrimido[4,5-d]pyridazin-2-yl)piperazin-1-yl)acetonitrile;

6-(4-((2-(1,4-diazepan-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(1,4-diazepan-1-yl)-5-oxo-5,6-dihydropyrimido[4,5-d]pyridazin-4-yl)amino)phenyl)piperidin-4-yl)acetic acid;

1-(4-((2-(1,4-diazepan-1-yl)-5-oxo-5,6-dihydropyrimido[4,5-d]pyridazin-4-yl)amino)phenyl)piperidine-4-carboxylic acid;

1-(4-((2-(1,4-diazepan-1-yl)-5-oxo-5,6-dihydropyrimido[4,5-d]pyridazin-4-yl)amino)benzyl)piperidine-4-carboxylic acid;

6-(4-((2-(4-(2-cyanoacetyl)piperazin-1-yl)-5-oxo-5,6-dihydropyrimido[4,5-d]pyridazin-4-yl)amino)phenyl)-6-azaspiro[2.5]octane-1-carboxylic acid;

2-(1-(4-((2-(4-(2-cyanoacetyl)piperazin-1-yl)-5-oxo-5,6-dihydropyrimido[4,5-d]pyridazin-4-yl)amino)phenyl)piperidin-4-yl)acetic acid;

1-(4-((2-(4-(2-cyanoacetyl)piperazin-1-yl)-5-oxo-5,6-dihydropyrimido[4,5-d]pyridazin-4-yl)amino)phenyl)piperidine-4-carboxylic acid;

1-(4-((2-(4-(2-cyanoacetyl)piperazin-1-yl)-5-oxo-5,6-dihydropyrimido[4,5-d]pyridazin-4-yl)amino)benzyl)piperidine-4-carboxylic acid;

3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperazin-1-yl)-3-oxopropanenitrile;

2-(1-(4-((2-(4-(2-cyanoacetyl)piperazin-1-yl)-5-oxo-5,6-dihydropyrimido[4,5-d]pyridazin-4-yl)amino)benzyl)piperidin-4-yl)acetic acid;

4-((4-((4-((2H-tetrazol-5-yl)methyl)piperidin-1-yl)methyl)phenyl)amino)-2-(4-(2-isocyanoacetyl)piperazin-1-yl)pyrimido[4,5-d]pyridazin-5(6H)-one;

6-(4-((2-(1-(2-cyanoacetyl)piperidin-4-yl)-5-oxo-5,6-dihydropyrimido[4,5-d]pyridazin-4-yl)amino)phenyl)-6-azaspiro[2.5]octane-1-carboxylic acid;

2-(1-(4-((2-(1-(2-cyanoacetyl)piperidin-4-yl)-5-oxo-5,6-dihydropyrimido[4,5-d]pyridazin-4-yl)amino)phenyl)piperidin-4-yl)acetic acid;

1-(4-((2-(1-(2-cyanoacetyl)piperidin-4-yl)-5-oxo-5,6-dihydropyrimido[4,5-d]pyridazin-4-yl)amino)phenyl)piperidine-4-carboxylic acid;

1-(4-((2-(1-(2-cyanoacetyl)piperidin-4-yl)-5-oxo-5,6-dihydropyrimido[4,5-d]pyridazin-4-yl)amino)benzyl)piperidine-4-carboxylic acid;

3-(4-(4-((4-((4-(2H-tetrazol-5-yl)piperidin-1-yl)methyl)phenyl)amino)-5-oxo-5,6-dihydropyrimido[4,5-d]pyridazin-2-yl)piperidin-1-yl)-3-oxopropanenitrile;

2-(1-(4-((2-(1-(2-cyanoacetyl)piperidin-4-yl)-5-oxo-5,6-dihydropyrimido[4,5-d]pyridazin-4-yl)amino)benzyl)piperidin-4-yl)acetic acid;

4-((4-((4-((2H-tetrazol-5-yl)methyl)piperidin-1-yl)methyl)phenyl)amino)-2-(1-(2-isocyanoacetyl)piperidin-4-yl)pyrimido[4,5-d]pyridazin-5(6H)-one;

2-(4-(5-((2-(azepan-1-yl)-5-oxo-5,6-dihydropyrimido[4,5-d]pyridazin-4-yl)amino)pyridin-2-yl)piperazin-1-yl)acetic acid;

2-(4-(4-((2-(azepan-1-yl)-5-oxo-5,6-dihydropyrimido[4,5-d]pyridazin-4-yl)amino)phenyl)-1,4-diazepan-1-yl)acetic acid;

2-(1-(4-((4-(4-(2-hydroxypropan-2-yl)piperidin-1-yl)phenyl)amino)-5-oxo-5,6-dihydropyrimido[4,5-d]pyridazin-2-yl)piperidin-4-yl)acetonitrile;

3-(1-(4-((2-(4-(cyanomethyl)piperidin-1-yl)-5-oxo-5,6-dihydropyrimido[4,5-d]pyridazin-4-yl)amino)phenyl)piperidin-4-yl)propanoic acid;

6-(5-((2-(4-(cyanomethyl)piperidin-1-yl)-5-oxo-5,6-dihydropyrimido[4,5-d]pyridazin-4-yl)amino)pyridin-2-yl)-6-azaspiro[2.5]octane-1-carboxylic acid;

1-(5-oxo-4-((4-(2-(piperazin-1-yl)ethoxy)phenyl)amino)-5,6-dihydropyrimido[4,5-d]pyridazin-2-yl)piperidine-4-carbonitrile;

2-(1-(5-oxo-4-((4-(2-(piperazin-1-yl)ethoxy)phenyl)amino)-5,6-dihydropyrimido[4,5-d]pyridazin-2-yl)piperidin-4-yl)acetonitrile;

2-(azepan-1-yl)-4-((4-(2-(4-ethylpiperazin-1-yl)ethoxy)phenyl)amino)pyrimido[4,5-d]pyridazin-5(6H)-one;

2-phenyl-4-((4-(2-(piperazin-1-yl)ethoxy)phenyl)amino)pyrimido[4,5-d]pyridazin-5(6H)-one;

4-((4-(2-(piperazin-1-yl)ethoxy)phenyl)amino)-2-(piperidin-1-yl)pyrimido[4,5-d]pyridazin-5(6H)-one;

2-(4-(4-((5-oxo-2-(piperidin-1-yl)-5,6-dihydropyrimido[4,5-d]pyridazin-4-yl)amino)phenyl)-1,4-diazepan-1-yl)acetic acid;

6-(4-((2-(4-methylpiperidin-1-yl)-5-oxo-5,6-dihydropyrimido[4,5-d]pyridazin-4-yl)amino)phenyl)-6-azaspiro[2.5]octane-1-carboxylic acid;

2-(4-methylpiperidin-1-yl)-4-((4-(2-(piperazin-1-yl)ethoxy)phenyl)amino)pyrimido[4,5-d]pyridazin-5(6H)-one hydrochloride;

2-(azepan-1-yl)-4-((4-(2-(3-oxopiperazin-1-yl)ethoxy)phenyl)amino)pyrimido[4,5-d]pyridazin-5(6H)-one;

6-(2-(4-((2-(azepan-1-yl)-5-oxo-5,6-dihydropyrimido[4,5-d]pyridazin-4-yl)amino)phenoxy)ethyl)-6-azaspiro[2.5]octane-1-carboxylic acid;

2-(azepan-1-yl)-4-((4-(2-(diethylamino)ethoxy)phenyl)amino)pyrimido[4,5-d]pyridazin-5(6H)-one;

2-(cyclohexyl(methyl)amino)-4-((4-(2-(piperazin-1-yl)ethoxy)phenyl)amino)pyrimido[4,5-d]pyridazin-5(6H)-one;

2-(1-(4-((2-(cyclohexyl(methyl)amino)-5-oxo-5,6-dihydropyrimido[4,5-d]pyridazin-4-yl)amino)phenyl)piperidin-4-yl)acetic acid;

2-(4-(4-((2-(4-(cyanomethyl)piperidin-1-yl)-5-oxo-5,6-dihydropyrimido[4,5-d]pyridazin-4-yl)amino)phenyl)piperazin-1-yl)acetic acid;

2-(1-(4-((2-(3-methoxyphenyl)-5-oxo-5,6-dihydropyrimido[4,5-d]pyridazin-4-yl)amino)phenyl)piperidin-4-yl)acetonitrile;

4-((4-(2-(1,4-diazepan-1-yl)ethoxy)phenyl)amino)-2-(azepan-1-yl)pyrimido[4,5-d]pyridazin-5(6H)-one;

2-(azepan-1-yl)-4-((4-(3-oxopiperazin-1-yl)phenyl)amino)pyrimido[4,5-d]pyridazin-5(6H)-one;

2-(3-methoxyphenyl)-4-((4-(2-(piperazin-1-yl)ethoxy)phenyl)amino)pyrimido[4,5-d]pyridazin-5(6H)-one;

2-(azepan-1-yl)-4-((4-(2-(dimethylamino)ethoxy)phenyl)amino)pyrimido[4,5-d]pyridazin-5(6H)-one;

2-(azepan-1-yl)-4-((4-(2-(piperidin-4-yl)ethoxy)phenyl)amino)pyrimido[4,5-d]pyridazin-5(6H)-one;

2-(1-(5-oxo-4-((4-(2-(piperidin-4-yl)ethoxy)phenyl)amino)-5,6-dihydropyrimido[4,5-d]pyridazin-2-yl)piperidin-4-yl)acetonitrile;

6-(4-((2-(cyclohexyl(methyl)amino)-5-oxo-5,6-dihydropyrimido[4,5-d]pyridazin-4-yl)amino)phenyl)-6-azaspiro[2.5]octane-1-carboxylic acid;

4-((4-(2-(1,4-diazepan-1-yl)ethoxy)phenyl)amino)-2-(piperidin-1-yl)pyrimido[4,5-d]pyridazin-5(6H)-one;

2-(azepan-1-yl)-4-((4-(2-(4-hydroxypiperidin-1-yl)ethoxy)phenyl)amino)pyrimido[4,5-d]pyridazin-5(6H)-one;

2-(azepan-1-yl)-4-((4-(3-(piperazin-1-yl)propyl)phenyl)amino)pyrimido[4,5-d]pyridazin-5(6H)-one;

2-(1-(5-oxo-4-((4-(3-(piperazin-1-yl)propyl)phenyl)amino)-5,6-dihydropyrimido[4,5-d]pyridazin-2-yl)piperidin-4-yl)acetonitrile;

2-(azepan-1-yl)-4-((4-(4-ethyl-3-oxopiperazin-1-yl)phenyl)amino)pyrimido[4,5-d]pyridazin-5(6H)-one;

2-morpholino-4-((4-(2-(piperazin-1-yl)ethoxy)phenyl)amino)pyrimido[4,5-d]pyridazin-5(6H)-one;

2-(2,6-dimethylmorpholino)-4-((4-(2-(piperazin-1-yl)ethoxy)phenyl)amino)pyrimido[4,5-d]pyridazin-5(6H)-one;

2-(1-(4-((4-(4-ethyl-3-oxopiperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(3-(4-hydroxypiperidin-1-yl)propyl)phenyl)amino)pyrimido[4,5-d]pyridazin-5(6H)-one;

2-(azepan-1-yl)-4-((4-(4-ethylpiperazin-1-yl)phenyl)amino)pyrimido[4,5-d]pyridazin-5(6H)-one;

4-((6-(2-(piperazin-1-yl)ethoxy)pyridin-3-yl)amino)-2-(piperidin-1-yl)pyrimido[4,5-d]pyridazin-5(6H)-one;

2-(azepan-1-yl)-4-((6-(2-(piperazin-1-yl)ethoxy)pyridin-3-yl)amino)pyrimido[4,5-d]pyridazin-5(6H)-one;

4-((4-(2-(4-hydroxypiperidin-1-yl)ethoxy)phenyl)amino)-2-(piperidin-1-yl)pyrimido[4,5-d]pyridazin-5(6H)-one;

2-(azepan-1-yl)-4-((4-(2-(4-hydroxy-4-methylpiperidin-1-yl)ethoxy)phenyl)amino)pyrimido[4,5-d]pyridazin-5(6H)-one;

2-(1-(4-((4-(2-(4-hydroxy-4-methylpiperidin-1-yl)ethoxy)phenyl)amino)-5-oxo-5,6-dihydropyrimido[4,5-d]pyridazin-2-yl)piperidin-4-yl)acetonitrile;

2-(azepan-1-yl)-4-((4-(4-hydroxypiperidin-1-yl)phenyl)amino)pyrimido[4,5-d]pyridazin-5(6H)-one;

2-(1-(4-((4-(4-ethylpiperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(2-(diisopropylamino)ethoxy)phenyl)amino)pyrimido[4,5-d]pyridazin-5(6H)-one;

2-(1-(4-((4-(4-hydroxypiperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-(2-hydroxyethyl)piperazin-1-yl)phenyl)amino)pyrimido[4,5-d]pyridazin-5(6H)-one;

2-(1-(4-((4-(4-(2-hydroxyethyl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(piperazin-1-yl)phenyl)amino)pyrimido[4,5-d]pyridazin-5(6H)-one;

2-(1-(5-oxo-4-((4-(piperazin-1-yl)phenyl)amino)-5,6-dihydropyrimido[4,5-d]pyridazin-2-yl)piperidin-4-yl)acetonitrile;

2-(azepan-1-yl)-4-((4-(4-(3-hydroxypropyl)piperidin-1-yl)phenyl)amino)pyrimido[4,5-d]pyridazin-5(6H)-one;

2-(azepan-1-yl)-4-((4-(4-(2-hydroxyethyl)piperidin-1-yl)phenyl)amino)pyrimido[4,5-d]pyridazin-5(6H)-one;

2-(1-(4-((4-(4-(2-hydroxyethyl)piperidin-1-yl)phenyl)amino)-5-oxo-5,6-dihydropyrimido[4,5-d]pyridazin-2-yl)piperidin-4-yl)acetonitrile;

2-(1-(4-((4-(2-(4-ethylpiperazin-1-yl)ethyl)phenyl)amino)-5-oxo-5,6-dihydropyrimido[4,5-d]pyridazin-2-yl)piperidin-4-yl)acetonitrile;

2-(azepan-1-yl)-4-((4-(2-(piperazin-1-yl)ethyl)phenyl)amino)pyrimido[4,5-d]pyridazin-5(6H)-one;

4-((4-(2-aminoethoxy)phenyl)amino)-2-(azepan-1-yl)pyrimido[4,5-d]pyridazin-5(6H)-one;

2-(1-(4-((4-(2-aminoethoxy)phenyl)amino)-5-oxo-5,6-dihydropyrimido[4,5-d]pyridazin-2-yl)piperidin-4-yl)acetonitrile;

2-(azepan-1-yl)-4-((4-(2-(4-hydroxypiperidin-1-yl)ethyl)phenyl)amino)pyrimido[4,5-d]pyridazin-5(6H)-one;

2-(azepan-1-yl)-4-((4-(4-(hydroxymethyl)piperidin-1-yl)phenyl)amino)pyrimido[4,5-d]pyridazin-5(6H)-one;

2-(azepan-1-yl)-4-((4-(2-(4-(hydroxymethyl)piperidin-1-yl)ethoxy)phenyl)amino)pyrimido[4,5-d]pyridazin-5(6H)-one;

2-(1-(2-(4-((2-(azepan-1-yl)-5-oxo-5,6-dihydropyrimido[4,5-d]pyridazin-4-yl)amino)piperidin-1-yl)ethyl)piperidin-4-yl)acetonitrile;

2-(1-(4-((4-(4-(3-hydroxypropyl)piperidin-1-yl)phenyl)amino)-5-oxo-5,6-dihydropyrimido[4,5-d]pyridazin-2-yl)piperidin-4-yl)acetonitrile;

2-(4-(4-((2-(azepan-1-yl)-5-oxo-5,6-dihydropyrimido[4,5-d]pyridazin-4-yl)amino)phenyl)piperazin-1-yl)acetonitrile;

2-(1-(4-((4-(4-(cyanomethyl)piperazin-1-yl)phenyl)amino)-5-oxo-5,6-dihydropyrimido[4,5-d]pyridazin-2-yl)piperidin-4-yl)acetonitrile;

3-(4-(4-((2-(azepan-1-yl)-5-oxo-5,6-dihydropyrimido[4,5-d]pyridazin-4-yl)amino)phenyl)piperazin-1-yl)propanoic acid;

2-(azepan-1-yl)-4-((4-(2-(4-ethylpiperazin-1-yl)ethyl)phenyl)amino)pyrimido[4,5-d]pyridazin-5(6H)-one;

2-(azepan-1-yl)-4-((4-(2-(4-hydroxy-4-methylpiperidin-1-yl)ethyl)phenyl)amino)pyrimido[4,5-d]pyridazin-5(6H)-one;

2-(azepan-1-yl)-4-((4-(2-(4-(2-hydroxyethyl)piperazin-1-yl)ethyl)phenyl)amino)pyrimido[4,5-d]pyridazin-5(6H)-one;

2-(1-(4-((4-(2-(4-(2-hydroxyethyl)piperazin-1-yl)ethyl)phenyl)amino)-5-oxo-5,6-dihydropyrimido[4,5-d]pyridazin-2-yl)piperidin-4-yl)acetonitrile;

2-(4-(4-((2-(4-(cyanomethyl)piperidin-1-yl)-5-oxo-5,6-dihydropyrimido[4,5-d]pyridazin-4-yl)amino)phenyl)piperazin-1-yl)-2-methylpropanoic acid;

2-(azepan-1-yl)-4-((4-(4-(2-hydroxy-2-methylpropanoyl)piperazin-1-yl)phenyl)amino)pyrimido[4,5-d]pyridazin-5(6H)-one;

3-(4-(4-((2-(azepan-1-yl)-5-oxo-5,6-dihydropyrimido[4,5-d]pyridazin-4-yl)amino)phenyl)piperazin-1-yl)-3-oxopropanenitrile;

2-(1-(4-((4-(4-(hydroxymethyl)piperidin-1-yl)phenyl)amino)-5-oxo-5,6-dihydropyrimido[4,5-d]pyridazin-2-yl)piperidin-4-yl)acetonitrile;

2-(azepan-1-yl)-4-((6-(4-hydroxypiperidin-1-yl)pyridin-3-yl)amino)pyrimido[4,5-d]pyridazin-5(6H)-one;

2-(1-(4-((4-(2-(4-(hydroxymethyl)piperidin-1-yl)ethoxy)phenyl)amino)-5-oxo-5,6-dihydropyrimido[4,5-d]pyridazin-2-yl)piperidin-4-yl)acetonitrile;

(phosphonooxy)methyl 6-(4-((2-(azepan-1-yl)-5-oxo-5,6-dihydropyrimido[4,5-d]pyridazin-4-yl)amino)phenyl)-6-azaspiro[2.5]octane-1-carboxylate;

3-(4-(4-((2-(4-(cyanomethyl)piperidin-1-yl)-5-oxo-5,6-dihydropyrimido[4,5-d]pyridazin-4-yl)amino)phenyl)piperazin-1-yl)propanoic acid;

2-(azepan-1-yl)-4-((6-(piperazin-1-yl)pyridin-3-yl)amino)pyrimido[4,5-d]pyridazin-5(6H)-one;

2-(azepan-1-yl)-4-((4-(2-(2-hydroxyethyl)-2H-tetrazol-5-yl)phenyl)amino)pyrimido[4,5-d]pyridazin-5(6H)-one;

2-(1-(4-((4-(4-(2-hydroxy-2-methylpropanoyl)piperazin-1-yl)phenyl)amino)-5-oxo-5,6-dihydropyrimido[4,5-d]pyridazin-2-yl)piperidin-4-yl)acetonitrile;

2-(1-(4-((4-(2-(diethylamino)ethoxy)phenyl)amino)-5-oxo-5,6-dihydropyrimido[4,5-d]pyridazin-2-yl)piperidin-4-yl)acetonitrile;

2-(azepan-1-yl)-4-((4-(2-ethyl-2H-tetrazol-5-yl)phenyl)amino)pyrimido[4,5-d]pyridazin-5(6H)-one;

2-(1-(4-((4-(2-ethyl-2H-tetrazol-5-yl)phenyl)amino)-5-oxo-5,6-dihydropyrimido[4,5-d]pyridazin-2-yl)piperidin-4-yl)acetonitrile;

4-((4-(2H-tetrazol-5-yl)phenyl)amino)-2-(azepan-1-yl)pyrimido[4,5-d]pyridazin-5(6H)-one;

2-(1-(4-((6-(4-ethylpiperazin-1-yl)pyridin-3-yl)amino)-5-oxo-5,6-dihydropyrimido[4,5-d]pyridazin-2-yl)piperidin-4-yl)acetonitrile;

2-(azepan-1-yl)-4-((6-(4-ethylpiperazin-1-yl)pyridin-3-yl)amino)pyrimido[4,5-d]pyridazin-5(6H)-one;

2-(4-(5-oxo-4-((4-(2-(piperazin-1-yl)ethoxy)phenyl)amino)-5,6-dihydropyrimido[4,5-d]pyridazin-2-yl)piperazin-1-yl)acetonitrile;

2-(1-(5-oxo-4-((6-(piperazin-1-yl)pyridin-3-yl)amino)-5,6-dihydropyrimido[4,5-d]pyridazin-2-yl)piperidin-4-yl)acetonitrile;

2-(1-(4-((2-(azepan-1-yl)-5-oxo-5,6-dihydropyrimido[4,5-d]pyridazin-4-yl)amino)phenyl)piperidin-3-yl)acetic acid;

2-(1-(4-((2-(azepan-1-yl)-5-oxo-5,6-dihydropyrimido[4,5-d]pyridazin-4-yl)amino)phenyl)piperidin-3-yl)acetic acid;

3-(4-(5-((2-(azepan-1-yl)-5-oxo-5,6-dihydropyrimido[4,5-d]pyridazin-4-yl)amino)pyridin-2-yl)piperazin-1-yl)-3-oxopropanenitrile;

2-(5-(4-((2-(azepan-1-yl)-5-oxo-5,6-dihydropyrimido[4,5-d]pyridazin-4-yl)amino)phenyl)-2H-tetrazol-2-yl)acetic acid;

2-(azepan-1-yl)-4-((6-(4-(2-hydroxyethyl)piperidin-1-yl)pyridin-3-yl)amino)pyrimido[4,5-d]pyridazin-5(6H)-one;

3-(4-(5-((2-(4-(cyanomethyl)piperidin-1-yl)-5-oxo-5,6-dihydropyrimido[4,5-d]pyridazin-4-yl)amino)pyridin-2-yl)piperazin-1-yl)-3-oxopropanenitrile;

2-(azepan-1-yl)-4-((6-(4-(2-hydroxy-2-methylpropanoyl)piperazin-1-yl)pyridin-3-yl)amino)pyrimido[4,5-d]pyridazin-5(6H)-one;

2-(azepan-1-yl)-4-((4-(2-(4-(2-hydroxyethyl)piperazin-1-yl)ethoxy)phenyl)amino)pyrimido[4,5-d]pyridazin-5(6H)-one;

3-(4-(4-((2-(4-(cyanomethyl)piperidin-1-yl)-5-oxo-5,6-dihydropyrimido[4,5-d]pyridazin-4-yl)amino)phenyl)piperazin-1-yl)-3-oxopropanenitrile;

2-(5-(4-((2-(4-(cyanomethyl)piperidin-1-yl)-5-oxo-5,6-dihydropyrimido[4,5-d]pyridazin-4-yl)amino)phenyl)-2H-tetrazol-2-yl)acetic acid;

2-(azepan-1-yl)-4-((6-(4-methylpiperazin-1-yl)pyridin-3-yl)amino)pyrimido[4,5-d]pyridazin-5(6H)-one;

2-(1-(4-((6-(4-methylpiperazin-1-yl)pyridin-3-yl)amino)-5-oxo-5,6-dihydropyrimido[4,5-d]pyridazin-2-yl)piperidin-4-yl)acetonitrile;

4-((4-(4-((2H-tetrazol-5-yl)methyl)piperidin-1-yl)phenyl)amino)-2-(azepan-1-yl)pyrimido[4,5-d]pyridazin-5(6H)-one;

2-(1-(4-((4-(2H-tetrazol-5-yl)phenyl)amino)-5-oxo-5,6-dihydropyrimido[4,5-d]pyridazin-2-yl)piperidin-4-yl)acetonitrile;

2-(1-(4-((4-(4-((2H-tetrazol-5-yl)methyl)piperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-methylpiperazin-1-yl)phenyl)amino)pyrimido[4,5-d]pyridazin-5(6H)-one;

2-(1-(4-((4-(4-methylpiperazin-1-yl)phenyl)amino)-5-oxo-5,6-dihydropyrimido[4,5-d]pyridazin-2-yl)piperidin-4-yl)acetonitrile;

2-(1-(5-((2-(4-(cyanomethyl)piperidin-1-yl)-5-oxo-5,6-dihydropyrimido[4,5-d]pyridazin-4-yl)amino)pyridin-2-yl)piperidin-3-yl)acetic acid;

2-(1-(4-((2-(4-(cyanomethyl)piperidin-1-yl)-5-oxo-5,6-dihydropyrimido[4,5-d]pyridazin-4-yl)amino)phenyl)piperidin-3-yl)acetic acid;

2-(1-(4-((6-(4-(2-hydroxy-2-methylpropanoyl)piperazin-1-yl)pyridin-3-yl)amino)-5-oxo-5,6-dihydropyrimido[4,5-d]pyridazin-2-yl)piperidin-4-yl)acetonitrile;

4-((6-(4-((2H-tetrazol-5-yl)methyl)piperidin-1-yl)pyridin-3-yl)amino)-2-(azepan-1-yl)pyrimido[4,5-d]pyridazin-5(6H)-one;

2-(1-(4-((6-(4-((2H-tetrazol-5-yl)methyl)piperidin-1-yl)pyridin-3-yl)amino)-5-oxo-5,6-dihydropyrimido[4,5-d]pyridazin-2-yl)piperidin-4-yl)acetonitrile;

2-(4-(4-((2-(azepan-1-yl)-5-oxo-5,6-dihydropyrimido[4,5-d]pyridazin-4-yl)amino)phenoxy)piperidin-1-yl)acetic acid;

2-(azepan-1-yl)-4-((4-(4-(2-methoxyethyl)piperazin-1-yl)phenyl)amino)pyrimido[4,5-d]pyridazin-5(6H)-one;

2-(1-(4-((4-(4-(2-methoxyethyl)piperazin-1-yl)phenyl)amino)-5-oxo-5,6-dihydropyrimido[4,5-d]pyridazin-2-yl)piperidin-4-yl)acetonitrile;

2-(1-(4-((4-(4-(2-amino ethyl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(1-(hydroxymethyl)-6-azaspiro[2.5]octan-6-yl)phenyl)amino)pyrimido[4,5-d]pyridazin-5(6H)-one;

2-(1-(4-((4-(1-(hydroxymethyl)-6-azaspiro[2.5]octan-6-yl)phenyl)amino)-5-oxo-5,6-dihydropyrimido[4,5-d]pyridazin-2-yl)piperidin-4-yl)acetonitrile;

2-(azepan-1-yl)-4-((4-(4-(3-hydroxypropyl)piperazin-1-yl)phenyl)amino)pyrimido[4,5-d]pyridazin-5(6H)-one;

2-(1-(4-((4-(4-(3-hydroxypropyl)piperazin-1-yl)phenyl)amino)-5-oxo-5,6-dihydropyrimido[4,5-d]pyridazin-2-yl)piperidin-4-yl)acetonitrile;

2-(4-(4-((2-(4-(cyanomethyl)piperidin-1-yl)-5-oxo-5,6-dihydropyrimido[4,5-d]pyridazin-4-yl)amino)phenoxy)piperidin-1-yl)acetic acid;

2-(azepan-1-yl)-4-((4-(4-(2-hydroxyethyl)-1,4-diazepan-1-yl)phenyl)amino)pyrimido[4,5-d]pyridazin-5(6H)-one;

2-(1-(4-((4-(4-(2-hydroxyethyl)-1,4-diazepan-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-(1-hydroxy-2-methylpropan-2-yl)piperazin-1-yl)phenyl)amino)pyrimido[4,5-d]pyridazin-5(6H)-one;

2-(1-(4-((4-(4-(1-hydroxy-2-methylpropan-2-yl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-(2-(dimethylamino)ethyl)piperazin-1-yl)phenyl)amino)pyrimido[4,5-d]pyridazin-5(6H)-one;

2-(1-(4-((4-(4-(2-(dimethylamino)ethyl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(2-(4-ethylpiperazin-1-yl)-2-oxoethoxy)phenyl)amino)pyrimido[4,5-d]pyridazin-5(6H)-one;

2-(1-(4-((4-(2-(4-ethylpiperazin-1-yl)-2-oxoethoxy)phenyl)amino)-5-oxo-5,6-dihydropyrimido[4,5-d]pyridazin-2-yl)piperidin-4-yl)acetonitrile;

2-(1-(4-((4-(2-(4-methylpiperazin-1-yl)-2-oxoethoxy)phenyl)amino)-5-oxo-5,6-dihydropyrimido[4,5-d]pyridazin-2-yl)piperidin-4-yl)acetonitrile;

2-(azepan-1-yl)-4-((4-(3-(2-hydroxyethyl)piperidin-1-yl)phenyl)amino)pyrimido[4,5-d]pyridazin-5(6H)-one;

2-(azepan-1-yl)-4-((4-(4-(2,3-dihydroxypropyl)piperazin-1-yl)phenyl)amino)pyrimido[4,5-d]pyridazin-5(6H)-one;

2-(1-(4-((4-(4-(2,3-dihydroxypropyl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-(2-fluoroethyl)piperazin-1-yl)phenyl)amino)pyrimido[4,5-d]pyridazin-5(6H)-one;

2-(1-(4-((4-(4-(2-fluoroethyl)piperazin-1-yl)phenyl)amino)-5-oxo-5,6-dihydropyrimido[4,5-d]pyridazin-2-yl)piperidin-4-yl)acetonitrile;

2-(azepan-1-yl)-4-((6-(3-hydroxypiperidin-1-yl)pyridin-3-yl)amino)pyrimido[4,5-d]pyridazin-5(6H)-one;

2-(1-(4-((6-(3-hydroxypiperidin-1-yl)pyridin-3-yl)amino)-5-oxo-5,6-dihydropyrimido[4,5-d]pyridazin-2-yl)piperidin-4-yl)acetonitrile;

2-(azepan-1-yl)-4-((4-(4,4-difluoropiperidin-1-yl)phenyl)amino)pyrimido[4,5-d]pyridazin-5(6H)-one;

2-(1-(4-((4-(4,4-difluoropiperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(3-hydroxypiperidin-1-yl)phenyl)amino)pyrimido[4,5-d]pyridazin-5(6H)-one;

2-(1-(4-((4-(3-hydroxypiperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(2-(4-methylpiperazin-1-yl)-2-oxoethoxy)phenyl)amino)pyrimido[4,5-d]pyridazin-5(6H)-one;

2-(1-(4-((4-(3-(hydroxymethyl)piperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(3-(hydroxymethyl)piperidin-1-yl)phenyl)amino)pyrimido[4,5-d]pyridazin-5(6H)-one;

2-(1-(4-((4-(3-(2-hydroxyethyl)piperidin-1-yl)phenyl)amino)-5-oxo-5,6-dihydropyrimido[4,5-d]pyridazin-2-yl)piperidin-4-yl)acetonitrile;

2-(1-(4-((4-(4-methoxypiperidin-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-methoxypiperidin-1-yl)phenyl)amino)pyrimido[4,5-d]pyridazin-5(6H)-one;

2-(azepan-1-yl)-4-((4-(4-fluoropiperidin-1-yl)phenyl)amino)pyrimido[4,5-d]pyridazin-5(6H)-one;

2-(1-(4-((4-(4-fluoropiperidin-1-yl)phenyl)amino)-5-oxo-5,6-dihydropyrimido[4,5-d]pyridazin-2-yl)piperidin-4-yl)acetonitrile;

2-(1-(4-((4-((1-(2-hydroxyethyl)piperidin-4-yl)oxy)phenyl)amino)-5-oxo-5,6-dihydropyrimido[4,5-d]pyridazin-2-yl)piperidin-4-yl)acetonitrile;

2-(azepan-1-yl)-4-((4-(piperidin-4-yloxy)phenyl)amino)pyrimido[4,5-d]pyridazin-5(6H)-one hydrochloride;

2-(1-(4-((4-(2-hydroxyethoxy)phenyl)amino)-5-oxo-5,6-dihydropyrimido[4,5-d]pyridazin-2-yl)piperidin-4-yl)acetonitrile;

2-(azepan-1-yl)-4-((4-(2-hydroxyethoxy)phenyl)amino)pyrimido[4,5-d]pyridazin-5(6H)-one;

2-(1-(4-((4-(3-hydroxypropoxy)phenyl)amino)-5-oxo-5,6-dihydropyrimido[4,5-d]pyridazin-2-yl)piperidin-4-yl)acetonitrile;

2-(azepan-1-yl)-4-((4-(3-hydroxypropoxy)phenyl)amino)pyrimido[4,5-d]pyridazin-5(6H)-one;

2-(1-(4-((4-(4-(1-hydroxy-2-methylpropan-2-yl)-1,4-diazepan-1-yl)phenyl)amino)-5-oxo-5,6-dihydropyrimido[4,5-d]pyridazin-2-yl)piperidin-4-yl)acetonitrile;

2-(azepan-1-yl)-4-((4-(4-(2-fluoroethyl)piperidin-1-yl)phenyl)amino)pyrimido[4,5-d]pyridazin-5(6H)-one;

2-(1-(4-((4-(4-(2-fluoroethyl)piperidin-1-yl)phenyl)amino)-5-oxo-5,6-dihydropyrimido[4,5-d]pyridazin-2-yl)piperidin-4-yl)acetonitrile;

2-(1-(4-((3,5-dimethoxyphenyl)amino)-5-oxo-5,6-dihydropyrimido[4,5-d]pyridazin-2-yl)piperidin-4-yl)acetonitrile;

2-(1-(5-oxo-4-((4-(trifluoromethoxy)phenyl)amino)-5,6-dihydropyrimido[4,5-d]pyridazin-2-yl)piperidin-4-yl)acetonitrile;

2-(azepan-1-yl)-4-((3,5-dimethoxyphenyl)amino)pyrimido[4,5-d]pyridazin-5(6H)-one;

2-(azepan-1-yl)-4-((4-(trifluoromethoxy)phenyl)amino)pyrimido[4,5-d]pyridazin-5(6H)-one;

3-(4-((2-(azepan-1-yl)-5-oxo-5,6-dihydropyrimido[4,5-d]pyridazin-4-yl)amino)phenyl)propanoic acid;

3-(4-((2-(4-(cyanomethyl)piperidin-1-yl)-5-oxo-5,6-dihydropyrimido[4,5-d]pyridazin-4-yl)amino)phenyl)propanoic acid;

2-(azepan-1-yl)-4-((4-(bis(2-hydroxyethyl)amino)phenyl)amino)pyrimido[4,5-d]pyridazin-5(6H)-one;

2-(1-(4-((4-(bis(2-hydroxyethyl)amino)phenyl)amino)-5-oxo-5,6-dihydropyrimido[4,5-d]pyridazin-2-yl)piperidin-4-yl)acetonitrile;

2-(azepan-1-yl)-4-((4-(3-hydroxypropyl)phenyl)amino)pyrimido[4,5-d]pyridazin-5(6H)-one;

2-(1-(4-((4-(3-hydroxypropyl)phenyl)amino)-5-oxo-5,6-dihydropyrimido[4,5-d]pyridazin-2-yl)piperidin-4-yl)acetonitrile;

2-(azepan-1-yl)-4-((3-(hydroxymethyl)phenyl)amino)pyrimido[4,5-d]pyridazin-5(6H)-one;

2-(1-(4-((3-(hydroxymethyl)phenyl)amino)-5-oxo-5,6-dihydropyrimido[4,5-d]pyridazin-2-yl)piperidin-4-yl)acetonitrile;

2-(1-(4-((4-fluorophenyl)amino)-5-oxo-5,6-dihydropyrimido[4,5-d]pyridazin-2-yl)piperidin-4-yl)acetonitrile;

2-(azepan-1-yl)-4-((4-fluorophenyl)amino)pyrimido[4,5-d]pyridazin-5(6H)-one;

2-(azepan-1-yl)-4-((4-((1-hydroxy-2-methylpropan-2-yl)oxy)phenyl)amino)pyrimido[4,5-d]pyridazin-5(6H)-one;

2-(1-(4-((4-((1-hydroxy-2-methylpropan-2-yl)oxy)phenyl)amino)-5-oxo-5,6-dihydropyrimido[4,5-d]pyridazin-2-yl)piperidin-4-yl)acetonitrile;

2-(4-((2-(azepan-1-yl)-5-oxo-5,6-dihydropyrimido[4,5-d]pyridazin-4-yl)amino)phenoxy)-2-methylpropanoic acid;

2-(4-((2-(4-(cyanomethyl)piperidin-1-yl)-5-oxo-5,6-dihydropyrimido[4,5-d]pyridazin-4-yl)amino)phenoxy)-2-methylpropanoic acid;

2-(azepan-1-yl)-4-((3,4-dimethoxyphenyl)amino)pyrimido[4,5-d]pyridazin-5(6H)-one;

2-(1-(4-((3,4-dimethoxyphenyl)amino)-5-oxo-5,6-dihydropyrimido[4,5-d]pyridazin-2-yl)piperidin-4-yl)acetonitrile;

2-(azepan-1-yl)-4-((3-methoxyphenyl)amino)pyrimido[4,5-d]pyridazin-5(6H)-one;

2-(1-(4-((3-methoxyphenyl)amino)-5-oxo-5,6-dihydropyrimido[4,5-d]pyridazin-2-yl)piperidin-4-yl)acetonitrile;

2-(azepan-1-yl)-4-((4-(2-hydroxyethyl)phenyl)amino)pyrimido[4,5-d]pyridazin-5(6H)-one;

2-(1-(4-((4-(2-hydroxyethyl)phenyl)amino)-5-oxo-5,6-dihydropyrimido[4,5-d]pyridazin-2-yl)piperidin-4-yl)acetonitrile;

2-(azepan-1-yl)-4-((4-(2-methoxyethoxy)phenyl)amino)pyrimido[4,5-d]pyridazin-5(6H)-one;

2-(1-(4-((4-(2-methoxyethoxy)phenyl)amino)-5-oxo-5,6-dihydropyrimido[4,5-d]pyridazin-2-yl)piperidin-4-yl)acetonitrile;

2-(1-(5-oxo-4-((3,4,5-trimethoxyphenyl)amino)-5,6-dihydropyrimido[4,5-d]pyridazin-2-yl)piperidin-4-yl)acetonitrile;

2-(azepan-1-yl)-4-(benzo[d][1,3]dioxol-5-ylamino)pyrimido[4,5-d]pyridazin-5(6H)-one;

2-(1-(4-(benzo[d][1,3]dioxol-5-ylamino)-5-oxo-5,6-dihydropyrimido[4,5-d]pyridazin-2-yl)piperidin-4-yl)acetonitrile;

2-(azepan-1-yl)-4-((4-((1-(2-hydroxyethyl)piperidin-4-yl)oxy)phenyl)amino)pyrimido[4,5-d]pyridazin-5(6H)-one;

sodium (2-(4-(cyanomethyl)piperidin-1-yl)-4-((4-(4-hydroxypiperidin-1-yl)phenyl)amino)-5-oxopyrimido[4,5-d]pyridazin-6(5H)-yl)methyl phosphate;

2-(azepan-1-yl)-4-((4-(hydroxymethyl)phenyl)amino)pyrimido[4,5-d]pyridazin-5(6H)-one;

2-(1-(4-((4-(hydroxymethyl)phenyl)amino)-5-oxo-5,6-dihydropyrimido[4,5-d]pyridazin-2-yl)piperidin-4-yl)acetonitrile;

2-(1-(4-((4-(methylsulfonyl)phenyl)amino)-5-oxo-5,6-dihydropyrimido[4,5-d]pyridazin-2-yl)piperidin-4-yl)acetonitrile;

2-(azepan-1-yl)-4-((4-(methylsulfonyl)phenyl)amino)pyrimido[4,5-d]pyridazin-5(6H)-one;

2-(1-(4-((1H-benzo[d][1,2,3]triazol-5-yl)amino)-5-oxo-5,6-dihydropyrimido[4,5-d]pyridazin-2-yl)piperidin-4-yl)acetonitrile;

2-(1-(5-oxo-4-((2-oxo-2,3-dihydro-1H-benzo[d]imidazol-5-yl)amino)-5,6-dihydropyrimido[4,5-d]pyridazin-2-yl)piperidin-4-yl)acetonitrile;

2-(1-(4-((4-(3-fluoropropyl)phenyl)amino)-5-oxo-5,6-dihydropyrimido[4,5-d]pyridazin-2-yl)piperidin-4-yl)acetonitrile;

2-(1-(4-((4-(difluoromethoxy)phenyl)amino)-5-oxo-5,6-dihydropyrimido[4,5-d]pyridazin-2-yl)piperidin-4-yl)acetonitrile; or 4-((1H-benzo[d][1,2,3]triazol-5-yl)amino)-2-(azepan-1-yl)pyrimido[4,5-d]pyridazin-5(6H)-one.

23. The pharmaceutical composition of claim 1, wherein the one or more excipients are selected from the group consisting of adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizing agents, sweeteners, surfactants, suspending agents, thickening agents, penetration enhancers, and viscosity regulators.

24. The pharmaceutical composition of claim 1, wherein the one or more excipients comprise a pH adjustor.

25. The pharmaceutical composition of claim 1, wherein the one or more excipients comprise a coating.

26. The pharmaceutical composition of claim 1, wherein the composition is formulated for administration to a patient by a modified-release delivery device.

27. The pharmaceutical composition of claim 26, wherein the composition is formulated for extended release to the patient.

28. The pharmaceutical composition of claim 26, wherein the composition is formulated for immediate release to the patient.

29. The pharmaceutical composition of claim 23, wherein the emulsifiers comprise polyoxyethylene fatty acid esters.

30. The pharmaceutical composition of claim 23, wherein the pH adjustors comprise sodium hydroxide.

31. The pharmaceutical composition of claim 23, wherein the sweeteners comprise one or more of saccharin and syrups.

32. The pharmaceutical composition of claim 23, wherein the thickening agents comprise one or more of carboxypolymethylene and hydroxypropylmethylcellulose.

33. The pharmaceutical composition of claim 23, wherein the penetration enhancers comprise one or more of hydroxypolyethoxydodecane, DMSO, DMAC and DDM.

* * * * *